US007078421B2

(12) United States Patent
Zhao et al.

(10) Patent No.: US 7,078,421 B2
(45) Date of Patent: Jul. 18, 2006

(54) SUBSTITUTED PHENYLACETIC ACIDS

(75) Inventors: Zuchun Zhao, Pleasanton, CA (US); Xin Chen, San Ramon, CA (US); Jianchao Wang, Castro Valley, CA (US); Hongbin Sun, Hayward, CA (US); Jack Shih-Chieh Liang, Mountain View, CA (US)

(73) Assignee: Metabolex, Inc., Hayward, CA (US)

( * ) Notice: Subject to any disclaimer, the term of this patent is extended or adjusted under 35 U.S.C. 154(b) by 254 days.

(21) Appl. No.: 10/394,487

(22) Filed: Mar. 19, 2003

(65) Prior Publication Data

US 2004/0029933 A1 Feb. 12, 2004

Related U.S. Application Data

(60) Provisional application No. 60/366,961, filed on Mar. 20, 2002.

(51) Int. Cl.
*A61K 31/4192* (2006.01)
*C07D 249/18* (2006.01)
*C07D 249/20* (2006.01)

(52) U.S. Cl. ....................... 514/359; 548/257; 548/260

(58) Field of Classification Search ................ 548/257; 1/260; 514/359
See application file for complete search history.

(56) References Cited

U.S. PATENT DOCUMENTS 3,072,585 A * 1/1963 Milionis et al. ............... 525/7
3,444,299 A 5/1969 Wood et al.
3,469,009 A 9/1969 Klingbail
3,558,778 A 1/1971 Klingbail
3,658,829 A 4/1972 Nakamura et al.
3,674,836 A 7/1972 Creger
3,876,791 A 4/1975 Hubbard et al.
4,001,268 A 1/1977 Kovar et al.
4,338,330 A 7/1982 Gillet et al.
4,508,882 A 4/1985 Yoshida et al.
4,528,311 A 7/1985 Beard et al.
4,714,762 A 12/1987 Hoefle et al.
4,863,802 A 9/1989 Moore et al.
4,891,396 A 1/1990 Avar et al.
4,910,211 A 3/1990 Imamura et al.
5,132,429 A 7/1992 Narita et al.
5,284,599 A 2/1994 Iwaki et al.
5,476,946 A 12/1995 Linker et al.
5,496,826 A 3/1996 Watson et al.
5,500,332 A 3/1996 Vishwakarma et al.
5,516,914 A 5/1996 Winter et al.
5,554,759 A 9/1996 Vishwakarma
5,700,819 A 12/1997 Aotsuka et al.
5,766,834 A 6/1998 Chen et al.
5,874,431 A 2/1999 Stevens et al.
5,942,626 A 8/1999 Winter et al.
6,013,659 A 1/2000 Goldfarb et al.
6,034,246 A 3/2000 Stevens et al.
6,037,393 A 3/2000 Okumura et al.
6,184,235 B1 2/2001 Connor et al.
6,201,000 B1 3/2001 Luther et al.
6,248,768 B1 6/2001 Yamada et al.
6,506,747 B1 1/2003 Betageri et al.

FOREIGN PATENT DOCUMENTS

EP 0 077 938 A2 5/1983
EP 0 105 494 A2 4/1984
EP 0 306 708 A1 3/1989
EP 1 162 196 A1 12/2001
JP 53-15325 A2 2/1978
JP 53-71071 A 6/1978
JP 60-109578 A 6/1986
WO WO 98/23252 A1 6/1998
WO WO 99/11627 A1 3/1999
WO WO 00/35886 A3 6/2000

OTHER PUBLICATIONS

Safak et al., *FABAD Farm Bilimer Derg.*, 8(1):19-29 (1983).
Varma et al., *Indian J. Chem.*, Sect B, 27B(5):438-42 (1988).
Huang et al., *Wuhan Daxue Xuebao, Ziran Kexueban*, 41(2):142-8 (1995).
El-Sherief et al., Bull. Fac. Sci. Assiut Univ. B, 24(1):111-23 (1995).
Qu et al. *Wuhan Univ. J. Nat. Sci.*, 1(2):283-284 (1996).
Qu et al. *Wujan Univ. J. Nat. Sci.*, 3(2):201-204 (1998).

* cited by examiner

*Primary Examiner*—Laura L. Stockton
(74) *Attorney, Agent, or Firm*—Townsend and Townsend and Crew LLP

(57) ABSTRACT

Substituted phenylacetic acids, phenylethanols and related compounds are provided that are useful in treating or controlling a number of diseases associated with glucose metabolism, lipid metabolism and insulin secretion.

31 Claims, 9 Drawing Sheets

,  ,  ,  ,

,  ,  ,  ,

,  ,  ,

,  ,  and

IIa

IIb

IIc

IId

IIe

IIf

IIg

,

IIh

,

IIi

IIj

,

IIk

,

III

IIm

IIn

IIo

IIp

,

IIq

,

IIr

IIs

IIt

,

IIu

,

IIv

IIw

IIx

IIy

IIz

,

IIaa

,

IIab

IIac

IIad

IIae

IIaf

IIag

IIah

IIai

IIaj

IIak

IIal

IIam

IIan

IIao

IIap

IIaq

IIar Q = O
IIas Q = S
IIat Q = NH or NR

IIax Q = O
IIay Q = S
IIaz Q = NH or NR

IIIa

,

IIIb

IIIc

IIId

IIIe

IIIf

IIIg

,

IIIh

,

IIIi

IIIj

,

IIIk

,

IIIl

IIIm

,

IIIn

,

IIIo

IIIp

IIIq

IIIr

IIIs

,

IIIt

,

IIIu

IIIv

,

IIIw

,

IIIx

IIIaa

,

IIIab

,

IIIac

IIIad

IIIae

IIIaf

,

IIIag

IIIah

Glucose lowering effect of selected compounds in ob/ob mice

SUBSTITUTED PHENYLACETIC ACIDS

CROSS-REFERENCES TO RELATED APPLICATIONS

This application claims the benefit of Provisional application Ser. No. 60/366,961 filed Mar. 20, 2002, the contents of which are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996), and all references cited therein. According to the American Diabetes Association, diabetes mellitus is estimated to affect approximately 6% of the world population. Uncontrolled hyperglycemia is associated with increased and premature mortality due to an increased risk for microvascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: Type 1 diabetes (formerly referred to as insulin-dependent diabetes or IDDM); and Type 2 diabetes (formerly referred to as non-insulin dependent diabetes or NIDDM).

Type 1 diabetes is the result of an absolute deficiency of insulin, the hormone which regulates glucose utilization. This insulin deficiency is usually characterized by β-cell destruction within the Islets of Langerhans in the pancreas, which usually leads to absolute insulin deficiency. Type 1 diabetes has two forms: Immune-Mediated Diabetes Mellitus, which results from a cellular mediated autoimmune destruction of the β cells of the pancreas; and Idiopathic Diabetes Mellitus, which refers to forms of the disease that have no known etiologies.

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes, with hyperlipidemia being an important precipitating factor for these diseases.

Hyperlipidemia is a condition generally characterized by an abnormal increase in serum lipids in the bloodstream and, as noted above, is an important risk factor in developing atherosclerosis and heart disease. For a review of disorders of lipid metabolism, see, e.g., Wilson, J. et al., (ed.), *Disorders of Lipid Metabolism*, Chapter 23, Textbook of Endocrinology, 9$^{th}$ Edition, (W.B. Sanders Company, Philadelphia, Pa. U.S.A. 1998; this reference and all references cited therein are herein incorated by reference). Serum lipoproteins are the carriers for lipids in the circulation. They are classified according to their density: chylomicrons; very low-density lipoproteins (VLDL); intermediate density lipoproteins (IDL); low density lipoproteins (LDL); and high density lipoproteins (HDL). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. *Ann. Chim. Med.* (1927) 5: 1061–1079). Epidemiological studies since then have confirmed the association and have shown a several-fold increase in coronary deaths among diabetic subjects when compared with nondiabetic subjects (see, e.g., Garcia, M. J. et al., *Diabetes* (1974) 23: 105–11 (1974); and Laakso, M. and Lehto, S., *Diabetes Reviews* (1997) 5(4): 294–315). Several lipoprotein abnormalities have been described among diabetic subjects (Howard B., et al., *Artherosclerosis* (1978) 30: 153–162).

What is needed in the art are new compounds and methods useful for the treatment of insulin resistance, Type 2 diabetes, hyperlipidemia and hyperuricemia. The present invention fulfills this and other needs by providing such compounds, compositions and methods for alleviating insulin resistance, Type 2 diabetes, hyperlipidemia and hyperuricemia.

BRIEF SUMMARY OF THE INVENTION

In one aspect, the present invention provides compounds having the formula:

Ia

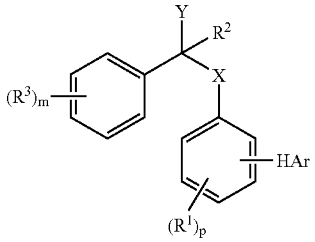

and

Ib

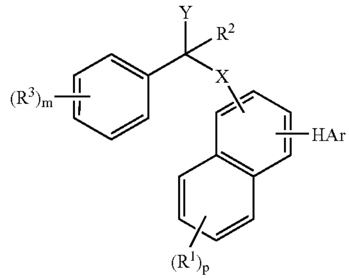

in which the letter X is selected from O, S, SO, $SO_2$ and NR, wherein R is H, $(C_1-C_8)$alkyl, $COR^a$, $COOR^a$ and $CONR^aR^b$ wherein $R^a$ and $R^b$ are each independently selected from H and $(C_1-C_8)$alkyl; the letter Y represents $CH_2OR^c$, $CO_2R^c$, CHO, $CONR^cR^m$, $CH({=}NR^c)$, $CH({=}NOR^c)$ or a carboxylic acid surrogate, wherein $R^c$ is selected from H, $(C_1-C_8)$alkyl, $(C_3-C_8)$alkenyl, $(C_3-C_8)$alkynyl, $(C_3-C_7)$cycloalkyl, $(C_4-C_8)$cycloalkyl-alkyl, aryl, aryl$(C_1-C_8)$alkyl and $(C_1-C_8)$alkylene-Z, wherein Z is selected from $COR^d$, $COOR^d$, $NR^dR^e$, $NR^dCONR^eR^f$, $NR^dCOR^e$, $NR^dCOOR^e$ and $CONR^dR^e$ wherein $R^d$, $R^e$ and $R^f$ are each independently selected from H, $(C_1-C_8)$alkyl and phenyl, or optionally two of $R^d$, $R^e$ and $R^f$ when attached to the same nitrogen atom are combined to form a five- or six-membered ring; and wherein $R^m$ is selected from H, $(C_1-C_8)$alkyl, aryl, OH and $SO_2R^n$, wherein $R^n$ is selected from $(C_1-C_8)$alkyl, $(C_1-C_8)$haloalkyl, $(C_1-C_8)$aralkyl, $(C_2-C_8)$heteroalkyl, aryl, heteroaryl, $(C_1-C_8)$alkoxy, aryloxy, alkylamino, dialkylamino, arylamino, diarylamino, haloalkylamino and di(haloalkyl) amino, and $R^m$ and $R^c$ are optionally combined with the nitrogen atom to which each is attached to form a five- or six-membered ring.

HAr represents a heteroaryl moiety, optionally substituted with from one to three substituents independently selected from halogen, hydroxy, $(C_1-C_8)$alkyl, aryl$(C_1-C_8)$alkyl, $(C_1-C_8)$alkoxy, $(C_2-C_8)$alkenyl, $(C_2-C_8)$alkynyl, $(C_3-C_7)$cycloalkyl, $(C_4-C_8)$cycloalkyl-alkyl, $(C_1-C_8)$heteroalkyl, $(C_2-C_5)$heterocyclyl, aryl, aryloxy, heterosubstituted $(C_3-C_7)$cycloalkyl, heteroalkyl substituted $(C_3-C_7)$cycloalkyl, $(C_1-C_8)$haloalkyl, $O(C_1-C_8)$haloalkyl, nitro, cyano, $CO_2R^g$, $COR^g$, $NR^gR^h$, $S(O)_qR^g$, $SO_2NR^gR^h$, $NR^gCONR^hR^i$, $NR^gCOR^h$, $NR^gCOOR^h$ and $CONR^gR^h$, wherein $R^g$, $R^h$ and $R^i$ are each independently selected from H and $(C_1-C_8)$alkyl, or optionally two of $R^g$, $R^h$ and $R^i$ when attached to the same nitrogen atom are combined to form a five- or six-membered ring, and the subscript q is an integer of from 0 to 2.

A variety of heteroaryl groups provide compounds having the desired activity. In particular, the heteroaryl groups can be monocyclic or fused bicyclic heteroaryl groups. More particularly, one group of suitable monocyclic heteroaryl groups are provided in FIG. 1A. In this Figure, the line extending from the ring indicates the point of attachment to the remainder of the compound and can be made through any available valence on the ring. Other examples of heteroaryl groups are provided in FIG. 1B, which illustrates preferred fused-bicyclic heteroaryl groups, wherein attachment to the remainder of the compound can take place through an available valence on either ring.

Returning to formulae Ia and Ib, the subscripts m and p indicate the presence of substituents on their repective rings, wherein each substituent present can be the same or different from any other substituent. More particularly, the subscript m is an integer of from 0 to 4, and the subscript p is an integer of from 0 to 3. More preferably the subscript m is an integer of from 0 to 3, and the subscript p is an integer of from 0 to 3. Still more preferably, the subscript m is an integer of from 0 to 2, and the subscript p is an integer of from 0 to 2. Most preferably, the subscript m is 0, 1 or 2 and the subscript p is 1 or 2.

Each $R^1$ and $R^3$ represents a substituent independently selected from halogen, hydroxy, $(C_1-C_8)$alkyl, $(C_2-C_8)$alkenyl, $(C_2-C_8)$alkynyl, $(C_1-C_8)$alkoxy, $(C_3-C_7)$cycloalkyl, $(C_4-C_8)$cycloalkyl-alkyl, $(C_1-C_8)$haloalkyl, $(C_1-C_8)$heteroalkyl, $(C_2-C_5)$heterocyclyl, heterosubstituted$(C_3-C_7)$cycloalkyl, heteroalkyl substituted $(C_3-C_7)$cycloalkyl, $O(C_1-C_8)$haloalkyl, nitro, cyano, phenyl, O-phenyl, $NR^j$-phenyl, $S(O)_r$-phenyl, $COR^j$, $COOR^j$, $NR^jR^k$, $S(O)_rR^j$, $SO_2NR^jR^k$, $NR^jCONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from H, $(C_1-C_8)$alkyl and $(C_1-C_8)$haloalkyl, or optionally two of $R^j$, $R^k$ and $R^l$ when attached to the same nitrogen atom are combined to form a five- or six-membered ring, and the subscript r is an integer of from 0 to 2. The subscript m is an integer of from 0 to 4 and the subscript p is an integer of from 0 to 3.

The symbol $R^2$ represents a member selected from H, $(C_1-C_8)$alkyl, $(C_1-C_8)$haloalkyl, $(C_1-C_8)$aralkyl and $(C_1-C_4)$alkylene-Z, wherein Z is as defined above.

In addition to compounds having formula Ia or Ib above, the present invention further includes all salts thereof, and particularly, pharmaceutically acceptable salts thereof. Still further, the invention includes compounds that are single isomers of the above formula (e.g., single enantiomers of compounds having a single chiral center), as well as prodrug forms thereof.

In other aspects, the present invention provides compositions containing one or more compounds of Formula Ia or Ib, as well as methods for the use of such compounds and compositions, either alone or in combination with other pharmaceutical agents as provided in detail below. In particular, the present invention provides methods of using the compounds and/or compositions for the treatment of type II diabetes, hyperlipidemia, hyperuricemia, and for the modulation of insulin resistance. Additionally, the present invention provides methods of using the compounds and/or compositions for the treatment of diseases modulated by any of the isoforms of peroxisome proliferation activated receptor (PPAR).

Still further, the present invention provides compositions and methods as noted, wherein the compound used is a single isomer of a compound of Formula Ia or Ib, or a prodrug form thereof.

DETAILED DESCRIPTION OF THE INVENTION

Abbreviations and Definitions

Figure 1A:
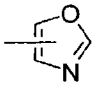
FIG. 1A provides selected monocyclic heteroaryl groups while FIG. 1B provides selected fused bicyclic heteroaryl groups. Each of the groups is optionally substituted with $R^4$ substituents that can be the same or different.
Figure 1A:
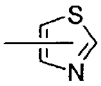
Figure 1A:
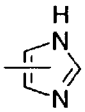
Figure 1A:
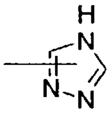
Figure 1A:
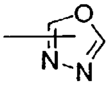
Figure 1A:
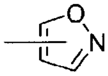
Figure 1A:
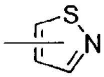
Figure 1A:
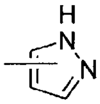
Figure 1A:
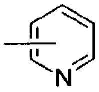
Figure 1A:
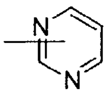
Figure 1A:
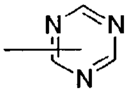
Figure 1A:
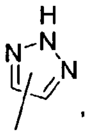
Figure 1A:
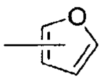
Figure 1A:
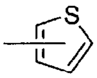
Figure 1A:
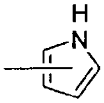

The abbreviations used herein are conventional, unless otherwise defined.

Unless otherwise stated, the following terms used in the specification and claims have the meanings given below:

"Alkyl" refers to a linear saturated monovalent hydrocarbon radical or a branched saturated monovalent hydrocarbon radical having the number of carbon atoms indicated in the prefix. For example, $(C_1-C_6)$alkyl is meant to include methyl, ethyl, n-propyl, 2-propyl, tert-butyl, pentyl, and the like. For each of the definitions herein (e.g., alkyl, alkenyl, alkoxy, aralkyloxy), when a prefix is not included to indicate the number of main chain carbon atoms in an alkyl portion, the radical or portion thereof will have six or fewer main chain carbon atoms.

"Alkylene" refers to a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene, and the like.

"Alkenyl" refers to a linear monovalent hydrocarbon radical or a branched monovalent hydrocarbon radical having the number of carbon atoms indicated in the prefix and containing at least one double bond, but no more than three double bonds. For example, $(C_2-C_6)$alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, $(C_2-C_6)$alkynyl is meant to include ethynyl, propynyl, and the like.

"Alkoxy", "aryloxy" or "aralkyloxy" refers to a radical —OR wherein R is an alkyl, aryl or arylalkyl, respectively, as defined herein, e.g., methoxy, phenoxy, benzyloxy, and the like.

"Aryl" refers to a monovalent monocyclic or bicyclic aromatic hydrocarbon radical of 6 to 10 ring atoms which is substituted independently with one to four substituents, preferably one, two, or three substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl), $-(CR'R'')_n-COOR$ (where n is an integer from 0 to 5, R' and R'' are independently hydrogen or alkyl, and R is hydrogen, alkyl, cycloalkyl, cycloalkylalkyl, phenyl or phenylalkyl) or $-(CR'R'')_n-CONR^xR^y$ (where n is an integer from 0 to 5, R' and R'' are independently hydrogen or alkyl, and $R^x$ and $R^y$ are independently selected from hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the substituted forms thereof.

"Aralkyl" or "Aryl$(C_1-C_x)$alkyl" refers to the radical $-R^xR^y$ where $R^x$ is an alkylene group (having eight or fewer main chain carbon atoms) and $R^y$ is an aryl group as defined above. Thus, "aralkyl" refers to groups such as, for example, benzyl, phenylethyl, 3-(4-nitrophenyl)-2-methylbutyl, and the like. Similarly, "Aralkenyl" means a radical $-R^xR^y$ where $R^x$ is an alkenylene group (an alkylene group having one or two double bonds) and $R^y$ is an aryl group as defined above, e.g., styryl, 3-phenyl-2-propenyl, and the like.

"Cycloalkyl" refers to a monovalent cyclic hydrocarbon radical of three to seven ring carbons. The cycloalkyl group may have one double bond and may also be optionally substituted independently with one, two, or three substituents selected from alkyl, optionally substituted phenyl, or $-C(O)R^z$ (where $R^z$ is hydrogen, alkyl, haloalkyl, amino, mono-alkylamino, di-alkylamino, hydroxy, alkoxy, or optionally substituted phenyl). More specifically, the term cycloalkyl includes, for example, cyclopropyl, cyclohexyl, cyclohexenyl, phenylcyclohexyl, 4-carboxycyclohexyl, 2-carboxamidocyclohexenyl, 2-dimethylaminocarbonyl-cyclohexyl, and the like.

"Cycloalkyl-alkyl" means a radical $-R^xR^y$ wherein $R^x$ is an alkylene group and $R^y$ is a cycloalkyl group as defined herein, e.g., cyclopropylmethyl, cyclohexenylpropyl, 3-cyclohexyl-2-methylpropyl, and the like. The prefix indicating the number of carbon atoms (e.g., $C_4-C_{10}$) refers to the total number of carbon atoms from both the cycloalkyl portion and the alkyl portion.

"Haloalkyl" refers to an alkyl group which is substituted with one or more same or different halo atoms, e.g., $-CH_2Cl$, $-CF_3$, $-CH_2CF_3$, $-CH_2CCl_3$, and the like, and further includes those alkyl groups such as perfluoroalkyl in which all hydrogen atoms are replaced by fluorine atoms. The prefix "halo" and the term "halogen" when used to describe a substituent, refer to —F, —Cl, —Br and —I.

"Heteroalkyl" means an alkyl radical as defined herein with one, two or three substituents independently selected from cyano, $-OR^w$, $-NR^xR^y$, and $-S(O)_nR^z$ (where n is an integer from 0 to 2), with the understanding that the point of attachment of the heteroalkyl radical is through a carbon atom of the heteroalkyl radical. $R^w$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. $R^x$ is hydrogen, alkyl, cycloalkyl, cycloalkyl-alkyl, aryl or aralkyl. $R^y$ is hydrogen, alkyl, cycloalkyl, cycloalkyl-alkyl, aryl, aralkyl, alkoxycarbonyl, aryloxycarbonyl, carboxamido, mono- or di-alkylcarbamoyl or alkylsulfonyl. $R^z$ is hydrogen (provided that n is 0), alkyl, cycloalkyl, cycloalkyl-alkyl, aryl, aralkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^w$, $R^x$,$R^y$, and $R^z$ can be further substituted by amino, fluorine, alkylamino, di-alkylamino, OH or alkoxy. Additionally, the prefix indicating the number of carbon atoms (e.g., $C_1$–$C_{10}$) refers to the total number of carbon atoms in the portion of the heteroalkyl group exclusive of the cyano, —$OR^w$, —$NR^xR^y$, or —$S(O)_nR^z$ portions.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —$(CR'R")_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or —$(CR'R")_n$—$CONR^xR^y$ (where n is an integer from 0 to 5, R' and R" are independently hydrogen or alkyl, and $R^x$ and $R^y$ are, independently of each other, hydrogen, alkyl, cycloalkyl, cycloalkyl-alkyl, phenyl or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heterocyclyl" or "cycloheteroalkyl" means a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, cycloalkyl, cycloalkyl-alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —$(CR'R")_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —$(CR'R")^n$—$CONR^xR^y$ (where n is an integer from 0 to 5, R' and R" are independently hydrogen or alkyl, $R^x$ and $R^y$ are, independently of each other, hydrogen, alkyl, cycloalkyl, cycloalkylalkyl, phenyl or phenylalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$–$C_{10}$) refers to the total number of carbon atoms in the portion of the cycloheteroalkyl or heterocyclyl group exclusive of the number of heteroatoms.

"Heterocyclylalkyl" or "Cycloheteroalkyl-alkyl" means a radical —$R^xR^y$ where $R^x$ is an alkylene group and $R^y$ is a heterocyclyl group as defined herein, e.g., tetrahydropyran-2-ylmethyl, 4-methylpiperazin-1-ylethyl, 3-piperidinylmethyl, and the like.

"Heterosubstituted cycloalkyl" means a cycloalkyl group wherein one, two, or three hydrogen atoms are replaced by substituents independently selected from the group consisting of cyano, hydroxy, alkoxy, amino, acylamino, mono-alkylamino, di-alkylamino, or —$SO_nR$ (where n is an integer from 0 to 2 and when n is 0, R is hydrogen or alkyl and when n is 1 or 2, R is alkyl, cycloalkyl, cycloalkylalkyl, aryl, aralkyl, heteroaryl, amino, acylamino, mono-alkylamino, di-alkylamino, or hydroxyalkyl). Examples include 4-hydroxycyclohexyl, 2-aminocyclohexyl etc.

"Heteroalkyl substituted cycloalkyl" means a cycloalkyl group wherein one, two, or three hydrogen atoms are replaced independently by heteroalkyl groups, with the understanding that the heteroalkyl group is attached to the cycloalkyl group via a carbon-carbon bond. Examples include 1-hydroxymethyl-cyclopent-1-yl, 2-hydroxymethyl-cyclohex-2-yl and the like.

"Heteroalkyl substituted heterocyclyl" means a heterocyclyl group wherein one, two, or three hydrogen atoms are replaced independently by heteroalkyl groups, with the understanding that the heteroalkyl group is attached to the heterocyclyl group via a carbon-carbon bond. Examples include 4-hydroxymethyl-piperidin-1-yl, and the like.

"Optionally substituted phenyl" means a phenyl ring which is optionally substituted independently with one to four substituents, preferably one or two substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —$(CR'R")_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R")_n$—$CONR^xR^y$ (where n is an integer from 0 to 5, R' and R" are independently hydrogen or alkyl, and $R^x$ and $R^y$ are, independently of each other, hydrogen, alkyl, cycloalkyl, cycloalkylalkyl, phenyl or phenylalkyl).

For each of the definitions above, the term "di-alkylamino" refers to an amino moiety bearing two alkyl groups that can be the same, or different.

As used herein, the term "carboxylic acid surrogate" refers to those moieties that are used as surrogates for a carboxylic acid moiety. Such groups are generally known to one of skill in the art (see, for example, The Practice of Medicinal Chemistry; Wermuth, C. G., ed., Academic Press, New York, 1996, page 203). Suitable isosteres or surrogates include —$C(O)NHSO_2R$ wherein R can be alkyl, haloalkyl, heteroalkyl, aralkyl, aryl, heteroaryl, heterocyclyl, alkoxy, haloalkoxy, aryloxy, alkylamino, haloalkylamino, dialkylamino, dihaloalkylamino, arylamino, diarylamino, arakylamino, diarakylamino or other groups to provide an overall acidic character to the moiety; sulfonic acids; sulfinic acids; phosphonic acids; phosphinic acids; activated sulfonamides (e.g., —$SO_2NHX$ wherein X is an electron withdrawing group relative to an alkyl group, such as an acyl group or aryl group; activated carboxamides (e.g., —C(O)NHCN); hydroxamic acids (—C(O)NHOH); acidic heterocycles or substituted heterocycles (e.g., tetrazoles, triazoles, hydroxypyrazoles, hydroxyoxazoles, hydroxythiadiazoles); and acidic alcohols (e.g., —$C(CF_3)_2OH$ or —$CH(CF_3)OH$).

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Calm and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of Advanced Organic Chemistry, 4th edition J. March, John Wiley and Sons, New York, 1992).

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, 4-chlorobenzenesulfonic acid, 2-napthalene-sulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like.

"Prodrugs" means any compound which releases an active parent drug according to Formula Ia or Ib in vivo when such prodrug is administered to a mammalian subject. Prodrugs of a compound of Formula Ia or Ib are prepared by modifying functional groups present in the compound of Formula Ia or Ib in such a way that the modifications may be cleaved in vivo to release the parent compound. Prodrugs include compounds of Formula Ia or Ib wherein a hydroxy, amino, or sulfhydryl group in a compound of Formula Ia or Ib is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, carbamates (e.g., N,N-dimethylaminocarbonyl) of hydroxy functional groups in compounds of Formula Ia or Ib, and the like.

"Protecting group" refers to a grouping of atoms that when attached to a reactive group in a molecule masks, reduces or prevents that reactivity. Examples of protecting groups can be found in T. W. Greene and P. G. Wuts, Protective Groups in Organic Chemistry, (Wiley, 2nd ed. 1991) and Harrison and Harrison et al., Compendium of Synthetic Organic Methods, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes:

(1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "mammal" includes, without limitation, humans, domestic animals (e.g., dogs or cats), farm animals (cows, horses, or pigs), monkeys, rabbits, mice, and laboratory animals.

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M., *J. Basic & Clin. Phys. & Pharm.* (1998) 9: 387–406 and Flier, *J. Ann Rev. Med.* (1983) 34: 145–60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plaminogen activator inhibitor-1), has been referred to as "Syndrome X" (see, e.g., Reaven, G. M., *Physiol. Rev.* (1995) 75: 473–486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes.

The term "secondary diabetes" is diabetes resulting from other identifiable etiologies which include: genetic defects of β cell function (e.g., maturity onset-type diabetes of youth, referred to as "MODY," which is an early-onset form of Type 2 diabetes with autosomal inheritance; see, e.g., Fajans S. et al., *Diabet. Med.* (1996) (9 Suppl 6): S90–5 and Bell, G. et al., *Annu. Rev. Physiol.* (1996) 58: 171–86; genetic defects in insulin action; diseases of the exocrine pancreas (e.g., hemochromatosis, pancreatitis, and cystic fibrosis); certain endocrine diseases in which excess hormones interfere with insulin action (e.g., growth hormone in acromegaly and cortisol in Cushing's syndrome); certain drugs that suppress insulin secretion (e.g., phenytoin) or inhibit insulin action (e.g., estrogens and glucocorticoids); and diabetes caused by infection (e.g., rubella, Coxsackie, and CMV); as well as other genetic syndromes.

The guidelines for diagnosis for Type 2 diabetes, impaired glucose tolerance, and gestational diabetes have been outlined by the American Diabetes Association (see, e.g., The Expert Committee on the Diagnosis and Classification of Diabetes Mellitus, *Diabetes Care*, (1999) Vol 2 (Suppl 1): S5–19).

The term "hyperinsulinemia" refers to the presence of an abnormally elevated level of insulin in the blood. Similarly, the term "hyperuricemia" refers to the presence of an abnormally elevated level of uric acid in the blood. The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "secretagogue" means a substance or compound that stimulates secretion. For example, an insulin secretagogue is a substance or compound that stimulates secretion of insulin.

The term "hemoglobin" or "Hb" refers to a respiratory pigment present in erythrocytes, which is largely responsible for oxygen transport. A hemoglobin molecule comprises four polypeptide subunits (two α chain systems and two β chain systems, respectively). Each subunit is formed by association of one globin protein and one heme molecule which is an iron-protoporphyrin complex. The major class of hemoglobin found in normal adult hemolysate is adult hemoglobin (referred to as "HbA"; also referred to $HbA_0$ for distinguishing it from glycated hemoglobin, which is referred to as "$HbA_1$," described infra) having $\alpha_2\beta_2$ subunits. Trace components such as $HbA_2$ ($\alpha_2\delta_2$) can also be found in normal adult hemolysate.

Among classes of adult hemoglobin HbAs, there is a glycated hemoglobin (referred to as "$HbA_1$," or "glycosylated hemoglobin"), which may be further fractionated into $HbA_{1a1}$, $HbA_{1a2}$, $HbA_{1b}$, and $HbA_{1c}$ with an ion exchange resin fractionation. All of these subclasses have the same primary structure, which is stabilized by formation of an aldimine (Schiff base) by the amino group of N-terminal valine in the β subunit chain of normal hemoglobin HbA and glucose (or, glucose-6-phosphate or fructose) followed by formation of ketoamine by Amadori rearrangement.

The term "glycosylated hemoglobin" (also referred to as "$HbA_{1c}$,", "GHb", "hemoglobin-glycosylated", "diabetic control index" and "glycohemoglobin"; hereinafter referred to as "hemoglobin $A_{1c}$,") refers to a stable product of the nonenzymatic glycosylation of the β-chain of hemoglobin by plasma glucose. Hemoglobin $A_{1c}$ comprises the main portion of glycated hemoglobins in the blood. The ratio of glycosylated hemoglobin is proportional to blood glucose level. Therefore, hemoglobin $A_{1c}$ rate of formation directly increases with increasing plasma glucose levels. Since glycosylation occurs at a constant rate during the 120-day lifespan of an erythrocyte, measurement of glycosylated hemoglobin levels reflect the average blood glucose level for an individual during the preceding two to three months. Therefore determination of the amount of glycosylated hemoglobin $HbA_{1c}$ can be a good index for carbohydrate metabolism control. Accordingly, blood glucose levels of the last two months can be estimated on the basis of the ratio of $HbA_{1c}$ to total hemoglobin Hb. The analysis of the hemoglobin $A_{1c}$ in blood is used as a measurement enabling long-term control of blood glucose level (see, e.g., Jain, S., et al., *Diabetes* (1989) 38: 1539–1543; Peters A., et al., *JAMA* (1996) 276: 1246–1252).

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206–242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels. Similarly, the term "antiuricemic" refers to the lowering of excessive uric acid concentrations in blood to desired levels.

The term "modulate" refers to the treating, prevention, suppression, enhancement or induction of a function or condition. For example, the compounds of the present invention can modulate hyperlipidemia by lowering cholesterol in a human, thereby suppressing hyperlipidemia.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small of the intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form the low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/or elevated levels of lipoproteins (e.g., elevated levels of LDL, VLDL and depressed levels of HDL).

Exemplary Primary Hyperlipidemia include, but are not limited to, the following:

(1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of Type 1 diabetes, Type 2 diabetes, Cushing's syndrome, hypothroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index (BMI) greater than 27.8 kg/$m^2$ for men and 27.3 kg/$m^2$ for women (BMI equals weight (kg)/height ($m^2$). Obesity is linked to a variety of medical conditions including diabetes and hyperlipidemia. Obesity is also a known risk factor for the development of Type 2 diabetes (See, e.g., Barrett-Conner, E., *Epidemol. Rev.* (1989) 11: 172–181; and Knowler, et al., *Am. J. Clin. Nutr.* (1991) 53:1543–1551).

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

General

The present invention derives from the discovery that compounds of Formula Ia or Ib are useful in treating or controlling a number of diseases associated with glucose metabolism, lipid metabolism and insulin secretion. More particularly, the compounds of the invention are useful in treating insulin resistance, diabetes, hyperinsulinemia, hyperlipidemia, hyperuricemia and obesity. Without intending to be bound by theory, it is considered that the compounds of Formula Ia or Ib operate via modulation of receptor interactions associated with one or more isoforms of PPAR. As a result, the compounds will likely have utility in treating other diseases states or conditions associated with PPAR.

Compounds

In one aspect, the present invention provides compounds having the formula:

Ia

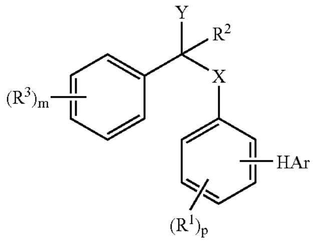

and

Ib

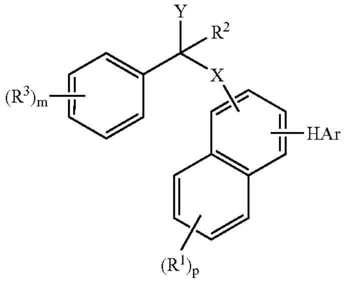

in which the letter X is selected from O, S, SO, $SO_2$ and NR, wherein R is H, $(C_1–C_8)$alkyl, $COR^a$, $COOR^a$ and $CONR^aR^b$ wherein $R^a$ and $R^b$ are each independently selected from H and $(C_1–C_8)$alkyl; the letter Y represents $CH_2OR^c$, $CO_2R^c$, CHO, $CONR^cR^m$, $CH({=}NR^c)$, $CH({=}NOR^c)$ or a carboxylic acid surrogate, wherein $R^c$ is selected from H, $(C_1–C_8)$alkyl, $(C_3–C_8)$alkenyl, $(C_3–C_8)$alkynyl, $(C_3–C_7)$cycloalkyl, $(C_4–C_8)$cycloalkyl-alkyl, aryl, aryl$(C_1–C_8)$alkyl and $(C_1–C_8)$alkylene-Z, wherein Z is selected from $COR^d$, $COOR^d$, $NR^dR^e$, $NR^dCONR^eR^f$, $NR^dCOR^e$, $NR^dCOOR^e$ and $CONR^dR^e$ wherein $R^d$, $R^e$ and $R^f$ are each independently selected from H, $(C_1–C_8)$alkyl and phenyl, or optionally two of $R^d$, $R^e$ and $R^f$ when attached to the same nitrogen atom are combined to form a five- or six-membered ring; and wherein $R^m$ is selected from H, $(C_1–C_8)$alkyl, aryl, OH and $SO_2R^n$, wherein $R^n$ is selected from $(C_1–C_8)$alkyl, $(C_1–C_8)$haloalkyl, aryl$(C_1–C_8)$alkyl, $(C_2–C_8)$heteroalkyl, aryl, heteroaryl, $(C_1–C_8)$alkoxy, aryloxy, alkylamino, dialkylamino, arylamino, diarylamino, haloalkylamino and di(haloalkyl)amino, and $R^m$ and $R^c$ are optionally combined with the nitrogen atom to which each is attached to form a five- or six-membered ring.

HAr represents a heteroaryl moiety, optionally substituted with from one to three substituents independently selected from halogen, hydroxy, $(C_1–C_8)$alkyl, aryl$(C_1–C_8)$alkyl, $(C_1–C_8)$alkoxy, $(C_2–C_8)$alkenyl, $(C_2–C_8)$alkynyl, $(C_3–C_7)$cycloalkyl, $(C_4–C_8)$cycloalkyl-alkyl $(C_1–C_8)$heteroalkyl, $(C_2–C_5)$heterocyclyl, aryl, heteroaryl, aryloxy, heterosubstituted$(C_3–C_7)$cycloalkyl, heteroalkyl substituted $(C_3–C_7)$cycloalkyl, $(C_1–C_8)$haloalkyl, $O(C_1–C_8)$haloalkyl, nitro, cyano, $CO_2R^g$, $COR^g$, $NR^gR^h$, $S(O)_qR^g$, $SO_2NR^gR^h$, $NR^gCONR^hR^i$, $NR^gCOR^h$, $NR^gCOOR^h$ and $CONR^gR^h$, wherein $R^g$, $R^h$ and $R^i$ are each independently selected from H and $(C_1–C_8)$alkyl, or optionally two of $R^g$, $R^h$ and $R^i$ when attached to the same nitrogen atom are combined to form a five- or six-membered ring, and the subscript q is an integer of from 0 to 2.

Figure 1B:
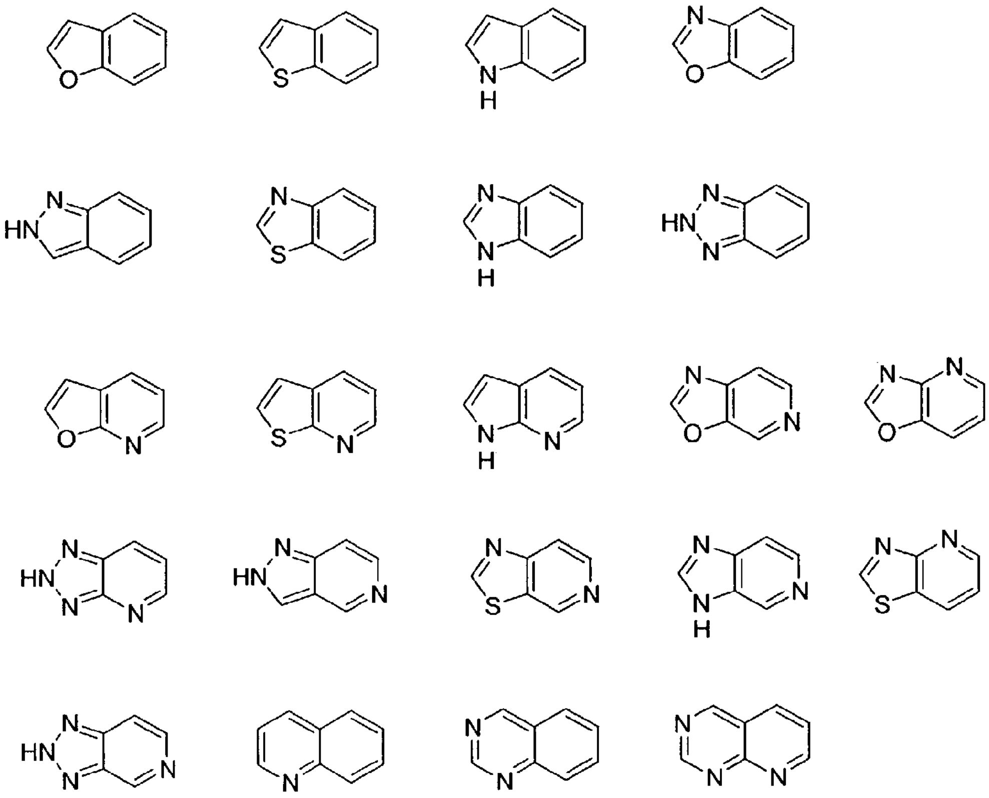
FIG. 1 illustrates a variety of heteroaryl groups (HAr) useful in compounds of formula I.

A variety of heteroaryl groups provide compounds having the desired activity. In particular, the heteroaryl groups can be monocyclic or fused bicyclic heteroaryl groups. More particularly, one group of suitable monocyclic heteroaryl groups are provided in FIG. 1A. In this Figure, the line extending from the ring indicates the point of attachment to the remainder of the compound and can be made through any available valence on the ring. Other examples of heteroaryl groups are provided in FIG. 1B, which illustrates preferred fused-bicyclic heteroaryl groups, wherein attachment to the remainder of the compound can take place through an available valence on either ring.

Returning to Formula Ia or Ib, the subscripts m and p indicate the presence of substituents on their repective rings, wherein each substituted present can be the same or different from any other substituent. More particularly, the subscript m is an integer of from 0 to 4, and the subscript p is an integer of from 0 to 3. More preferably the subscript m is an integer of from 0 to 3, and the subscript p is an integer of from 1 to 3. Still more preferably, the subscript m is 0, 1, 2 or 3 and the subscript p is 1 or 2.

Each $R^1$ and $R^3$ represents a substituent independently selected from halogen, hydroxy, $(C_1–C_8)$alkyl, $(C_2–C_8)$alkenyl, $(C_2–C_8)$alkynyl, $(C_1–C_8)$alkoxy, $(C_3–C_7)$cycloalkyl, $(C_4–C_8)$cycloalkyl-alkyl, $(C_1–C_8)$haloalkyl, $(C_1–C_8)$heteroalkyl, $(C_2–C_5)$heterocyclyl, heterosubstituted$(C_3–C_7)$cycloalkyl, heteroalkyl substituted $(C_3–C_7)$cycloalkyl, $O(C_1–C_8)$haloalkyl, nitro, cyano, phenyl, O-phenyl, $NR^j$-phenyl, $S(O)_r$-phenyl, $COR^j$, $COOR^j$, $NR^jR^k$, $S(O)_rR^j$, $SO_2NR^jR^k$, $NR^jCONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from H, $(C_1–C_8)$alkyl and $(C_1–C_8)$haloalkyl, or optionally two of $R^j$, $R^k$ and $R^l$ when attached to the same nitrogen atom are combined to form a five- or six-membered ring, and the subscript r is an integer of from 0 to 2. The subscript m is an integer of from 0 to 4 and the subscript p is an integer of from 0 to 3.

The symbol $R^2$ represents a member selected from H, $(C_1–C_8)$alkyl, $(C_1–C_8)$haloalkyl, aryl$(C_1–C_8)$alkyl and $(C_1–C_4)$alkylene-Z, wherein Z is as defined above.

In addition to compounds having formula Ia or Ib above, the present invention further includes all salts thereof, and particularly, pharmaceutically acceptable salts thereof. Still further, the invention includes compounds that are single isomers of the above formula (e.g., single enantiomers of compounds having a single chiral center), as well as prodrug forms thereof.

In certain preferred embodiments, Y is $CH_2OR^c$, $CO_2R^c$, a carboxylic acid surrogate or CHO. Preferred carboxylic acid surrogates included tetrazol-5-yl and the group $CONR^cR'''$ wherein $R'''$ is $SO_2R''$. Still more preferably, the carboxylic acid surrogate is tetrazol-5-yl or $CONHSO_2R''$. A further preferred group of embodiments are those in which Y is $CO_2R^c$, a carboxylic acid surrogate or $CH_2OR^c$.

A number of groups of embodiments are preferred and are set forth below.

In a first group of embodiments, Y is $CO_2R^c$, a carboxylic acid surrogate (preferably those provided above) or $CH_2OR^c$; HAr is a fused bicyclic heteroaryl moiety, wherein each of the HAr groups is optionally substituted with from one to three substituents independently selected from the group consisting of halogen, $(C_1–C_4)$alkyl, $(C_1–C_4)$haloalkyl, $(C_1–C_8)$heteroalkyl $(C_1–C_4)$alkoxy, $O(C_1–C_4)$haloalkyl, aryl$(C_1–C_4)$alkyl, aryl$(C_1–C_4)$haloalkyl, aryl, heteroaryl, aryloxy, nitro, cyano, $CO_2R^g$, $COR^g$ and $CONR^gR^h$. Still further preferred, within this group of embodiments, are compounds wherein X is O, S or NH, with compounds in which $R^2$ is H, $CH_3$ or $CF_3$ being further preferred. Even further preferred are those compounds wherein HAr is attached to the 2- or 3-position of the ring bearing X and is selected from:

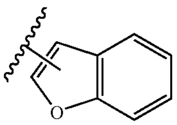,
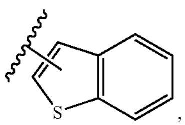,
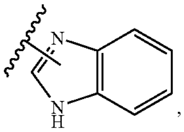,
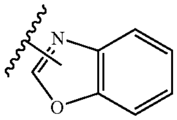,
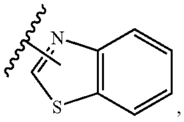,
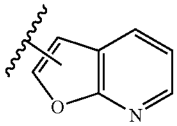,
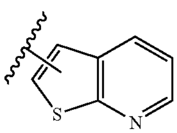,
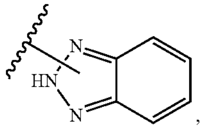,
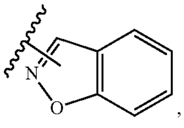,
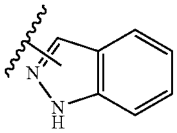,
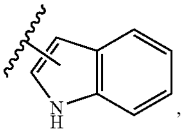,
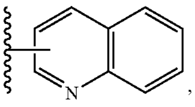,
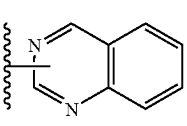,
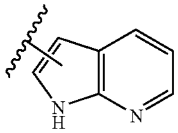, -continued

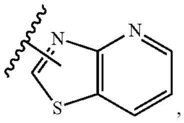,
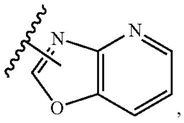,
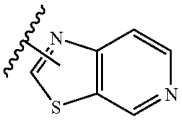
and
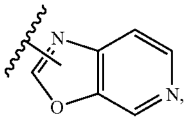, wherein each of the HAr groups is optionally substituted with from one to three substituents independently selected from halogen, $(C_1–C_4)$alkyl, $(C_1–C_4)$haloalkyl, $(C_1–C_8)$heteroalkyl $(C_1–C_4)$alkoxy, $O(C_1–C_4)$haloalkyl, aryl$(C_1–C_4)$alkyl, aryl$(C_1–C_4)$haloalkyl, aryl, heteroaryl, aryloxy, nitro, cyano, $CO_2R^g$, $COR^g$ and $CONR^gR^h$, and wherein the wavy line indicates the point of attached to the ring bearing X through attachment to any available ring member in either ring of HAr. In preferred embodiments below, these substituents are provided as the group $—(R^4)_s$ wherein each $R^4$ is halogen, $(C_1–C_4)$alkyl, $(C_1–C_4)$haloalkyl, $(C_1–C_8)$heteroalkyl $(C_1–C_4)$alkoxy, $O(C_1–C_4)$haloalkyl, aryl$(C_1–C_4)$alkyl, aryl$(C_1–C_4)$haloalkyl, aryl, heteroaryl, aryloxy, nitro, cyano, $CO_2R^g$, $COR^g$ and $CONR^gR^h$, and the subscipt s is an integer of from 0 to 3, indicating that the substituent is optional (s is 0) or present (s is 1, 2 or 3). When multiple substituents are present, each is selected independently of the others.

Turning next to other substituents of formula Ia and Ib, each $R^3$ is preferably, halogen, $(C_1–C_4)$alkyl, $O(C_1–C_4)$alkyl, $(C_1–C_4)$haloalkyl, $O(C_1–C_4)$haloalkyl, nitro, cyano, phenyl, O-phenyl, $NR^j$-phenyl or $S(O)_r$-phenyl and each $R^1$ is preferably halogen, $(C_1–C_4)$alkyl, $O(C_1–C_4)$alkyl, $(C_1–C_4)$haloalkyl, $O(C_1–C_4)$haloalkyl, nitro, cyano, phenyl, O-phenyl, $NR^j$-phenyl or $S(O)_r$-phenyl. More preferably, the subscript m is is an integer of from 0 to 2; each $R^3$ is independently selected from halogen, $(C_1–C_4)$alkyl, $O(C_1–C_4)$alkyl, $(C_1–C_4)$haloalkyl, $O(C_1–C_4)$haloalkyl, nitro, cyano, phenyl, O-phenyl, $NR^j$-phenyl or $S(O)_r$-phenyl; and the subscript p is an integer of from 0 to 2, with $R^1$ being independently selected from halogen, $(C_1–C_4)$alkyl, $O(C_1–C_4)$alkyl, $(C_1–C_4)$haloalkyl, $O(C_1–C_4)$haloalkyl, nitro, cyano, phenyl, O-phenyl, $NR^j$-phenyl or $S(O)_r$-phenyl.

In a particularly preferred group of embodiments, the compounds have a formula selected from:

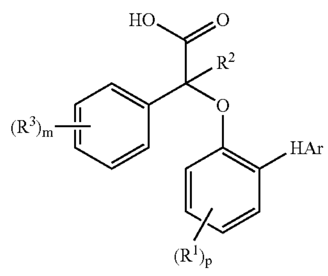

-continued

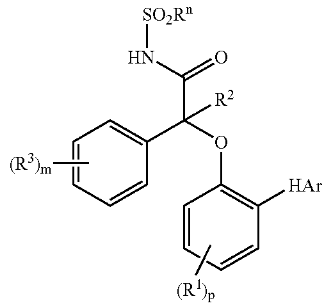

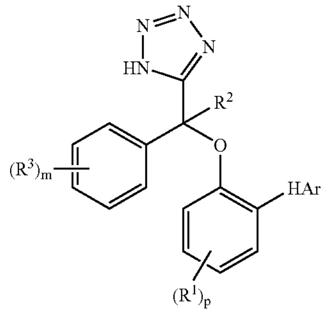

and

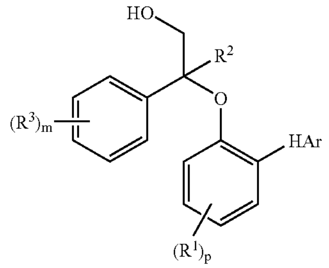

wherein the subscript m is an integer of from 0 to 2, the subscript p is an integer of from 0 to 2, and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl; and $R^n$ is $(C_1-C_8)$alkyl, $(C_1-C_8)$ haloalkyl, aryl$(C_1-C_8)$alkyl, $(C_1-C_8)$heteroalkyl, aryl, heteroaryl, $(C_1-C_8)$alkoxy, aryloxy, alkylamino, dialkylamino, arylamino, diarylamino, haloalkylamino and di(haloalkyl) amino.

Still further preferred are those embodiments in which HAr is selected from

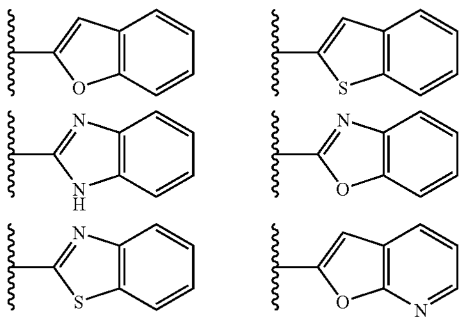

-continued

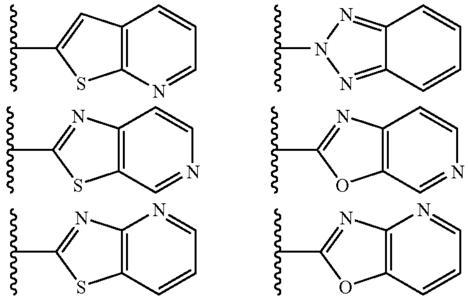

wherein each of the HAr groups is optionally substituted with from one to three substituents independently selected from halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

Even further preferred are those embodiments in which HAr is selected from

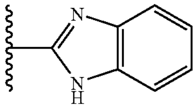, 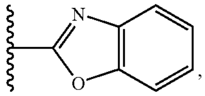, 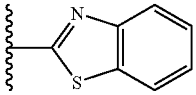, 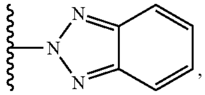, 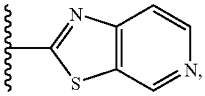, 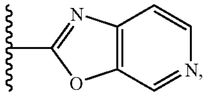, 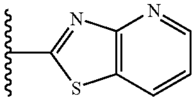 and 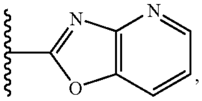, wherein each of the HAr groups is optionally substituted with from one to three substituents independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$. In certain most preferred embodiments, HAr is an optionally substituted 2-benzoxazolyl; $R^2$ is H or $CH_3$; the subscript m is 0 or 1, and p is 1 or 2; and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$. In other most preferred embodiments, HAr is an optionally substituted 2-benzothiazolyl; $R^2$ is H or $CH_3$; the subscript m is 0 or 1, and p is 1 or 2; and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$. In still other most preferred embodiments, HAr is an optionally substituted 2-benzotriazolyl; $R^2$ is H or $CH_3$; the subscript m is 0 or 1, and p is 1 or 2; and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

In a second group of embodiments, Y is $CO_2R^c$, a carboxylic acid surrogate or $CH_2OR^c$; HAr is a monocyclic heteroaryl moiety, wherein each of the HAr groups is optionally substituted with from one to three substituents independently selected from halogen, $(C_1–C_4)$alkyl, $(C_1–C_8)$heteroalkyl, $(C_1–C_4)$alkoxy, $(C_1–C_4)$haloalkyl, $O(C_1–C_4)$haloalkyl, aryl$(C_1–C_4)$alkyl, aryl, heteroaryl, nitro, cyano, $CO_2R^g$, $COR^g$ and $CONR^gR^h$. In preferred embodiments below, these substituents are provided as the group —$(R^4)_s$ wherein each $R^4$ is selected from the group of substituents provided above, and the subscript s is an integer of from 0 to 3, indicating that the substituent is absent (s is 0) or present (s is 1, 2 or 3). When multiple substituents are present, each is selected independently of the others. Still further preferred, within this group of embodiments, are compounds wherein X is O, S or NH, with compounds in which $R^2$ is H, $CH_3$ or $CF_3$ being further preferred. Even further preferred are those compounds wherein HAr is attached to the 2- or 3-position of the phenyl ring bearing X and is selected from the group consisting of

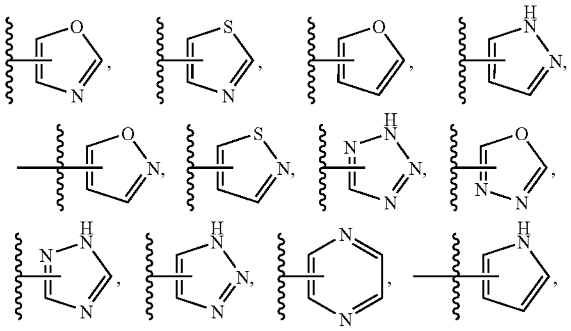

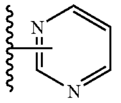

and

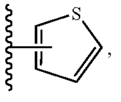

wherein each of said HAr groups is optionally substituted with from one to three substituents independently selected from the group consisting of halogen, $(C_1–C_4)$alkyl, $(C_1–C_8)$heteroalkyl, $(C_1–C_4)$alkoxy, $(C_1–C_4)$haloalkyl, $O(C_1–C_4)$haloalkyl, aryl$(C_1–C_4)$alkyl, aryl, heteroaryl, nitro, cyano, $CO_2R^g$, $COR^g$ and $CONR^gR^h$, and the wavy line indicates the attachment to the ring bearing X. That is, HAr is preferably attached to a carbon atom directly adjacent to the $sp^2$-carbon bearing X (an ortho-position), or is attached to a carbon atom one place removed from the $sp^2$-carbon bearing X (a meta-position).

Turning next to other substituents of formula Ia and Ib, each $R^3$ is preferably, halogen, $(C_1–C_4)$alkyl, $O(C_1–C_4)$ alkyl, $(C_1–C_4)$haloalkyl, $O(C_1–C_4)$haloalkyl, nitro, cyano, phenyl, O-phenyl, $NR^j$-phenyl or $S(O)_r$-phenyl and each $R^1$ is preferably halogen, $(C_1–C_4)$alkyl, $O(C_1–C_4)$alkyl, $(C_1–C_4)$haloalkyl, $O(C_1–C_4)$haloalkyl, nitro, cyano, phenyl, O-phenyl, $NR^j$-phenyl or $S(O)_r$-phenyl. More preferably, the subscript m is is an integer of from 0 to 2; each $R^3$ is independently selected from halogen, $(C_1–C_4)$alkyl, $O(C_1–C_4)$alkyl, $(C_1–C_4)$haloalkyl, $O(C_1–C_4)$haloalkyl, nitro, cyano, phenyl, O-phenyl, $NR^j$-phenyl or $S(O)_r$-phenyl; and the subscript p is an integer of from 0 to 2, with $R^1$ being independently selected from halogen, $(C_1–C_4)$alkyl, $O(C_1–C_4)$alkyl, $(C_1–C_4)$haloalkyl, $O(C_1–C_4)$haloalkyl, nitro, cyano, phenyl, O-phenyl, $NR^j$-phenyl or $S(O)_r$-phenyl.

In a particularly preferred group of embodiments, the compounds have a formula selected from:

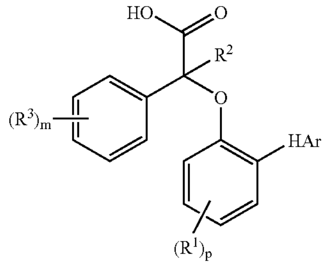

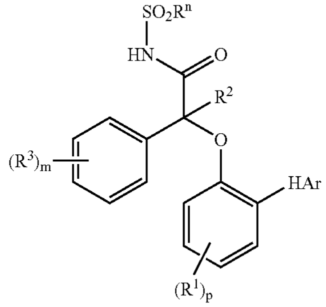

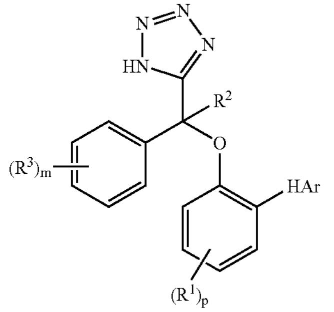

and

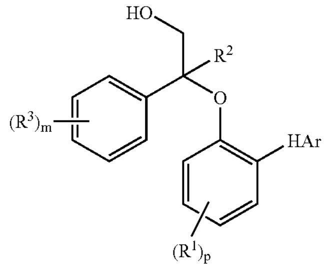

wherein the subscript m is an integer of from 0 to 2, the subscript p is an integer of from 0 to 2, and $R^1$ and $R^3$ are each independently selected from the group consisting of halogen, $(C_1–C_4)$alkyl, $(C_1–C_4)$alkoxy, $(C_1–C_4)$haloalkyl, $O(C_1–C_4)$haloalkyl, nitro, cyano, phenyl, O-phenyl, $NR^j$-phenyl and $S(O)_r$-phenyl; and $R^n$ is $(C_1–C_8)$alkyl, $(C_1–C_8)$ haloalkyl, aryl$(C_1–C_8)$alkyl, $(C_1–C_8)$heteroalkyl, aryl, heteroaryl, $(C_1–C_8)$alkoxy, aryloxy, alkylamino, dialkylamino, arylamino, diarylamino, haloalkylamino and di(haloalkyl) amino.

Still further preferred are those embodiments in which HAr is selected from

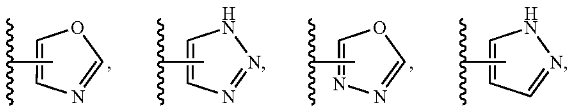

-continued

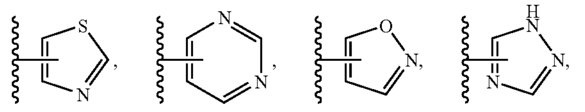

and

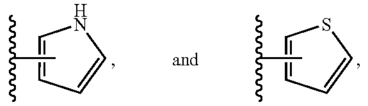

wherein each of the HAr groups is optionally substituted with from one to three substituents independently selected from halogen, $(C_1–C_4)$alkyl, $(C_1–C_8)$heteroalkyl, $(C_1–C_4)$alkoxy, $(C_1–C_4)$haloalkyl, $O(C_1–C_4)$haloalkyl, aryl$(C_1–C_4)$alkyl, aryl, heteroaryl, nitro, cyano, $CO_2R^g$, $COR^g$ and $CONR^gR^h$.

Even further preferred are those embodiments in which HAr is selected from the group consisting of

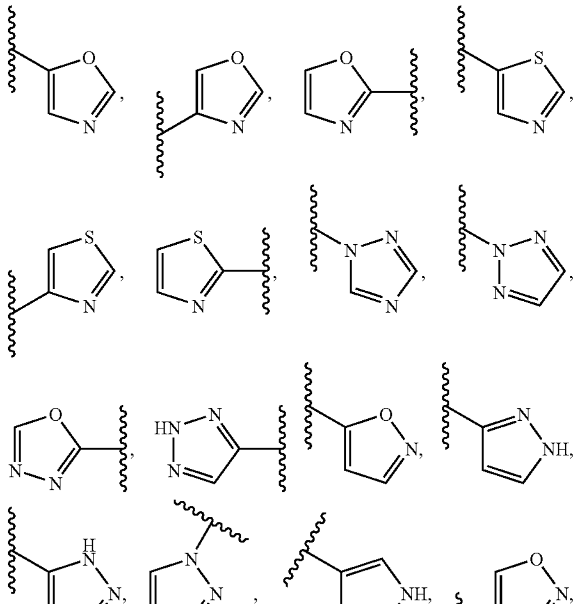

and

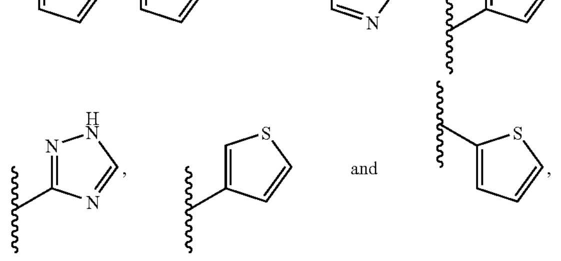

wherein each of the HAr groups is optionally substituted with from one to three substituents independently selected from halogen, $(C_1–C_4)$alkyl, $(C_1–C_8)$heteroalkyl, $(C_1–C_4)$alkoxy, $(C_1–C_4)$haloalkyl, $O(C_1–C_4)$haloalkyl, aryl$(C_1–C_4)$alkyl, aryl, heteroaryl, nitro, cyano, $CO_2R^g$, $COR^g$ and $CONR^gR^h$. In the most preferred embodiments, $R^1$ and $R^3$ are each independently selected from F, Cl, Br, $(C_1–C_4)$alkyl, $(C_1–C_4)$alkoxy, $(C_1–C_4)$haloalkyl, $O(C_1–C_4)$haloalkyl, CN, $NO_2$ and phenyl. Within this most preferred group of embodiments, certain optionally substituted HAr groups are further preferred. In one of these groups HAr is optionally substituted 2-, 4- or 5-thiazolyl wherein the thiazolyl is optionally substituted with from one to two substituents selected from the group consisting of F, Cl, Br, $(C_1–C_4)$alkyl, aryl$(C_1–C_4)$alkyl, $(C_1–C_4)$alkoxy, $(C_1–C_4)$haloalkyl, $O(C_1–C_4)$haloalkyl, CN and phenyl; $R^2$ is H or $CH_3$; the subscript m is 0 or 1 and p is 1 or 2; and $R^1$ and $R^3$ are each independently selected from the group consisting of F, Cl, Br, $(C_1–C_4)$alkyl, $(C_1–C_4)$alkoxy, $(C_1–C_4)$haloalkyl, $O(C_1–C_4)$haloalkyl, CN, $NO_2$ and phenyl. In another of these groups, HAr is selected from the group consisting of optionally substituted 1, 3, 4 or 5-pyrazolyl wherein the pyrazolyl is optionally substituted with from one to two substituents selected from the group consisting of F, Cl, Br, $(C_1–C_4)$alkyl, aryl$(C_1–C_4)$alkyl, $(C_1–C_4)$alkoxy, $(C_1–C_4)$haloalkyl, $O(C_1–C_4)$haloalkyl, CN and phenyl; $R^2$ is H or $CH_3$; the subscript m is 0 or 1 and p is 1 or 2; and $R^1$ and $R^3$ are each independently selected from the group consisting of F, Cl, Br, $(C_1–C_4)$alkyl, $(C_1–C_4)$alkoxy, $(C_1–C_4)$haloalkyl, $O(C_1–C_4)$haloalkyl, CN, $NO_2$ and phenyl. In still other groups, HAr is optionally substituted 2-, 4- or 5-oxazolyl wherein the oxazolyl is optionally substituted with from one to two substituents selected from the group consisting of F, Cl, Br, $(C_1–C_4)$alkyl, aryl$(C_1–C_4)$alkyl, $(C_1–C_4)$alkoxy, $(C_1–C_4)$haloalkyl, $O(C_1–C_4)$haloalkyl, CN and phenyl; $R^2$ is H or $CH_3$; the subscript m is 0 or 1 and p is 1 or 2; and $R^1$ and $R^3$ are each independently selected from the group consisting of F, Cl, Br, $(C_1–C_4)$alkyl, $(C_1–C_4)$alkoxy, $(C_1–C_4)$haloalkyl, $O(C_1–C_4)$haloalkyl, CN, $NO_2$ and phenyl.

Figure 2:
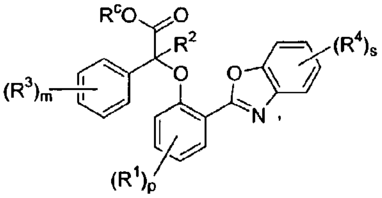
FIG. 2 illustrates a family of preferred sub-generic formulae for compounds of the invention wherein HAr is benzoxazol-2-yl; benzothiazol-2-yl and benzimidazol-2-yl.
Figure 2:
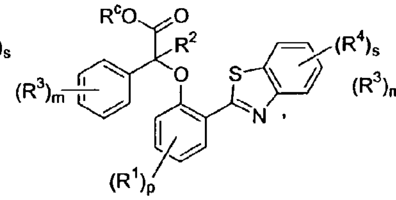
Figure 2:
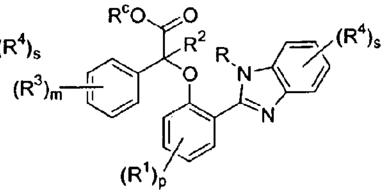
Figure 2:
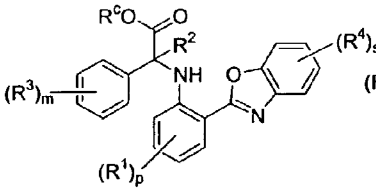
Figure 2:
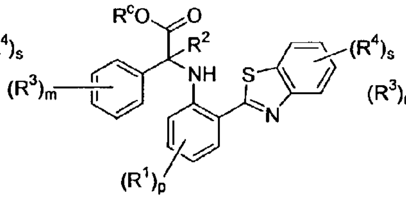
Figure 2:
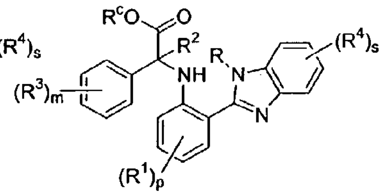
Figure 2:
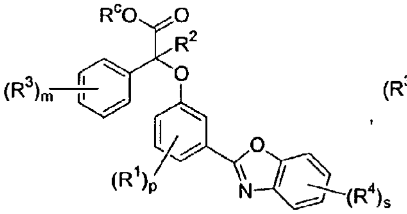
Figure 2:
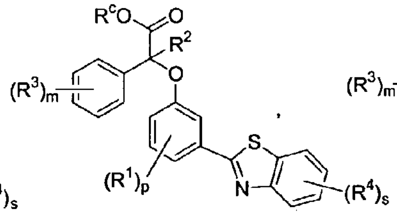
Figure 2:
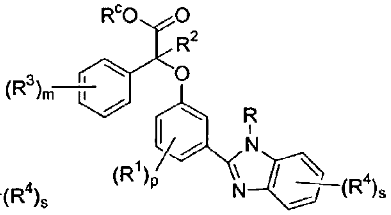
Figure 2:
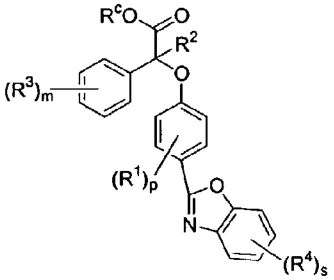
Figure 2:
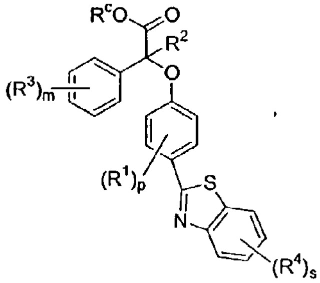
Figure 2:
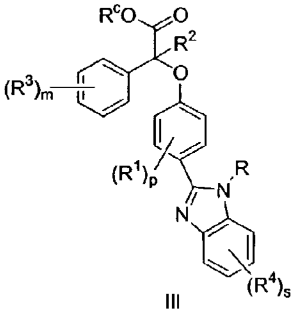
Figure 3:
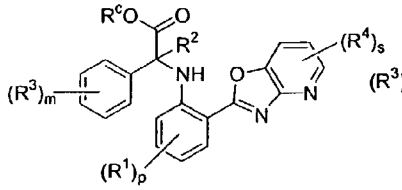
FIG. 3 illustrates another family of preferred sub-generic formulae for compounds of the invention, wherein HAr is a fused bicyclic heteroaryl group.
Figure 3:
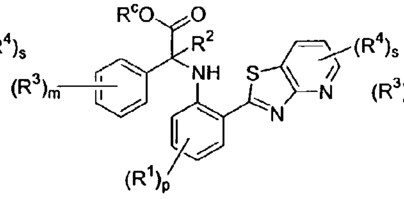
Figure 3:
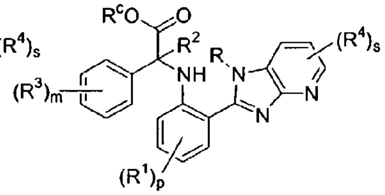
Figure 3:
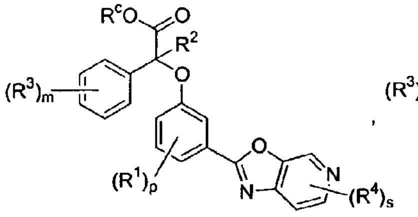
Figure 3:
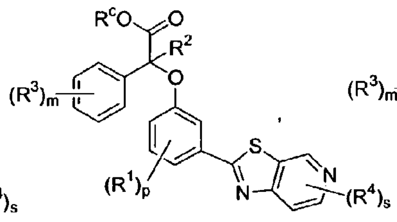
Figure 3:
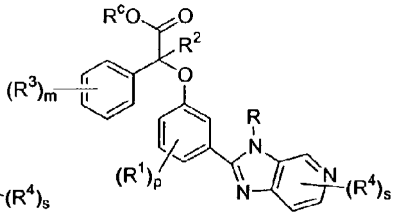
Figure 3:
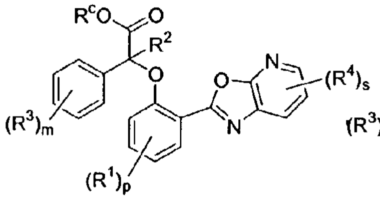
Figure 3:
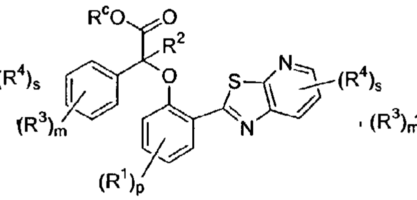
Figure 3:
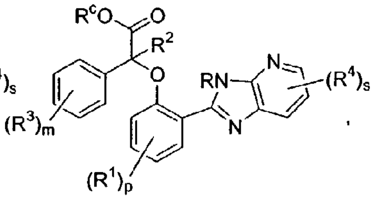
Figure 3:
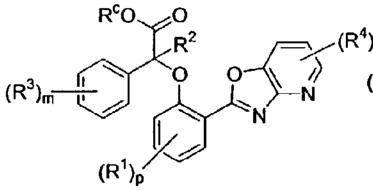
Figure 3:
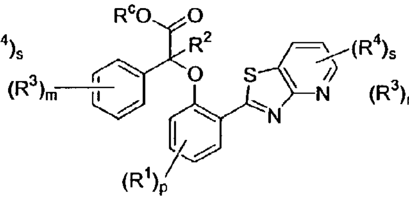
Figure 3:
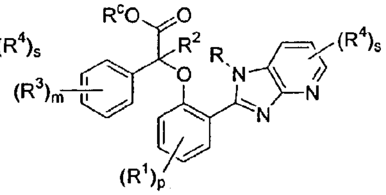
Figure 3:
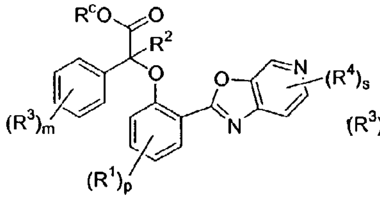
Figure 3:
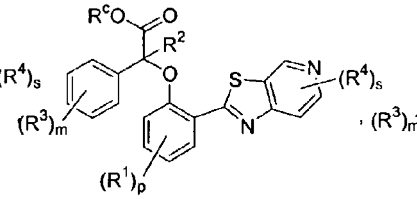
Figure 3:
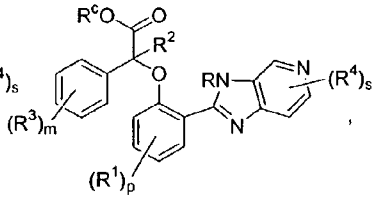
Figure 4A:
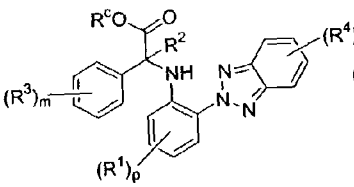
FIG. 4 illustrates yet another family of preferred sub-generic formulae for compounds of the invention wherein HAr is benzoxazol-2-yl, benzothiazol-2-yl and benzotriazol-2-yl (see FIG. 4A).
FIG. 4B illustrates other preferred compounds having carboxylic acid surrogates in place of $CO_2R^c$.
Figure 4A:
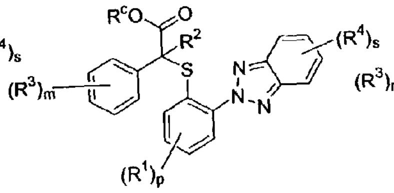
Figure 4A:
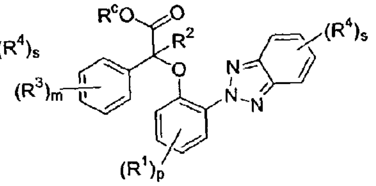
Figure 4A:
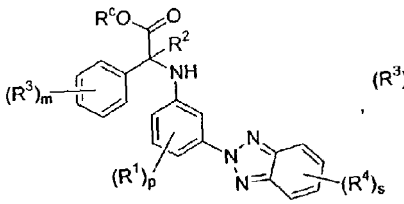
Figure 4A:
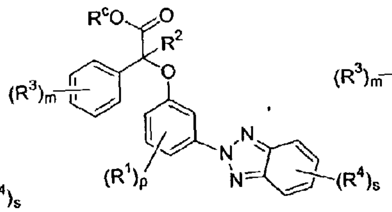
Figure 4A:
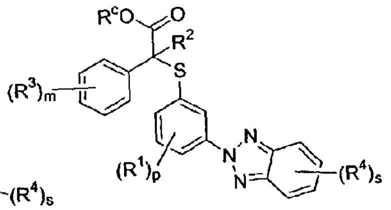
Figure 4A:
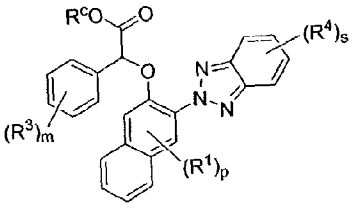
Figure 4A:
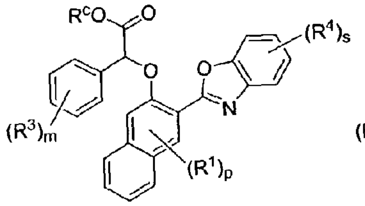
Figure 4A:
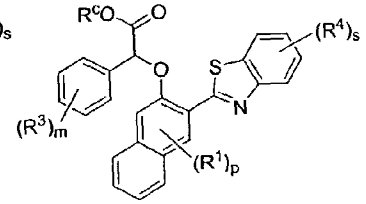
Figure 4A:
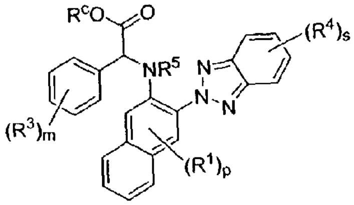
Figure 4A:
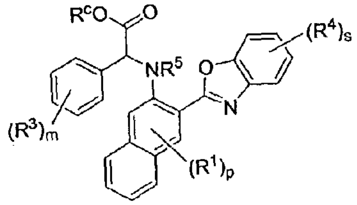
Figure 4A:
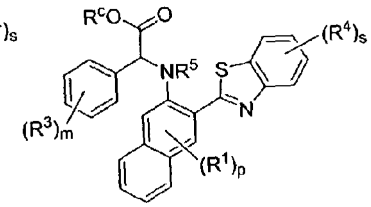

Other preferred groups of embodiments are provided by each of formula IIa through IIam, in FIGS. 2, 3, and 4A, wherein each of $R^c$, $R^1$, $R^2$, $R^3$, $R^4$, $R^5$ and the subscripts m, p and s have the meanings provided above with regard to their most general embodiments. The group provided as R which is attached to nitrogen in certain formulae is intended to be H or another $R^4$ moiety that can be the same or different from the remaining $R^4$ moieties. Preferred members of $R^c$, $R^1$, $R^3$, $R^4$, and the subscripts m, p and s are those that are provided above as preferred for each of these groups with respect to the fused bicyclic HAr moieties. Further preferred for each of IIa through IIam are those compounds in which p is 0, 1 or 2; m is 0, 1, or 2; each $R^1$ and $R^3$ when present is selected from F, Cl, Br, $(C_1–C_4)$alkoxy, $(C_1–C_4)$alkyl, $(C_1–C_4)$haloalkyl, $O(C_1–C_4)$haloalkyl, CN and $NO_2$; s is 0 or 1; $R^c$ is H or $(C_1–C_4)$alkyl; $R^2$ is H, $CH_3$ or $CF_3$. In the most preferred embodiments for each of IIa through IIam, p is 1 or 2, more preferably 1; m is 0, 1, or 2, more preferably 0 or 1; each $R^1$ and $R^3$ when present is selected from F, Cl, Br, $CF_3$ and $OCH_3$; s is 0 or 1; $R^c$ is H; $R^2$ is H or $CH_3$.

Figure 4B:
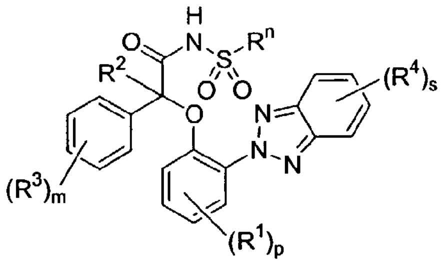
Figure 4B:
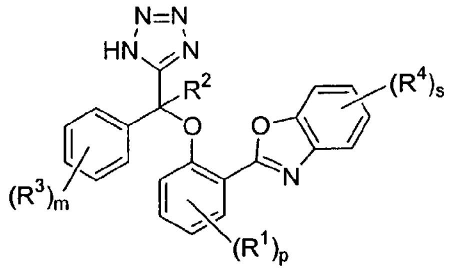
Figure 4B:
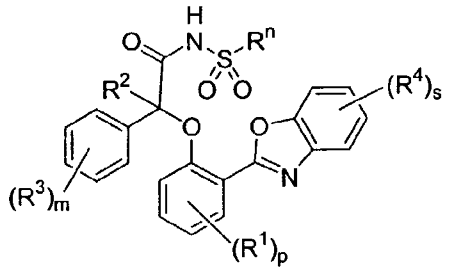
Figure 4B:
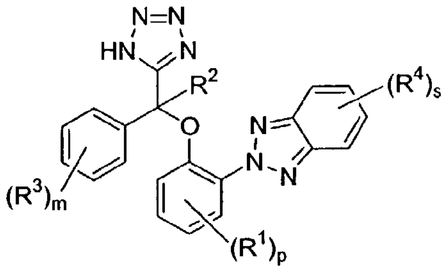
Figure 4B:
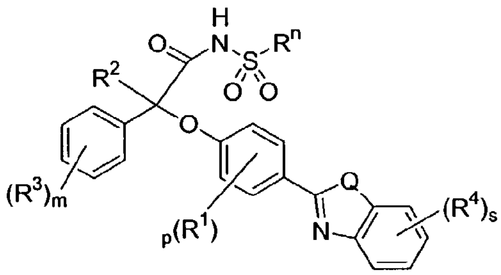
Figure 4B:
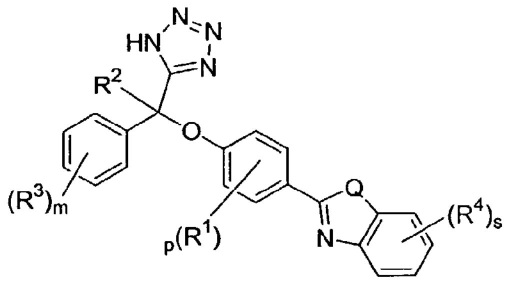

Still other preferred groups of embodiments are provided by each of formula IIan through IIaz, in FIG. 4B, wherein each of $R^1$, $R^2$, $R^3$, $R^4$ $R''$ and the subscripts m, p and s have the meanings provided above with regard to their most general embodiments. Preferred members of $R^1$, $R^2$, $R^3$, $R^4$, $R''$ and the subscripts m, p and s are those that are provided above for each of these groups with respect to the fused bicyclic HAr moieties. Further preferred for each of IIan through IIaz are those compounds in which p is 0, 1 or 2; m is 0, 1, or 2; each $R^1$ and $R^3$ when present is selected from F, Cl, Br, $(C_1–C_4)$alkoxy, $(C_1–C_4)$alkyl, $O(C_1–C_4)$haloalkyl, $(C_1–C_4)$haloalkyl, CN and $NO_2$; $R''$ is $(C_1–C_8)$alkyl, $(C_1–C_8)$haloalkyl, aryl, alkylamino, dialkylamino or arylamino; s is 0 or 1; $R^2$ is H, $CH_3$ or $CF_3$. In the most preferred embodiments for each of IIan through IIaz, p is 1 or 2, more preferably 1; m is 0, 1, or 2, more preferably 0 or 1; each $R^1$ and $R^3$ when present is selected from F, Cl, Br, $CF_3$ and $OCH_3$; s is 0 or 1; $R^2$ is H or $CH_3$.

Figure 5A:
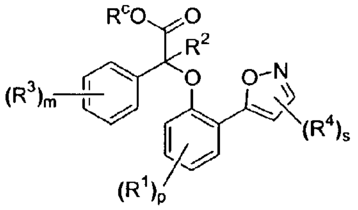
FIG. 5 illustrates yet another family of preferred sub-generic formulae for compounds of the invention wherein HAr is a monocyclic heteroaryl group selected from oxazolyl, isoxazolyl, thiazolyl, isothiazolyl, pyrazolyl and triazolyl (see FIGS. 5A and 5B).
FIG. 5C illustrates other preferred compounds having carboxylic acid surrogates in place of $CO_2R^c$.
Figure 5A:
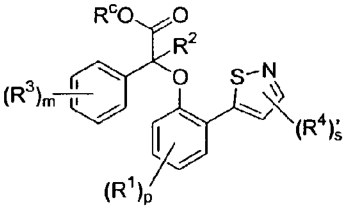
Figure 5A:
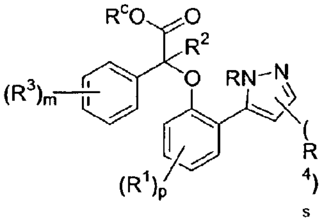
Figure 5A:
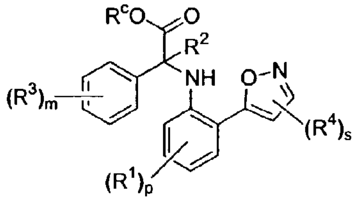
Figure 5A:
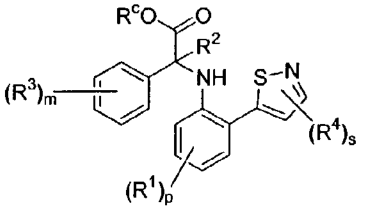
Figure 5A:
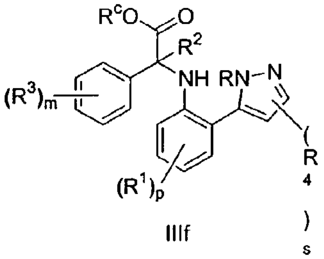
Figure 5A:
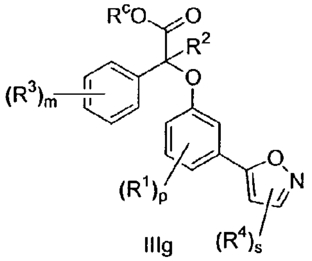
Figure 5A:
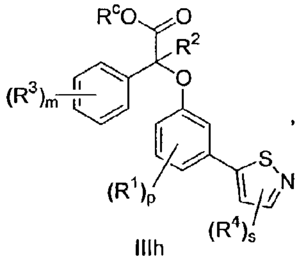
Figure 5A:
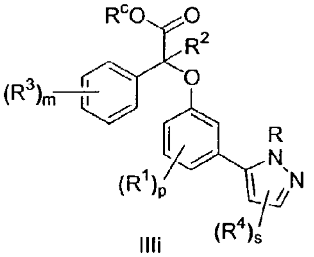
Figure 5A:
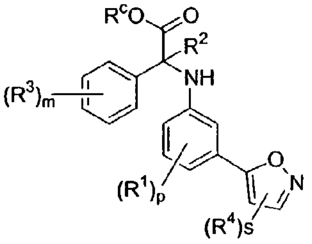
Figure 5A:
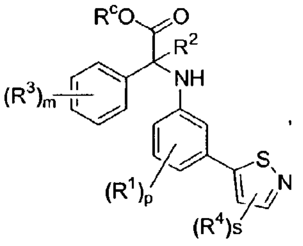
Figure 5A:
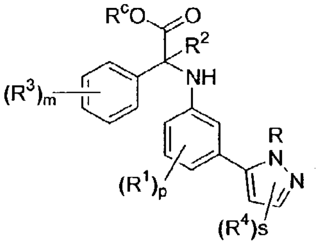
Figure 5B:
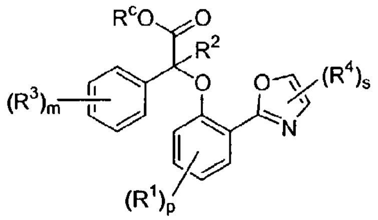
Figure 5B:
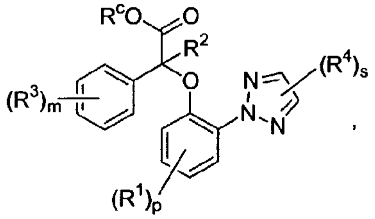
Figure 5B:
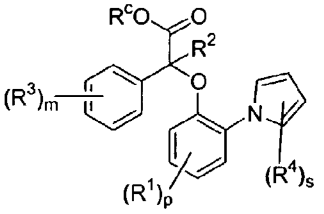
Figure 5B:
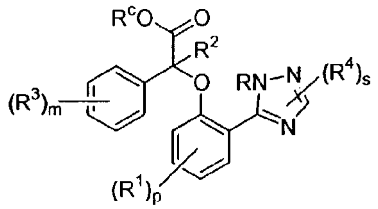
Figure 5B:
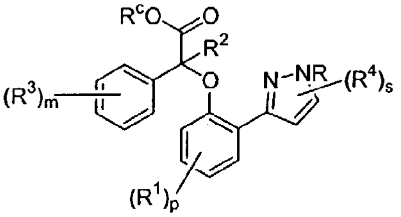
Figure 5B:
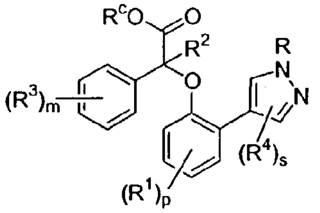
Figure 5B:
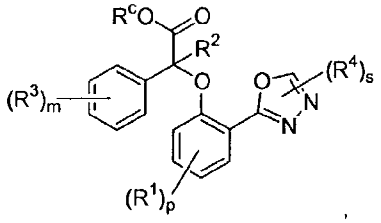
Figure 5B:
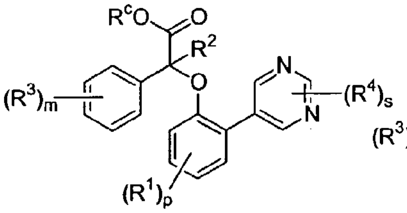
Figure 5B:
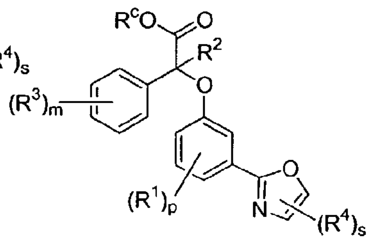
Figure 5B:
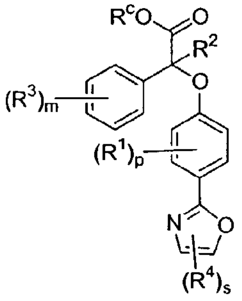
Figure 5B:
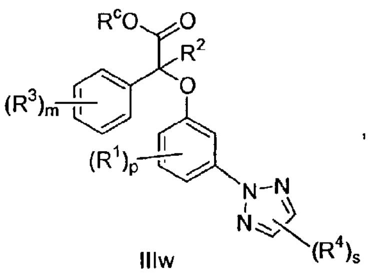
Figure 5B:
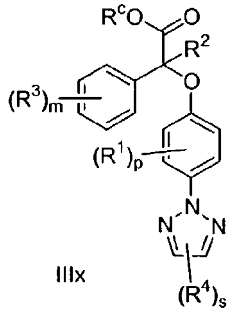

Still other preferred groups of embodiments are those having attached monocyclic heteroaryl groups as HAr in formula Ia and Ib and are provided by each of formula IIIa through IIIx, in FIGS. 5A and 5B, wherein each of $R^c$, $R^1$, $R^2$, $R^3$, $R^4$, and the subscripts m, p and s have the meanings provided above with regard to their most general embodiments. The group provided as R which is attached to nitrogen in certain formulae is intended to be H or another $R^4$ moiety that can be the same or different from the remaining $R^4$ moieties. Preferred members of $R^c$, $R^1$, $R^2$, $R^3$, $R^4$, and the subscripts m, p and s are those that are provided above for each of these groups with respect to monocyclic HAr moieties. Further preferred for each of IIIa through IIIx are those compounds in which p is 0, 1 or 2; m is 0, 1, or 2; each $R^1$ and $R^3$ when present is selected from F, Cl, Br, $(C_1$–$C_4)$alkoxy, $(C_1$–$C_4)$alkyl, $O(C_1$–$C_4)$haloalkyl, $(C_1$–$C_4)$ haloalkyl, CN and $NO_2$; s is 0, 1 or 2; $R^c$ is H or $(C_1$–$C_4)$ alkyl; $R^2$ is H, $CH_3$ or $CF_3$. In the most preferred embodiments for each of IIIa through IIIx, p is 1 or 2, more preferably 1; m is 0, 1, or 2, more preferably 0 or 1; each $R^1$ and $R^3$ when present is selected from F, Cl, Br, $CF_3$ and $OCH_3$; s is 0, 1 or 2; $R^c$ is H; $R^2$ is H or $CH_3$.

Figure 5C:
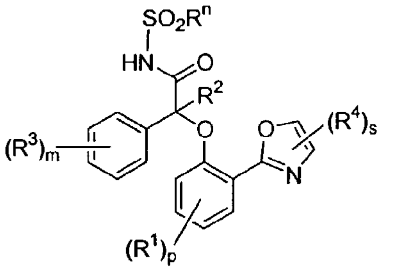
Figure 5C:
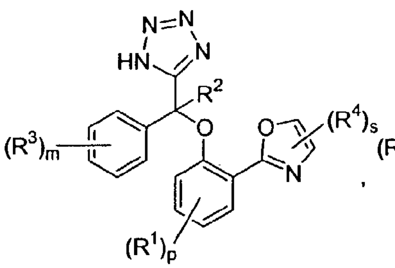
Figure 5C:
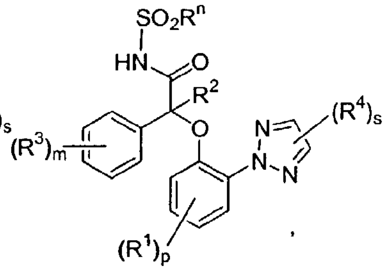
Figure 5C:
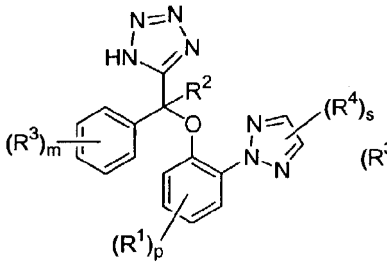
Figure 5C:
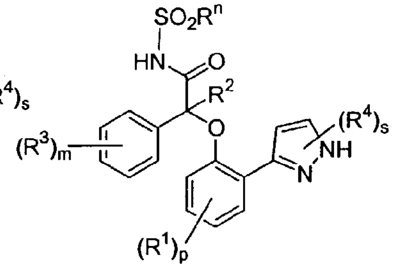
Figure 5C:
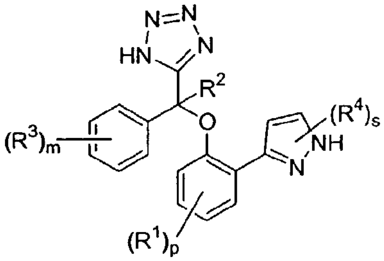
Figure 5C:
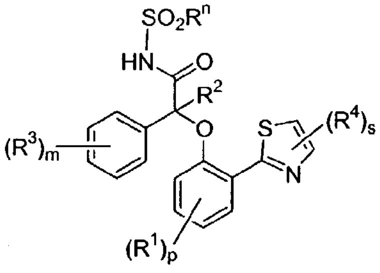
Figure 5C:
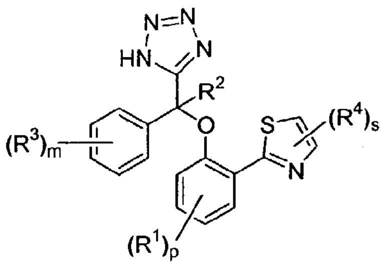

Still other preferred groups of embodiments are provided by each of formula IIIaa through IIIah in FIG. 5C, wherein each of $R^1$, $R^2$, $R^3$, $R^4$ $R''$ and the subscripts m, p and s have the meanings provided above with regard to their most general embodiments. Preferred members of $R^1$, $R^2$, $R^3$, $R^4$, $R''$ and the subscripts m, p and s are those that are provided above for each of these groups with respect to the monocyclic HAr moieties. Further preferred for each of IIIaa through IIIah are those compounds in which p is 0, 1 or 2; m is 0, 1, or 2; each $R^1$ and $R^3$ when present is selected from F, Cl, Br, $(C_1$–$C_4)$alkoxy, $(C_1$–$C_4)$alkyl, $O(C_1$–$C_4)$haloalkyl, $(C_1$–$C_4)$haloalkyl, CN and $NO_2$; $R''$ is $(C_1$–$C_8)$alkyl, $(C_1$–$C_8)$haloalkyl, aryl, alkylamino, dialkylamino, arylamino and diarylamino; s is 0, 1 or 2; and $R^2$ is H, $CH_3$ or $CF_3$. In the most preferred embodiments for each of IIIaa through IIIah, p is 1 or 2, more preferably 1; m is 0, 1, or 2, more preferably 0 or 1; each $R^1$ and $R^3$ when present is selected from F, Cl, Br, $CF_3$ and $OCH_3$; s is 0, 1 or 2; and $R^2$ is H or $CH_3$.

Still other preferred groups of embodiments are provided in the Examples and Tables below.

General Synthetic Routes to Compounds of the Invention

The compounds of the present invention can be prepared using methods generally outlined in Schemes 1–5.

Scheme 1

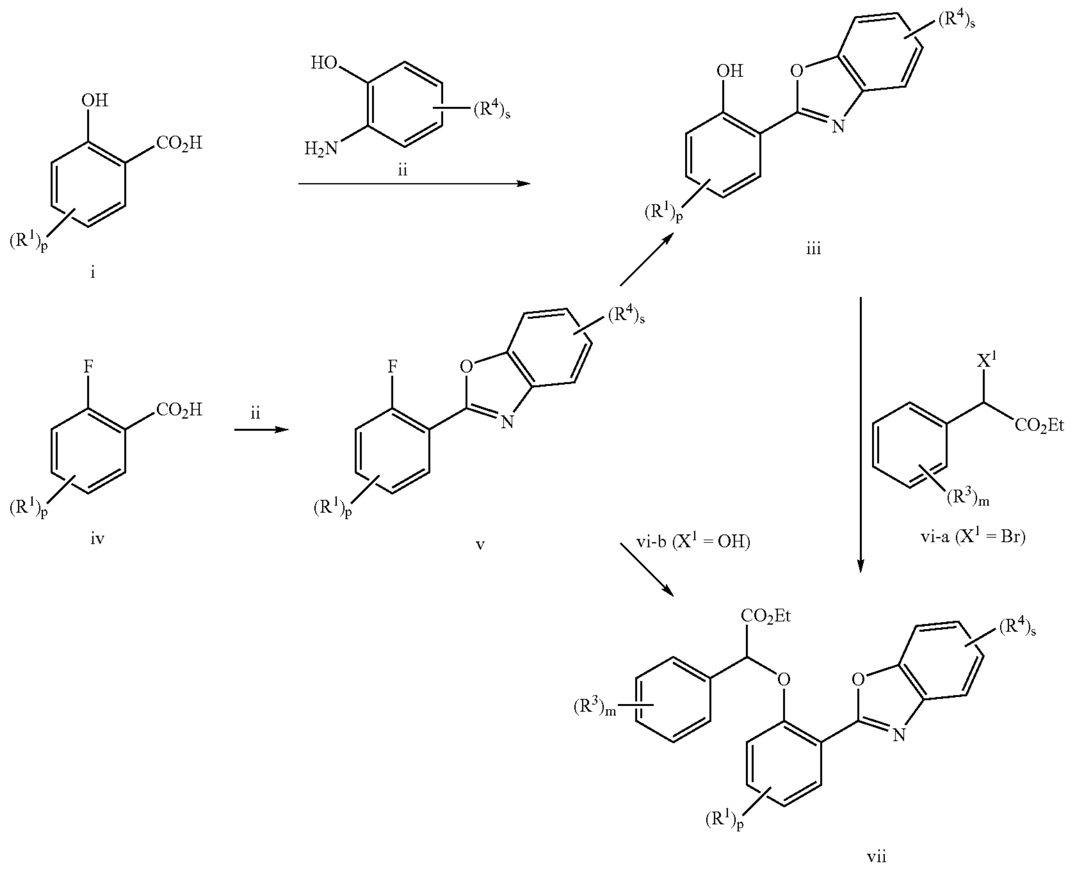

According to Scheme 1, salicylic acids of formula i (either commercially available or prepared according to known methods) are condensed with suitably substituted 2-aminophenols (ii) to provide a 2-(benzoxazol-2-yl)phenol (iii). Treatment of iii with a suitably substituted ethyl 2-bromophenylacetate (vi-a), generally in the presence of a base such as potassium carbonate, provides the target compound vii. Alternatively, 2-fluorobenzoic acids (iv) can be converted to the corresponding derivatives v which can then be converted to iii-and carried on through the scheme as noted, or, in certain embodiments, compounds of formula v can be converted directly into target compounds vii using 2-hydroxyphenylacetic acid derivatives (vi-b). The latter route is particularly useful for the compounds of formula vii in which $R^1$ substituents increase the reactivity of the ring toward fluorine displacement. Additionally, in the above Scheme as well as in Formulae II and III, below, each $R^4$ (the subscript s being an integer of from 0 to 4), is meant to include any of the HAr substituents provided above.

Structural isomers, having the benzoxazolyl ring attached at either the 3-position or the 4-position relative to the phenolic hydroxy group in compound iii can be prepared from the corresponding 3-hydroxybenzoic acids and 4-hydroxybenzoic acids.

In a similar manner, compounds of formula Ia wherein X is NH can be prepared as follows.

Scheme 2

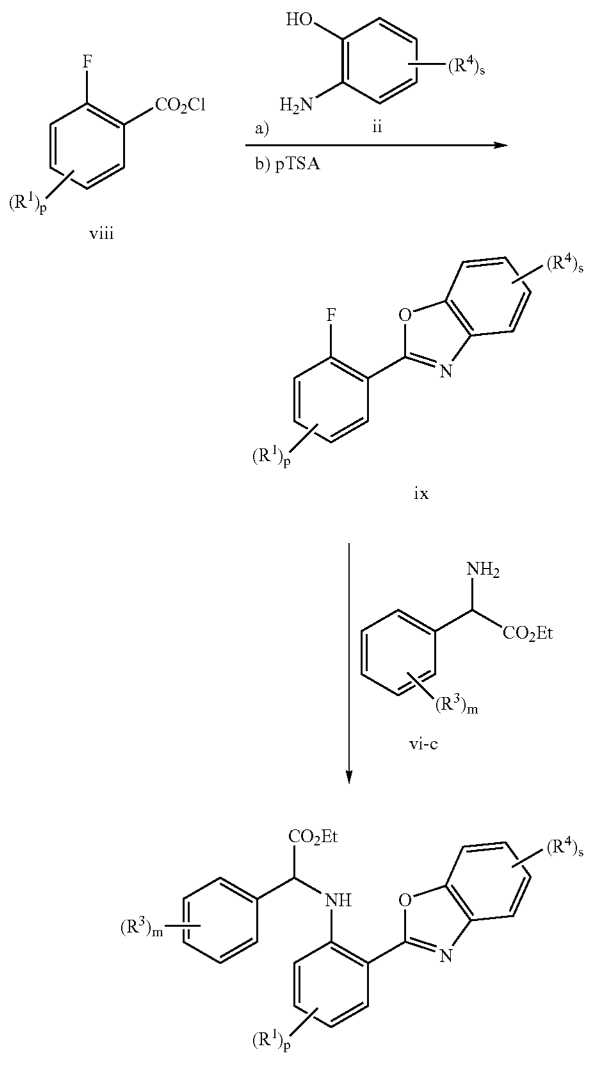

viii ii ix vi-c x

Here, a 2-fluorobenzoic acid or benzoyl chloride (viii) serves as the starting material. The acid chloride is treated with 2-aminophenols (ii) to provide substituted aryl fluorides, ix. Treatment of ix with the suitably substituted ethyl 2-aminophenylacetate (vi-c) provides the target compound x.

Still further, the general schemes outlined in Scheme 1 and Scheme 2 can be used to prepare compounds of Formula Ia in which HAr is benzothiazolyl. To obtain these compounds, the 2-aminophenols (ii) are replaced by the corresponding 2-aminothiophenols. More specific details are provided in the examples below.

Preparation of compounds of Formula Ia in which HAr is a suitably substituted benzimidazole can be prepared according to the general methods outlined in Scheme 3.

Scheme 3

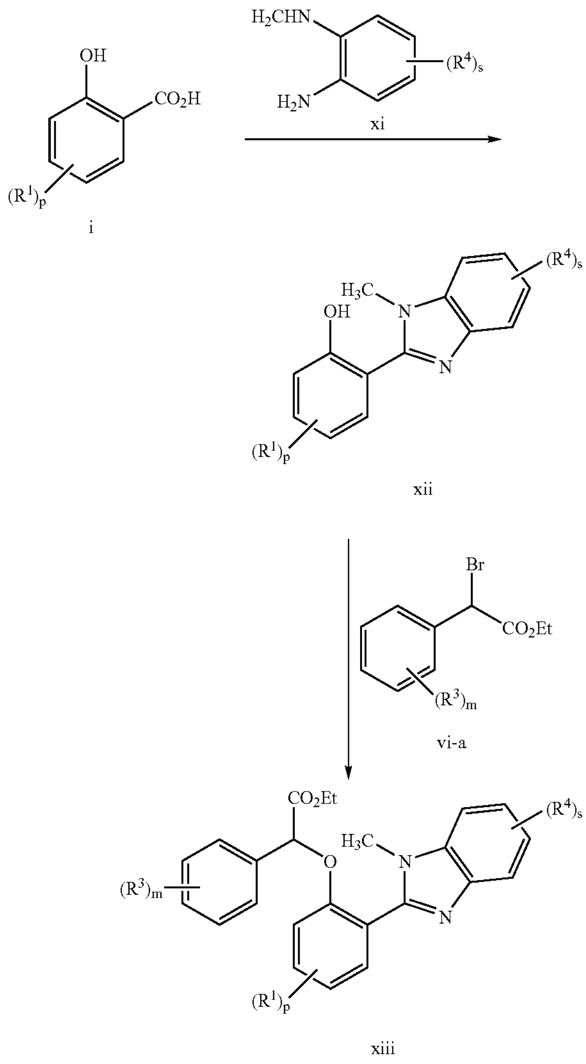

i xi xii vi-a xiii

In Scheme 3, salicylic acid derivatives of formula i are condensed with N-methyl-1,2-phenylenediamine derivatives (xi) to provide benzimidazolyl-substituted phenols of formula xii. Conversion of xii to the desired products (xiii) can be accomplished using suitably substituted ethyl 2-bromophenylacetate (vi-a, in Scheme 1). Additionally, while the synthetic route is illustrated for the preparation of N-methyl benzimidazole compounds, the invention is not so limited and derivatives are contemplated wherein the N-methyl is replaced by hydrogen or by other $(C_1-C_8)$alkyl groups.

In each of Schemes 1, 2 and 3, the position of the heteroaryl ring portion can be changed depending on the starting benzoic acids i and viii.

Related compounds can be prepared in a similar manner beginning with, for example, appropriately substituted 2-(5-isoxazolyl)phenols, many of which are available from commercial sources or can be prepared according to literature methods (see Scheme 4).

Scheme 4

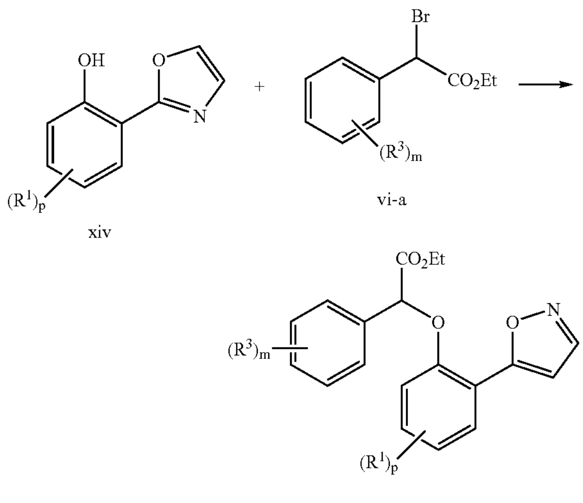

xiv vi-a xv

Similarly, compounds of Formula Ia in which HAr is a pyrazolyl group can be prepared from the corresponding pyrazolylphenols (see Scheme 5).

Scheme 5

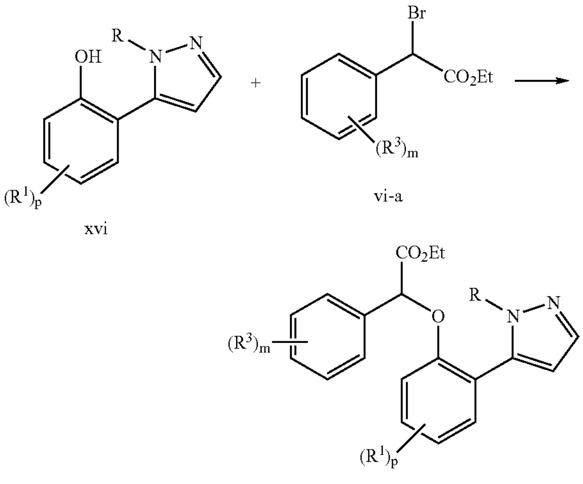

xvi vi-a xvii

In each of Scheme 1–5, reaction conditions (e.g., amounts of reactants, solvents, temperatures and workup conditions) can be selected using the Examples below as a guide.

Preparation of Alcohols, Esters and Aldehydes

The above general synthesis schemes are provided to illustrate the prepared of compounds of Formula Ia or Ib in which Y is a carboxylic acid or ester. Conversion of each of these groups into the corresponding alcohols, ethers, or aldehydes can be accomplished using methods generally known to one of skill in the art. Several methods for reduction (and oxidation) are provided below as illustrative of the processess to used in preparing additional compounds of the invention.

Conversion of Carboxylic Acids into Aldehydes, Carbinols and Carbinol Esters.

The carboxylic acids of this invention can be converted into the corresponding aldehydes, carbinols and carbinol esters by a number of methods, including the routes A-E shown in Scheme 6. The method to be used in a given case depends on the nature of R, and the substituents thereon. A variety of useful methods are described in Larock, Comprehensive Organic Transformations, VCH Publishers Inc, New York (1989). In particular, methods are described for converting acyl chlorides 2 to aldehydes 3 (p 620), aldehydes 3 to carbinols 4 (p 528ff), esters 5 to aldehydes 3 (p 621), esters 5 to carbinols 4 (p 549), carboxylic acids 1 to carbinols 4 (p 548), carbinols 4 to aldehydes 3 (p 604) and carbinols 4 to esters 6 (p 966).

In method A, Scheme 6, the carboxylic acid 1 is first converted into the corresponding acid chloride 2. This transformation is effected by reacting the acid 1 with oxalyl chloride, phosphorus pentachloride, or, preferably, thionyl chloride. The reaction is conducted in an aprotic solvent such as dichloromethane, tetrahydrofuran or, preferably, 1,2-dichloroethane. The acid chloride 2 is then converted into the aldehyde 3 by chemical reduction, such as by the use of sodium borohydride in DMF at −70° C., as described in *Tetrahedron Lett.* 22:11 (1981), or, more preferably by hydrogenation using 5% palladium on barium sulfate as catalyst (see, for example, *J. Amer. Chem. Soc.*, 108:2608 (1986)). The reaction is conducted in an aprotic solvent such as toluene or, preferably, xylene. The aldehyde 3 is converted into the carbinol 4 by reduction, for example by reaction with 9-BBN, lithium aluminum tritertiarybutoxy hydride, or more preferably sodium borohydride, (see, *J. Amer. Chem. Soc.* 71:122 (1949)). The reaction is conducted in a protic solvent such as ethanol, or preferably, isopropanol.

In method B, Scheme 6, the carboxylic acid is first converted into an ester 5, in which $R^1$ is lower alkyl. This conversion is effected by reacting the acid with a diazoalkane such as diazomethane, or preferably, with a lower alkanol, such as ethanol, in the presence of an acid catalyst. The ester 5 is then converted into the aldehyde 3 by reduction, for example, by the use of sodium aluminum hydride or preferably, diisobutyl aluminum hydride (see, for example, *Synthesis*, 617 (1975)). The reaction is conducted in a non-polar solvent such as benzene or, preferably, toluene.

The ester 5 is converted into the carbinol 4 by reduction with lithium aluminum hydride or, preferably, with lithium borohydride (see, *J. Amer. Chem. Soc.*, 109:1186 (1987)). The reaction is conducted in an ethereal solvent such as dioxan or, preferably, tetrahydrofuran.

In method C, Scheme 6, the carboxylic acid 1 is converted into the carbinol 4. This conversion is effected by reacting the carboxylic acid with a reducing agent such as lithium aluminum hydride or, preferably, with diborane, as described in Organic Syntheses, 64:104 (1985). The reaction is conducted in an ethereal solvent such as dioxan or, preferably, tetrahydrofuran.

In method D, Scheme 6, the carbinol 4 is converted into the aldehyde 3. This conversion is effected by reacting the carbinol with an oxidizing agent such as dicyclohexylcarbodiimide/dimethylsulfoxide, or, preferably, with pyridinium chlorochromate, as described in *Synthesis*, 245 (1982). The reaction is conducted in an aprotic solvent such as dichloromethane or, preferably, 1,2-dichloroethane, optionally in the presence of celite, as described in J. Org. Chem., 50:2626 (1985).

In method E, Scheme 6, the carbinol 4 is converted into the ester 6. This transformation is effected by an esterification reaction, for example by reacting the carbinol 4 with a carboxylic anhydride $(R^2CO)_2O$, or, preferably, with an acyl chloride $R^2COCl$. The reaction is conducted in an aprotic solvent such as dichloromethane or, preferably, tetrahydrofuran, in the presence of an organic base such as triethylamine or, preferably, pyridine.

Scheme 6

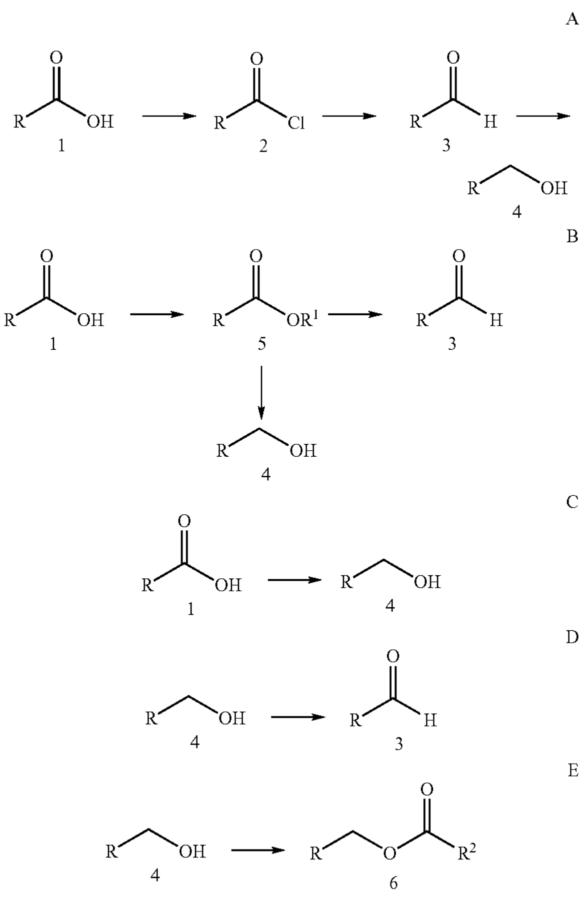

Resolution of Isomers (Enantiomers)

For many compounds of the present invention, a single chiral center is present (at the carbon atom bearing $R^2$), resulting in racemic mixtures of enantiomers. As noted above, the present invention farther includes compounds, compositions and methods wherein a single isomer (or single enantiomer) is provided or used. Methods of preparing chiral compounds are provided in the Examples. Alternatively, mixtures of enantiomers can be separated into their individual isomers via methods such as salt formation and crystallization with chiral bases, chiral chromatography (e.g., hplc using commercially available columns for chiral resolution) and via methods such as simulated moving bed chromatography (see, for example, U.S. Pat. No. 5,518,625).

In certain preferred embodiments of the invention, the (−)-isomer of the compound of formula Ia or Ib is used, which is substantially free of its (+)-isomer. In this context, "substantially free" refers to a compound that is contaminated by less than about 20%, more preferably 10%, still more preferably 5%, even more preferably 2% and most preferably less than about 1% of the undesired isomer. In other preferred embodiments of the invention, the (+)-isomer of the compound of formula Ia or Ib is used, which is substantially free of its (−)-isomer.

Prodrug Forms of the Compounds of the Invention

In some embodiments, the compounds of the invention are present in a prodrug form. In particular, the invention also provides, for example, compounds of Formula Ia or Ib in which Y is $—CO_2H$ which has been esterified to form $—CO_2R''$, wherein R" is selected from alkyl, heteroalkyl, aryl, heteroaryl, phenyl-lower alkyl, benzamido-lower alkyl, di-lower alkylamino-lower alkyl, ureido-lower alkyl, N'-lower alkyl-ureido-lower alkyl, carbamoyl-lower alkyl, halophenoxy substituted lower alkyl and carbamoyl substituted phenyl.

Examples of such R" groups include, without limitation, the following: $C_1$–$C_5$ alkyl, $C_1$–$C_8$-cyclic alkyl, $C_2$–$C_5$ alkenyl, and $C_2$–$C_5$ alkynyl, wherein the groups are optionally substituted with one or more halogen atoms; phenyl, naphthyl and pyridyl, wherein the groups are optionally substituted with one or more substituents selected from the group consisting of halo, $C_1$–$C_4$ alkyl, $C_1$–$C_4$ alkoxy, $—NO_2$, $—S(O)_{m1}(C_1\text{–}C_5\text{alkyl})$, —OH, $—NR^{3a}R^{4a}$, $—CO_2R^{5a}$, $—CONR^{3a}R^{4a}$, $—NR^{3a}COR^{4a}$, $—NR^{3a}CONR^{3a}R^{4a}$ and $—C_{v1}F_{w1}$; $—(CHR^{3a})R^{4a}$; $—R^{5a}OR^{3a}$; $—R^{5a}O_2CR^{6a}NR^{3a}R^{4a}$; $—R^{8a}COR^{6a}$; $—R^{7a}NR^{3a}COR^{4a}$; $—R^{7a}NR^{3a}R^{4a}$; $—(CH_2)_{o1}CH(R^{3a})(CH_2)_{q1}O_2CR^{9a}$; $—(CH_2)_{o1}CH(R^{3a})(CH_2)_{q1}NR^{4a}COR^{9a}$; $—(CH_2)_{o1}CH(R^{3a})(CH_2)_{q1}NR^{4a}CONR^{3a}R^{4a}$; $—(CH_2)_{o1}CH(R^{3a})(CH_2)_{q1}NR^{4a}COOR^{10a}$; $—(CH_2)_{o1}CH(R^{3a})(CH_2)_{q1}NR^{4a}SO_2R^{11a}$; $—(CHR^{3a})_{p1}CO_2R^{12a}$; $—(CHR^{3a})_{p1}NR^{3a}R^{4a}$; $—(CHR^{3a})_{s1}CONR^{13a}R^{4a}$

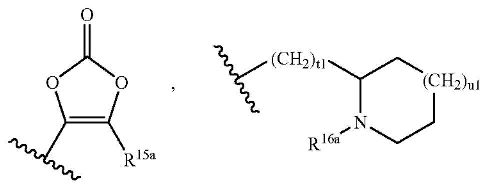

and

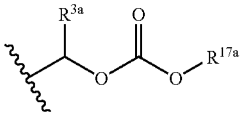

Subscripts m1, o1, q1, s1, t1, u1, v1 and w1 are integers as follows: m1 is 0 to 2; o1 and q1 are 0 to 5; p1 is 1 to 5; s1 is 1 to 3; t1 is 1 to 5; u1 is 0 to 1; v1 is 1 to 3; and w1 is 1 to (2v1+1). $R^{3a}$ and $R^{4a}$ are independently H, $C_1$–$C_5$ alkyl, phenyl or benzyl. $R^{5a}$ is H, $C_1$–$C_5$ alkyl or $—NR^{3a}R^{4a}$. $R^{6a}$ is phenyl, naphthyl, pyridyl, imidazolyl, indoxyl, indolizinyl, oxazolyl, thiazolyl, thienyl, pyrimidyl, or 1-pyrazolyl optionally substituted with one or more substituents selected from the group consisting of halo, $C_1$–$C_4$ alkyl, $C_1$–$C_4$ alkoxy, $—NO_2$, $—S(O)_{m1}(C_1\text{–}C_5\text{alkyl})$, —OH, $—NR^{3a}R^{4a}$, $—CO_2R^{5a}$, $—CONR^{3a}R^{4a}$, $—NR^{3a}COR^{4a}$, $—NR^{5a}CONR^{3a}R^{4a}$ and $—C_{v1}F_{w1}$. $R^{7a}$ is a $C_1$–$C_8$ saturated or unsaturated, straight-chain, branched or cyclic alkylene or alkylidene group optionally substituted with one or more groups selected from halo, hydroxyl, thiol, amino, monoalkyl amino, dialkyl amino, acylamino, carboxyl, alkylcarboxyl, acyl, aryl, aroyl, aralkyl, cyano, nitro, alkoxy, alkenyloxy, alkylcarbonyloxy and arylcarbonyloxy. $R^{8a}$ is a $C_1$–$C_8$ straight-chain or branched alkylene or alkylidene optionally substituted with one or more groups selected from amino, monoalkyl amino, dialkyl amino, acylamino, hydroxyl, thiol, methylthiol, carboxyl and phenyl. $R^{9a}$ and $R^{10a}$ are independently H, $C_1$–$C_5$ alkyl, optionally substituted with one or more groups consisting of $C_1$–$C_5$ alkoxy, aryl and heteroaryl, wherein the aryl is phenyl or naphthyl optionally substituted with one or more substituents selected from the group consisting of halo, $C_1$–$C_4$ alkyl, $C_1$–$C_4$ alkoxy, —$NO_2$, —$S(O)_{m1}(C_1$–$C_5$alkyl), —OH, —$NR^{3a}R^{4a}$, —$CO_2R^{5a}$, —$CONR^{3a}R^{4a}$, —$NR^{3a}COR^{4a}$, —$NR^{3a}CONR^{3a}R^{4a}$ and —$C_{v1}F_{w1}$, and wherein the heteroaryl is pyridyl optionally substituted with one or more substituents selected from the group consisting of halo, $C_1$–$C_4$ alkyl, $C_1$–$C_4$ alkoxy, —$NO_2$, —$S(O)_{m1}(C_1$–$C_5$alkyl), —OH, —$NR^{3a}R^{4a}$, —$CO_2R^{5a}$, —$CONR^{3a}R^{4a}$, —$NR^{3a}COR^{4a}$, —$NR^{3a}CONR^{3a}R^{4a}$ and —$C_{v1}F_{w1}$. $R^{11a}$ is methyl or phenyl, wherein the phenyl is optionally substituted with methyl and/or —$NO_2$. $R^{12a}$ is H, $C_1$–$C_5$ alkyl, phenyl, benzyl, naphthyl or pyridyl, wherein the $C_1$–$C_5$ alkyl, phenyl, naphthyl, benzyl and pyridyl are optionally substituted with one or more substituents selected from the group consisting of halo, $C_1$–$C_4$ alkyl, $C_1$–$C_4$ alkoxy, —$NO_2$, —$S(O)_{m1}(C_1$–$C_5$alkyl), —OH, —$NR^{3a}R^{4a}$, —$CO_2R^{5a}$, —$CONR^{3a}R^{4a}$, —$NR^{3a}COR^{4a}$, —$NR^{3a}CONR^{3a}R^{4a}$ and —$C_{v1}F_{w1}$. $R^{13a}$ and $R^{14}$ are independently the following: alkyl, alkenyl, aryl, aralkyl or cycloalkyl, wherein the groups are optionally substituted with one or more substituents selected from the group consisting of halo, $C_1$–$C_4$ alkyl, $C_1$–$C_4$ alkoxy, —$NO_2$, —$S(O)_{m1}(C_1$–$C_5$alkyl), —OH, —$NR^{3a}R^{4a}$, —$CO_2R^{5a}$, —$CONR^{3a}R^{4a}$, —$NR^{3a}COR^{4a}$, —$NR^{3a}CONR^{3a}R^{4a}$, —$CH_2NR^{3a}R^{4a}$, $OOCR^{18a}$ and —$C_{v1}F_{w1}$; and wherein $R^{13a}$ and $R^{14a}$ are included as —$(CHR^{3a})CONR^{13a}R^{14a}$ wherein $NR^{13a}R^{14a}$ is

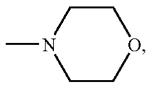, 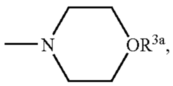, 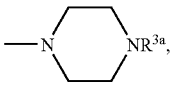,

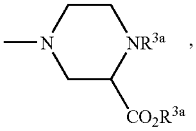, 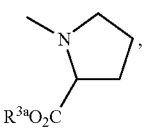, 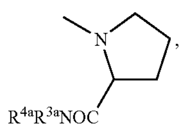,

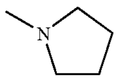, 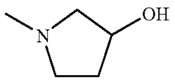, 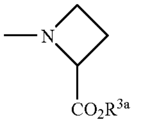 or

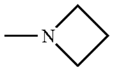

$R^{15a}$ is $C_{v1}F_{w1}$ or $C_1$–$C_5$ alkyl, wherein $C_1$–$C_5$ alkyl is optionally substituted with the following substituents: $C_1$–$C_5$ alkoxy; phenyl, optionally substituted with one or more substituents selected from the group consisting of halo, $C_1$–$C_4$ alkyl, $C_1$–$C_4$ alkoxy, —$NO_2$, —$S(O)_{m1}(C_1$–$C_5$alkyl), —OH, —$NR^{3a}R^{4a}$, —$CO_2R^{5a}$, —$CONR^{3a}R^{4a}$, —$NR^{3a}COR^{4a}$, —$NR^{3a}CONR^{3a}R^{4a}$ and —$C_{v1}F_{w1}$; benzyl, optionally substituted with one or more substituents selected from the group consisting of halo, $C_1$–$C_4$ alkyl, $C_1$–$C_4$ alkoxy, —$NO_2$, —$S(O)_{m1}(C_1$–$C_5$alkyl), —OH, —$NR^{3a}R^{4a}$, —$CO_2R^{5a}$, —$CONR^{3a}R^{4a}$, —$NR^{3a}COR^{4a}$, —$NR^{3a}CONR^{3a}R^{4a}$ and —$C_{v1}F_{w1}$. $R^{16a}$ is H, $C_1$–$C_5$ alkyl or benzyl. $R^{17a}$ is $C_1$–$C_5$ alkyl, $C_3$–$C^8$ cyclic alkyl, phenyl or benzyl. $R^{18a}$ is H, alkyl, aryl, aralkyl or cycloalkyl, where the group is optionally substituted with one or more substituents selected from the group consisting of halo, $C_1$–$C_4$ alkyl, $C_1$–$C_4$ alkoxy, —$NO_2$, —$S(O)_{m1}(C_1$–$C_5$alkyl), —OH, $NR^{3a}R^{4a}$, —$CO_2R^{5a}$, —$CONR^{3a}R^{4a}$, —$NR^{3a}COR^{4a}$, —$NR^{3a}CONR^{3a}R^{4a}$ and —$C_{v1}F_{w1}$.

Pharmaceutical Compositions and Methods of Treating Diseases and Conditions

In accordance with the present invention, a therapeutically effective amount of a compound of Formula Ia or Ib can be used for the preparation of a pharmaceutical composition useful for treating diabetes, treating hyperlipidemia, treating hyperuricemia, treating obesity, lowering triglyceride levels, lowering cholesterol levels, raising the plasma level of high density lipoprotein, and for treating, preventing or reducing the risk of developing atherosclerosis.

The compositions of the invention can include compounds of Formula Ia or Ib, pharmaceutically acceptable salts thereof, or a hydrolyzable precursor thereof. In general, the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of Type 2 diabetes.

The compounds of Formula Ia or Ib that are used in the methods of the present invention can be incorporated into a variety of formulations for therapeutic administration. More particularly, the compounds of Formula Ia or Ib can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a local rather than systemic manner, in a depot or sustained release formulation. In addition, the compounds can be administered in a liposome.

The compounds of Formula Ia or Ib can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. Compounds of Formula Ia or Ib can be administered alone, in combination with each other, or they can be used in combination with other known compounds (see Combination Therapy below).

Suitable formulations for use in the present invention are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527–1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds of Formula Ia or Ib can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide (DMSO) also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al. 1975 In: *The Pharmacological Basis of Therapeutics*, Ch. 1).

The amount of active compound that can be combined with a carrier material to produce a single dosage form will vary depending upon the disease treated, the mammalian species, and the particular mode of administration. However, as a general guide, suitable unit doses for the compounds of the present invention can, for example, preferably contain between 100 mg to about 3000 mg of the active compound. A preferred unit dose is between 500 mg to about 1500 mg. A more preferred unit dose is between 500 to about 1000 mg. Such unit doses can be administered more than once a day, for example 2, 3, 4, 5 or 6 times a day, but preferably 1 or 2 times per day, so that the total daily dosage for a 70 kg adult is in the range of 0.1 to about 250 mg per kg weight of subject per administration. A preferred dosage is 5 to about 250 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

A typical dosage can be one 10 to about 1500 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to interrupt, adjust, or terminate therapy in conjunction with individual patient response.

Combination Therapy

As noted above, the compounds of the present invention will, in some instances, be used in combination with other therapeutic agents to bring about a desired effect. Selection of additional agents will, in large part, depend on the desired target therapy (see, e.g., Turner, N. et al. *Prog. Drug Res.* (1998) 51: 33–94; Hafffer, S. *Diabetes Care* (1998) 21: 160–178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165–71; United Kingdom Prospective Diabetes Study Group: UKPDS 28, *Diabetes Care* (1998) 21: 87–92; Bardin, C. W.,(ed.), Current Therapy in Endocrinology and Metabolism, $6^{th}$ Edition (Mosby—Year Book, Inc., St. Louis, Mo. 1997); Chiasson, J. et al., *Ann. Intern. Med.* (1994) 121: 928–935; Coniff, R. et al., *Clin. Ther.* (1997) 19: 16–26; Coniff, R. et al., *Am. J. Med.* (1995) 98: 443–451; and Iwamoto, Y. et al., *Diabet. Med.* (1996) 13 365–370; Kwiterovich, P. *Am. J. Cardiol* (1998) 82(12A): 3U–17U). These studies indicate that diabetes and hyperlipidemia modulation can be further improved by the addition of a second agent to the therapeutic regimen. Combination therapy includes administration of a single pharmaceutical dosage formulation which contains a compound having the general structure of Formula Ia or Ib and one or more additional active agents, as well as administration of a compound of Formula Ia or Ib and each active agent in its own separate pharmaceutical dosage formulation. For example, a compound of Formula Ia or Ib and an HMG-CoA reductase inhibitor can be administered to the human subject together in a single oral dosage composition, such as a tablet or capsule, or each agent can be administered in separate oral dosage formulations. Where separate dosage formulations are used, a compound of Formula Ia or Ib and one or more additional active agents can be administered at essentially the same time (i.e., concurrently), or at separately staggered times (i.e., sequentially). Combination therapy is understood to include all these regimens.

An example of combination therapy that modulates (prevents the onset of the symptoms or complications associated) atherosclerosis, wherein a compound of Formula Ia or Ib is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the compounds of Formula Ia or Ib can be administered in combination with more than one additional active agent, for example, a combination of a compound of Formula Ia or Ib with an HMG-CoA reductase inhibitor (e.g., lovastatin, simvastatin and pravastatin) and aspirin, or a compound of Formula Ia or Ib with an HMG-CoA reductase inhibitor and a β blocker.

Another example of combination therapy can be seen in treating obesity or obesity-related disorders, wherein the compounds of Formula Ia or Ib can be effectively used in combination with, for example, phenylpropanolamine, phentermine, diethylpropion, mazindol; fenfluramine, dexfenfluramine, phentiramine, $\beta_3$ adrenoceptor agonist agents; sibutramine, gastrointestinal lipase inhibitors (such as orlistat), and leptins. Other agents used in treating obesity or obesity-related disorders wherein the compounds of Formula Ia or Ib can be effectively used in combination with, for example, neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Still another example of combination therapy can be seen in modulating diabetes (or treating diabetes and its related symptoms, complications, and disorders), wherein the compounds of Formula Ia or Ib can be effectively used in combination with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

A further example of combination therapy can be seen in modulating hyperlipidemia (treating hyperlipidemia and its related complications), wherein the compounds of Formula Ia or Ib can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E, or vitamin C.

Additionally, an effective amount of a compound of Formula Ia or Ib and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozil; vitamin $B_6$ and the pharmaceutically acceptable salts thereof, vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, $\beta_3$ adrenergic receptor agonists; sulfonylureas, biguanides, α-glucosidase inhibitors, other insulin secretogogues, and insulin can be used together for the preparation of a pharmaceutical composition useful for the above-described treatments.

Kits

In addition, the present invention provides for kits with unit doses of the compounds of Formula Ia or Ib, either in oral or injectable doses. In addition to the containers containing the unit doses will be an informational package insert describing the use and attendant benefits of the drugs in alleviating symptoms and/or complications associated with Type 2 diabetes as well as in alleviating hyperlipidemia and hyperuricemia, or for alleviating conditions dependent on PPAR. Preferred compounds and unit doses are those described herein above.

For the compositions, methods and kits provided above, one of skill in the art will understand that preferred compounds for use in each are those compounds that are preferred above and particularly those compounds provided in formulae Ia through IIat, and IIIa through IIIt in FIGS. 2, 3, 4A, 4B, 5A, 5B and 5C. Still further preferred compounds for the compositions, methods and kits are those compounds provided in the Examples below.

EXAMPLES

Experimental Section

General Methods. All operations involving moisture and/or oxygen sensitive materials were conducted under an atmosphere of dry nitrogen in pre-dried glassware. Unless noted otherwise, materials were obtained from commercially available sources and used without further purification.

Flash chromatography was performed on E. Merck silica gel 60 (240–400 mesh) according to the protocol of Still, Kahn, and Mitra (*J. Org. Chem.* 1978, 43, 2923). Thin layer chromatography was performed using precoated plates purchased from E. Merck (silica gel 60 $PF_{254}$, 0.25 mm) and spots were visualized with long-wave ultraviolet light followed by an appropriate staining reagent.

Nuclear magnetic resonance (NMR) spectra were recorded on a Varian Inova-400 resonance spectrometer. $^1H$ NMR chemical shifts are given in parts per million (δ) downfield from tetramethylsilane (TMS) using TMS or the residual solvent signal ($CHCl_3$=δ7.24, DMSO=β2.50) as internal standard. $^1H$ NMR information is tabulated in the following format: number of protons, multiplicity (s, singlet; d, doublet; t, triplet; q, quartet; m, multiplet), coupling constant(s) (J) in hertz, and, in selected cases, position assignment. The prefix app is occasionally applied in cases where the true signal multiplicity was unresolved and br indicates the signal in question was broadened.

Combustion analyses were performed by Robertson Microlit Laboratories, Inc. (Madison, N.J.) and optical rotations were measured on Perkin-Elmer 241 MC polarimeter and reported as: $[\alpha]^T_\lambda$ (c=(g/100 mL), solvent).

Two routes are illustrated below which are useful in preparing the coumpounds disclosed in this invention. In Route I, α-bromo-phenylacetate S-1 was treated with a phenol, aniline or benzenethiol S-2 under basic condition to yield α-phenoxy-, α-phenylamino- or α-phenylsulfanyl-phenylacetate S-3. Hydrolysis of S-3 under basic condition yielded the corresponding acid S-4. Alternatively, S-3 was alkylated with a corresponding alkyl halide followed by basic hydrolysis to afford the alkylated acid S-5. In route B, intermediates S-7 with an electron withdrawing $R_1$ such as 4-$CF_3$ were treated with α-hydroxy, amino, or mercapto-phenyl acetic acid S-6 under strongly basic condition to afford phenylacetic acid S-8 directly.

FIG. 1.
General Reaction Schemes

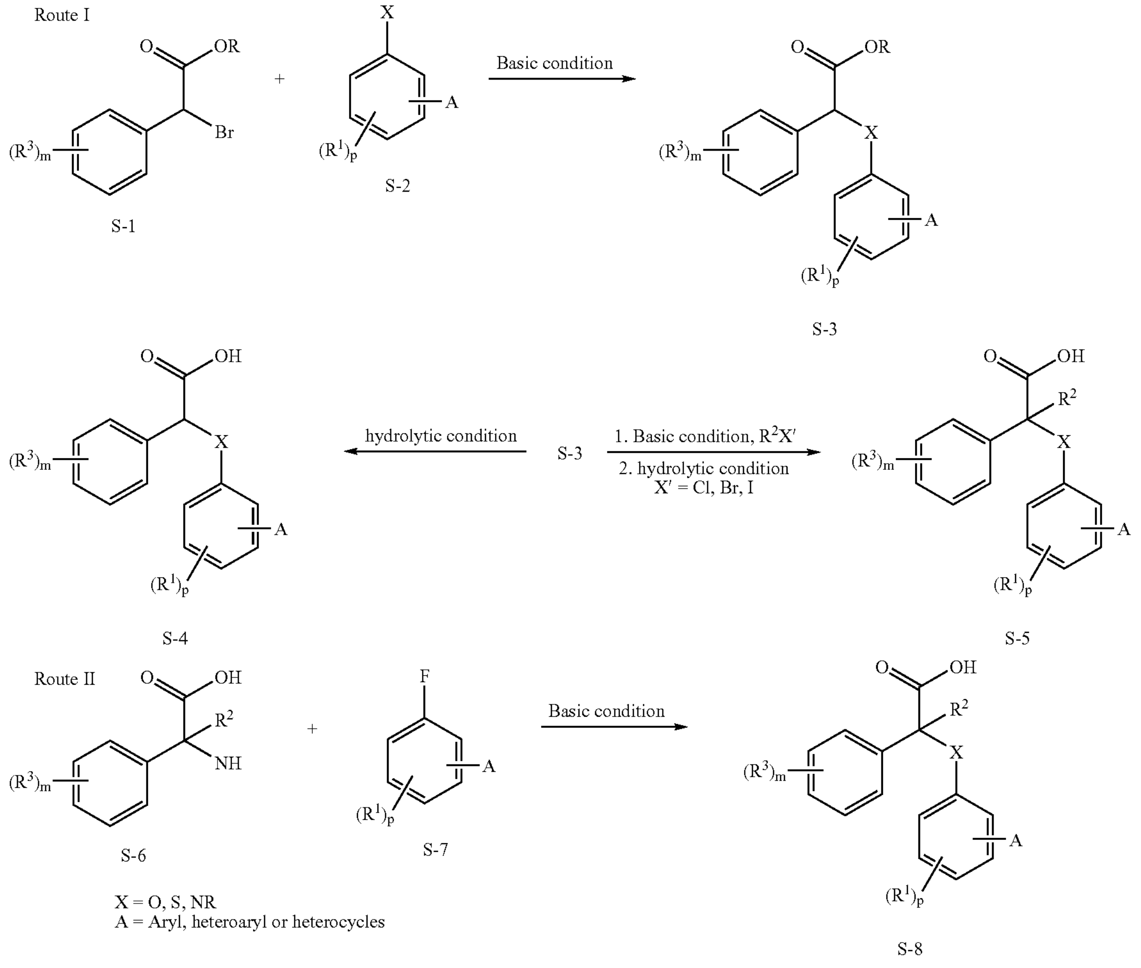

The compounds listed in Tables 1 through Table 12 were either synthesized or can be synthesized by the reaction routes and examples illustrated throughout the experimental section. All the intermediates and final products can be prepared by known procedures or by those skilled in the arts.

TABLE 1

2-Benzooxazole analogs

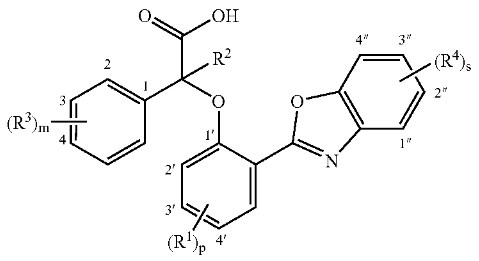

Compound I-X and Ia-X

| Compound | $R^2$ | $(R^3)_m$ | $(R^1)_p$ | $(R^4)_s$ | Configuration |
|---|---|---|---|---|---|
| I-1 | H | 4-Cl | H | H | R/S |
| I-2 | H | 3-OPh | H | H | R/S |
| I-3 | H | 3-$CF_3$ | H | H | R/S |
| I-4 | H | 3-Cl | H | H | R/S |
| I-5 | H | 4-OMe | H | H | R/S |
| I-6 | H | 4-$CF_3$ | H | H | R/S |
| I-7 | H | 4-Br | H | H | R/S |
| I-8 | H | H | H | H | R/S |
| I-9 | H | 4-F | H | H | R/S |
| I-10 | H | 2,3-di-F | H | H | R/S |
| I-11 | H | 2,4-di-F | H | H | R/S |
| I-12 | H | 2,5-di-F | H | H | R/S |
| I-13 | H | 2,6-di-F | H | H | R/S |
| I-14 | H | 3,4-di-F | H | H | R/S |
| I-15 | H | 3,5-di-F | H | H | R/S |
| I-16 | H | 2,3,5-tri-F | H | H | R/S |
| I-17 | H | 4-Et | H | H | R/S |
| I-18 | H | 4-Cl | H | 2"-Me | R/S |
| I-19 | H | 3-$CF_3$ | H | 2"-Me | R/S |
| I-20 | H | 3-OPh | H | 2"-Me | R/S |
| I-21 | H | 3-Cl | H | 2"-Me | R/S |
| I-22 | H | 4-OMe | H | 2"-Me | R/S |
| I-23 | H | 4-$CF_3$ | H | 2"-Me | R/S |
| I-24 | H | 4-Br | H | 2"-Me | R/S |
| I-25 | H | H | H | 2"-Me | R/S |
| I-26 | H | 4-F | H | 2"-Me | R/S |
| I-27 | H | 4-Et | H | 2"-Me | R/S |
| I-28 | H | 4-Cl | H | 2"-Ph | R/S |
| I-29 | H | 3-$CF_3$ | H | 2"-Ph | R/S |
| I-30 | H | 3-OPh | H | 2"-Ph | R/S |
| I-31 | H | 3-Cl | H | 2"-Ph | R/S |
| I-32 | H | 4-OMe | H | 2"-Ph | R/S |
| I-33 | H | 4-$CF_3$ | H | 2"-Ph | R/S |
| I-34 | H | 4-Br | H | 2"-Ph | R/S |
| I-35 | H | H | H | 2"-Ph | R/S |
| I-36 | H | 4-F | H | 2"-Ph | R/S |
| I-37 | H | 4-Et | H | 2"-Ph | R/S |
| I-38 | H | 4-Cl | H | 2"-Cl | R/S |
| I-39 | H | 3-$CF_3$ | H | 2"-Cl | R/S |
| I-40 | H | 3-OPh | H | 2"-Cl | R/S |
| I-41 | H | 3-Cl | H | 2"-Cl | R/S |
| I-42 | H | 4-OMe | H | 2"-Cl | R/S |
| I-43 | H | 4-$CF_3$ | H | 2"-Cl | R/S |
| I-44 | H | 4-Br | H | 2"-Cl | R/S |
| I-45 | H | H | H | 2"-Cl | R/S |
| I-46 | H | 4-F | H | 2"-Cl | R/S |
| I-47 | H | 4-Et | H | 2"-Cl | R/S |
| I-48 | H | 4-Cl | H | 2"-$OCF_3$ | R/S |
| I-49 | H | 3-$CF_3$ | H | 2"-$OCF_3$ | R/S |
| I-50 | H | 3-OPh | H | 2"-$OCF_3$ | R/S |
| I-51 | H | 3-Cl | H | 2"-$OCF_3$ | R/S |
| I-52 | H | 4-OMe | H | 2"-$OCF_3$ | R/S |
| I-53 | H | 4-$CF_3$ | H | 2"-$OCF_3$ | R/S |
| I-54 | H | 4-Br | H | 2"-$OCF_3$ | R/S |
| I-55 | H | H | H | 2"-$OCF_3$ | R/S |
| I-56 | H | 4-F | H | 2"-$OCF_3$ | R/S |
| I-57 | H | 4-Et | H | 2"-$OCF_3$ | R/S |
| I-58 | H | 4-Cl | H | 3"-Me | R/S |
| I-59 | H | 3-$CF_3$ | H | 3"-Me | R/S |

TABLE 1-continued

2-Benzooxazole analogs

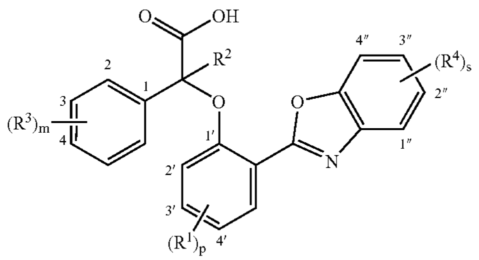

Compound I-X and Ia-X

| Compound | $R^2$ | $(R^3)_m$ | $(R^1)_p$ | $(R^4)_s$ | Configuration |
|---|---|---|---|---|---|
| I-60 | H | 3-OPh | H | 3"-Me | R/S |
| I-61 | H | 3-Cl | H | 3"-Me | R/S |
| I-62 | H | 4-OMe | H | 3"-Me | R/S |
| I-63 | H | 4-$CF_3$ | H | 3"-Me | R/S |
| I-64 | H | 4-Br | H | 3"-Me | R/S |
| I-65 | H | H | H | 3"-Me | R/S |
| I-66 | H | 4-F | H | 3"-Me | R/S |
| I-67 | H | 4-Et | H | 3"-Me | R/S |
| I-68 | H | 4-Cl | H | 3"-OMe | R/S |
| I-69 | H | 3-$CF_3$ | H | 3"-OMe | R/S |
| I-70 | H | 3-OPh | H | 3"-OMe | R/S |
| I-71 | H | 3-Cl | H | 3"-OMe | R/S |
| I-72 | H | 4-OMe | H | 3"-OMe | R/S |
| I-73 | H | 4-$CF_3$ | H | 3"-OMe | R/S |
| I-74 | H | 4-Br | H | 3"-OMe | R/S |
| I-75 | H | H | H | 3"-OMe | R/S |
| I-76 | H | 4-F | H | 3"-OMe | R/S |
| I-77 | H | 4-Et | H | 3"-OMe | R/S |
| I-78 | H | 4-Cl | H | 3"-Cl | R/S |
| I-79 | H | 3-$CF_3$ | H | 3"-Cl | R/S |
| I-80 | H | 3-OPh | H | 3"-Cl | R/S |
| I-81 | H | 3-Cl | H | 3"-Cl | R/S |
| I-82 | H | 4-OMe | H | 3"-Cl | R/S |
| I-83 | H | 4-$CF_3$ | H | 3"-Cl | R/S |
| I-84 | H | 4-Br | H | 3"-Cl | R/S |
| I-85 | H | H | H | 3"-Cl | R/S |
| I-86 | H | 4-F | H | 3"-Cl | R/S |
| I-87 | H | 4-Et | H | 3"-Cl | R/S |
| I-88 | H | 4-Cl | 4'-$CF_3$ | H | R/S |
| I-89 | H | 3-$CF_3$ | 4'-$CF_3$ | H | R/S |
| I-90 | H | 3-OPh | 4'-$CF_3$ | H | R/S |
| I-91 | H | 4-$CF_3$ | 4'-$CF_3$ | H | R/S |
| I-92 | H | H | 4'-$CF_3$ | H | R/S |
| I-93 | H | 4-OMe | 4'-$CF_3$ | H | R/S |
| I-94 | H | 3-Cl | 4'-$CF_3$ | H | R/S |
| I-95 | H | 3,4-diF | 4'-$CF_3$ | H | R/S |
| I-96 | H | 3-OMe | 4'-$CF_3$ | H | R/S |
| I-97 | H | 2,3,6-tri-F | 4'-$CF_3$ | H | R/S |
| I-98 | H | 3-Ph | 4'-$CF_3$ | H | R/S |
| I-99 | H | 4-Br | 4'-$CF_3$ | H | R/S |
| I-100 | H | 3-$NO_2$ | 4'-$CF_3$ | H | R/S |
| I-101 | H | 3,4-methylenedioxy | 4'-$CF_3$ | H | R/S |
| I-102 | H | 4-F | 4'-$CF_3$ | H | R/S |
| I-103 | H | 2,3-di-F | 4'-$CF_3$ | H | R/S |
| I-104 | H | 2,4-di-F | 4'-$CF_3$ | H | R/S |
| I-105 | H | 2,5-di-F | 4'-$CF_3$ | H | R/S |
| I-106 | H | 2,6-di-F | 4'-$CF_3$ | H | R/S |
| I-107 | H | 3,4-di-F | 4'-$CF_3$ | H | R/S |
| I-108 | H | 3,5-di-F | 4'-$CF_3$ | H | R/S |
| I-109 | H | 2,3,5-tri-F | 4'-$CF_3$ | H | R/S |
| I-110 | H | 4-Et | 4'-$CF_3$ | H | R/S |
| I-111 | H | 2-Cl | 4'-$CF_3$ | H | R/S |
| I-112 | Et | H | 4'-$CF_3$ | H | R/S |
| I-113 | H | 4-iPr | 4'-$CF_3$ | H | R/S |
| I-114 | H | 4-$CF_3$ | 4'-$CF_3$ | H | R/S |
| I-115 | H | 3-Br | 4'-$CF_3$ | H | R/S |
| I-116 | H | 4-MeS | 4'-$CF_3$ | H | R/S |
| I-117 | H | 4-$NO_2$ | 4'-$CF_3$ | H | R/S |

TABLE 1-continued

2-Benzooxazole analogs

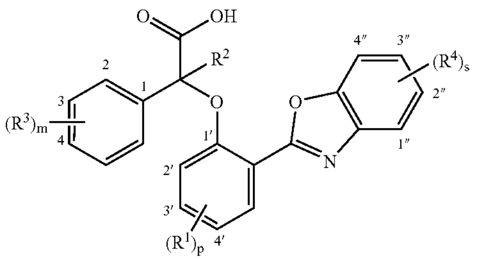

Compound I-X and Ia-X

| Compound | $R^2$ | $(R^3)_m$ | $(R^1)_p$ | $(R^4)_s$ | Configuration |
|---|---|---|---|---|---|
| I-118 | H | 2,5-di-Me | 4'-$CF_3$ | H | R/S |
| I-119 | H | H | 4'-$CF_3$ | 2"-Me | R/S |
| I-120 | H | 3-$CF_3$ | 4'-$CF_3$ | 2"-Me | R/S |
| I-121 | H | 3-OPh | 4'-$CF_3$ | 2"-Me | R/S |
| I-122 | H | 3-Cl | 4'-$CF_3$ | 2"-Me | R/S |
| I-123 | H | 4-OMe | 4'-$CF_3$ | 2"-Me | R/S |
| I-124 | H | 4-$CF_3$ | 4'-$CF_3$ | 2"-Me | R/S |
| I-125 | H | 4-Br | 4'-$CF_3$ | 2"-Me | R/S |
| I-126 | H | 4-Cl | 4'-$CF_3$ | 2"-Me | R/S |
| I-127 | H | 4-F | 4'-$CF_3$ | 2"-Me | R/S |
| I-128 | H | 4-Et | 4'-$CF_3$ | 2"-Me | R/S |
| I-129 | H | 4-Cl | 4'-$CF_3$ | 2"-Ph | R/S |
| I-130 | H | 3-$CF_3$ | 4'-$CF_3$ | 2"-Ph | R/S |
| I-131 | H | 3-OPh | 4'-$CF_3$ | 2"-Ph | R/S |
| I-132 | H | 3-Cl | 4'-$CF_3$ | 2"-Ph | R/S |
| I-133 | H | 4-OMe | 4'-$CF_3$ | 2"-Ph | R/S |
| I-134 | H | 4-$CF_3$ | 4'-$CF_3$ | 2"-Ph | R/S |
| I-135 | H | 4-Br | 4'-$CF_3$ | 2"-Ph | R/S |
| I-136 | H | H | 4'-$CF_3$ | 2"-Ph | R/S |
| I-137 | H | 4-F | 4'-$CF_3$ | 2"-Ph | R/S |
| I-138 | H | 4-Et | 4'-$CF_3$ | 2"-Ph | R/S |
| I-139 | H | 4-Cl | 4'-$CF_3$ | 2"-Cl | R/S |
| I-140 | H | 3-$CF_3$ | 4'-$CF_3$ | 2"-Cl | R/S |
| I-141 | H | 3-OPh | 4'-$CF_3$ | 2"-Cl | R/S |
| I-142 | H | 3-Cl | 4'-$CF_3$ | 2"-Cl | R/S |
| I-143 | H | 4-OMe | 4'-$CF_3$ | 2"-Cl | R/S |
| I-144 | H | 4-$CF_3$ | 4'-$CF_3$ | 2"-Cl | R/S |
| I-145 | H | 4-Br | 4'-$CF_3$ | 2"-Cl | R/S |
| I-146 | H | H | 4'-$CF_3$ | 2"-Cl | R/S |
| I-147 | H | 4-F | 4'-$CF_3$ | 2"-Cl | R/S |
| I-148 | H | 4-Et | 4'-$CF_3$ | 2"-Cl | R/S |
| I-149 | H | 4-Cl | 4'-$CF_3$ | 2"-$OCF_3$ | R/S |
| I-150 | H | 3-$CF_3$ | 4'-$CF_3$ | 2"-$OCF_3$ | R/S |
| I-151 | H | 3-OPh | 4'-$CF_3$ | 2"-$OCF_3$ | R/S |
| I-152 | H | 3-Cl | 4'-$CF_3$ | 2"-$OCF_3$ | R/S |
| I-153 | H | 4-OMe | 4'-$CF_3$ | 2"-$OCF_3$ | R/S |
| I-154 | H | 4-$CF_3$ | 4'-$CF_3$ | 2"-$OCF_3$ | R/S |
| I-155 | H | 4-Br | 4'-$CF_3$ | 2"-$OCF_3$ | R/S |
| I-156 | H | H | 4'-$CF_3$ | 2"-$OCF_3$ | R/S |
| I-157 | H | 4-F | 4'-$CF_3$ | 2"-$OCF_3$ | R/S |
| I-158 | H | 4-Et | 4'-$CF_3$ | 2"-$OCF_3$ | R/S |
| I-159 | H | 4-Cl | 4'-$CF_3$ | 3"-Me | R/S |
| I-160 | H | 3-$CF_3$ | 4'-$CF_3$ | 3"-Me | R/S |
| I-161 | H | 3-OPh | 4'-$CF_3$ | 3"-Me | R/S |
| I-162 | H | 3-Cl | 4'-$CF_3$ | 3"-Me | R/S |
| I-163 | H | 4-OMe | 4'-$CF_3$ | 3"-Me | R/S |
| I-164 | H | 4-$CF_3$ | 4'-$CF_3$ | 3"-Me | R/S |
| I-165 | H | 4-Br | 4'-$CF_3$ | 3"-Me | R/S |
| I-166 | H | H | 4'-$CF_3$ | 3"-Me | R/S |
| I-167 | H | 4-F | 4'-$CF_3$ | 3"-Me | R/S |
| I-168 | H | 4-Et | 4'-$CF_3$ | 3"-Me | R/S |
| I-169 | H | 4-Cl | 4'-$CF_3$ | 3"-OMe | R/S |
| I-170 | H | 3-$CF_3$ | 4'-$CF_3$ | 3"-OMe | R/S |
| I-171 | H | 3-OPh | 4'-$CF_3$ | 3"-OMe | R/S |
| I-172 | H | 3-Cl | 4'-$CF_3$ | 3"-OMe | R/S |
| I-173 | H | 4-OMe | 4'-$CF_3$ | 3"-OMe | R/S |
| I-174 | H | 4-$CF_3$ | 4'-$CF_3$ | 3"-OMe | R/S |
| I-175 | H | 4-Br | 4'-$CF_3$ | 3"-OMe | R/S |
| I-176 | H | H | 4'-$CF_3$ | 3"-OMe | R/S |

TABLE 1-continued

2-Benzooxazole analogs

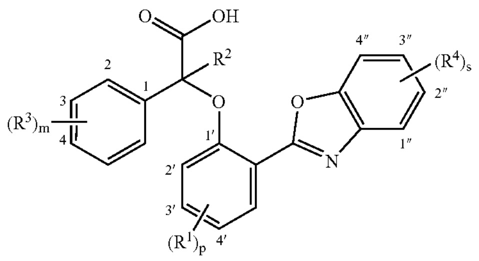

Compound I-X and Ia-X

| Compound | $R^2$ | $(R^3)_m$ | $(R^1)_p$ | $(R^4)_s$ | Configuration |
|---|---|---|---|---|---|
| I-177 | H | 4-F | 4'-$CF_3$ | 3"-OMe | R/S |
| I-178 | H | 4-Et | 4'-$CF_3$ | 3"-OMe | R/S |
| I-179 | H | 4-Cl | 4'-$CF_3$ | 3"-Cl | R/S |
| I-180 | H | 3-$CF_3$ | 4'-$CF_3$ | 3"-Cl | R/S |
| I-181 | H | 3-OPh | 4'-$CF_3$ | 3"-Cl | R/S |
| I-182 | H | 3-Cl | 4'-$CF_3$ | 3"-Cl | R/S |
| I-183 | H | 4-OMe | 4'-$CF_3$ | 3"-Cl | R/S |
| I-184 | H | 4-$CF_3$ | 4'-$CF_3$ | 3"-Cl | R/S |
| I-185 | H | 4-Br | 4'-$CF_3$ | 3"-Cl | R/S |
| I-186 | H | H | 4'-$CF_3$ | 3"-Cl | R/S |
| I-187 | H | 4-F | 4'-$CF_3$ | 3"-Cl | R/S |
| I-188 | H | 4-Et | 4'-$CF_3$ | 3"-Cl | R/S |
| I-189 | H | H | 4'-$CF_3$ | 4"-$CF_3$ | R/S |
| I-190 | H | 4-Cl | 4'-Cl | H | R/S |
| I-191 | H | 3-$CF_3$ | 4'-Cl | H | R/S |
| I-192 | H | H | 4'-Cl | H | R/S |
| I-193 | H | 4-OMe | 4'-Cl | H | R/S |
| I-194 | H | 3-Cl | 4'-Cl | H | R/S |
| I-195 | H | 4-Br | 4'-Cl | H | R/S |
| I-196 | H | 3-Ph | 4'-Cl | H | R/S |
| I-197 | H | 4-Cl | 4'-Cl | H | R/S |
| I-198 | H | 4-$CF_3$ | 4'-Cl | H | R/S |
| I-199 | H | 4-F | 4'-Cl | H | R/S |
| I-200 | H | 2,3-di-F | 4'-Cl | H | R/S |
| I-201 | H | 2,4-di-F | 4'-Cl | H | R/S |
| I-202 | H | 2,5-di-F | 4'-Cl | H | R/S |
| I-203 | H | 2,6-di-F | 4'-Cl | H | R/S |
| I-204 | H | 3,4-di-F | 4'-Cl | H | R/S |
| I-205 | H | 3,5-di-F | 4'-Cl | H | R/S |
| I-206 | H | 2,3,5-tri-F | 4'-Cl | H | R/S |
| I-207 | H | 4-Et | 4'-Cl | H | R/S |
| I-208 | H | 3-OMe | 4'-Cl | 4"-Cl | R/S |
| I-209 | H | 4-Cl | 4'-Cl | 2"-Me | R/S |
| I-210 | H | 3-$CF_3$ | 4'-Cl | 2"-Me | R/S |
| I-211 | H | 3-OPh | 4'-Cl | 2"-Me | R/S |
| I-212 | H | 3-Cl | 4'-Cl | 2"-Me | R/S |
| I-213 | H | 4-OMe | 4'-Cl | 2"-Me | R/S |
| I-214 | H | 4-$CF_3$ | 4'-Cl | 2"-Me | R/S |
| I-215 | H | 4-Br | 4'-Cl | 2"-Me | R/S |
| I-216 | H | H | 4'-Cl | 2"-Me | R/S |
| I-217 | H | 4-F | 4'-Cl | 2"-Me | R/S |
| I-218 | H | 4-Et | 4'-Cl | 2"-Me | R/S |
| I-219 | H | 4-Cl | 4'-Cl | 2"-Ph | R/S |
| I-220 | H | 3-$CF_3$ | 4'-Cl | 2"-Ph | R/S |
| I-221 | H | 3-OPh | 4'-Cl | 2"-Ph | R/S |
| I-222 | H | 3-Cl | 4'-Cl | 2"-Ph | R/S |
| I-223 | H | 4-OMe | 4'-Cl | 2"-Ph | R/S |
| I-224 | H | 4-$CF_3$ | 4'-Cl | 2"-Ph | R/S |
| I-225 | H | 4-Br | 4'-Cl | 2"-Ph | R/S |
| I-226 | H | H | 4'-Cl | 2"-Ph | R/S |
| I-227 | H | 4-F | 4'-Cl | 2"-Ph | R/S |
| I-228 | H | 4-Et | 4'-Cl | 2"-Ph | R/S |
| I-229 | H | 4-Cl | 4'-Cl | 2"-Cl | R/S |
| I-230 | H | 3-$CF_3$ | 4'-Cl | 2"-Cl | R/S |
| I-231 | H | 3-OPh | 4'-Cl | 2"-Cl | R/S |
| I-232 | H | 3-Cl | 4'-Cl | 2"-Cl | R/S |
| I-233 | H | 4-OMe | 4'-Cl | 2"-Cl | R/S |
| I-234 | H | 4-$CF_3$ | 4'-Cl | 2"-Cl | R/S |
| I-235 | H | 4-Br | 4'-Cl | 2"-Cl | R/S |

TABLE 1-continued

2-Benzooxazole analogs

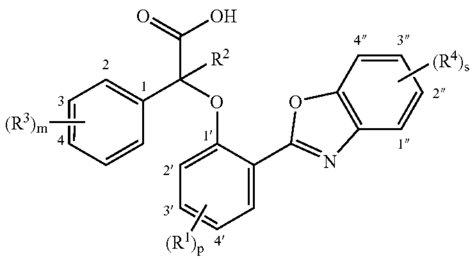

Compound I-X and Ia-X

| Compound | $R^2$ | $(R^3)_m$ | $(R^1)_p$ | $(R^4)_s$ | Configuration |
|---|---|---|---|---|---|
| I-236 | H | H | 4'-Cl | 2"-Cl | R/S |
| I-237 | H | 4-F | 4'-Cl | 2"-Cl | R/S |
| I-238 | H | 4-Et | 4'-Cl | 2"-Cl | R/S |
| I-239 | H | 4-Cl | 4'-Cl | 2"-$OCF_3$ | R/S |
| I-240 | H | 3-$CF_3$ | 4'-Cl | 2"-$OCF_3$ | R/S |
| I-241 | H | 3-OPh | 4'-Cl | 2"-$OCF_3$ | R/S |
| I-242 | H | 3-Cl | 4'-Cl | 2"-$OCF_3$ | R/S |
| I-243 | H | 4-OMe | 4'-Cl | 2"-$OCF_3$ | R/S |
| I-244 | H | 4-$CF_3$ | 4'-Cl | 2"-$OCF_3$ | R/S |
| I-245 | H | 4-Br | 4'-Cl | 2"-$OCF_3$ | R/S |
| I-246 | H | H | 4'-Cl | 2"-$OCF_3$ | R/S |
| I-247 | H | 4-F | 4'-Cl | 2"-$OCF_3$ | R/S |
| I-248 | H | 4-Et | 4'-Cl | 2"-$OCF_3$ | R/S |
| I-249 | H | 4-Cl | 4'-Cl | 3"-Me | R/S |
| I-250 | H | 3-$CF_3$ | 4'-Cl | 3"-Me | R/S |
| I-251 | H | 3-OPh | 4'-Cl | 3"-Me | R/S |
| I-252 | H | 3-Cl | 4'-Cl | 3"-Me | R/S |
| I-253 | H | 4-OMe | 4'-Cl | 3"-Me | R/S |
| I-254 | H | 4-$CF_3$ | 4'-Cl | 3"-Me | R/S |
| I-255 | H | 4-Br | 4'-Cl | 3"-Me | R/S |
| I-256 | H | H | 4'-Cl | 3"-Me | R/S |
| I-257 | H | 4-F | 4'-Cl | 3"-Me | R/S |
| I-258 | H | 4-Et | 4'-Cl | 3"-Me | R/S |
| I-259 | H | 4-Cl | 4'-Cl | 3"-OMe | R/S |
| I-260 | H | 3-$CF_3$ | 4'-Cl | 3"-OMe | R/S |
| I-261 | H | 3-OPh | 4'-Cl | 3"-OMe | R/S |
| I-262 | H | 3-Cl | 4'-Cl | 3"-OMe | R/S |
| I-263 | H | 4-OMe | 4'-Cl | 3"-OMe | R/S |
| I-264 | H | 4-$CF_3$ | 4'-Cl | 3"-OMe | R/S |
| I-265 | H | 4-Br | 4'-Cl | 3"-OMe | R/S |
| I-266 | H | H | 4'-Cl | 3"-OMe | R/S |
| I-267 | H | 4-F | 4'-Cl | 3"-OMe | R/S |
| I-268 | H | 4-Et | 4'-Cl | 3"-OMe | R/S |
| I-269 | H | 4-Cl | 4'-Cl | 3"-Cl | R/S |
| I-270 | H | 3-$CF_3$ | 4'-Cl | 3"-Cl | R/S |
| I-271 | H | 3-OPh | 4'-Cl | 3"-Cl | R/S |
| I-271 | H | 3-Cl | 4'-Cl | 3"-Cl | R/S |
| I-272 | H | 4-OMe | 4'-Cl | 3"-Cl | R/S |
| I-273 | H | 4-$CF_3$ | 4'-Cl | 3"-Cl | R/S |
| I-274 | H | 4-Br | 4'-Cl | 3"-Cl | R/S |
| I-275 | H | H | 4'-Cl | 3"-Cl | R/S |
| I-276 | H | 4-F | 4'-Cl | 3"-Cl | R/S |
| I-277 | H | 4-Et | 4'-Cl | 3"-Cl | R/S |
| I-278 | H | 3-$CF_3$ | 4'-$CF_3$ | 4"-Cl | R/S |
| I-279 | H | 4-OMe | 4'-$CF_3$ | 4"-Cl | R/S |
| I-280 | H | 4-Cl | 4'-$CF_3$ | 4"-Cl | R/S |
| I-281 | H | 4-$CF_3$ | 4'-$CF_3$ | 4"-Cl | R/S |
| I-282 | H | 4-Br | 4'-$CF_3$ | 4"-Cl | R/S |
| I-283 | H | H | 4'-$CF_3$ | 4"-Cl | R/S |
| I-284 | H | 3-Cl | 4'-Me | H | R/S |
| I-285 | H | 3-$CF_3$ | 4'-Me | H | R/S |
| I-286 | H | 3-OPh | 4'-Me | H | R/S |
| I-287 | H | 4-OMe | 4'-Me | H | R/S |
| I-288 | H | 4-Cl | 4'-Me | H | R/S |
| I-289 | H | 4-$CF_3$ | 4'-Me | H | R/S |
| I-290 | H | 4-Br | 4'-Me | H | R/S |
| I-291 | H | H | 4'-Me | H | R/S |
| I-292 | H | 4-F | 4'-Me | H | R/S |
| I-293 | H | 2,3-di-F | 4'-Me | H | R/S |

TABLE 1-continued

2-Benzooxazole analogs

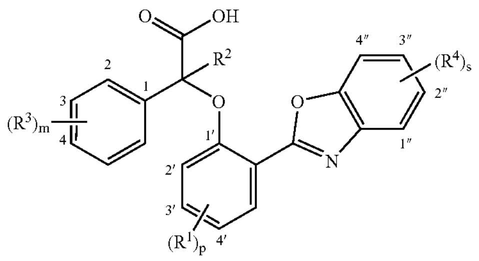

Compound I-X and Ia-X

| Compound | $R^2$ | $(R^3)_m$ | $(R^1)_p$ | $(R^4)_s$ | Configuration |
|---|---|---|---|---|---|
| I-294 | H | 2,4-di-F | 4'-Me | H | R/S |
| I-295 | H | 2,5-di-F | 4'-Me | H | R/S |
| I-296 | H | 2,6-di-F | 4'-Me | H | R/S |
| I-297 | H | 3,4-di-F | 4'-Me | H | R/S |
| I-298 | H | 3,5-di-F | 4'-Me | H | R/S |
| I-299 | H | 2,3,5-tri-F | 4'-Me | H | R/S |
| I-300 | H | 4-Et | 4'-Me | H | R/S |
| I-301 | H | 3-Cl | 4'-t-Bu | H | R/S |
| I-302 | H | 3-$CF_3$ | 4'-t-Bu | H | R/S |
| I-303 | H | 3-OPh | 4'-t-Bu | H | R/S |
| I-304 | H | 4-OMe | 4'-t-Bu | H | R/S |
| I-305 | H | 4-Cl | 4'-t-Bu | H | R/S |
| I-306 | H | 4-$CF_3$ | 4'-t-Bu | H | R/S |
| I-307 | H | 4-Br | 4'-t-Bu | H | R/S |
| I-308 | H | H | 4'-t-Bu | H | R/S |
| I-309 | H | 4-F | 4'-t-Bu | H | R/S |
| I-310 | H | 2,3-di-F | 4'-t-Bu | H | R/S |
| I-311 | H | 2,4-di-F | 4'-t-Bu | H | R/S |
| I-312 | H | 2,5-di-F | 4'-t-Bu | H | R/S |
| I-313 | H | 2,6-di-F | 4'-t-Bu | H | R/S |
| I-314 | H | 3,4-di-F | 4'-t-Bu | H | R/S |
| I-315 | H | 3,5-di-F | 4'-t-Bu | H | R/S |
| I-316 | H | 2,3,5-tri-F | 4'-t-Bu | H | R/S |
| I-317 | H | 4-Et | 4'-t-Bu | H | R/S |
| I-318 | H | 3-Cl | 4'-Br | H | R/S |
| I-319 | H | 3-$CF_3$ | 4'-Br | H | R/S |
| I-320 | H | 3-OPh | 4'-Br | H | R/S |
| I-321 | H | 4-OMe | 4'-Br | H | R/S |
| I-322 | H | 4-Cl | 4'-Br | H | R/S |
| I-323 | H | 4-$CF_3$ | 4'-Br | H | R/S |
| I-324 | H | 4-Br | 4'-Br | H | R/S |
| I-325 | H | H | 4'-Br | H | R/S |
| I-326 | H | 4-F | 4'-Br | H | R/S |
| I-327 | H | 2,3-di-F | 4'-Br | H | R/S |
| I-328 | H | 2,4-di-F | 4'-Br | H | R/S |
| I-329 | H | 2,5-di-F | 4'-Br | H | R/S |
| I-330 | H | 2,6-di-F | 4'-Br | H | R/S |
| I-331 | H | 3,4-di-F | 4'-Br | H | R/S |
| I-332 | H | 3,5-di-F | 4'-Br | H | R/S |
| I-333 | H | 4-Et | 4'-Br | H | R/S |
| I-334 | H | 2,3,6-tri-F | 4'-Br | H | R/S |
| I-335 | H | 3-Cl | 4',6'-di Cl | H | R/S |
| I-336 | H | 3-$CF_3$ | 4',6'-di Cl | H | R/S |
| I-337 | H | 3-OPh | 4',6'-di Cl | H | R/S |
| I-338 | H | 4-OMe | 4',6'-di Cl | H | R/S |
| I-339 | H | 4-Cl | 4',6'-di Cl | H | R/S |
| I-340 | H | 4-$CF_3$ | 4',6'-di Cl | H | R/S |
| I-341 | H | 4-Br | 4',6'-di Cl | H | R/S |
| I-342 | H | H | 4',6'-di Cl | H | R/S |
| I-343 | H | 4-F | 4',6'-di Cl | H | R/S |
| I-344 | H | 4-Et | 4',6'-di Cl | H | R/S |
| I-345 | H | 3-Cl | 4'-(2,4-diF-Ph) | H | R/S |
| I-346 | H | 3-$CF_3$ | 4'-(2,4-diF-Ph) | H | R/S |
| I-347 | H | 3-OPh | 4'-(2,4-diF-Ph) | H | R/S |
| I-348 | H | 4-OMe | 4'-(2,4-diF-Ph) | H | R/S |
| I-349 | H | 4-Cl | 4'-(2,4-diF-Ph) | H | R/S |
| I-350 | H | 4-$CF_3$ | 4'-(2,4-diF-Ph) | H | R/S |
| I-351 | H | 4-Br | 4'-(2,4-diF-Ph) | H | R/S |
| I-352 | H | H | 4'-(2,4-diF-Ph) | H | R/S |

TABLE 1-continued

2-Benzooxazole analogs

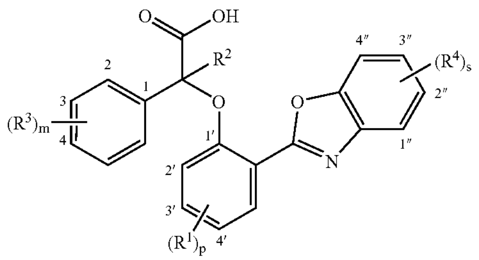

Compound I-X and Ia-X

| Compound | $R^2$ | $(R^3)_m$ | $(R^1)_p$ | $(R^4)_s$ | Configuration |
|---|---|---|---|---|---|
| I-353 | H | 4-F | 4'-(2,4-diF-Ph) | H | R/S |
| I-354 | H | 4-Et | 4'-(2,4-diF-Ph) | H | R/S |
| I-355 | H | 3-Cl | 4'-(1H-pyrrol-yl) | H | R/S |
| I-356 | H | $3-CF_3$ | 4'-(1H-pyrrol-yl) | H | R/S |
| I-357 | H | 3-OPh | 4'-(1H-pyrrol-yl) | H | R/S |
| I-358 | H | 4-OMe | 4'-(1H-pyrrol-yl) | H | R/S |
| I-359 | H | 4-Cl | 4'-(1H-pyrrol-yl) | H | R/S |
| I-360 | H | $4-CF_3$ | 4'-(1H-pyrrol-yl) | H | R/S |
| I-361 | H | 4-Br | 4'-(1H-pyrrol-yl) | H | R/S |
| I-362 | H | H | 4'-(1H-pyrrol-yl) | H | R/S |
| I-363 | H | 4-F | 4'-(1H-pyrrol-yl) | H | R/S |
| I-364 | H | 4-Et | 4'-(1H-pyrrol-yl) | H | R/S |
| I-365 | H | $3-CF_3$ | $4'-CF_3$ | H | (+) |
| I-366 | H | $3-CF_3$ | $4'-CF_3$ | H | (−) |
| I-367 | H | $3-CF_3$ | 4'-Cl | H | (+) |
| I-368 | H | $3-CF_3$ | 4'-Cl | H | (−) |
| I-369 | H | H | $4'-CF_3$ | H | S |
| I-370 | H | H | $4'-CF_3$ | H | R |
| I-371 | H | 3-Cl | $4'-CF_3$ | H | S |
| I-372 | H | 4-Cl | $4'-CF_3$ | H | (+) |
| I-373 | H | 4-Cl | $4'-CF_3$ | H | (−) |
| I-374 | H | 3-Cl | 4'-Cl | H | (+) |
| I-375 | H | 3-Cl | 4'-Cl | H | (−) |
| I-376 | H | 3-Ph | $4'-CF_3$ | H | R/S |
| I-377 | H | H | 4'-Cl | H | (+) |
| I-378 | H | H | 4'-Cl | H | (−) |
| I-379 | H | 3-F,5-F | $4'-CF_3$ | H | R/S |
| I-380 | H | 3-F,4-F | $4'-CF_3$ | H | R/S |
| Ia-1 | Me | 4-Cl | H | H | R/S |
| Ia-2 | Me | $3-CF_3$ | H | H | R/S |
| Ia-3 | Me | 3-OPh | H | H | R/S |
| Ia-4 | Me | 3-Cl | H | H | R/S |
| Ia-5 | Me | 4-OMe | H | H | R/S |
| Ia-6 | Me | $4-CF_3$ | H | H | R/S |
| Ia-7 | Me | 4-Br | H | H | R/S |
| Ia-8 | Me | H | H | H | R/S |
| Ia-9 | Me | 4-F | H | H | R/S |
| Ia-10 | Me | 2,3-di-F | H | H | R/S |
| Ia-11 | Me | 2,4-di-F | H | H | R/S |
| Ia-12 | Me | 2,5-di-F | H | H | R/S |
| Ia-13 | Me | 2,6-di-F | H | H | R/S |
| Ia-14 | Me | 3,4-di-F | H | H | R/S |
| Ia-15 | Me | 3,5-di-F | H | H | R/S |
| Ia-16 | Me | 2,3,5-tri-F | H | H | R/S |
| Ia-17 | Me | 4-Et | H | H | R/S |
| Ia-18 | Me | 4-Cl | H | 2"-Me | R/S |
| Ia-19 | Me | $3-CF_3$ | H | 2"-Me | R/S |
| Ia-20 | Me | 3-OPh | H | 2"-Me | R/S |
| Ia-21 | Me | 3-Cl | H | 2"-Me | R/S |
| Ia-22 | Me | 4-OMe | H | 2"-Me | R/S |
| Ia-23 | Me | $4-CF_3$ | H | 2"-Me | R/S |
| Ia-24 | Me | 4-Br | H | 2"-Me | R/S |
| Ia-25 | Me | H | H | 2"-Me | R/S |
| Ia-26 | Me | 4-F | H | 2"-Me | R/S |
| Ia-27 | Me | 4-Et | H | 2"-Me | R/S |
| Ia-28 | Me | 4-Cl | H | 2"-Ph | R/S |
| Ia-29 | Me | $3-CF_3$ | H | 2"-Ph | R/S |
| Ia-30 | Me | 3-OPh | H | 2"-Ph | R/S |
| Ia-31 | Me | 3-Cl | H | 2"-Ph | R/S |

TABLE 1-continued

2-Benzooxazole analogs

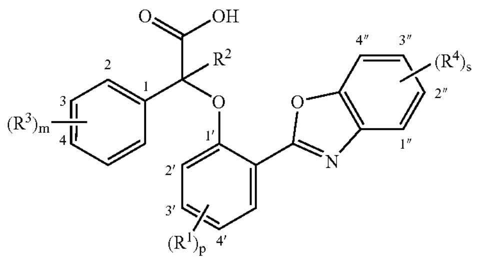

Compound I-X and Ia-X

| Compound | $R^2$ | $(R^3)_m$ | $(R^1)_p$ | $(R^4)_s$ | Configuration |
|---|---|---|---|---|---|
| Ia-32 | Me | 4-OMe | H | 2"-Ph | R/S |
| Ia-33 | Me | 4-$CF_3$ | H | 2"-Ph | R/S |
| Ia-34 | Me | 4-Br | H | 2"-Ph | R/S |
| Ia-35 | Me | H | H | 2"-Ph | R/S |
| Ia-36 | Me | 4-F | H | 2"-Ph | R/S |
| Ia-37 | Me | 4-Et | H | 2"-Ph | R/S |
| Ia-38 | Me | 4-Cl | H | 2"-Cl | R/S |
| Ia-39 | Me | 3-$CF_3$ | H | 2"-Cl | R/S |
| Ia-40 | Me | 3-OPh | H | 2"-Cl | R/S |
| Ia-41 | Me | 3-Cl | H | 2"-Cl | R/S |
| Ia-42 | Me | 4-OMe | H | 2"-Cl | R/S |
| Ia-43 | Me | 4-$CF_3$ | H | 2"-Cl | R/S |
| Ia-44 | Me | 4-Br | H | 2"-Cl | R/S |
| Ia-45 | Me | H | H | 2"-Cl | R/S |
| Ia-46 | Me | 4-F | H | 2"-Cl | R/S |
| Ia-47 | Me | 4-Et | H | 2"-Cl | R/S |
| Ia-48 | Me | 4-Cl | H | 2"-$OCF_3$ | R/S |
| Ia-49 | Me | 3-$CF_3$ | H | 2"-$OCF_3$ | R/S |
| Ia-50 | Me | 3-OPh | H | 2"-$OCF_3$ | R/S |
| Ia-51 | Me | 3-Cl | H | 2"-$OCF_3$ | R/S |
| Ia-52 | Me | 4-OMe | H | 2"-$OCF_3$ | R/S |
| Ia-53 | Me | 4-$CF_3$ | H | 2"-$OCF_3$ | R/S |
| Ia-54 | Me | 4-Br | H | 2"-$OCF_3$ | R/S |
| Ia-55 | Me | H | H | 2"-$OCF_3$ | R/S |
| Ia-56 | Me | 4-F | H | 2"-$OCF_3$ | R/S |
| Ia-57 | Me | 4-Et | H | 2"-$OCF_3$ | R/S |
| Ia-58 | Me | 4-Cl | H | 3"-Me | R/S |
| Ia-59 | Me | 3-$CF_3$ | H | 3"-Me | R/S |
| Ia-60 | Me | 3-OPh | H | 3"-Me | R/S |
| Ia-61 | Me | 3-Cl | H | 3"-Me | R/S |
| Ia-62 | Me | 4-OMe | H | 3"-Me | R/S |
| Ia-63 | Me | 4-$CF_3$ | H | 3"-Me | R/S |
| Ia-64 | Me | 4-Br | H | 3"-Me | R/S |
| Ia-65 | Me | H | H | 3"-Me | R/S |
| Ia-66 | Me | 4-F | H | 3"-Me | R/S |
| Ia-67 | Me | 4-Et | H | 3"-Me | R/S |
| Ia-68 | Me | 4-Cl | H | 3"-OMe | R/S |
| Ia-69 | Me | 3-$CF_3$ | H | 3"-OMe | R/S |
| Ia-70 | Me | 3-OPh | H | 3"-OMe | R/S |
| Ia-71 | Me | 3-Cl | H | 3"-OMe | R/S |
| Ia-72 | Me | 4-OMe | H | 3"-OMe | R/S |
| Ia-73 | Me | 4-$CF_3$ | H | 3"-OMe | R/S |
| Ia-74 | Me | 4-Br | H | 3"-OMe | R/S |
| Ia-75 | Me | H | H | 3"-OMe | R/S |
| Ia-76 | Me | 4-F | H | 3"-OMe | R/S |
| Ia-77 | Me | 4-Et | H | 3"-OMe | R/S |
| Ia-78 | Me | 4-Cl | H | 3"-Cl | R/S |
| Ia-79 | Me | 3-$CF_3$ | H | 3"-Cl | R/S |
| Ia-80 | Me | 3-OPh | H | 3"-Cl | R/S |
| Ia-81 | Me | 3-Cl | H | 3"-Cl | R/S |
| Ia-82 | Me | 4-OMe | H | 3"-Cl | R/S |
| Ia-83 | Me | 4-$CF_3$ | H | 3"-Cl | R/S |
| Ia-84 | Me | 4-Br | H | 3"-Cl | R/S |
| Ia-85 | Me | H | H | 3"-Cl | R/S |
| Ia-86 | Me | 4-F | H | 3"-Cl | R/S |
| Ia-87 | Me | 4-Et | H | 3"-Cl | R/S |
| Ia-88 | Me | 4-Cl | 4'-$CF_3$ | H | R/S |
| Ia-89 | Me | 3-$CF_3$ | 4'-$CF_3$ | H | R/S |
| Ia-90 | Me | 3-OPh | 4'-$CF_3$ | H | R/S |

TABLE 1-continued

2-Benzooxazole analogs

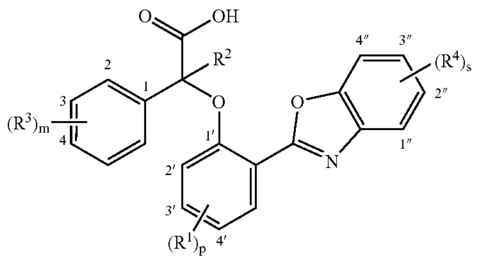

Compound I-X and Ia-X

| Compound | $R^2$ | $(R^3)_m$ | $(R^1)_p$ | $(R^4)_s$ | Configuration |
|---|---|---|---|---|---|
| Ia-91 | Me | 4-$CF_3$ | 4'-$CF_3$ | H | R/S |
| Ia-92 | Me | 4-iPr | 4'-$CF_3$ | H | R/S |
| Ia-93 | Me | H | 4'-$CF_3$ | H | R/S |
| Ia-94 | Me | 4-OMe | 4'-$CF_3$ | H | R/S |
| Ia-95 | Me | 3-$CF_3$ | 4'-$CF_3$ | H | R/S |
| Ia-96 | Me | 3-Cl | 4'-$CF_3$ | H | R/S |
| Ia-97 | Me | 3-OMe | 4'-$CF_3$ | H | R/S |
| Ia-98 | Me | 4-Cl | 4'-$CF_3$ | H | R/S |
| Ia-99 | Me | 4-Br | 4'-$CF_3$ | H | R/S |
| Ia-100 | Me | 3-$NO_2$ | 4'-$CF_3$ | H | R/S |
| Ia-101 | Me | 3,4-methylenedioxy | 4'-$CF_3$ | H | R/S |
| Ia-102 | Me | 4-F | 4'-$CF_3$ | H | R/S |
| Ia-103 | Me | 2,3-di-F | 4'-$CF_3$ | H | R/S |
| Ia-104 | Me | 2,4-di-F | 4'-$CF_3$ | H | R/S |
| Ia-105 | Me | 2,5-di-F | 4'-$CF_3$ | H | R/S |
| Ia-106 | Me | 2,6-di-F | 4'-$CF_3$ | H | R/S |
| Ia-107 | Me | 3,4-di-F | 4'-$CF_3$ | H | R/S |
| Ia-108 | Me | 3,5-di-F | 4'-$CF_3$ | H | R/S |
| Ia-109 | Me | 2,3,5-tri-F | 4'-$CF_3$ | H | R/S |
| Ia-110 | Me | 4-Et | 4'-$CF_3$ | H | R/S |
| Ia-111 | Me | 2-Cl | 4'-$CF_3$ | H | R/S |
| Ia-112 | Me | 3-Br | 4'-$CF_3$ | H | R/S |
| Ia-113 | Me | 4-tBu | 4'-$CF_3$ | H | R/S |
| Ia-114 | Me | 3-F | 4'-$CF_3$ | H | R/S |
| Ia-115 | Me | 4-Me | 4'-$CF_3$ | H | R/S |
| Ia-116 | Me | 4-MeS | 4'-$CF_3$ | H | R/S |
| Ia-117 | Me | 4-$NO_2$ | 4'-$CF_3$ | H | R/S |
| Ia-118 | Me | 2,5-di-Me | 4'-$CF_3$ | H | R/S |
| Ia-119 | Me | 4-Cl | 4'-$CF_3$ | 2"-Me | R/S |
| Ia-120 | Me | 3-$CF_3$ | 4'-$CF_3$ | 2"-Me | R/S |
| Ia-121 | Me | 3-OPh | 4'-$CF_3$ | 2"-Me | R/S |
| Ia-122 | Me | 3-Cl | 4'-$CF_3$ | 2"-Me | R/S |
| Ia-123 | Me | 4-OMe | 4'-$CF_3$ | 2"-Me | R/S |
| Ia-124 | Me | 4-$CF_3$ | 4'-$CF_3$ | 2"-Me | R/S |
| Ia-125 | Me | 4-Br | 4'-$CF_3$ | 2"-Me | R/S |
| Ia-126 | Me | H | 4'-$CF_3$ | 2"-Me | R/S |
| Ia-127 | Me | 4-F | 4'-$CF_3$ | 2"-Me | R/S |
| Ia-128 | Me | 4-Et | 4'-$CF_3$ | 2"-Me | R/S |
| Ia-129 | Me | 4-Cl | 4'-$CF_3$ | 2"-Ph | R/S |
| Ia-130 | Me | 3-$CF_3$ | 4'-$CF_3$ | 2"-Ph | R/S |
| Ia-131 | Me | 3-OPh | 4'-$CF_3$ | 2"-Ph | R/S |
| Ia-132 | Me | 3-Cl | 4'-$CF_3$ | 2"-Ph | R/S |
| Ia-133 | Me | 4-OMe | 4'-$CF_3$ | 2"-Ph | R/S |
| Ia-134 | Me | 4-$CF_3$ | 4'-$CF_3$ | 2"-Ph | R/S |
| Ia-135 | Me | 4-Br | 4'-$CF_3$ | 2"-Ph | R/S |
| Ia-136 | Me | H | 4'-$CF_3$ | 2"-Ph | R/S |
| Ia-137 | Me | 4-F | 4'-$CF_3$ | 2"-Ph | R/S |
| Ia-138 | Me | 4-Et | 4'-$CF_3$ | 2"-Ph | R/S |
| Ia-139 | Me | 4-Cl | 4'-$CF_3$ | 2"-Cl | R/S |
| Ia-140 | Me | 3-$CF_3$ | 4'-$CF_3$ | 2"-Cl | R/S |
| Ia-141 | Me | 3-OPh | 4'-$CF_3$ | 2"-Cl | R/S |
| Ia-142 | Me | 3-Cl | 4'-$CF_3$ | 2"-Cl | R/S |
| Ia-143 | Me | 4-OMe | 4'-$CF_3$ | 2"-Cl | R/S |
| Ia-144 | Me | 4-$CF_3$ | 4'-$CF_3$ | 2"-Cl | R/S |
| Ia-145 | Me | 4-Br | 4'-$CF_3$ | 2"-Cl | R/S |
| Ia-146 | Me | H | 4'-$CF_3$ | 2"-Cl | R/S |
| Ia-147 | Me | 4-F | 4'-$CF_3$ | 2"-Cl | R/S |
| Ia-148 | Me | 4-Et | 4'-$CF_3$ | 2"-Cl | R/S |

TABLE 1-continued

2-Benzooxazole analogs

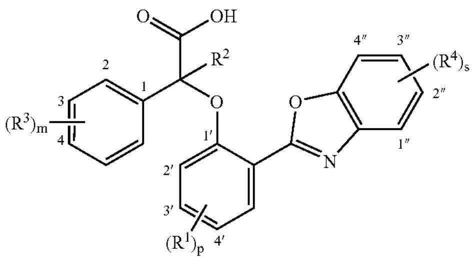

Compound I-X and Ia-X

| Compound | $R^2$ | $(R^3)_m$ | $(R^1)_p$ | $(R^4)_s$ | Configuration |
|---|---|---|---|---|---|
| Ia-149 | Me | 4-Cl | 4'-$CF_3$ | 2"-$OCF_3$ | R/S |
| Ia-150 | Me | 3-$CF_3$ | 4'-$CF_3$ | 2"-$OCF_3$ | R/S |
| Ia-151 | Me | 3-OPh | 4'-$CF_3$ | 2"-$OCF_3$ | R/S |
| Ia-152 | Me | 3-Cl | 4'-$CF_3$ | 2"-$OCF_3$ | R/S |
| Ia-153 | Me | 4-OMe | 4'-$CF_3$ | 2"-$OCF_3$ | R/S |
| Ia-154 | Me | 4-$CF_3$ | 4'-$CF_3$ | 2"-$OCF_3$ | R/S |
| Ia-155 | Me | 4-Br | 4'-$CF_3$ | 2"-$OCF_3$ | R/S |
| Ia-156 | Me | H | 4'-$CF_3$ | 2"-$OCF_3$ | R/S |
| Ia-157 | Me | 4-F | 4'-$CF_3$ | 2"-$OCF_3$ | R/S |
| Ia-158 | Me | 4-Et | 4'-$CF_3$ | 2"-$OCF_3$ | R/S |
| Ia-159 | Me | 4-Cl | 4'-$CF_3$ | 3"-Me | R/S |
| Ia-160 | Me | 3-$CF_3$ | 4'-$CF_3$ | 3"-Me | R/S |
| Ia-161 | Me | 3-OPh | 4'-$CF_3$ | 3"-Me | R/S |
| Ia-162 | Me | 3-Cl | 4'-$CF_3$ | 3"-Me | R/S |
| Ia-163 | Me | 4-OMe | 4'-$CF_3$ | 3"-Me | R/S |
| Ia-164 | Me | 4-$CF_3$ | 4'-$CF_3$ | 3"-Me | R/S |
| Ia-165 | Me | 4-Br | 4'-$CF_3$ | 3"-Me | R/S |
| Ia-166 | Me | H | 4'-$CF_3$ | 3"-Me | R/S |
| Ia-167 | Me | 4-F | 4'-$CF_3$ | 3"-Me | R/S |
| Ia-168 | Me | 4-Et | 4'-$CF_3$ | 3"-Me | R/S |
| Ia-169 | Me | 4-Cl | 4'-$CF_3$ | 3"-OMe | R/S |
| Ia-170 | Me | 3-$CF_3$ | 4'-$CF_3$ | 3"-OMe | R/S |
| Ia-171 | Me | 3-OPh | 4'-$CF_3$ | 3"-OMe | R/S |
| Ia-172 | Me | 3-Cl | 4'-$CF_3$ | 3"-OMe | R/S |
| Ia-173 | Me | 4-OMe | 4'-$CF_3$ | 3"-OMe | R/S |
| Ia-174 | Me | 4-$CF_3$ | 4'-$CF_3$ | 3"-OMe | R/S |
| Ia-175 | Me | 4-Br | 4'-$CF_3$ | 3"-OMe | R/S |
| Ia-176 | Me | H | 4'-$CF_3$ | 3"-OMe | R/S |
| Ia-177 | Me | 4-F | 4'-$CF_3$ | 3"-OMe | R/S |
| Ia-178 | Me | 4-Et | 4'-$CF_3$ | 3"-OMe | R/S |
| Ia-179 | Me | 4-Cl | 4'-$CF_3$ | 3"-Cl | R/S |
| Ia-180 | Me | 3-$CF_3$ | 4'-$CF_3$ | 3"-Cl | R/S |
| Ia-181 | Me | 3-OPh | 4'-$CF_3$ | 3"-Cl | R/S |
| Ia-182 | Me | 3-Cl | 4'-$CF_3$ | 3"-Cl | R/S |
| Ia-183 | Me | 4-OMe | 4'-$CF_3$ | 3"-Cl | R/S |
| Ia-184 | Me | 4-$CF_3$ | 4'-$CF_3$ | 3"-Cl | R/S |
| Ia-185 | Me | 4-Br | 4'-$CF_3$ | 3"-Cl | R/S |
| Ia-186 | Me | H | 4'-$CF_3$ | 3"-Cl | R/S |
| Ia-187 | Me | 4-F | 4'-$CF_3$ | 3"-Cl | R/S |
| Ia-188 | Me | 4-Et | 4'-$CF_3$ | 3"-Cl | R/S |
| Ia-189 | Me | H | 4'-$CF_3$ | 4"-$CF_3$ | R/S |
| Ia-190 | Me | 3-Cl | 4'-$CF_3$ | 4"-Cl | R/S |
| Ia-191 | Me | 3-$CF_3$ | 4'-Cl | H | R/S |
| Ia-192 | Me | 3-Cl | 4'-Cl | H | R/S |
| Ia-193 | Me | H | 4'-Cl | H | R/S |
| Ia-194 | Me | 4-OMe | 4'-Cl | H | R/S |
| Ia-195 | Me | 3-OMe | 4'-Cl | H | R/S |
| Ia-196 | Me | 4-Br | 4'-Cl | H | R/S |
| Ia-197 | Me | 3-Ph | 4'-Cl | H | R/S |
| Ia-198 | Me | 4-Cl | 4'-Cl | H | R/S |
| Ia-199 | Me | 4-$CF_3$ | 4'-Cl | H | R/S |
| Ia-200 | Me | 4-F | 4'-Cl | H | R/S |
| Ia-201 | Me | 2,3-di-F | 4'-Cl | H | R/S |
| Ia-202 | Me | 2,4-di-F | 4'-Cl | H | R/S |
| Ia-203 | Me | 2,5-di-F | 4'-Cl | H | R/S |
| Ia-204 | Me | 2,6-di-F | 4'-Cl | H | R/S |
| Ia-205 | Me | 3,4-di-F | 4'-Cl | H | R/S |
| Ia-206 | Me | 3,5-di-F | 4'-Cl | H | R/S |
| Ia-207 | Me | 2,3,5-tri-F | 4'-Cl | H | R/S |

TABLE 1-continued

2-Benzooxazole analogs

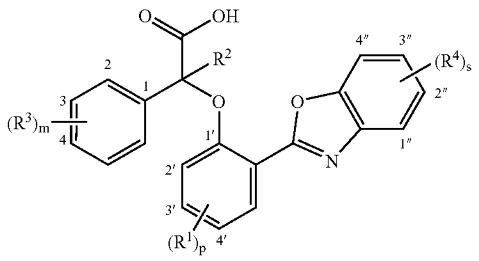

Compound I-X and Ia-X

| Compound | $R^2$ | $(R^3)_m$ | $(R^1)_p$ | $(R^4)_s$ | Configuration |
|---|---|---|---|---|---|
| Ia-208 | Me | 4-Et | 4'-Cl | H | R/S |
| Ia-209 | Me | 4-Cl | 4'-Cl | 2"-Me | R/S |
| Ia-210 | Me | 3-$CF_3$ | 4'-Cl | 2"-Me | R/S |
| Ia-211 | Me | 3-OPh | 4'-Cl | 2"-Me | R/S |
| Ia-212 | Me | 3-Cl | 4'-Cl | 2"-Me | R/S |
| Ia-213 | Me | 4-OMe | 4'-Cl | 2"-Me | R/S |
| Ia-214 | Me | 4-$CF_3$ | 4'-Cl | 2"-Me | R/S |
| Ia-215 | Me | 4-Br | 4'-Cl | 2"-Me | R/S |
| Ia-216 | Me | H | 4'-Cl | 2"-Me | R/S |
| Ia-217 | Me | 4-F | 4'-Cl | 2"-Me | R/S |
| Ia-218 | Me | 4-Et | 4'-Cl | 2"-Me | R/S |
| Ia-219 | Me | 4-Cl | 4'-Cl | 2"-Ph | R/S |
| Ia-220 | Me | 3-$CF_3$ | 4'-Cl | 2"-Ph | R/S |
| Ia-221 | Me | 3-OPh | 4'-Cl | 2"-Ph | R/S |
| Ia-222 | Me | 3-Cl | 4'-Cl | 2"-Ph | R/S |
| Ia-223 | Me | 4-OMe | 4'-Cl | 2"-Ph | R/S |
| Ia-224 | Me | 4-$CF_3$ | 4'-Cl | 2"-Ph | R/S |
| Ia-225 | Me | 4-Br | 4'-Cl | 2"-Ph | R/S |
| Ia-226 | Me | H | 4'-Cl | 2"-Ph | R/S |
| Ia-227 | Me | 4-F | 4'-Cl | 2"-Ph | R/S |
| Ia-228 | Me | 4-Et | 4'-Cl | 2"-Ph | R/S |
| Ia-229 | Me | 4-Cl | 4'-Cl | 2"-Cl | R/S |
| Ia-230 | Me | 3-$CF_3$ | 4'-Cl | 2"-Cl | R/S |
| Ia-231 | Me | 3-OPh | 4'-Cl | 2"-Cl | R/S |
| Ia-232 | Me | 3-Cl | 4'-Cl | 2"-Cl | R/S |
| Ia-233 | Me | 4-OMe | 4'-Cl | 2"-Cl | R/S |
| Ia-234 | Me | 4-$CF_3$ | 4'-Cl | 2"-Cl | R/S |
| Ia-235 | Me | 4-Br | 4'-Cl | 2"-Cl | R/S |
| Ia-236 | Me | H | 4'-Cl | 2"-Cl | R/S |
| Ia-237 | Me | 4-F | 4'-Cl | 2"-Cl | R/S |
| Ia-238 | Me | 4-Et | 4'-Cl | 2"-Cl | R/S |
| Ia-239 | Me | 4-Cl | 4'-Cl | 2"-$OCF_3$ | R/S |
| Ia-240 | Me | 3-$CF_3$ | 4'-Cl | 2"-$OCF_3$ | R/S |
| Ia-241 | Me | 3-OPh | 4'-Cl | 2"-$OCF_3$ | R/S |
| Ia-242 | Me | 3-Cl | 4'-Cl | 2"-$OCF_3$ | R/S |
| Ia-243 | Me | 4-OMe | 4'-Cl | 2"-$OCF_3$ | R/S |
| Ia-244 | Me | 4-$CF_3$ | 4'-Cl | 2"-$OCF_3$ | R/S |
| Ia-245 | Me | 4-Br | 4'-Cl | 2"-$OCF_3$ | R/S |
| Ia-246 | Me | H | 4'-Cl | 2"-$OCF_3$ | R/S |
| Ia-247 | Me | 4-F | 4'-Cl | 2"-$OCF_3$ | R/S |
| Ia-248 | Me | 4-Et | 4'-Cl | 2"-$OCF_3$ | R/S |
| Ia-249 | Me | 4-Cl | 4'-Cl | 3"-Me | R/S |
| Ia-250 | Me | 3-$CF_3$ | 4'-Cl | 3"-Me | R/S |
| Ia-251 | Me | 3-OPh | 4'-Cl | 3"-Me | R/S |
| Ia-252 | Me | 3-Cl | 4'-Cl | 3"-Me | R/S |
| Ia-253 | Me | 4-OMe | 4'-Cl | 3"-Me | R/S |
| Ia-254 | Me | 4-$CF_3$ | 4'-Cl | 3"-Me | R/S |
| Ia-255 | Me | 4-Br | 4'-Cl | 3"-Me | R/S |
| Ia-256 | Me | H | 4'-Cl | 3"-Me | R/S |
| Ia-257 | Me | 4-F | 4'-Cl | 3"-Me | R/S |
| Ia-258 | Me | 4-Et | 4'-Cl | 3"-Me | R/S |
| Ia-259 | Me | 4-Cl | 4'-Cl | 3"-OMe | R/S |
| Ia-260 | Me | 3-$CF_3$ | 4'-Cl | 3"-OMe | R/S |
| Ia-261 | Me | 3-OPh | 4'-Cl | 3"-OMe | R/S |
| Ia-262 | Me | 3-Cl | 4'-Cl | 3"-OMe | R/S |
| Ia-263 | Me | 4-OMe | 4'-Cl | 3"-OMe | R/S |
| Ia-264 | Me | 4-$CF_3$ | 4'-Cl | 3"-OMe | R/S |
| Ia-265 | Me | 4-Br | 4'-Cl | 3"-OMe | R/S |
| Ia-266 | Me | H | 4'-Cl | 3"-OMe | R/S |

TABLE 1-continued

2-Benzooxazole analogs

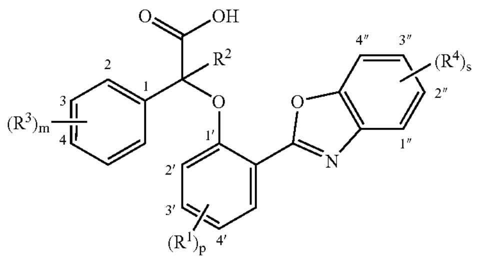

Compound I-X and Ia-X

| Compound | $R^2$ | $(R^3)_m$ | $(R^1)_p$ | $(R^4)_s$ | Configuration |
|---|---|---|---|---|---|
| Ia-267 | Me | 4-F | 4'-Cl | 3''-OMe | R/S |
| Ia-268 | Me | 4-Et | 4'-Cl | 3''-OMe | R/S |
| Ia-269 | Me | 4-Cl | 4'-Cl | 3''-Cl | R/S |
| Ia-270 | Me | 3-$CF_3$ | 4'-Cl | 3''-Cl | R/S |
| Ia-271 | Me | 3-OPh | 4'-Cl | 3''-Cl | R/S |
| Ia-271 | Me | 3-Cl | 4'-Cl | 3''-Cl | R/S |
| Ia-272 | Me | 4-OMe | 4'-Cl | 3''-Cl | R/S |
| Ia-273 | Me | 4-$CF_3$ | 4'-Cl | 3''-Cl | R/S |
| Ia-274 | Me | 4-Br | 4'-Cl | 3''-Cl | R/S |
| Ia-275 | Me | H | 4'-Cl | 3''-Cl | R/S |
| Ia-276 | Me | 4-F | 4'-Cl | 3''-Cl | R/S |
| Ia-277 | Me | 4-Et | 4'-Cl | 3''-Cl | R/S |
| Ia-278 | Me | 3-$CF_3$ | 4'-$CF_3$ | 4''-Cl | R/S |
| Ia-279 | Me | 4-OMe | 4'-$CF_3$ | 4''-Cl | R/S |
| Ia-280 | Me | 4-Cl | 4'-$CF_3$ | 4''-Cl | R/S |
| Ia-281 | Me | 4-$CF_3$ | 4'-$CF_3$ | 4''-Cl | R/S |
| Ia-282 | Me | 4-Br | 4'-$CF_3$ | 4''-Cl | R/S |
| Ia-283 | Me | H | 4'-$CF_3$ | 4''-Cl | R/S |
| Ia-284 | Me | 3-Cl | 4'-Me | H | R/S |
| Ia-285 | Me | 3-$CF_3$ | 4'-Me | H | R/S |
| Ia-286 | Me | 3-OPh | 4'-Me | H | R/S |
| Ia-287 | Me | 4-OMe | 4'-Me | H | R/S |
| Ia-288 | Me | 4-Cl | 4'-Me | H | R/S |
| Ia-289 | Me | 4-$CF_3$ | 4'-Me | H | R/S |
| Ia-290 | Me | 4-Br | 4'-Me | H | R/S |
| Ia-291 | Me | H | 4'-Me | H | R/S |
| Ia-292 | Me | 4-F | 4'-Me | H | R/S |
| Ia-293 | Me | 2,3-di-F | 4'-Me | H | R/S |
| Ia-294 | Me | 2,4-di-F | 4'-Me | H | R/S |
| Ia-295 | Me | 2,5-di-F | 4'-Me | H | R/S |
| Ia-296 | Me | 2,6-di-F | 4'-Me | H | R/S |
| Ia-297 | Me | 3,4-di-F | 4'-Me | H | R/S |
| Ia-298 | Me | 3,5-di-F | 4'-Me | H | R/S |
| Ia-299 | Me | 2,3,5-tri-F | 4'-Me | H | R/S |
| Ia-300 | Me | 4-Et | 4'-Me | H | R/S |
| Ia-301 | Me | 3-Cl | 4'-t-Bu | H | R/S |
| Ia-302 | Me | 3-$CF_3$ | 4'-t-Bu | H | R/S |
| Ia-303 | Me | 3-OPh | 4'-t-Bu | H | R/S |
| Ia-304 | Me | 4-OMe | 4'-t-Bu | H | R/S |
| Ia-305 | Me | 4-Cl | 4'-t-Bu | H | R/S |
| Ia-306 | Me | 4-$CF_3$ | 4'-t-Bu | H | R/S |
| Ia-307 | Me | 4-Br | 4'-t-Bu | H | R/S |
| Ia-308 | Me | H | 4'-t-Bu | H | R/S |
| Ia-309 | Me | 4-F | 4'-t-Bu | H | R/S |
| Ia-310 | Me | 2,3-di-F | 4'-t-Bu | H | R/S |
| Ia-311 | Me | 2,4-di-F | 4'-t-Bu | H | R/S |
| Ia-312 | Me | 2,5-di-F | 4'-t-Bu | H | R/S |
| Ia-313 | Me | 2,6-di-F | 4'-t-Bu | H | R/S |
| Ia-314 | Me | 3,4-di-F | 4'-t-Bu | H | R/S |
| Ia-315 | Me | 3,5-di-F | 4'-t-Bu | H | R/S |
| Ia-316 | Me | 2,3,5-tri-F | 4'-t-Bu | H | R/S |
| Ia-317 | Me | 4-Et | 4'-t-Bu | H | R/S |
| Ia-318 | Me | 3-Cl | 4'-Br | H | R/S |
| Ia-319 | Me | 3-$CF_3$ | 4'-Br | H | R/S |
| Ia-320 | Me | 3-OPh | 4'-Br | H | R/S |
| Ia-321 | Me | 4-OMe | 4'-Br | H | R/S |
| Ia-322 | Me | 4-Cl | 4'-Br | H | R/S |
| Ia-323 | Me | 4-$CF_3$ | 4'-Br | H | R/S |
| Ia-324 | Me | 4-Br | 4'-Br | H | R/S |

TABLE 1-continued

2-Benzooxazole analogs

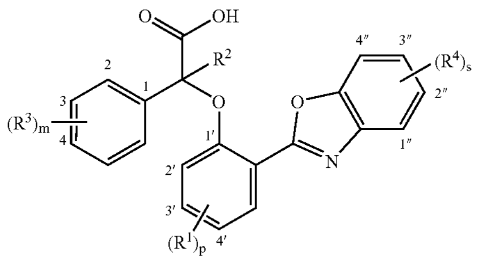

Compound I-X and Ia-X

| Compound | $R^2$ | $(R^3)_m$ | $(R^1)_p$ | $(R^4)_s$ | Configuration |
|---|---|---|---|---|---|
| Ia-325 | Me | H | 4'-Br | H | R/S |
| Ia-326 | Me | 4-F | 4'-Br | H | R/S |
| Ia-327 | Me | 2,3-di-F | 4'-Br | H | R/S |
| Ia-328 | Me | 2,4-di-F | 4'-Br | H | R/S |
| Ia-329 | Me | 2,5-di-F | 4'-Br | H | R/S |
| Ia-330 | Me | 2,6-di-F | 4'-Br | H | R/S |
| Ia-331 | Me | 3,4-di-F | 4'-Br | H | R/S |
| Ia-332 | Me | 3,5-di-F | 4'-Br | H | R/S |
| Ia-333 | Me | 4-Et | 4'-Br | H | R/S |
| Ia-334 | Me | 2,3,6-tri-F | 4'-Br | H | R/S |
| Ia-335 | Me | 3-Cl | 4',6'-di Cl | H | R/S |
| Ia-336 | Me | 3-$CF_3$ | 4',6'-di Cl | H | R/S |
| Ia-337 | Me | 3-OPh | 4',6'-di Cl | H | R/S |
| Ia-338 | Me | 4-OMe | 4',6'-di Cl | H | R/S |
| Ia-339 | Me | 4-Cl | 4',6'-di Cl | H | R/S |
| Ia-340 | Me | 4-$CF_3$ | 4',6'-di Cl | H | R/S |
| Ia-341 | Me | 4-Br | 4',6'-di Cl | H | R/S |
| Ia-342 | Me | H | 4',6'-di Cl | H | R/S |
| Ia-343 | Me | 4-F | 4',6'-di Cl | H | R/S |
| Ia-344 | Me | 4-Et | 4',6'-di Cl | H | R/S |
| Ia-345 | Me | 3-Cl | 4'-(2,4-diF-Ph) | H | R/S |
| Ia-346 | Me | 3-$CF_3$ | 4'-(2,4-diF-Ph) | H | R/S |
| Ia-347 | Me | 3-OPh | 4'-(2,4-diF-Ph) | H | R/S |
| Ia-348 | Me | 4-OMe | 4'-(2,4-diF-Ph) | H | R/S |
| Ia-349 | Me | 4-Cl | 4'-(2,4-diF-Ph) | H | R/S |
| Ia-350 | Me | 4-$CF_3$ | 4'-(2,4-diF-Ph) | H | R/S |
| Ia-351 | Me | 4-Br | 4'-(2,4-diF-Ph) | H | R/S |
| Ia-352 | Me | H | 4'-(2,4-diF-Ph) | H | R/S |
| Ia-353 | Me | 4-F | 4'-(2,4-diF-Ph) | H | R/S |
| Ia-354 | Me | 4-Et | 4'-(2,4-diF-Ph) | H | R/S |
| Ia-355 | Me | 3-Cl | 4'-(1H-pyrrol-yl) | H | R/S |
| Ia-356 | Me | 3-$CF_3$ | 4'-(1H-pyrrol-yl) | H | R/S |
| Ia-357 | Me | 3-OPh | 4'-(1H-pyrrol-yl) | H | R/S |
| Ia-358 | Me | 4-OMe | 4'-(1H-pyrrol-yl) | H | R/S |
| Ia-359 | Me | 4-Cl | 4'-(1H-pyrrol-yl) | H | R/S |
| Ia-360 | Me | 4-$CF_3$ | 4'-(1H-pyrrol-yl) | H | R/S |
| Ia-361 | Me | 4-Br | 4'-(1H-pyrrol-yl) | H | R/S |
| Ia-362 | Me | H | 4'-(1H-pyrrol-yl) | H | R/S |
| Ia-363 | Me | 4-F | 4'-(1H-pyrrol-yl) | H | R/S |
| Ia-364 | Me | 4-Et | 4'-(1H-pyrrol-yl) | H | R/S |
| Ia-365 | Me | H | 4'-$CF_3$ | H | S |
| Ia-366 | Me | H | 4'-$CF_3$ | H | R |

1. Synthesis of substituted α-bromo-phenylacetates

Scheme 1 illustrates the general preparative routes for the synthesis of substituted α-bromo-phenylacetates, α-hydroxy-phenylacetic acids and α-hydroxy-phenylacetates. All of the intermediates can be prepared by known procedures or by those skilled in the arts.

Scheme 1.
Synthesis of substituted α-bromo-phenylacetate, α-hydroxy-phenylacetic acid and α-hydroxy-phenylacetate

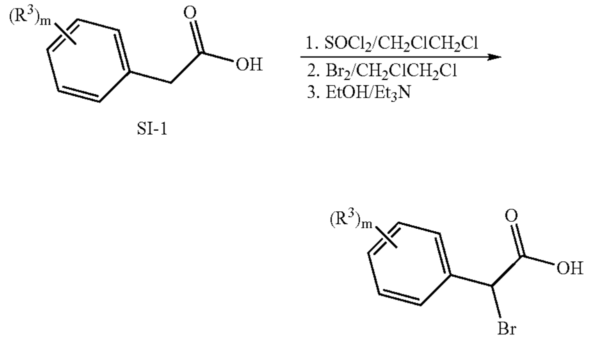

SI-1

SBr-X

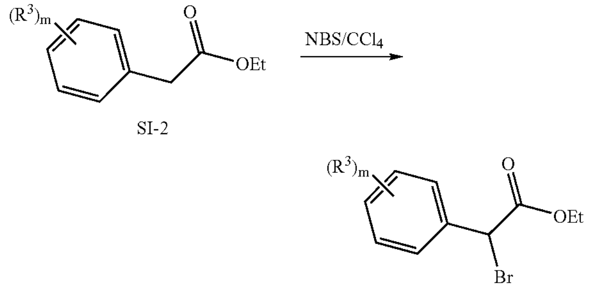

SI-2

SBr-X

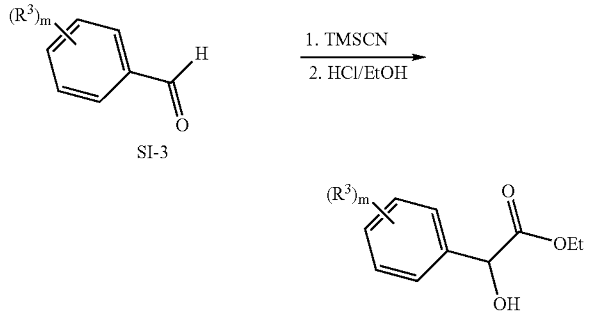

SI-3

SOR-X

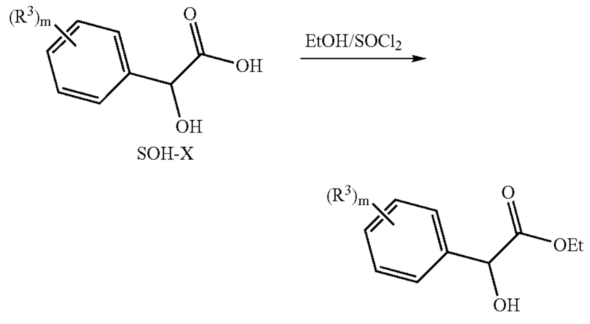

SOH-X

SI-4

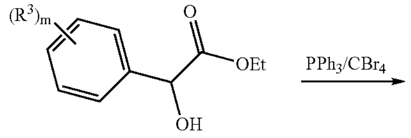

SI-4

-continued

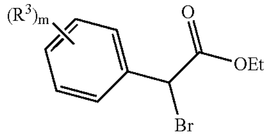

SBr-X

Example 1

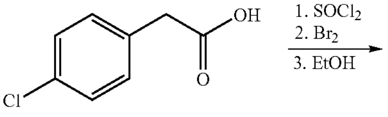

SI-5

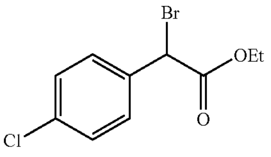

SBr-1

A 2 L three neck roundbottom flask was equipped with an efficient condenser attached to an acid scrubber, a magnetic stir bar, and was placed under nitrogen. 4-Chlorophenylacetic acid (200 g) and 1000 mL of 1,2-dichloroethane were added, followed by thionyl chloride (103.6 mL). The condenser was cooled with 4° C. water. The mixture was heated to an internal temperature of 55–60° C. Gas evolution was observed and the solid dissolved as the internal temperature rose to 55–60° C. over 45 min. Bromine (66 mL) was added and the mixture was maintained at 55–60° C. for 18 h. The internal temperature was then raised to 80–85° C. over 1.5 h and heating was continued for 18 h. The solution was cooled to room temperature, and 247 mL of ethanol was added slowly at 0° C. The solution was washed with water and dried over anhydrous sodium sulfate. The solvent was removed to give 270 g of crude product compound SBr-1, which was used without further purification. $^1H$ NMR (400 MHz, $CDCl_3$): δ 7.50–7.33 (dd, 4H), 5.29 (s, 1H), 4.24 (q, 2H), 1.28 (t, 3H).

Example 2

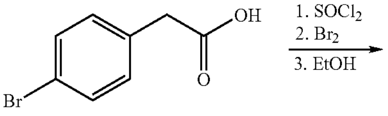

SI-6

-continued

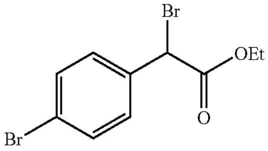

SBr-2

In the same manner as that described in Example 1, compound SBr-2 can be prepared from commercially available SI-6.

Example 3

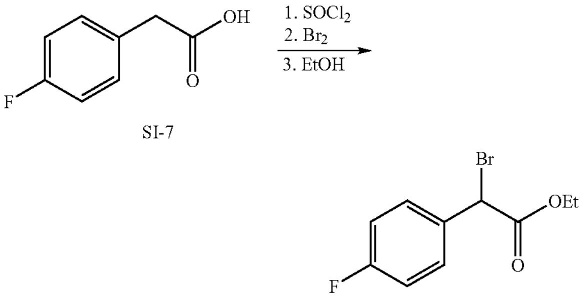

SI-7

SBr-3

In the same manner as that described in Example 1, compound SBr-3 can be prepared from commercially available SI-7.

Example 4

SBr-4

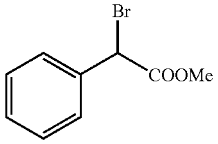

Compound SBr-4 was purchasd from Aldrich Chemicals Inc., USA

Example 5

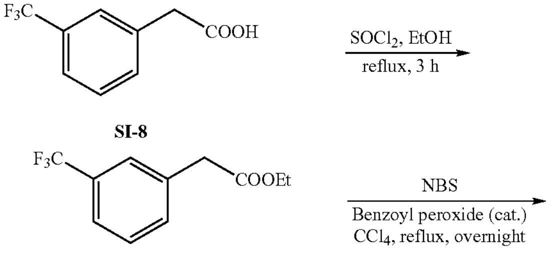

SI-8

SI-9

-continued

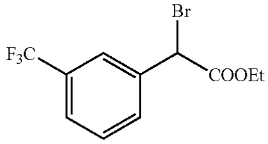

SBr-5

To a solution of (α,α,α-trifluoro-m-tolyl)acetic acid SI-8 (202.36 g, 0.99 mol) in absolute ethanol (1.0 L) at 0° C. was added thionyl chloride (79 mL, 1.05 mol), and the resulting solution was refluxed for 3 h. Concentration in vacuo gave a residue which was partitioned between EtOAc and water. The organic layer was washed with sat. $NaHCO_3$ and brine, dried over $Na_2SO_4$ and concentrated in vacuo to afford 220.1 g (96%) of crude ethyl ester SI-9 as a pale yellow liquid. To a mixture of crude ethyl ester SI-9 (119.15 g, ca. 0.51 mol) and NBS (100.48 g, 0.56 mol) in $CCL_4$ (1.0 L) was added benzoyl peroxide (1.0 g). The resulting mixture was heated at 75° C. for 20 min. and then refluxed at 90° C. overnight (14 h) until the brown mixture became nearly colorless with white precipitate. The mixture was cooled to 0° C., filtered through a pad of celite, and concentrated in vacuo to afford 151.27 g (95%) of bromide SBr-5 as a pale brown liquid. The product was sufficiently pure to be used directly in the subsequent substitution reaction. This product was also prepared by refluxing (α,α,α-trifluoro-m-tolyl)acetic acid SI-8 with bromine in the presence of $SOCl_2$, and then quenching with EtOH. $^1H$ NMR (400 MHz, $CDCl_3$): δ 7.80 (1H, s), 7.77 (1H, d, J=7.6 Hz), 7.61 (1H, d, J=8.0 Hz), 7.51 (1H, t, J=7.8 Hz), 5.35 (1H, s), 4.26 (2H, q), 1.30 (3H, t).

Example 6

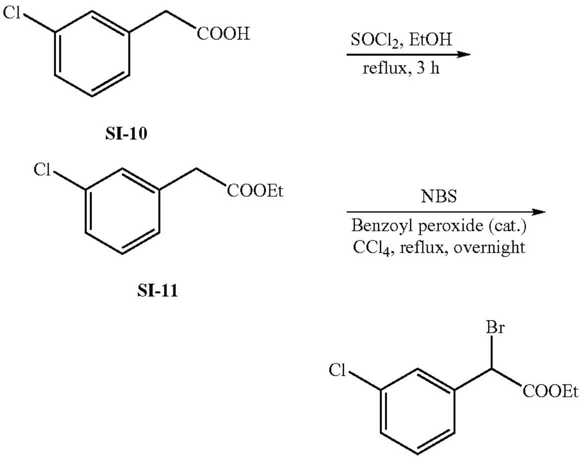

SI-10

SI-11

SBr-6

In the same manner as that described in Example 5, compound SBr-6 was prepared from commercially available SI-10. $^1$HNMR (400 MHz, $CDCl_3$): δ 7.58 (m, 1H), 7.42 (m, 2H), 7.30 (m, 2H), 5.29 (s, 1H), 4.26 (m, 2H), 1.30 (t, 3H).

Example 7

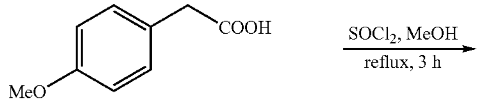

SI-12

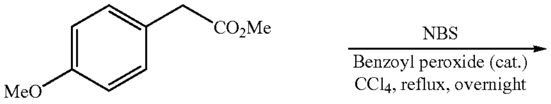

SI-13

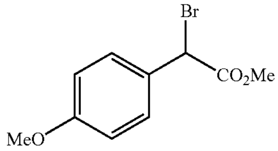

SBr-7

In the same manner as that described in Example 5, compound SBr-7 was prepared from commercially available SI-12. $^1$HNMR (400 MHz, $CDCl_3$): δ 7.43 (d, 2H), 6.88 (d, 2H), 5.38 (s, 1H), 3.81 (s, 3H), 3.79 (s, 3H).

Example 8

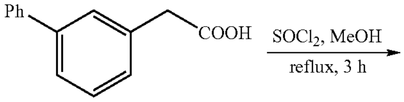

SI-14

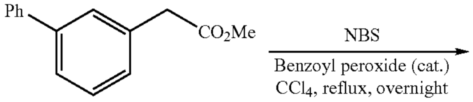

SI-15

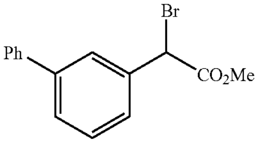

SBr-8

In the same manner as that described in Example 5, compound SBr-8 was prepared from commercially available SI-14. $^1$H NMR (400 MHz, $CDCl_3$): δ 7.62–7.35 (m, 9H), 5.41 (s, 1H), 3.82 (s, 3H).

Example 9

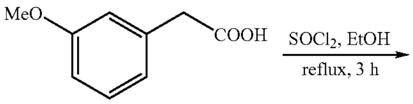

SI-16

-continued

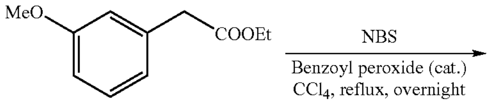

SI-17

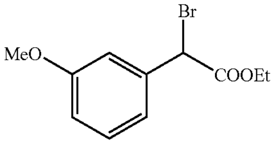

SBr-9

In the same manner as that described in Example 5, compound SBr-9 was prepared from commercially available SI-16. $^1$HNMR (400 MHz, $CDCl_3$): δ 7.28 (m, 1H), 7.09 (m, 1H), 6.88 (m, 1H), 6.72 (m, 1H), 5.33 (s, 1H), 4.26 (m, 2H), 3.80 (s, 3H), 1.29 (t, 3H).

Example 10

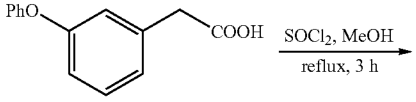

SI-18

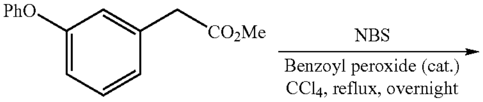

SI-19

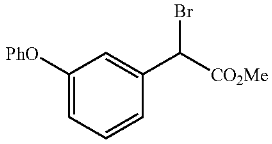

SBr-10

In the same manner as that described in Example 5, compound SBr-10 was prepared from commercially available SI-18. $^1$H NMR (400 MHz, $CDCl_3$): δ 7.40–6.98 (m, 9H), 5.30 (s, 1H), 3.80 (s, 3H).

Example 11

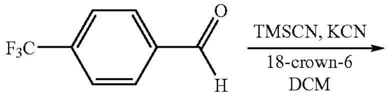

SI-20

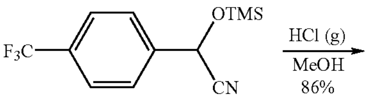

SI-21

-continued

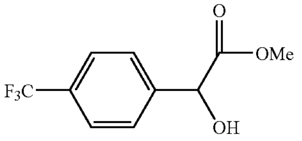

SI-22

To a mixture of 4-(trifluoromethyl)-benzaldehyde SI-20 (25 g), a catalytic amount of KCN and 18-crown-6 in dichloromethane (150 mL) was added slowly TMSCN (21.0 mL) at 0° C. The reaction mixture was stirred at room temperature overnight and washed with aqueous sodium bicarbonate solution. The solvent was removed under vacuum to give a crude cyano product.

The above cyano product was dissolved in methanol, and HCl gas was then bulbed through for several minutes at 0° C. The solution was stirred overnight at room temperature, neutralized with aqueous NaOH solution, concentrated, and extracted with ethyl acetate. The organic solution was dried over anhydrous sodium sulfate and concentrated. Purification with flash column chromatography (hexanes/ethyl acetate 1/5) gave the desired hydroxyl product SI-22 (28.75 g, 86%) as a colorless oil. $^{1}$H-NMR (DMSO, 400 MHz): δ 7.58 (m, 4H), 5.21 (s, 1H), 3.70 (s, 3H).

Example 12

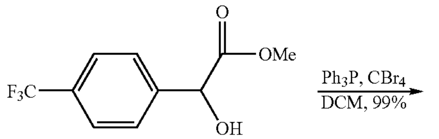

SI-22

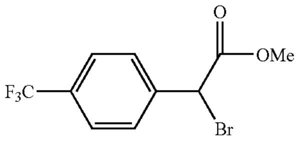

SBr-11

To a solution of hydroxyl ester SI-22 (28 g) in dichloromethane (250 mL) containing triphenylphosphine (31.4 g) was slowly added carbon tetrabromide (40 g) at 0° C., and then the solution was stirred at room temperature overnight. The solution was concentrated and diluted with ethyl acetate/hexanes (2/3, 300 mL). A white precipitate was formed and filtered out. The solvent was removed, and the residue was purified by flash column chromatography (hexane/ethyl acetate 5/1) to give the bromide product SBr-11 (35 g, 99%) as a colorless oil. $^{1}$H-NMR (DMSO, 400 MHz): δ 7.78 (m, 4H), 6.10 (s, 1H), 3.68 (s, 3H).

Example 13

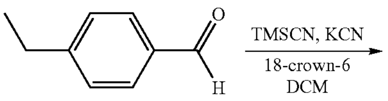

SI-23

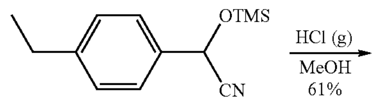

SI-24

-continued

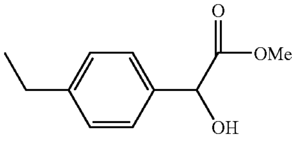

SI-25

In the same manner as that described in Example 11, compound SI-25 was prepared from commercially available SI-23 as a colorless oil. $^{1}$H NMR (400 MHz, $CDCl_3$): δ 7.31 (d, 2H), 7.19 (d, 2H), 5.99 (d, 1H), 5.10 (d, 1H), 3.59 (s, 3H), 2.58 (q, 2H), 1.16 (t, 3H).

Example 14

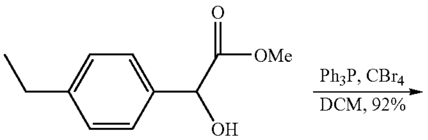

SI-25

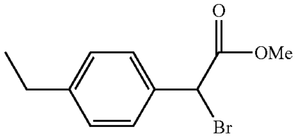

SBr-12

In the same manner as that described in Example 12, compound SBr-12 was prepared from SI-25. $^{1}$H NMR (400 MHz, $CDCl_3$): δ 7.46 (d, 2H), 7.24 (d, 2H), 5.91 (s, 1H), 3.71 (s, 3H), 2.58 (q, 2H), 1.16 (t, 3H).

Example 15

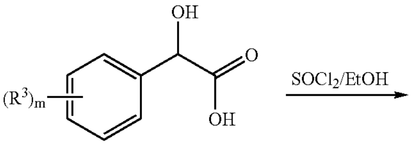

SOH-X

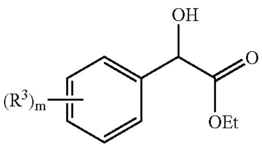

SI-26

$R^3$=H, 4-Cl, 3-$CF_3$, 3-OPh, 4-$CF_3$, 4-OMe, 3-$CF_3$, 3-Cl, 3-OMe, 4-Cl, 4-Br, 3-$NO_2$, 3,4-methylenedioxy, 4-F, 2,3-di-F, 2,4-di-F, 2,5-di-F, 2,6-di-F, 3,4-di-F, 3,5di-F, 2,3,5-tri-F, 2,3,6-tri-F, 2-Cl, MeO, 4-Me, 4-MeS, 4-$NO_2$, 2,5-di-Me Differently substituted α-hydroxy phenyl acetic acids SOH-X were purchased from a variety of commercial suppliers. The free acids can then be refluxed in absolute ethanol with 1–2 equivalent of thionyl chloride to afford esters SI-26 after evaporation of the solvent. Alternatively, SI-26 can be prepared from the corresponding aldehydes as described in Examples 11 and 13.

Example 16

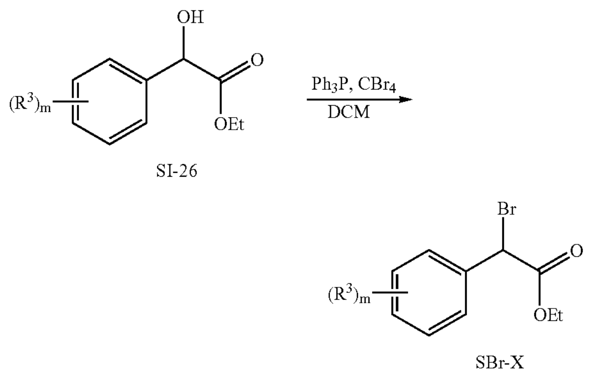

SI-26

SBr-X $R^3$=H, 4-Cl, 3-$CF_3$, 3-OPh, 4-OMe, 3-$CF_3$, 3-Cl, 3-OMe, 4-Cl, 4-Br, 3-$NO_2$, 3,4-methylenedioxy, 4-F, 2,3-di-F, 2,4-di-F, 2,5-di-F, 2,6-di-F, 3,4-di-F, 3,5-di-F, 2,3,5-tri-F, 2,3,6-tri-F, 2-Cl, MeO, 4-Me, 4-MeS, 4-$NO_2$, 2,5-di-Me In the same manner as that described in Example 12 and 14, compound SBr-X can be prepared from SI-26.

2. Synthesis of 2-benzooxazol-2-yl-phenols

Scheme 2 illustrates the general route for preparing 2-benzooxazol-2-yl-phenols or 2-benzooxazol-2-yl-phenylfluorides. Generally, 2-fluoro or 2-hydroxyl benzoic acid was transformed to the corresponding acyl chloride. The acyl chorides were then reacted with aminophenols and were further dehydrated to afford the corresponding 2-benzooxazol-2-yl-phenols or 2-benzooxazol-2-yl-phenylfluorides. 2-benzooxazol-2-yl-phenylfluorides were converted to 2-benzooxazol-2-yl-phenols by reacting with sodium methoxide followed by demethylation. All of the intermediates can be prepared by known procedures or by those skilled in the arts.

Scheme 2
Synthesis of 2-benzoxazoyl phenols and 2-bezoxazoyl florides

A

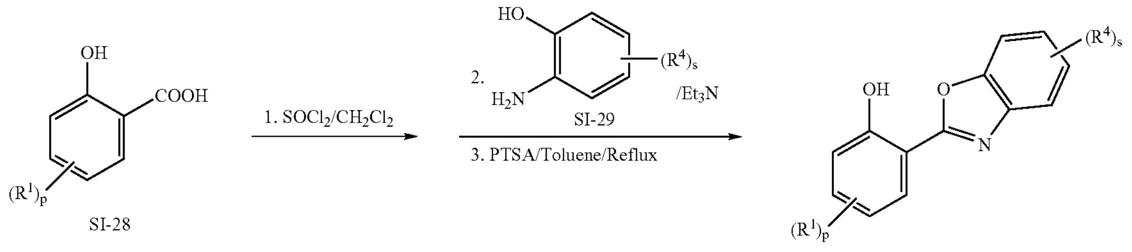

SI-28

SI-29

PhOH-X

B

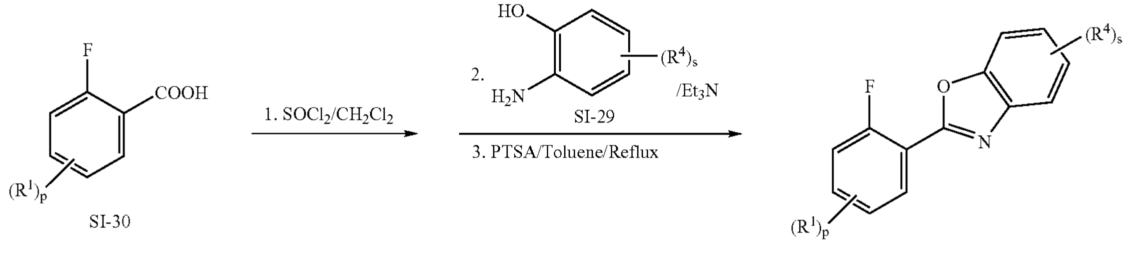

SI-30

SI-29

PhF-X

C

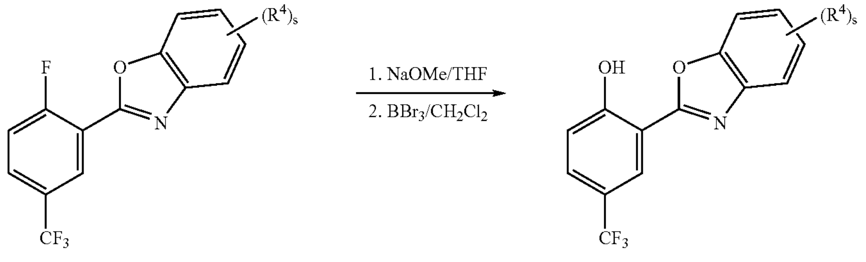

SI-31

PhOH-X

Example 17

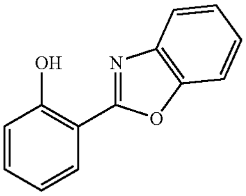

PhOH-1

Compound PhOH-1 was purchased from Aldrich Chemicals Inc., USA.

Example 18

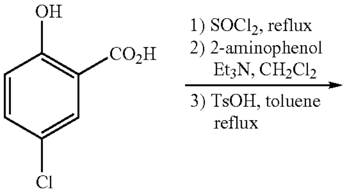

SI-32

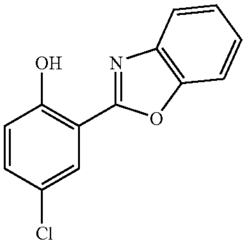

PhOH-2

A mixture of SI-32 (19.24 g, 0.111 mol) and $SOCl_2$ (30 mL) was refluxed for 2 h. The mixture was concentrated to dryness and further dried under vaccum. To the residue was added 2-aminophenol (18.2 g, 0.167 mol) in $CH_2Cl_2$ (500 mL). To the solution was slowly added $Et_3N$ (31 mL, 0.22 mol) at 0° C. and the reaction was allowed to warm to room temperature and stirred overnight. The reaction mixture was concentrated to dryness. To the residue was added 1N HCl (400 mL), which was extracted with EtOAc. The organic layer was washed with 1N HCl and brine, dried and concentrated to give a brown solid (28.4 g), which was used for the next reaction without further purification.

A mixture of the above crude product (28.4 g) and TsOH monohydrate (10 g) in toluene (700 mL) was refluxed overnight using a Dean-Stark apparatus. The reaction mixture was concentrated to dryness. Recrystallization of the residue from MeOH gave phenol PhOH-2 as an off-white solid (20.9 g, 77%). $^1$HNMR (d-DMSO, 400 MHz) δ11.22 (s, 1H), 7.98 (s, 1H), 7.85 (m, 2H), 7.53–7.45 (m, 3H), 7.16 (d, 1H).

Example 19

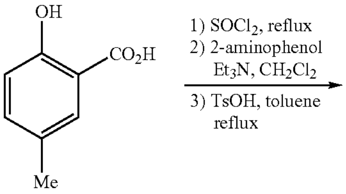

SI-33

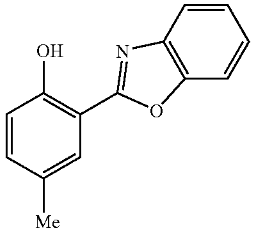

PhOH-3

In the same manner as that described in Example 18 compound PhOH-3 can be prepared from commercially available SI-33.

Example 20

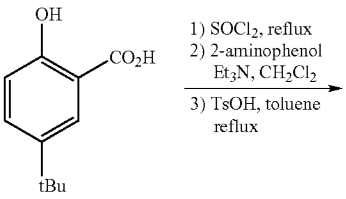

SI-34

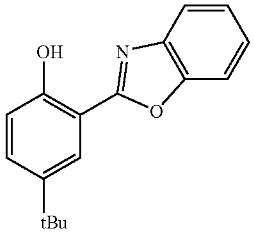

PhOH-4

In the same manner as that described in Example 18 compound PhOH-4 can be prepared from commercially available SI-34.

Example 21

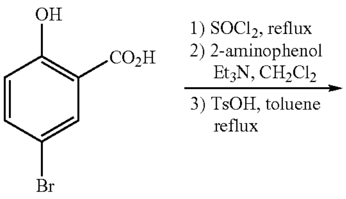

SI-35

-continued

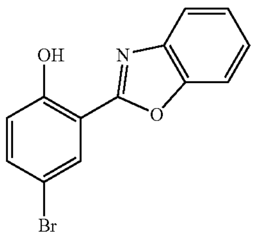

PhOH-5

In the same manner as that described in Example 18 compound PhOH-5 can be prepared from commercially available SI-35.

Example 22

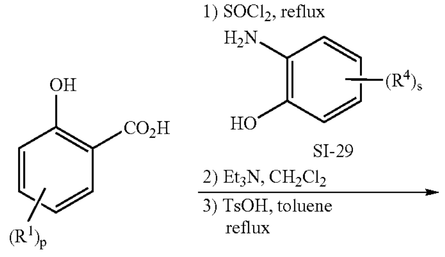

SI-28 SI-29

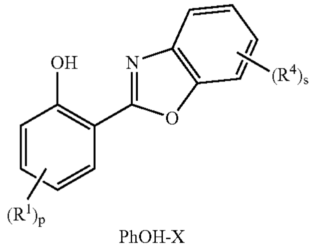

PhOH-X $R^1$ = H, 4′-$CF_3$, 4′-Cl, 4′-Me, 4′-tBu, 4′-Br, 4′,6′-diCl, 4′-(1H-pyrrol-yl), 4′-(1H-pyrrol-yl) etc.
$R^4$ = H, 2″-$OCF_3$, 2″-Cl, 2″-Me, 2″-Ph, 3″-Me, 3″-OMe, 3″-Cl, etc.

In the same manner as that described in Example 18 compound PhOH-X can be prepared from commercially available SI-28.

Example 23

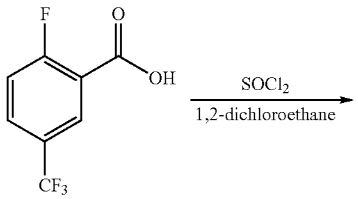

SI-36

-continued

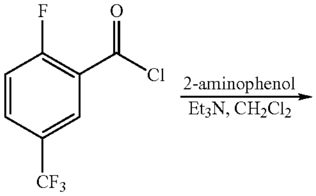

SI-37

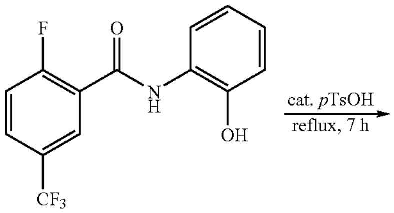

SI-38

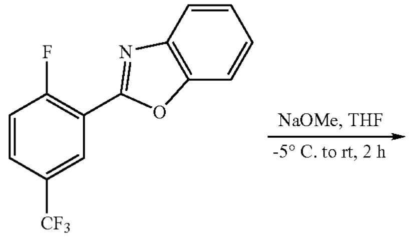

PhF-1

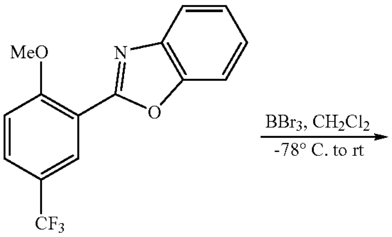

SI-39

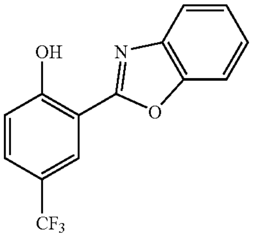

PhOH-6

2-Fluoro-5-(trifluoromethyl)benzoyl chloride SI-37 was commercially obtained from Aldrich, or prepared by refluxing a solution of 2-fluoro-5-(trifluoromethylmethyl)benzoid acid SI-36 (116.71 g, 0.56 mol) and thionyl chloride (81.0 mL, 1.11 mol) in 1,2-dichloroethane (250 mL) at 80° C. for 0.5 h. Step A. To a solution of 2-fluoro-5-(trifluoromethyl) benzoyl chloride SI-37 (25.7 g, 0.11 mol) and 2-aminophenol (13.87 g, 0.13 mol) in $CH_2Cl_2$ (350 mL) at 0° C. was added $Et_3N$ (18 mL, 0.13 mol). The resulting mixture was stirred at 0° C. to rt overnight, diluted with EtOAc and washed with water. The organic layer was washed with water and brine, dried over $Na_2SO_4$ and concentrated in vacuo to afford crude SI-38 (35 g). Step B. To a suspension of unpurified SI-38 (35 g, 0.11 mol) in toluene (500 mL) was added TsOH monohydrate (6.78 g, 0.035 mol). The resulting suspension was refluxed at 80° C. with a Dean-Stork condenser for 7 h. The reaction mixture was cooled to rt, concentrated in vacuo, diluted with EtOAc, washed with $H_2O$, then washed with sat. $NaHCO_3$ and brine, dried over $Na_2SO_4$ and concentrated in vacuo to afford crude PhF-1 (31.66 g, 99% over two steps) as an off-white solid. $^1H$ NMR (400 MHz, $CDCl_3$): δ 8.56 (1H, d, J=6.0 Hz), 7.85–7.87 (1H, m), 7.78–7.81 (1H, m), 7.64–7.67 (1H, m), 7.41–7.44 (3H, m) ppm. Step C. To a solution of unpurified PhF-1 (31.62 g, 0.11 mol) in THF (200 mL) at −5° C. was added NaOMe (8.95 g, 0.16 mol). The resulting solution was warmed up to rt, and stirred at rt for 1.5 h, quenched with sat. $NH_4Cl$, and diluted with EtOAc. The organic layer was separated and washed with $H_2O$ and sat. $NH_4Cl$, dried over $Na_2SO_4$ and concentrated in vacuo to afford crude SI-39 (31.89 g) as an off-white solid. This product was sufficiently pure to be used directly in the subsequent demethylation reaction, and the analytical pure SI-39 can be obtained by recrystalization from $CH_2Cl_2$. $^1H$ NMR (400 MHz, $CDCl_3$): δ 8.44 (1H, s), 7.84–7.86 (1H, m), 7.77 (1H, d, J=8.8 Hz), 7.62–7.64 (1H, m), 7.36–7.41 (2H, m), 7.18 (1H, d, J=8.8 Hz) ppm. Step D. A solution of unpurified SI-39 (32.89 g, 0.11 mol) in anhy. $CH_2Cl_2$ (500 mL) at −78° C. was treated with $BBr_3$ (17 mL, 0.18 mol). The resultant cloudy solution was warmed to −10° C. over 2 h and stirred at rt for another 2 h. The reaction mixture was cooled to 0° C. and quenched with water. Concentration in vacuo gave a residue which was partitioned between EtOAc and water. The organic layer was washed with water, sat. $NaHCO_3$ and brine, dried over $Na_2SO_4$ and concentrated in vacuo to afford crude PhOH-6 (31.31 g, 99.7% over 2 steps) as a white solid. This product was sufficiently pure to be used directly in the subsequent displacement reaction without further purification. $^1H$ NMR (400 MHz, $CDCl_3$): δ 11.90 (1H, s, ArOH), 8.33 (1H, s), 7.75–7.78 (1H, m), 7.64–7.69 (2H, m), 7.42–7.45 (2H, m), 7.22 (1H, d, J=8.4 Hz).

Example 24

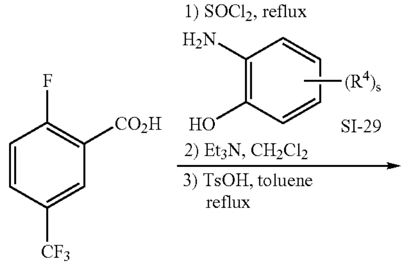

SI-36

-continued

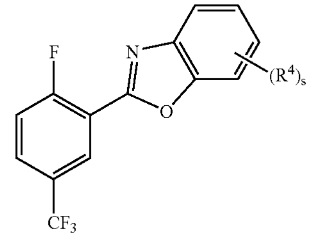

PhF-2

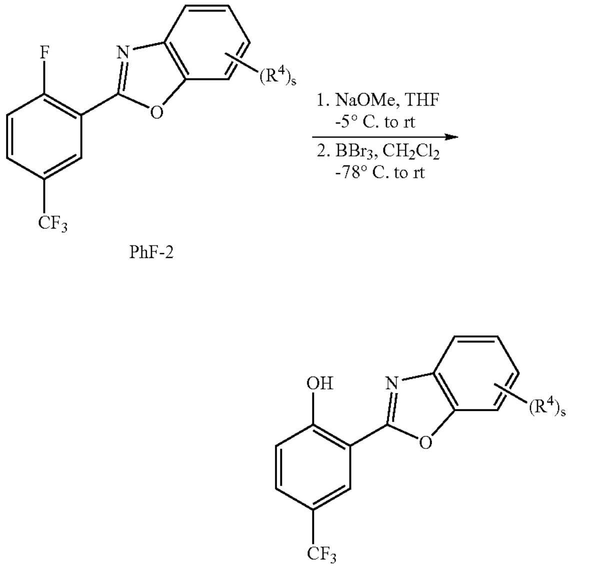

PhF-2

PhOH-7

$R^4$ = H, 2″-$OCF_3$, 2″-Cl, 2″-Me, 2″-Ph, 3″-Me, 3″-OMe, 3″-Cl, etc.

In the same manner as that described in Example 23 compound PhF-2 and PhOH-7 can be prepared from commercially available SI-36 and SI-29.

3. Synthesis of Compounds I and Ia in Table 1

One or two routes illustrated in Scheme 3 were used to prepare the compounds I and Ia listed in Table 1. In route A, α-bromo-phenylacetate was treated with 2-benzoxazoyl-phenol under basic condition to yield α-phenoxy-phenylacetate SI-40. Hydrolysis of SI-40 under basic condition yielded α-phenoxy-phenylacetic acid I-X. Alternatively, SI-40 was alkylated with a corresponding alkyl halide followed by basic hydrolysis to afford α-phenoxy-phenylacetic acid Ia-X. In route B, intermediates PhF-X with an electron withdrawing $R^1$ such as a 4-$CF_3$ group were treated with α-hydroxy-phenyl acetic acid SOH-X under strongly basic condition to afford α-phenoxy-phenylacetic acid I-X or Ia-X directly. All of the intermediates can be prepared by known procedures or by those skilled in the arts.

Scheme 3
Synthesis of compounds I and Ia listed in table 1.
Route A
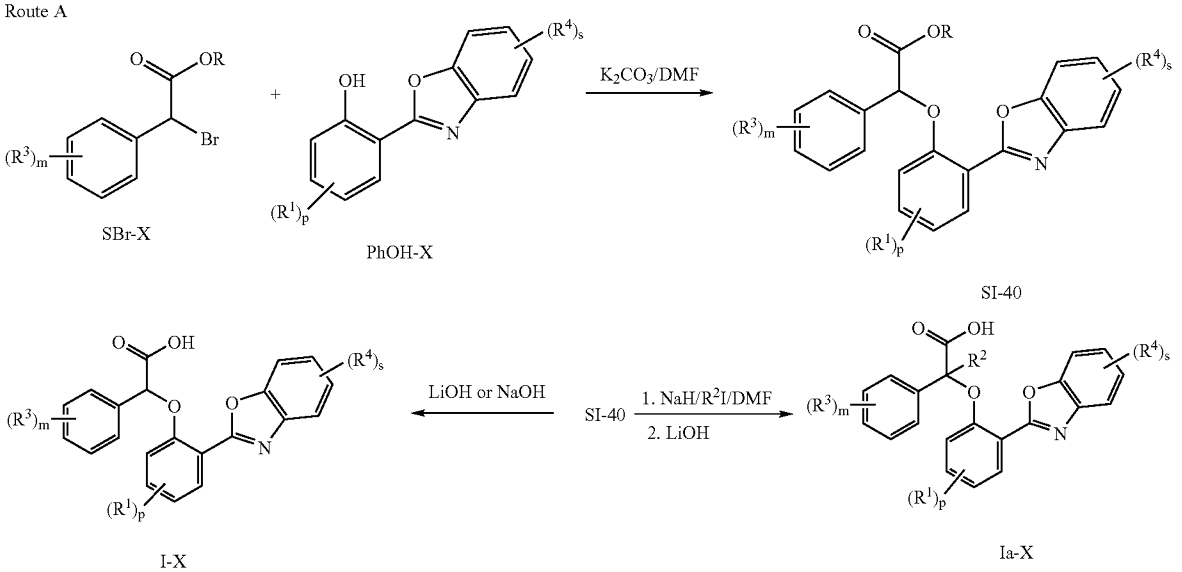
SBr-X, PhOH-X, SI-40, I-X, SI-40, Ia-X
Route B
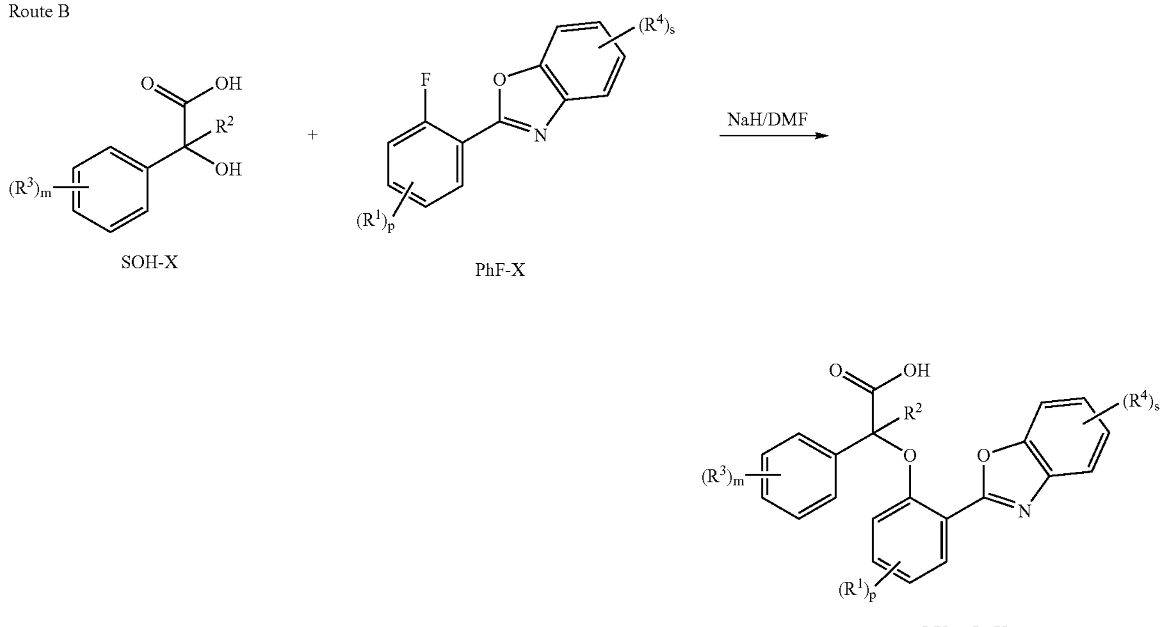
SOH-X, PhF-X, I-X or Ia-X
Example 25
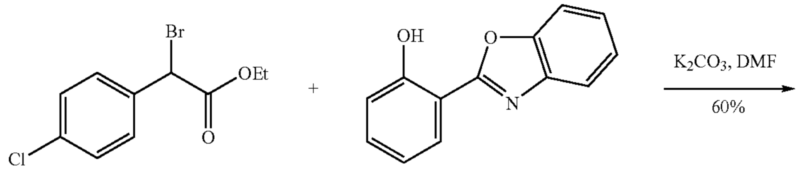
SBr-I, PhOH-1

-continued

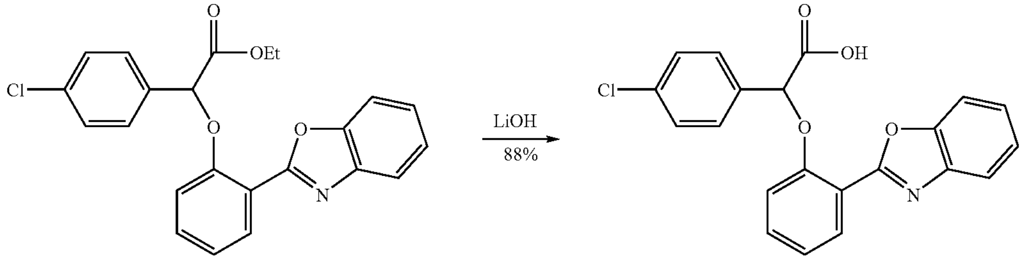

SI-41 I-1

A mixture of bromo ester SBr-1 (5.0 g), phenol PhOH-1 (4.1 g), and $K_2CO_3$ (3.9 g in DMF was stirred at room temperature overnight until no starting material was left as judged by TLC. The reaction mixture was diluted with water and extracted with ethyl acetate. The organic solution was dried over anhydrous $Na_2SO_4$ and concentrated. The residue was purified with flash chromatography (ethyl acetate/hexanes 1:5) to give the desired ester SI-41 (4.6 g) as a colorless oil. $^1$H NMR (400 MHz, $CDCl_3$): δ 8.22–6.98 (m, 12H), 5.79 (s, 1H), 4.18 (q, 2H), 1.17 (t, 3H).

The ester (1.0 g) was dissolved in THF (5 mL), and mixed with a LiOH solution (1.0 N, 20 mL). The mixture was stirred at room temperature overnight and extracted with ethyl acetate. The organic solution was washed with 0.1 N HCl, and dried over anhydrous $Na_2SO_4$ and concentrated. Purification with flash chromatography (ethyl acetate) gave the desired acid I-1 (0.82 g) as a white solid. $^1$H NMR (400 MHz, DMSO): δ 8.10–7.12 (m, 12H), 5.42 (s, 1H).

Example 26

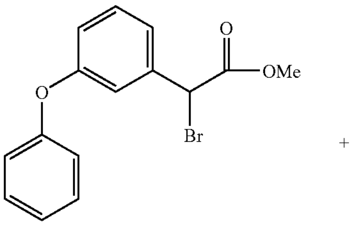

SBr-10

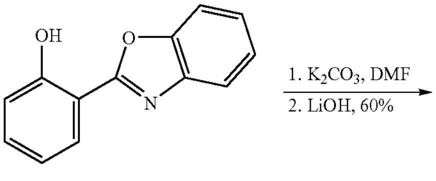

PhOH-1

-continued

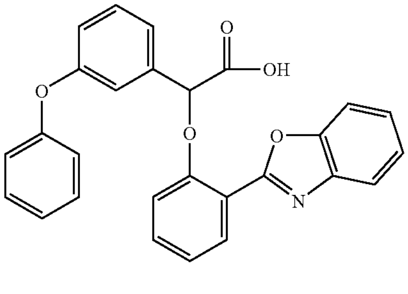

I-2

In the same manner as that described in Example 25 compound I-2 was prepared from SBr-10 and PhOH-1 as a white solid. $^1$H NMR (400 MHz, DMSO): δ 8.24–6.82 (m, 17H), 5.44 (s, 1H).

Example 27

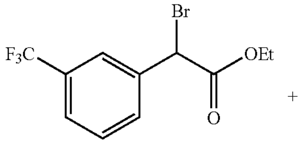

SBr-5

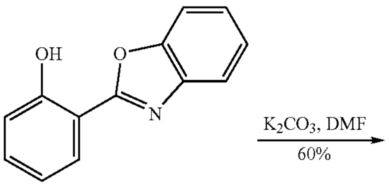

PhOH-1

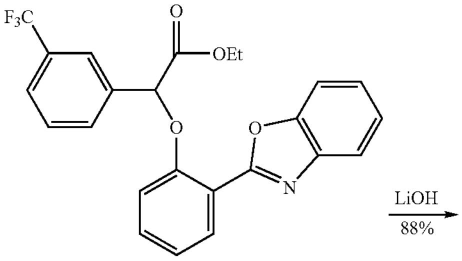

SI-42

-continued

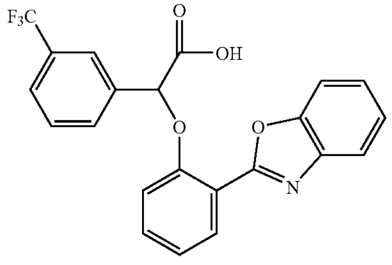

I-3

In the same manner as that described in Example 25 compound I-3 was prepared from SBr-5 and PhOH-1.

Example 28

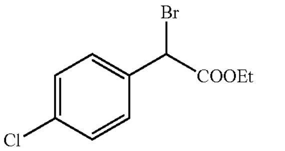

+

SBr-1

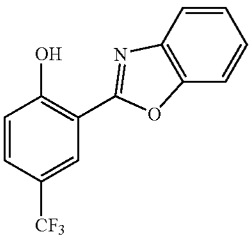

PhOH-6

$K_2CO_3$
DMF, rt.

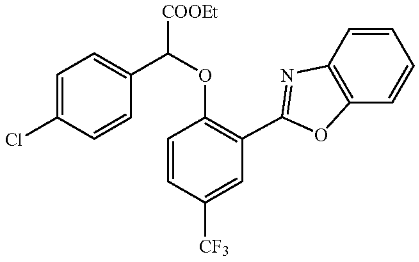

SI-44

LiOH
$THF/H_2O$

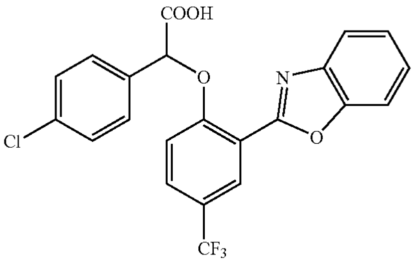

I-88

Step A: To a solution of phenol PhOH-6 (0.9882 g, 3.54 mmol) in DMF (10 mL) was added $K_2CO_3$ (0.92 g, 6.66 mmol) followed by bromide SBr-1 (1.20 g, 4.57 mmol). After stirring for 0.5 h at rt, the reaction mixture was diluted with EtOAc and water. The organic layer was washed with sat. $NaHCO_3$ and brine, dried over $Na_2SO_4$ and concentrated in vacuo. Purification via recrystallization from $CH_2Cl_2$ afforded ester SI-44 (1.3698 g) as a snow-white solid. $^1H$ NMR (400 MHz, $CDCl_3$): δ 8.55 (1H, s), 7.82–7.85 (1H, m), 7.78 (2H, dd, J=8.4, 2.0 Hz), 7.71 (1H, d, J=8.8 Hz), 7.60–7.62 (1H, m), 7.39–7.45 (4H, m), 7.05 (1H, d, J=8.8 Hz), 5.84 (1H, s), 4.18–4.23 (2H, m), 1.17–1.21 (3H, m). Step B. To a solution of ester SI-44 (0.9658 g, 2.03 mmol) in $THF/H_2O$ (20 mL/5 mL) at rt was added lithium hydroxide monohydrate (0.43 g, 10.25 mmol). The resulting solution was stirred at rt for 1 h, quenched with 1N aqueous HCl and extracted with EtOAc. The organic layer was washed with brine, dried over $Na_2SO_4$ and concentrated in vacuo to afford acid I-88 (0.8842 g) as a white solid. $^1H$ NMR (400 MHz, DMSO-$d_6$): δ 8.41 (1H, d, J=2.0 Hz), 7.99 (1H, dd, J=9.2, 2.0 Hz), 7.89 (1H, dd, J=6.8, 2.0 Hz), 7.83–7.86 (1H, m), 7.83 (2H, d, J=8.6 Hz), 7.59 (2H, d, J=8.6 Hz), 7.43–7.50 (2H, m), 7.40 (1H, d, J=8.8 Hz), 6.34 (1H, s).

Example 29

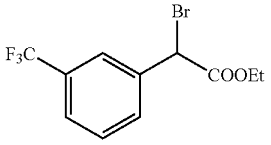

+

SBr-5

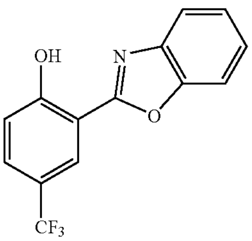

PhOH-6

$K_2CO_3$
DMF, rt

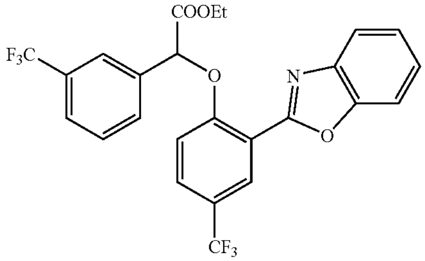

SI-45

LiOH
$THF/H_2O$

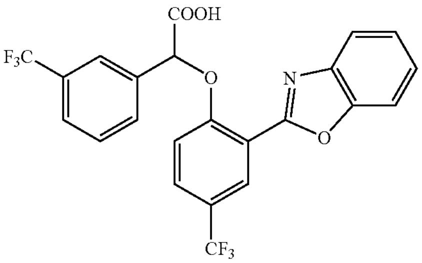

I-89

In the same manner as that described in Example 28 compound I-89 was prepared from SBr-5 and PhOH-6 as a white solid. $^1H$ NMR (400 MHz, DMSO-$d_6$): δ 8.40 (1H, d, J=2.0 Hz), 8.35 (1H, s), 8.04 (1H, d, J=7.6 Hz), 7.97 (1H, dd, J=8.8, 2.4 Hz), 7.82 (1H, dd, J=6.8, 2.4 Hz), 7.75–7.77 (1H, m), 7.74 (1H, d, J=4.4 Hz), 7.69 (2H, t, J=7.8 Hz), 7.43–7.50 (2H, m), 7.39 (1H, d, J=9.2 Hz), 6.27 (1H, s) ppm.

Example 30
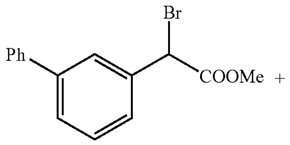
SBr-8
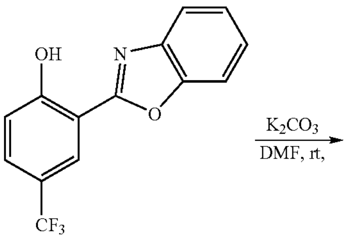
PhOH-6
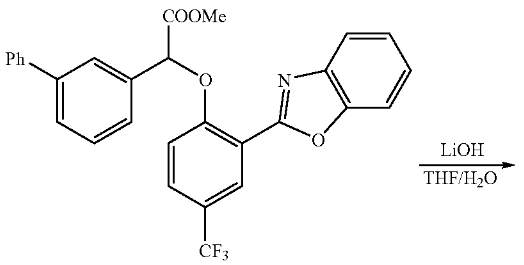
SI-46
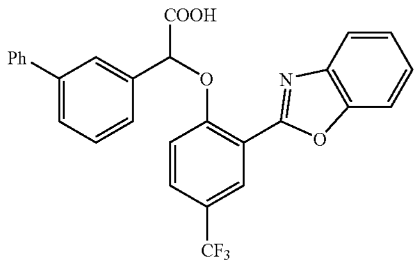
I-90
In the same manner as that described in Example 28 compound I-90 was prepared from SBr-8 and PhOH-6. $^1$H NMR (400 MHz, DMSO): δ 8.40–6.40 (m, 16H), 5.42 (s, 1H).
Example 31
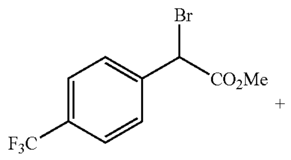
SBr-11
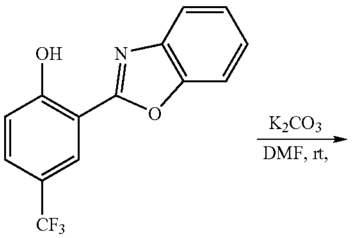
PhOH-6
-continued
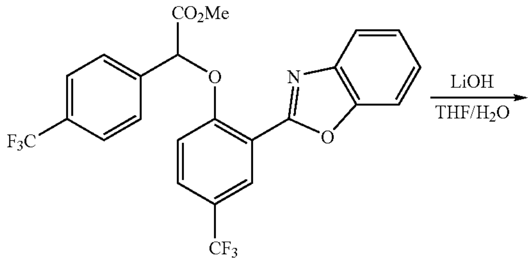
SI-47
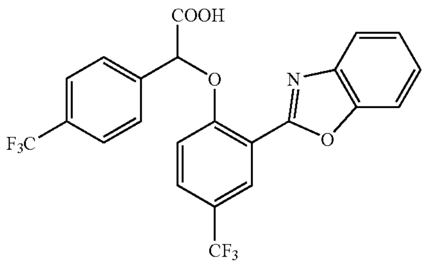
I-91
In the same manner as that described in Example 28 compound I-91 was prepared from SBr-11 and PhOH-6. $^1$H NMR (400 MHz, DMSO): δ 8.42–7.40 (m, 11H), 6.47 (s, 1H).
Example 32
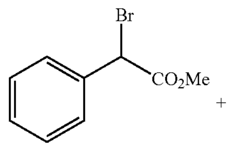
SBr-4
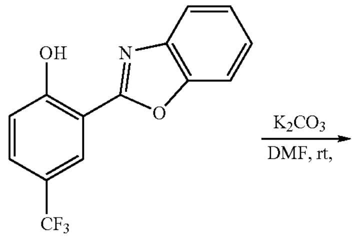
PhOH-6
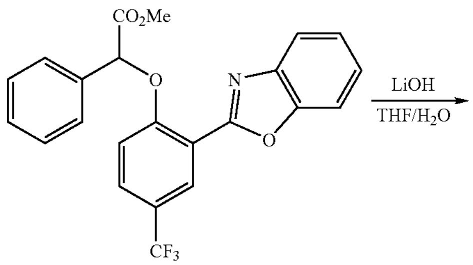
SI-48

-continued

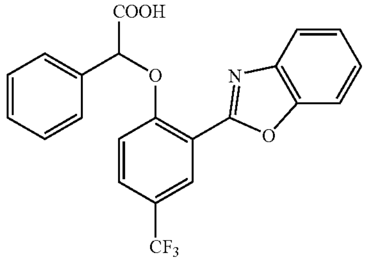

I-92

In the same manner as that described in Example 28 compound I-92 was prepared from SBr-4 and PhOH-6. $^1$H NMR (400 MHz, DMSO-$d_6$): δ 8.39 (1H, s), 7.99 (1H, d, J=8.8 Hz), 7.86 (1H, d, J=7.2 Hz), 7.77–7.79 (3H, m), 7.40–7.49 (6H, m), 6.27 (1H, s) ppm.

Example 33

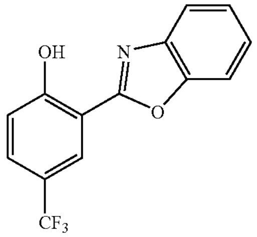

PhOH-6

+

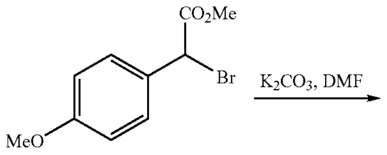

SBr-7

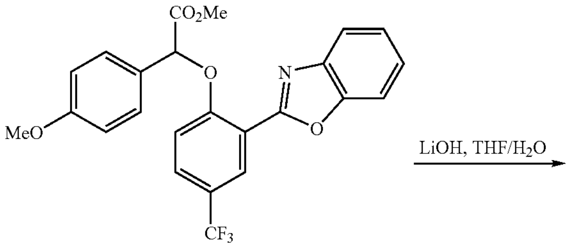

SI-49

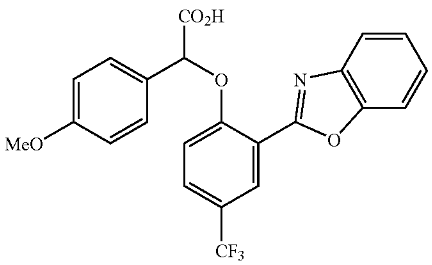

I-93

In the same manner as that described in Example 28 compound I-93 was prepared from SBr-7 and PhOH-6 as a white solid. $^1$HNMR (d-DMSO, 400 MHz) δ 13.42 (br, 1H), 8.41 (s, 1H), 8.00 (d, 1H), 7.82 (dd, 2H), 7.70 (d, 2H), 7.42 (m, 3H), 7.05 (d, 2H), 6.22 (s, 1H), 3.79 (s, 3H).

Example 34

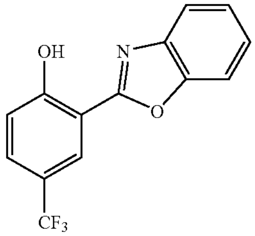

PhOH-6

+

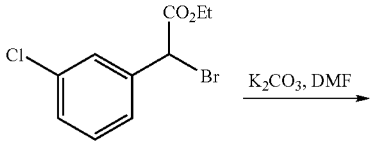

SBr-6

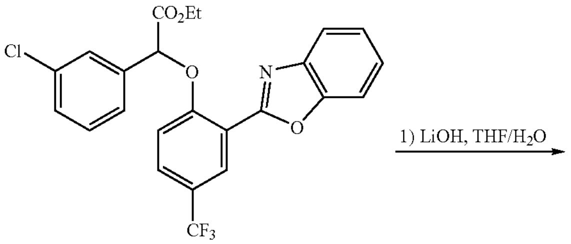

SI-50

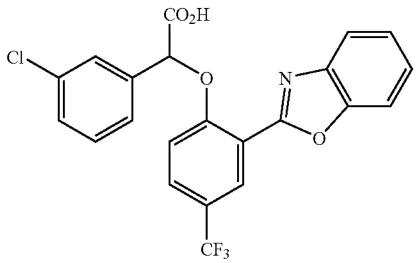

I-94

In the same manner as that described in Example 28 compound I-94 was prepared from SBr-6 and PhOH-6 as a white solid. $^1$HNMR (d-DMSO, 400 MHz) δ 13.68 (br, 1H), 8.43 (d, 1H), 8.11 (s, 1H), 8.21 (dd, 1H), 7.89 (m, 1H), 7.83 (m, 1H), 7.70 (d, 1H), 7.50 (m, 4H), 7.42 (d, 1H), 6.40 (s, 1H).

Example 35

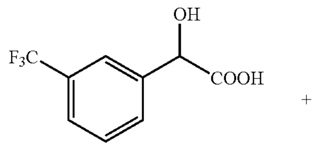

SOH-1

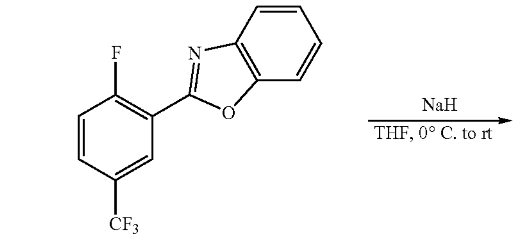

PhF-1

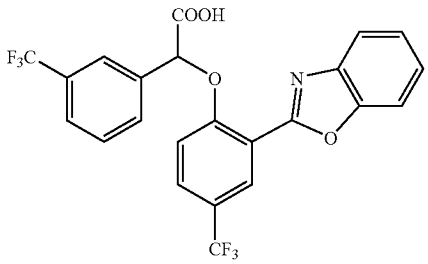

I-89

To a solution of 3-(trifluoromethyl)mandelic acid SOH-1 (4.8251 g, 0.022 mol) in THF (50 mL) at 0° C. was added NaH (Aldrich, 60%, 4.928 g, 0.055 mol). After stirring for 0.5 h, fluoride PhF-1 (6.1618 g, 0.022 mol) was added, and then warmed up and stirred at rt overnight. The reaction mixture was cooled to 0° C. and quenched with sat. $NH_4Cl$ (aq.), diluted with EtOAc and water. The organic layer was washed with brine, dried over $Na_2SO_4$, concentrated in vacuo. Purification via recrystallization from iPrOH (rinsed with 10% EtOAc/hexanes) afforded I-89 (9.80 g, 92%) as a white solid.

Example 36

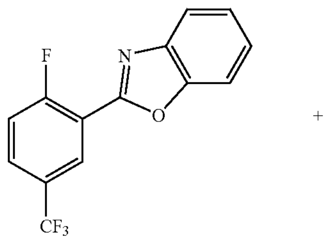

PhF-1

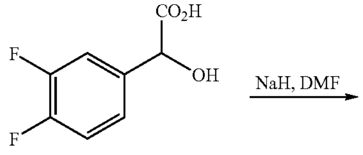

SOH-2

-continued

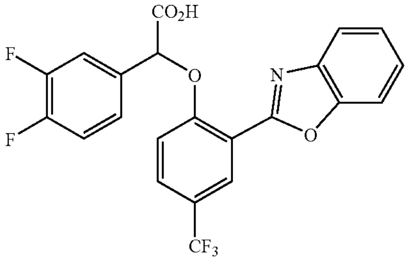

I-95

To a solution of PhF-1 (1.49 g, 5.32 mmol) and SOH-2 (1 g, 5.32 mmol) in DMF (20 mL) was added NaH (60%, 0.43 g, 10.64 mmol) in one portion at −10° C., and the reaction mixture was slowly warmed to room temperature over 0.5 h. After stirring at room temperature for additional 2 h, the mixture was poured into a mixture of ice and 1 N HCl solution, filtered, washed with water and dried. Recrystallization from MeOH gave I-95 as a white solid (1.94 g). $^1$HNMR (d-DMSO, 400 MHz) δ 8.42 (d, 1H), 7.99 (m, 2H), 7.85 (m, 1H), 7.79 (d, 1H), 7.58 (m, 2H), 7.49 (m, 2H), 7.44 (d, 1H), 6.38 (s, 1H).

Example 37

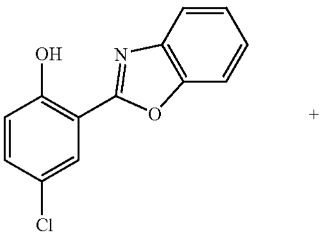

PhOH-2

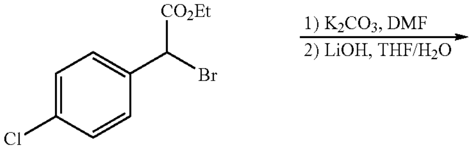

SBr-1

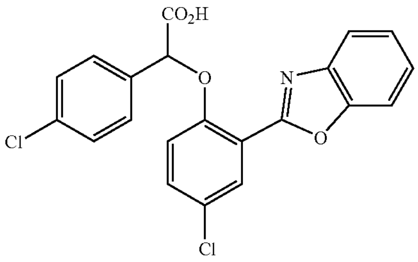

I-190

In the same manner as that described in Example 28 compound I-190 was prepared from SBr-1 and PhOH-2 as a white solid. $^1$HNMR (d-DMSO, 400 MHz) δ 13.6 (br, 1H), 8.10 (d, 1H), 7.84 (m, 4H), 7.66 (dd, 1H), 7.57 (m, 2H), 7.45 (m, 2H), 7.24 (d, 1H), 6.20 (s, 1H).

Example 38

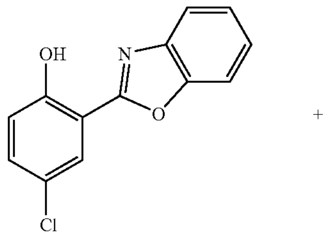

PhOH-2

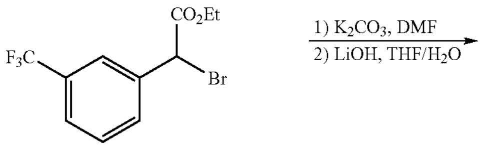

SBr-5

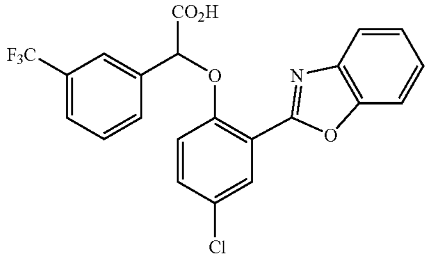

I-191

In the same manner as that described in Example 28 compound I-191 was prepared from SBr-5 and PhOH-2 as a white solid. $^1$HNMR (d-DMSO, 400 MHz) δ 13.70 (br, 1H), 8.34 (s, 1H), 8.15 (d, 1H), 8.02 (d, 1H), 7.85–7.71 (m, 5H), 7.50 (m, 2H), 7.29 (d, 1H), 6.40 (s, 1H).

Example 39

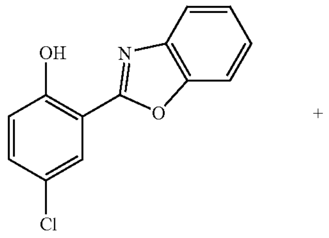

PhOH-2

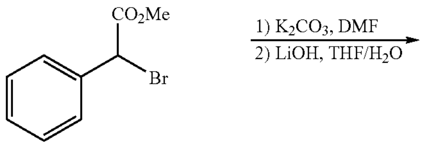

SBr-4

-continued

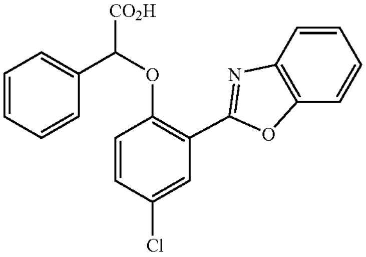

I-192

In the same manner as that described in Example 28 compound I-192 was prepared from SBr-4 and PhOH-2 as a white solid. $^1$HNMR (d-DMSO, 400 MHz) δ 13.45 (br, 1H), 8.10 (d, 1H), 7.85 (dd, 1H), 7.75 (m, 3H), 7.67 (dd, 1H), 7.47 (m, 4H), 7.40 (m, 1H), 7.24 (d, 1H), 6.13 (s, 1H).

Example 40

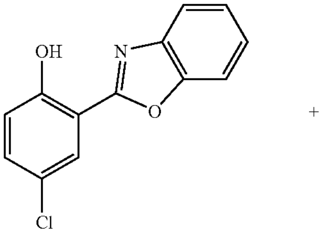

PhOH-2

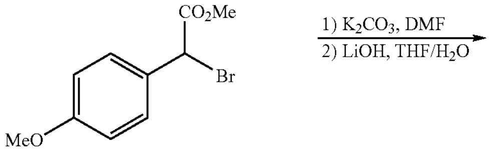

SBr-7

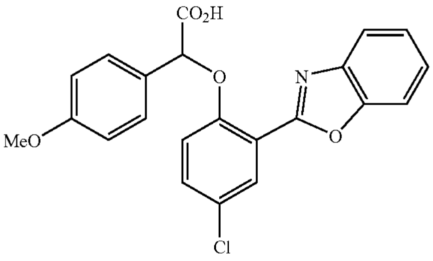

I-193

In the same manner as that described in Example 28 compound I-193 was prepared from SBr-7 and PhOH-2 as a white solid. $^1$HNMR (d-DMSO, 400 MHz) δ 13.30 (br, 1H), 8.09 (d, 1H), 7.82 (m, 2H), 7.65 (d, 3H), 7.45 (m, 2H), 7.22 (d, 1H), 7.01 (d, 2H), 6.60 (s, 1H).

Example 41

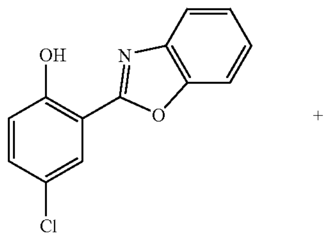

PhOH-2

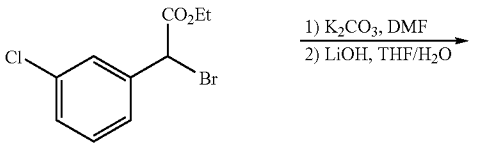

SBr-6

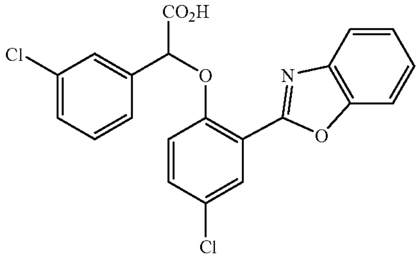

I-194

In the same manner as that described in Example 28 compound I-194 was prepared from SBr-6 and PhOH-2 as a white solid. $^1$HNMR (d-DMSO, 400 MHz) δ 13.60 (br, 1H), 8.13 (d, 1H), 8.07 (s, 1H), 7.87 (m, 1H), 7.80 (m, 1H), 7.68 (m, 2H), 7.48 (m, 4H), 7.23 (d, 1H), 6.24 (s, 1H).

Example 42

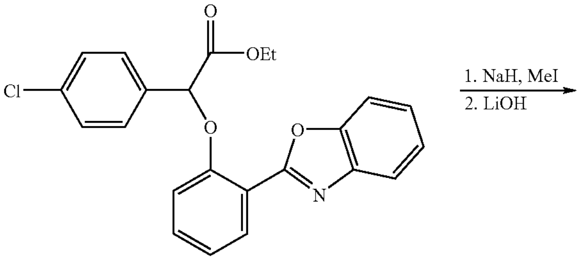

SI-41

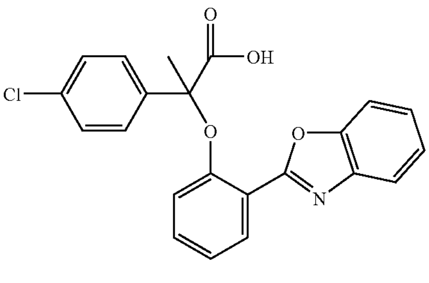

Ia-1

To a suspension of NaH (0.44 g) in DMF was added dropwise a solution of ester SI-41(3.0 g) in DMF at 0° C. The reaction mixture was stirred at the same temperature for 30 min, then MeI (0.6 mL) was introduced via syringe. The solution was stirred for one hour, quenched with water, extracted with ethyl acetate. Purification with column chromatography (hexanes/ethyl acetate 5:1) gave the methylated ester (2.1 g).

The above ester was dissolved in THF (5 mL), and mixed with a LiOH solution (1.0 N, 20 mL). The mixture was stirred at room temperature overnight, and extracted with ethyl acetate. The organic solution was washed with 0.5 N HCl, dried over anhydrous $Na_2SO_4$, and concentrated. Purification with flash chromatography (ethyl acetate) gave the desired acid Ia-1 (1.6 g, 80%) as a white solid. $^1$H NMR (400 MHz, DMSO): δ 7.70–6.61 (m, 12H), 3.30 (s, 3H).

Example 43

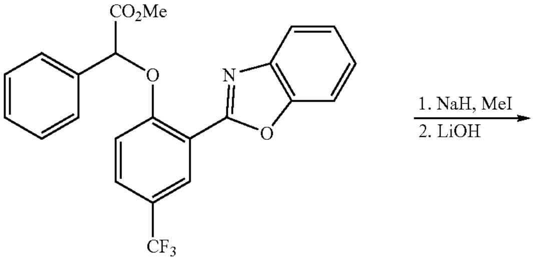

SI-48

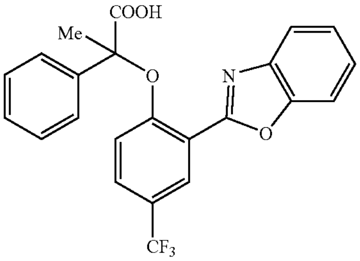

Ia-93

In the same manner as that described in Example 42 compound Ia-93 was prepared from SI-48. $^1$H NMR (d-DMSO, 400 MHz) δ 13.85 (br, 1H), 8.38 (d, 1H), 7.90–7.87 (m, 2H), 7.83–7.79 (m, 3H), 7.52–7.42 (m, 4H), 7.36 (m, 1H), 7.07 (d, 1H), 2.0 (s, 3H).

Example 44

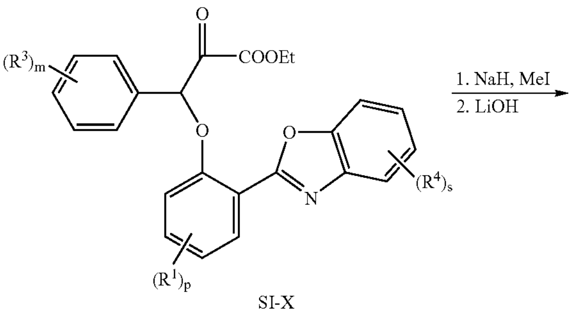

SI-X

-continued

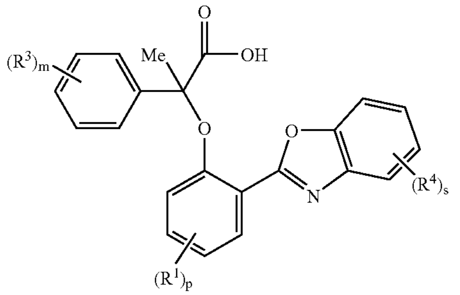

Ia-X $R^3$ = 4-Cl, 3-$CF_3$, 3-OPh, 3-Cl, 4-OMe, 4-$CF_3$, 4-Br, H, 4-F, 4-Et
$R^1$ = H, 4′-$CF_3$, 4′-Cl, 4′-Me, 4′-t-Bu, 4′-Br, 4′6′-di-Cl, 4′-(2,4-diF-Ph), 4′-(1H-pyrrol-yl)
$R^4$ = 2″-Me, 2″-Ph, 2″-Cl 2″$OCF_3$, 3″-Me, 3″-OMe, 3″-Cl In the same manner as that described in Example 42 the rest of Ia-X listed in Table 1 can be prepared from SI-X.

4. Enantioselective Synthesis and Enantiomer Separation

One or more routes illustrated in Scheme 4 was or can be used to prepare the individual enantiomers of compound I-X and Ia-X listed in Table 1. In route A, an enantiomerically pure α-hydroxy-phenyl acetic acid was treated with flouro compounds PhF-X with an electron withdrawing group such as $CF_3$ under strongly basic condition to afford enantiomerically enriched compounds. In route B, racemic compounds were resolved into single enantiomers by seperation on a chiral HPLC. In route C, racemic compounds were resolved into single enantiomers by recrystalization with a chiral amine.

Scheme 4
Preparation of enantiomerically pure I-X or Ia-X.

A

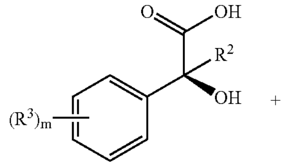

SOH-X

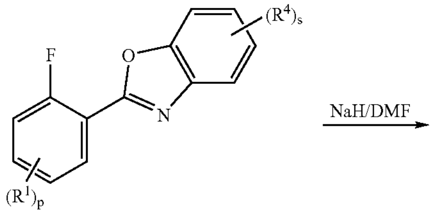

PhF-X

-continued

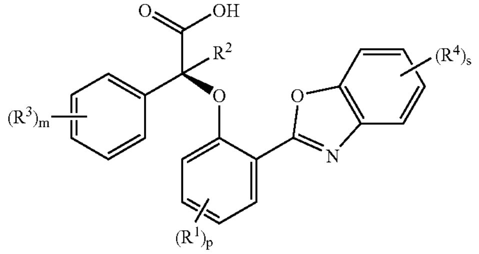

I-X or Ia-X

B

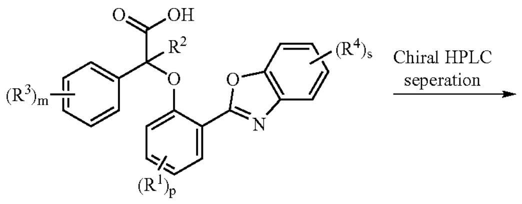

I-X or Ia-X (-)-enantiomer + (+)-enantiomer

C

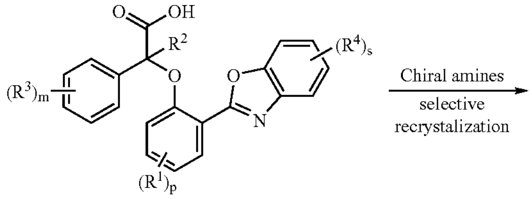

I-X or Ia-X (-)-enantiomer + (+)-enantiomer

Example 45

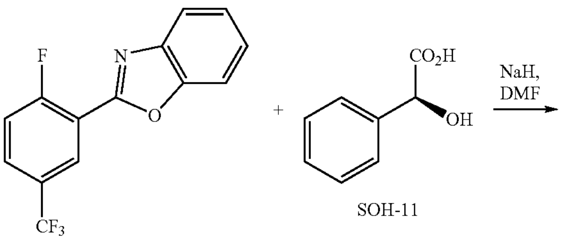

PhF-1 SOH-11

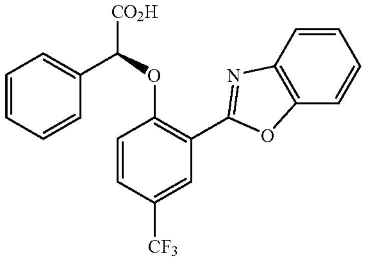

I-369

To a solution of PhF-1 (5.26 g, 0.0187 mol) and SOH-11 (3.132 g, 0.0206 mol) in DMF (100 mL) was added NaH (60%, 1.484 g, 0.0371 mol) in one portion at −78° C., and the reaction mixture was slowly warmed to room temperature over 1 h. After stirring at room temperature for additional 1.5 h, the mixture was poured into a mixture of ice and 1 N HCl solution, filtered, washed with water and dried. Recrystallization from MeOH gave optically pure I-369 as a white solid (6.56 g). $^1$H NMR (d-DMSO, 400 MHz) δ 13.48 (br, 1H), 8.41 (d, 1H), 8.0 (dd, 1H), 7.86 (dd, 1H), 7.78 (m, 3H), 7.46 (m, 6H), 6.29 (s, 1H).

Example 46

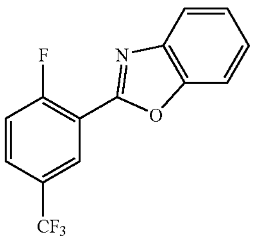

PhF-1

+

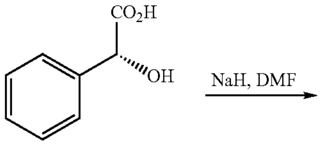

SOH-13

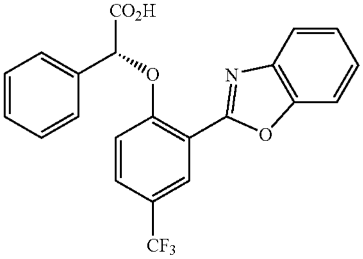

I-370

In the same manner as that described in Example 45 compound I-370 was prepared from PhF-1 and SOH-13. $^1$HNMR (d-DMSO, 400 MHz) δ 13.48 (br, 1H), 8.41 (d, 1H), 8.0 (dd, 1H), 7.86 (dd, 1H), 7.78 (m, 3H), 7.46 (m, 6H), 6.29 (s, 1H).

Example 47

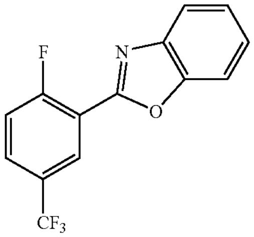

PhF-1

+

-continued

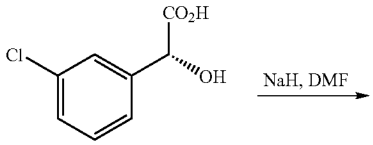

SOH-12

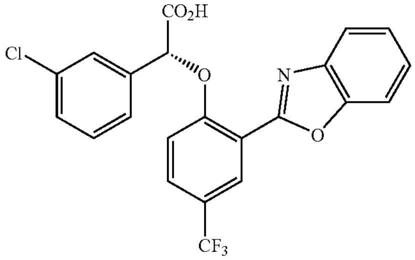

I-371

In the same manner as that described in Example 45 compound I-371 was prepared from PhF-1 and SOH-12. $^1$HNMR (d-DMSO, 400 MHz) δ 13.68 (br, 1H), 8.43 (d, 1H), 8.11 (s, 1H), 8.21 (dd, 1H), 7.89 (m, 1H), 7.83 (m, 1H), 7.70 (d, 1H), 7.50 (m, 4H), 7.42 (d, 1H), 6.40 (s, 1H). I-367 ee %>20%.

Example 48

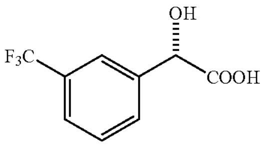

SOH-14

+

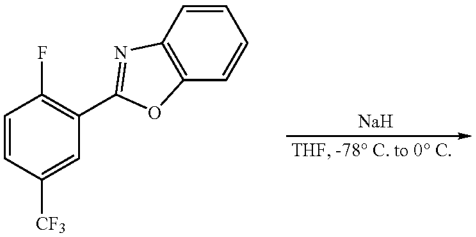

PhF-1

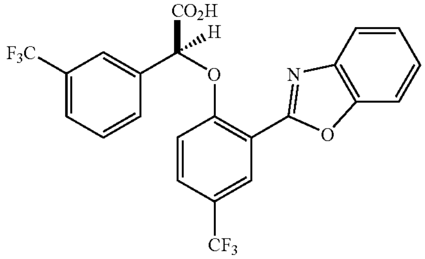

I-89

To a solution of 3-trifluoromethylmandelic acid SOH-14 (0.729 g, 3.31 mmol) in THF (20 mL) at −78° C. was added NaH (Aldrich, 60%, 0.594 g, 6.60 mmol). After warming up to −45° C. for 0.5 h, fluoride PhF-1 (0.9765 g, 3.47 mmol)

was added, and then warmed up to 0° C. overnight. The reaction was checked by chiral HPLC to find that two enantiomers were produced ((+)/(−)-isomer=6:4) with 80% conversion.

Example 49

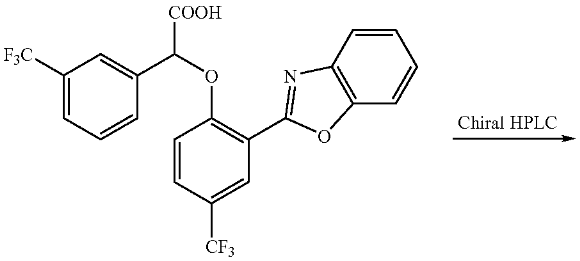

I-89

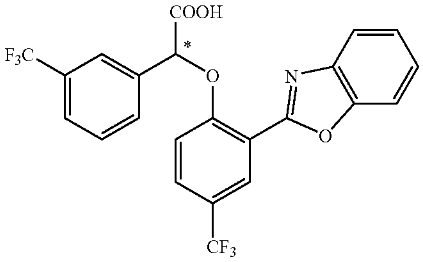

I-365
(+)-isomer

+

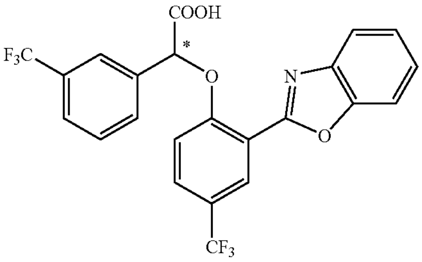

I-366
(-)-isomer

The two enantiomers were seperated by chiral HPLC using a 25 cm×21.1 mm Regis Technologies (R,R) WHELK-O 2 10/100 column at ambient temperature. Injected samples were 3.0 mL of 15.5 mg/mL solutions of the racemic I-89 in iPrOH/hexanes (1:1, v/v). The column was eluted with (15/85/0.1) iPrOH/hexanes/TFA at a flow rate of 30 mL/min. Detection was at 220 nm. The (+)-enantiomer I-365 eluted at 6 to 9 min, and the (−)-enantiomer I-366 at 9.5 to 12 min.

Example 50

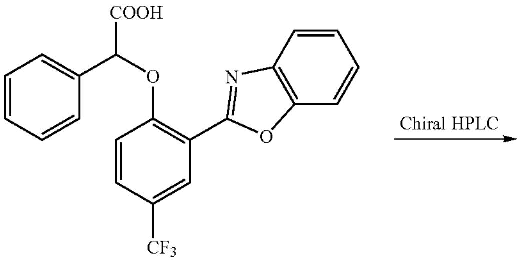

I-92

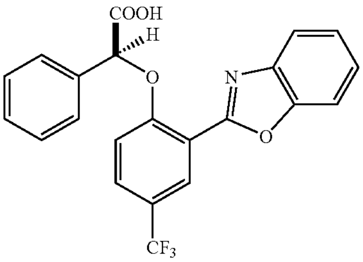

I-369

+

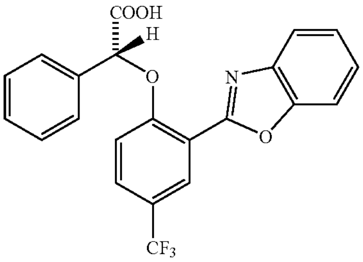

I-370

The two enantiomers were seperated by chiral HPLC using a 25 cm×21.1 mm Regis Technologies (R,R) WHELK-O 2 10/100 column at ambient temperature. Injected samples were 5.0 mL of 7 mg/mL solutions of the racemic I-92 in iPrOH/hexanes (6:4, v/v). The column was eluted with (25/75/0.1) iPrOH/hexanes/TFA at a flow rate of 30 mL/min. Detection was at 220 nm. The (S)-(+)-enantiomer I-369 eluted at 5 to 7 min, and the (R)-(−)-enantiomer I-370 at 8 to 10 min.

Example 51

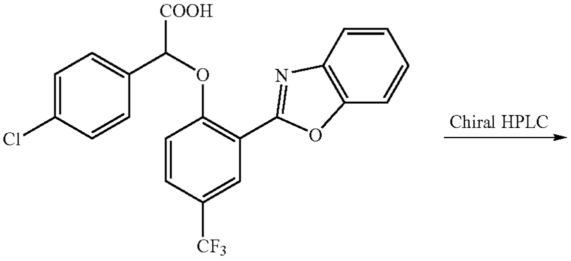

I-88

-continued

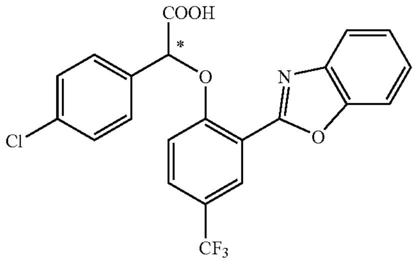

I-372
(+)-isomer

+

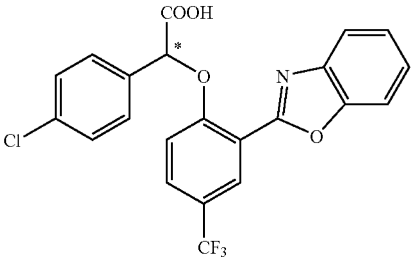

I-373
(-)-isomer

The two enantiomers were seperated by chiral HPLC using a 25 cm×21.1 mm Regis Technologies (R,R) WHELK-O 2 10/100 column at ambient temperature. Injected samples were 5.0 mL of 7 mg/mL solutions of the racemic I-88 in iPrOH/hexanes (6:4, v/v). The column was eluted with (25/75/0.1) iPrOH/hexanes/TFA at a flow rate of 30 mL/min. Detection was at 220 nm. The (+)-enantiomer I-372 eluted at 6 to 8 min, and the (−)-enantiomer I-373 at 9 to 11 min.

Example 52

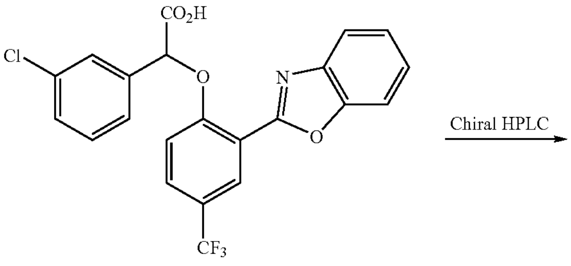

I-94

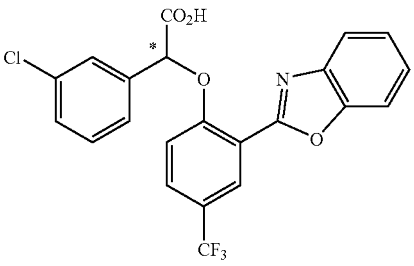

(+)-isomer

-continued

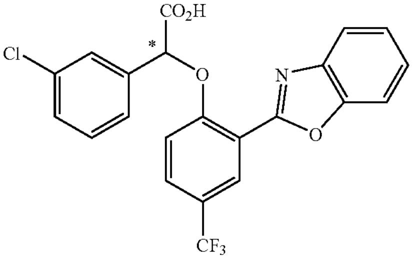

(-)-isomer

Racemic I-94 was resolved by chiral HPLC to give (+)-I-94 and (−)-I-94. HPLC methods and conditions, including eluents used, solvent flow rate and detection wavelength were: 20% iPrOH-80% Hexanes-0.1% TFA, 30 mL/min., λ=220 nm. For (+)-I-94: RT 5.5 min. For (−)-I-94: RT 9.5 min.

Example 53

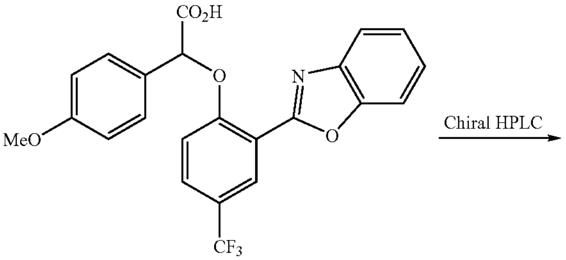

I-93

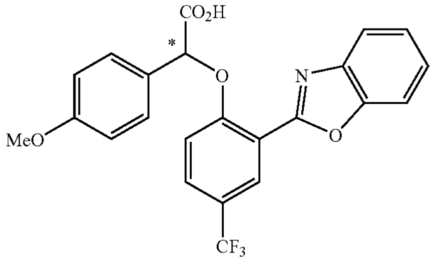

(+)-isomer

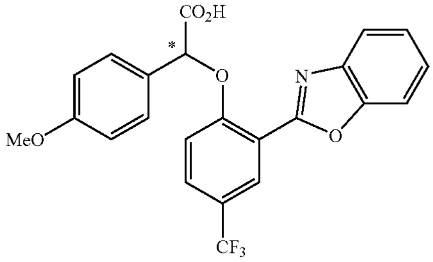

(-)-isomer

Racemic I-93 was resolved by chiral HPLC to give (+)-isomer and (−)-isomer. HPLC methods and conditions, including eluents used, solvent flow rate and detection wavelength were: 50% iPrOH-50% Hexanes-0.1% TFA, 30 mL/min., λ=220 nm. For (+)-isomer: RT 4.7 min. For (−)-isomer: RT 8.75 min.

Example 54

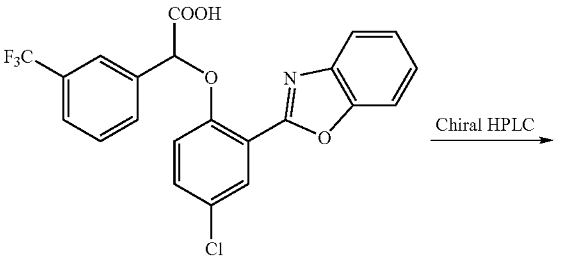

I-191

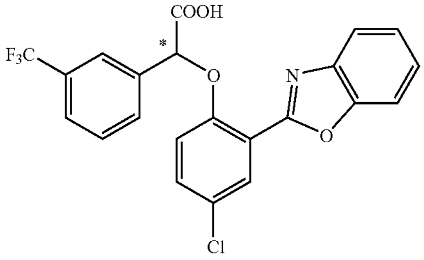

I-367
(+)-isomer

+

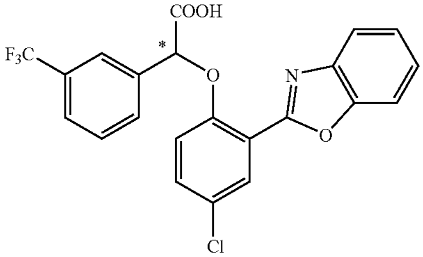

I-368
(-)-isomer

The two enantiomers were seperated by chiral HPLC using a 25 cm×21.1 mm Regis Technologies (R,R) WHELK-O 2 10/100 column at ambient temperature. Injected samples were 5.0 mL of 12 mg/mL solutions of the racemic I-191 in iPrOH/hexanes (4:6, v/v). The column was eluted with (15/85/0.1) iPrOH/hexanes/TFA at a flow rate of 30 mL/min. Detection was at 220 nm. The (+)-enantiomer I-367 eluted at 4 to 6 min, and the (−)-enantiomer I-368 at 7 to 9 min.

Example 55

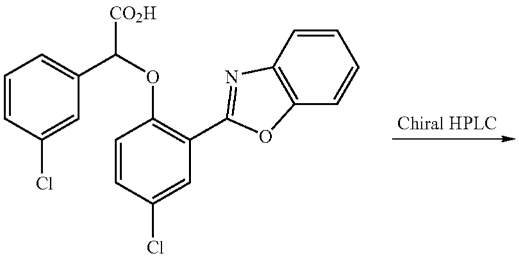

I-194

-continued

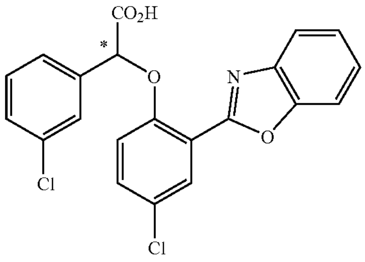

I-374
(+)-isomer

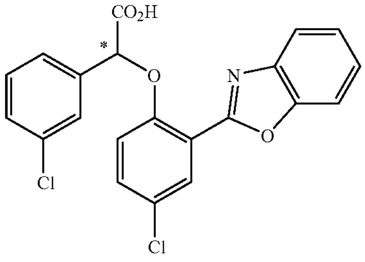

I-375
(-)-isomer

Racemic I-194 was resolved by chiral HPLC to give I-374 and I-375. HPLC methods and conditions, including eluents used, solvent flow rate and detection wavelength were: 35% iPrOH-65% Hexanes-0.1% TFA, 30 mL/min., λ=220 nm. For I-374: RT 4.7 min. For I-375: RT 6.7 min.

Example 56

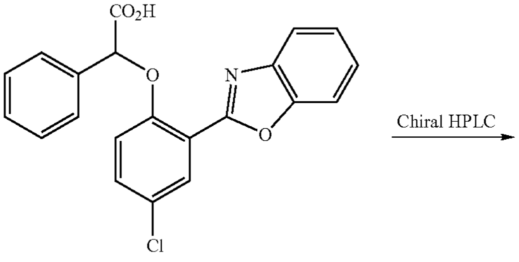

I-192

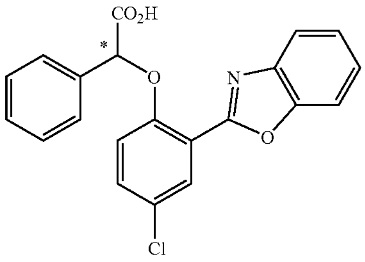

I-377
(+)-isomer

-continued

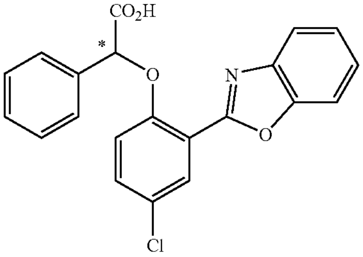

I-378
(-)-isomer

Racemic I-192 was resolved by chiral HPLC to give I-377 and I-378. HPLC methods and conditions, including eluents used, solvent flow rate and detection wavelength were: 50% iPrOH-50% Hexanes-0.1% TFA, 30 mL/min., λ=220 nm. For I-377: RT 5.4 min. For I-378: RT 7.8 min.

Example 57

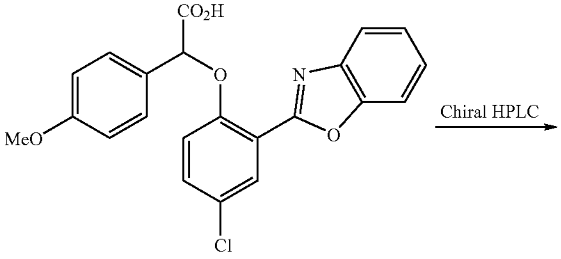

I-193

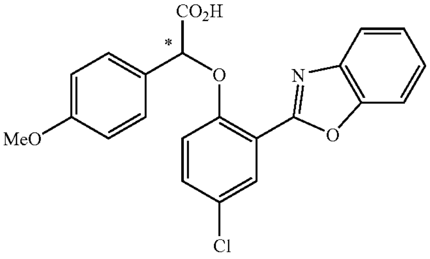

(+)-isomer

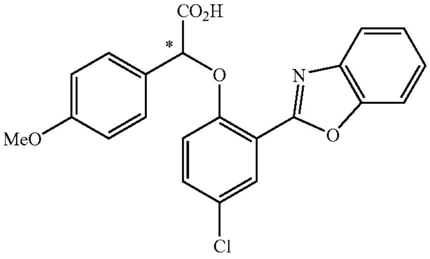

(-)-isomer

Racemic I-193 was resolved by chiral HPLC to give (+)-I-193 and (−)-I-193. HPLC methods and conditions, including eluents used, solvent flow rate and detection wavelength were: 50% iPrOH-50% Hexanes-0.1% TFA, 30 mL/min., λ=220 mu. For (+)-I-193: RT 5.5 min. For (−)-I-193: RT 11.5 min.

Example 58

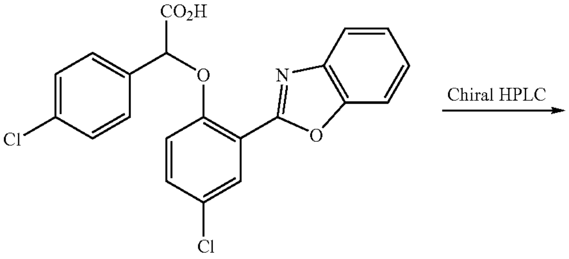

I-197

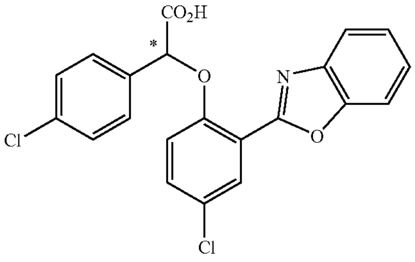

(+)-isomer

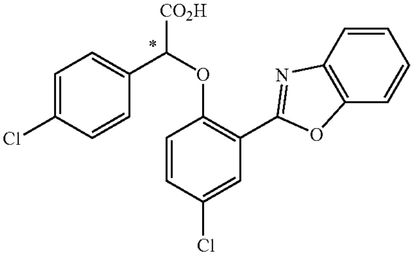

(-)-isomer

Racemic I-197 was resolved by chiral HPLC to give (+)-isomer and (−)-isomer. HPLC methods and conditions, including cluents used, solvent flow rate and detection wavelength were: 40% iPrOH-60% Hexanes-0.1% TFA, 30 mL/min., λ=220 nm. For (+)-isomer: RT 4.2 min. For (−)-isomer: RT 7.5 min.

Example 59

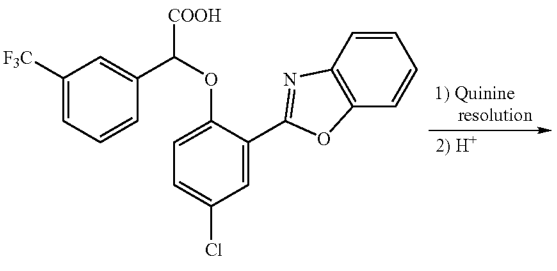

I-191

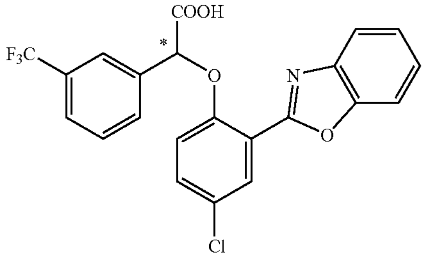

I-367
(+)-isomer

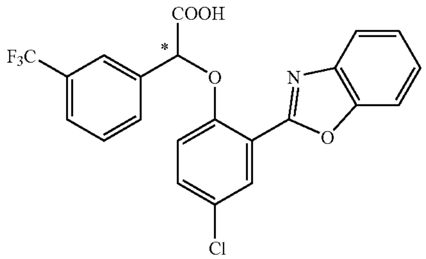

I-368
(-)-isomer

A suspension of I-191 (37.44 g, 0.084 mol) in 750 mL of EtOH 3A was heated to reflux at 90° C. (water-bath temperature) to give a cloudy solution, then cooled to ca. 80° C. Quinine (25.34 g, 0.078 mol) was added, and the resulting clear solution was stirred at 70–80° C. (internal solution temperature) and solid began to crash out of the hot solution. After stirring for 1 h at 70–80° C., and then cooled to 50° C. with stirring. The solid was collected by filtration and rinsed twice with EtOH 3A. The dried solid (ca. 33 g) had an 90–93% enantiomeric excess (ee) of the (+) enantiomer, and the mother liquor had an 85–90% enantiomeric excess (ee) of the (−) enantiomer. When this hot mother liquor was cooled to rt, a second crop solid (17.0 g) was obtained. This solid had a 99% ee of the (−)-enatiomer. Chiral HPLC analysis was carried out at $\lambda$=220 nm by injecting 10 µL of an approximately a 0.5 mg/mL solution of the sample dissolved in mobile phase onto a 25 cm×4.6 mm Regis Technologies (R,R) Whelk-O 1 5 µm column with a 1.5 mL/min flow of (25/75/0.1) iPrOH/hexanes/TFA. Under these conditions, (+) enantiomer I-367 eluted at 4.3 min, and (−) enantiomer at 5.8 min (approximate retention times). To the crude (+) salt (33 g) obtained above was added 520 mL of EtOH 3A, and the suspension was refluxed at 106° C. (oil-bath temperature) for 3 h, cooled to rt, filtered and rinsed twice with EtOH 3A. The white solid was dried to afford 28.32 g of the desired (+) enantiomer salt with an ee of 97–99%. To a suspension of the resolved salt (28 g) in 350 mL of EtOAc was added 45 mL of 2N $H_2SO_4$. After stirring for 10 min at rt, the resulting mixture was diluted with water (100 mL). The organic layer was separated and washed with water twice and then brine and dried over $Na_2SO_4$. After removal of solvents in vacuo and dried at 40–45° C./3 mmHg, 16.26 g of desired (+) enantiomer I-367 was obtained. Similarly, (+) enantiomer I-367 was also obtained by resolution of racemic I-191 using cinchonidine (0.9 eq.) in EtOH 3A with 60% recovery of (+) enantiomer with a 97–99% ee.

Example 60

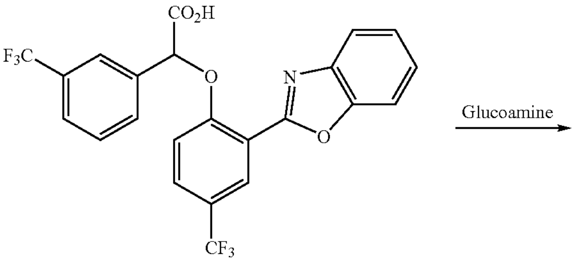

I-89

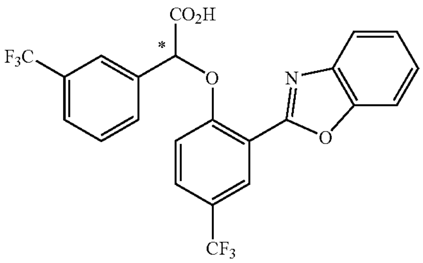

I-365
(+)-isomer

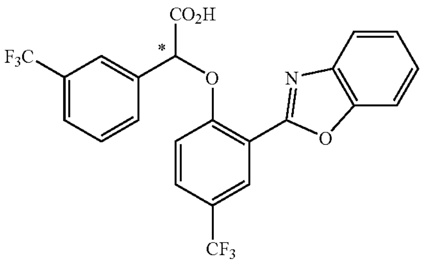

I-366
(-)-isomer (+) enantiomer I-365 and (−) enantiomer I-366 were obtained by resolution of racemic I-89 using N-methyl-D-glucamine (0.9 eq.) in EtOH 3A by a similar procedure as Example 59 above. Chiral HPLC analysis was carried out at $\lambda$=220 nrm by injecting 10 µL of a 0.5 mg/mL solution of the sample dissolved in mobile phase onto a 25 cm×4.6 mm Regis Technologies (R,R) Whelk-O 15 µm column with a 1.5 mL/min flow of (15/85/0.1) iPrOH/hexanes/TFA. Under these conditions, (+) enantiomer I-377 eluted at 4.5 min, and (−) enantiomer at 5.9 min (approximate retention times).

Example 61

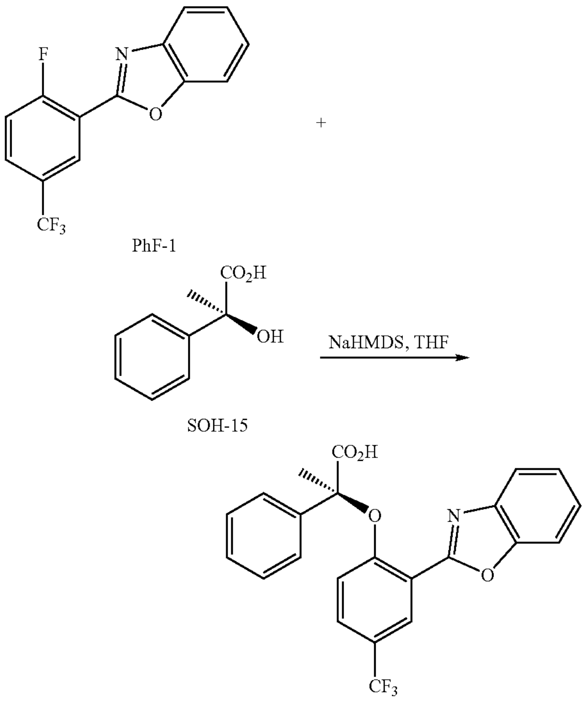

PhF-1

SOH-15

Ia-365

To a solution of SOH-15 (0.62 g, 3.73 mmol) in THF (10 mL) was added NaHMDS (1.0 M in THF, 7.83 mL) at −10° C. and the reaction was warmed to room temperature. After stirring at room temperature for 10 min., a solution of PhF-1 (1.05 g, 3.73 mmol) in THF (10 mL) was added. The reaction mixture was heated at 60° C. for 1 h, and then stirred overnight at room temperature. The reaction was quenched with 1 N HCl solution, extracted with EtOAc, washed with brine, dried and concentrated. The residue was purified by flash column (hexane/EtOAc 10:1) to give compound Ia-365 as a white solid (0.72 g, 45%). $^1$HNMR (d-DMSO, 400 MHz) δ 8.38 (d, 1H), 7.89 (m, 2H), 7.81 (m, 3H), 7.48 (m, 4H), 7.36 (m, 1H), 7.07 (d, 1H), 2.0 (s, 3H).

Example 62

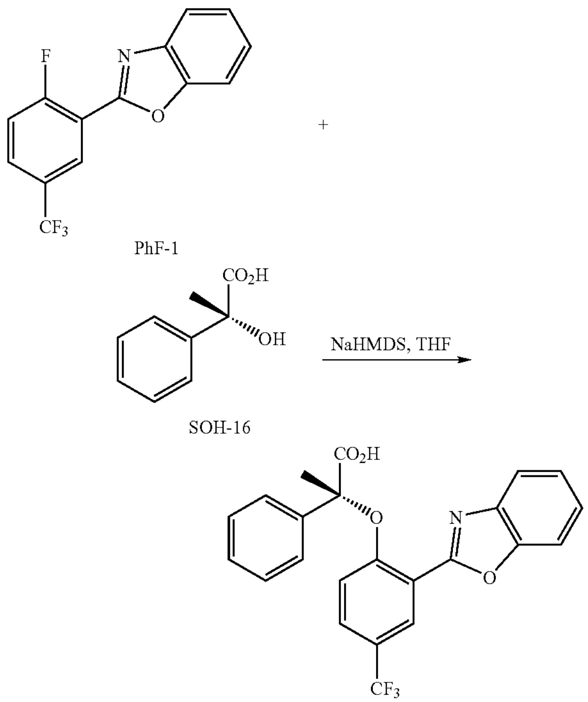

PhF-1

SOH-16

Ia-366

Ia-366 was obtained as a white solid from PhF-1 and SOH-16 in the same manner as that described in Example 61. $^1$HNMR (d-DMSO, 400 MHz) δ 8.38 (d, 1H), 7.89 (m, 2H), 7.81 (m, 3H), 7.48 (m, 4H), 7.36 (m, 1H), 7.07 (d, 1H), 2.0 (s, 3H).

TABLE 2

2-benzothiazole analogs

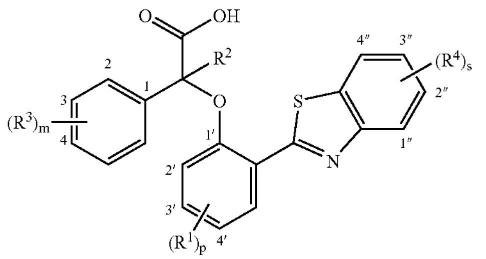

Compounds II and IIa

| Compound | $R^2$ | $(R^3)_m$ | $(R^1)_p$ | $(R^4)_s$ | Configuration |
|---|---|---|---|---|---|
| II-1 | H | 4-Cl | H | H | R/S |
| II-2 | H | 3-$CF_3$ | H | H | R/S |
| II-3 | H | 3-OPh | H | H | R/S |
| II-4 | H | 3-Cl | H | H | R/S |
| II-5 | H | 4-OMe | H | H | R/S |

TABLE 2-continued 2-benzothiazole analogs

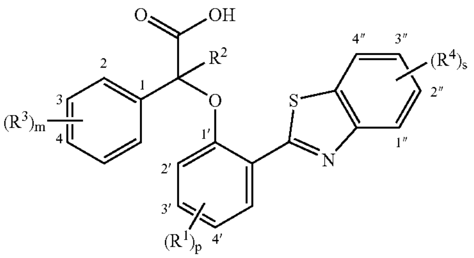

Compounds II and IIa

| Compound | $R^2$ | $(R^3)_m$ | $(R^1)_p$ | $(R^4)_s$ | Configuration |
|---|---|---|---|---|---|
| II-6 | H | 4-$CF_3$ | H | H | R/S |
| II-7 | H | 4-Br | H | H | R/S |
| II-8 | H | H | H | H | R/S |
| II-9 | H | 4-F | H | H | R/S |
| II-10 | H | 4-Et | H | H | R/S |
| II-11 | H | 4-Cl | H | 2"-Cl | R/S |
| II-12 | H | 3-$CF_3$ | H | 2"-Cl | R/S |
| II-13 | H | 3-OPh | H | 2"-Cl | R/S |
| II-14 | H | 3-Cl | H | 2"-Cl | R/S |
| II-15 | H | 4-OMe | H | 2"-Cl | R/S |
| II-16 | H | 4-$CF_3$ | H | 2"-Cl | R/S |
| II-17 | H | 4-Br | H | 2"-Cl | R/S |
| II-18 | H | H | H | 2"-Cl | R/S |
| II-19 | H | 4-F | H | 2"-Cl | R/S |
| II-20 | H | 4-Et | H | 2"-Cl | R/S |
| II-21 | H | H | 4'-$CF_3$ | H | R/S |
| II-22 | H | 3-$CF_3$ | 4'-$CF_3$ | H | R/S |
| II-23 | H | 3-OPh | 4'-$CF_3$ | H | R/S |
| II-24 | H | 4-$CF_3$ | 4'-$CF_3$ | H | R/S |
| II-25 | H | 4-Et | 4'-$CF_3$ | H | R/S |
| II-26 | H | 4-Cl | 4'-$CF_3$ | H | R/S |
| II-27 | H | 4-OMe | 4'-$CF_3$ | H | R/S |
| II-28 | H | 3-Br | 4'-$CF_3$ | H | R/S |
| II-29 | H | 3-Cl | 4'-$CF_3$ | H | R/S |
| II-30 | H | 3-OMe | 4'-$CF_3$ | H | R/S |
| II-31 | H | 4-Me | 4'-$CF_3$ | H | R/S |
| II-32 | H | 4-Br | 4'-$CF_3$ | H | R/S |
| II-33 | H | 3-$NO_2$ | 4'-$CF_3$ | H | R/S |
| II-34 | H | 3,4-methylenedioxy | 4'-$CF_3$ | H | R/S |
| II-35 | H | 4-F | 4'-$CF_3$ | H | R/S |
| II-36 | H | 2,3-di-F | 4'-$CF_3$ | H | R/S |
| II-37 | H | 2,4-di-F | 4'-$CF_3$ | H | R/S |
| II-38 | H | 2,5-di-F | 4'-$CF_3$ | H | R/S |
| II-40 | H | 2,6-di-F | 4'-$CF_3$ | H | R/S |
| II-41 | H | 3,4-di-F | 4'-$CF_3$ | H | R/S |
| II-42 | H | 3,5-di-F | 4'-$CF_3$ | H | R/S |
| II-43 | H | 2,3,5-tri-F | 4'-$CF_3$ | H | R/S |
| II-44 | H | 4-MeS | 4'-$CF_3$ | H | R/S |
| II-45 | H | 4-$NO_2$ | 4'-$CF_3$ | H | R/S |
| II-46 | H | 2,5-di-Me | 4'-$CF_3$ | H | R/S |
| II-47 | H | 4-Cl | 4'-$CF_3$ | 2"-Cl | R/S |
| II-48 | H | 3-$CF_3$ | 4'-$CF_3$ | 2"-Cl | R/S |
| II-49 | H | 3-OPh | 4'-$CF_3$ | 2"-Cl | R/S |
| II-50 | H | 3-Cl | 4'-$CF_3$ | 2"-Cl | PJS |
| II-51 | H | 4-OMe | 4'-$CF_3$ | 2"-Cl | R/S |
| II-52 | H | 4-$CF_3$ | 4'-$CF_3$ | 2"-Cl | R/S |
| II-53 | H | 4-Br | 4'-$CF_3$ | 2"-Cl | R/S |
| II-54 | H | H | 4'-$CF_3$ | 2"-Cl | R/S |
| II-55 | H | 4-F | 4'-$CF_3$ | 2"-Cl | R/S |
| II-56 | H | 4-Et | 4'-$CF_3$ | 2"-Cl | R/S |
| II-57 | H | 4-Cl | 4'-$CF_3$ | 2"-$CF_3$ | R/S |
| II-58 | H | 3-$CF_3$ | 4'-$CF_3$ | 2"-$CF_3$ | R/S |
| II-59 | H | 3-OPh | 4'-$CF_3$ | 2"-$CF_3$ | R/S |
| II-60 | H | 3-Cl | 4'-$CF_3$ | 2"-$CF_3$ | R/S |
| II-61 | H | 4-OMe | 4'-$CF_3$ | 2"-$CF_3$ | R/S |
| II-62 | H | 4-$CF_3$ | 4'-$CF_3$ | 2"-$CF_3$ | R/S |
| II-63 | H | 4-Br | 4'-$CF_3$ | 2"-$CF_3$ | R/S |
| II-64 | H | H | 4'-$CF_3$ | 2"-$CF_3$ | R/S |
| II-65 | H | 4-F | 4'-$CF_3$ | 2"-$CF_3$ | R/S |

TABLE 2-continued 2-benzothiazole analogs

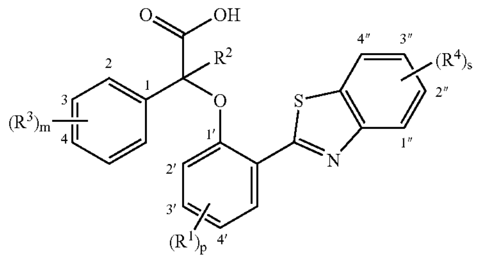

Compounds II and IIa

| Compound | $R^2$ | $(R^3)_m$ | $(R^1)_p$ | $(R^4)_s$ | Configuration |
|---|---|---|---|---|---|
| II-66 | H | 4-Et | 4'-$CF_3$ | 2"-$CF_3$ | R/S |
| II-67 | H | 3-Cl | 4',6'-di Cl | H | R/S |
| II-68 | H | 3-$CF_3$ | 4',6'-di Cl | H | R/S |
| II-69 | H | 3-OPh | 4',6'-di Cl | H | R/S |
| II-70 | H | 4-OMe | 4',6'-di Cl | H | R/S |
| II-71 | H | 4-Cl | 4',6'-di Cl | H | R/S |
| II-72 | H | 4-$CF_3$ | 4',6'-di Cl | H | R/S |
| II-73 | H | 4-Br | 4',6'-di Cl | H | R/S |
| II-74 | H | H | 4',6'-di Cl | H | R/S |
| II-75 | H | 4-F | 4',6'-di Cl | H | R/S |
| II-76 | H | 4-Et | 4',6'-di Cl | H | R/S |
| II-77 | H | 3-Cl | 4'-(2,4-diF-Ph) | H | R/S |
| II-78 | H | 3-$CF_3$ | 4'-(2,4-diF-Ph) | H | R/S |
| II-79 | H | 3-OPh | 4'-(2,4-diF-Ph) | H | R/S |
| II-80 | H | 4-OMe | 4'-(2,4-diF-Ph) | H | R/S |
| II-81 | H | 4-Cl | 4'-(2,4-diF-Ph) | H | R/S |
| II-82 | H | 4-$CF_3$ | 4'-(2,4-diF-Ph) | H | R/S |
| II-83 | H | 4-Br | 4'-(2,4-diF-Ph) | H | R/S |
| II-84 | H | H | 4'-(2,4-diF-Ph) | H | R/S |
| II-85 | H | 4-F | 4'-(2,4-diF-Ph) | H | R/S |
| II-86 | H | 4-Et | 4'-(2,4-diF-Ph) | H | R/S |
| II-87 | H | 3-Cl | 4'-(1H-pyrrol-yl) | H | R/S |
| II-88 | H | 3-$CF_3$ | 4'-(1H-pyrrol-yl) | H | R/S |
| II-89 | H | 3-OPh | 4'-(1H-pyrrol-yl) | H | R/S |
| II-90 | H | 4-OMe | 4'-(1H-pyrrol-yl) | H | R/S |
| II-91 | H | 4-Cl | 4'-(1H-pyrrol-yl) | H | R/S |
| II-92 | H | 4-$CF_3$ | 4'-(1H-pyrrol-yl) | H | R/S |
| II-93 | H | 4-Br | 4'-(1H-pyrrol-yl) | H | R/S |
| II-94 | H | H | 4'-(1H-pyrrol-yl) | H | R/S |
| II-95 | H | 4-F | 4'-(1H-pyrrol-yl) | H | R/S |
| II-96 | H | 4-Et | 4'-(1H-pyrrol-yl) | H | R/S |
| II-97 | H | 4-Cl | 4'-Cl | H | R/S |
| II-98 | H | 3-$CF_3$ | 4"-Cl | H | R/S |
| II-99 | H | 3-OPh | 4'-Cl | H | R/S |
| II-100 | H | 3-Cl | 4'-Cl | H | R/S |
| II-101 | H | 4-OMe | 4'-Cl | H | R/S |
| II-102 | H | 4-$CF_3$ | 4'-Cl | H | R/S |
| II-103 | H | 4-Br | 4'-Cl | H | R/S |
| II-104 | H | H | 4'-Cl | H | R/S |
| II-105 | H | 4-F | 4'-Cl | H | R/S |
| II-106 | H | 4-Et | 4'-Cl | H | R/S |
| II-107 | H | 4-Cl | 4'-Cl | 2"-Cl | R/S |
| II-108 | H | 3-$CF_3$ | 4'-Cl | 2"-Cl | R/S |
| II-109 | H | 3-OPh | 4'-Cl | 2"-Cl | R/S |
| II-110 | H | 3-Cl | 4'-Cl | 2"-Cl | R/S |
| II-112 | H | 4-OMe | 4'-Cl | 2"-Cl | R/S |
| II-113 | H | 4-$CF_3$ | 4'-Cl | 2"-Cl | R/S |
| II-114 | H | 4-Br | 4'-Cl | 2"-Cl | R/S |
| II-115 | H | H | 4'-Cl | 2"-Cl | R/S |
| II-116 | H | 4-F | 4'-Cl | 2"-Cl | R/S |
| II-117 | H | 4-Et | 4'-Cl | 2"-Cl | R/S |
| II-118 | H | 4-Cl | 4'-Cl | 2"-$CF_3$ | R/S |
| II-119 | H | 3-$CF_3$ | 4'-Cl | 2"-$CF_3$ | R/S |
| II-120 | H | 3-OPh | 4'-Cl | 2"-$CF_3$ | R/S |
| II-121 | H | 3-Cl | 4'-Cl | 2"-$CF_3$ | R/S |
| II-122 | H | 4-OMe | 4'-Cl | 2"-$CF_3$ | R/S |
| II-123 | H | 4-$CF_3$ | 4'-Cl | 2"-$CF_3$ | R/S |
| II-124 | H | 4-Br | 4'-Cl | 2"-$CF_3$ | R/S |
| II-125 | H | H | 4'-Cl | 2"-$CF_3$ | R/S |
| II-126 | H | 4-F | 4'-Cl | 2"-$CF_3$ | R/S |

TABLE 2-continued 2-benzothiazole analogs

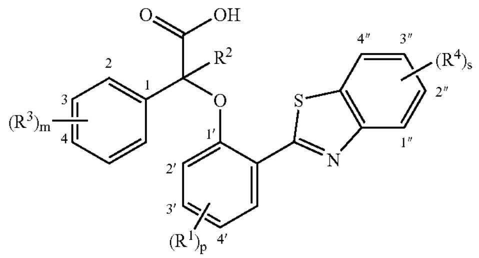

Compounds II and IIa

| Compound | $R^2$ | $(R^3)_m$ | $(R^1)_p$ | $(R^4)_s$ | Configuration |
|---|---|---|---|---|---|
| II-127 | H | 4-Et | 4'-Cl | 2"-$CF_3$ | R/S |
| II-128 | H | 3-Cl | 4'-Me | H | R/S |
| II-129 | H | 3-$CF_3$ | 4'-Me | H | R/S |
| II-130 | H | 3-OPh | 4'-Me | H | R/S |
| II-131 | H | 4-OMe | 4'-Me | H | R/S |
| II-132 | H | 4-Cl | 4'-Me | H | R/S |
| II-133 | H | 4-$CF_3$ | 4'-Me | H | R/S |
| II-134 | H | 4-Br | 4'-Me | H | R/S |
| II-135 | H | H | 4'-Me | H | R/S |
| II-136 | H | 4-F | 4'-Me | H | R/S |
| II-137 | H | 4-Et | 4'-Me | H | R/S |
| II-138 | H | 3-Cl | 4'-tBu | H | R/S |
| II-139 | H | 3-$CF_3$ | 4'-tBu | H | R/S |
| II-140 | H | 3-OPh | 4'-tBu | H | R/S |
| II-141 | H | 4-OMe | 4'-tBu | H | R/S |
| II-142 | H | 4-Cl | 4'-tBu | H | R/S |
| II-143 | H | 4-$CF_3$ | 4'-tBu | H | R/S |
| II-144 | H | 4-Br | 4'-tBu | H | R/S |
| II-145 | H | H | 4'-tBu | H | R/S |
| II-146 | H | 4-F | 4'-tBu | H | R/S |
| II-147 | H | 4-Et | 4'-tBu | H | R/S |
| II-148 | H | 3-Cl | 4'-Br | H | R/S |
| II-149 | H | 3-$CF_3$ | 4'-Br | H | R/S |
| II-150 | H | 3-OPh | 4'-Br | H | R/S |
| II-151 | H | 4-OMe | 4'-Br | H | R/S |
| II-152 | H | 4-Cl | 4'-Br | H | R/S |
| II-153 | H | 4-$CF_3$ | 4'-Br | H | R/S |
| II-154 | H | 4-Br | 4'-Br | H | R/S |
| II-155 | H | H | 4'-Br | H | R/S |
| II-156 | H | 4-F | 4'-Br | H | R/S |
| II-157 | H | 4-Et | 4'-Br | H | R/S |
| IIa-1 | Me | 4-Cl | H | H | R/S |
| IIa-2 | Me | 3-$CF_3$ | H | H | R/S |
| IIa-3 | Me | 3-OPh | H | H | R/S |
| IIa-4 | Me | 3-Cl | H | H | R/S |
| IIa-5 | Me | 4-OMe | H | H | R/S |
| IIa-6 | Me | 4-$CF_3$ | H | H | R/S |
| IIa-7 | Me | 4-Br | H | H | R/S |
| IIa-8 | Me | H | H | H | R/S |
| IIa-9 | Me | 4-F | H | H | R/S |
| IIa-10 | Me | 4-Et | H | H | R/S |
| IIa-11 | Me | 4-Cl | H | 2"-Cl | R/S |
| IIa-12 | Me | 3-$CF_3$ | H | 2"-Cl | R/S |
| IIa-13 | Me | 3-OPh | H | 2"-Cl | R/S |
| IIa-14 | Me | 3-Cl | H | 2"-Cl | R/S |
| IIa-15 | Me | 4-OMe | H | 2"-Cl | R/S |
| IIa-16 | Me | 4-$CF_3$ | H | 2"-Cl | R/S |
| IIa-17 | Me | 4-Br | H | 2"-Cl | R/S |
| IIa-18 | Me | H | H | 2"-Cl | R/S |
| IIa-19 | Me | 4-F | H | 2"-Cl | R/S |
| IIa-20 | Me | 4-Et | H | 2"-Cl | R/S |
| IIa-21 | Me | 4-Cl | 4'-$CF_3$ | H | R/S |
| IIa-22 | Me | 3-OPh | 4'-$CF_3$ | H | R/S |
| IIa-23 | Me | 3-$CF_3$ | 4'-$CF_3$ | H | R/S |
| IIa-24 | Me | H | 4'-$CF_3$ | H | R/S |
| IIa-25 | Me | 4-OMe | 4'-$CF_3$ | H | R/S |
| IIa-26 | Me | 4-$CF_3$ | 4'-$CF_3$ | H | R/S |
| IIa-27 | Me | 3-Cl | 4'-$CF_3$ | H | R/S |
| IIa-28 | Me | 3-OMe | 4'-$CF_3$ | H | R/S |
| IIa-29 | Me | 4-Br | 4'-$CF_3$ | H | R/S |

TABLE 2-continued 2-benzothiazole analogs

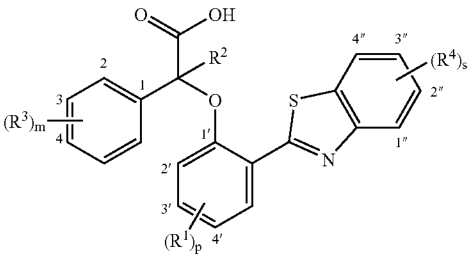

Compounds II and IIa

| Compound | $R^2$ | $(R^3)_m$ | $(R^1)_p$ | $(R^4)_s$ | Configuration |
|---|---|---|---|---|---|
| IIa-30 | Me | 3-$NO_2$ | 4'-$CF_3$ | H | R/S |
| IIa-31 | Me | 3,4-methylenedioxy | 4'-$CF_3$ | H | R/S |
| IIa-32 | Me | 4-F | 4'-$CF_3$ | H | R/S |
| IIa-33 | Me | 2,3-di-F | 4'-$CF_3$ | H | R/S |
| IIa-34 | Me | 2,4-di-F | 4'-$CF_3$ | H | R/S |
| IIa-35 | Me | 2,5-di-F | 4'-$CF_3$ | H | R/S |
| IIa-36 | Me | 2,6-di-F | 4'-$CF_3$ | H | R/S |
| IIa-37 | Me | 3,4-di-F | 4'-$CF_3$ | H | R/S |
| IIa-38 | Me | 3,5-di-F | 4'-$CF_3$ | H | R/S |
| IIa-40 | Me | 2,3,5-tri-F | 4'-$CF_3$ | H | R/S |
| IIa-41 | Me | 4-Et | 4'-$CF_3$ | H | R/S |
| IIa-42 | Me | H | 4'-$CF_3$ | H | R/S |
| IIa-43 | Me | 4-Me | 4'-$CF_3$ | H | R/S |
| IIa-44 | Me | 4-MeS | 4'-$CF_3$ | H | R/S |
| IIa-45 | Me | 4-$NO_2$ | 4'-$CF_3$ | H | R/S |
| IIa-46 | Me | 2,5-di-Me | 4'-$CF_3$ | H | R/S |
| IIa-47 | Me | 4-Cl | 4'-$CF_3$ | 2"-Cl | R/S |
| IIa-48 | Me | 3-$CF_3$ | 4'-$CF_3$ | 2"-Cl | R/S |
| IIa-49 | Me | 3-OPh | 4'-$CF_3$ | 2"-Cl | R/S |
| IIa-50 | Me | 3-Cl | 4'-$CF_3$ | 2"-Cl | R/S |
| IIa-51 | Me | 4-OMe | 4'-$CF_3$ | 2"-Cl | R/S |
| IIa-52 | Me | 4-$CF_3$ | 4'-$CF_3$ | 2"-Cl | R/S |
| IIa-53 | Me | 4-Br | 4'-$CF_3$ | 2"-Cl | R/S |
| IIa-54 | Me | H | 4'-$CF_3$ | 2"-Cl | R/S |
| IIa-55 | Me | 4-F | 4'-$CF_3$ | 2"-Cl | R/S |
| IIa-56 | Me | 4-Et | 4'-$CF_3$ | 2"-Cl | R/S |
| IIa-57 | Me | 4-Cl | 4'-$CF_3$ | 2"-$CF_3$ | R/S |
| IIa-58 | Me | 3-$CF_3$ | 4'-$CF_3$ | 2"-$CF_3$ | R/S |
| IIa-59 | Me | 3-OPh | 4'-$CF_3$ | 2"-$CF_3$ | R/S |
| IIa-60 | Me | 3-Cl | 4'-$CF_3$ | 2"-$CF_3$ | R/S |
| IIa-61 | Me | 4-OMe | 4'-$CF_3$ | 2"-$CF_3$ | R/S |
| IIa-62 | Me | 4-$CF_3$ | 4'-$CF_3$ | 2"-$CF_3$ | R/S |
| IIa-63 | Me | 4-Br | 4'-$CF_3$ | 2"-$CF_3$ | R/S |
| IIa-64 | Me | H | 4'-$CF_3$ | 2"-$CF_3$ | R/S |
| ILa-65 | Me | 4-F | 4'-$CF_3$ | 2"-$CF_3$ | R/S |
| IIa-66 | Me | 4-Et | 4'-$CF_3$ | 2"-$CF_3$ | R/S |
| IIa-67 | Me | 3-Cl | 4',6'-di Cl | H | R/S |
| IIa-68 | Me | 3-$CF_3$ | 4',6'-di Cl | H | R/S |
| IIa-69 | Me | 3-OPh | 4',6'-di Cl | H | R/S |
| IIa-70 | Me | 4-OMe | 4',6'-di Cl | H | R/S |
| IIa-71 | Me | 4-Cl | 4',6'-di Cl | H | R/S |
| IIa-72 | Me | 4-$CF_3$ | 4',6'-di Cl | H | R/S |
| IIa-73 | Me | 4-Br | 4',6'-di Cl | H | R/S |
| IIa-74 | Me | H | 4',6'-di Cl | H | R/S |
| IIa-75 | Me | 4-F | 4',6'-di Cl | H | R/S |
| IIa-76 | Me | 4-Et | 4',6'-di Cl | H | R/S |
| IIa-77 | Me | 3-Cl | 4'-(2,4-diF-Ph) | H | R/S |
| IIa-78 | Me | 3-$CF_3$ | 4'-(2,4-diF-Ph) | H | R/S |
| IIa-79 | Me | 3-OPh | 4'-(2,4-diF-Ph) | H | R/S |
| IIa-80 | Me | 4-OMe | 4'-(2,4-diF-Ph) | H | R/S |
| IIa-81 | Me | 4-Cl | 4'-(2,4-diF-Ph) | H | R/S |
| IIa-82 | Me | 4-$CF_3$ | 4'-(2,4-diF-Ph) | H | R/S |
| IIa-83 | Me | 4-Br | 4'-(2,4-diF-Ph) | H | R/S |
| IIa-84 | Me | H | 4'-(2,4-diF-Ph) | H | R/S |
| IIa-85 | Me | 4-F | 4'-(2,4-diF-Ph) | H | R/S |
| IIa-86 | Me | 4-Et | 4'-(2,4-diF-Ph) | H | R/S |
| IIa-87 | Me | 3-Cl | 4'-(1H-pyrrol-yl) | H | R/S |
| IIa-88 | Me | 3-$CF_3$ | 4'-(1H-pyrrol-yl) | H | R/S |
| IIa-89 | Me | 3-OPh | 4'-(1H-pyrrol-yl) | H | R/S |

TABLE 2-continued 2-benzothiazole analogs

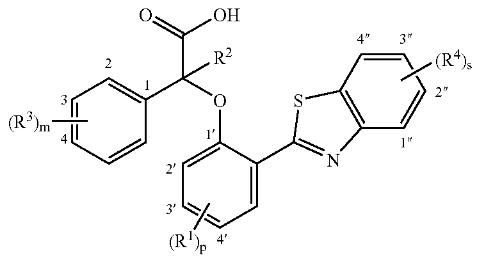

Compounds II and IIa

| Compound | $R^2$ | $(R^3)_m$ | $(R^1)_p$ | $(R^4)_s$ | Configuration |
|---|---|---|---|---|---|
| IIa-90 | Me | 4-OMe | 4'-(1H-pyrrol-yl) | H | R/S |
| IIa-91 | Me | 4-Cl | 4'-(1H-pyrrol-yl) | H | R/S |
| IIa-92 | Me | 4-$CF_3$ | 4'-(1H-pyrrol-yl) | H | R/S |
| IIa-93 | Me | 4-Br | 4'-(1H-pyrrol-yl) | H | R/S |
| IIa-94 | Me | H | 4'-(1H-pyrrol-yl) | H | R/S |
| IIa-95 | Me | 4-F | 4'-(1H-pyrrol-yl) | H | R/S |
| IIa-96 | Me | 4-Et | 4'-(1H-pyrrol-yl) | H | R/S |
| IIa-97 | Me | 4-Cl | 4'-Cl | H | R/S |
| IIa-98 | Me | 3-$CF_3$ | 4'-Cl | H | R/S |
| IIa-99 | Me | 3-OPh | 4'-Cl | H | R/S |
| IIa-100 | Me | 3-Cl | 4'-Cl | H | R/S |
| IIa-101 | Me | 4-OMe | 4'-Cl | H | R/S |
| IIa-102 | Me | 4-$CF_3$ | 4'-Cl | H | R/S |
| IIa-103 | Me | 4-Br | 4'-Cl | H | R/S |
| IIa-104 | Me | H | 4'-Cl | H | R/S |
| IIa-105 | Me | 4-F | 4'-Cl | H | R/S |
| IIa-106 | Me | 4-Et | 4'-Cl | H | R/S |
| IIa-107 | Me | 4-Cl | 4'-Cl | 2"-Cl | R/S |
| IIa-108 | Me | 3-$CF_3$ | 4'-Cl | 2"-Cl | R/S |
| IIa-109 | Me | 3-OPh | 4'-Cl | 2"-Cl | R/S |
| IIa-110 | Me | 3-Cl | 4'-Cl | 2"-Cl | R/S |
| IIa-112 | Me | 4-OMe | 4'-Cl | 2"-Cl | R/S |
| IIa-113 | Me | 4-$CF_3$ | 4'-Cl | 2"-Cl | R/S |
| IIa-114 | Me | 4-Br | 4'-Cl | 2"-Cl | R/S |
| IIa-115 | Me | H | 4'-Cl | 2"-Cl | R/S |
| IIa-116 | Me | 4-F | 4'-Cl | 2"-Cl | R/S |
| IIa-117 | Me | 4-Et | 4'-Cl | 2"-Cl | R/S |
| IIa-118 | Me | 4-Cl | 4'-Cl | 2"-$CF_3$ | R/S |
| IIa-119 | Me | 3-$CF_3$ | 4'-Cl | 2"-$CF_3$ | R/S |
| IIa-120 | Me | 3-OPh | 4'-Cl | 2"-$CF_3$ | R/S |
| IIa-121 | Me | 3-Cl | 4'-Cl | 2"-$CF_3$ | R/S |
| IIa-122 | Me | 4-OMe | 4'-Cl | 2"-$CF_3$ | R/S |
| IIa-123 | Me | 4-$CF_3$ | 4'-Cl | 2"-$CF_3$ | R/S |
| IIa-124 | Me | 4-Br | 4'-Cl | 2"-$CF_3$ | R/S |
| IIa-125 | Me | H | 4'-Cl | 2"-$CF_3$ | R/S |
| IIa-126 | Me | 4-F | 4'-Cl | 2"-$CF_3$ | R/S |
| IIa-127 | Me | 4-Et | 4'-Cl | 2"-$CF_3$ | R/S |
| IIa-128 | Me | 3-Cl | 4'-Me | H | R/S |
| IIa-129 | Me | 3-$CF_3$ | 4'-Me | H | R/S |
| IIa-130 | Me | 3-OPh | 4'-Me | H | R/S |
| IIa-131 | Me | 4-OMe | 4'-Me | H | R/S |
| IIa-132 | Me | 4-Cl | 4'-Me | H | R/S |
| IIa-133 | Me | 4-$CF_3$ | 4'-Me | H | R/S |
| IIa-134 | Me | 4-Br | 4'-Me | H | R/S |
| IIa-135 | Me | H | 4'-Me | H | R/S |
| IIa-136 | Me | 4-F | 4'-Me | H | R/S |
| IIa-137 | Me | 4-Et | 4'-Me | H | R/S |
| IIa-138 | Me | 3-Cl | 4'-tBu | H | R/S |
| IIa-139 | Me | 3-$CF_3$ | 4'-tBu | H | R/S |
| IIa-140 | Me | 3-OPh | 4'-tBu | H | R/S |
| IIa-141 | Me | 4-OMe | 4'-tBu | H | R/S |
| IIa-142 | Me | 4-Cl | 4'-tBu | H | R/S |
| IIa-143 | Me | 4-$CF_3$ | 4 '-tBu | H | R/S |
| IIa-144 | Me | 4-Br | 4'-tBu | H | R/S |
| IIa-145 | Me | H | 4'-tBu | H | R/S |
| IIa-146 | Me | 4-F | 4'-tBu | H | R/S |
| IIa-147 | Me | 4-Et | 4'-tBu | H | R/S |
| IIa-148 | Me | 3-Cl | 4'-Br | H | R/S |
| IIa-149 | Me | 3-$CF_3$ | 4'-Br | H | R/S |
| IIa-150 | Me | 3-OPh | 4'-Br | H | R/S |

TABLE 2-continued 2-benzothiazole analogs

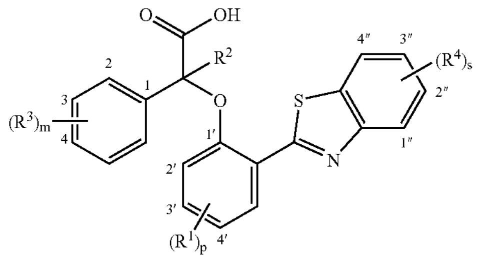

Compounds II and IIa

| Compound | $R^2$ | $(R^3)_m$ | $(R^1)_p$ | $(R^4)_s$ | Configuration |
|---|---|---|---|---|---|
| IIa-151 | Me | 4-OMe | 4'-Br | H | R/S |
| IIa-152 | Me | 4-Cl | 4'-Br | H | R/S |
| IIa-153 | Me | 4-$CF_3$ | 4'-Br | H | R/S |
| IIa-154 | Me | 4-Br | 4'-Br | H | R/S |
| IIa-155 | Me | H | 4'-Br | H | R/S |
| IIa-156 | Me | 4-F | 4'-Br | H | R/S |
| IIa-157 | Me | 4-Et | 4'-Br | H | R/S |

5. Synthesis of 2-benzothiazol-2-yl-phenols

The 2-benzothiazol-2-yl-phenol or 2-benzothiazol-2-yl-phenylfluorides used for the preparation of compounds II-X and IIa-X were prepared in the same manner as that described for the synthesis of 2-benzooxazol-2-yl-phenols and 2-benzooxazol-2-yl-phenylfluorides illustrated in Scheme II or can be prepared by those skilled in the arts.

Example 63

PhOH-11

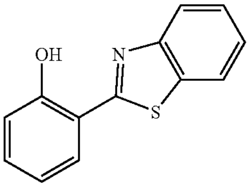

Compound PhOH-11 was purchased from Aldrich Chemicals Inc., USA.

Example 64

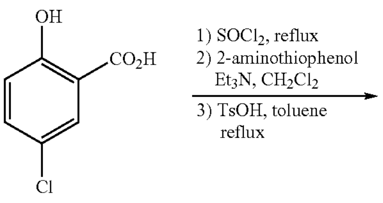

SI-32

-continued

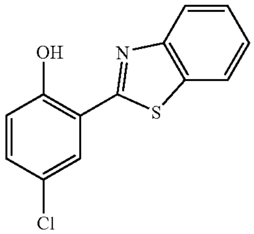

PhOH-12

A mixture of SI-32 (67 g, 0.388 mol) and $SOCl_2$ (42 mL, 0.582) was refluxed for 2 h. The mixture was concentrated to dryness and put on high vaccum for a while. To the residue was added THF (700 mL) and then 2-aminothiophenol (53.4 g, 0.427 mol) was added slowly at 0° C. To the resulted solution was added dropwise $Et_3N$ (82 mL, 0.582 mol) at 0° C., then warmed to room temperature and stirred overnight. The reaction mixture was acidified by addding 2N HCl and concentrated, to the residue was added water, filtered and washed with water to give a solid (98 g), which was used for the next reaction without further purification.

A mixture of the above crude product (98 g) and $TsOH.H_2O$ (12.5 g) in toluene (500 mL) was refluxed for 4 hours using Dean-Stark apparatus. The reaction mixture was cooled to room temperature. Filtration and washing with MeOH gave phenol PhOH-12 as an off-white solid (90 g, 89%). $^1$HNMR (d-DMSO, 400 MHz) δ 11.69 (s, 1H), 8.20 (d, 1H), 8.08 (d, 1H), 8.04 (d, 1H), 7.53–7.39 (m, 3H), 7.08 (d, 1H).

Example 65

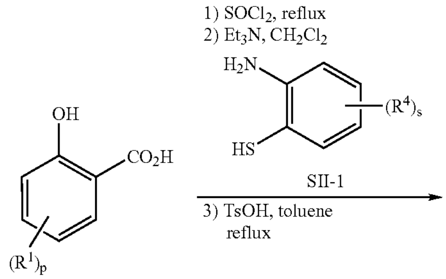

SI-28

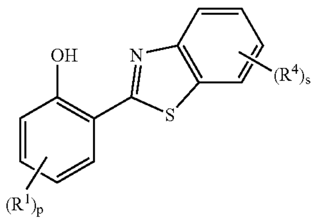

PhOH-X $R^1$ = H, 4'-$CF_3$, 4'-Cl, 4'-Me, 4'-tBu, 4'-Br, 4',6'-diCl, 4'-(1H-pyrrol-yl), 4'-(1H-pyrrol-yl) etc.
$R^4$ = H, 2"-Cl, 2"-$CF_3$ etc.

In the same manner as that described in Example 64 compound PhOH-X can be prepared from commercially available SI-28.

Example 66

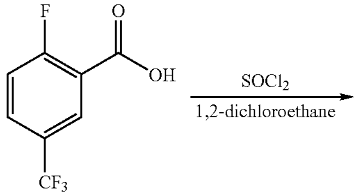

SI-36

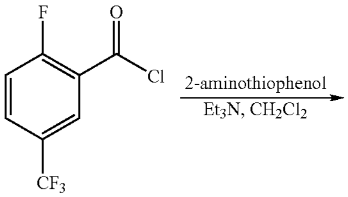

SI-37

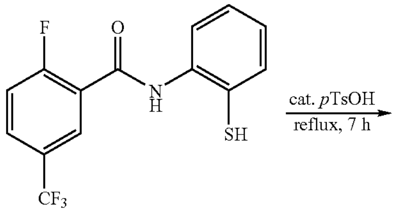

SII-2

-continued

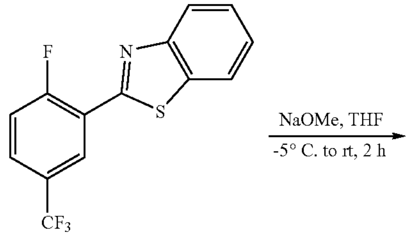

PhF-4

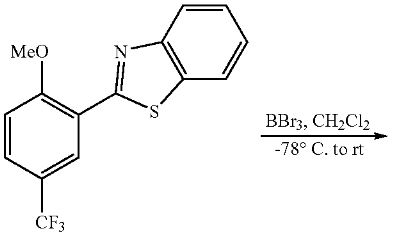

SII-3

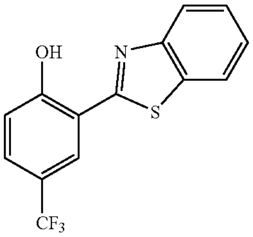

PhOH-16

In the same manner as that described in Example 23 compound PhF-4 and PhOH-16 were prepared from commercially available SI-36 and 2-aminothiophenol.

Example 67

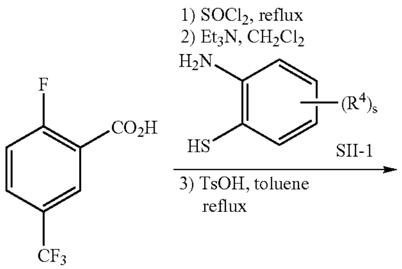

SI-36

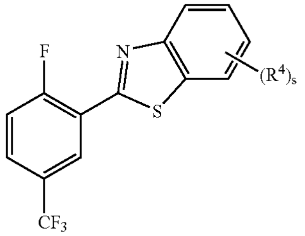

PhF-5

-continued

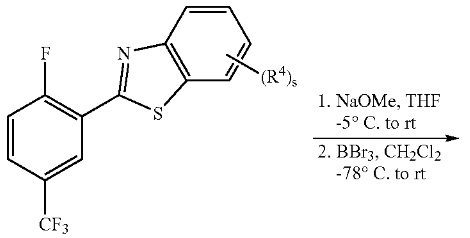

PhF-5

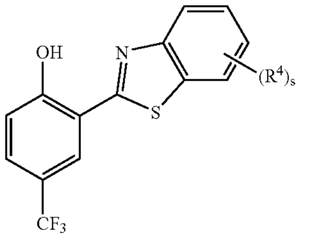

PhOH-17

$R^4$ = H, 2"-Cl, 2"-$CF_3$,

In the same manner as that described in Example 23 compound PhF-5 and PhOH-17 can be prepared from commercially available SI-36 and SII-1.

6. Synthesis of Compounds II and Ia in Table 2

Compounds II and IIa were or can be prepared in the same manner as that described for the synthesis of compounds I and Ia.

Example 68

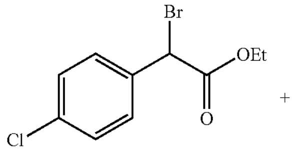

SBr-1

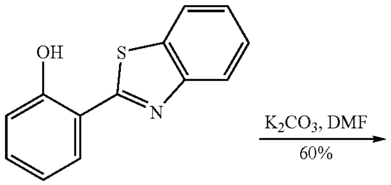

PhOH-11

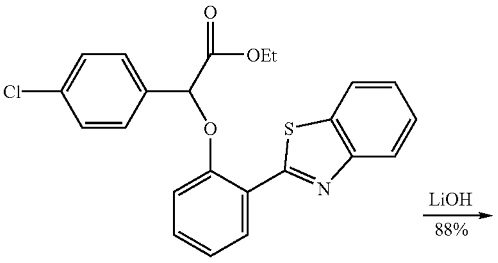

SII-4

-continued

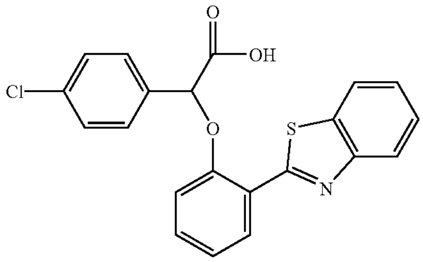

II-1

In the same manner as that described in Example 28 compound II-1 was prepared from SBr-6 and PhOH-11. $^1$HNMR (d-DMSO, 400 MHz) δ 8.44 (d, 1H), 8.17 (s, 1H), 8.07 (m, 3H), 7.83 (m, 1H), 7.75 (m, 1H), 7.55 (m, 2H), 7.47 (m, 1H), 7.31 (m, 1H), 7.22 (m, 1H), 6.51 (s, 1H).

Example 69

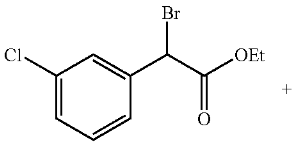

SBr-6

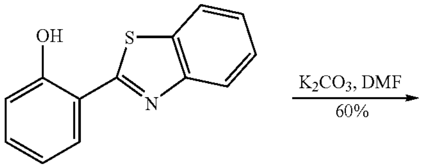

PhOH-11

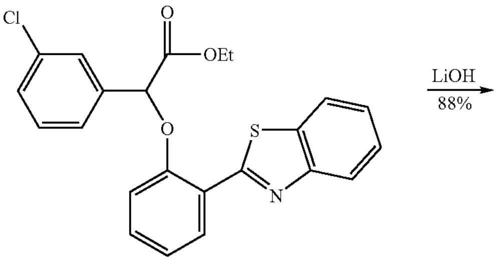

SII-5

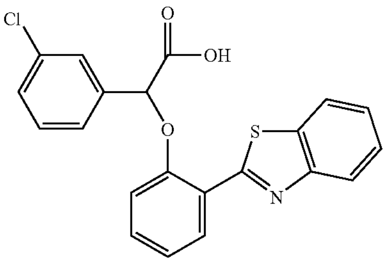

II-4

In the same manner as that described in Example 28 compound II-4 was prepared as a white solid (1.18 g). $^1$HNMR (d-DMSO, 400 MHz) δ 8.43 (ds, 1H), 8.07 (m, 2H), 7.79 (m, 1H), 7.67 (m, 1H), 7.54–7.41 (m, 5H), 7.26 (d, 1H), 7.19 (m, 1H), 6.35 (s, 1H).

Example 70

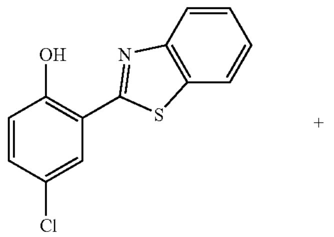

PhOH-12

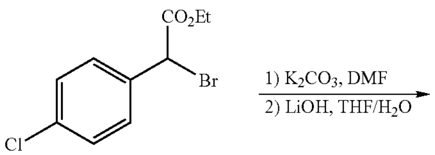

SBr-1

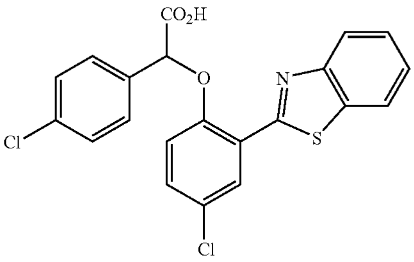

II-97

In the same manner as that described in Example 28 compound II-97 was prepared from SBr-1 and PhOH-12. II-97: $^1$HNMR (d-DMSO, 400 MHz) δ 13.62 (br, 1H), 8.40 (d, 1H), 8.10 (dd, 2H), 7.72 (d, 2H), 7.60–7.53 (m, 5H), 7.45 (m, 1H), 7.31 (d, 1H), 6.38 (s, 1H).

Example 71

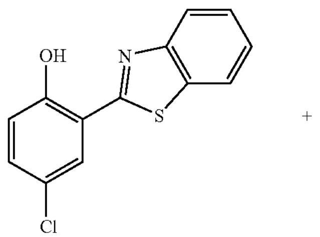

PhOH-12

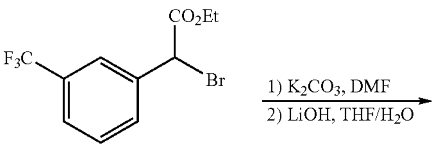

SBr-5

-continued

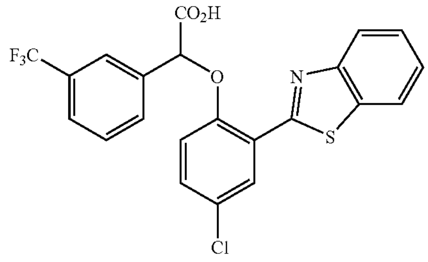

II-98

In the same manner as that described in Example 28 compound II-98 was prepared from SBr-5 and PhOH-12. $^1$HNMR (400 MHz, DMSO-d$6_1$): δ 8.38 (d, 1H), 8.11–8.00 (m, 4H), 7.83 (d, 1H), 7.73 (m, 1H), 7.63 (dd, 1H), 7.58 (m, 1H), 7.68 (m, 1H), 7.34 (d, 1H), 6.52 (s, 1H).

Example 72

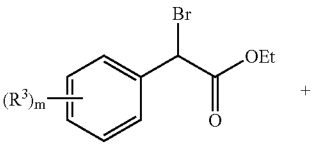

SBr-X

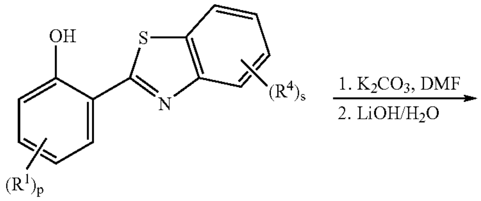

PhOH-X

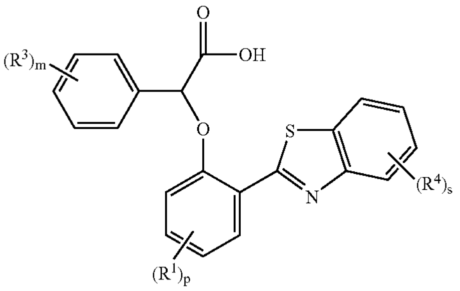

II-11 to II-157

$R^3$ = 4-Cl, 3-$CF_3$, 3-OPh, 3-Cl, 4-OMe, 4-$CF_3$, 4-Br, H, 4-F, 4-Et
$R^1$ = H, 4′-$CF_3$, 4′,6′-diCl, 4′-(2,4-diF)Ph, 4′-(1H)-pyrrolyl, 4′-Cl, 4′-Me, 4′-tBu, 4′-Br,
$R^4$ = 2″-Cl In the same manner as that described in Example 28 the rest of compound II-X can be prepared from SBr-X and PhOH-X.

Example 73

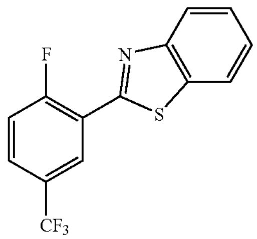

+

PHF-4

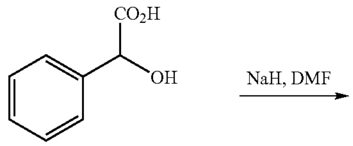

SOH-3

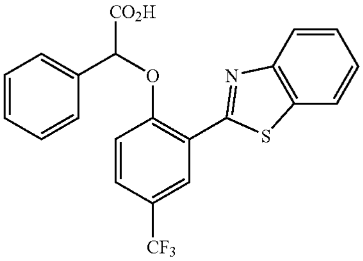

II-26

In the same manner as that described in Example 35 compound II-26 was prepared from SOH-3 and PhF-4. II-26: $^1$HNMR (d-DMSO, 400 MHz) δ 13.60 (br, 1H), 8.71 (s, 1H), 8.12 (m, 2H), 7.90 (m, 1H), 7.71 (m, 2H), 7.54 (m, 1H), 7.46 (m, 5H), 6.44 (s, 1H).

Example 74

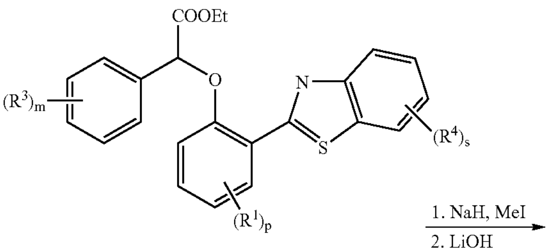

SII-12

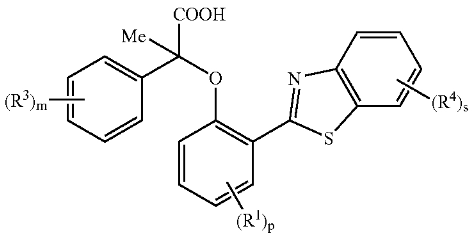

IIa-1 to IIa-157

-continued $R^3$ = 4-Cl, 3-$CF_3$, 3-OPh, 3-Cl, 4-OMe, 4-$CF_3$, 4-Br, H, 4-F, 4-Et, 2,3-di-F, 2,4-di-F, 2,5-di-F, 2,6-di-F, 3,4-di-F, 3,5-di-F, 2,3,5-tri-F, 3-OMe, 3-$NO_2$, 3,4-methylenedioxy, 2,3,6-tri-F, 2-Cl, 4-iPr, 4-Me, 4-MeS, 4-$NO_2$, 2,5-di-Me, 4-Et.
$R^1$ = H, 4′-$CF_3$, 4′-Cl, 4′-Br, 4′-Me, 4′-tBu, 4′,6′-diCl, 4′-(1H-pyrrol-yl), 4′-(1H-pyrrol-yl) etc.
$R^4$ = H, 2-Cl, 2-$CF_3$ In the same manner as that described in Example 42 compound IIa-1 to IIa-157 can be prepared from SI-55.

7. Enantioselective Synthesis and Enantiomer Separation

The enantiomers of compounds II-X and IIa-X were or can be obtained in the same manner as that decribed in Section 4 and Example 45 to Example 62.

Example 75

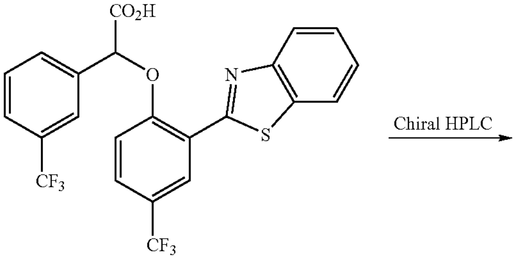

II-22

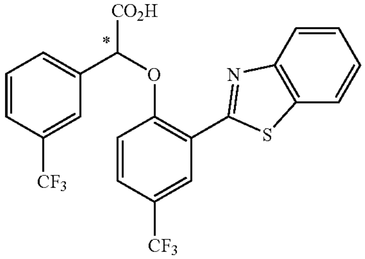

(+)-II-22

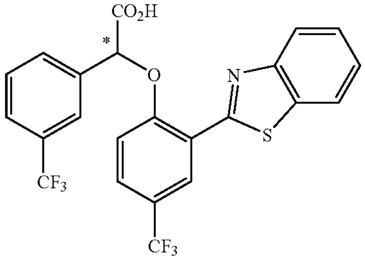

(-)-II-22

(+)-II-22 and (−)-II-22 was separated in the same manner as described in Example 49.

Example 76

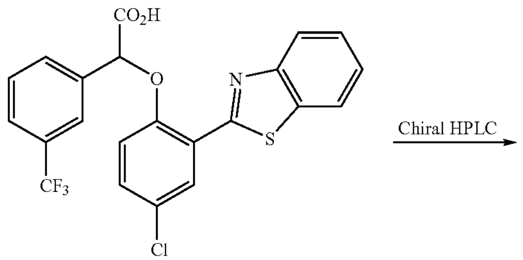

II-98

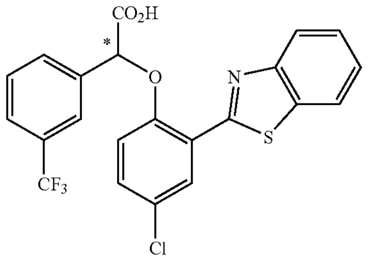

(+)-II-98

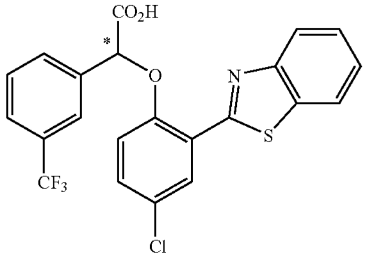

(-)-II-98

(+)-II-98 and (−)-II-98 was separated in the same manner as described in Example 49

TABLE 3

2-benzooxazole and 2-benzothiazole analogs

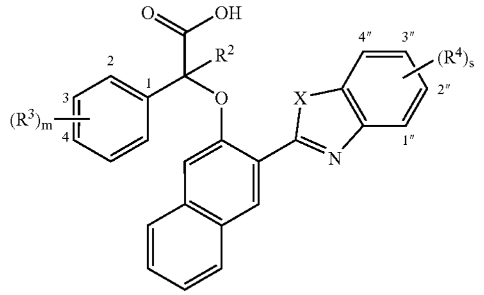

Compounds III

| Compound | $R^2$ | $(R^3)_m$ | X | $(R^4)_s$ | Configuration |
|---|---|---|---|---|---|
| III-1 | H | 4-Cl | O | H | R/S |
| III-2 | H | 3-$CF_3$ | O | H | R/S |
| III-3 | H | 3-OPh | O | H | R/S |
| III-4 | H | 3-Cl | O | H | R/S |
| III-5 | H | 4-OMe | O | H | R/S |
| III-6 | H | 4-$CF_3$ | O | H | R/S |
| III-7 | H | 4-Br | O | H | R/S |
| III-8 | H | H | O | H | R/S |
| III-9 | H | 4-F | O | H | R/S |
| III-10 | H | 4-Et | O | H | R/S |
| III-11 | H | 4-Cl | S | H | R/S |

TABLE 3-continued 2-benzooxazole and 2-benzothiazole analogs

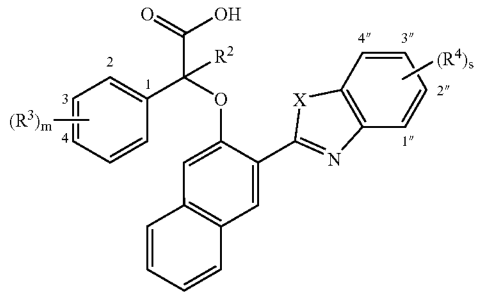

Compounds III

| Compound | $R^2$ | $(R^3)_m$ | X | $(R^4)_s$ | Configuration |
|---|---|---|---|---|---|
| III-12 | H | 3-$CF_3$ | S | H | R/S |
| III-13 | H | 3-OPh | S | H | R/S |
| III-14 | H | 3-Cl | S | H | R/S |
| III-15 | H | 4-OMe | S | H | R/S |
| III-16 | H | 4-$CF_3$ | S | H | R/S |
| III-17 | H | 4-Br | S | H | R/S |
| III-18 | H | H | S | H | R/S |
| III-19 | H | 4-F | S | H | R/S |
| III-10 | H | 4-Et | S | H | R/S |

Example 77

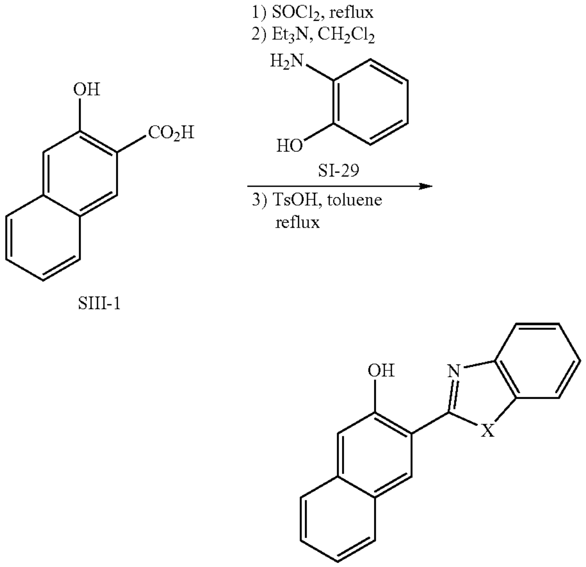

X = O, PhOH-18a
X = S, PhOH-19a

In the same manner as that described in Example 18 compound PhOH-18a, 19a can be prepared from commercially available SI-29 and SIII-1.

Example 78

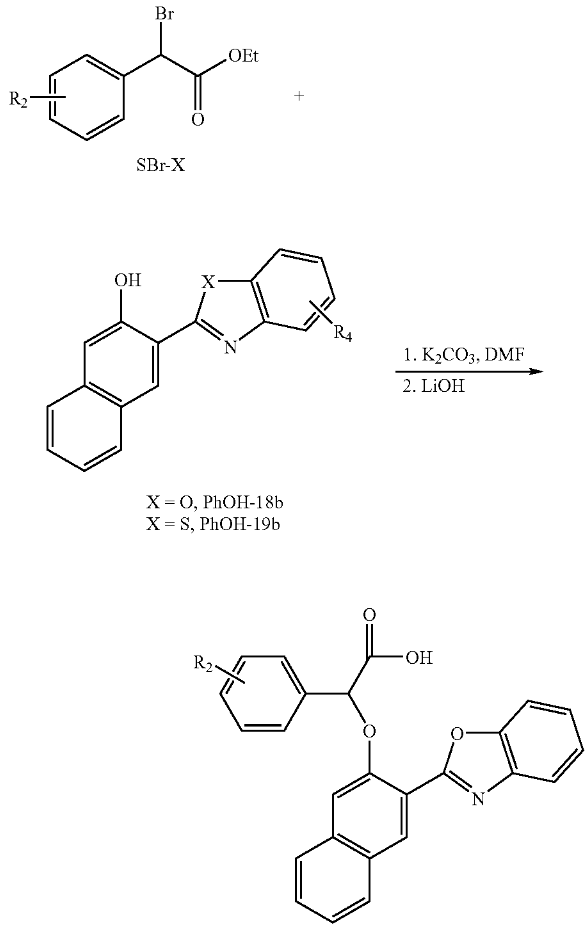

SBr-X

X = O, PhOH-18b
X = S, PhOH-19b

III-X $R_2$ = 4-Cl, 3-$CF_3$, 3-OPh, 3-Cl, 4-OMe, 4-$CF_3$, 4-Br, 4-F, 4-Et

In the same manner as that described in Example 28 compound III-X can be prepared from commercially available SBr-X and PhOH-18a, 19a.

TABLE 4

3-benzooxazole and 3-benzothiazole analogs

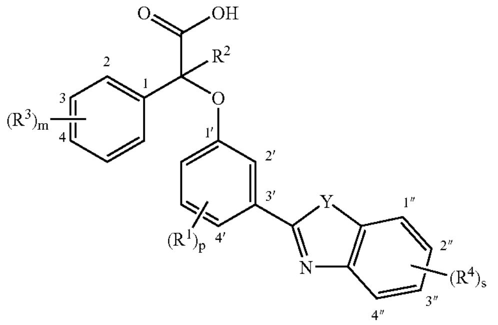

Compounds IV

| | $R^2$ | $(R^3)_m$ | $(R^1)_p$ | $(R^4)_s$ | Y | Configuration |
|---|---|---|---|---|---|---|
| IV-1 | H | 4-Cl | H | H | 0 | R/S |
| IV-2 | H | 3-$CF_3$ | H | H | O | R/S |

TABLE 4-continued 3-benzooxazole and 3-benzothiazole analogs

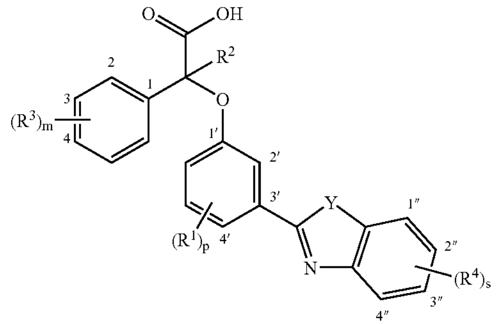

Compounds IV

| | $R^2$ | $(R^3)_m$ | $(R^1)_p$ | $(R^4)_s$ | Y | Configuration |
|---|---|---|---|---|---|---|
| IV-3 | H | 3-OPh | H | H | O | R/S |
| IV-4 | H | 3-Cl | H | H | O | R/S |
| IV-5 | H | 4-$CF_3$ | H | H | O | R/S |
| IV-6 | H | 3-OMe | H | H | O | R/S |
| IV-7 | H | 4-OMe | H | H | O | R/S |
| IV-8 | H | 3-F, 5-F | H | H | O | R/S |
| IV-9 | H | 2-F, 4-F | H | H | O | |
| IV-10 | H | 4-Et | H | H | O | |
| IV-11 | H | 4-Cl | 2-Me | H | O | R/S |
| IV-12 | H | 3-$CF_3$ | 2-Me | H | O | R/S |
| IV-13 | H | 3-OPh | 2-Me | H | O | R/S |
| IV-14 | H | 3-Cl | 2-Me | H | O | R/S |
| IV-15 | H | 4-$CF_3$ | 2-Me | H | O | R/S |
| IV-16 | H | 3-OMe | 2-Me | H | O | R/S |
| IV-17 | H | 4-OMe | 2-Me | H | O | R/S |
| IV-18 | H | 3-F, 5-F | 2-Me | H | O | R/S |
| IV-19 | H | 2-F, 4-F | 2-Me | H | O | |
| IV-20 | H | 4-Et | 2-Me | H | O | |
| IV-21 | H | 4-Cl | H | H | S | |
| IV-22 | H | 4-Cl | 2-Me | H | S | R/S |

Example 79

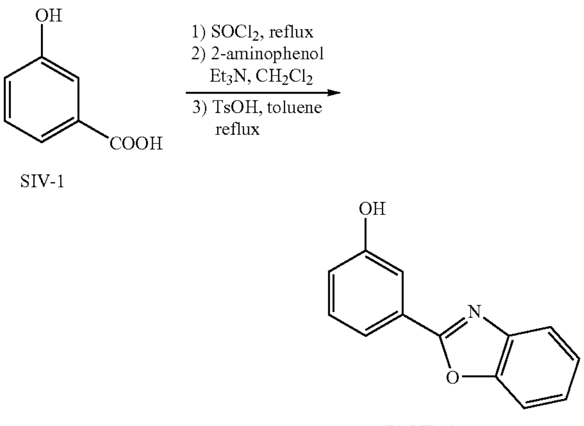

SIV-1

PhOH-18

In the same manner as that described in Example 18, PhOH-18 can be prepared from SIV-1.

Example 80

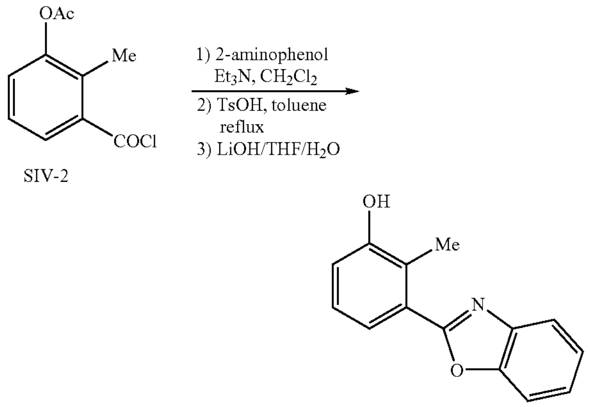

SIV-2

PhOH-19

In the same manner as that described in Example 18, PhOH-19 was prepared from SIV-2. PhOH-19: $^1$H NMR ($CDCl_3$, 400 MHz) δ 7.82 (m, 1H), 7.71 (d, 1H), 7.61 (m, 1H), 7.39 (m, 2H), 7.23 (m, 1H), 6.98 (d, 1H), 5.40 (br, 1H), 2.69 (s, 3H).

Example 81

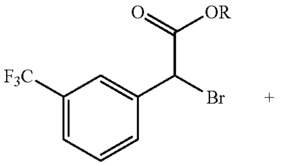

SBr-2

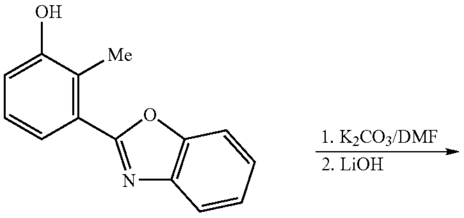

PhOH-19

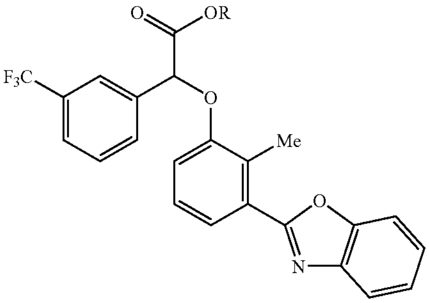

IV-11

In the same manner as that described in Example 28 compound IV-11 was prepared from SBr-2 and PhOH-19.

Example 82

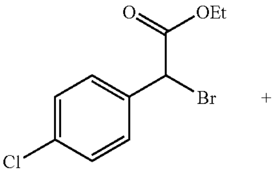

SBr-1

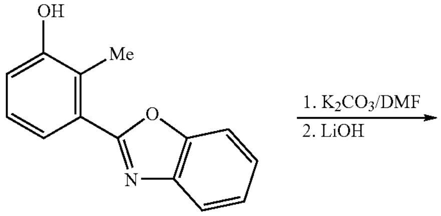

PhOH-19

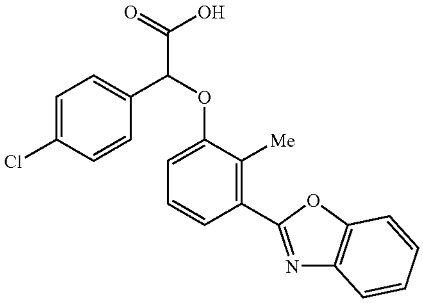

IV-11

In the same manner as that described in Example 28 compound IV-12 was prepared from SBr-1 and PhOH-19. IV-11: $^1$HNMR (d-DMSO, 400 MHz) δ 13.41 (br, 1H), 7.83 (d, 1H), 7.80 (d, 1H), 7.65 (m, 3H), 7.52 (d, 2H), 7.46–7.39 (m, 2H), 7.35 (m, 1H), 7.16 (d, 1H), 6.05 (s, 1H), 2.69 (s, 3H).

Example 83

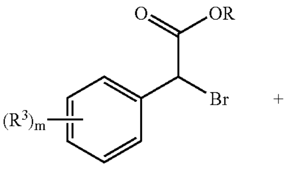

SBr-X

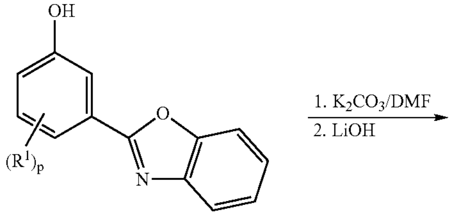

PhOH-X
Y = O, S

-continued

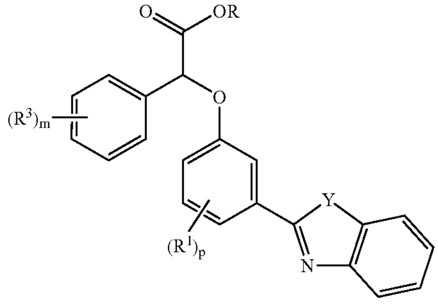

IV-X

In the same manner as that described in Example 28 the rest of IV-X listed Table 4 can be prepared.

TABLE 5

4-benzooxazole and 4-benzothiazole analogs

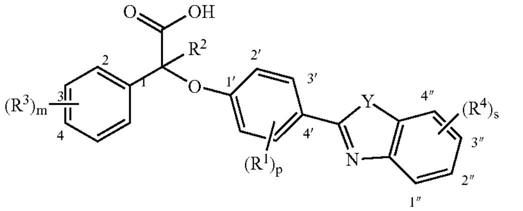

Compounds V

| | $R^2$ | $(R^3)_m$ | $(R^1)_p$ | $(R^4)_s$ | Y | Configuration |
|---|---|---|---|---|---|---|
| V-1 | H | 3-$CF_3$ | H | H | O | R/S |
| V-2 | H | 4-Cl | H | H | O | R/S |
| V-3 | H | 3-OPh | H | H | O | R/S |
| V-4 | H | 3-Cl | H | H | O | R/S |
| V-5 | H | 4-$CF_3$ | H | H | O | R/S |
| V-6 | H | 3-OMe | H | H | O | R/S |
| V-7 | H | 4-OMe | H | H | O | R/S |
| V-8 | H | 3-F, 5-F | H | H | O | R/S |
| V-9 | H | 2-F, 4-F | H | H | O | |
| V-10 | H | 4-Et | H | H | O | |
| V-11 | H | 4-Cl | H | H | S | |

Example 84

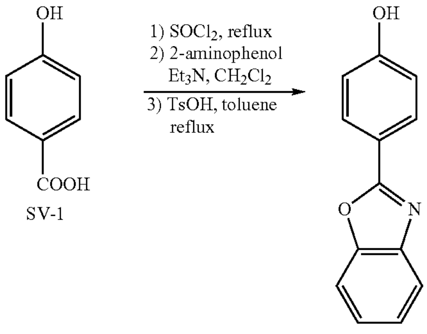

SV-1

PhOH-20

In the same manner as that described in Example 18, PhOH-20 was prepared from SV-1. PhOH-20: $^1H$ NMR (d-DMSO, 400 MHz) δ 10.36 (br, 1H), 8.05 (d, 2H), 7.75 (m, 2H), 7.38 (d, 2H), 6.97 (d, 2H).

Example 85

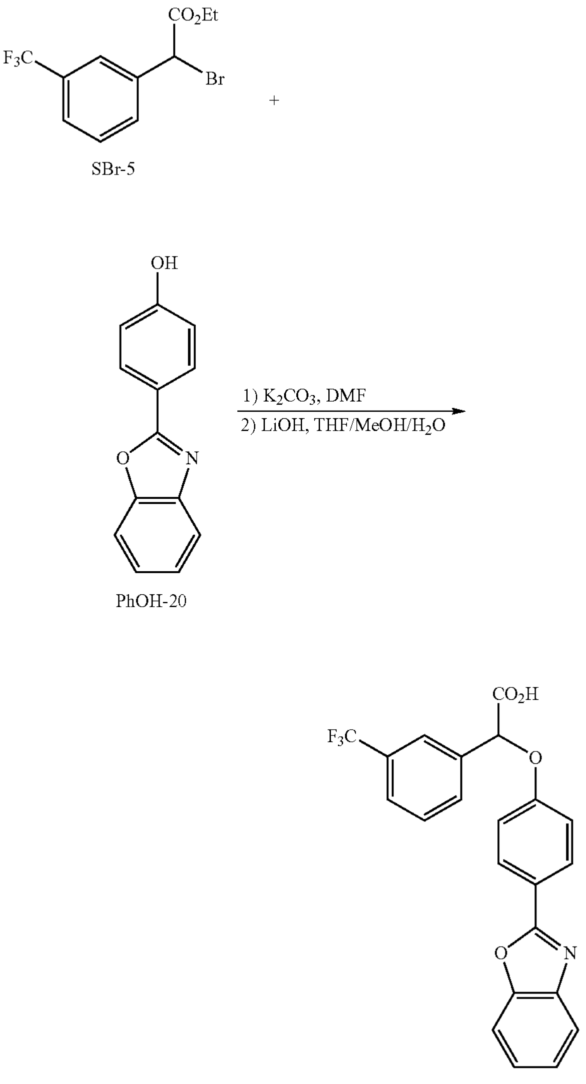

SBr-5

PhOH-20

V-1

In the same manner as that described in Example 28 compound V-1 was prepared from SBr-5 and PhOH-20. $^1H$ NMR (d-DMSO, 400 MHz) δ 13.60 (br, 1H), 8.19 (d, 2H), 7.90 (m, 2H), 7.75 (m, 4H), 7.40 (m, 2H), 7.22 (d, 2H), 6.22 (s, 1H).

Example 86

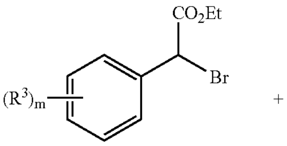

SBr-X

-continued

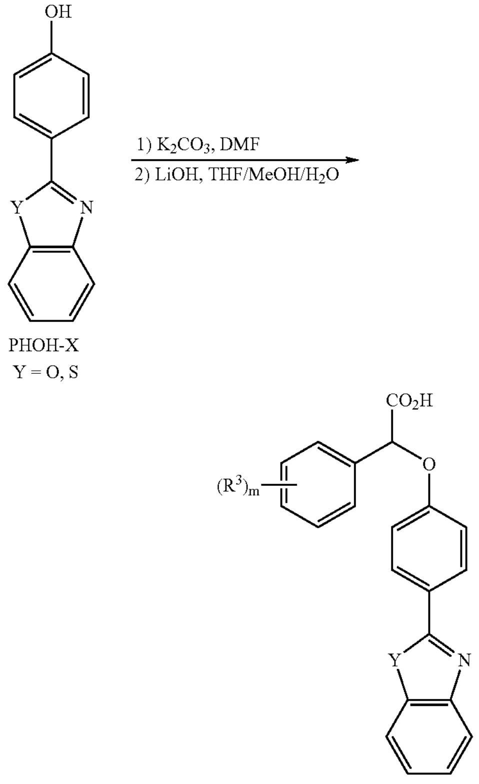

PHOH-X
Y = O, S

V-2 to 11

In the same manner as that described in Example 28 compound V-2 to V-11 can be prepared from SBr-X and PhOH-X.

TABLE 6

2-benzooxazole and 2-benzothiazole anilino analogs

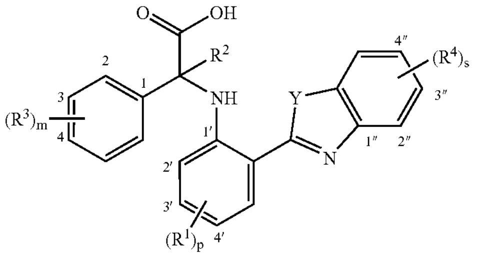

Compounds VI and VIa

| Compound | $R^2$ | $(R^3)_m$ | $(R^1)_p$ | $(R^4)_s$ | Y | Configuration |
|---|---|---|---|---|---|---|
| VI-1 | H | 4-Cl | H | H | O | R/S |
| VI-2 | H | 3-$CF_3$ | H | H | O | R/S |
| VI-3 | H | 3-OPh | H | H | O | R/S |
| VI-4 | H | 3-Cl | H | H | O | R/S |
| VI-5 | H | 4-OMe | H | H | O | R/S |
| VI-6 | H | 4-$CF_3$ | H | H | O | R/S |
| VI-7 | H | 4-Br | H | H | O | R/S |
| VI-8 | H | H | H | H | O | R/S |
| VI-9 | H | 4-F | H | H | O | R/S |
| VI-10 | H | 4-Et | H | H | O | R/S |
| VI-11 | H | 4-Cl | 5'-$CF_3$ | H | O | R/S |
| VI-12 | H | 3-$CF_3$ | 5'-$CF_3$ | H | O | R/S |
| VI-13 | H | 3-OPh | 5'-$CF_3$ | H | O | R/S |
| VI-14 | H | 3-Cl | 5'-$CF_3$ | H | O | R/S |
| VI-15 | H | 4-OMe | 5'-$CF_3$ | H | O | R/S |

TABLE 6-continued 2-benzooxazole and 2-benzothiazole anilino analogs

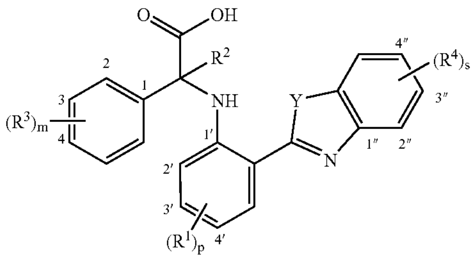

Compounds VI and VIa

| Compound | $R^2$ | $(R^3)_m$ | $(R^1)_p$ | $(R^4)_s$ | Y | Configuration |
|---|---|---|---|---|---|---|
| VI-16 | H | 4-$CF_3$ | 5'-$CF_3$ | H | O | R/S |
| VI-17 | H | 4-Br | 5'-$CF_3$ | H | O | R/S |
| VI-18 | H | H | 5'-$CF_3$ | H | O | R/S |
| VI-19 | H | 4-F | 5'-$CF_3$ | H | O | R/S |
| VI-20 | H | 4-Et | 5'-$CF_3$ | H | O | R/S |
| VI-21 | H | 3-$CF_3$ | 4'-Cl | H | O | R/S |
| VI-22 | H | 3-Cl | 4'-Cl | H | O | R/S |
| VI-23 | H | H | 4'-Cl | H | O | R/S |
| VI-24 | H | 4-OMe | 4'-Cl | H | O | R/S |
| VI-25 | H | 3-OMe | 4'-Cl | H | O | R/S |
| VI-26 | H | 4-Br | 4'-Cl | H | O | R/S |
| VI-27 | H | 3-Ph | 4'-Cl | H | O | R/S |
| VI-28 | H | 4-Cl | 4'-Cl | H | O | R/S |
| VI-29 | H | 4-$CF_3$ | 4'-Cl | H | O | R/S |
| VI-30 | H | 4-F | 4'-Cl | H | O | R/S |
| VI-31 | H | 4-Et | 4'-Cl | H | O | R/S |
| VI-32 | H | 3-Cl | 4'-Br | H | O | R/S |
| VI-33 | H | 3-$CF_3$ | 4'-Br | H | O | R/S |
| VI-34 | H | 3-OPh | 4'-Br | H | O | R/S |
| VI-35 | H | 4-OMe | 4'-Br | H | O | R/S |
| VI-36 | H | 4-Cl | 4'-Br | H | O | R/S |
| VI-37 | H | 4-$CF_3$ | 4'-Br | H | O | R/S |
| VI-38 | H | 4-Br | 4'-Br | H | O | R/S |
| VI-39 | H | H | 4'-Br | H | O | R/S |
| VI-40 | H | 4-F | 4'-Br | H | O | R/S |
| VI-41 | H | 4-Et | 4'-Br | H | O | R/S |
| VI-42 | H | 3-Cl | 4'-F | H | O | R/S |
| VI-43 | H | 3-$CF_3$ | 4'-F | H | O | R/S |
| VI-44 | H | 3-OPh | 4'-F | H | O | R/S |
| VI-45 | H | 4-OMe | 4'-F | H | O | R/S |
| VI-46 | H | 4-Cl | 4'-F | H | O | R/S |
| VI-47 | H | 4-$CF_3$ | 4'-F | H | O | R/S |
| VI-48 | H | 4-Br | 4'-F | H | O | R/S |
| VI-49 | H | H | 4'-F | H | O | R/S |
| VI-50 | H | 4-F | 4'-F | H | O | R/S |
| VI-51 | H | 4-Et | 4'-F | H | O | R/S |
| VI-52 | H | 3-Cl | 3',4'-diF | H | O | R/S |
| VI-53 | H | 3-$CF_3$ | 3',4'-diF | H | O | R/S |
| VI-54 | H | 3-OPh | 3',4'-diF | H | O | R/S |
| VI-55 | H | 4-OMe | 3',4'-diF | H | O | R/S |
| VI-56 | H | 4-Cl | 3',4'-diF | H | O | R/S |
| VI-57 | H | 4-$CF_3$ | 3',4'-diF | H | O | R/S |
| VI-58 | H | 4-Br | 3',4'-diF | H | O | R/S |
| VI-59 | H | H | 3',4'-diF | H | O | R/S |
| VI-60 | H | 4-F | 3',4'-diF | H | O | R/S |
| VI-61 | H | 4-Et | 3',4'-diF | H | O | R/S |
| VI-62 | H | 4-$CF_3$ | 4'-$CF_3$ | H | O | R/S |
| VI-63 | H | H | 4'-$CF_3$ | H | O | R/S |
| VI-64 | H | 4-OMe | 4'-$CF_3$ | H | O | R/S |
| VI-65 | H | 3-$CF_3$ | 4'-$CF_3$ | H | O | R/S |
| VI-66 | H | 3-Cl | 4'-$CF_3$ | H | O | R/S |
| VI-67 | H | 4-Me | 4'-$CF_3$ | H | O | R/S |
| VI-68 | H | 4-Cl | 4'-$CF_3$ | H | O | R/S |
| VI-69 | H | 4-Br | 4'-$CF_3$ | H | O | R/S |
| VI-70 | H | 4-iPr | 4'-$CF_3$ | H | O | R/S |
| VI-71 | H | 4-Cl | H | H | S | R/S |
| VI-72 | H | 3-$CF_3$ | H | H | S | R/S |
| VI-73 | H | 3-OPh | H | H | S | R/S |
| VI-74 | H | 3-Cl | H | H | S | R/S |
| VI-75 | H | 4-OMe | H | H | S | R/S |

TABLE 6-continued 2-benzooxazole and 2-benzothiazole anilino analogs

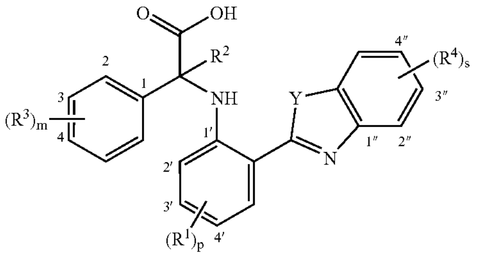

Compounds VI and VIa

| Compound | $R^2$ | $(R^3)_m$ | $(R^1)_p$ | $(R^4)_s$ | Y | Configuration |
|---|---|---|---|---|---|---|
| VI-76 | H | 4-$CF_3$ | H | H | S | R/S |
| VI-77 | H | 4-Br | H | H | S | R/S |
| VI-78 | H | H | H | H | S | R/S |
| VI-79 | H | 4-F | H | H | S | R/S |
| VI-80 | H | 4-Et | H | H | S | R/S |
| VI-81 | H | 3-$CF_3$ | 4'-Cl | H | S | R/S |
| VI-82 | H | 3-Cl | 4'-Cl | H | S | R/S |
| VI-83 | H | H | 4'-Cl | H | S | R/S |
| VI-84 | H | 4-OMe | 4'-Cl | H | S | R/S |
| VI-85 | H | 3-OMe | 4'-Cl | H | S | R/S |
| VI-86 | H | 4-Br | 4'-Cl | H | S | R/S |
| VI-87 | H | 3-Ph | 4'-Cl | H | S | R/S |
| VL-88 | H | 4-Cl | 4'-Cl | H | S | R/S |
| VI-89 | H | 4-$CF_3$ | 4'-Cl | H | S | R/S |
| VI-90 | H | 4-F | 4'-Cl | H | S | R/S |
| VI-91 | H | 4-Et | 4'-Cl | H | S | R/S |
| VI-92 | H | 4-$CF_3$ | 4'-$CF_3$ | H | S | R/S |
| VI-93 | H | H | 4'-$CF_3$ | H | S | R/S |
| VI-94 | H | 4-OMe | 4'-$CF_3$ | H | S | R/S |
| VI-95 | H | 3-$CF_3$ | 4'-$CF_3$ | H | S | R/S |
| VI-96 | H | 3-Cl | 4'-$CF_3$ | H | S | R/S |
| VI-97 | H | 4-Me | 4'-$CF_3$ | H | S | R/S |
| VI-98 | H | 4-Cl | 4'-$CF_3$ | H | S | R/S |
| VI-99 | H | 4-Br | 4'-$CF_3$ | H | S | R/S |
| VI-100 | H | 4-iPr | 4'-$CF_3$ | H | S | R/S |
| VIa-1 | Me | H | 4'-$CF_3$ | H | S | R/S |
| VIa-2 | Me | H | 4'-$CF_3$ | H | S | R/S |

8. Synthesis of 2-benzooxazole and 2-benzothiazole anilines

The 2-benzooxazole and 2-benzothiazole anilines used for the preparation of compounds VI and VIa were prepared in the same manner as that described for the synthesis of 2-benzooxazol-2-yl-phenols illustrated in Scheme 2 or by those skilled in the art.

Scheme 5
Synthesis of 2-benzooxazole and 2-benzothiazole anilines

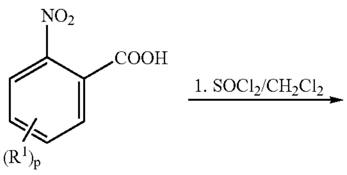

SVI-1

-continued

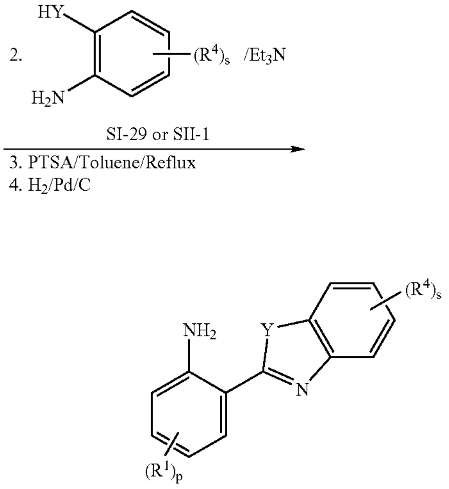

PhNH$_2$-X
Y = O, S

Example 87

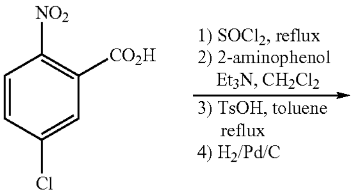

SVI-2

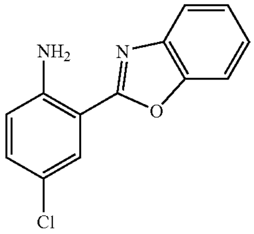

PhNH$_2$-1

In the similar manner as that described in Example 18, PhNH$_2$-1 can be prepared from SVI-2.

Example 88

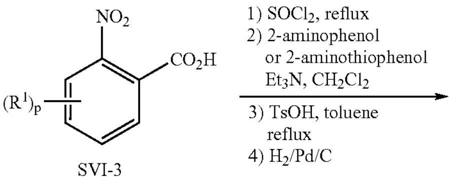

SVI-3

-continued

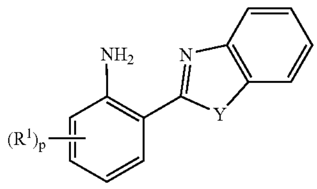

$PhNH_2$—X
Y = O, S $R^1$ = H, 5′-$CF_3$, 5′-Cl, ′5-F, 4′-Cl, 4′-Me, 4′-OMe, 4′-Br, 4′-F, 3′,4′-diF, ′4-$CF_3$

In the similar manner as that described in Example 18, $PhNH_2$-X can be prepared 5 from SVI-3.

9. Synthesis of Compounds VI and VIa in Table 6

Compounds VI-X and VIa-X were or can be prepared in the same manner as that described for the synthesis of compounds I-X and Ia-X.

Example 89

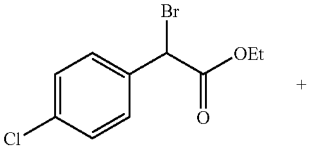

SBr-1

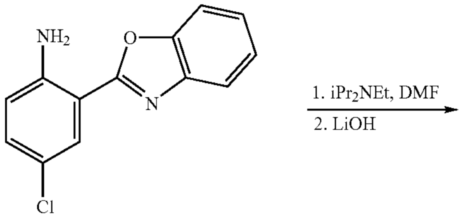

$PhNH_2$-1

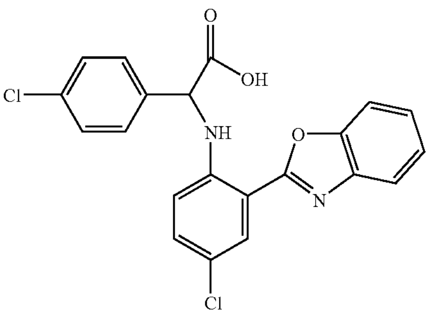

VI-28

In the same manner as that described in Example 28 compound VI-28 was prepared from SBr-1 and $PhNH_2$-1.

Example 90

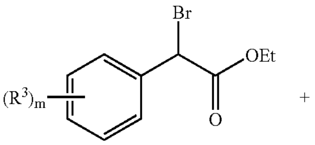

SBr-X

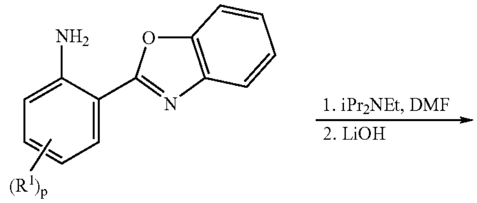

$PhNH_2$-X

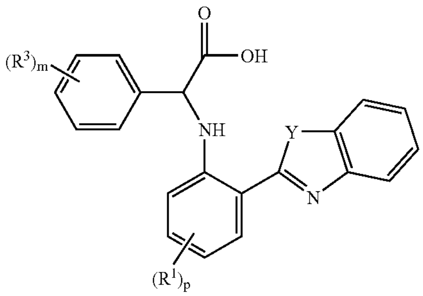

VI-X
Y = O, S

R3 = 3-$CF_3$, 3-Cl, H, 4-OMe, 3-OMe, 4-Br, 3-Ph, 4-Cl, 4-$CF_3$, 4-F, 4-Et
R1 = H, 5′-$CF_3$, 5′-Cl, ′5-F, 4′-Cl, 4′-Me, 4′-OMe, 4′-Br, 4′-F, 3′, 4′-diF, 3′, 4′-diOMe, ′4-$CF_3$

In the same manner as that described in Example 28 the rest of compounds VI-X in Table 6 can be prepared from SBr-X and $PhNH_2$-X.

Example 91

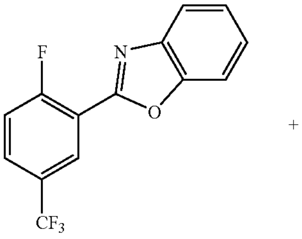

PhF-1

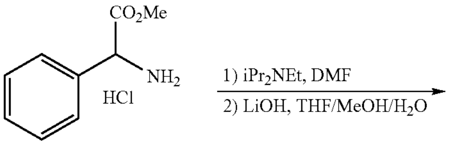

SVI-4

-continued

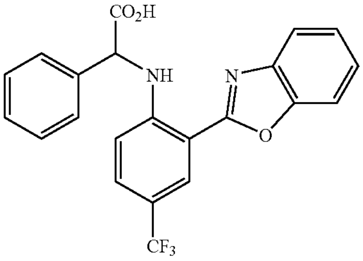

VI-63

A mixture of PhF-1 (1.124 g, 4.0 mmol), SVI-4 (0.914 g, 4.40 mmol) and $iPr_2NEt$ (1.32 mL, 7.6 mmol) in DMF (10 mL) was heated at 100° C. for 24 h. After cooling to room temperature the mixture was poured into a mixture of ice and waterand extracted with EtOAc. The organic layer was washed with brine, dried and concentrated. The residue was recrystallized from MeOH to give a white solid (0.6 g).

To the above product in THF/MeOH (15 mL/30 mL) was added 1M LiOH solution (10 mL). The mixture was heated at 70° C. for 0.5 h, cooled to room temperature and quenched by adding 1 N HCl (10 mL). The mixture was concentrated and extracted with EtOAc. The organic layer washed with water, dried and concentrated. Crystallization from MeOH gave VI-63 as a white solid (0.45 g). $^1H$ NMR (d-DMSO, 400 MHz) δ 9.87 (d, 1H), 8.28 (d, 1H), 7.85 (m, 2H), 7.60 (dd, 1H), 7.50 (m, 7H), 6.83 (d, 1H), 5.61 (d, 1H).

Example 92

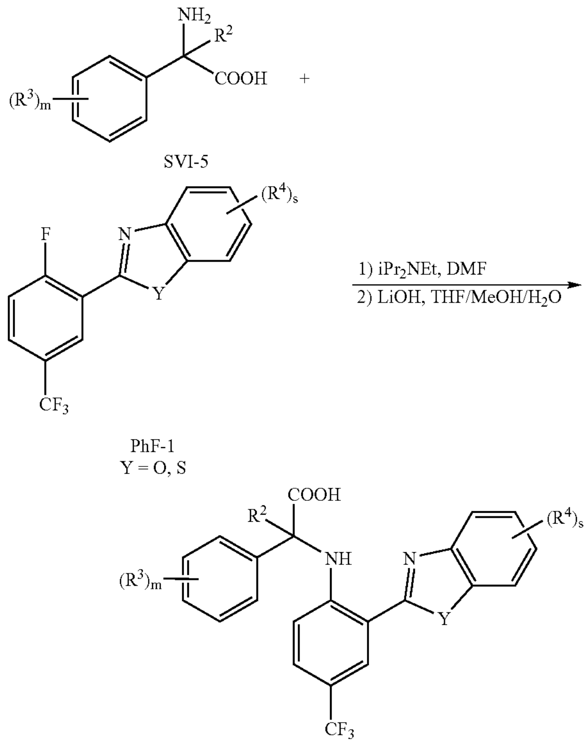

SVI-5

+

PhF-1
Y = O, S

VI 70 to VI-80
VI-90 to VI-100

-continued $R^2$ = H, Me
$R^3$ = 2′-Cl, 3′-Br, 3-Cl-4-F, 3,5-di$CF_3$, 4-$CF_3$, H, 4-OMe, 3-$CF_3$, 3-Cl, 4-Me, 4-Cl, 4-Br, 4-iPr.
$R^4$ = H, 5′-$CF_3$, 5′-Cl, ′5-F, 4′-Cl, 4′-Me, 4′-OMe, 4′-Br, 4′-F, 3′,4′-diF, 3′, 4′-diOMe, ′4-$CF_3$ In the same manner as that described in Example 91 compound VI-70 to VI-80 and VI-90 to VI-100 in Table 6 can be prepared from SVI-5 and PhF-1.

10. Enantioselective Synthesis and Enantiomers Separations

The individual enantiomers of compounds VI-X and VIa-X listed in Table 6 can be obtained in the same manner as that described in Section 4 and Example 45 to Example 62.

TABLE 7

2-benzooxazole and 2-benzothiazole anilino analogs

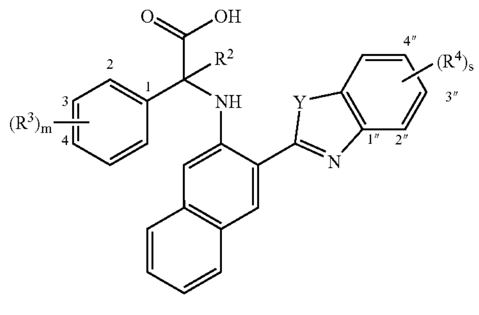

Compounds VII

| Compound | $R^2$ | $(R^3)_m$ | $(R^4)_s$ | Y | Configuration |
|---|---|---|---|---|---|
| VII-1 | H | 4-Cl | H | O | R/S |
| VII-2 | H | 3-$CF_3$ | H | O | R/S |
| VII-3 | H | 3-OPh | H | O | R/S |
| VII-4 | H | 3-Cl | H | O | |
| VII-5 | H | 4-OMe | H | O | |
| VII-6 | H | 4-$CF_3$ | H | O | |
| VII-7 | H | 4-Br | H | O | |
| VII-8 | H | H | H | O | |
| VII-9 | H | 4-F | H | O | |
| VII-10 | H | 4-Et | H | O | |
| VII-11 | H | 4-Cl | H | S | |

All the compounds listed in Table 7 can be prepared with proper starting materials in the same manner as that described for the synthesis of compounds listed in Table 6.

TABLE 8

2-Benzoimidazole analogs

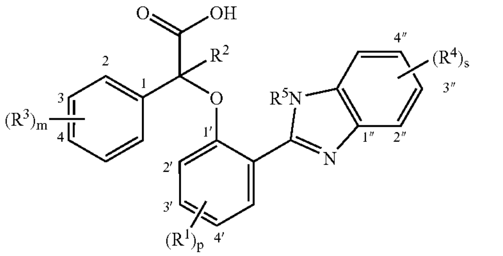

Compounds VIII

| Compound | $R^2$ | $(R^3)_m$ | $(R^1)_p$ | $(R^4)_s$ | $R^5$ | Configuration |
|---|---|---|---|---|---|---|
| VIII-1 | H | 4-Cl | H | H | Me | R/S |
| VIII-2 | H | 3-$CF_3$ | H | H | Me | R/S |
| VIII-3 | H | 3-OPh | H | H | Me | R/S |
| VIII-4 | H | 3-Cl | H | H | Me | R/S |
| VIII-5 | H | 4-OMe | H | H | Me | R/S |
| VIII-6 | H | 4-$CF_3$ | H | H | Me | R/S |
| VIII-7 | H | 4-Br | H | H | Me | R/S |
| VIII-8 | H | H | H | H | Me | R/S |
| VIII-9 | H | 4-F | H | H | Me | R/S |
| VIII-10 | H | 4-Et | H | H | Me | R/S |
| VIII-11 | H | 4-Cl | 4'-Cl | H | Me | R/S |
| VIII-12 | H | 3-$CF_3$ | 4'-Cl | H | Me | R/S |
| VIII-13 | H | 3-OPh | 4'-Cl | H | Me | R/S |
| VIII-14 | H | 3-Cl | 4'-Cl | H | Me | R/S |
| VIII-15 | H | 4-OMe | 4'-Cl | H | Me | R/S |
| VIII-16 | H | 4-$CF_3$ | 4'-Cl | H | Me | R/S |
| VIII-17 | H | 4-Br | 4'-Cl | H | Me | R/S |
| VIII-18 | H | H | 4'-Cl | H | Me | R/S |
| VIII-19 | H | 4-F | 4'-Cl | H | Me | R/S |
| VIII-20 | H | 4-Et | 4'-Cl | H | Me | R/S |
| VIII-21 | H | 4-Cl | 4'-Cl | 2"-Cl | Me | R/S |
| VIII-22 | H | 3-$CF_3$ | 4'-Cl | 2"-Cl | Me | R/S |
| VIII-23 | H | 3-OPh | 4'-Cl | 2"-Cl | Me | R/S |
| VIII-24 | H | 3-Cl | 4'-Cl | 2"-Cl | Me | R/S |
| VIII-25 | H | 4-OMe | 4'-Cl | 2"-Cl | Me | R/S |
| VIII-26 | H | 4-$CF_3$ | 4'-Cl | 2"-Cl | Me | R/S |
| VIII-27 | H | 4-Br | 4'-Cl | 2"-Cl | Me | R/S |
| VIII-28 | H | H | 4'-Cl | 2"-Cl | Me | R/S |
| VIII-29 | H | 4-F | 4'-Cl | 2"-Cl | Me | R/S |
| VIII-30 | H | 4-Et | 4'-Cl | 2"-Cl | Me | R/S |

11. Synthesis of 2-Benzoimidazol-2-yl-phenol

Scheme 6 illustrates the general route for preparing 2-benzoimidazol-2-yl-phenols. Generally, hydroxyl benzoic acids were treated with o-phenylenediamines under strongly dehydration conditions to afford the corresponding benzoimidazol-2-yl-phenols.

Scheme 6

Synthesis of benzoimidazol-2-yl-phenols

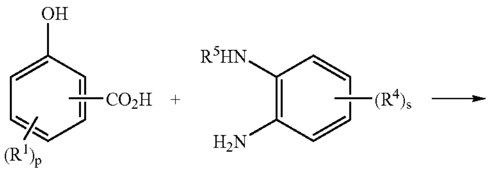

SVIII-1 SVIII-2

-continued

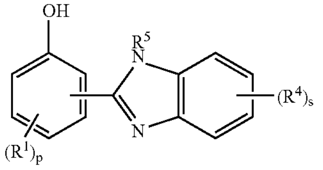

PhOH-X

Example 93

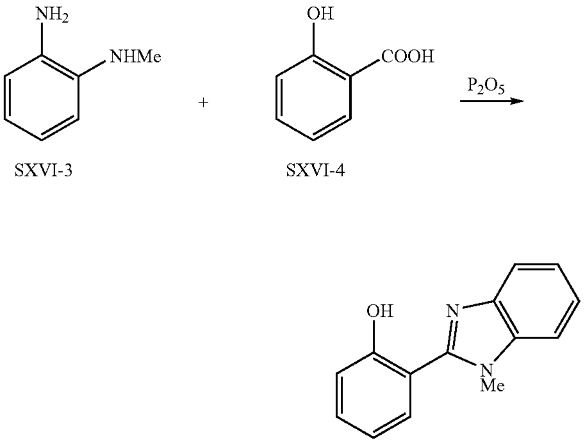

SXVI-3 SXVI-4

PhOH-21

PhOH-21 was prepared according to the literature procedure [Youji Huaxue, (1), 32–5; 1986]

Example 94

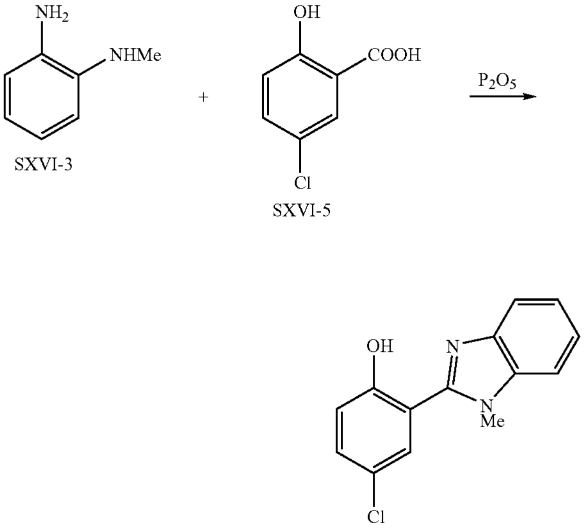

SXVI-3 SXVI-5

PhOH-22

PhOH-22 can be prepared in the same manner as that described for the synthesis of PhOH-21 in Example 93.

Example 95

PhOH-23

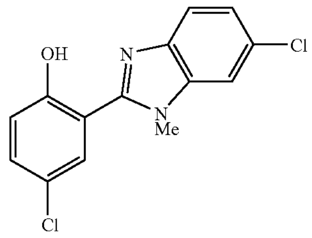

PhOH-23 was prepared according to the literature procedure [*Indian J. Chem., Sect. B.* 19B (11), 967–9; 1980]

Example 96

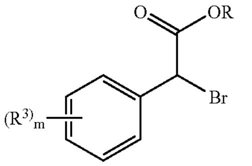

SBr-X

+

-continued

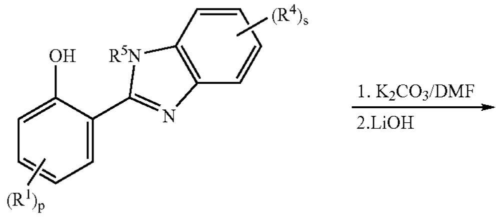

PhOH-20, 21, 22

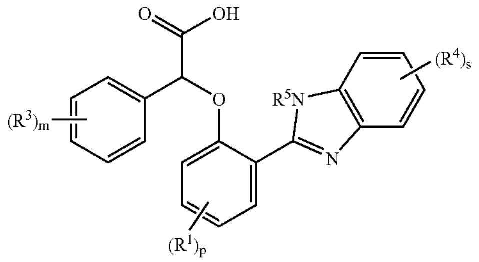

XVI-X

Compounds VIII-X can be prepared with SBr-X and PhOH-21, 22, and 23 in the same manner as that described in Example 28.

TABLE 9

2-isooxazole analogs

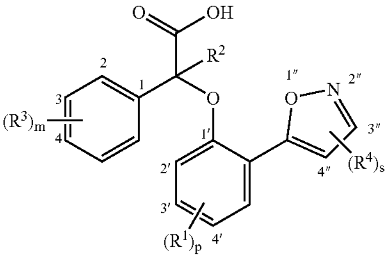

Compounds IX and IXa

| Compound | $R^2$ | $(R^3)_m$ | $(R^1)_p$ | $(R^4)_s$ | Configuration |
|---|---|---|---|---|---|
| IX-1 | H | 3-Cl | 4-H | H | R/S |
| IX-2 | H | 3-$CF_3$ | 4-H | H | R/S |
| IX-3 | H | 3-OPh | 4-H | H | R/S |
| IX-4 | H | 4-OMe | 4-H | H | R/S |
| IX-5 | H | 4-Cl | 4-H | H | R/S |
| IX-6 | H | 4-$CF_3$ | 4-H | H | R/S |
| IX-7 | H | 4-Br | 4-H | H | R/S |
| IX-8 | H | H | 4-H | H | R/S |
| IX-9 | H | 4-Et | 4-H | H | R/S |
| IX-10 | H | 3-Cl | 4-Me | H | R/S |
| IX-11 | H | 3-$CF_3$ | 4-Me | H | R/S |
| IX-12 | H | 3-OPh | 4-Me | H | R/S |
| IX-13 | H | 4-OMe | 4-Me | H | R/S |
| IX-14 | H | 4-Cl | 4-Me | H | R/S |
| IX-15 | H | 4-$CF_3$ | 4-Me | H | R/S |
| IX-16 | H | 4-Br | 4-Me | H | R/S |
| IX-17 | H | H | 4-Me | H | R/S |
| IX-18 | H | 4-Et | 4-Me | H | R/S |
| IX-19 | H | 3-Cl | 4-Cl | H | R/S |
| IX-20 | H | 3-$CF_3$ | 4-Cl | H | R/S |
| IX-21 | H | 3-OPh | 4-Cl | H | R/S |
| IX-22 | H | 4-OMe | 4-Cl | H | R/S |

TABLE 9-continued 2-isooxazole analogs

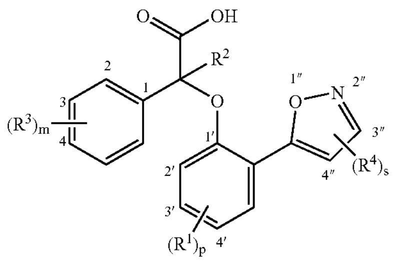

Compounds IX and IXa

| Compound | $R^2$ | $(R^3)_m$ | $(R^1)_p$ | $(R^4)_s$ | Configuration |
|---|---|---|---|---|---|
| IX-23 | H | 4-Cl | 4-Cl | H | R/S |
| IX-24 | H | 4-$CF_3$ | 4-Cl | H | R/S |
| IX-25 | H | 4-Br | 4-Cl | H | R/S |
| IX-26 | H | H | 4-Cl | H | R/S |
| IX-27 | H | 4-Et | 4-Cl | H | R/S |
| IX-28 | H | 3-Cl | 4-Br | H | R/S |
| IX-29 | H | 3-$CF_3$ | 4-Br | H | R/S |
| IX-30 | H | 3-OPh | 4-Br | H | R/S |
| IX-31 | H | 4-OMe | 4-Br | H | R/S |
| IX-32 | H | 4-Cl | 4-Br | H | R/S |
| IX-33 | H | 4-$CF_3$ | 4-Br | H | R/S |
| IX-34 | H | 4-Br | 4-Br | H | R/S |
| IX-35 | H | H | 4-Br | H | R/S |
| IX-36 | H | 4-Et | 4-Br | H | R/S |
| IX-37 | H | 3-Cl | 4-Cl, 5-Me | H | R/S |
| IX-38 | H | 3-$CF_3$ | 4-Cl, 5-Me | H | R/S |
| IX-39 | H | 3-OPh | 4-Cl, 5-Me | H | R/S |
| IX-40 | H | 4-OMe | 4-Cl, 5-Me | H | R/S |
| IX-41 | H | 4-Cl | 4-Cl, 5-Me | H | R/S |
| IX-42 | H | 4-$CF_3$ | 4-Cl, 5-Me | H | R/S |
| IX-43 | H | 4-Br | 4-Cl, 5-Me | H | R/S |
| IX-44 | H | H | 4-Cl, 5-Me | H | R/S |
| IX-45 | H | 4-Et | 4-Cl, 5-Me | H | R/S |
| IX-46 | H | 3-Cl | 4-Cl, 6-Cl | H | R/S |
| IX-47 | H | 3-$CF_3$ | 4-Cl, 6-Cl | H | R/S |
| IX-48 | H | 3-OPh | 4-Cl, 6-Cl | H | R/S |
| IX-49 | H | 4-OMe | 4-Cl, 6-Cl | H | R/S |
| IX-50 | H | 4-Cl | 4-Cl, 6-Cl | H | R/S |
| IX-5 1 | H | 4-$CF_3$ | 4-Cl, 6-Cl | H | R/S |
| IX-52 | H | 4-Br | 4-Cl, 6-Cl | H | R/S |
| IX-53 | H | H | 4-Cl, 6-Cl | H | R/S |
| IX-54 | H | 4-Et | 4-Cl, 6-Cl | H | R/S |
| IX-55 | H | 3-Cl | H | 3-(2-benzofuranyl) | R/S |
| LX-56 | H | 3-$CF_3$ | H | 3-(2-benzofuranyl) | R/S |
| IX-57 | H | 3-OPh | H | 3-(2-benzofuranyl) | R/S |
| IX-58 | H | 4-OMe | H | 3-(2-benzofuranyl) | R/S |
| IX-59 | H | 4-Cl | H | 3-(2-benzofuranyl) | R/S |
| IX-60 | H | 4-$CF_3$ | H | 3-(2-benzofuranyl) | R/S |
| IX-61 | H | 4-Br | H | 3-(2-benzofuranyl) | R/S |
| IX-62 | H | H | H | 3-(2-benzofuranyl) | R/S |
| IX-63 | H | 4-Et | H | 3-(2-benzofuranyl) | R/S |
| IX-64 | H | 3-$CF_3$ | 4-Cl | H | – |
| IX-65 | H | 3-$CF_3$ | 4-Cl | H | + |
| IXa-1 | Me | 3-Cl | 4-Cl | H | R/S |
| IXa-2 | Me | 3-$CF_3$ | 4-Cl | H | R/S |
| IXa-3 | Me | 3-OPh | 4-Cl | H | R/S |
| IXa-4 | Me | 4-OMe | 4-Cl | H | R/S |
| IXa-5 | Me | 4-Cl | 4-Cl | H | R/S |

TABLE 9-continued 2-isooxazole analogs

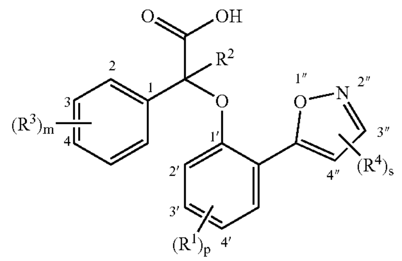

Compounds IX and IXa

| Compound | $R^2$ | $(R^3)_m$ | $(R^1)_p$ | $(R^4)_s$ | Configuration |
|---|---|---|---|---|---|
| IXa-6 | Me | 4-$CF_3$ | 4-Cl | H | R/S |
| IXa7 | Me | 4-Br | 4-Cl | H | R/S |

12. 2-isooxazoyl phenols

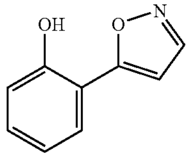

PhOH-24

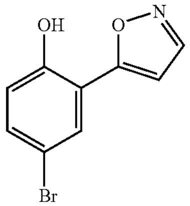

PhOH-25

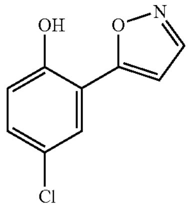

PhOH-26

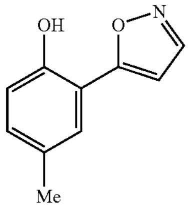

PhOH-27

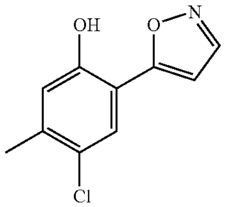

PhOH-28

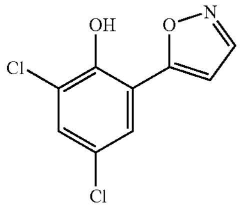

PhOH-29

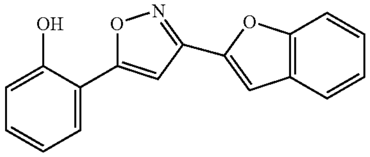

PhOH-30

PhOH-24 to PhOH-30 were purchased from different commercial sources.

Example 97

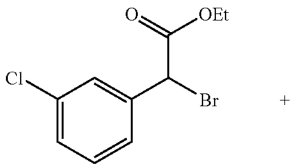

SBr-6

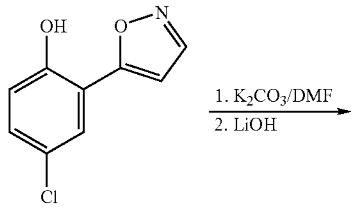

PhOH-26

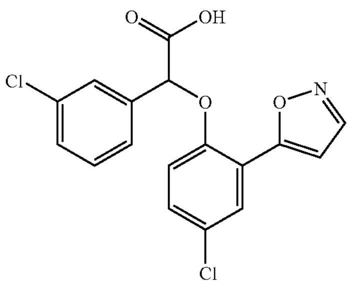

IX-19

In the same manner as that described in Example 28 compound IX-23 was prepared from SBr-1 and PhOH-26. $^1$HNMR (400 MHz, d-DMSO$d_6$): δ 8.76 (d, 1H), 7.87 (d, 1H), 7.59 (s, 1H), 7.66 1M, 4H1), 7.36 (s, 1H), 7.17 (d, 1H), 6.27) (s, 1H).

Example 98

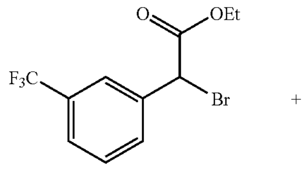

SBr-5

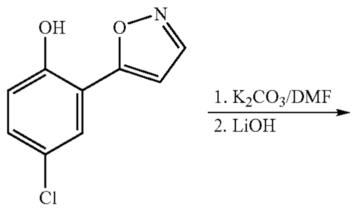

PhOH-26

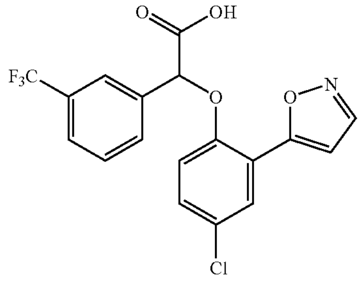

IX-20

In the same manner as that described in Example 28 compound IX-20 was prepared from SBr-5 and PhOH-26. IX-20: $^1$H NMR (d-DMSO, 400 MHz) δ 13.69 (br, 1H), 8.76 (d, 1H), 7.87 (d, 1H), 7.59 (s, 1H), 7.48–7.43 (m, 4H), 7.36 (s, 1H), 7.16 (d, 1H), 6.27 (s, 1H).

Example 99

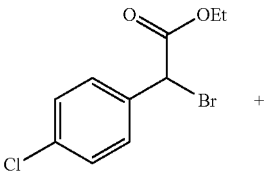

SBr-1

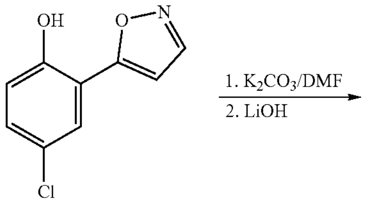

PhOH-26

-continued

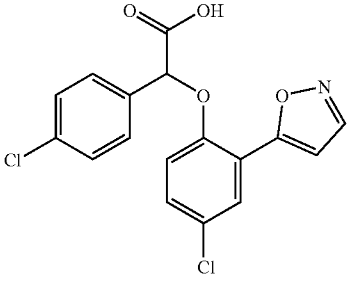

IX-23

In the same manner as that described in Example 28 compound IX-23 was prepared from SBr-1 and PhOH-26. $^1$H NMR (d-DMSO, 400 MHz) δ (8.74 (d, 1H), 7.87 (d, 1H), 7.52 (m, 2H), 7.45 (m, 3H), 7.33 (d, 1H), 7.14 (d, 1H), 6.27 (s, 1H).

Example 100

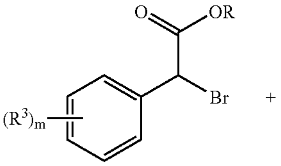

SBr-X

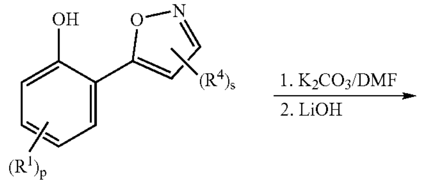

PhOH-24 to 30

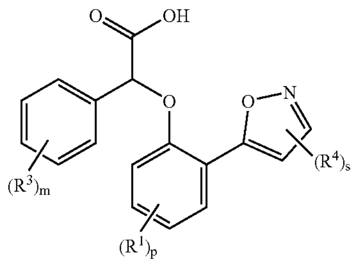

IX-X $R^3$ = 3-$CF_3$, 3-Cl, 3-OPh, H, 4-OMe, 4-Cl, 4-$CF_3$, 4-Br, 4-Et
$R^1$ = H, 4′-Me, 4′-Cl, 4′-Br, 4′-Cl, 5′-Me, 4′-Cl-6′-Cl
$R^4$ = H, 3″-(2-benzofuranyl)

In the same manner as that described in Example 28, the rest of compounds IX-X can be prepared.

Example 101

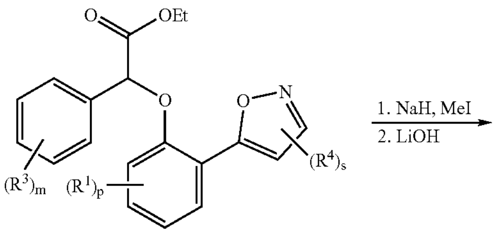

SIX-1

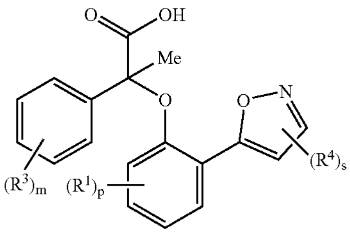

IXa-X $R^3$ = 3-$CF_3$, 3-Cl, 3-OPh, H, 4-OMe, 4-Cl, 4-$CF_3$, 4-Br, 4-Et
$R^1$ = H, 4′-Me, 4′-Cl, 4′-Br, 4′-Cl, 5′-Me, 4′-Cl-6′-Cl
$R^4$ = H, 3″-(2-benzofuranyl)

In the same manner as that described in Example 42 compound IXa-X can be prepared from SIX-1.

Example 102

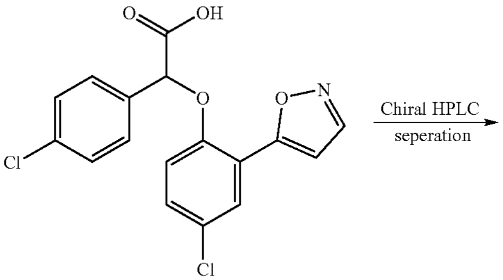

(+/-)-IX-23

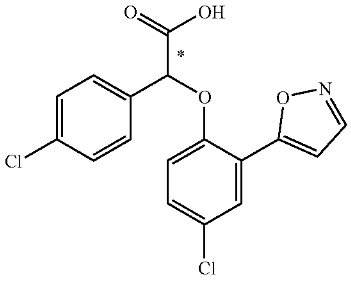

(+)-IX-23

-continued

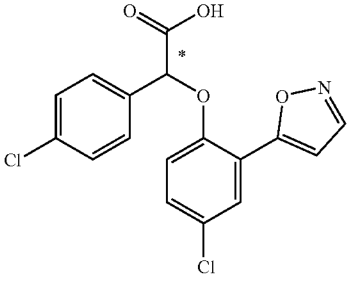

(-)-IX-23

Racemic IX-23 was resolved by chiral HPLC to give (+)-IX-23 and (−)-IX-23. HPLC methods and conditions, including eluents used, solvent flow rate and detection wavelength were: 20% iPrOH-80% Hexanes-0.1% TFA, 30 mL/min., $\lambda$=220 nm. For (+)-IX-23: RT 6.7 min. For (−)-IX-23: RT 7.0 min.

Example 103

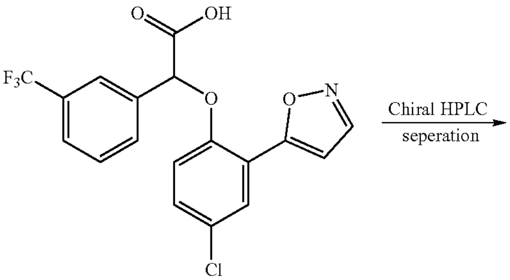

(+/-)-IX-20

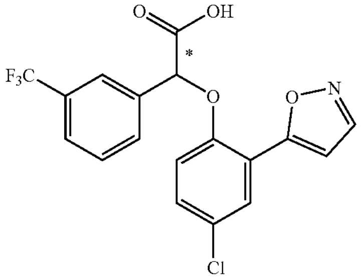

(+)-IX-20

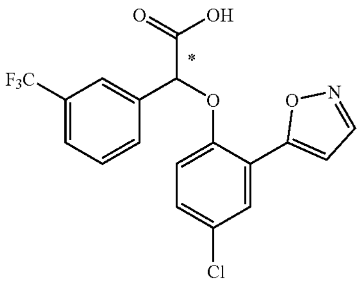

(-)-IX-20

Racemic IX-20 was resolved by chiral HPLC to give (+)-IX-20 and (−)-IX-20. HPLC methods and conditions, including eluents used, solvent flow rate and detection wavelength were: 20% iPrOH-80% Hexanes-0.1% TFA, 30 mL/min., $\lambda$=220 nm. For (+)-IX-20: RT 6.6 min. For (−)-IX-20: RT 6.9 min.

TABLE 10

2-pyrroyl analogs

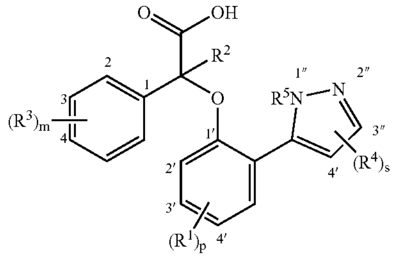

Compounds X and Xa

| Compound | $R^2$ | $(R^3)_m$ | $(R^1)_p$ | $(R^4)_s$ | $R^5$ | Configuration |
|---|---|---|---|---|---|---|
| X-1 | H | 4-Cl | 4'-Cl | H | H | R/S |
| X-2 | H | 3-$CF_3$ | 4'-Cl | H | H | R/S |
| X-3 | H | 3-OPh | 4'-Cl | H | H | R/S |
| X-4 | H | 4-OMe | 4'-Cl | H | H | R/S |
| X-5 | H | 3-Cl | 4'-Cl | H | H | R/S |
| X-6 | H | 4-$CF_3$ | 4'-Cl | H | H | R/S |
| X-7 | H | 4-Br | 4'-Cl | H | H | R/S |
| X-8 | H | H | 4'-Cl | H | H | R/S |
| X-9 | H | 3-Cl | 4-F | H | Me | R/S |
| X-10 | H | 3-$CF_3$ | 4-F | H | Me | R/S |
| X-11 | H | 3-OPh | 4-F | H | Me | R/S |
| X-12 | H | 4-OMe | 4-F | H | Me | R/S |
| X-13 | H | 4-Cl | 4-F | H | Me | R/S |
| X-14 | H | 4-$CF_3$ | 4-F | H | Me | R/S |
| X-15 | H | 4-Br | 4-F | H | Me | R/S |
| X-16 | H | H | 4-F | H | Me | R/S |
| X-17 | H | 3-Cl | 4-Cl | H | Ph | R/S |
| X-18 | H | 3-$CF_3$ | 4-Cl | H | Ph | R/S |
| X-19 | H | 3-OPh | 4-Cl | H | Ph | R/S |
| X-20 | H | 4-OMe | 4-Cl | H | Ph | R/S |
| X-21 | H | 4-Cl | 4-Cl | H | Ph | R/S |
| X-22 | H | 4-$CF_3$ | 4-Cl | H | Ph | R/S |
| X-23 | H | 4-Br | 4-Cl | H | Ph | R/S |
| X-24 | H | H | 4-Cl | H | Ph | R/S |
| X-25 | H | 3-Cl | 4-Br | H | Ph | R/S |
| X-26 | H | 3-$CF_3$ | 4-Br | H | Ph | R/S |
| X-27 | H | 3-OPh | 4-Br | H | Ph | R/S |
| X-28 | H | 4-OMe | 4-Br | H | Ph | R/S |
| X-29 | H | 4-Cl | 4-Br | H | Ph | R/S |
| X-30 | H | 4-$CF_3$ | 4-Br | H | Ph | R/S |
| X-31 | H | 4-Br | 4-Br | H | Ph | R/S |
| X-32 | H | H | 4-Br | H | Ph | R/S |
| X-33 | H | 3-Cl | 4-Cl, 6-Cl | H | Me | R/S |
| X-34 | H | 3-$CF_3$ | 4-Cl, 6-Cl | H | Me | R/S |
| X-35 | H | 3-OPh | 4-Cl, 6-Cl | H | Me | R/S |
| X-36 | H | 4-OMe | 4-Cl, 6-Cl | H | Me | R/S |
| X-37 | H | 4-Cl | 4-Cl, 6-Cl | H | Me | R/S |
| X-38 | H | 4-$CF_3$ | 4-Cl, 6-Cl | H | Me | R/S |
| X-39 | H | 4-Br | 4-Cl, 6-Cl | H | Me | R/S |
| X-40 | H | H | 4-Cl, 6-Cl | H | Me | R/S |
| X-41 | H | 3-Cl | 4-Me | H | Ph | R/S |
| X-42 | H | 3-$CF_3$ | 4-Me | H | Ph | R/S |
| X-43 | H | 3-OPh | 4-Me | H | Ph | R/S |
| X-44 | H | 4-OMe | 4-Me | H | Ph | R/S |
| X-45 | H | 4-Cl | 4-Me | H | Ph | R/S |
| X-46 | H | 4-$CF_3$ | 4-Me | H | Ph | R/S |
| X-47 | H | 4-Br | 4-Me | H | Ph | R/S |
| X-48 | H | H | 4-Me | H | Ph | R/S |
| X-49 | H | 3-Cl | 4-Cl, 5-Me | H | Ph | R/S |
| X-50 | H | 3-$CF_3$ | 4-Cl, 5-Me | H | Ph | R/S |
| X-51 | H | 3-OPh | 4-Cl, 5-Me | H | Ph | R/S |
| X-52 | H | 4-OMe | 4-Cl, 5-Me | H | Ph | R/S |

TABLE 10-continued 2-pyrroyl analogs

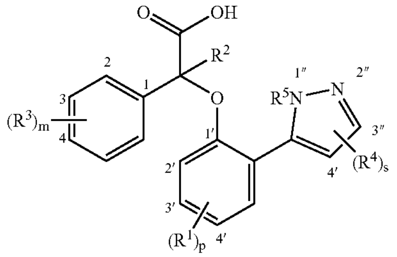

Compounds X and Xa

| Compound | $R^2$ | $(R^3)_m$ | $(R^1)_p$ | $(R^4)_s$ | $R^5$ | Configuration |
|---|---|---|---|---|---|---|
| X-53 | H | 4-Cl | 4-Cl, 5-Me | H | Ph | R/S |
| X-54 | H | 4-$CF_3$ | 4-Cl, 5-Me | H | Ph | R/S |
| X-55 | H | 4-Br | 4-Cl, 5-Me | H | Ph | R/S |
| X-56 | H | H | 4-Cl, 5-Me | H | Ph | R/S |
| X-57 | H | 3-Cl | H | H | Me | R/S |
| X-58 | H | 3-$CF_3$ | H | H | Me | R/S |
| X-59 | H | 3-OPh | H | H | Me | R/S |
| X-60 | H | 4-OMe | H | H | Me | R/S |
| X-61 | H | 4-Cl | H | H | Me | R/S |
| X-62 | H | 4-$CF_3$ | H | H | Me | R/S |
| X-63 | H | 4-Br | H | H | Me | R/S |
| X-64 | H | H | H | H | Me | R/S |
| X-65 | H | 3-Cl | H | H | Ph | R/S |
| X-66 | H | 3-$CF_3$ | H | H | Ph | R/S |
| X-67 | H | 3-OPh | H | H | Ph | R/S |
| X-68 | H | 4-OMe | H | H | Ph | R/S |
| X-69 | H | 4-Cl | H | H | Ph | R/S |
| X-70 | H | 4-$CF_3$ | H | H | Ph | R/S |
| X-71 | H | 4-Br | H | H | Ph | R/S |
| X-72 | H | H | H | H | Ph | R/S |
| Xa-1 | Me | 3-Cl | 4-Cl | H | Ph | R/S |
| Xa-2 | Me | 3-$CF_3$ | 4-Cl | H | Ph | R/S |
| Xa-3 | Me | 3-OPh | 4-Cl | H | Ph | R/S |
| Xa-4 | Me | 4-OMe | 4-Cl | H | Ph | R/S |
| Xa-5 | Me | 4-Cl | 4-Cl | H | Ph | R/S |
| Xa-6 | Me | 4-$CF_3$ | 4-Cl | H | Ph | R/S |
| Xa-7 | Me | 4-Br | 4-Cl | H | Ph | R/S |
| Xa-8 | Me | H | 4-Cl | H | Ph | R/S |

13. 2-pyrazolyl phenols

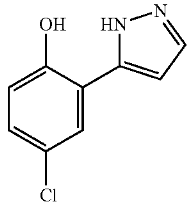

PhOH-31

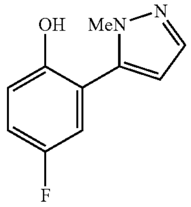

PhOH-32

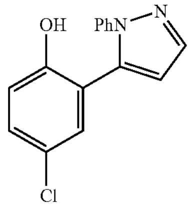

PhOH-33

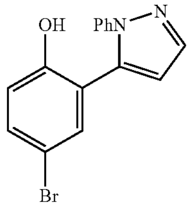

PhOH-34

-continued

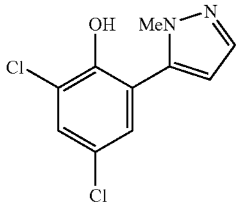
PhOH-35

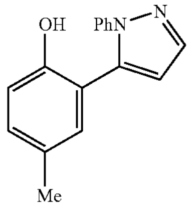
PhOH-36

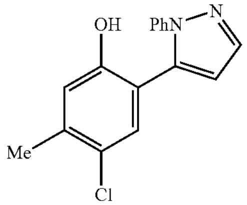
PhOH-37

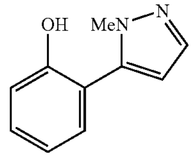
PhOH-38

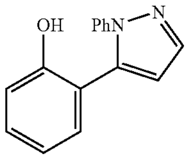
PhOH-39

PhOH-31 to PhOH-39 were purchased from different commercial sources.

Example 104

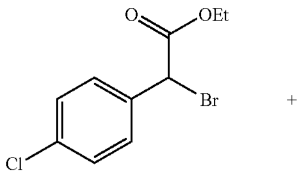
SBr-1

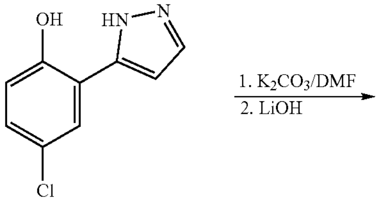

PhOH-31

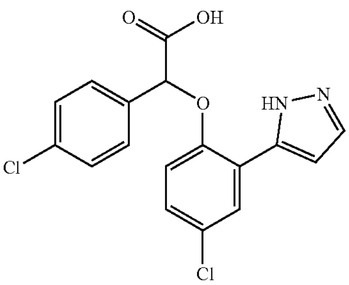
X-1

In the same manner as that described in Example 28 compound X-1 was prepared from SBr-1 and PhOH-31. $^1H$ NMR ($CDCl_3$, 400 MHz) δ 7.50–7.42 (m, 6H), 7.18 (dd, 1H), 6.96 (d, 1H), 6.63 (d, 1H), 6.20 (s, 1H).

Example 105

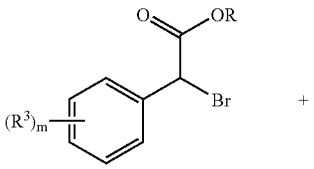
SBr-X

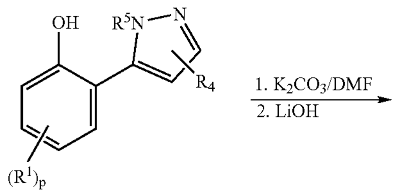

PhOH-31 to 39

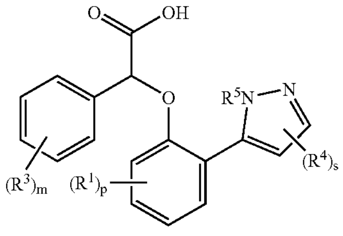
X $R^3$ = 3-$CF_3$, 3-Cl, 3-OPh, H, 4-OMe, 4-Cl, 4-$CF_3$, 4-Br
$R^1$ = H, 4'-F, 4'-Me, 4'-Cl, 4'-Br, 4'-Cl-5'- Me-, 4'-Cl-6'-Cl
$R^4$ = H
$R^5$ = H, Me, Ph The rest of compounds X listed in Table 10 can be prepared in the same manner as that described in Example 28.

Example 106

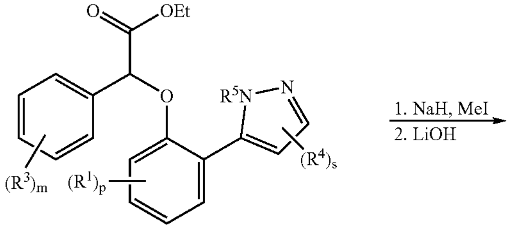

X

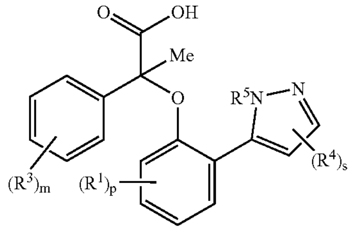
Xa $R^3$ = 3-$CF_3$, 3-Cl, 3-OPh, H, 4-OMe, 4-Cl, 4-$CF_3$, 4-Br
$R^1$ = H, 4'-F, 4'-Me, 4'-Cl, 4'-Br, 4'-Cl-5'- Me-, 4'-Cl-6'-Cl
$R^4$ = H
$R^5$ = H, Me, Ph Compounds Xa listed in Table 10 can be prepared in the same manner as that described in Example 42.

TABLE 11

2-Benzotriazole analogs

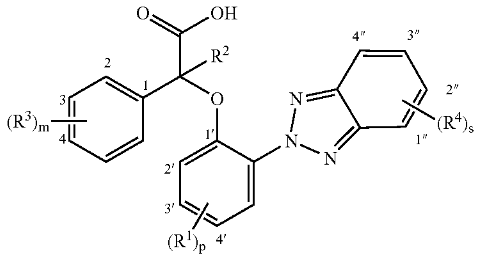

Compounds XI and XIa

| Compound | $R^2$ | $(R^3)_m$ | $(R^1)_p$ | $(R^4)_s$ | Configuration |
|---|---|---|---|---|---|
| XI-1 | H | 3-Cl | 4-Me | H | R/S |
| XI-2 | H | 3-$CF_3$ | 4-Me | H | R/S |
| XI-3 | H | 3-OPh | 4-Me | H | R/S |
| XI-4 | H | 4-OMe | 4-Me | H | R/S |
| XI-5 | H | 4-Cl | 4-Me | H | R/S |
| XI-6 | H | 4-$CF_3$ | 4-Me | H | R/S |
| XI-7 | H | 4-Br | 4-Me | H | R/S |
| XI-8 | H | H | 4-Me | H | R/S |
| XI-9 | H | 4-Et | 4-Me | H | R/S |
| XI-10 | H | 3-Cl | 4-t-octyl | H | R/S |
| XI-11 | H | 3-$CF_3$ | 4-t-octyl | H | R/S |
| XI-12 | H | 3-OPh | 4-t-octyl | H | R/S |
| XI-13 | H | 4-OMe | 4-t-octyl | H | R/S |
| XI-14 | H | 4-Cl | 4-t-octyl | H | R/S |
| XI-15 | H | 4-$CF_3$ | 4-t-octyl | H | R/S |
| XI-16 | H | 4-Br | 4-t-octyl | H | R/S |
| XI-17 | H | H | 4-t-octyl | H | R/S |
| XI-18 | H | 4-Et | 4-t-octyl | H | R/S |
| XI-19 | H | 3-Cl | 4-Cl | H | R/S |
| XI-20 | H | 3-$CF_3$ | 4-Cl | H | R/S |
| XI-21 | H | 3-OPh | 4-Cl | H | R/S |
| XI-22 | H | 4-OMe | 4-Cl | H | R/S |
| XI-23 | H | 4-Cl | 4-Cl | H | R/S |
| XI-24 | H | 4-$CF_3$ | 4-Cl | H | R/S |
| XI-25 | H | 4-Br | 4-Cl | H | R/S |
| XI-26 | H | H | 4-Cl | H | R/S |
| XI-27 | H | 4-Et | 4-Cl | H | R/S |
| XI-28 | H | 3-Cl | 4-Br | H | R/S |
| XI-29 | H | 3-$CF_3$ | 4-Br | H | R/S |
| XI-30 | H | 3-OPh | 4-Br | H | R/S |
| XI-31 | H | 4-OMe | 4-Br | H | R/S |
| XI-32 | H | 4-Cl | 4-Br | H | R/S |
| XI-33 | H | 4-$CF_3$ | 4-Br | H | R/S |
| XI-34 | H | 4-Br | 4-Br | H | R/S |
| XI-35 | H | H | 4-Br | H | R/S |
| XI-36 | H | 4-Et | 4-Br | H | R/S |
| XI-37 | H | 3-Cl | 4-t-Bu | H | R/S |
| XI-38 | H | 3-$CF_3$ | 4-t-Bu | H | R/S |
| XI-39 | H | 3-OPh | 4-t-Bu | H | R/S |
| XI-40 | H | 4-OMe | 4-t-Bu | H | R/S |
| XI-41 | H | 4-Cl | 4-t-Bu | H | R/S |
| XI-42 | H | 4-$CF_3$ | 4-t-Bu | H | R/S |
| XI-43 | H | 4-Br | 4-t-Bu | H | R/S |
| XI-44 | H | H | 4-t-Bu | H | R/S |
| XI-45 | H | 4-Et | 4-t-Bu | H | R/S |
| XI-46 | H | 3-Cl | 4'-$CF_3$ | H | R/S |
| XI-47 | H | 3-$CF_3$ | 4'-$CF_3$ | H | R/S |
| XI-48 | H | 3-OPh | 4'-$CF_3$ | H | R/S |
| XI-49 | H | 4-OMe | 4'-$CF_3$ | H | R/S |
| XI-50 | H | 4-Cl | 4'-$CF_3$ | H | R/S |
| XI-51 | H | 4-$CF_3$ | 4'-$CF_3$ | H | R/S |
| XI-52 | H | 4-Br | 4'-$CF_3$ | H | R/S |
| XI-53 | H | H | 4'-$CF_3$ | H | R/S |
| XI-54 | H | 4-Et | 4'-$CF_3$ | H | R/S |
| XI-55 | H | 3-Cl | 2',4'-di-t-Bu | H | R/S |
| XI-56 | H | 3-$CF_3$ | 2',4'-di-t-Bu | H | R/S |
| XI-57 | H | 3-OPh | 2',4'-di-t-Bu | H | R/S |

TABLE 11-continued

2-Benzotriazole analogs

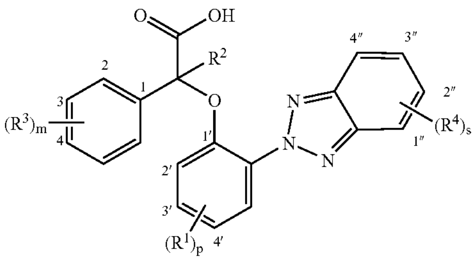

Compounds XI and XIa

| Compound | $R^2$ | $(R^3)_m$ | $(R^1)_p$ | $(R^4)_s$ | Configuration |
|---|---|---|---|---|---|
| XI-58 | H | 4-OMe | 2',4'-di-t-Bu | H | R/S |
| XI-59 | H | 4-Cl | 2',4'-di-t-Bu | H | R/S |
| XI-60 | H | 4-$CF_3$ | 2',4'-di-t-Bu | H | R/S |
| XI-61 | H | 4-Br | 2',4'-di-t-Bu | H | R/S |
| XI-62 | H | H | 2',4'-di-t-Bu | H | R/S |
| XI-63 | H | 4-Et | 2',4'-di-t-Bu | H | R/S |
| XI-64 | H | 3-Cl | 2'-t-Bu, 4'-Me | 2"-Cl | R/S |
| XI-65 | H | 3-$CF_3$ | 2'-t-Bu, 4'-Me | 2"-Cl | R/S |
| XI-66 | H | 3-OPh | 2'-t-Bu, 4'-Me | 2"-Cl | R/S |
| XI-67 | H | 4-OMe | 2'-t-Bu, 4'-Me | 2"-Cl | R/S |
| XI-68 | H | 4-Cl | 2'-t-Bu, 4'-Me | 2"-Cl | R/S |
| XI-69 | H | 4-$CF_3$ | 2'-t-Bu, 4'-Me | 2"-Cl | R/S |
| XI-70 | H | 4-Br | 2'-t-Bu, 4'-Me | 2"-Cl | R/S |
| XI-71 | H | H | 2'-t-Bu, 4'-Me | 2"-Cl | R/S |
| XI-72 | H | 4-Et | 2'-t-Bu, 4'-Me | 2"-Cl | R/S |
| XI-73 | H | 4-$CF_3$ | 4'-Cl | H | (−) |
| XI-74 | H | 4-$CF_3$ | 4'-Cl | H | (+) |
| XI-75 | H | 4-Cl | 4'-Cl | H | (−) |
| XI-76 | H | 4-Cl | 4'-Cl | H | (+) |
| XIa-1 | Me | 3-Cl | 4-Me | H | R/S |
| XIa-2 | Me | 3-$CF_3$ | 4-Me | H | R/S |
| XIa-3 | Me | 3-OPh | 4-Me | H | R/S |
| XIa-4 | Me | 4-OMe | 4-Me | H | R/S |
| XIa-5 | Me | 4-Cl | 4-Me | H | R/S |
| XIa-6 | Me | 4-$CF_3$ | 4-Me | H | R/S |
| XIa-7 | Me | 4-Br | 4-Me | H | R/S |
| XIa-8 | Me | H | 4-Me | H | R/S |
| XIa-9 | Me | 4-Et | 4-Me | H | R/S |
| XIa-10 | Me | 3-Cl | 4-t-octyl | H | R/S |
| XIa-11 | Me | 3-$CF_3$ | 4-t-octyl | H | R/S |
| XIa-12 | Me | 3-OPh | 4-t-octyl | H | R/S |
| XIa-13 | Me | 4-OMe | 4-t-octyl | H | R/S |
| XIa-14 | Me | 4-Cl | 4-t-octyl | H | R/S |
| XIa-15 | Me | 4-$CF_3$ | 4-t-octyl | H | R/S |
| XIa-16 | Me | 4-Br | 4-t-octyl | H | R/S |
| XIa-17 | Me | H | 4-t-octyl | H | R/S |
| XIa-18 | Me | 4-Et | 4-t-octyl | H | R/S |
| XIa-19 | Me | 3-Cl | 4-Cl | H | R/S |
| XIa-20 | Me | 3-$CF_3$ | 4-Cl | H | R/S |
| XIa-21 | Me | 3-OPh | 4-Cl | H | R/S |
| XIa-22 | Me | 4-OMe | 4-Cl | H | R/S |
| XIa-23 | Me | 4-Cl | 4-Cl | H | R/S |
| XIa-24 | Me | 4-$CF_3$ | 4-Cl | H | R/S |
| XIa-25 | Me | 4-Br | 4-Cl | H | R/S |
| XIa-26 | Me | H | 4-Cl | H | R/S |
| XIa-27 | Me | 4-Et | 4-Cl | H | R/S |
| XIa-28 | Me | 3-Cl | 4-Br | H | R/S |
| XIa-29 | Me | 3-$CF_3$ | 4-Br | H | R/S |
| XIa-30 | Me | 3-OPh | 4-Br | H | R/S |
| XIa-31 | Me | 4-OMe | 4-Br | H | R/S |
| XIa-32 | Me | 4-Cl | 4-Br | H | R/S |
| XIa-33 | Me | 4-$CF_3$ | 4-Br | H | R/S |
| XIa-34 | Me | 4-Br | 4-Br | H | R/S |
| XIa-35 | Me | H | 4-Br | H | R/S |
| XIa-36 | Me | 4-Et | 4-Br | H | R/S |
| XIa-37 | Me | 3-Cl | 4-t-Bu | H | R/S |
| XIa-38 | Me | 3-$CF_3$ | 4-t-Bu | H | R/S |
| XIa-39 | Me | 3-OPh | 4-t-Bu | H | R/S |

TABLE 11-continued

2-Benzotriazole analogs

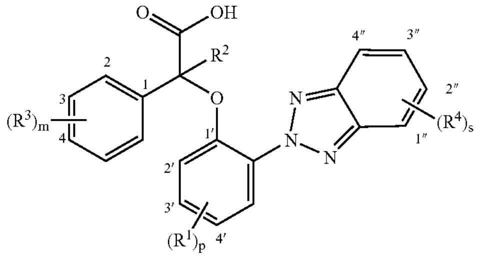

Compounds XI and XIa

| Compound | $R^2$ | $(R^3)_m$ | $(R^1)_p$ | $(R^4)_s$ | Configuration |
|---|---|---|---|---|---|
| XIa-40 | Me | 4-OMe | 4-t-Bu | H | R/S |
| XIa-41 | Me | 4-Cl | 4-t-Bu | H | R/S |
| XIa-42 | Me | 4-$CF_3$ | 4-t-Bu | H | R/S |
| XIa-43 | Me | 4-Br | 4-t-Bu | H | R/S |
| XIa-44 | Me | H | 4-t-Bu | H | R/S |
| XIa-45 | Me | 4-Et | 4-t-Bu | H | R/S |
| XIa-46 | Me | 3-Cl | 4'-$CF_3$ | H | R/S |
| XIa-47 | Me | 3-$CF_3$ | 4'-$CF_3$ | H | R/S |
| XIa-48 | Me | 3-OPh | 4'-$CF_3$ | H | R/S |
| XIa-49 | Me | 4-OMe | 4'-$CF_3$ | H | R/S |
| XIa-50 | Me | 4-Cl | 4'-$CF_3$ | H | R/S |
| XIa-51 | Me | 4-$CF_3$ | 4'-$CF_3$ | H | R/S |
| XIa-52 | Me | 4-Br | 4'-$CF_3$ | H | R/S |
| XIa-53 | Me | H | 4'-$CF_3$ | H | R/S |
| XIa-54 | Me | 4-Et | 4'-$CF_3$ | H | R/S |
| XIa-55 | Me | 3-Cl | 2',4'-di-t-Bu | H | R/S |
| XIa-56 | Me | 3-$CF_3$ | 2',4'-di-t-Bu | H | R/S |
| XIa-57 | Me | 3-OPh | 2',4'-di-t-Bu | H | R/S |
| XIa-58 | Me | 4-OMe | 2',4'-di-t-Bu | H | R/S |
| XIa-59 | Me | 4-Cl | 2',4'-di-t-Bu | H | R/S |
| XIa-60 | Me | 4-$CF_3$ | 2',4'-di-t-Bu | H | R/S |
| XIa-61 | Me | 4-Br | 2',4'-di-t-Bu | H | R/S |
| XIa-62 | Me | H | 2',4'-di-t-Bu | H | R/S |
| XIa-63 | Me | 4-Et | 2',4'-di-t-Bu | H | R/S |
| XIa-64 | Me | 3-Cl | 2'-t-Bu, 4'-Me | 2"-Cl | R/S |
| XIa-65 | Me | 3-$CF_3$ | 2'-t-Bu, 4'-Me | 2"-Cl | R/S |
| XIa-66 | Me | 3-OPh | 2'-t-Bu, 4'-Me | 2"-Cl | R/S |
| XIa-67 | Me | 4-OMe | 2'-t-Bu, 4'-Me | 2"-Cl | R/S |
| XIa-68 | Me | 4-Cl | 2'-t-Bu, 4'-Me | 2"-Cl | R/S |
| XIa-69 | Me | 4-$CF_3$ | 2'-t-Bu, 4'-Me | 2"-Cl | R/S |
| XIa-70 | Me | 4-Br | 2'-t-Bu, 4'-Me | 2"-Cl | R/S |
| XIa-71 | Me | H | 2'-t-Bu, 4'-Me | 2"-Cl | R/S |
| XIa-72 | Me | 4-Et | 2'-t-Bu, 4'-Me | 2"-Cl | R/S |
| XIa-73 | Me | 4-$CF_3$ | 4'-Cl | H | (−) |
| XIa-74 | Me | 4-$CF_3$ | 4'-Cl | H | (+) |
| XIa-75 | Me | 4-Cl | 4'-Cl | H | (−) |
| XIa-76 | Me | 4-Cl | 4'-Cl | H | (+) |

14. 2-Benzotriazol-2-yl-phenols

PhOH-40

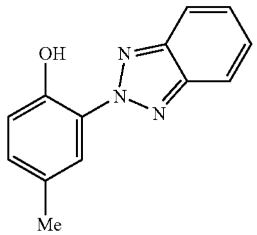

-continued

PhOH-41

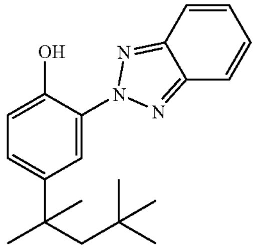

PhOH-42

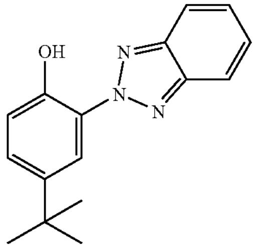

PhOH-43

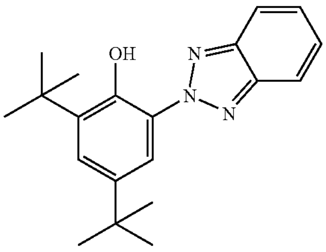

PhOH-44

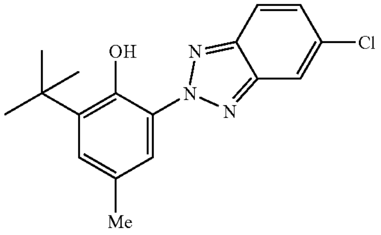

PhOH-40 to PhOH-44 were purchased from different commercial sources.

Example 107

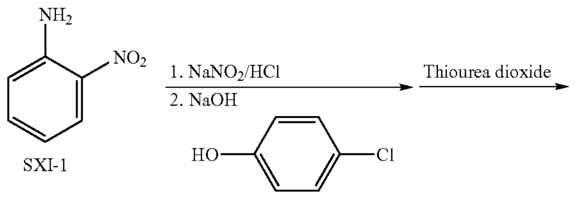

SXI-1

-continued

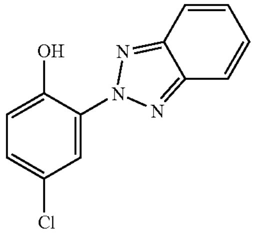

PhOH-45

Nitro aniline (138.13 g) was mixed with 500 mL of concentrated HCl and stirred for several min. When all the aniline was dissolved, the solution was cooled down to room temperature and diluted with water (300 mL), and then a solution of $NaNO_2$ (69 g) in 250 mL of water was dropwise added at 0° C. The solution became a clear and yellowish solution. The diazonium salt solution was added slowly to a solution of phenol (128.5 g) in water (800 mL) containing 80 g of NaOH at 0° C. When the addition was complete, the reaction mixture was stand for several hours, a black precipitate was formed and filtered. The solid was dissolved in ethyl acetate, washed with brine, dried over anhydrous $Na_2SO_4$. The solution was concentrated to give 133.5 g of nitroazophenol product as light yellow solid. The mother liquor was concentrated again to give another 65 g of the nitroazophenol product. $^1$H-NMR (400 MHz, $CDCl_3$): δ 10.98 (s, 1H), 8.20–7.05 (m, 7H).

A mixture of nitroazophenol (40 g), thiourea dioxide (30 g), 500 mL of NaOH solution (4 N) and 500 mL ethanol was stirred for half an hour at 80° C., and then 15 g of thiourea dioxide was added. The solution was stirred for another one hour, diluted with ice-water, extracted with ethyl acetate, dried over anhydrous $Na_2SO_4$. The solution was concentrated to give 21 g of PhOH-45 as a white solid. $^1$H-NMR (400 MHz, $CDCl_3$): δ 11.25 (s, 1H), 8.40–7.15 (m, 7H).

Example 108

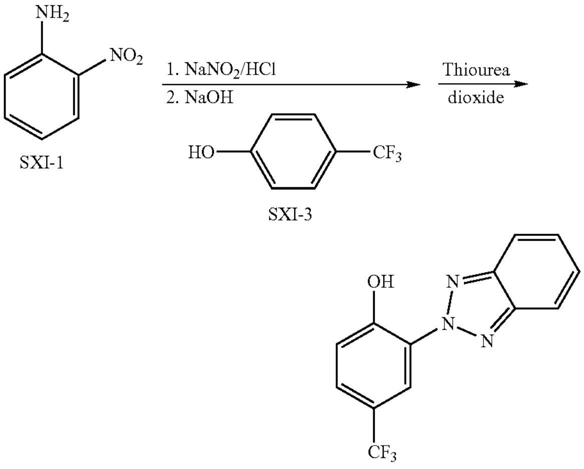

SXI-1

SXI-3

PhOH-46

In the same manner as that described in Example 107, PhOH-46 was prepared from phenol SXI-3. $^1$H-NMR (400 MHz, $CDCl_3$): δ 11.78 (s, 1H), 8.71–7.23 (m, 7H).

Example 109

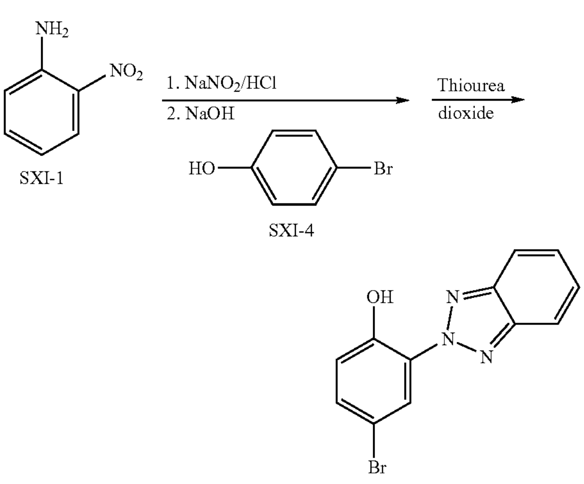

SXI-1

SXI-4

PhOH-47

PhOH-47 can be prepared from SXI-1 and SXI-4 in the same manner as that described in Example 107.

15. Synthesis of Compounds XI and XMa in Table 11

Compounds XI and XMa were or can be prepared in the same manner as that described for the synthesis of compounds I-X and Ia-X.

Example 110

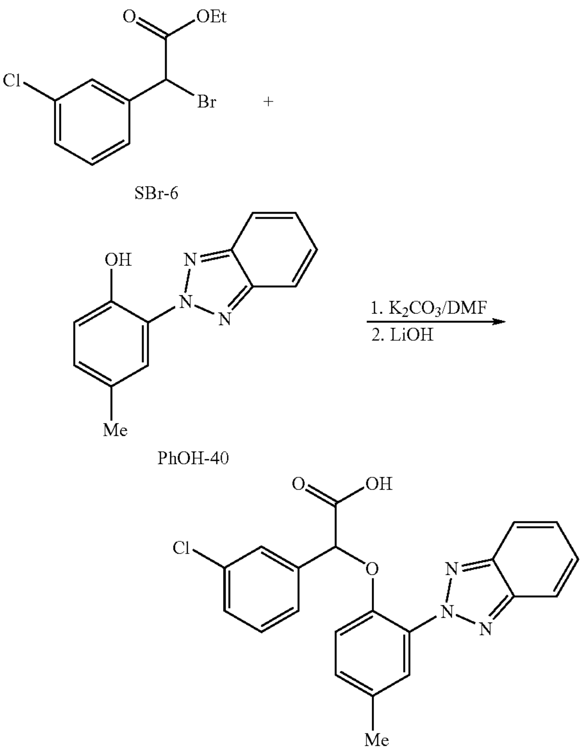

SBr-6

PhOH-40

XI-1

XI-1 was prepared from SBr-6 and PhOH-40 in the same manner as that described in Example 28. $^1$H-NMR (d-DMSO, 400 MHz) δ 8.15 (m, 2H), 7.63 (d, 1H), 7.57 (m, 3H), 7.40 (m, 4H), 7.20 (d, 1H), 6.15 (s, 1H), 2.38 (s, 3H).

Example 111

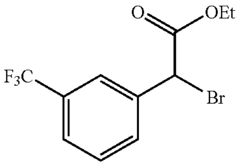

SBr-5

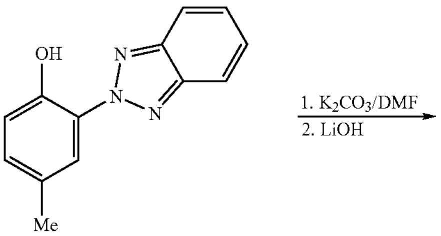

PhOH-40

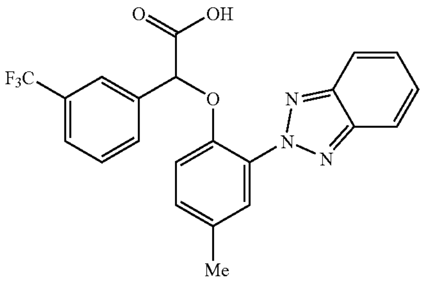

XI-2

XI-2 was prepared from SBr-5 and PhOH-40 in the same manner as that described in Example 28. $^1$H NMR (400 MHz, DMSO-$d_6$): δ 7.98 (2H, dd, J=6.6, 3.2 Hz), 7.72 (2H, d, J=6.0 Hz), 7.66 (1H, d, J=8.4 Hz), 7.60 (1H, d, J=2.4 Hz), 7.57 (1H, d, J=7.6 Hz), 7.51 (2H, dd, J=6.6, 3.2 Hz), 7.39 (1H, dd, J=8.8, 2.0 Hz), 7.19 (1H, d, J=8.8 Hz), 616 (1H, s), 2.40 (3H, s).

Example 112

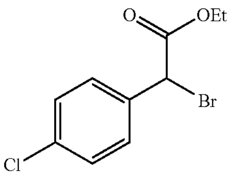

SBr-1

-continued

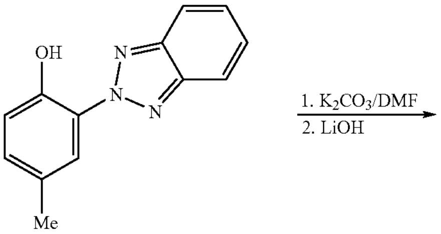

PhOH-40

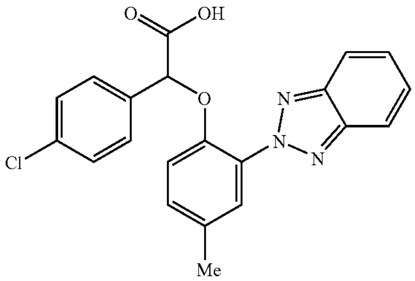

XI-5

XI-5 was prepared from SBr-1 and PhOH-40 in the same manner as that described in Example 28. $^1$H NMR (400 MHz, DMSO-$d_6$): δ 8.02 (2H, dd, J=6.8, 3.2 Hz), 7.56 (1H, dd, J=3.2, 0.8 Hz), 7.50 (2H, dd, J=6.8, 3.2 Hz), 7.41–7.44 (2H, m), 7.34–7.37 (3H, m), 7.14 (1H, d, J=8.8 Hz), 5.92 (1H, s), 2.32 (3H, s).

Example 113

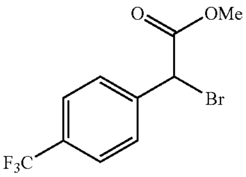

SBr-11

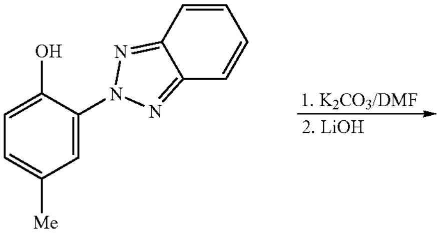

PhOH-40

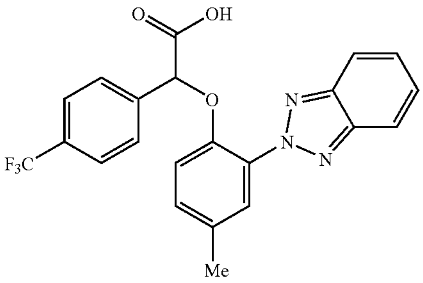

XI-6

XI-6 was prepared from SBr-11 and PhOH-40 in the same manner as that described in Example 28. $^1$HNMR (400 MHz, $CDCl_3$): δ 11.25 (br, 1H), 8.0–6.90 (m, 11H), 5.90 (s, 1H).

Example 114

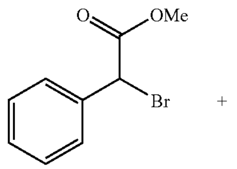

SBr-4

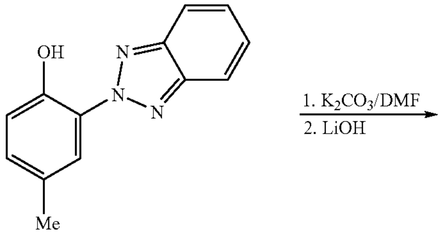

PhOH-40

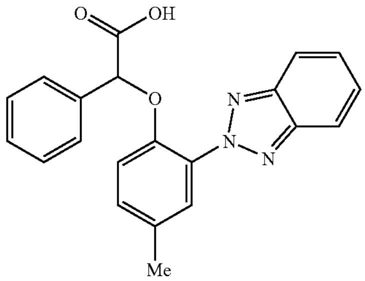

XI-8

XI-8 was prepared from SBr-4 and PhOH-40 in the same manner as that described in Example 28. $^1$HNMR (CDCl3, 400 MHz) δ 7.96 (m, 3H), 7.54–7.46 (m, 7H), 7.12 (d, 1H), 6.96 (d, 1H), 5.84 (s, 1H), 2.35 (s, 3H).

Example 115

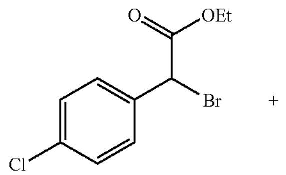

SBr-1

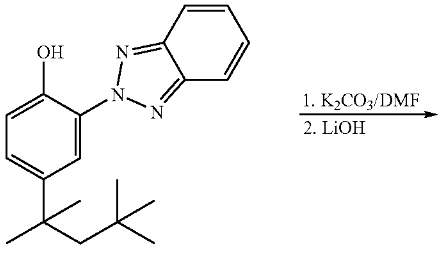

PhOH-41

-continued

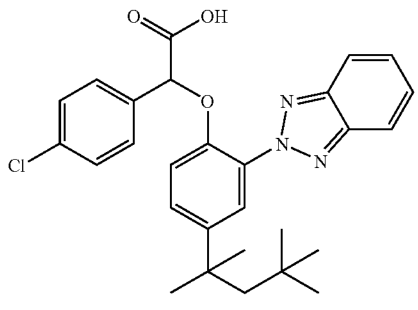

XI-14

XI-14 was prepared from SBr-1 and PhOH-41 in the same manner as that described in Example 28. $^1$HNMR (400 MHz, DMSO): δ 8.10–7.15 (m, 11H), 6.0 (s, 1H), 1.70 (s, 2H), 1.32 (s, 6H), 0.68 (s, 9H).

Example 116

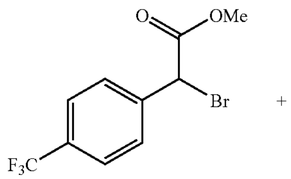

SBr-11

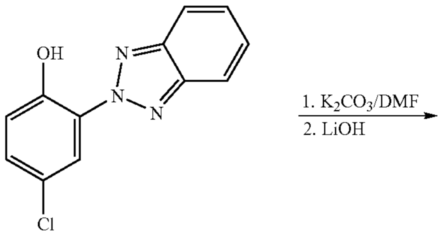

PhOH-45

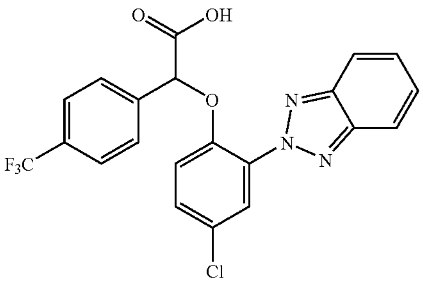

XI-24

XI-24 was prepared from SBr-11 and PhOH-45 in the same manner as that described in Example 28. $^1$H-NMR (400 MHz, DMSO): δ 13.58 (s, 1H), 8.06–7.33 (m, 11H), 6.25 (s, 1H).

Example 117
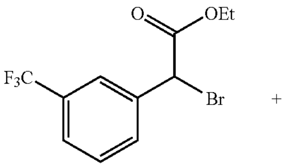
SBr-5
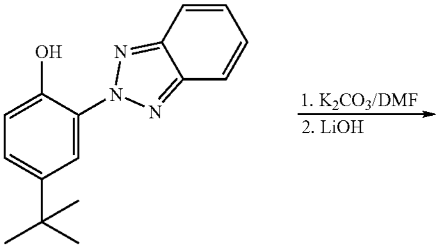
PhOH-42
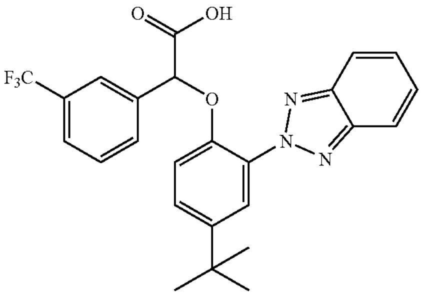
XI-38
XI-38 was prepared from SBr-5 and PhOH-42 in the same manner as that described in Example 28.
Example 118
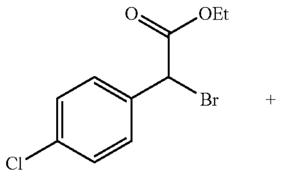
SBr-1
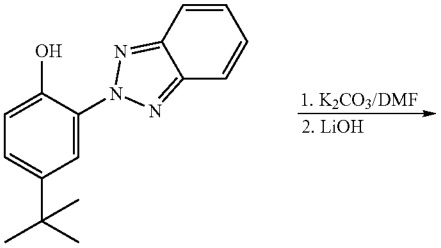
PhOH-42
-continued
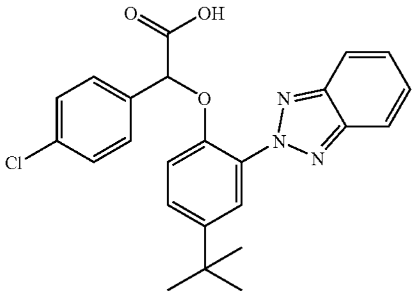
XI-41
XI-41 was prepared from SBr-1 and PhOH-42 in the same manner as that described in Example 28.
Example 119
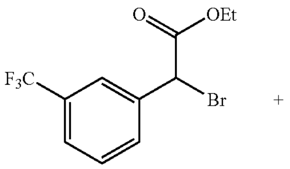
SBr-5
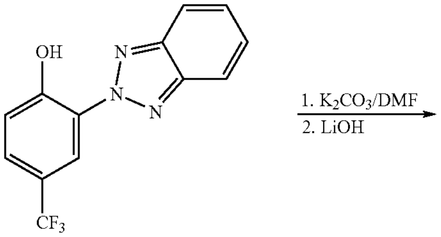
PhOH-46
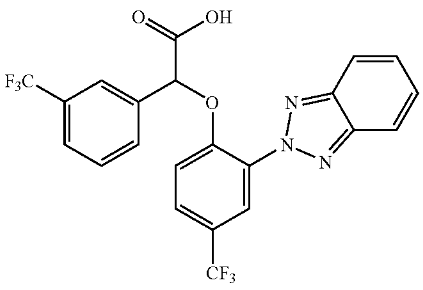
XI-47
XI-47 was prepared from SBr-5 and PhOH-46 in the same manner as that described in Example 28. $^1$H-NMR (400 MHz, DMSO): δ 8.22–7.45 (m, 11H), 6.42 (s, 1H).

Example 120

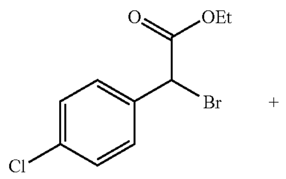

SBr-1

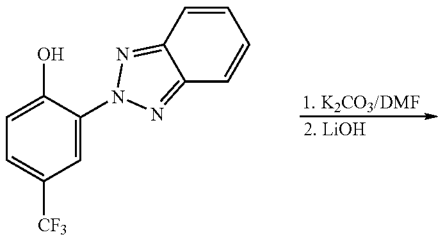

PhOH-46

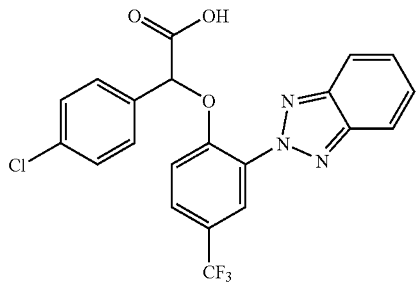

XI-50

XI-50 was prepared from SBr-1 and PhOH-46 in the same manner as that described in Example 28. $^1$H-NMR (400 MHz, DMSO): δ 8.20–7.40 (m, 11H), 6.22 9s, 1H).

Example 121

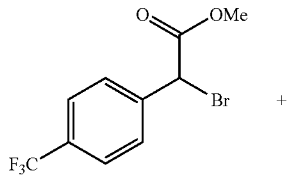

SBr-11

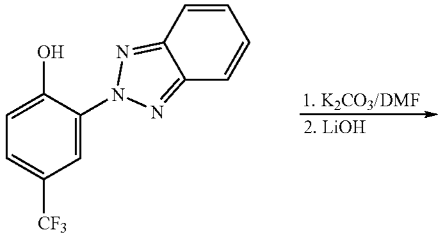

PhOH-46

-continued

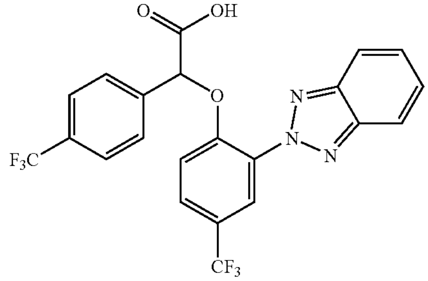

XI-51

XI-51 was prepared from SBr-11 and PhOH-46 in the same manner as that described in Example 28. $^1$H-NMR (400 MHz, DMSO): δ 8.22–7.45 (m, 11H), 6.40 (s, 1H).

Example 122

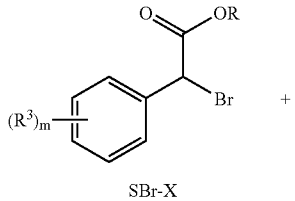

SBr-X

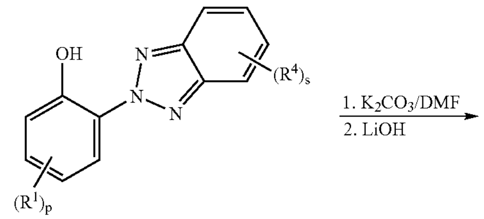

PhOH-X

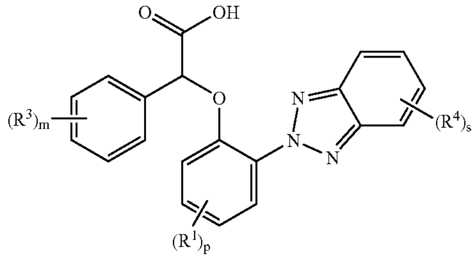

XI-X $R^3$ = 3-$CF_3$, 3-Cl, 3-OPh, H, 4-OMe, 4-Cl, 4-$CF_3$, 4-Br, 4-Et
$R^1$ = H, 4′-t-octyl, 4′-tBu, 4′-Me, 4′-Cl, 4′-Br, 2′,4′-di-t-Bu, 4′-$CF_3$
$R^4$ = H, 2″-Cl The rest of XI can be prepared from SBr-X and PhOH-X in the same manner as that described in Example 28.

Example 123

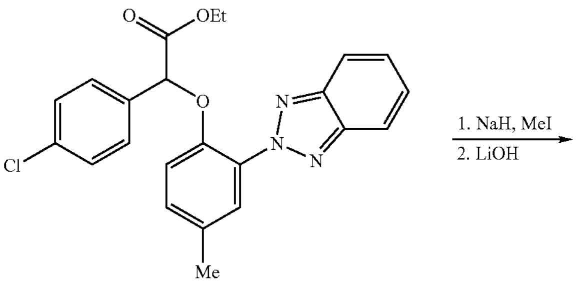

SXI-5

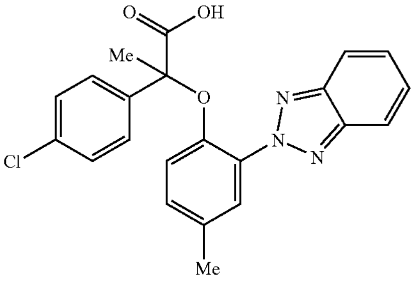

XIa-5

XIa-5 was prepared from SXI-5 in the same manner as that described in Example 42. $^1$H NMR (400 MHz, DMSO-$d_6$): δ 8.02 (2H, dd, J=6.8, 3.2 Hz), 7.58 (1H, s), 7.51 (2H, dd, J=6.8, 3.2 Hz), 7.36 (3H, t, J=8.8 Hz), 7.24 (2H, d, J=8.4 Hz), 6.94 (1H, d, J=8.4 Hz), 2.38 (3H, s), 1.78 (3H, s).

Example 124

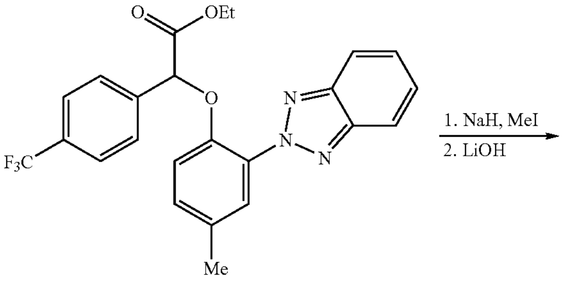

SXI-6

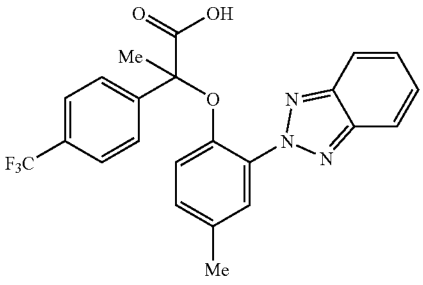

XIa-6

XIa-6 was prepared from SXI-6 in the same manner as that described in Example 42. $^1$H-NMR (400 MHz, DMSO): δ 8.00–6.98 (m, 11H), 2.32 (s, 3H), 1.70 (s, 3H).

Example 125

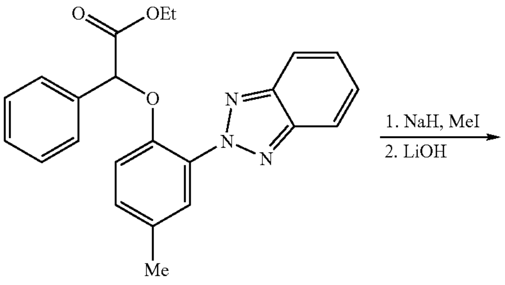

SXI-7

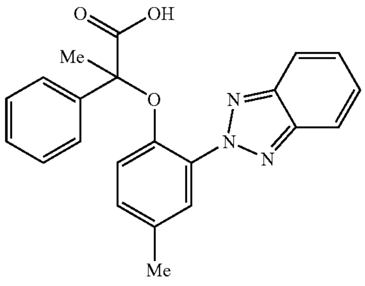

XIa-8

XIa-8 was prepared from SXI-7 in the same manner as that described in Example 42. $^1$H NMR ($CDCl_3$, 400 MHz) δ 13.41 (br, 1H), 8.03 (m, 2H), 7.58 (d, 1H), 7.53–7.49 (m, 2H), 7.36 (dd, 1H), 7.32 (m, 2H), 7.19 (m, 3H), 6.93 (d, 1H), 2.35 (s, 3H), 1.67 (s, 3H).

Example 126

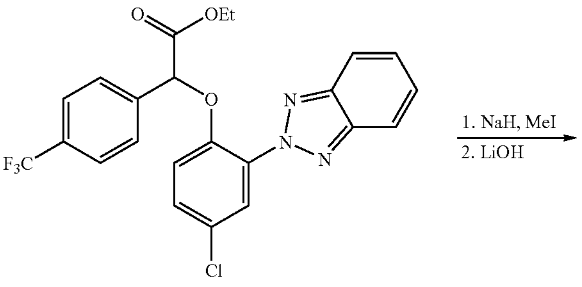

SXI-8

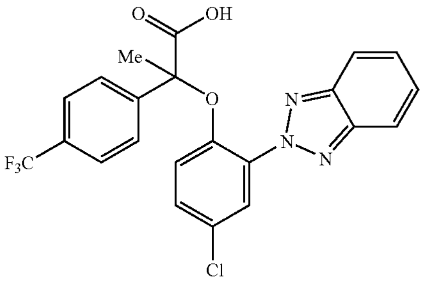

XIa-24

XIa-24 was prepared from SXI-8 in the same manner as that described in Example 42.

Example 127

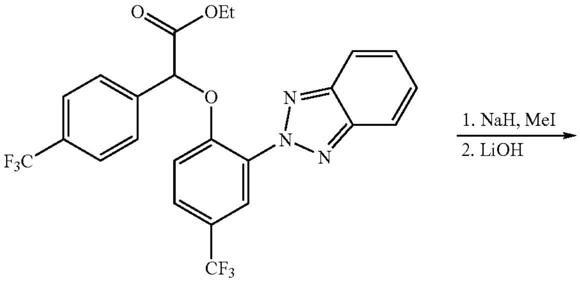

SXI-10

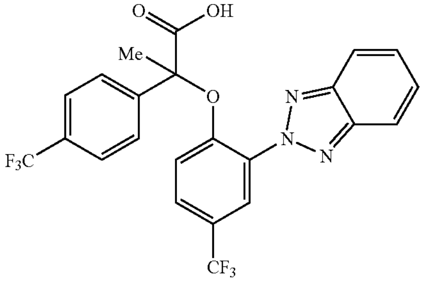

XIa-51

XIa-51 was prepared from SXI-10 in the same manner as that described in Example 42. $^1$H-NMR (400 MHz, DMSO): δ 8.10–7.22 (m, 11H), 2.42 (s, 3H), 1.70 (s, 3H).

Example 128

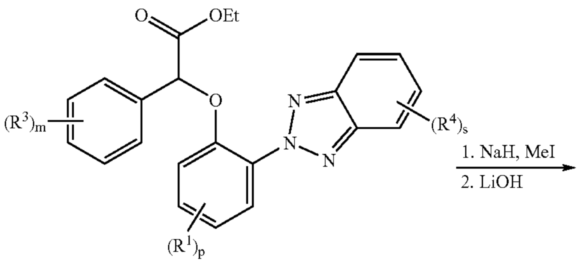

SXI-11

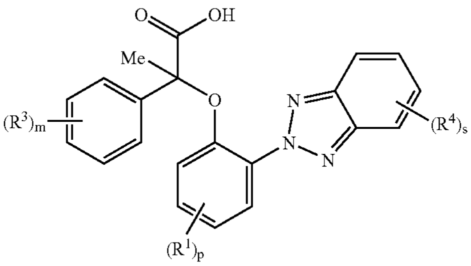

XIa-X $R^3$ = 3-$CF_3$, 3-Cl, 3-OPh, H, 4-OMe, 4-Cl, 4-$CF_3$, 4-Br, 4-Et
$R^1$ = H, 4′-t-octyl, 4′-tBu, 4′-Me, 4′-Cl, 4′-Br, 2′,4′-di-t-Bu, 4′-$CF_3$
$R^4$ = H, 2″-Cl The rest of XIa-X can be prepared from SXI-11 in the same manner as that described in Example 42.

16. Enantiomer Separation

The enantiomers of compounds XI and XIa were or can be obtained in the same manner as that described in Section 4 and Example 49 to Example 62.

Example 129

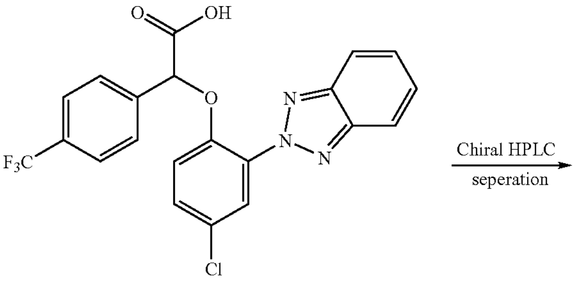

(+/-)-XI-24

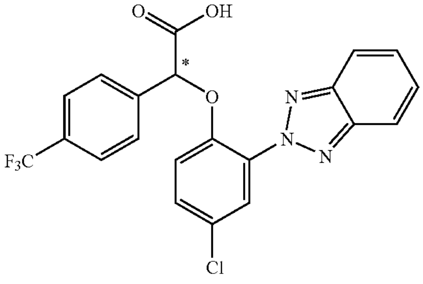

(+)-XI-24

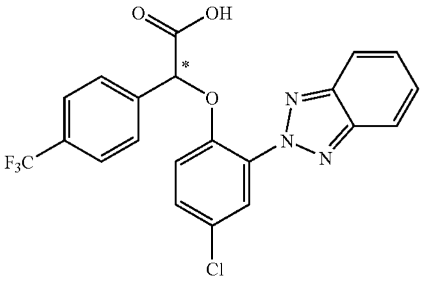

(-)-XI-24

Racemic XI-24 was resolved by chiral HPLC to give (+)-XI-24 and (−)-XI-24. HPLC methods and conditions, including eluents used, solvent flow rate and detection wavelength were: 20% iPrOH-80% Hexanes-0.1% TFA, 30 mL/min., λ=220 nm. For (+)-XI-24: RT 4.60 min. For (−)-XI-24: RT 5.11 min.

Example 130

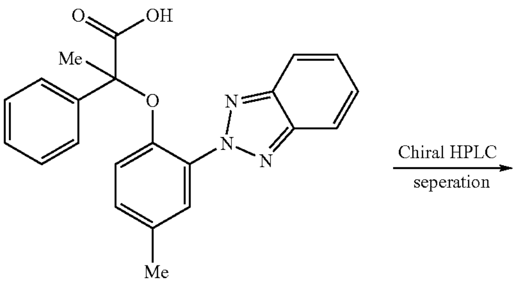

(+/-)-XIa-8

-continued

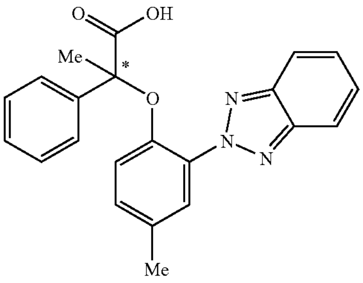

(+)-XIa-8

-continued

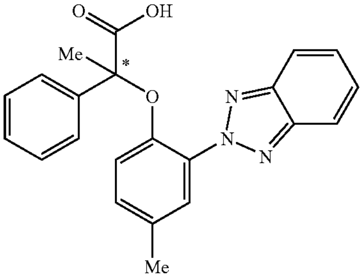

(-)-XIa-8

Racemic XIa-8 was resolved by chiral HPLC to give (+)-XIa-8 and (−)-XIa-8. HPLC methods and conditions, including eluents used, solvent flow rate and detection wavelength were: 25% iPrOH-75% Hexanes-0.1% TFA, 30 mL/min., λ=220 nm. For (+)-XIa-8: RT 4.75 min. For (−)-XIa-8: RT 6.05 min.

TABLE 12

2-Hetero-aryl analogs

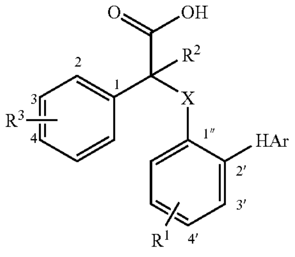

Compounds XII and XIIa

| Compound | $R^1$ | $R^2$ | $R^3$ | X | HAr | Configuration |
|---|---|---|---|---|---|---|
| XII-1 | H | H | 3-Cl | O | 2-Benzofuran-2-yl | R/S |
| XII-2 | H | H | 3-$CF_3$ | O | 2-Benzofuran-2-yl | R/S |
| XII-3 | H | H | 4-Cl | O | 2-Benzofuran-2-yl | R/S |
| XII-4 | H | H | 4-$CF_3$ | O | 2-Benzofuran-2-yl | R/S |
| XII-5 | H | H | H | O | 2-Benzofuran-2-yl | R/S |
| XII-6 | H | H | 3-Cl | O | 2-(1H-Indol-2-yl) | R/S |
| XII-7 | H | H | 3-$CF_3$ | O | 2-(1H-Indol-2-yl) | R/S |
| XII-8 | H | H | 4-Cl | O | 2-(1H-Indol-2-yl) | R/S |
| XII-9 | H | H | 4-$CF_3$ | O | 2-(1H-Indol-2-yl) | R/S |
| XII-10 | H | H | H | O | 2-(1H-Indol-2-yl) | R/S |
| XII-11 | H | H | 3-Cl | O | 2-(3-Methyl-benzo[b]thiophen-2-yl) | R/S |
| XII-12 | H | H | 3-$CF_3$ | O | 2-(3-Methyl-benzo[b]thiophen-2-yl) | R/S |
| XII-13 | H | H | 4-Cl | O | 2-(3-Methyl-benzo[b]thiophen-2-yl) | R/S |
| XII-14 | H | H | 4-$CF_3$ | O | 2-(3-Methyl-benzo[b]thiophen-2-yl) | R/S |
| XII-15 | H | H | H | O | 2-(3-Methyl-benzo[b]thiophen-2-yl) | R/S |
| XII-16 | 4-Cl | H | 3-Cl | O | 2-(5-Chloro-benzofuran-2-yl) | R/S |
| XII-17 | 4-Cl | H | 3-$CF_3$ | O | 2-(5-Chloro-benzofuran-2-yl) | R/S |
| XII-18 | 4-Cl | H | 4-Cl | O | 2-(5-Chloro-benzofuran-2-yl) | R/S |
| XII-19 | 4-Cl | H | 4-$CF_3$ | O | 2-(5-Chloro-benzofuran-2-yl) | R/S |
| XLI-20 | 4-Cl | H | H | O | 2-(5-Chloro-benzofuran-2-yl) | R/S |
| XII-21 | H | H | 3-Cl | O | 2-Quinolin-2-yl | R/S |
| XII-22 | H | H | 3-$CF_3$ | O | 2-Quinolin-2-yl | R/S |
| XII-23 | H | H | 4-Cl | O | 2-Quinolin-2-yl | R/S |

TABLE 12-continued

2-Hetero-aryl analogs

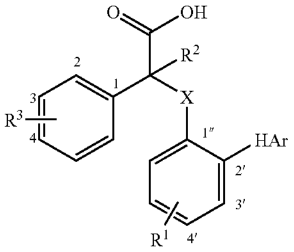

Compounds XII and XIIa

| Compound | $R^1$ | $R^2$ | $R^3$ | X | HAr | Configuration |
|---|---|---|---|---|---|---|
| XII-24 | H | H | 4-$CF_3$ | O | 2-Quinolin-2-yl | R/S |
| XII-25 | H | H | H | O | 2-Quinolin-2-yl | R/S |
| XII-26 | H | H | 3-Cl | O | 2-Thiophen-2-yl | R/S |
| XII-27 | H | H | 3-$CF_3$ | O | 2-Thiophen-2-yl | R/S |
| XII-28 | H | H | 4-Cl | O | 2-Thiophen-2-yl | R/S |
| XII-29 | H | H | 4-$CF_3$ | O | 2-Thiophen-2-yl | R/S |
| XII-30 | H | H | H | O | 2-Thiophen-2-yl | R/S |
| XII-31 | H | H | 3-Cl | O | 2-(1H-Pyrrol-2-yl) | R/S |
| XII-32 | H | H | 3-$CF_3$ | O | 2-(1H-Pyrrol-2-yl) | R/S |
| XII-33 | H | H | 4-Cl | O | 2-(1H-Pyrrol-2-yl) | R/S |
| XII-34 | H | H | 4-$CF_3$ | O | 2-(1H-Pyrrol-2-yl) | R/S |
| XII-35 | H | H | H | O | 2-(1H-Pyrrol-2-yl) | R/S |
| XII-36 | H | H | 3-Cl | NH | 2-(5-Methyl-furan-2-yl) | R/S |
| XII-37 | H | H | 3-$CF_3$ | NH | 2-(5-Methyl-furan-2-yl) | R/S |
| XII-38 | H | H | 4-Cl | NH | 2-(5-Methyl-furan-2-yl) | R/S |
| XII-39 | H | H | 4-$CF_3$ | NH | 2-(5-Methyl-furan-2-yl) | R/S |
| XII-40 | H | H | H | NH | 2-(5-Methyl-furan-2-yl) | R/S |
| XII-41 | H | H | 3-Cl | NH | 2-(1H-Indol-2-yl) | R/S |
| XII-42 | H | H | 3-$CF_3$ | NH | 2-(1H-Indol-2-yl) | R/S |
| XII-43 | H | H | 4-Cl | NH | 2-(1H-Indol-2-yl) | R/S |
| XII-44 | H | H | 4-$CF_3$ | NH | 2-(1H-Indol-2-yl) | R/S |
| XII-45 | H | H | H | NH | 2-(1H-Indol-2-yl) | R/S |
| XII-46 | H | H | 3-Cl | NH | 2-Benzo[b]thiophen-2-yl | R/S |
| XII-47 | H | H | 3-$CF_3$ | NH | 2-Benzo[b]thiophen-2-yl | R/S |
| XII-48 | H | H | 4-Cl | NH | 2-Benzo[b]thiophen-2-yl | R/S |
| XII-49 | H | H | 4-$CF_3$ | NH | 2-Benzo[b]thiophen-2-yl | R/S |
| XII-50 | H | H | H | NH | 2-Benzo[b]thiophen-2-yl | R/S |
| XII-51 | H | H | 3-Cl | NH | 2-Quinolin-2-yl | R/S |
| XII-52 | H | H | 3-$CF_3$ | NH | 2-Quinolin-2-yl | R/S |
| XII-53 | H | H | 4-Cl | NH | 2-Quinolin-2-yl | R/S |
| XII-54 | H | H | 4-$CF_3$ | NH | 2-Quinolin-2-yl | R/S |
| XII-55 | H | H | H | NH | 2-Quinolin-2-yl | R/S |
| XII-56 | H | H | 3-Cl | NH | 2-Thiophen-2-yl | R/S |
| XII-57 | H | H | 3-$CF_3$ | NH | 2-Thiophen-2-yl | R/S |
| XII-58 | H | H | 4-Cl | NH | 2-Thiophen-2-yl | R/S |
| XII-59 | H | H | 4-$CF_3$ | NH | 2-Thiophen-2-yl | R/S |
| XII-60 | H | H | H | NH | 2-Thiophen-2-yl | R/S |
| XII-61 | H | H | 3-Cl | NH | 2-Furan-2-yl | R/S |
| XII-62 | H | H | 3-$CF_3$ | NH | 2-Furan-2-yl | R/S |
| XII-63 | H | H | 4-Cl | NH | 2-Furan-2-yl | R/S |
| XII-64 | H | H | 4-$CF_3$ | NH | 2-Furan-2-yl | R/S |
| XII-65 | H | H | H | NH | 2-Furan-2-yl | R/S |
| XIIa-1 | H | H | 3-Cl | O | 2-Benzofuran-2-yl | R/S |
| XIIa-2 | H | H | 3-$CF_3$ | O | 2-Benzofuran-2-yl | R/S |
| XIIa-3 | H | H | 4-Cl | O | 2-Benzofuran-2-yl | R/S |
| XIIa-4 | H | H | 4-$CF_3$ | O | 2-Benzofuran-2-yl | R/S |
| XIIa-5 | H | H | H | O | 2-Benzofuran-2-yl | R/S |
| XIIa-6 | H | H | 3-Cl | O | 2-Thiophen-2-yl | R/S |
| XIIa-7 | H | H | 3-$CF_3$ | O | 2-Thiophen-2-yl | R/S |
| XIIa-8 | H | H | 4-Cl | O | 2-Thiophen-2-yl | R/S |
| XIIa-9 | H | H | 4-$CF_3$ | O | 2-Thiophen-2-yl | R/S |
| XIIa-10 | H | H | H | O | 2-Thiophen-2-yl | R/S |
| XIIa-11 | H | H | 3-Cl | O | 2-(3-Methyl-benzo[b]thiophen-2-yl) | R/S |

TABLE 12-continued

2-Hetero-aryl analogs

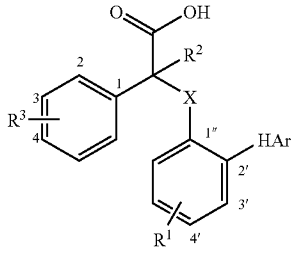

Compounds XII and XIIa

| Compound | $R^1$ | $R^2$ | $R^3$ | X | HAr | Configuration |
|---|---|---|---|---|---|---|
| XIIa-12 | H | H | 3-$CF_3$ | O | 2-(3-Methyl-benzo[b]thiophen-2-yl) | R/S |
| XIIa-13 | H | H | 4-Cl | O | 2-(3-Methyl-benzo[b]thiophen-2-yl) | R/S |
| XIIa-14 | H | H | 4-$CF_3$ | O | 2-(3-Methyl-benzo[b]thiophen-2-yl) | R/S |
| XIIa-15 | H | H | H | O | 2-(3-Methyl-benzo[b]thiophen-2-yl) | R/S |
| XIIa-16 | 4-Cl | H | 3-Cl | O | 2-(5-Chloro-benzofuran-2-yl) | R/S |
| XIIa-17 | 4-Cl | H | 3-$CF_3$ | O | 2-(5-Chloro-benzofuran-2-yl) | R/S |
| XIIa-18 | 4-Cl | H | 4-Cl | O | 2-(5-Chloro-benzofuran-2-yl) | R/S |
| XIIa-19 | 4-Cl | H | 4-$CF_3$ | O | 2-(5-Chloro-benzofuran-2-yl) | R/S |
| XIIa-20 | 4-Cl | H | H | O | 2-(5-Chloro-benzofuran-2-yl) | R/S |

17. 2-hetero-aryl-phenols

PhOH-48

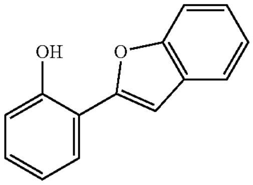

J. Amer. Chem. Soc.; 55; 1933; 3040, 3047

PhOH-49

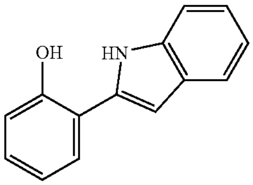

Can. J. Chem.; 63; 1985; 632–635

-continued

PhOH-50

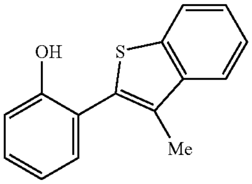

J. Chem. Res. Miniprint; 8; 1981; 2756–2771

PhOH-51

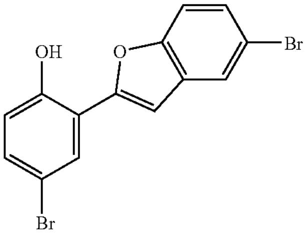

J. Org. Chem.; 55; 1990; 1240–1248

-continued

PhOH-52

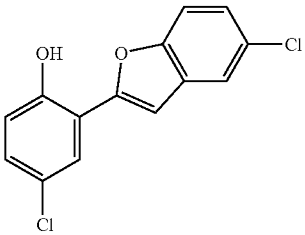

J. Org. Chem.; 55; 1990; 1240–1248

PhOH-53

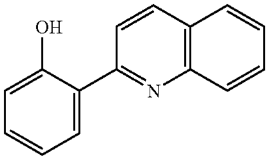

J. Chem. Soc; 1959; 1579, 1585

PhOH-54

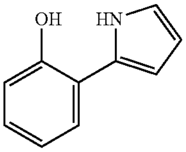

J. Org. Chem; 63; 1998; 5031–5041

PhOH-55

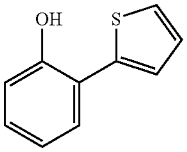

J. heterocycl. chem.; 22; 1985; 1667–1669

PhOH-48 to PhOH-55 can be prepared according to the literature procedures cited.

18. 2-Hetero-aryl anilines $PhNH_2$-2

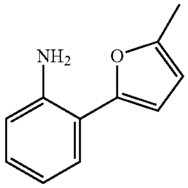

Comcercially available

-continued $PhNH_2$-3

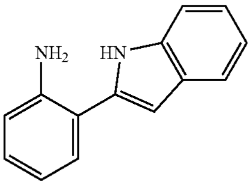

Comcercially available $PhNH_2$-4

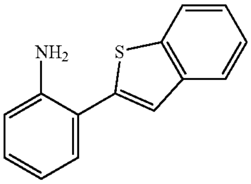

J. Chem. Soc. Perkin Trans. 1; 1972; 2023–2030

$PhNH_2$-5

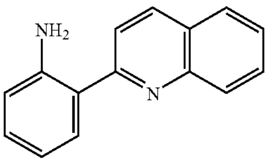

Synth. Commum.; 29; 22; 1999; 3959–3970

$PhNH_2$-6

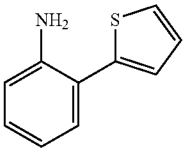

J. Amer. Chem. Soc.; 73; 1951; 2626, 2629

$PhNH_2$-7

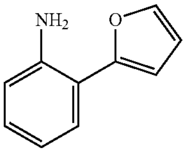

J. Amer. Chem. Soc.; 75; 1953; 6335

$PhNH_2$-2 to $PhNH_2$-7 can be either purchased from different commercial sources or they can be prepared according the literature procedures cited.

19. Synthesis of Compounds XII and XIa in Table 12

Compounds XII-X and XIIa-X were or can be prepared with SBr-X and PhOH-48 to PhOH-55 and with SBr-X and $PhNH_2$-2 to $PhNH_2$-7 in the same manner as that described for the synthesis of compounds I-X and Ia-X.

TABLE 13

Aza-beuzooxazole and aza-benzothiazole analogs

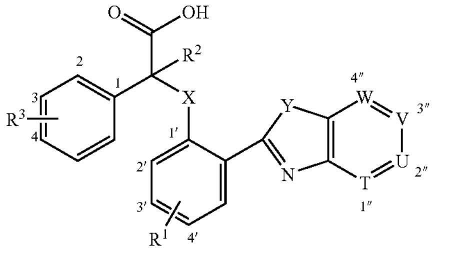

Compound XIII

| Compound | $R^1$ | $R^2$ | $R^3$ | X | Y | T, U, V, W, |
|---|---|---|---|---|---|---|
| XIII-1 | H | H | 3-Cl | O | O | T=N U=V=W=CH |
| XIII-2 | H | H | 3-$CF_3$ | O | O | T=N U=V=W=CH |
| XIII-3 | H | H | 4-Cl | O | O | T=N U=V=W=CH |
| XIII-4 | H | H | 4-$CF_3$ | O | O | T=N U=V=W=CH |
| XIII-5 | H | H | H | O | O | T=N U=V=W=CH |
| XIII-6 | H | H | 3-Cl | O | O | W=N T=U=V=CH |
| XIII-7 | H | H | 3-$CF_3$ | O | O | W=N T=U=V=CH |
| XIII-8 | H | H | 4-Cl | O | O | W=N T=U=V=CH |
| XIII-9 | H | H | 4-$CF_3$ | O | O | W=N T=U=V=CH |
| XIII-10 | H | H | H | O | O | W=N T=U=V=CH |
| XIII-11 | H | H | 3-Cl | O | O | U=N T=V=W=CH |
| XIII-12 | H | H | 3-$CF_3$ | O | O | U=N T=V=W=CH |
| XIII-13 | H | H | 4-Cl | O | O | U=N T=V=W=CH |
| XIII-14 | H | H | 4-$CF_3$ | O | O | U=N T=V=W=CH |
| XIII-15 | H | H | H | O | O | U=N T=V=W=CH |
| XIII-16 | 4'-Cl | H | 3-Cl | O | O | T=N U=V=W=CH |
| XIII-17 | 4'-Cl | H | 3-$CF_3$ | O | O | T=N U=V=W=CH |
| XIII-18 | 4'-Cl | H | 4-Cl | O | O | T=N U=V=W=CH |
| XIII-19 | 4'-Cl | H | 4-$CF_3$ | O | O | T=N U=V=W=CH |
| XILI-20 | 4'-Cl | H | H | O | O | T=N U=V=W=CH |
| XIII-21 | 4'-Cl | H | 3-Cl | O | O | W=N T=U=V=CH |
| XIII-22 | 4'-Cl | H | 3-$CF_3$ | O | O | W=N T=U=V=CH |
| XIII-23 | 4'-Cl | H | 4-Cl | O | O | W=N T=U=V=CH |
| XIII-24 | 4'-Cl | H | 4-$CF_3$ | O | O | W=N T=U=V=CH |
| XIII-25 | 4'-Cl | H | H | O | O | W=N T=U=V=CH |
| XIII-26 | 4'-Cl | H | 3-Cl | O | O | U=N T=V=W=CH |
| XIII-27 | 4'-Cl | H | 3-$CF_3$ | O | O | U=N T=V=W=CH |
| XIII-28 | 4'-Cl | H | 4-Cl | O | O | U=N T=V=W=CH |
| XIII-29 | 4'-Cl | H | 4-$CF_3$ | O | O | U=N T=V=W=CH |

TABLE 13-continued

Aza-beuzooxazole and aza-benzothiazole analogs

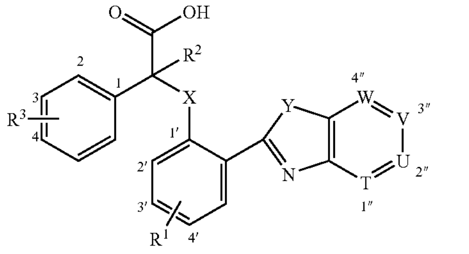

Compound XIII

| Compound | $R^1$ | $R^2$ | $R^3$ | X | Y | T, U, V, W, |
|---|---|---|---|---|---|---|
| XIII-30 | 4'-Cl | H | H | O | O | U=N T=V=W=CH |
| XIII-31 | 4'-$CF_3$ | H | 3-Cl | O | O | T=N U=V=W=CH |
| XIII-32 | 4'-$CF_3$ | H | 3-$CF_3$ | O | O | T=N U=V=W=CH |
| XIII-33 | 4'-$CF_3$ | H | 4-Cl | O | O | T=N U=V=W=CH |
| XIII-34 | 4'-$CF_3$ | H | 4-$CF_3$ | O | O | T=N U=V=W=CH |
| XIII-35 | 4'-$CF_3$ | H | H | O | O | T=N U=V=W=CH |
| XIII-36 | 4'-$CF_3$ | H | 3-Cl | O | O | W=N T=U=V=CH |
| XIII-37 | 4'-$CF_3$ | H | 3-$CF_3$ | O | O | W=N T=U=V=CH |
| XIII-38 | 4'-$CF_3$ | H | 4-Cl | O | O | W=N T=U=V=CH |
| XIII-39 | 4'-$CF_3$ | H | 4-$CF_3$ | O | O | W=N T=U=V=CH |
| XIII-40 | 4'-$CF_3$ | H | H | O | O | W=N T=U=V=CH |
| XIII-41 | 4'-$CF_3$ | H | 3-Cl | O | O | U=N T=V=W=CH |
| XIII-42 | 4'-$CF_3$ | H | 3-$CF_3$ | O | O | U=N T=V=W=CH |
| XIII-43 | 4'-$CF_3$ | H | 4-Cl | O | O | U=N T=V=W=CH |
| XIII-44 | 4'-$CF_3$ | H | 4-$CF_3$ | O | O | U=N T=V=W=CH |
| XIII-45 | 4'-$CF_3$ | H | H | O | O | U=N T=V=W=CH |
| XIII-46 | 4'-Cl | H | 3-Cl | O | S | W=N T=U=V=CH |
| XIII-47 | 4'-Cl | H | 3-$CF_3$ | O | S | W=N T=U=V=CH |
| XIII-48 | 4'-Cl | H | 4-Cl | O | S | W=N T=U=V=CH |
| XIII-49 | 4'-Cl | H | 4-$CF_3$ | O | S | W=N T=U=V=CH |
| XIII-50 | 4'-Cl | H | H | O | S | W=N T=U=V=CH |
| XIII-51 | 4'-$CF_3$ | H | 3-Cl | O | S | W=N T=U=V=CH |
| XIII-52 | 4'-$CF_3$ | H | 3-$CF_3$ | O | S | W=N T=U=V=CH |
| XIII-53 | 4'-$CF_3$ | H | 4-Cl | O | S | W=N T=U=W=CH |
| XIII-54 | 4'-$CF_3$ | H | 4-$CF_3$ | O | S | W=N T=U=V=CH |
| XIII-55 | 4'-$CF_3$ | H | H | O | S | W=N T=U=V=CH |
| XIII-56 | H | H | 3-Cl | NH | O | T=N U=V=W=CH |
| XIII-57 | H | H | 3-$CF_3$ | NH | O | T=N U=V=W=CH |
| XIII-58 | H | H | 4-Cl | NH | O | T=N U=V=W=CH |

TABLE 13-continued

Aza-beuzooxazole and aza-benzothiazole analogs

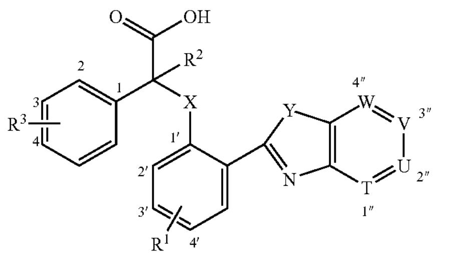

Compound XIII

| Compound | $R^1$ | $R^2$ | $R^3$ | X | Y | T, U, V, W, |
|---|---|---|---|---|---|---|
| XIII-59 | H | H | 4-$CF_3$ | NH | O | T=N<br>U=V=W=CH |
| XIII-60 | H | H | H | NH | O | T=N<br>U=V=W=CH |
| XIII-61 | H | H | 3-Cl | NH | O | W=N<br>T=U=V=CH |
| XIII-62 | H | H | 3-$CF_3$ | NH | O | W=N<br>T=U=V=CH |
| XIII-63 | H | H | 4-Cl | NH | O | W=N<br>T=U=V=CH |
| XIII-64 | H | H | 4-$CF_3$ | NH | O | W=N<br>T=U=V=CH |
| XIII-65 | H | H | H | NH | O | W=N<br>T=U=V=CH |
| XIII-66 | H | H | 3-Cl | NH | O | U=N<br>T=V=W=CH |
| XIII-67 | H | H | 3-$CF_3$ | NH | O | U=N<br>T=V=W=CH |
| XIII-68 | H | H | 4-Cl | NH | O | U=N<br>T=V=W=CH |
| XIII-69 | H | H | 4-$CF_3$ | NH | O | U=N<br>T=V=W=CH |
| XIII-70 | H | H | H | NH | O | U=N<br>T=V=W=CH |
| XIII-71 | 4'-Cl | H | 3-Cl | NH | O | T=N<br>U=V=W=CH |
| XIII-72 | 4'-Cl | H | 3-$CF_3$ | NH | O | T=N<br>U=V=W=CH |
| XIII-73 | 4'-Cl | H | 4-Cl | NH | O | T=N<br>U=V=W=CH |
| XIII-74 | 4'-Cl | H | 4-$CF_3$ | NH | O | T=N<br>U=V=W=CH |
| XIII-75 | 4'-Cl | H | H | NH | O | T=N<br>U=V=W=CH |
| XIII-76 | 4'-Cl | H | 3-Cl | NH | O | W=N<br>T=U=V=CH |
| XIII-77 | 4'-Cl | H | 3-$CF_3$ | NH | O | W=N<br>T=U=V=CH |
| XIII-78 | 4'-Cl | H | 4-Cl | NH | O | W=N<br>T=U=V=CH |
| XIII-79 | 4'-Cl | H | 4-$CF_3$ | NH | O | W=N<br>T=U=V=CH |
| XIII-80 | 4'-Cl | H | H | NH | O | W=N<br>T=U=V=CH |
| XIII-81 | 4'-Cl | H | 3-Cl | NH | O | U=N<br>T=V=W=CH |
| XIII-82 | 4'-Cl | H | 3-$CF_3$ | NH | O | U=N<br>T=V=W=CH |
| XIII-83 | 4'-Cl | H | 4-Cl | NH | O | U=N<br>T=W=W=CH |
| XIII-84 | 4'-Cl | H | 4-$CF_3$ | NH | O | U=N<br>T=V=W=CH |
| XIII-85 | 4'-Cl | H | H | NH | O | U=N<br>T=V=W=CH |
| XIII-86 | 4'-$CF_3$ | H | 3-Cl | NH | O | T=N<br>U=V=W=CH |
| XIII-87 | 4'-$CF_3$ | H | 3-$CF_3$ | NH | O | T=N<br>U=V=W=CH |

TABLE 13-continued

Aza-beuzooxazole and aza-benzothiazole analogs

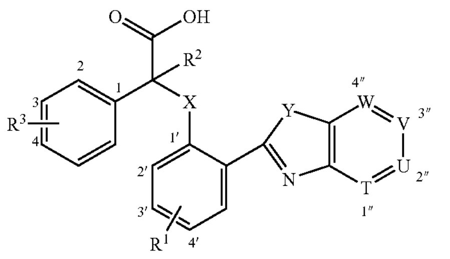

Compound XIII

| Compound | $R^1$ | $R^2$ | $R^3$ | X | Y | T, U, V, W, |
|---|---|---|---|---|---|---|
| XIII-88 | 4'-$CF_3$ | H | 4-Cl | NH | O | T=N<br>U=V=W=CH |
| XIII-89 | 4'-$CF_3$ | H | 4-$CF_3$ | NH | O | T=N<br>U=V=W=CH |
| XIII-90 | 4'-$CF_3$ | H | H | NH | O | T=N<br>U=V=W=CH |
| XIII-91 | 4'-$CF_3$ | H | 3-Cl | NH | O | W=N<br>T=U=V=CH |
| XIII-92 | 4'-$CF_3$ | H | 3-$CF_3$ | NH | O | W=N<br>T=U=V=CH |
| XIII-93 | 4'-$CF_3$ | H | 4-Cl | NH | O | W=N<br>T=U=V=CH |
| XIII-94 | 4'-$CF_3$ | H | 4-$CF_3$ | NH | O | W=N<br>T=U=V=CH |
| XIII-95 | 4'-$CF_3$ | H | H | NH | O | W=N<br>T=U=V=CH |
| XIII-96 | 4'-$CF_3$ | H | 3-Cl | NH | O | U=N<br>T=V=W=CH |
| XIII-97 | 4'-$CF_3$ | H | 3-$CF_3$ | NH | O | U=N<br>T=V=W=CH |
| XIII-98 | 4'-$CF_3$ | H | 4-Cl | NH | O | U=N<br>T=V=W=CH |
| XIII-99 | 4'-$CF_3$ | H | 4-$CF_3$ | NH | O | U=N<br>T=V=W=CH |
| XIII-100 | 4'-$CF_3$ | H | H | NH | O | U=N<br>T=V=W=CH |
| XIII-101 | 4'-Cl | H | 3-Cl | NH | S | W=N<br>T=U=V=CH |
| XIII-102 | 4'-Cl | H | 3-$CF_3$ | NH | S | W=N<br>T=U=N=CH |
| XIII-103 | 4'-Cl | H | 4-Cl | NH | S | W=N<br>T=U=V=CH |
| XIII-104 | 4'-Cl | H | 4-$CF_3$ | NH | S | W=N<br>T=U=V=CH |
| XIII-105 | 4'-Cl | H | H | NH | S | W=N<br>T=U=V=CH |
| XIII-106 | 4'-$CF_3$ | H | 3-Cl | NH | S | W=N<br>T=U=V=CH |
| XIII-107 | 4'-$CF_3$ | H | 3-$CF_3$ | NH | S | W=N<br>T=U=V=CH |
| XIII-108 | 4'-$CF_3$ | H | 4-Cl | NH | S | W=N<br>T=U=V=CH |
| XIII-109 | 4'-$CF_3$ | H | 4-$CF_3$ | NH | S | W=N<br>T=U=V=CH |
| XIII-110 | 4'-$CF_3$ | H | H | NH | S | W=N<br>T=U=V=CH |

20. Synthesis of aza-benzooxazole and aza-benzothiazole phenols and anilines

The Aza-benzooxazole and Aza-benzothiazole Phenols and Anilines used for the preparation of compounds XIII can be prepared in the same manner as that described for the synthesis of 2-benzooxazol-2-yl-phenols illustrated in Scheme II or by those skilled in the arts.

Scheme 7
Synthesis of aza-benzooxazole and aza-benzothiazole phenols and anilines
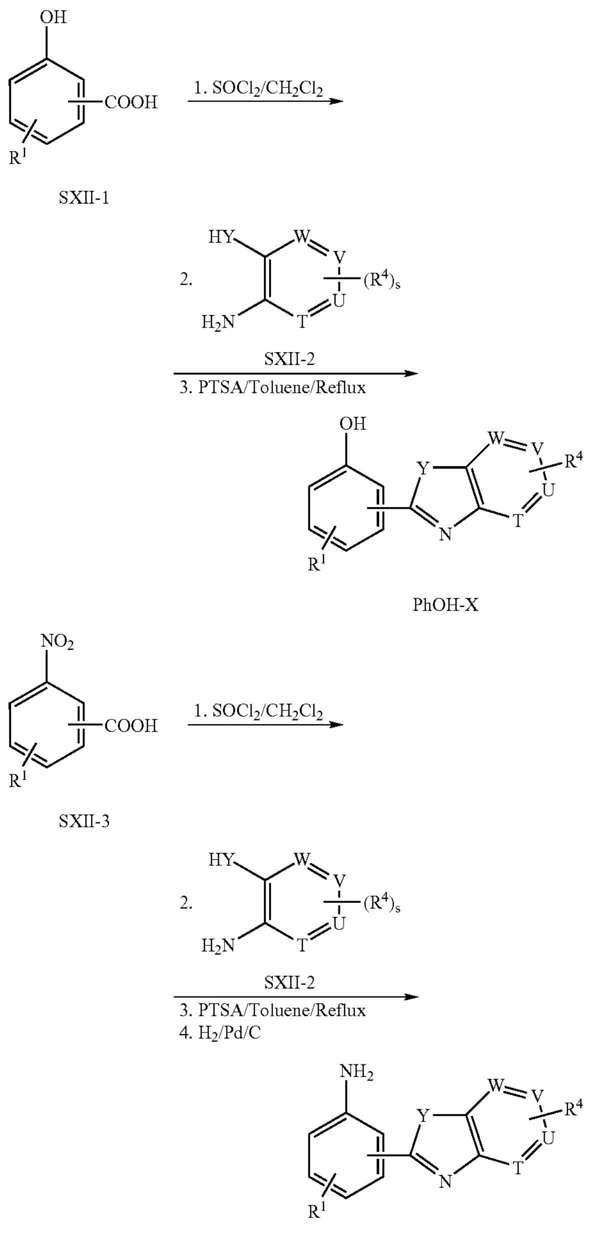
Y = O, S
T = $CR^4$, CH, N; U = $CR^4$, CH, N; V = $CR^4$, CH, N; W = $CR^4$, CH, N;
$R^1$ = H, 4′-Cl, 4′-Me, 4′-OMe, 4′-Br, 4′-F, 3′,4′-diF, 3′,4′-diOMe, ′4-$CF_3$
$R^4$ = H, halo, haloalkyl, alkyl, Oalkyl etc.
PhOH-56
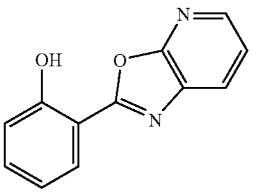
-continued
PhOH-57
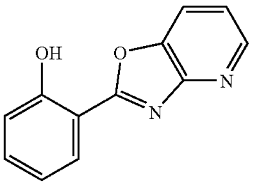
PhOH-58
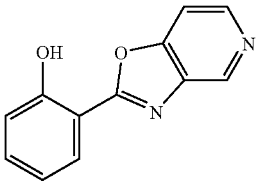
PhOH-59
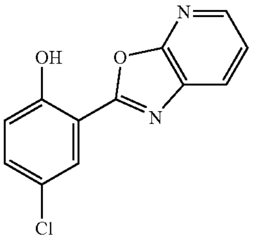
PhOH-60
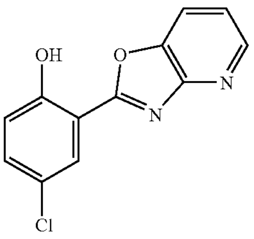
PhOH-61
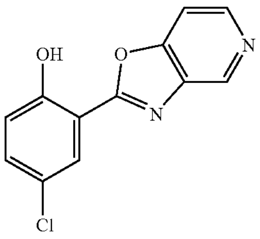
PhOH-62
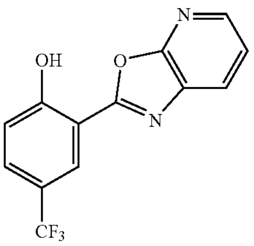
PhOH-63
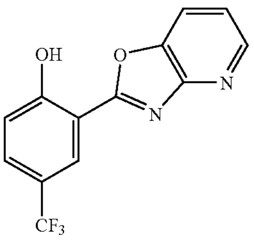

-continued
PhOH-64
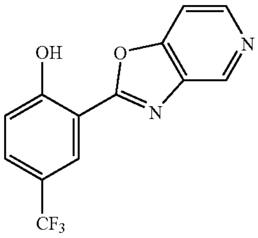
PhOH-65
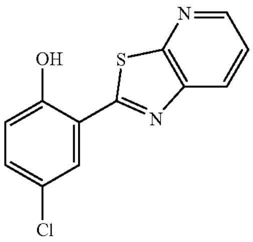
PhOH-66
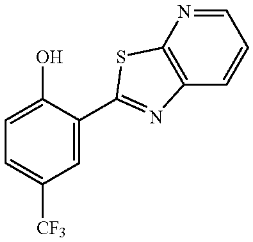
PhOH-56 to PhOH-66 can be prepared according to Scheme7 with readily available aza-2-amino-phenols and aza-2-amino-benzenethiol.
$PhNH_2$-8
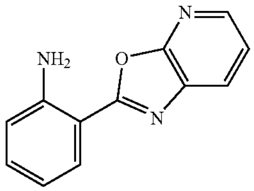
$PhNH_2$-9
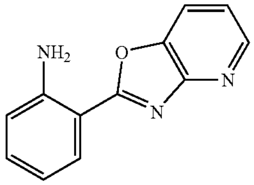
$PhNH_2$-10
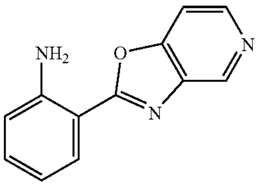
-continued
$PhNH_2$-11
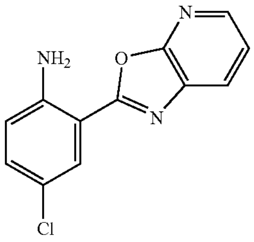
$PhNH_2$-12
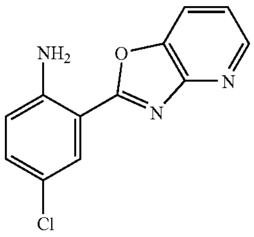
$PhNH_2$-13
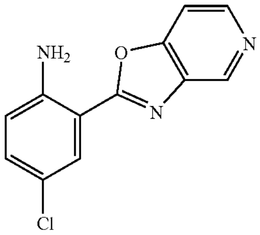
$PhNH_2$-14
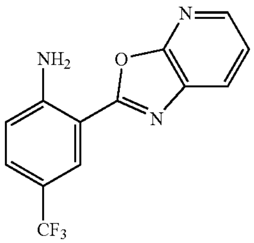
$PhNH_2$-15
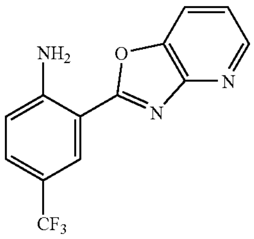
$PhNH_2$-16
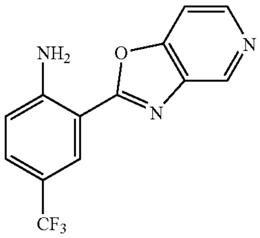

-continued

PhNH$_2$-17

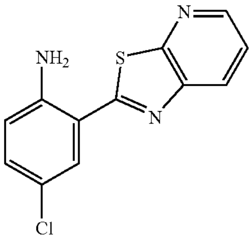

-continued

PhNH$_2$-18

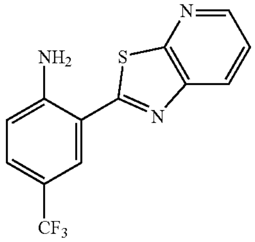

PhNH$_2$-8 to PhNH$_2$-18 can be prepared according to Scheme7 with readily available aza-2-amino-phenols and aza-2-amino-benzenethiol.

21. Synthesis of Compounds XIII in Table 13

Compounds XIII can be prepared with SBr-X and PhOH-56 to PhOH-66 and with SBr-X and PhNH$_2$-8 to PhNH$_2$-18 in the same manner as that described for the synthesis of compounds I-X and Ia-X.

TABLE 14

Prodrugs

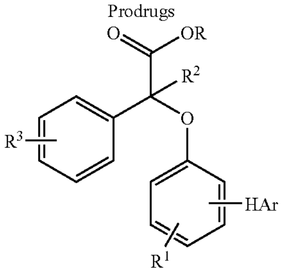

Compounds XIV

| Compound | $R^1$ | $R^2$ | $R^3$ | HAr | Racemic or enantiomer | R |
|---|---|---|---|---|---|---|
| XIV-1 | 4'-$CF_3$ | H | 4-Cl | 2-benzooxazole | +/− | $CH_2CH_2NHAc$ |
| XIV-2 | 4'-$CF_3$ | H | 3-$CF_3$ | 2-benzooxazole | +/− | $CH_2CH_2NHAc$ |
| XIV-3 | 4'-$CF_3$ | H | 3-$CF_3$ | 2-benzooxazole | + | $CH_2CH_2NHAc$ |
| XIV-4 | 4'-$CF_3$ | H | 3-$CF_3$ | 2-benzooxazole | − | $CH_2CH_2NHAc$ |
| XIV-5 | 4'-$CF_3$ | H | 3-Cl | 2-benzooxazole | +/− | $CH_2CH_2NHAc$ |
| XIV-6 | 4'-$CF_3$ | H | 4-$CF_3$ | 2-benzooxazole | +/− | $CH_2CH_2NHAc$ |
| XIV-7 | 4'-$CF_3$ | H | H | 2-benzooxazole | +/− | $CH_2CH_2NHAc$ |
| XIV-8 | 4'-$CF_3$ | H | H | 2-benzooxazole | + | $CH_2CH_2NHAc$ |
| XIV-9 | 4'-$CF_3$ | H | H | 2-benzooxazole | − | $CH_2CH_2NHAc$ |
| XIV-10 | 4'-Cl | H | 4-Cl | 2-benzooxazole | +/− | $CH_2CH_2NHAc$ |
| XIV-11 | 4'-Cl | H | 3-$CF_3$ | 2-benzooxazole | +/− | $CH_2CH_2NHAc$ |
| XIV-12 | 4'-Cl | H | 3-$CF_3$ | 2-benzooxazole | + | $CH_2CH_2NHAc$ |
| XIV-13 | 4'-Cl | H | 3-$CF_3$ | 2-benzooxazole | − | $CH_2CH_2NHAc$ |
| XIV-14 | 4'-Cl | H | 3-Cl | 2-benzooxazole | +/− | $CH_2CH_2NHAc$ |
| XIV-15 | 4'-Cl | H | 4-$CF_3$ | 2-benzooxazole | +/− | $CH_2CH_2NHAc$ |
| XIV-16 | 4'-Cl | H | H | 2-benzooxazole | +/− | $CH_2CH_2NHAc$ |
| XIV-17 | 4'-$CF_3$ | Me | 4-Cl | 2-benzooxazole | +/− | $CH_2CH_2NHAc$ |
| XIV-18 | 4'-$CF_3$ | Me | 3-$CF_3$ | 2-benzooxazole | +/− | $CH_2CH_2NHAc$ |
| XIV-19 | 4'-$CF_3$ | Me | 3-Cl | 2-benzooxazole | +/− | $CH_2CH_2NHAc$ |
| XIV-20 | 4'-$CF_3$ | Me | 4-$CF_3$ | 2-benzooxazole | +/− | $CH_2CH_2NHAc$ |
| XIV-21 | 4'-$CF_3$ | Me | H | 2-benzooxazole | +/− | $CH_2CH_2NHAc$ |
| XIV-22 | 4'-Cl | Me | 4-Cl | 2-benzooxazole | +/− | $CH_2CH_2NHAc$ |
| XIV-23 | 4'-Cl | Me | 3-$CF_3$ | 2-benzooxazole | +/− | $CH_2CH_2NHAc$ |
| XIV-24 | 4'-Cl | Me | 3-Cl | 2-benzooxazole | +/− | $CH_2CH_2NHAc$ |
| XIV-25 | 4'-Cl | Me | 4-$CF_3$ | 2-benzooxazole | +/− | $CH_2CH_2NHAc$ |
| XIV-26 | 4'-Cl | Me | H | 2-benzooxazole | +/− | $CH_2CH_2NHAc$ |
| XIV-27 | 4'-$CF_3$ | H | 3-$CF_3$ | 2-benzothiazole | +/− | $CH_2CH_2NHAc$ |
| XIV-28 | 4'-Cl | H | 3-$CF_3$ | 2-benzothiazole | +/− | $CH_2CH_2NHAc$ |
| XIV-29 | 4'-$CF_3$ | H | 4-Cl | 2-benzothiazole | +/− | $CH_2CH_2NHAc$ |
| XIV-30 | 4'-Cl | H | 4-Cl | 2-benzothiazole | +/− | $CH_2CH_2NHAc$ |

TABLE 14-continued

Prodrugs

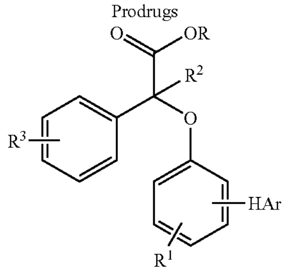

Compounds XIV

| Compound | $R^1$ | $R^2$ | $R^3$ | HAr | Racemic or enantiomer | R |
|---|---|---|---|---|---|---|
| XIV-31 | 4'-$CF_3$ | Me | 3-$CF_3$ | 2-benzothiazole | +/− | $CH_2CH_2NHAc$ |
| XIV-32 | 4'-Cl | Me | 3-$CF_3$ | 2-benzothiazole | +/− | $CH_2CH_2NHAc$ |
| XIV-33 | 4'-$CF_3$ | Me | 4-Cl | 2-benzothiazole | +/− | $CH_2CH_2NHAc$ |
| XIV-34 | 4'-Cl | Me | 4-Cl | 2-benzothiazole | +/− | $CH_2CH_2NHAc$ |
| XIV-35 | 4'-$CF_3$ | H | 4-Cl | 2-benzotriazole | +/− | $CH_2CH_2NHAc$ |
| XIV-36 | 4'-$CF_3$ | H | 3-$CF_3$ | 2-benzotriazole | +/− | $CH_2CH_2NHAc$ |
| XIV-37 | 4'-$CF_3$ | H | 3-Cl | 2-benzotriazole | +/− | $CH_2CH_2NHAc$ |
| XIV-38 | 4'-$CF_3$ | H | 4-$CF_3$ | 2-benzotriazole | +/− | $CH_2CH_2NHAc$ |
| XIV-39 | 4'-$CF_3$ | H | H | 2-benzotriazole | +/− | $CH_2CH_2NHAc$ |
| XIV-40 | 4'-Cl | H | 4-Cl | 2-benzotriazole | +/− | $CH_2CH_2NHAc$ |
| XIV-41 | 4'-Cl | H | 3-$CF_3$ | 2-benzotriazole | +/− | $CH_2CH_2NHAc$ |
| XIV-42 | 4'-Cl | H | 3-Cl | 2-benzotriazole | +/− | $CH_2CH_2NHAc$ |
| XIV-43 | 4'-Cl | H | 4-$CF_3$ | 2-benzotriazole | +/− | $CH_2CH_2NHAc$ |
| XIV-44 | 4'-Cl | H | H | 2-benzotriazole | +/− | $CH_2CH_2NHAc$ |
| XIV-45 | 4'-$CF_3$ | Me | 4-Cl | 2-benzotriazole | +/− | $CH_2CH_2NHAc$ |
| XIV-46 | 4'-$CF_3$ | Me | 3-$CF_3$ | 2-benzotriazole | +/− | $CH_2CH_2NHAc$ |
| XIV-47 | 4'-$CF_3$ | Me | 3-Cl | 2-benzotriazole | +/− | $CH_2CH_2NHAc$ |
| XIV-48 | 4'-$CF_3$ | Me | 4-$CF_3$ | 2-benzotriazole | +/− | $CH_2CH_2NHAc$ |
| XIV-49 | 4'-$CF_3$ | Me | H | 2-benzotriazole | +/− | $CH_2CH_2NHAc$ |
| XIV-50 | 4'-Cl | Me | 4-Cl | 2-benzotriazole | +/− | $CH_2CH_2NHAc$ |
| XIV-51 | 4'-Cl | Me | 3-$CF_3$ | 2-benzotriazole | +/− | $CH_2CH_2NHAc$ |
| XIV-52 | 4'-Cl | Me | 3-Cl | 2-benzotriazole | +/− | $CH_2CH_2NHAc$ |
| XIV-53 | 4'-Cl | Me | 4-$CF_3$ | 2-benzotriazole | +/− | $CH_2CH_2NHAc$ |
| XIV-54 | 4'-Cl | Me | H | 2-benzotriazole | +/− | $CH_2CH_2NHAc$ |
| XIV-55 | 4'-$CF_3$ | H | 4-Cl | 2-benzooxazole | +/− | $CH_2COOEt$ |
| XIV-56 | 4'-$CF_3$ | H | 3-$CF_3$ | 2-benzooxazole | +/− | $CH_2COOEt$ |
| XIV-57 | 4'-$CF_3$ | H | 3-$CF_3$ | 2-benzooxazole | + | $CH_2COOEt$ |
| XIV-58 | 4'-$CF_3$ | H | 3-$CF_3$ | 2-benzooxazole | − | $CH_2COOEt$ |
| XIV-59 | 4'-$CF_3$ | H | 3-Cl | 2-benzooxazole | +/− | $CH_2COOEt$ |
| XIV-60 | 4'-$CF_3$ | H | 4-$CF_3$ | 2-benzooxazole | +/− | $CH_2COOEt$ |
| XIV-61 | 4'-$CF_3$ | H | H | 2-benzooxazole | +/− | $CH_2COOEt$ |
| XIV-62 | 4'-$CF_3$ | H | H | 2-benzooxazole | + | $CH_2COOEt$ |
| XIV-63 | 4'-$CF_3$ | H | H | 2-benzooxazole | − | $CH_2COOEt$ |
| XIV-64 | 4'-Cl | H | 4-Cl | 2-benzooxazole | +/− | $CH_2COOEt$ |
| XIV-65 | 4'-Cl | H | 3-$CF_3$ | 2-benzooxazole | +/− | $CH_2COOEt$ |
| XIV-66 | 4'-Cl | H | 3-$CF_3$ | 2-benzooxazole | + | $CH_2COOEt$ |
| XIV-67 | 4'-Cl | H | 3-$CF_3$ | 2-benzooxazole | − | $CH_2COOEt$ |
| XIV-68 | 4'-Cl | H | 3-Cl | 2-benzooxazole | +/− | $CH_2COOEt$ |
| XIV-69 | 4'-Cl | H | 4-$CF_3$ | 2-benzooxazole | +/− | $CH_2COOEt$ |
| XIV-70 | 4'-Cl | H | H | 2-benzooxazole | +/− | $CH_2COOEt$ |
| XIV-71 | 4'-$CF_3$ | Me | 4-Cl | 2-benzooxazole | +/− | $CH_2COOEt$ |
| XIV-72 | 4'-$CF_3$ | Me | 3-$CF_3$ | 2-benzooxazole | +/− | $CH_2COOEt$ |
| XIV-73 | 4'-$CF_3$ | Me | 3-Cl | 2-benzooxazole | +/− | $CH_2COOEt$ |
| XIV-74 | 4'-$CF_3$ | Me | 4-$CF_3$ | 2-benzooxazole | +/− | $CH_2COOEt$ |
| XIV-75 | 4'-$CF_3$ | Me | H | 2-benzooxazole | +/− | $CH_2COOEt$ |
| XIV-76 | 4'-Cl | Me | 4-Cl | 2-benzooxazole | +/− | $CH_2COOEt$ |
| XIV-77 | 4'-Cl | Me | 3-$CF_3$ | 2-benzooxazole | +/− | $CH_2COOEt$ |
| XIV-78 | 4'-Cl | Me | 3-Cl | 2-benzooxazole | +/− | $CH_2COOEt$ |
| XIV-79 | 4'-Cl | Me | 4-$CF_3$ | 2-benzooxazole | +/− | $CH_2COOEt$ |
| XIV-80 | 4'-Cl | Me | H | 2-benzooxazole | +/− | $CH_2COOEt$ |
| XIV-81 | 4'-$CF_3$ | H | 3-$CF_3$ | 2-benzothiazole | +/− | $CH_2COOEt$ |
| XIV-82 | 4'-Cl | H | 3-$CF_3$ | 2-benzothiazole | +/− | $CH_2COOEt$ |
| XIV-83 | 4'-$CF_3$ | H | 4-Cl | 2-benzothiazole | +/− | $CH_2COOEt$ |
| XIV-84 | 4'-Cl | H | 4-Cl | 2-benzothiazole | +/− | $CH_2COOEt$ |
| XIV-85 | 4'-$CF_3$ | Me | 3-$CF_3$ | 2-benzothiazole | +/− | $CH_2COOEt$ |
| XIV-86 | 4'-Cl | Me | 3-$CF_3$ | 2-benzothiazole | +/− | $CH_2COOEt$ |
| XIV-87 | 4'-$CF_3$ | Me | 4-Cl | 2-benzothiazole | +/− | $CH_2COOEt$ |
| XIV-88 | 4'-Cl | Me | 4-Cl | 2-benzothiazole | +/− | $CH_2COOEt$ |
| XIV-89 | 4'-$CF_3$ | H | 4-Cl | 2-benzotriazole | +/− | $CH_2COOEt$ |

TABLE 14-continued

Prodrugs

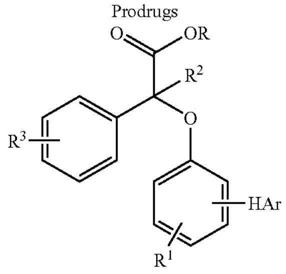

Compounds XIV

| Compound | $R^1$ | $R^2$ | $R^3$ | HAr | Racemic or enantiomer | R |
|---|---|---|---|---|---|---|
| XIV-90 | 4'-$CF_3$ | H | 3-$CF_3$ | 2-benzotriazole | +/− | $CH_2COOEt$ |
| XIV-91 | 4'-$CF_3$ | H | 3-Cl | 2-benzotriazole | +/− | $CH_2COOEt$ |
| XIV-92 | 4'-$CF_3$ | H | 4-$CF_3$ | 2-benzotriazole | +/− | $CH_2COOEt$ |
| XIV-93 | 4'-$CF_3$ | H | H | 2-benzotriazole | +/− | $CH_2COOEt$ |
| XIV-94 | 4'-Cl | H | 4-Cl | 2-benzotriazole | +/− | $CH_2COOEt$ |
| XIV-95 | 4'-Cl | H | 3-$CF_3$ | 2-benzotriazole | +/− | $CH_2COOEt$ |
| XIV-96 | 4'-Cl | H | 3-Cl | 2-benzotriazole | +/− | $CH_2COOEt$ |
| XIV-97 | 4'-Cl | H | 4-$CF_3$ | 2-benzotriazole | +/− | $CH_2COOEt$ |
| XIV-98 | 4'-Cl | H | H | 2-benzotriazole | +/− | $CH_2COOEt$ |
| XIV-99 | 4'-$CF_3$ | Me | 4-Cl | 2-benzotriazole | +/− | $CH_2COOEt$ |
| XIV-100 | 4'-$CF_3$ | Me | 3-$CF_3$ | 2-benzotriazole | +/− | $CH_2COOEt$ |
| XIV-101 | 4'-$CF_3$ | Me | 3-Cl | 2-benzotriazole | +/− | $CH_2COOEt$ |
| XIV-102 | 4'-$CF_3$ | Me | 4-$CF_3$ | 2-benzotriazole | +/− | $CH_2COOEt$ |
| XIV-103 | 4'-$CF_3$ | Me | H | 2-benzotriazole | +/− | $CH_2COOEt$ |
| XIV-104 | 4'-Cl | Me | 4-Cl | 2-benzotriazole | +/− | $CH_2COOEt$ |
| XIV-105 | 4'-Cl | Me | 3-$CF_3$ | 2-benzotriazole | +/− | $CH_2COOEt$ |
| XIV-106 | 4'-Cl | Me | 3-Cl | 2-benzotriazole | +/− | $CH_2COOEt$ |
| XIV-107 | 4'-Cl | Me | 4-$CF_3$ | 2-benzotriazole | +/− | $CH_2COOEt$ |
| XIV-108 | 4'-Cl | Me | H | 2-benzotriazole | +/− | $CH_2COOEt$ |
| XIV-109 | 4'-$CF_3$ | H | 4-Cl | 2-benzooxazole | +/− | Et |
| XIV-110 | 4'-$CF_3$ | H | 3-$CF_3$ | 2-benzooxazole | +/− | Et |
| XIV-111 | 4'-$CF_3$ | H | 3-$CF_3$ | 2-benzooxazole | + | Et |
| XIV-112 | 4'-$CF_3$ | H | 3-$CF_3$ | 2-benzooxazole | − | Et |
| XIV-113 | 4'-$CF_3$ | H | 3-Cl | 2-benzooxazole | +/− | Et |
| XIV-114 | 4'-$CF_3$ | H | 4-$CF_3$ | 2-benzooxazole | +/− | Et |
| XIV-115 | 4'-$CF_3$ | H | H | 2-benzooxazole | +/− | Et |
| XIV-116 | 4'-$CF_3$ | H | H | 2-benzooxazole | + | Et |
| XIV-117 | 4'-$CF_3$ | H | H | 2-benzooxazole | − | Et |
| XIV-118 | 4'-Cl | H | 4-Cl | 2-benzooxazole | +/− | Et |
| XIV-119 | 4'-Cl | H | 3-$CF_3$ | 2-benzooxazole | +/− | Et |
| XIV-120 | 4'-Cl | H | 3-$CF_3$ | 2-benzooxazole | + | Et |
| XIV-121 | 4'-Cl | H | 3-$CF_3$ | 2-benzooxazole | − | Et |
| XIV-122 | 4'-Cl | H | 3-Cl | 2-benzooxazole | +/− | Et |
| XIV-123 | 4'-Cl | H | 4-$CF_3$ | 2-benzooxazole | +/− | Et |
| XIV-124 | 4'-Cl | H | H | 2-benzooxazole | +/− | Et |
| XIV-125 | 4'-$CF_3$ | Me | 4-Cl | 2-benzooxazole | +/− | Et |
| XIV-126 | 4'-$CF_3$ | Me | 3-$CF_3$ | 2-benzooxazole | +/− | Et |
| XIV-127 | 4'-$CF_3$ | Me | 3-Cl | 2-benzooxazole | +/− | Et |
| XIV-128 | 4'-$CF_3$ | Me | 4-$CF_3$ | 2-benzooxazole | +/− | Et |
| XIV-129 | 4'-$CF_3$ | Me | H | 2-benzooxazole | +/− | Et |
| XIV-130 | 4'-Cl | Me | 4-Cl | 2-benzooxazole | +/− | Et |
| XIV-131 | 4'-Cl | Me | 3-$CF_3$ | 2-benzooxazole | +/− | Et |
| XIV-132 | 4'-Cl | Me | 3-Cl | 2-benzooxazole | +/− | Et |
| XIV-133 | 4'-Cl | Me | 4-$CF_3$ | 2-benzooxazole | +/− | Et |
| XIV-134 | 4'-Cl | Me | H | 2-benzooxazole | +/− | Et |
| XIV-135 | 4'-$CF_3$ | H | 3-$CF_3$ | 2-benzothiazole | +/− | Et |
| XIV-136 | 4'-Cl | H | 3-$CF_3$ | 2-benzothiazole | +/− | Et |
| XIV-137 | 4'-$CF_3$ | H | 4-Cl | 2-benzothiazole | +/− | Et |
| XIV-138 | 4'-Cl | H | 4-Cl | 2-benzothiazole | +/− | Et |
| XIV-139 | 4'-$CF_3$ | Me | 3-$CF_3$ | 2-benzothiazole | +/− | Et |
| XIV-140 | 4'-Cl | Me | 3-$CF_3$ | 2-benzothiazole | +/− | Et |
| XIV-141 | 4'-$CF_3$ | Me | 4-Cl | 2-benzothiazole | +/− | Et |
| XIV-142 | 4'-Cl | Me | 4-Cl | 2-benzothiazole | +/− | Et |
| XIV-143 | 4'-$CF_3$ | H | 4-Cl | 2-benzotriazole | +/− | Et |
| XIV-144 | 4'-$CF_3$ | H | 3-$CF_3$ | 2-benzotriazole | +/− | Et |
| XIV-145 | 4'-$CF_3$ | H | 3-Cl | 2-benzotriazole | +/− | Et |
| XIV-146 | 4'-$CF_3$ | H | 4-$CF_3$ | 2-benzotriazole | +/− | Et |
| XIV-147 | 4'-$CF_3$ | H | H | 2-benzotriazole | +/− | Et |
| XIV-148 | 4'-Cl | H | 4-Cl | 2-benzotriazole | +/− | Et |

TABLE 14-continued

Prodrugs

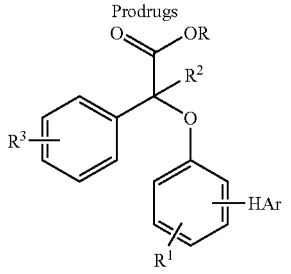

Compounds XIV

| Compound | $R^1$ | $R^2$ | $R^3$ | HAr | Racemic or enantiomer | R |
|---|---|---|---|---|---|---|
| XIV-149 | 4'-Cl | H | 3-$CF_3$ | 2-benzotriazole | +/− | Et |
| XIV-150 | 4'-Cl | H | 3-Cl | 2-benzotriazole | +/− | Et |
| XIV-151 | 4'-Cl | H | 4-$CF_3$ | 2-benzotriazole | +/− | Et |
| XIV-152 | 4'-Cl | H | H | 2-benzotriazole | +/− | Et |
| XIV-153 | 4'-$CF_3$ | Me | 4-Cl | 2-benzotriazole | +/− | Et |
| XIV-154 | 4'-$CF_3$ | Me | 3-$CF_3$ | 2-benzotriazole | +/− | Et |
| XIV-155 | 4'-$CF_3$ | Me | 3-Cl | 2-benzotriazole | +/− | Et |
| XIV-156 | 4'-$CF_3$ | Me | 4-$CF_3$ | 2-benzotriazole | +/− | Et |
| XIV-157 | 4'-$CF_3$ | Me | H | 2-benzotriazole | +/− | Et |
| XIV-158 | 4'-Cl | Me | 4-Cl | 2-benzotriazole | +/− | Et |
| XIV-159 | 4'-Cl | Me | 3-$CF_3$ | 2-benzotriazole | +/− | Et |
| XIV-160 | 4'-Cl | Me | 3-Cl | 2-benzotriazole | +/− | Et |
| XIV-161 | 4'-Cl | Me | 4-$CF_3$ | 2-benzotriazole | +/− | Et |
| XIV-162 | 4'-Cl | Me | H | 2-benzotriazole | +/− | Et |

22. Synthesis of Compound XIV-X Listed in Table 14.

Compounds XIV-X listed in Table 14 were or can be prepared with SBr-14, 15, 16, 17 and 18 and PhOH-X in the same manner as described in Example 28 Step A. Alternatively, they were or can be prepared from esterification of the corresponding acids in the same manner as that described in Examples 136 to 138.

Example 131

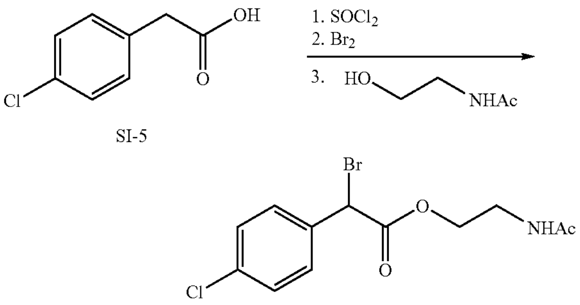

SI-5

SBr-14

A 500 mL three neck roundbottom flask was equipped with an efficient condenser attached to an acid scrubber, a magnetic stir bar, and placed under argon. 4-Chlorophenylacetic acid SI-5 (99.9 g, 0.50 mole) was charged, followed by thionyl chloride (50.0 mL (81.6 g), 0.68 mole). The condenser was cooled with 4° C. water. The mixture was heated to an internal temperature of 55–60° C. Gas evolution was observed and the solids dissolved as the internal temperature rose to 55–60° C. over 45 min. The mixture was then stirred at 55–60° C. for 45 min. Bromine (33.0 mL (102.4 g), 0.65 mole) was charged and the mixture maintained at 55–60° C. for 18 h. The internal temperature was then raised to 80–85° C. over 1.5 h and heating continued for 18 h (based on other runs, the reaction is complete after 6–7 h). The mixture was cooled to 20–25° C. and anhydrous dichloromethane (500 mL) added. In a separate flask was place 2-acetylethanolamine (190 mL (213 g), 2.07 mole) and anhydrous dichloromethane (500 mL) under argon and the mixture cooled to 2.8° C. To this was added the acyl halide solution at such a rate as to keep the internal temperature below 21° C. (caution: exothermic). After the addition was complete (approx. 20 min.), the mixture was stirred in the cold bath for 0.5 h, at which time the internal temperature was 4.8° C. This mixture was carefully added to 1.5 L water containing sodium bicarbonate (148 g, 1.8 mole) at such a rate that frothing was moderate. The pH at the end of the addition (15 min.) was 7, by pH paper. Sodium thiosulfate (18.7 g, 0.12 mole) was added in portions and gas evolution was observed. Bromine was found to be absent at this time by testing with a Peroxide 100 (quantifix) strip. The layers were then partitioned in a separatory funnel (100 mL dichloromethane used in transfer), and the organic phase extracted with 250 mL water, dried over magnesium sulfate (17 g), and filtered. The filter cake was washed with dichloromethane (150 mL). Rotary evaporation and pumping at high vacuum afforded an oil, which was slurried in 100 mL hexane: ethyl acetate (70:30). Additional hexane (300 mL) was added until a white color formed in the top layer of the biphasic mixture. Vigorous agitation afforded a solid, which was filtered away from the supernatant to yield crude (2-acetamidoethyl)-4-chlorophenylbromoacetate SBr-14 (147 g) as a light tan solid.

Example 132
SBr-15
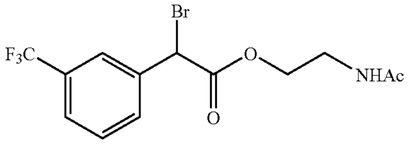
SBr-16
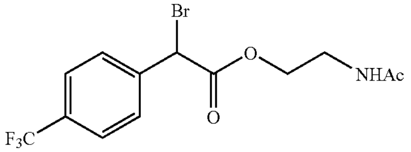
SBr-17
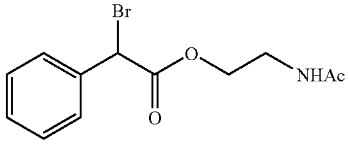
SBr-18
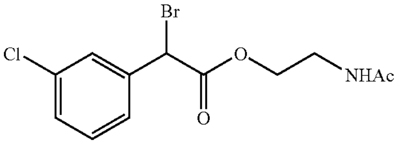
SBr-15, 16, 17, and 18 were prepared in the same manner as that described in Example 131.
Example 133
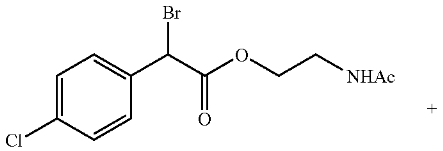
SBr-14
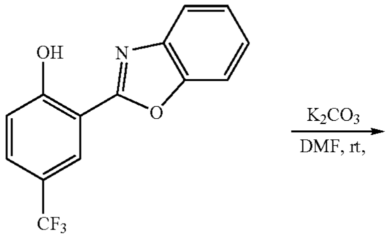
PhOH-6
-continued
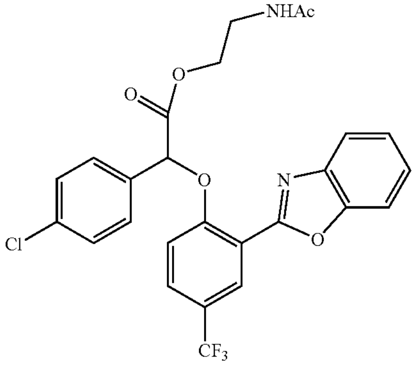
XIV-1
In the same manner as that described in Example 28 Step A, compound XIV-1 was prepared from SBr-14 and PhOH-6.
Example 134
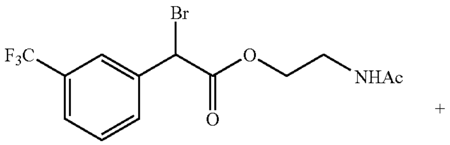
SBr-15
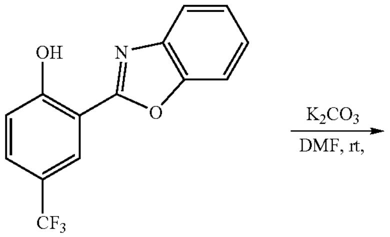
PhOH-6
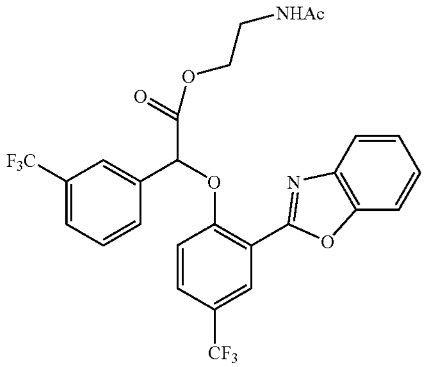
XIV-2
In the same manner as that described in Example 28 Step A, compound XIV-2 was prepared from SBr-15 and PhOH-6.

Example 135

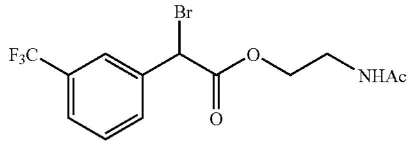

+

SBr-15

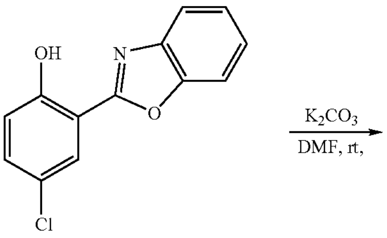

PhOH-2

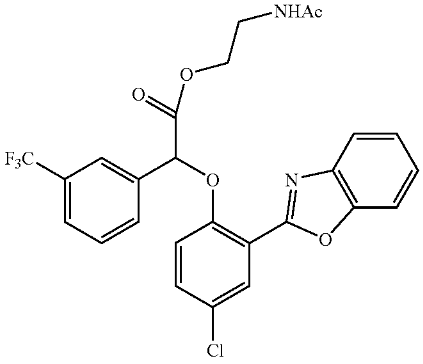

XIV-11

In the same manner as that described in Example 28 Step A, compound XIV-11 was prepared from SBr-15 and PhOH-2.

23. Enantiomers Preparation

The enantiomers of compounds XIV-X can be obtained from the corresponding enantiomerically pure acids with esterfication as that described in Example 136, Example 137 and Example 138. Alternatively, it can be obtained from the (+/−) racemic mixture with a chiral HPLC separation as that described in Section 4.

Example 136

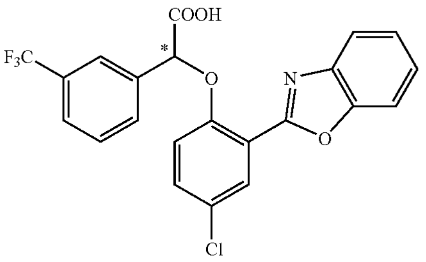

+

I-367
(+)-isomer

-continued

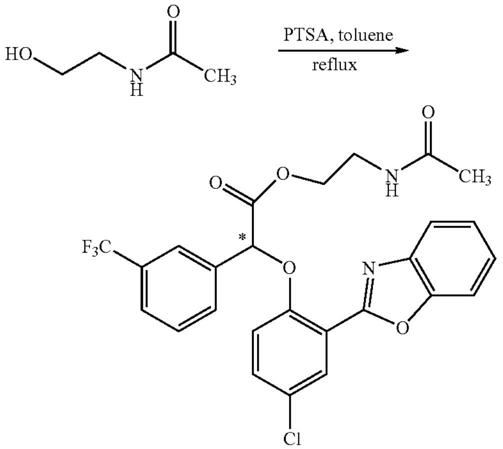

enantiomer 1

A mixture of I-367(11.74 g, ee>99.9%), N-acetylethanolamine (13.51 g) and TsOH monohydrate (0.25 g) in toluene (200 mL) was refluxed overnight using a Dean-Stark apparatus. The reaction mixture was concentrated to dryness, water was added, and the resultant mixture was stirred at room temperature for 0.5 h. Filtration and washing with water gave a off-white solid, which was recrystallized from iPrOH-hexanes to give enantiomer 1 as an white solid. $^1$HNMR (d-DMSO, 400 MHz) δ 8.33 (s, 1H), 8.13 (d, 1H), 8.01 (d, 1H), 7.82–7.65 (m, 6H), 7.48 (m, 2H), 7.30 (d, 1H), 6.48 (s, 1H), 4.16 (m, 1H), 4.02 (m, 1H), 3.27 (m, 1H), 3.18 (m, 1H), 1.69 (s, 3H).

Example 137

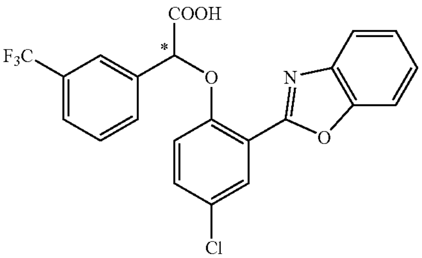

+

I-367
(+)-isomer

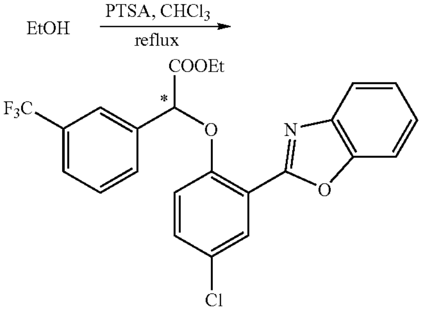

enantiomer 2

A mixture of I-367 (5.87 g, ee>99.9%), EtOH (150 mL) and TsOH monohydrate (0.125 g) was refluxed overnight. The reaction mixture was concentrated to afford enantiomer 2 as a white solid. $^1$HNMR (d-DMSO, 400 MHz) δ 8.32 (s, 1H), 8.11 (s, 1H), 8.01 (d, 1H), 7.82–7.65 (m, 5H), 7.48 (m, 2H), 7.30 (d, 1H), 6.48 (s, 1H), 4.08 (m, 2H), 1.02 (m, 3H).

Example 138

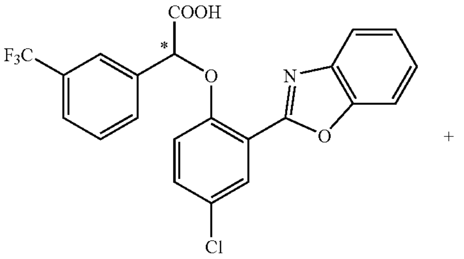

I-367
(+)-isomer

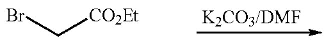

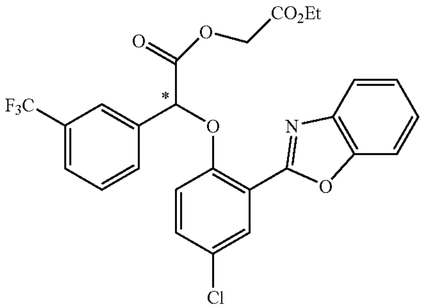

enantiomer 3

To a solution of(+)-I-367 (1.1546 g, 2.58 mmol) in DMF (10 mL) at 0° C. was added $K_2CO_3$ (0.3597 g, 2.60 mmol), and then followed by ethyl bromoacetate (0.30 mL, 2.70 mmol). After stirring for 40 min at 0° C., the reaction mixture was diluted with EtOAc and aq. $NH_4Cl/H_2O$. The organic layer was washed with aq. $NH_4Cl/H_2O$, and then brine/water, dried over $Na_2SO_4$, concentrated in vacuo. Purification via chromatography with EtOAc/hexanes (10% to 30%) to afford enantiomer 3 (1.0211 g, 74%) as a white solid. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 15 μm column with a 1.5 mL/min flow of (3/97/0.1) iPrOH/ hexanes/TFA. Under these conditions, enantiomer 3 eluted at 12.3 min, and the corresponding pro-drug ester of I-368 (-isomer) elutes at 13.1 min (approximate retention times). $^1$H NMR (400 MHz, $CDCl_3$): δ 8.36 (1H, s), 8.26 (1H, d, J=2.0 Hz), 7.98 (1H, d, J=7.6 Hz), 7.81 (1H, m), 7.69 (1H, d, J=7.2 Hz), 7.56 (2H, m), 7.46 (1H, m), 7.39 (2H, m), 7.12 (1H, d, J=8.4 Hz), 5.98 (1H, s), 4.93 (1H, d, J=15.6 Hz), 4.58 (1H, d, J=15.6 Hz), 4.14 (2H, m), 1.67 (3H, t, J=7.2 Hz) ppm.

Example 139

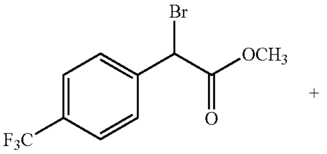

139-S1

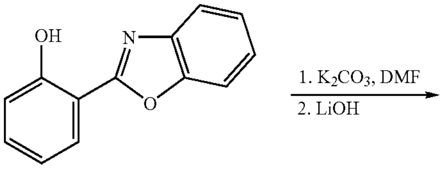

139-S2

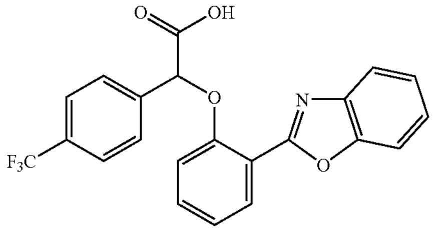

139 (I-6)

In the same manner as that described in Example 28 compound 139 was prepared from 139-S1 and 139-S2. $^1$HNMR (400 MHz, DMSO-$d_6$): δ 8.20–7.22 (m, 12H), 6.50 (s, 1H).

Example 140

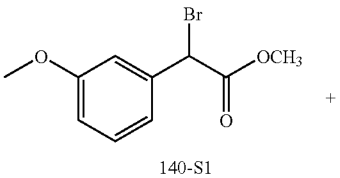

140-S1

-continued

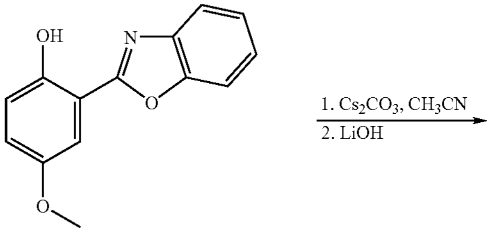

140-S2

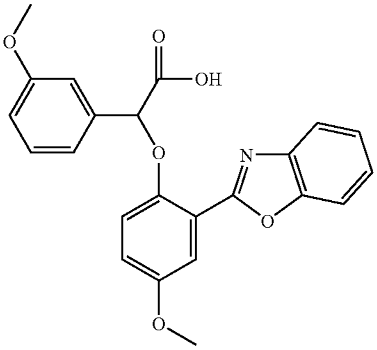

140

In the same manner as that described in Example 28 compound 140 was prepared from 140-S1 and 140-S2. $^1$HNMR (400 MHz, DMSO-$d_6$): δ 7.81–6.92 (m, 11H), 5.95 (s, 1H), 3.79 (s, 3H), 3.74 (s, 3H).

The two enantiomers of 140 were separated by HPLC. Column: PIRKLE COVALENT, (R,R) Whelk-O 2 10/100, 25 cm×21.1 mm. Flow: 30 mmin, 50% iPrOH/Hexanes-0. I% TFA.

Example 141

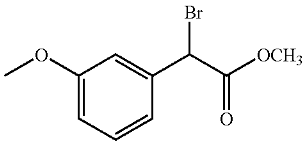

141-S1

+

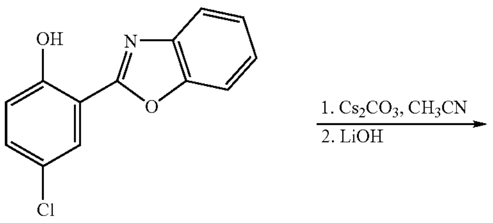

141-S2

-continued

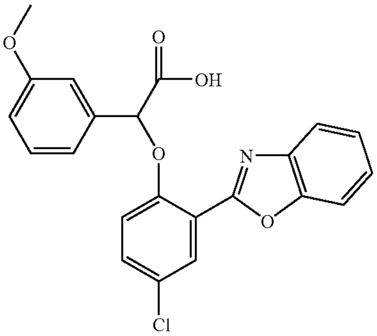

141

In the same manner as that described in Example 28 compound 141 was prepared from 141-S1 and 141-S2. $^1$H NMR (400 MHz, DMSO-$d_6$): δ 13.40 (br, 1H), 8.08–6.93 (m, 11H), 6.11 (s, 1H), 3.75 (s, 3H).

The two enantiomers of 141 were separated by HPLC. Column: PIRKLE COVALENT, (R,R) Whelk-C 2 10/100, 25 cm×21.1 mm. Flow: 30 ml/min, 50% iPrOH/Hexanes-0.1% TFA.

Example 142

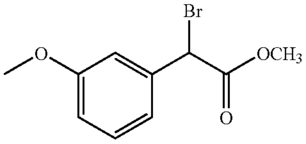

142-S1

+

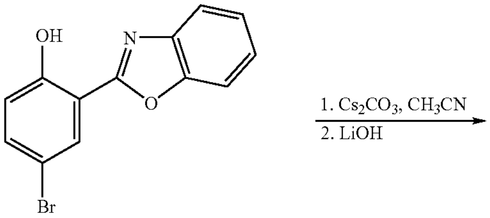

142-S2

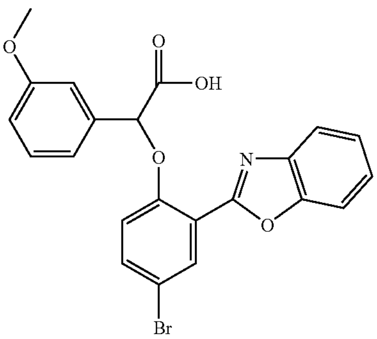

142

In the same manner as that described in Example 28 compound 142 was prepared from 142-S1 and 142-S2. $^{1}H$ NMR (400 MHz, DMSO-$d_6$): δ 8.20–6.93 (m, 11H), 6.11 (s, 1H), 3.75 (s, 3H).

The two enantiomers were separated by HPLC. Column: PIRKLE COVALENT, (R,R) Whelk-O 2 10/100, 25 cm×21.1 mm. Flow: 30 m/min, 50% iPrOH/Hexanes-0.1% TFA.

Example 143

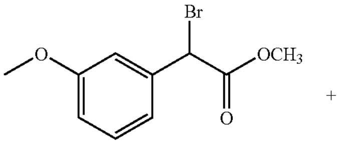

143-S1

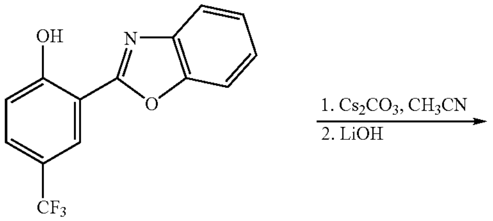

143-S2

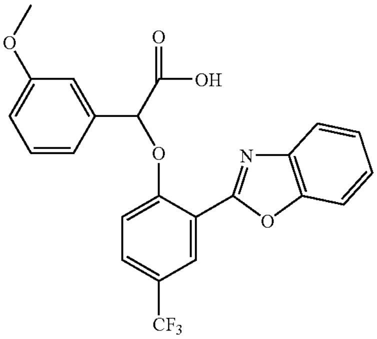

143 (I-96)

In the same manner as that described in Example 28 compound 143 was prepared from 143-S1 and 143-S2. $^{1}H$ NMR (400 MHz, DMSO-$d_6$): δ 8.38–6.95 (m, 11H), 6.26 (s, 1H), 3.75 (s, 3H).

The two enantiomers were separated by HPLC. Column: PIRKLE COVALENT, (R,R) Whelk-O 2 10/100, 25 cm×21.1 mm. Flow: 30 ml/min, 50% iPrOH/Hexanes-0.1% TFA.

Example 144

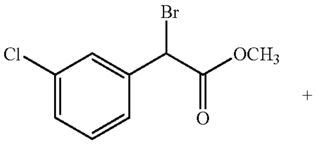

144-S1

-continued

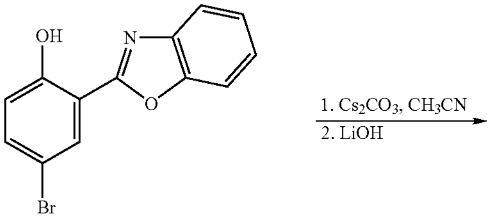

144-S2

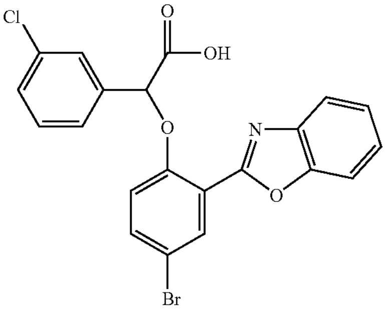

144 (I-318)

In the same manner as that described in Example 28 compound 144 was prepared from 144-S1 and 144-S2. $^{1}H$ NMR (400 MHz, DMSO-$d_6$): δ 8.25–7.16 (m, 11H), 6.23 (s, 1H).

The two enantiomers were separated by HPLC. Column: PIRKLE COVALENT, (R,R) Whelk-O 2 10/100, 25 cm×21.1 mm. Flow: 30 ml/min, 50% iPrOH/Hexanes-0.1% TFA.

Example 145

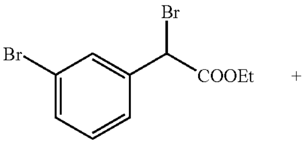

145-S1

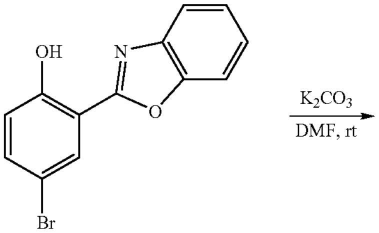

145-S2

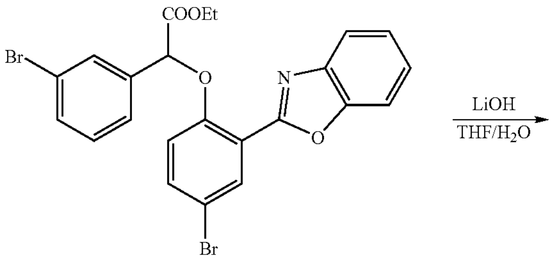

145-S3

-continued

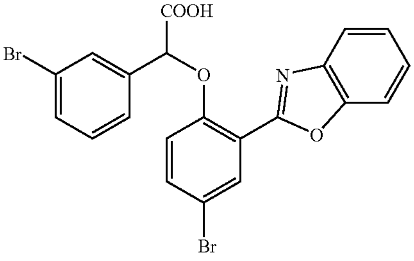

145

In the same manner as that described in Example 28 compound 145 was prepared from 145-S1 and 145-S2. $^1$H NMR (400 MHz, DMSO-$d_6$): δ 13.6 (1H, br, COOH), 8.25 (1H, d, J=2.8 Hz), 8.21 (1H, t, J=2.0 Hz), 7.88–7.90 (1H, m), 7.79–7.83 (2H, m), 7.69 (1H, d, J=7.6 Hz), 7.60–7.62 (1H, m), 7.41–7.50 (3H, m), 7.18 (1H, d, J=9.2 Hz), 6.24 (1H, s) ppm.

Example 146

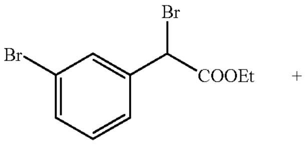

146-S1

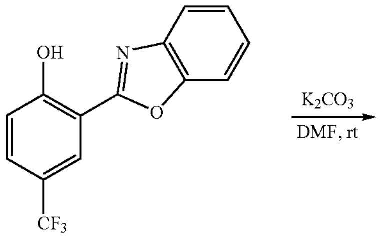

146-S2

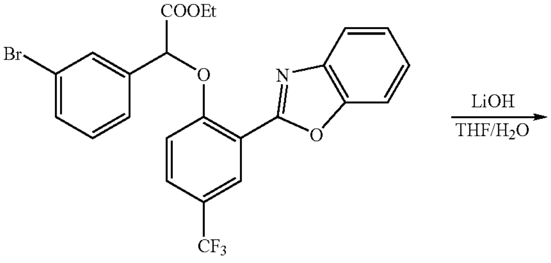

146-S3

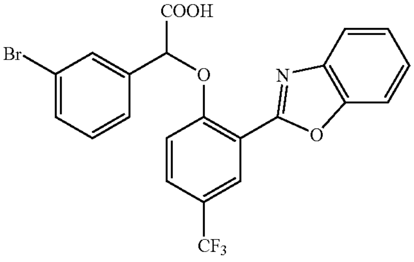

146 (I-115)

In the same manner as that described in Example 28 compound 146 was prepared from 146-S1 and 146-S2. $^1$H NMR (400 MHz, DMSO-$d_6$): δ 13.7 (1H, br, COOH), 8.42 (1H, s), 8.25 (1H, s), 8.02 (1H, d, J=9.2 Hz), 7.91 (1H, d, J=8.0 Hz), 7.84 (1H, d, J=7.2 Hz), 7.73 (1H, d, J=7.2 Hz), 7.62 (1H, d, J=8.4 Hz), 7.39–7.51 (4H, m), 6.38 (1H, s) ppm.

Example 147

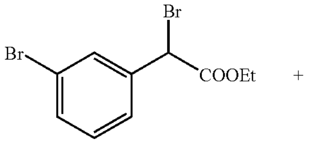

147-S1

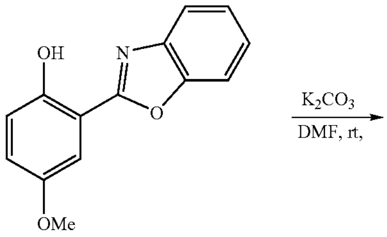

147-S2

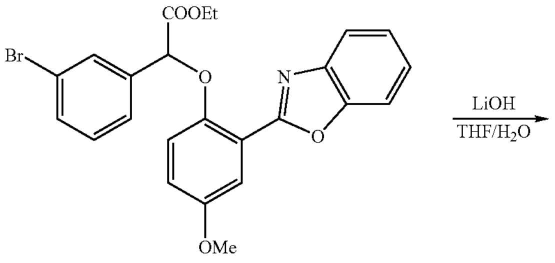

147-S3

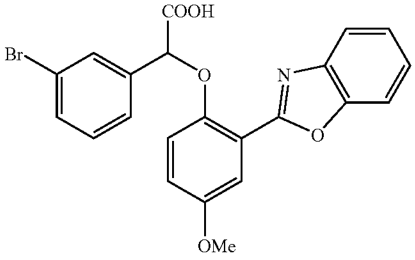

147

In the same manner as that described in Example 28 compound 147 was prepared from 147-S1 and 147-S2. $^1$H NMR (400 MHz, DMSO-$d_6$): δ 13.5 (1H, br, COOH), 8.16 (1H, s), 7.85–7.87 (1H, m), 7.77–7.80 (1H, m), 7.67 (1H, d, J=8.0 Hz), 7.64 (1H, d, J=3.2 Hz), 7.59 (1H, dd, J=7.2, 1.2 Hz), 7.39–7.49 (3H, m), 7.13–7.21 (2H, m), 6.08 (1H, s), 3.80 (3H, s) ppm.

Example 148

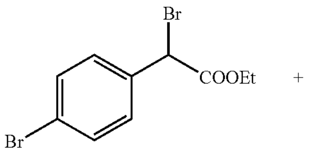

148-S1

-continued
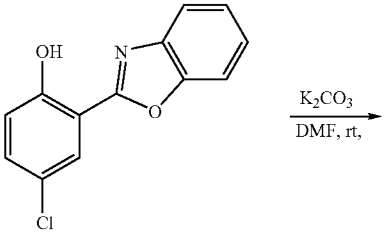
148-S2
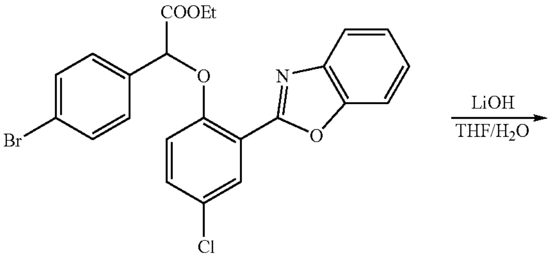
148-S3
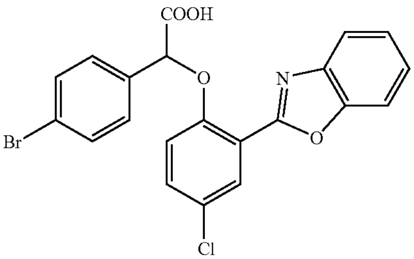
148 (I-195)
In the same manner as that described in Example 28 compound 148 was prepared from 148-S1 and 148-S2. NMR (400 MHz, DMSO-$d_6$): δ 13.5 (1H, br, COOH), 8.11 (1H, d, J=2.8 Hz), 7.86–7.88 (1H, m), 7.81–7.83 (1H, m), 7.65–7.75 (5H, m), 7.41–7.49 (2H, m), 7.23 (1H, d, J=9.6 Hz), 6.18 (1H, s) ppm.
Example 149
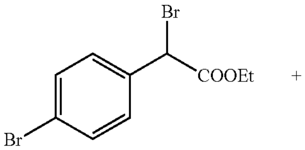
149-S1
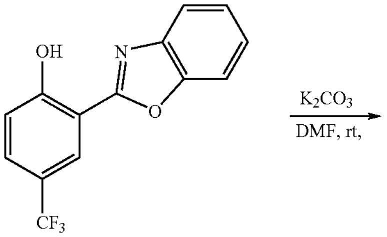
149-S2
-continued
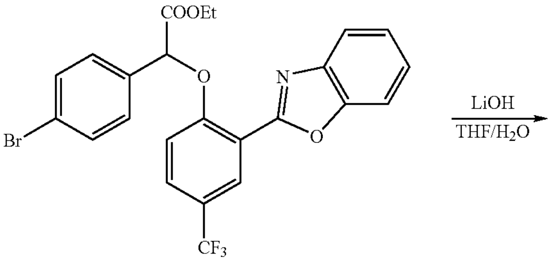
149-S3
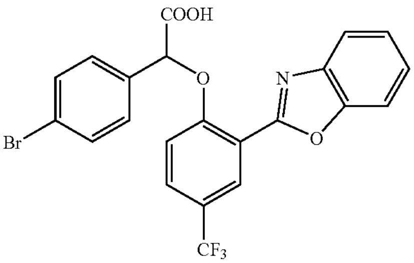
149 (I-99)
In the same manner as that described in Example 28 compound 149 was prepared from 149-S1 and 149-S2. [1]H. NMR (400 MHz, DMSO-$d_6$): δ 13.7 (1H, br, COOH), 8.41 (1H, s), 8.00 (1H, d, J=8.0 Hz), 7.90 (1H, d, J=8.0 Hz), 7.85 (1H, d, J=7.2 Hz), 7.78 (2H, d, J=8.6 Hz), 7.73 (2H, d, J=8.6 Hz), 7.39–7.51 (3H, m), 6.33 (1H, s) ppm.
Example 150
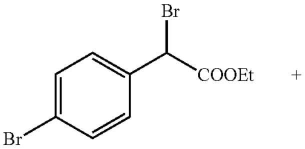
150-S1
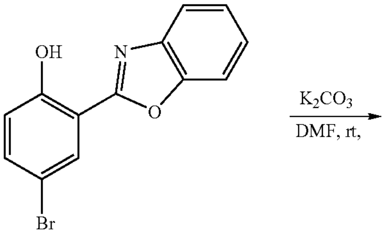
150-S2
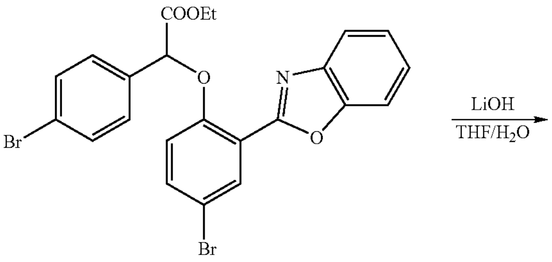
150-S3

-continued

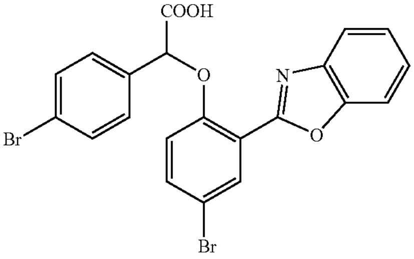

150 (I-324)

In the same manner as that described in Example 28 compound 150 was prepared from 150-S1 and 150-S2. $^1H$ NMR (400 MHz, DMSO-$d_6$): δ 13.5 (1H, br, COOH), 8.23 (1H, d, J=2.8 Hz), 7.69–7.88 (7H, m), 7.41–7.49 (2H, m), 7.17 (1H, d, J=9.2 Hz), 6.17 (1H, s) ppm.

Example 151

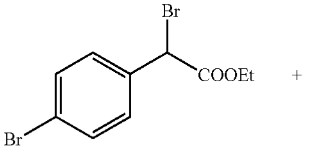

151-S1

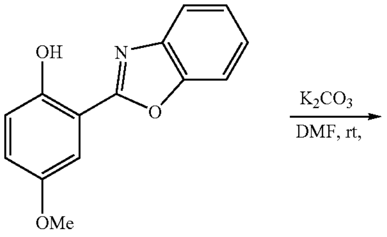

151-S2

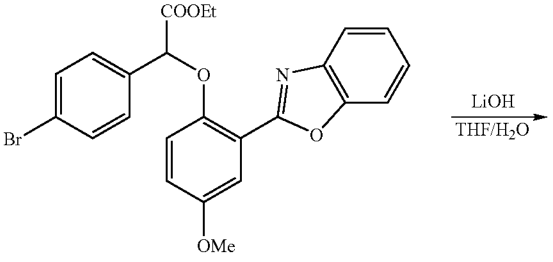

151-S3

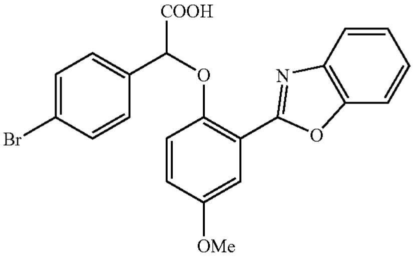

151

In the same manner as that described in Example 28 compound 151 was prepared from 151-S1 and 151-S2. $^1H$ NMR (400 MHz, DMSO-$d_6$): δ 13.4 (1H, br, COOH), 7.83–7.85 (1H, m), 7.77–7.80 (1H, m), 7.66–7.72 (4H, m), 7.62 (1H, d, J=3.2 Hz), 7.40–7.47 (2H, m), 7.11–7.19 (2H, m), 6.01 (1H, s), 3.81 (3H, s) ppm.

Example 152

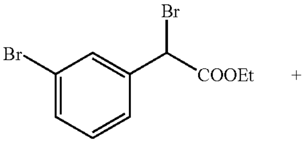

152-S1

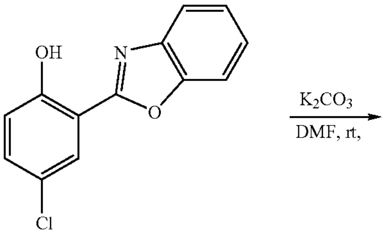

152-S2

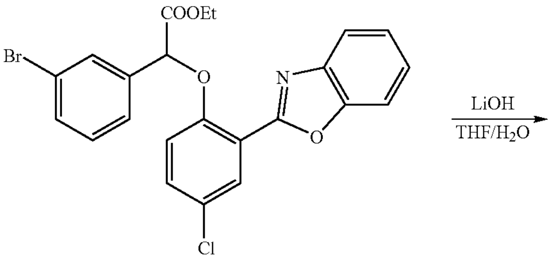

152-S3

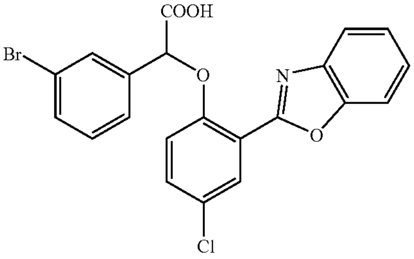

152

In the same manner as that described in Example 28 compound 152 was prepared from 152-S1 and 152-S2. $^1H$ NMR (400 MHz, DMSO-$d_6$): δ 13.6 (1H, br, COOH), 8.22 (1H, s), 8.13 (1H, d, J=2.8 Hz), 7.88–7.90 (1H, m), 7.81–7.83 (1H, m), 7.67–7.71 (2H, m), 7.60–7.62 (1H, m), 7.41–7.49 (3H, m), 7.23 (1H, d, J=9.2 Hz), 6.24 (1H, s) ppm.

Example 153

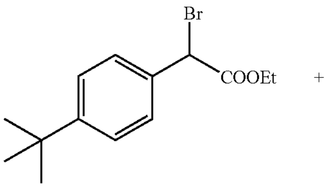

153-S1

-continued
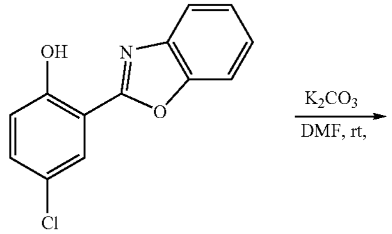
153-S2
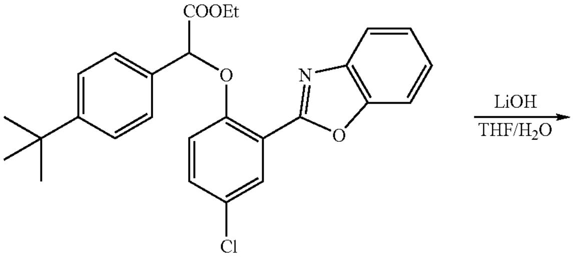
153-S3
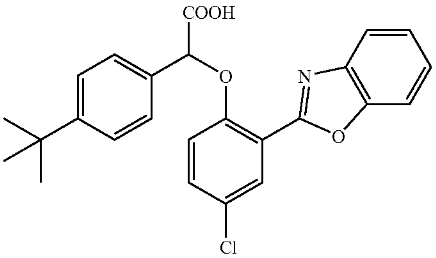
153
In the same manner as that described in Example 28 compound 153 was prepared from 153-S1 and 153-S2. $^{1}$H NMR (400 MHz, DMSO-$d_6$): δ 8.09 (d, J=2.4 Hz, 1H), 7.86 (m, 1H), 7.78 (m, 1H), 7.67 (m, 3H), 7.45–7.42 (m, 4H), 7.23 (d, J=9.2 Hz, 1H), 6.09 (s, 1H), 1.28 (s, 9H).
Example 154
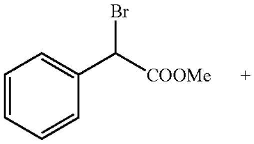
154-S1
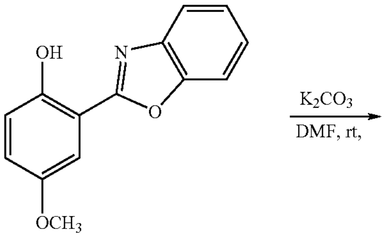
154-S2
-continued
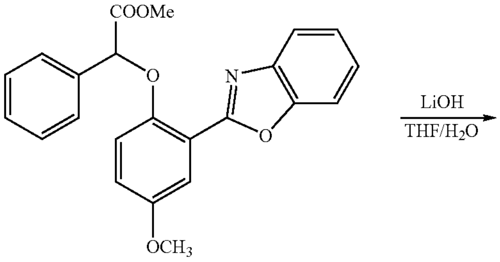
154-S3
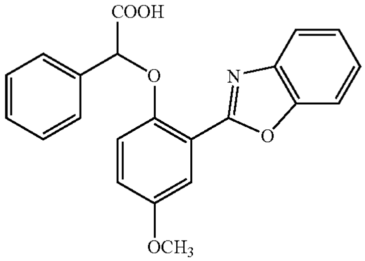
154
In the same manner as that described in Example 28 compound 154 was prepared from 154-S1 and 154-S2. $^{1}$H NMR (400 MHz, DMSO-$d_6$): δ 7.83 (m, 1H), 7.73 (m, 3H), 7.62 (d, J=2.4 Hz, 1H), 7.44 (m, 4H), 7.38 (m, 1H), 7.15 (m, 2H), 5.96 (s, 1H).
Example 155
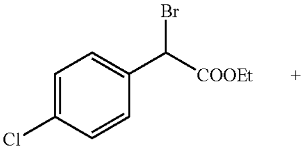
155-S1
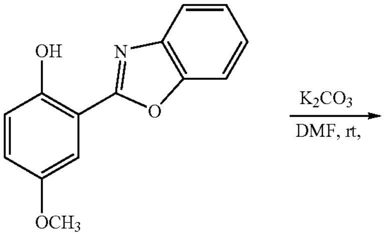
155-S2
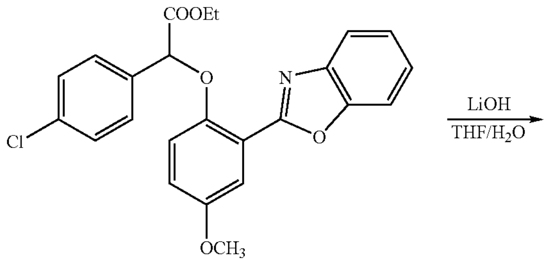
155-S3

-continued

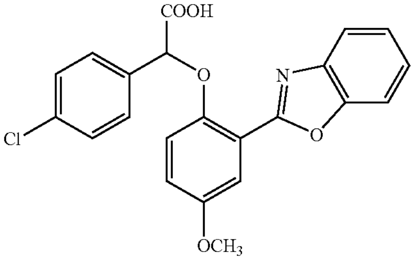

155

In the same manner as that described in Example 28 compound 155 was prepared from 155-S1 and 155-S2. $^1H$ NMR (400 MHz, DMSO-$d_6$): δ 7.85 (m, 1H), 7.76 (m, 3H), 7.63 (m, 1H), 7.55 (m, 2H), 7.44 (m, 2H), 7.17 (m, 2H), 6.03 (s, 1H).

Example 156

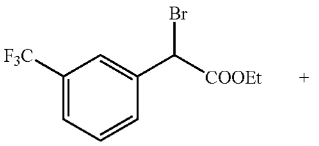

156-S1

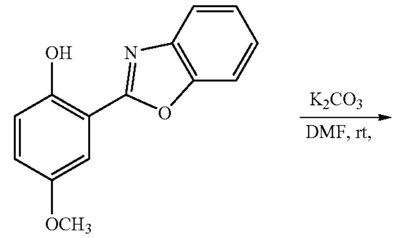

156-S2

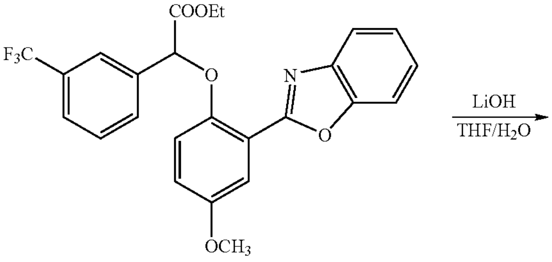

156-S3

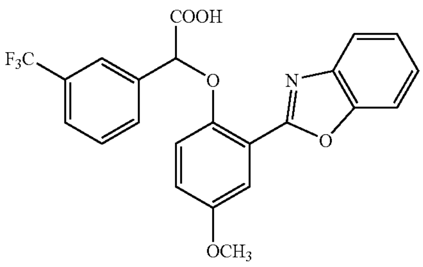

156

In the same manner as that described in Example 28 compound 156 was prepared from 156-S1 and 156-S2. $^1H$ NMR (400 MHz, DMSO-$d_6$): δ 8.27 (s, 1H), 7.99 (d, J=2.8 Hz, 1H), 7.81–7.75 (m, 2H), 7.71 (m, 2H), 7.63 (d, J=2.4 Hz, 1H), 7.47 (m, 2H), 7.20 (m, 2H), 6.26 (s, 1H).

Example 157

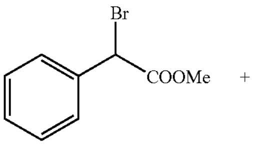

157-S1

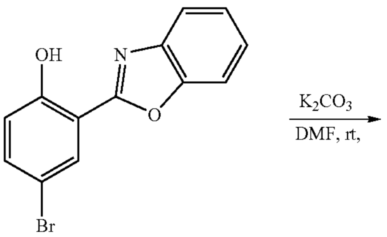

157-S2

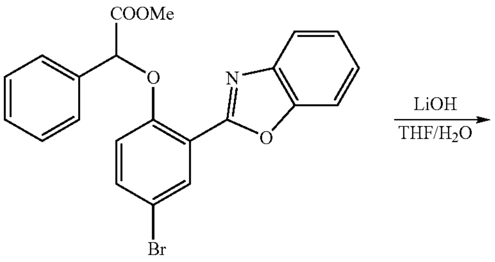

157-S3

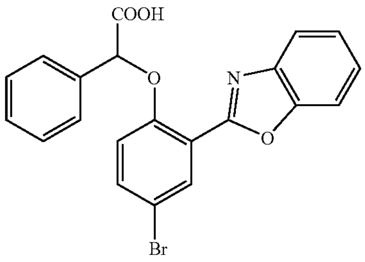

157 (I-325)

In the same manner as that described in Example 28 compound 157 was prepared from 157-S1 and 157-S2. $^1H$ NMR (400 MHz, DMSO-$d_6$): δ 13.40 (s, 1H), 8.22 (d, J=2.8 Hz, 1H), 7.85 (m, 1H), 7.79–7.74 (m, 4H), 7.48–7.38 (m, 5H), 7.19 (d, J=9.2 Hz, 1H), 6.14 (s, 1H).

Example 158

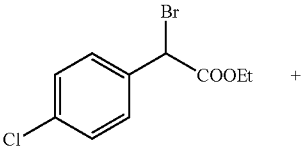

158-S1

-continued
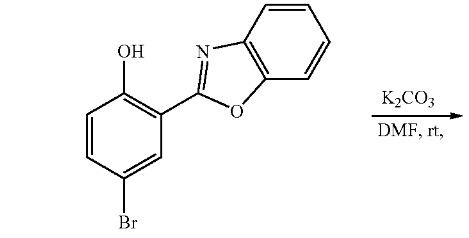
158-S2
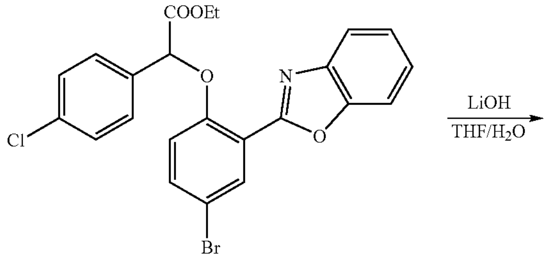
158-S3
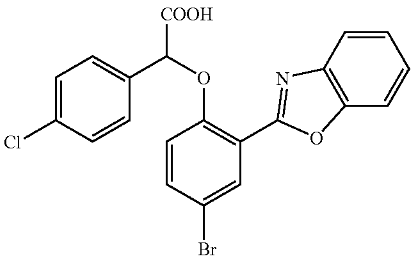
158 (I-322)
In the same manner as that described in Example 28 compound 158 was prepared from 158-S1 and 158-S2. $^1H$ NMR (400 MHz, DMSO-$d_6$): δ 8.23 (d, J=2.4 Hz, 1H), 7.87 (m, 1H), 7.79 (m, 4H), 7.58 (m, 2H), 7.47–7.42 (m, 2H), 7.18 (d, J=9.2 Hz, 1H), 6.20 (s, 1H).
Example 159
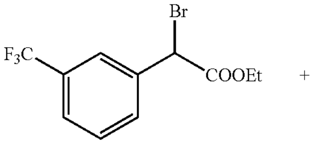
159-S1
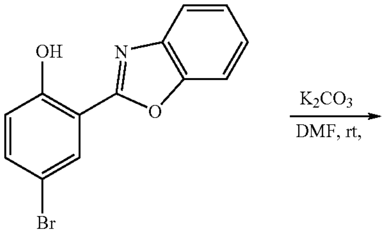
159-S2
-continued
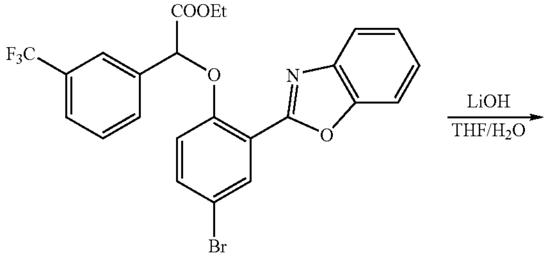
159-S3
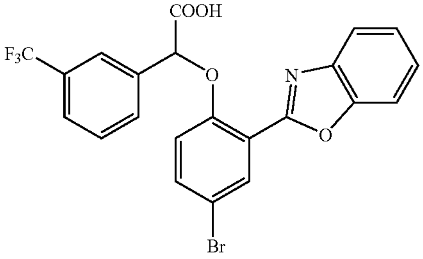
159 (I-318)
In the same manner as that described in Example 28 compound 159 was prepared from 159-S1 and 159-S2. $^1H$ NMR (400 MHz, DMSO-$d_6$): δ 8.32 (s, 1H), 8.25 (d, J=2.4 Hz, 1H), 8.03 (d, J=8 Hz, 1H), 7.83–7.71 (m, 5H), 7.48 (m, 2H), 7.26 (d, J=9.6 Hz, 1H), 6.38 (s, 1H).
Example 160
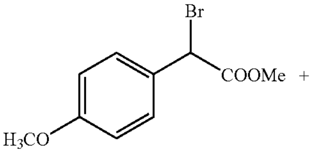
160-S1
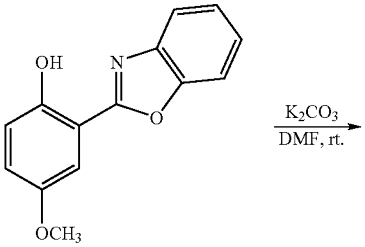
160-S2
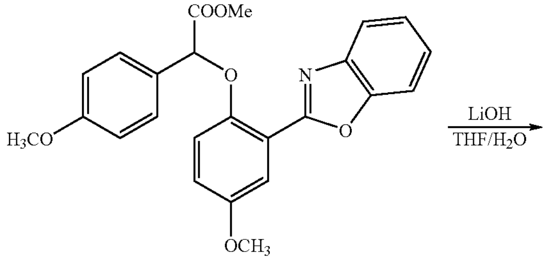
160-S3

-continued

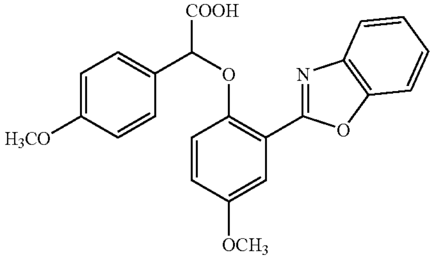

160

In the same manner as that described in Example 28 compound 160 was prepared from 160-S1 and 160-S2. $^1$H NMR (400 MHz, DMSO-$d_6$): δ 13.20 (s, 1H), 7.84 (m, 1H), 7.76 (m, 1H), 7.63 (m, 3H), 7.47–7.40 (m, 2H), 7.17–7.11 (m, 2H), 7.01 (m, 2H), 5.89 (s, 1H), 3.79 (s, 3H), 3.75 (s, 3H).

Example 161

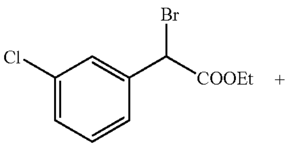

161-S3

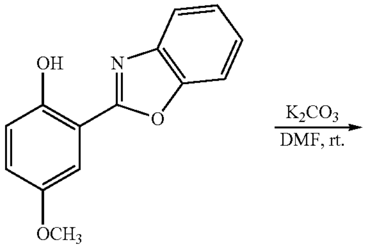

161-S2

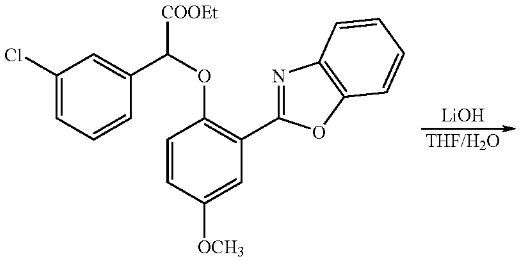

161-S1

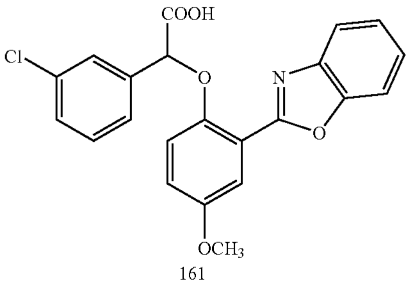

161

In the same manner as that described in Example 28 compound 161 was prepared from 161-S1 and 161-S2. $^1$H NMR (400 MHz, DMSO-$d_6$): δ 8.01 (m, 1H), 7.85 (m1H), 7.77 (m, 1H), 7.65 (m, 2H), 7.50–7.41 (m, 4H), 7.21 (dd, J=2.8 and 8.8 Hz, 1H), 7.13 (d, J=9.6 Hz, 1H), 6.08 (s, 1H), 3.80 (s, 3H).

Example 162

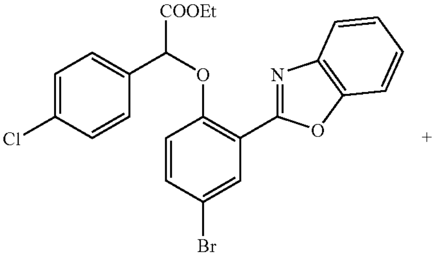

162-S1

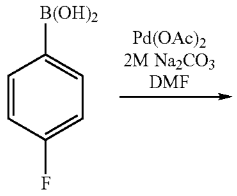

162-S2

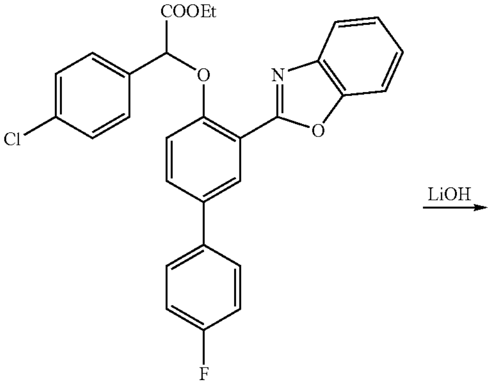

162-S3

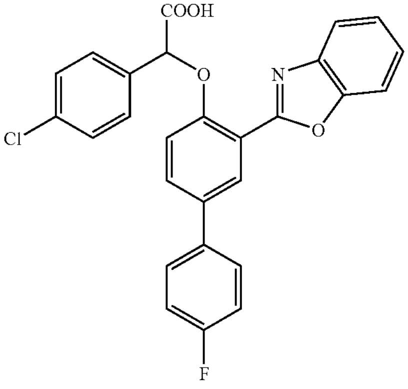

162

A mixture of ester 162-S1 (205 mg, 0.42 mmol), 4-fluorophenyl boronic acid (71 mg, 0.51 mmol), $Pd(OAc)_2$ (19 mg, 0.084 mmol), 2M $Na_2CO_3$ (0.42 mL) in DMF (9 mL) was stirred overnight at room temperature under nitrogen. The mixture was diluted with EtOAc, filtered, washed with brine, dried, and concentrated. Purification via flash column (hexane/EtOAc 5:1) gave ester 162-S3 as a white solid. $^1$H NMR (400 MHz, DMSO-$d_6$): δ 8.35 (d, J=2.8 Hz, 1H), 7.89

(m, 2H), 7.83 (m, 3H), 7.74 (m, 2H), 7.59 (m, 2H), 7.4 (m, 2H), 7.28 (m, 3H), 6.38 (s, 1H), 4.13 (m, 2H), 1.08 (t, J=7.2 Hz, 3H).

To a solution of the above ester (90 mg) in THF/MeOH (3 mL/3 mL) was added 1 M LiOH solution (1 mL). The resulting mixture was stirred at room temperature for 0.5 h, quenched with 1N aqueous HCl and concentrated to remove the organic solvents. To the residue was added water. The formed solid was filtered, washed with water, and dried to afford acid 162 (82 mg) as a white solid.

$^1$H NMR (400 MHz, DMSO-$d_6$): δ 8.35 (d, J=2.4 Hz, 1H), 7.90–7.78 (m, 5H), 7.74 (m, 2H), 7.57 (m, 2H), 7.48–7.41 (m, 2H), 7.32–7.26 (m, 3H), 6.23 (s, 1H).

Example 163

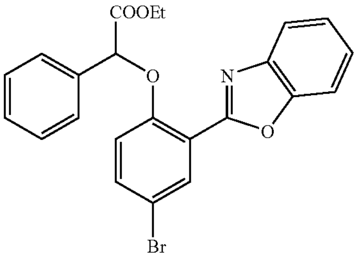

+

163-S1

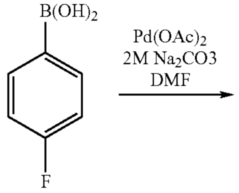

163-S2

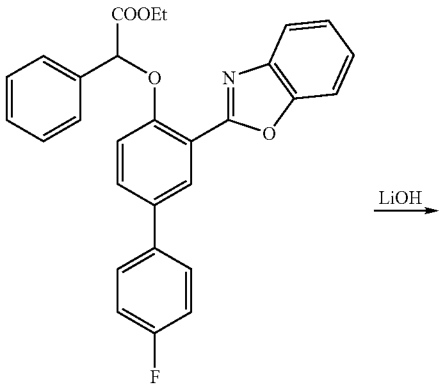

163-S3

-continued

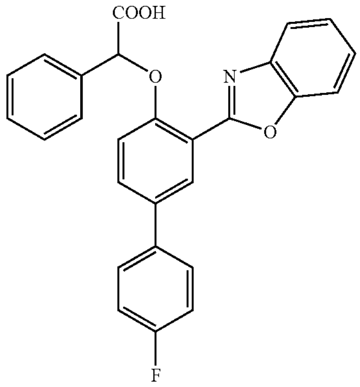

163

In the same manner as that described in Example 162 compound 163 was prepared from 163-S1 and 163-S2. $^1$H NMR (400 MHz, DMSO-$d_6$): δ 8.33 (d, J=2.4 Hz, 1H), 7.90 (dd, J=2.4 and 8.4 Hz, 1H), 7.84 (m, 1H), 7.79–7.74 (m, 5H), 7.49–7.36 (m, 5H), 7.29 (m, 3H), 6.16 (s, 1H).

Example 164

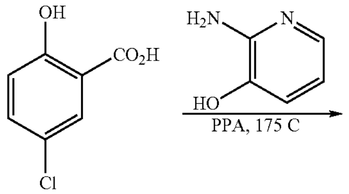

164-S1

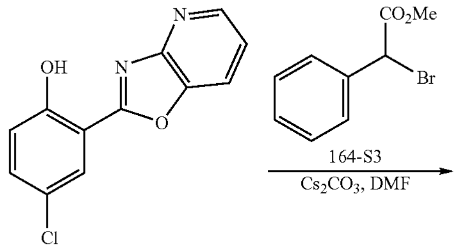

164-S2

-continued

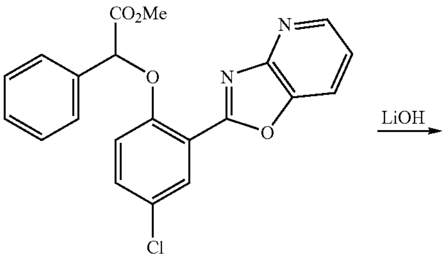

164-S4

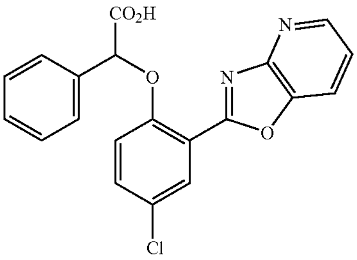

164 (XIII-3)

A mixture of 164-S1 (0.7 g), 2-amino-3-hydroxy-pyridine (0.45 g) and PPA (9.0 g) was heated for 1 h at 175° C. under nitrogen. The mixture was then poured into water, basified by adding saturated aqueous $NaHCO_3$ solution. The resulting mixture was extracted with EtOAc, washed with brine, dried and concentrated to give phenol 164-S2 as a pale yellow solid (265 mg). Pure product was obtained by recrystallization from MeOH. $^1H$ NMR (400 MHz, DMSO-$d_6$): δ 11.30 (s, 1H), 8.58 (m, 1H), 8.29 (m, 1H), 8.01 ((d, J=2.8 Hz, 1H), 7.55 (m, 2H), 7.19 (d, J=8.4 Hz, 1H).

A mixture of the above phenol 164-S2 (109 mg), bromide 164-S3 (121 mg), $Cs_2CO_3$ (172 mg) in DMF was stirred at room temperature for 3 h. The mixture was quenched with saturated aqueous $NH_4Cl$ solution, extracted with $Et_2O$. The organic layer was dried and concentrated. Purification via flash column (hexane/EtOAc 5:1) gave ester 164-S4 as colorless oil. $^1H$ NMR (400 MHz, $CDCl_3$): δ 8.64 (m, 1H), 8.34 (d, J=2.4 Hz, 1H), 7.86 (m, 1H), 7.76 (m, 2H), 7.47–7.42 (m, 4H), 7.38 (m, 1H), 6.93 (d, J=9.2 Hz, 1H), 5.78 (s, 1H), 3.72 (s, 3H).

To a solution of the above ester (40 mg) in THF/MeOH (3 mL/3 mL) was added 0.08 M LiOH solution (1.5 mL) at 0° C. The resulting mixture was stirred at 0° C. for 4 h, quenched with 0.5 N aqueous HCl and concentrated. The residue was extracted with EtOAc and the organic layer was dried and concentrated. Purification via flash column (5% to 20% iPrOH in hexanes containing 0.1% TFA) gave acid 164 as a white solid (22 mg). $^1H$ NMR (400 MHz, $CDCl_3$): δ 8.70 (m, 1H), 8.24 (d, J=2.8 Hz, 1H), 7.98 (m, 1H), 7.57 (m, 2H), 7.45–7.38 (m, 5H), 6.85 (d, J=8.4 Hz, 1H), 5.75 (s, 1H).

Example 165

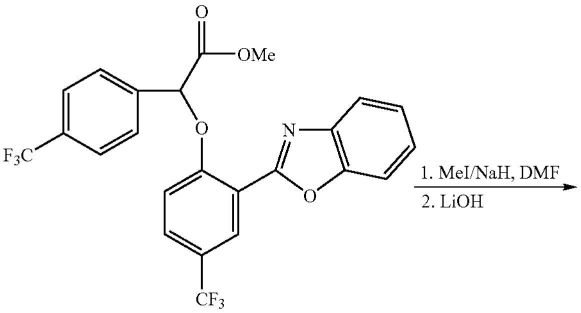

165-S1

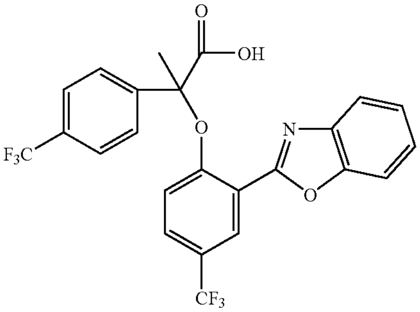

165 (Ia-91)

In the same manner as that described in Example 42 compound 165 was prepared from 165-S1. $^1H$ NMR (400 MHz, DMSO-$d_6$): δ 8.32–7.22 (m, 11H), 1.80 (s, 3H).

Example 166

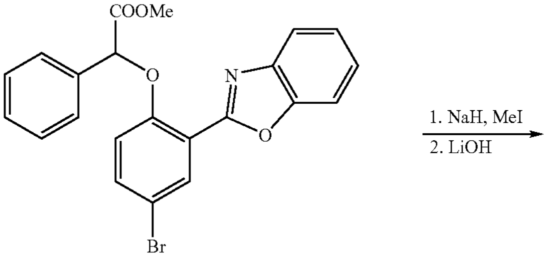

166-S1

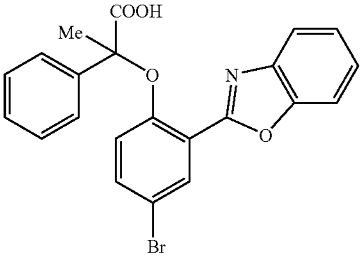

166 (Ia-325)

In the same manner as that described in Example 42 compound 166 was prepared from 166-S1. $^1H$ NMR (400 MHz, DMSO-$d_6$): δ 8.22 (d, J=2.4 Hz, 1H), 7.85 (m, 1H), 7.79 (m, 1H), 7.74 (m, 2H), 7.69 (dd, J=2.4 and 8.8 Hz, 1H), 7.51–7.32 (m, 5H), 6.85 (d, J=8.8 Hz, 1H), 1.95 (s, 3H).

Example 167

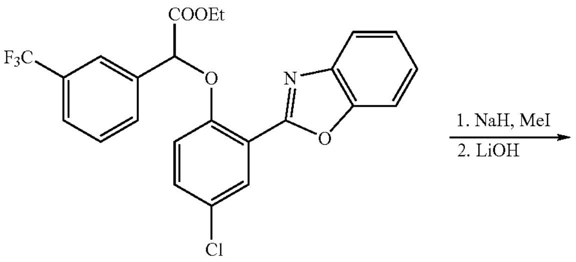

167-S1

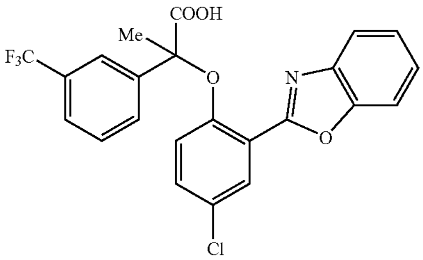

167 (Ia-191)

In the same manner as that described in Example 42 compound 167 was prepared from 167-S1. $^{1}H$ NMR (400 MHz, DMSO-$d_6$): δ 8.34 (s, 1H), 8.12 (m, H), 7.99 (m, 1H), 7.81 (m, 1H), 7.73–7.63 (m, 4H), 7.46 (m, 2H), 7.01 (d, J=8.8 Hz, 1H), 1.92 (s, 3H).

Example 168

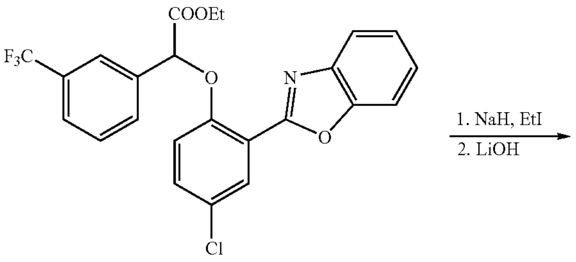

168-S1

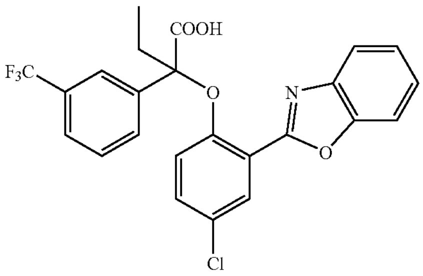

168

In the same manner as that described in Example 42 compound 168 was prepared from 168-S1. $^{1}H$ NMR (400 MHz, DMSO-$d_6$): δ 8.31 (s, 1H), 8.12 (d, J=2.4 Hz, 1H), 7.95 (m, 1H), 7.85 (m, 1H), 7.79 (m, 1H), 7.74 (m, 1H), 7.67 (m, 1H), 7.59 (m, 1H), 7.48 (m, 2H), 6.89 (d, J=8.8 Hz, 1H), 2.62 (m, 1H), 2.40 (m, 1H), 0.59 (t, J=6.8 Hz, 3H).

Example 169

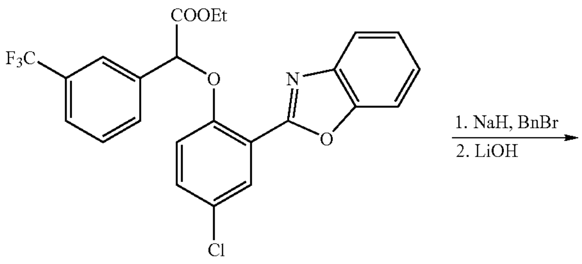

169-S1

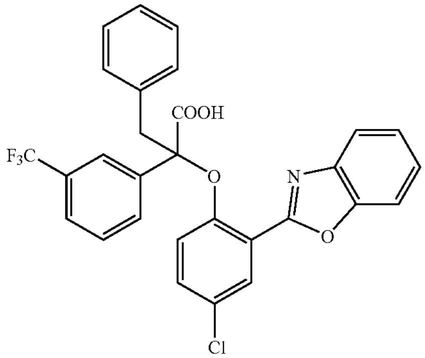

169

In the same manner as that described in Example 42 compound 169 was prepared from 169-S1. $^{1}H$ NMR (400 MHz, DMSO-$d_6$): δ 8.14 (s, 1H), 7.97 (d, J=2.8 Hz, 1H), 7.91 (d, J=8 Hz, 1H), 7.79 (m, 1H), 7.65 (m, 1H), 7.49 (dd, J=2.8 and 9.2 Hz, 1H), 7.48–7.37 (m, 4H), 7.17 (d, J=9.6 Hz, 1H), 6.79 (m, 1H), 6.72 (m, 2H), 6.54 (m, 2H), 3.75 (d, J=15.2 Hz, 1H), 3.54 (d, J=14.4 Hz, 1H).

Example 170

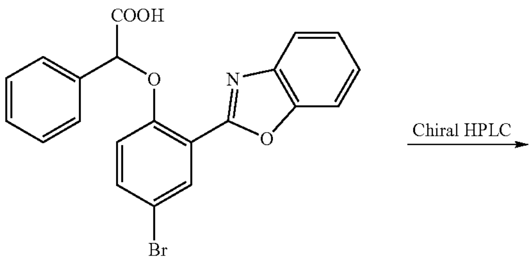

171

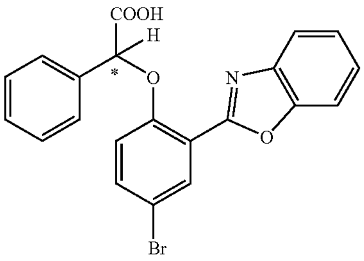

+

(+)-170 [(+)-I-325]

-continued

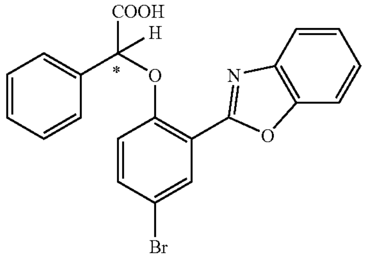

(-)-170 [(-)-I-325]

The two enantiomers were isolated by chiral HPLC using a 25 cm×21.1 mm Regis Technologies (R,R) WHELK-O 2 10/100 column at ambient temperature. The column was eluted with (50/50/0.1) iPrOH/hexanes/0.1%TFA at a flow of 30 mL/min.

Example 171

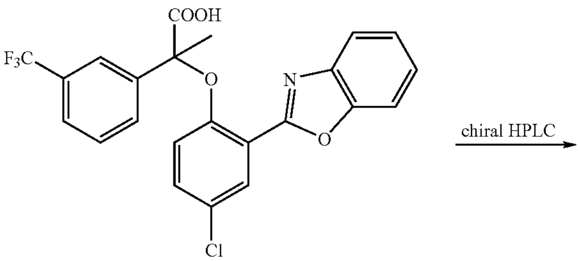

171

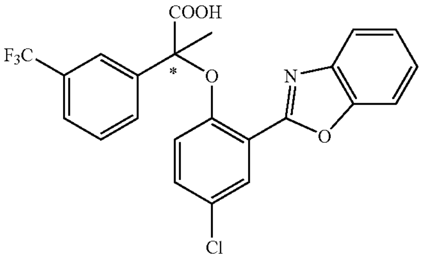

(+)-171 [(+)-Ia-191]

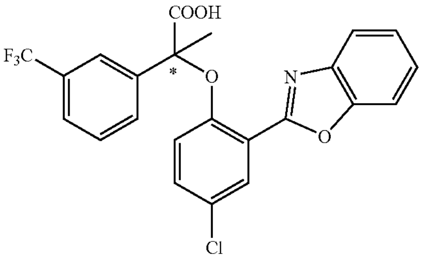

(-)-171 [(-)-Ia-191]

The two enantiomers were separated by chiral HPLC using a 25 cm×21.1 mm Regis Technologies (R,R) WHELK-O 2 10/100 column at ambient temperature. HPLC methods and condition: 25% iPrOH-75% Hexanes-0.1% TFA, 30 mL/min., λ=220 nm.

Example 172

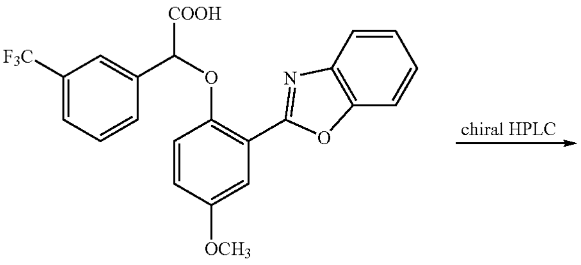

172

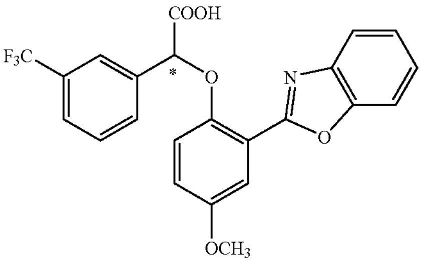

(+)-172

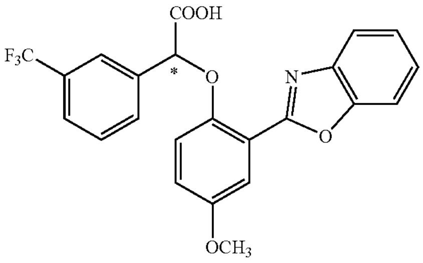

(-)-171

The two enantiomers were separated by chiral HPLC using a 25 cm×21.1 mm Regis Technologies (R,R) WHELK-O 2 10/100 column at ambient temperature. HPLC methods and conditions: 25% iPrOH-75% Hexanes-0.1% TFA, 30 mL/min., λ=220 nm.

Example 173

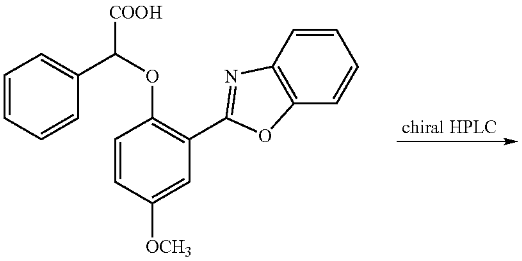

173

-continued

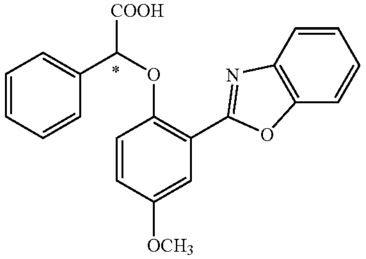

(+)-173

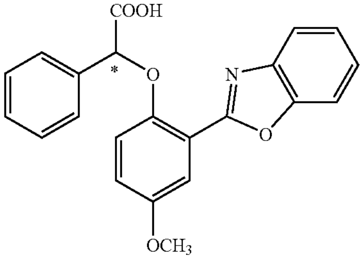

(-)-173

The two enantiomers were separated by chiral HPLC using a 25 cm×21.1 mm Regis Technologies (R,R) WHELK-O 2 10/100 column at ambient temperature. HPLC methods and conditions: 50% iPrOH-50% Hexanes-0.1% TFA, 30 mL/min., λ=220 nm.

Example 174

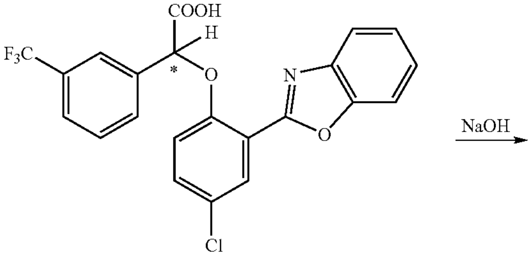

(+)-174

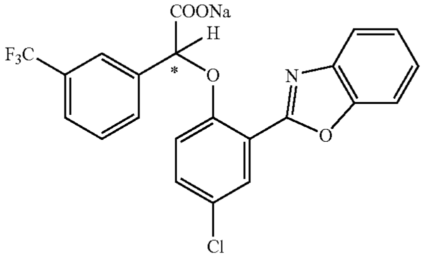

(+)-174 Na salt

A suspension of (+)-174 (1.80 g, 4.02 mol) in ca. 100 mL of $CH_3CN$ was heated until it was a clear solution, then cooled to rt. A solution of aq. NaOH (2N, 2.01 mL, 4.02 mmol) was added, and stripped off solvents in vacuo. The residue was dissolved in water and lyophilized to afford desired sodium salt (1.87 g) as a white solid. $^1$H NMR (400 MHz, DMSO-$d_6$): δ 8.33 (1H, s), 8.04–8.07 (2H, m), 7.81 (1H, m), 7.72 (1H, m), 7.59 (3H, m), 7.45 (2H, m), 7.12 (1H, d, J=9.2 Hz), 5.51 (1H, s) ppm.

Example 174A

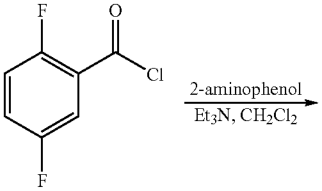

174A-S1

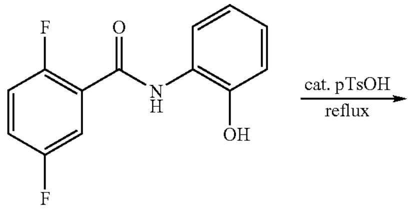

174A-S2

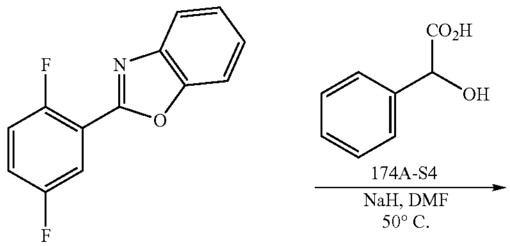

174A-S3

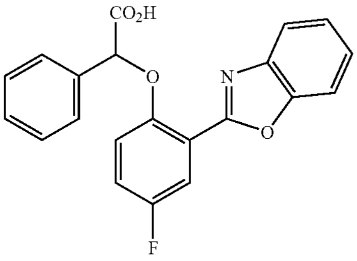

174A

To a solution of 2-aminophenol (10.64 g, 0.0975 mol) and $Et_3N$ (14.24 mL, 0.102 mol) in $CH_2Cl_2$ (200 mL) at 0° C. was added drop wise 2,5-difluoro-benzoyl chloride 174A-S1 (16.39 g, 0.093 mol). The resulting mixture was stirred at 0° C. to rt overnight, diluted with EtOAc and washed with 1N HCl and water. The organic layer was dried over $Na_2SO_4$ and concentrated in vacuo to afford crude 174A-S2 as a pale yellow solid. $^1$H NMR (400 MHz, DMSO-$d_6$): δ 10.06 (s, 1H), 9.52 (d, J=8.0 Hz), 8.0–6.79 (m, 7H).

To a suspension of the above crude product 174A-S2 in toluene (300 mL) was added pTsOH monohydrate (5.0 g). The resulting suspension was refluxed at 120° C. with a Dean-Stark condenser for 16 h. The reaction was cooled to rt, concentrated in vacuo, diluted with EtOAc, washed with sat. $NaHCO_3$ and brine, dried over $Na_2SO_4$ and concentrated in vacuo to afford 174A-S3 (18.73 g, 87% for two steps) as a pale yellow solid. $^1$H NMR (400 MHz, DMSO-$d_6$): δ 7.96 (m, 1H), 7.85–7.79 (m, 2H), 7.56 (m, 2H), 7.48–7.40 (m, 2H).

To a solution of 174A-S4 (1.88 g, 12.32 mmol) in DMF (30 mL) at 0° C. was added NaH (0.96 g, 24.03 mmol). The resulting mixture was warmed up to rt, and stirred at rt for 1 h. To this reaction mixture was added a solution of 174A-S3 (2.85 g, 12.32 mmol) in DMF (20 mL), and the resulting mixture was heated at 50° C. for 12 hrs. After cooling to r.t., the reaction mixture was quenched with cold 2 N HCl solutions, extracted EtOAc. The organic layer was washed with $H_2O$, dried over $Na_2SO_4$ and concentrated in vacuo. The residue was recrystallized from $Et_2O$ to afford 174A as a greenish solid (1.2 g). $^1H$ NMR (400 MHz, DMSO-$d_6$): δ 13.38 (br, 1H), 7.89–7.83 (m, 2H), 7.77–7.72 (m, 3H), 7.48–7.37 (m, 6H), 7.24 (m, 1H), 6.19 (s, 1H).

The two enantiomers were separated by HPLC. Column: PIRKLE COVALENT, (R,R) Whelk-O 2 10/100, 25 cm×21.1 mm. Flow: 30 ml/min, iPrOH/Hexanes-0.1% TFA.

Example 174B

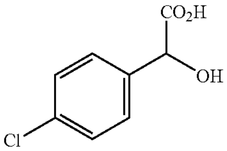

174B-S1

+

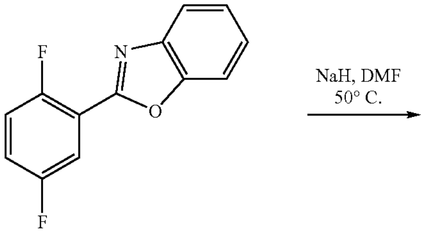

174A-S3

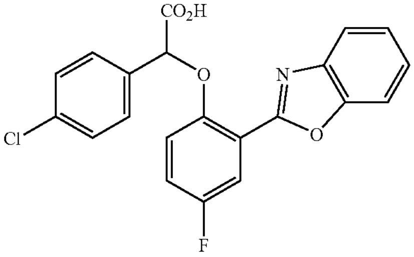

174B

In the same manner as that described in Example 174A compound 174B was prepared from 174A-S3 and 174B-S1. $^1H$ NMR (400 MHz, DMSO-$d_6$): δ 13.38 (br, 1H), 7.91–7.83 (m, 2H), 7.81–7.78 (m, 3H), 7.48–7.41 (m, 5H), 7.24 (m, 1H), 6.15 (s, 1H).

The two enantiomers were separated by HPLC. Column: PIRKLE COVALENT, (R,R) Whelk-O 2 10/100, 25 cm×21.1 mm. Flow: 30 ml/min, iPrOH/Hexanes-0.1% TFA.

Example 174C

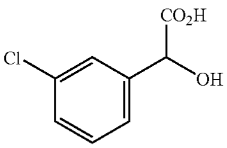

174C-S1

+

-continued

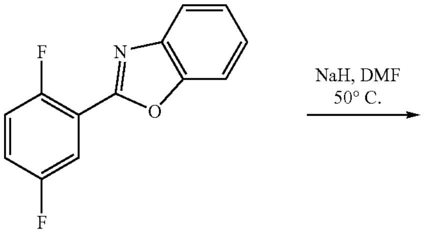

174A-S3

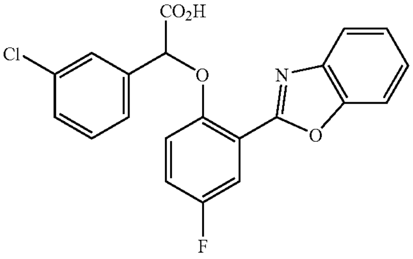

174C

In the same manner as that described in Example 174A compound 174C was prepared from 174A-S3 and 174C-S1. $^1H$ NMR (400 MHz, $CDCl_3$): δ 7.96 (m, 1H), 7.86 (m, 1H), 7.67 (m, 1H), 7.58 (m, 1H), 7.48 (m, 3H), 7.38 (m, 2H), 7.13 (m, 1H), 6.81 (m, 1H), 5.62 (s, 1H).

The two enantiomers were separated by HPLC. Column: PIRKLE COVALENT, (R,R) Whelk-O 2 10/100, 25 cm×21.1 mm. Flow: 30 ml/min, iPrOH/Hexanes-0.1% TFA.

Example 174D

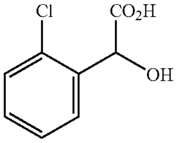

174D-S1

+

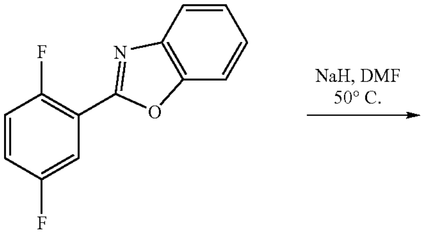

174A-S3

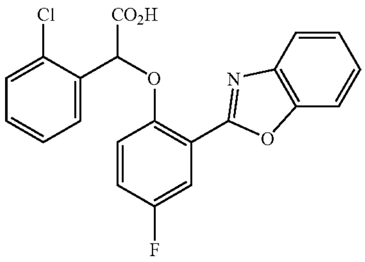

174D

In the same manner as that described in Example 174A compound 174D was prepared from 174A-S3 and 174D-S1. $^1$H NMR (400 MHz, $CDCl_3$): δ 7.93–7.86 (m, 2H), 7.66 (m, 1H), 7.55–7.46 (m, 4H), 7.37–7.33 (m, 2H), 7.15 (m, 1H), 6.82 (m, 1H), 6.18 (s, 1H).

The two enantiomers were separated by HPLC. Column: PIRKLE COVALENT, (R,R) Whelk-O 2 10/100, 25 cm×21.1 mm. Flow: 30 ml/min, iPrOH/Hexanes-0.1% TFA.

Example 174E

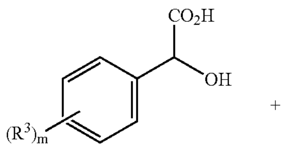

174F-S1

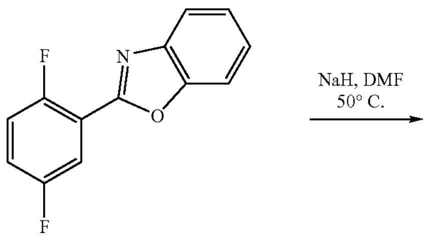

174A-S3

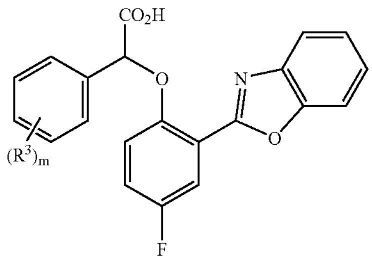

174E

In the same manner as that described in Example 174A compound 174F was prepared from 174A-S3 and 174F-S1.

Example 175

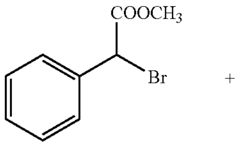

175-S1

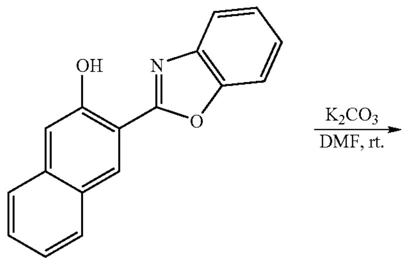

175-S2

-continued

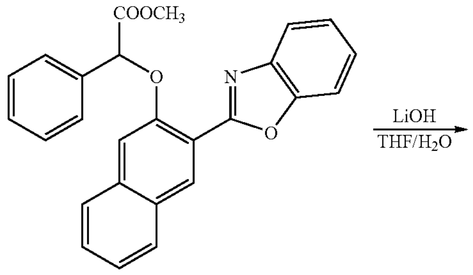

175-S3

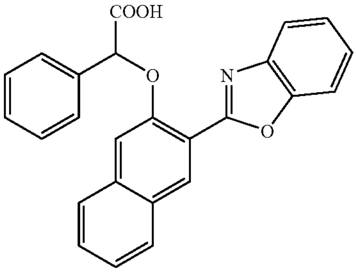

175 (III-8)

In the same manner as that described in Example 28 compound 175 was prepared from 175-S1 and 175-S2. $^1$H NMR (400 MHz, DMSO-$d_6$): δ 13.4 (1H, br, COOH), 8.80 (1H, s), 8.07 (1H, d, J=8.0 Hz), 7.86–7.88 (2H, m), 7.78–7.82 (3H, m), 7.60 (1H, td, J=7.8, 1.2 Hz), 7.55 (1H, s), 7.43–7.75 (5H, m), 7.39 (1H, tt, J=7.2, 1.2 Hz), 6.21 (1H, s)ppm.

Example 176

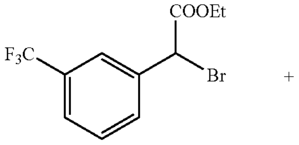

176-S1

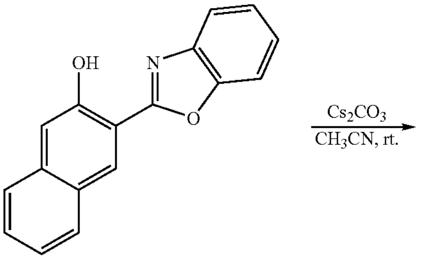

176-S2

-continued

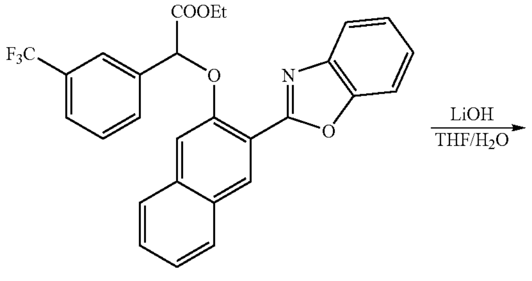

176-S3

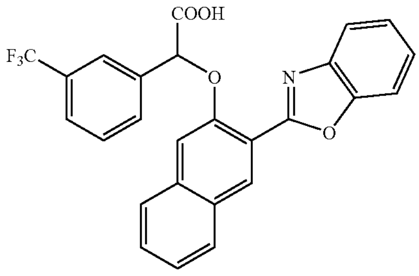

176 (III-2)

In the same manner as that described in Example 28 compound 176 was prepared from 176-S1 and 176-S2. $^1$H NMR (400 MHz, DMSO-$d_6$): δ 8.82 (1H, s), 8.41 (1H, s), 8.09 (2H, t, J=8.2 Hz), 7.88 (1H, d, J=8.0 Hz), 7.83–7.86 (1H, m), 7.77–7.80 (2H), 7.73 (1H, t, J=7.6 Hz), 7.61 (1H, td, J=6.8, 1.2 Hz), 7.58 (1H, s), 7.45–7.52 (3H, m), 6.43 (1H, s) ppm.

Example 177

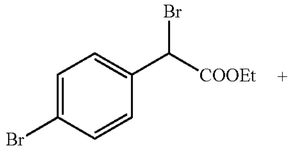

177-S1

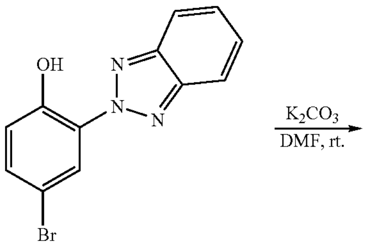

177-S2

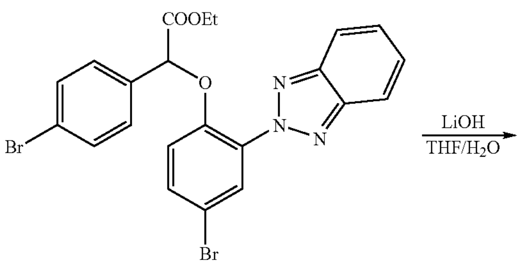

177-S3

-continued

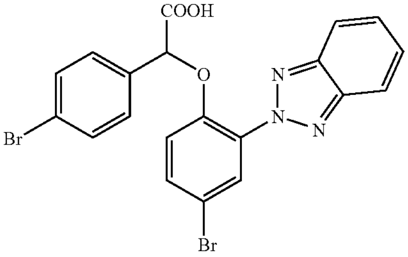

177 (XI-34)

In the same manner as that described in Example 28 compound 177 was prepared from 177-S1 and 177-S2. $^1$H NMR (400 MHz, DMSO-$d_6$): δ 13.5 (1H, br, COOH), 8.00–8.06 (3H, m), 7.78 (1H, dd, J=9.2, 2.4 Hz), 7.51–7.54 (4H, m), 7.36 (2H, d, J=8.4 Hz), 7.24 (1H, d, J=8.8 Hz), 6.07 (1H, s) ppm.

Example 178

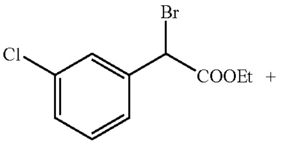

178-S1

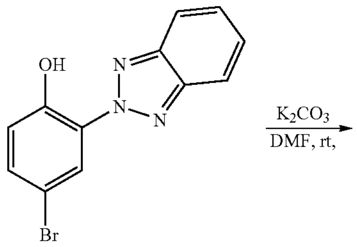

178-S2

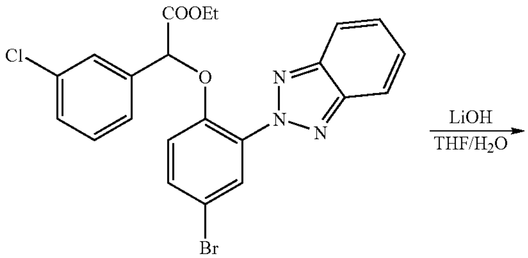

178-S3

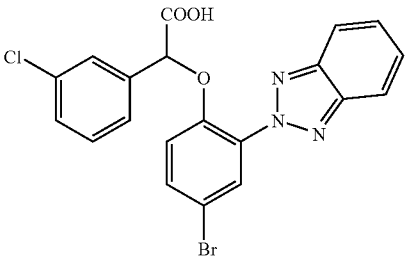

178 (XI-28)

In the same manner as that described in Example 28 compound 178 was prepared from 178-S1 and 178-S2. $^1$H NMR (400 MHz, DMSO-$d_6$): δ 8.01–8.06 (3H, m), 7.79

(1H, dd, J=8.8, 2.8 Hz), 7.51–7.56 (2H, m), 7.47 (1H, m), 7.35–7.37 (3H, m), 7.25 (1H, d, J=8.8 Hz), 6.13 (1H, s) ppm.

Example 179

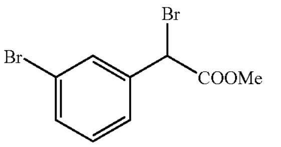
+

179-S1

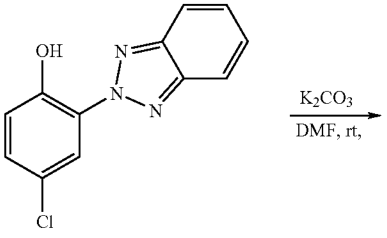

179-S2

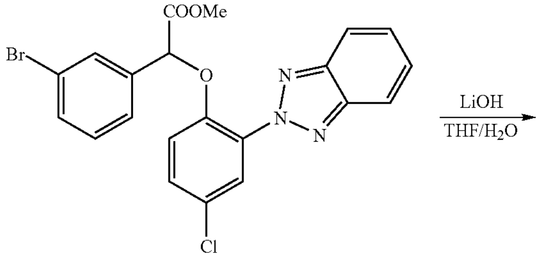

179-S3

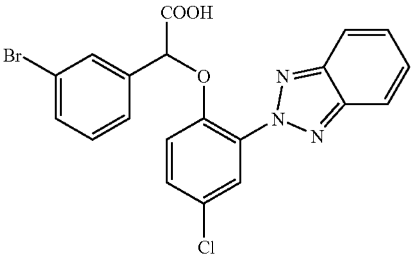

179

In the same manner as that described in Example 28 compound 179 was prepared from 179-S1 and 179-S2. $^1H$ NMR (400 MHz, DMSO-$d_6$): δ 8.03–8.06 (2H, m), 7.94 (1H, d, J=2.4 Hz), 7.68 (1H, dd, J=8.8, 2.8 Hz), 7.62 (1H, m), 7.48–7.54 (3H, m), 7.41 (1H, d, J=7.6 Hz), 7.26–7.32 (2H, m), 6.13 (1H, s) ppm.

Example 180

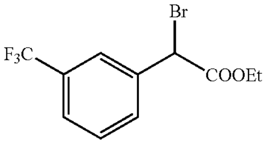
+

180-S1

-continued

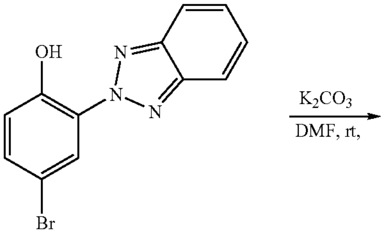

180-S2

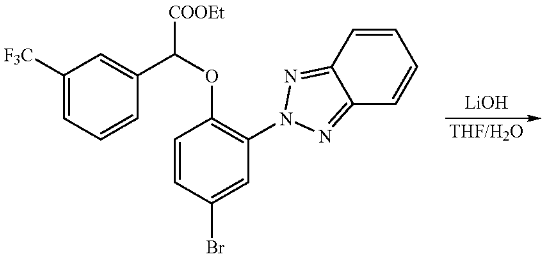

180-S3

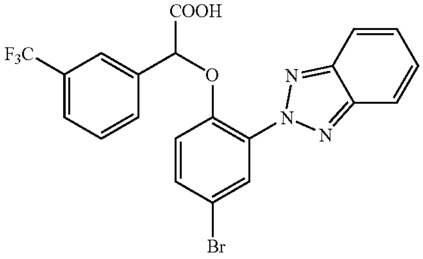

180 (XI-29)

In the same manner as that described in Example 28 compound 180 was prepared from 180-S1 and 180-S2. $^1H$ NMR (400 MHz, DMSO-$d_6$): δ 8.04 (1H, d, J=2.8 Hz), 7.97–8.02 (2H, m), 7.81 (1H, dd, J=8.8, 2.8 Hz), 7.71–7.73 (2H, m), 7.67 (1H, d, J=8.2 Hz), 7.58 (1H, d, J=8.2 Hz), 7.51–7.55 (2H, m), 7.29 (1H, d, J=8.8 Hz), 6.28 (1H, s) ppm.

Example 181

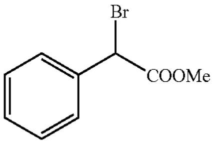
+

181-S1

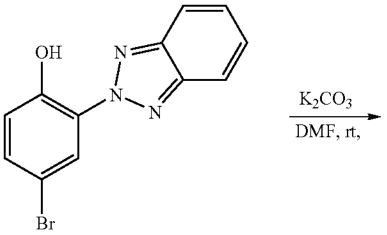

181-S2

-continued

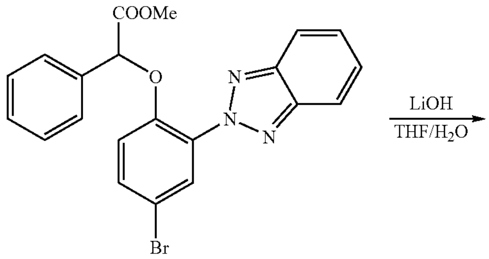

181-S3

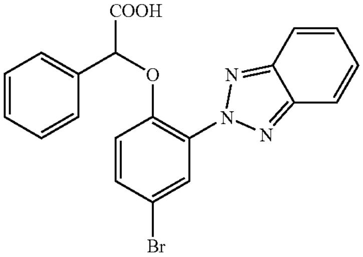

181 (XI-35)

In the same manner as that described in Example 28 compound 181 was prepared from 181-S1 and 181-S2. $^1H$ NMR (400 MHz, DMSO-$d_6$): δ 7.98–8.06 (2H, m), 7.98 (1H, d, J=2.4 Hz), 7.77 (1H, dd, J=9.2, 2.4 Hz), 7.50–7.55 (2H, m), 7.34–7.39 (2H, m), 7.27–7.31 (3H, m), 7.24 (1H, d, J=8.8 Hz), 6.03 (1H, s) ppm. The two enantiomers were isolated by chiral HPLC using a 25 cm×21.1 mm Regis Technologies (R,R) WHELK-O 2 10/100 column at ambient temperature. The column was eluted with (15/85/0.1) iPrOH/hexanes/TFA at a flow of 30 mL/min. Detection was at 220 nm. The (+)-181 eluted at 4.0 to 5.3 min, and the (−)-181 at 5.8 to 7.1 min.

Example 182

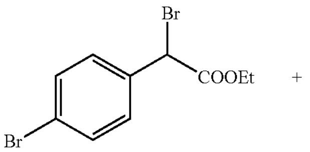

182-S1

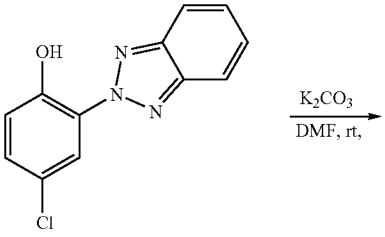

181-S2

-continued

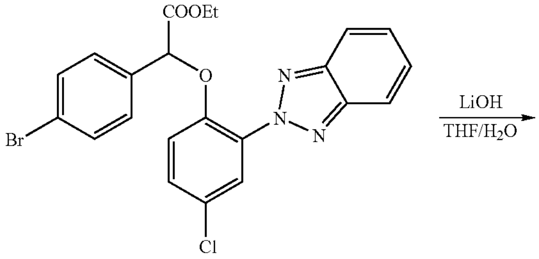

182-S3

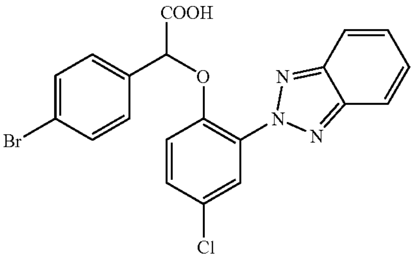

182 (XI-25)

In the same manner as that described in Example 28 compound 182 was prepared from 182-S1 and 182-S2. $^1H$ NMR (400 MHz, DMSO-$d_6$): δ 13.5 (1H, br, COOH), 8.04 (2H, q, J=3.2 Hz), 7.91 (1H, d, J=2.8 Hz), 7.66 (1H, dd, J=9.2, 2.8 Hz), 7.52–7.54 (4H, m), 7.36 (2H, d, J=8.4 Hz), 7.29 (1H, d, J=9.6 Hz), 6.09 (1H, s) ppm.

Example 183

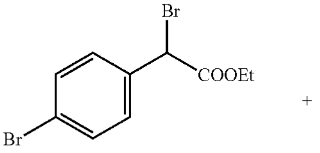

183-S1

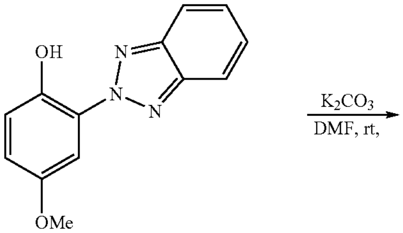

183-S2

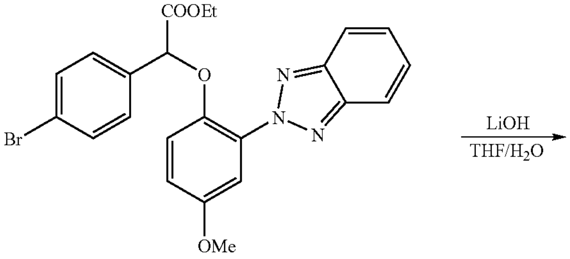

183-S3

-continued

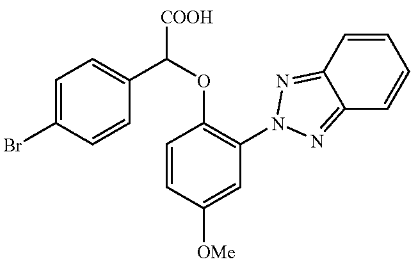

183

In the same manner as that described in Example 28 compound 183 was prepared from 183-S1 and 183-S2. $^1$H NMR (400 MHz, DMSO-$d_6$): δ 13.3 (1H, br, COOH), 8.02 (2H, q, J=3.2 Hz), 7.48–7.52 (4H, m), 7.32–7.35 (3H, m), 7.21 (1H, d, J=8.8 Hz), 7.14 (1H, dd, J=9.6, 3.2 Hz), 5.86 (1H, s), 3.77 (3H, s) ppm.

Example 184

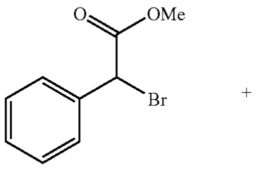

184-S1

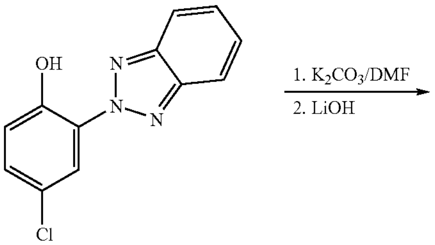

184-S2

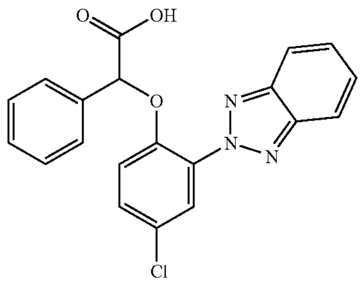

184 (XI-26)

In the same manner as that described in Example 28 compound 184 was prepared from 184-S1 and 184-S2. $^1$H NMR (400 MHz, DMSO-$d_6$): δ 8.04 (m, 2H), 7.88 (d, J=2.4 Hz, 1H), 7.67 (dd, J=2.8 and 9.2 Hz, 1H), 7.53 (m, 2H), 7.38 (m, 2H), 7.29 (m, 4H), 6.04 (s, 1H).

Example 185

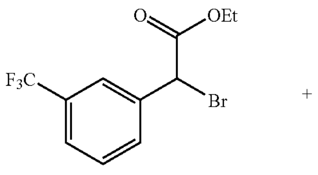

185-S1

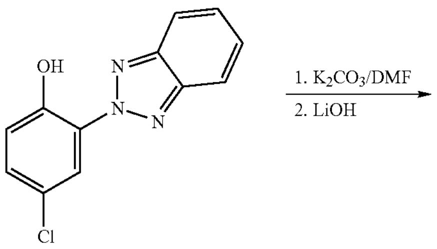

185-S2

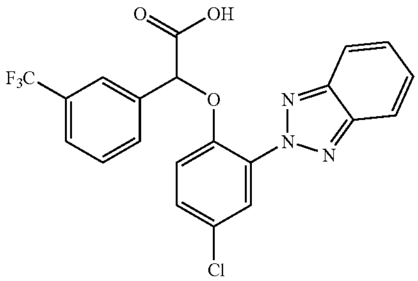

185 (XI-20)

In the same manner as that described in Example 28 compound 185 was prepared from 185-S1 and 185-S2. $^1$H NMR (400 MHz, DMSO-$d_6$): δ 8.02 (m, 2H), 7.96 (d, J=2.8 Hz, 1H), 7.74–7.66 (m, 4H), 7.60–7.51 (m, 3H), 7.37 (d, J=8.8 Hz, 1H), 6.29 (s, 1H).

Example 186

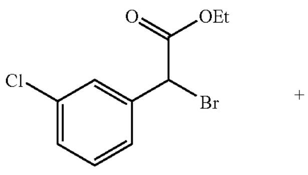

186-S1

-continued

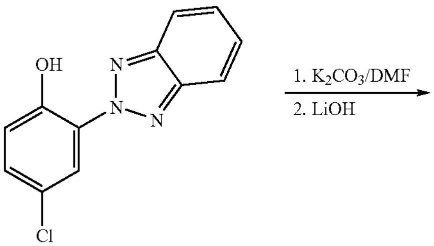

186-S2

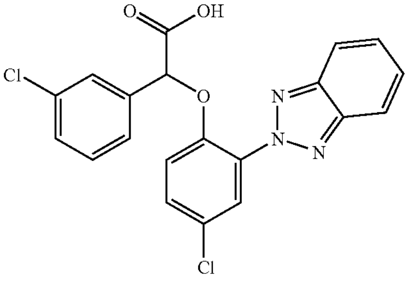

186 (XI-19)

In the same manner as that described in Example 28 compound 186 was prepared from 186-S1 and 186-S2.$^1$H NMR (400 MHz, DMSO-$d_6$): δ 8.05 (m, 2H), 7.94 (d, J=2.8 Hz, 1H), 7.69 (dd, J=2.8 and 8.8 Hz, 1H), 7.56–7.52 (m, 2H), 7.48 (s, 1H), 7.39–7.30 (m, 4H), 6.15 (s, 1H).

Example 187

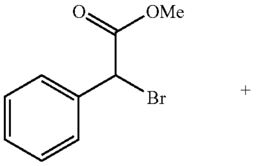

187-S1

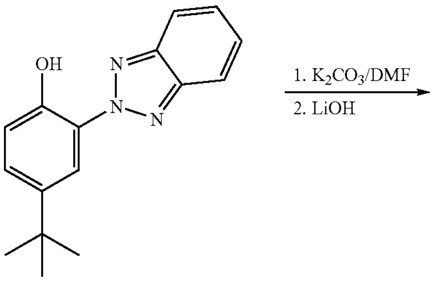

187-S2

-continued

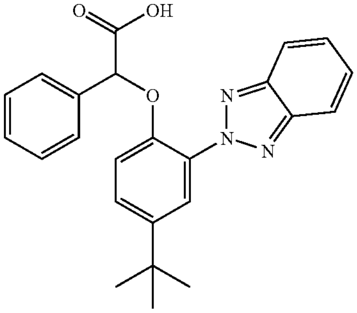

187 (XI-44)

In the same manner as that described in Example 28 compound 187 was prepared from 187-S1 and 187-S2. $^1$H NMR (400 MHz, DMSO-$d_6$): δ 8.04 (m, 2H), 7.67 (m, 1H), 7.57 (m, 1H), 7.50 (m, 2H), 7.40 (m, 2H), 7.28 (m, 3H), 7.17 (m, 1H), 5.94 (s, 1H), 1.30 (s, 9H).

Example 188

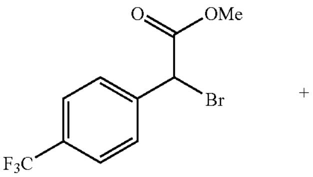

188-S1

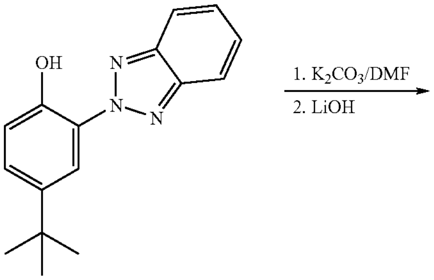

188-S2

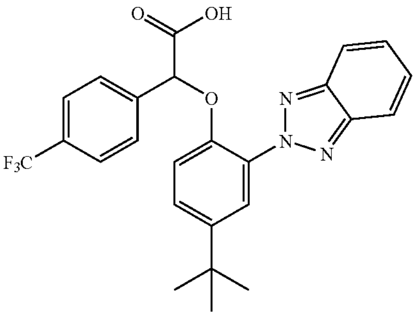

188 (XI-42)

In the same manner as that described in Example 28 compound 188 was prepared from 188-S1 and 188-S2. $^1$H NMR (400 MHz, $CDCl_3$): δ 8.18 (d, J=2.4 Hz, 1H), 8.01 (m, 2H), 7.69 (m, 4H), 7.54 (m, 2H), 7.44 (dd, J=2.4 and 8.8 Hz, 1H), 6.97 (d, J=8 Hz, 1H), 5.91 (s, 1H), 1.39 (s, 9H).

Example 189

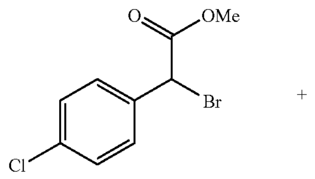

189-S1

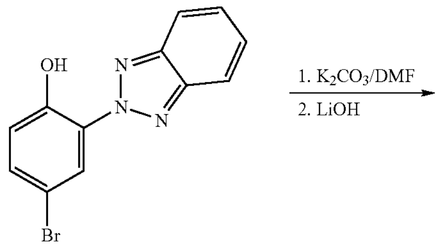

189-S2

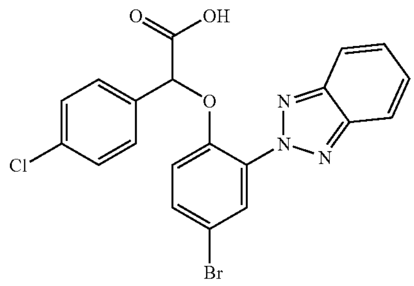

189 (XI-32)

In the same manner as that described in Example 28 compound 189 was prepared from 189-S1 and 189-S2. $^1$H NMR (400 MHz, DMSO-$d_6$): δ 8.0 (m, 2H), 7.94 (d, J=2.8 Hz, 1H), 7.74 (dd, J=2.4 and 8.8 Hz, 1H), 7.52 (m, 2H), 7.34 (m, 4H), 7.19 (d, J=8.8 Hz, 1H), 5.97 (s, 1H).

Example 190

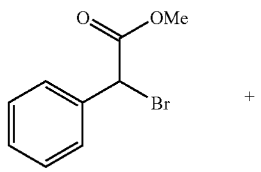

190-S1

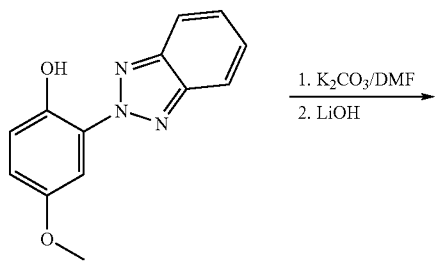

190-S2

-continued

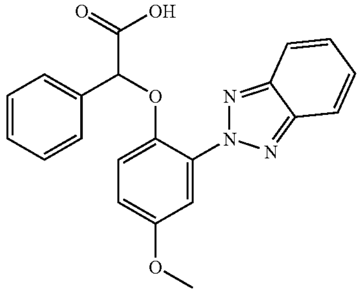

190

In the same manner as that described in Example 28 compound 190 was prepared from 190-S1 and 190-S2. $^1$H NMR (400 MHz, DMSO-$d_6$): δ 8.04 (m, 2H), 7.52 (m, 2H), 7.36(m, 2H), 7.33 (d, J=3.2 Hz, 1H), 7.27 (m, 3H), 7.21 (d, J=8.8 Hz, 1H), 7.13 (dd, J=3.2 and 9.2 Hz, 1H), 5.82 (s, 1H), 3.79 (s, 3H).

Example 191

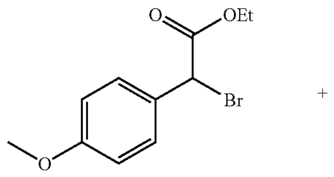

191-S1

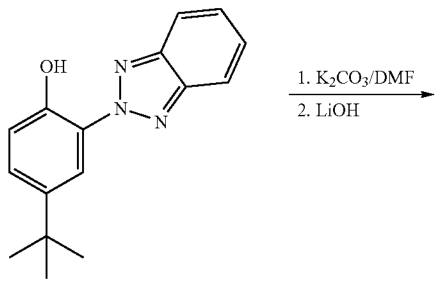

191-S2

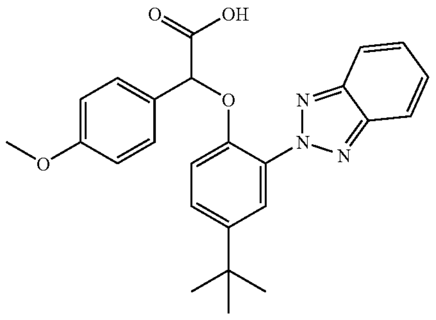

191 (XI-40)

In the same manner as that described in Example 28 compound 191 was prepared from 191-S1 and 191-S2. $^1$H NMR (400 MHz, $CDCl_3$): δ 8.12 (d, J=2.4 Hz, 1H), 8.01 (m, 2H), 7.54 (m, 2H), 7.42 (m, 3H), 7.06 (d, J=8.8 Hz, 1H), 6.90 (d, J=8.8 Hz, 2H), 5.82 (s, 1H), 3.79 (s, 3H), 1,38 (s, 9H).

Example 192

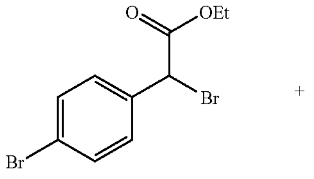

192-S1

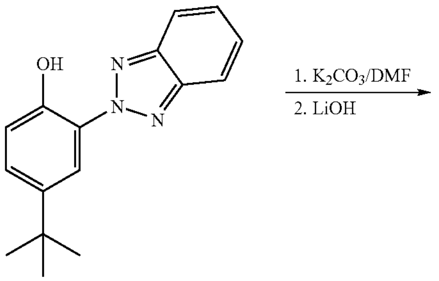

192-S2

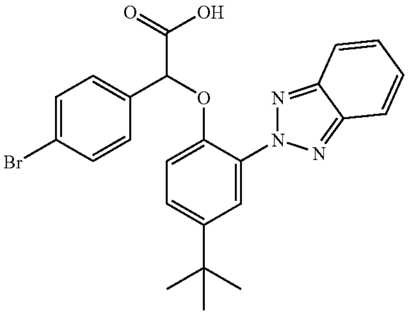

192 (XI-43)

In the same manner as that described in Example 28 compound 192 was prepared from 192-S1 and 192-S2. $^1$H NMR (400 MHz, DMSO-$d_6$): δ 8.04 (m, 2H), 7.69 (d, J=2.8 Hz, 1H), 7.58 (dd, J=2.4 and 8.8 Hz, 1H), 7.51 (m, 4H), 7.36 (m, 2H), 7.15 (d, J=8.8 Hz, 1H), 5.97 (s, 1H), 1.30 (s, 9H).

Example 193

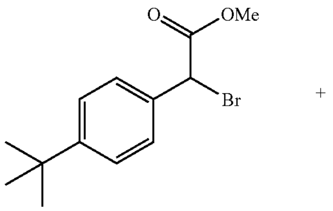

193-S1

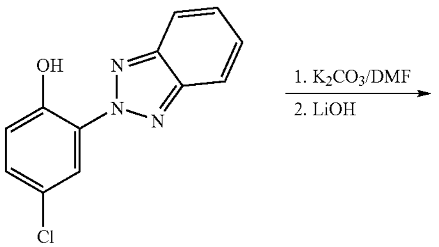

193-S2

-continued

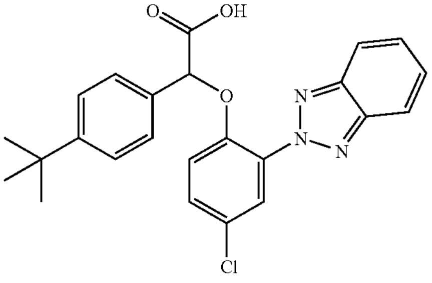

193

In the same manner as that described in Example 28 compound 193 was prepared from 193-S1 and 193-S2. $^1$H NMR (400 MHz, DMSO-$d_6$): δ 8.05 (m, 2H), 7.87 (d, J=2.8 Hz, 1H), 7.67 (dd, J=2.8 and 8.8 Hz, 1H), 7.52 (m, 2H), 7.31 (m, 5H), 5.99 (s, 1H), 1.21 (s, 9H).

Example 194

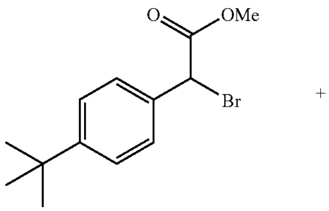

194-S1

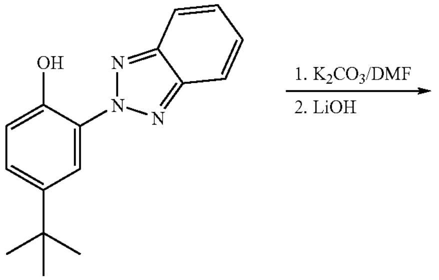

194-S2

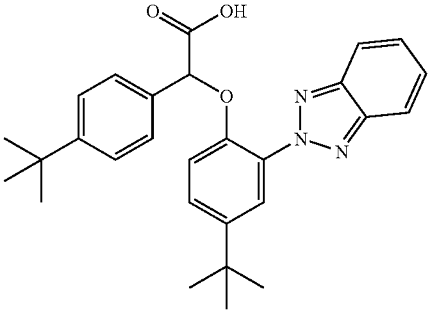

194

In the same manner as that described in Example 28 compound 194 was prepared from 194-S1 and 142-S2. $^1$H NMR (400 MHz, DMSO-$d_6$): δ 8.04 (m, 2H), 7.65 (d, J=2.8 Hz, 1H), 7.48 (dd, J=2.8 and 8.8 Hz, 1H), 7.51 (m, 2H), 7.30 (m, 4H), 7.18 (d, J=8.8 Hz, 1H), 5.89 (s, 1H), 1.30 (s, 9H), 1.23 (s, 9H).

Example 195

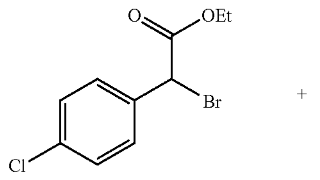

195-S1

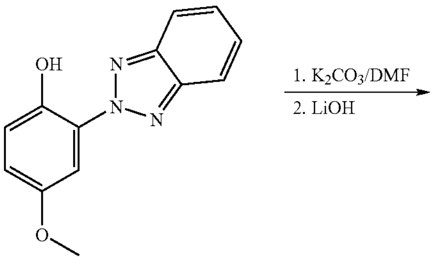

195-S2

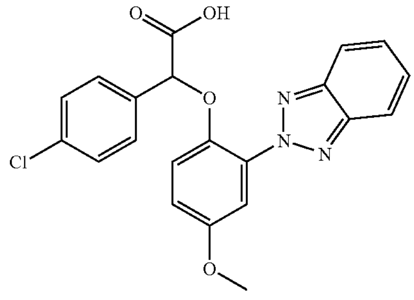

195

In the same manner as that described in Example 28 compound 195 was prepared from 195-S1 and 195-S2. $^1$H NMR (400 MHz, DMSO-$d_6$): δ 8.03 (m, 2H), 7.52 (m, 2H), 7.38 (m, 5H), 7.21 (d, J=8.8 Hz, 1H), 7.14 (dd, J=2.8 and 9.6 Hz, 1H), 5.87 (s, 1H), 3.77(s, 3H).

Example 196

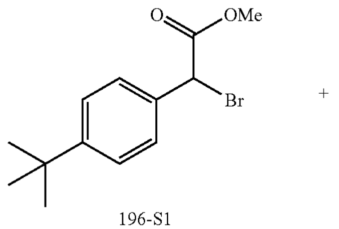

196-S1

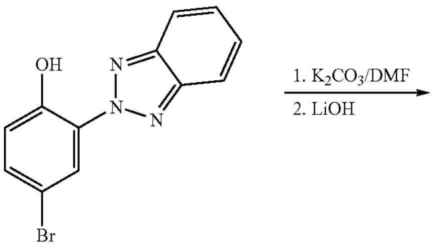

196-S2

-continued

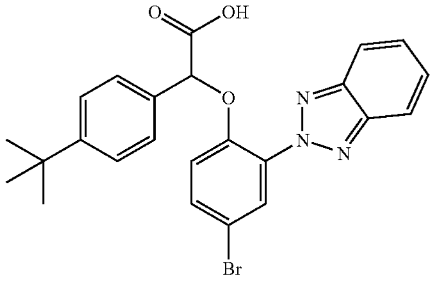

196

In the same manner as that described in Example 28 compound 196 was prepared from 196-S1 and 196-S2. $^1$H NMR (400 MHz, DMSO-$d_6$): δ 8.05 (m, 2H), 7.97 (d, J=2.8 Hz, 1H), 7.76 (dd, J=2.4 and 9.2 Hz, 1H), 7.54 (m, 2H), 7.36 (m, 2H), 7.31 (m, 4H), 7.24 (d, J=3.2 Hz, 1H), 5.99 (s, 1H), 1.22 (s, 9H).

Example 197

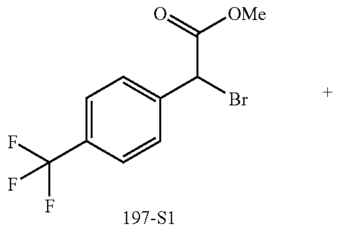

197-S1

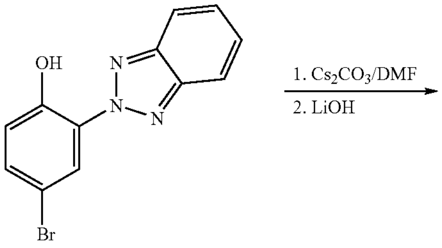

197-S2

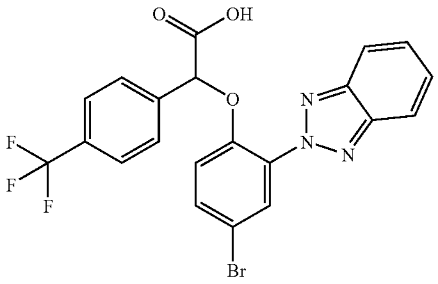

197 (XI-33)

In the same manner as that described in Example 28 compound 197 was prepared from 197-S1 and 197-S2. $^1$H NMR (400 MHz, $CDCl_3$): δ 8.39 (m, 1H), 7.98 (m, 2H), 7.67 (m, 4H), 7.55 (m, 2H), 7.48 (m, 1H), 6.88 (d, J=8.8 Hz, 1H), 5.87 (s, 1H).

Example 198

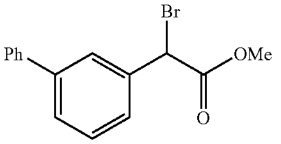

198-S1

+

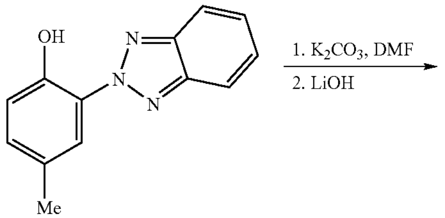

198-S2

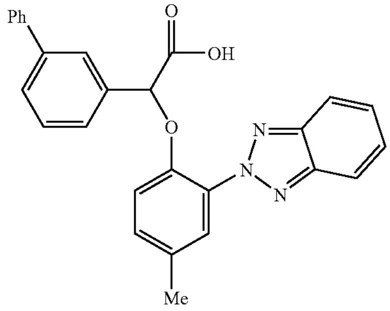

198

In the same manner as that described in Example 28 compound 198 was prepared from 198-S1 and 198-S2. $^1$H NMR (400 MHz, DMSO-$d_6$): δ 8.0–7.0 (m, 16H), 6.0 (s, 1H), 2.26 (s, 3H).

Example 199

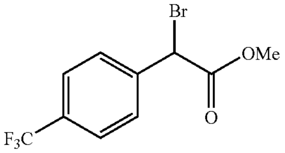

199-S1

+

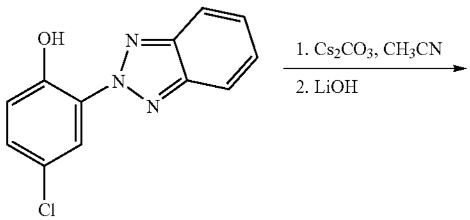

199-S2

-continued

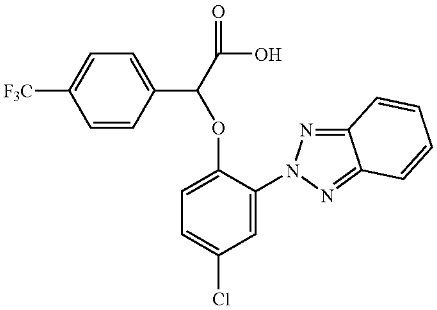

199 (XI-24)

In the same manner as that described in Example 28 compound 199 was prepared from 199-S1 and 199-S2. $^1$H NMR (400 MHz, DMSO-$d_6$): δ 8.06–7.33 (m, 11H), 6.24 (s, 1H).

The two enantiomers were separated by HPLC. Column: PIRKLE COVALENT, (R,R) Whelk-O 2 10/100, 25 cm×21.1 mm. Flow: 30 ml/min, 8% iPrOH/Hexanes-0.1% TFA.

Example 200

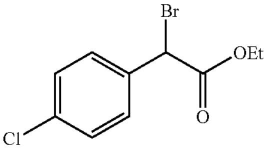

200-S1

+

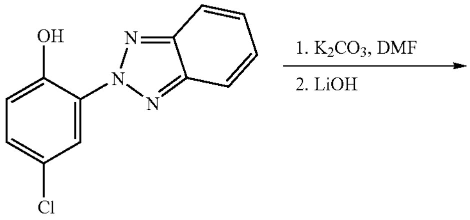

200-S2

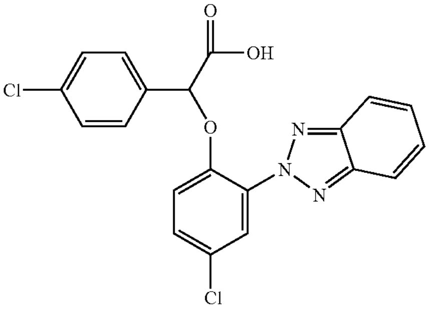

200 (XI-23)

In the same manner as that described in Example 28 compound 200 was prepared from 200-S1 and 200-S2. $^1$H NMR (400 MHz, DMSO-$d_6$): δ 8.05–7.28 (m, 16H), 6.09 (s, 1H).

The two enantiomers were separated by HPLC. Column: PIRKLE COVALENT, (R,R) Whelk-O 2 10/100, 25 cm×21.1 mm. Flow: 30 ml/min, 15% iPrOH/Hexanes-0.1% TFA.

Example 201

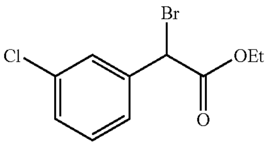

201-S1

+

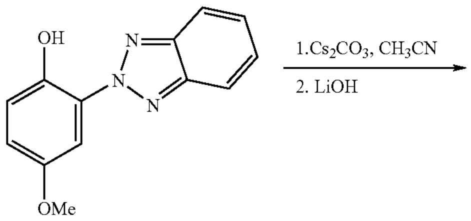

201-S2

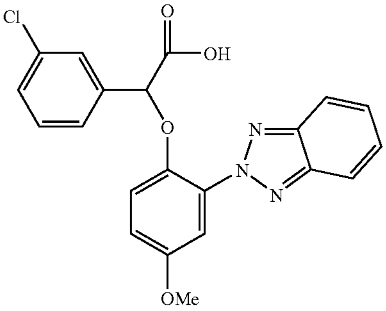

201

In the same manner as that described in Example 28 compound 201 was prepared from 201-S1 and 201-S2. $^1$H NMR (400 MHz, DMSO-$d_6$): δ 8.03–7.16 (m, 11H), 5.94 (s, 1H), 3.78 (s, 3H).

The two enantiomers were separated by HPLC. Column: PIKLE COVALENT, (R,R) Whelk-O 2 10/100, 25 cm×21.1 mm. Flow: 30 ml/min, 15% iPrOH/Hexanes-0.1% TFA.

Example 202

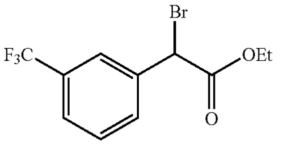

202-S1

+

-continued

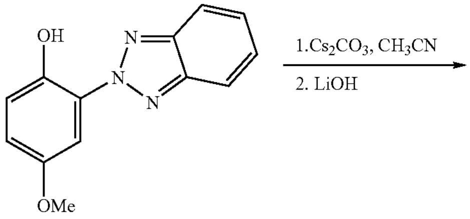

202-S2

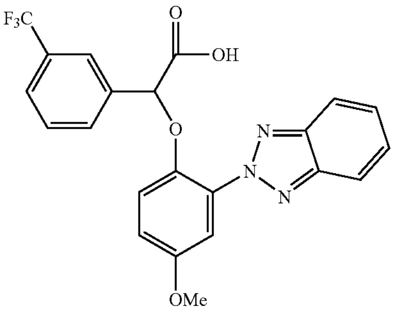

202

In the same manner as that described in Example 28 compound 202 was prepared from 202-S1 and 202-S2. $^1$H NMR (400 MHz, DMSO-$d_6$): δ 7.99–7.16 (m, 11H), 6.08 (s, 1H), 3.78 (s, 3H).

The two enantiomers were separated by chiral HPLC. Column: PIRKLE COVALENT, (R,R) Whelk-O 2 10/100, 25 cm×21.1 mm. Flow: 30 ml/min, 8% iPrOH/Hexanes-0.1% TFA.

Example 203

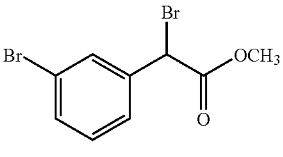

203-S1

+

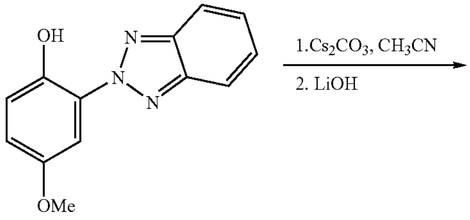

203-S2

-continued

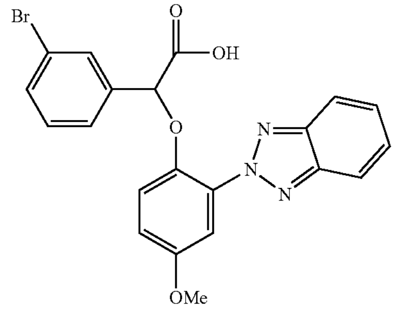

203

In the same manner as that described in Example 28 compound 203 was prepared from 203-S1 and 203-S2. $^1$H NMR (400 MHz, DMSO-$d_6$): δ 8.04–7.16 (m, 11H), 5.94 (s, 1H), 3.78 (s, 3H).

The two enantiomers were separated by chiral HPLC. Column: PIRKLE COVALENT, (R,R) Whelk-O 2 10/100, 25 cm×21.1 mm. Flow: 30 ml/min, 15% iPrOH/Hexanes-0.1% TFA.

Example 204

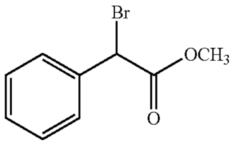

204-S1

+

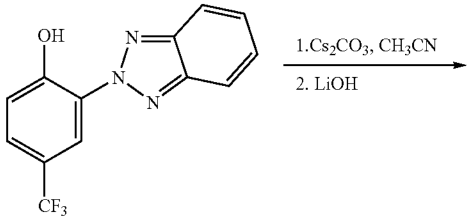

204-S2

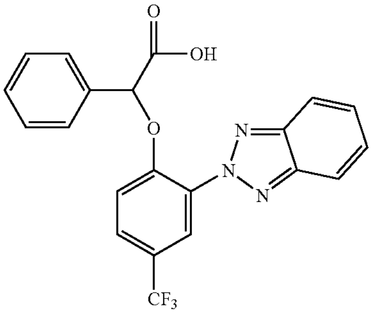

204 (XI-53)

In the same manner as that described in Example 28 compound 204 was prepared from 204-S1 and 204-S2. $^1$H NMR (400 MHz, DMSO-$d_6$): δ 8.17–7.29 (m, 12H), 6.20 (s, 1H).

The two enantiomers were separated by chiral HPLC. Column: PIRKLE COVALENT, (R,R) Whelk-O 2 10/100, 25 cm×21.1 mm. Flow: 30 ml/min, 10% iPrOH/Hexanes-0.1% TFA.

Example 205

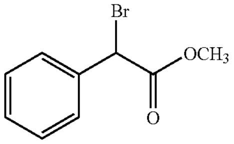

205-S1

+

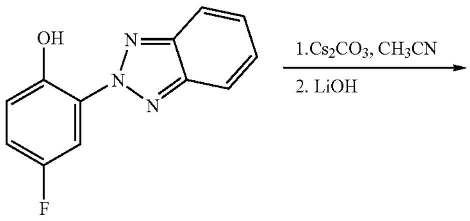

205-S2

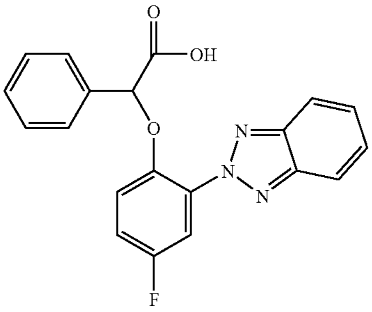

205

In the same manner as that described in Example 28 compound 205 was prepared from 205-S1 and 205-S2. $^1$H NMR (400 MHz, DMSO-$d_6$): δ 8.04–7.27 (m, 12H), 5.96 (s, 1H).

The two enantiomers were separated by chiral HPLC. Column: PIRKLE COVALENT, (R,R) Whelk-O 2 10/100, 25 cm×21.1 mm. Flow: 30 ml/min, 15% iPrOH/Hexanes-0.1% TFA.

Example 206

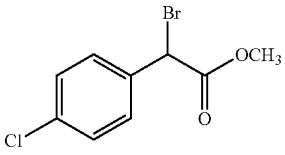

206-S1

+

-continued

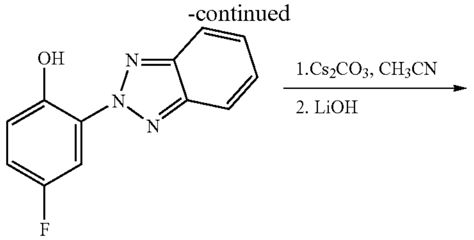

206-S2

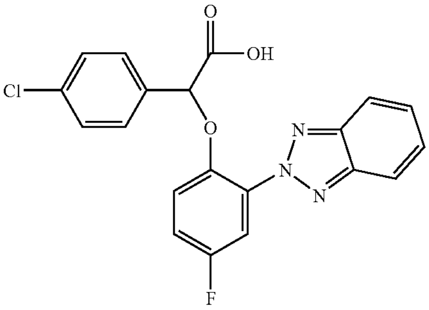

206

In the same manner as that described in Example 28 compound 206 was prepared from 206-S1 and 206-S2. $^{1}$H NMR (400 MHz, DMSO-$d_6$): δ 8.03–7.29 (m, 11H), 6.01(s, 1H).

Example 206A

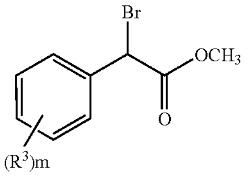

+

206A-S1

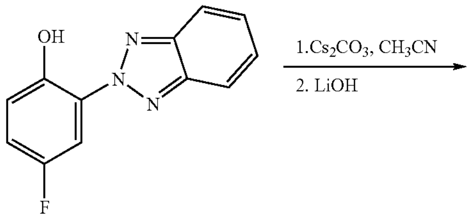

206A-S2

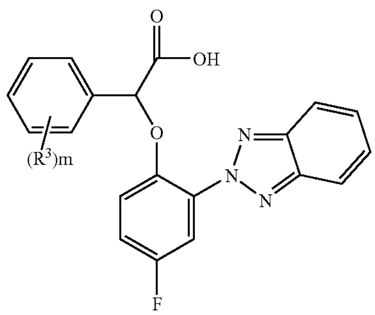

206A

In the same manner as that described in Example 28 compound 206A was prepared from 20A6-S1 and 206A-S2.

Example 207

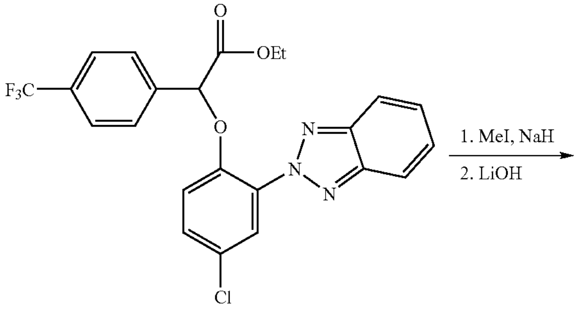

207-S1

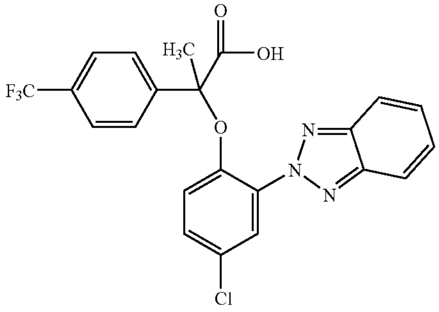

207 (XIa-24)

In the same manner as that described in Example 42 compound 207 was prepared from 207-S1. $^{1}$H NMR (400 MHz, DMSO-$d_6$): δ 8.05–7.08 (m, 11H), 1.76 (s, 3H).

The two enantiomers of 207 were separated by HPLC. Column: PIRKLE COVALENT, (R,R) Whelk-O 2 10/100, 25 cm×21.1 mm. Flow: 8 ml/min, 15% iPrOH/Hexanes-0.1% TFA.

Example 208

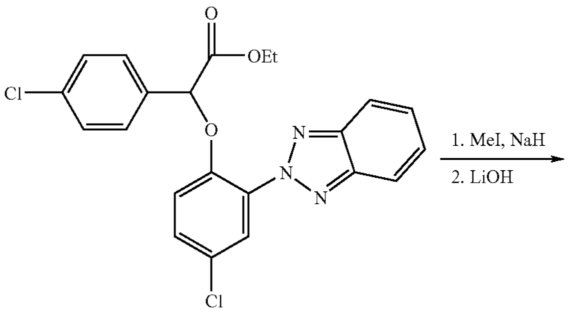

208-S1

-continued

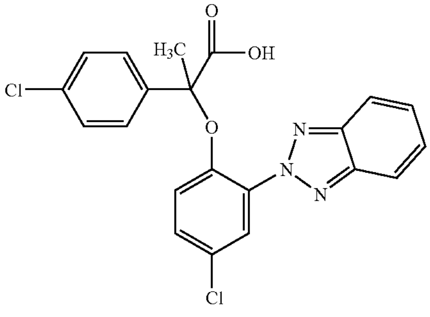

208 (XIa-23)

In the same manner as that described in Example 42 compound 208 was prepared from 208-S1. $^{1}$H NMR (400 MHz, DMSO-$d_6$): δ 8.06–7.03 (m, 16H), 1.72 (s, 3H).

The two enantiomers were separated by HPLC. Column: PIRKLE COVALENT, (R,R) Whelk-O 2 10/100, 25 cm×21.1 mm. Flow: 30 ml/min, 8% iPrOH/Hexanes-0.1% TFA.

Example 209

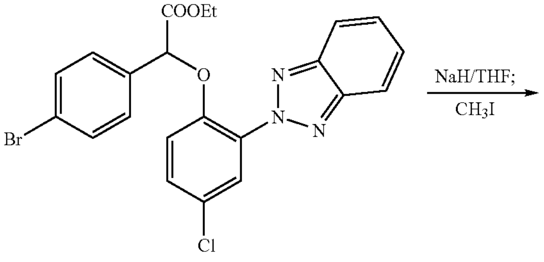

209-S1

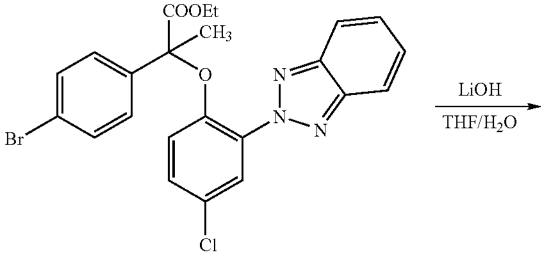

209-S2

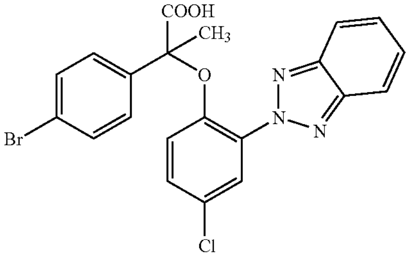

209 (XIa-25)

In the same manner as that described in Example 42 compound 209 was prepared from 209-S1. $^{1}$H NMR (400 MHz, DMSO-$d_6$): δ 13.7 (1H, br, COOH), 8.05 (2H, q, J=2.8 Hz), 7.94 (1H, d, J=2.4 Hz), 7.63 (1H, dd, J=8.8, 2.8 Hz), 7.52–7.55 (2H, m), 7.40–7.42 (2H, m), 7.32–7.35 (2H, m), 7.04 (1H, d, J=8.8 Hz), 1.72 (3H, s) ppm.

Example 210

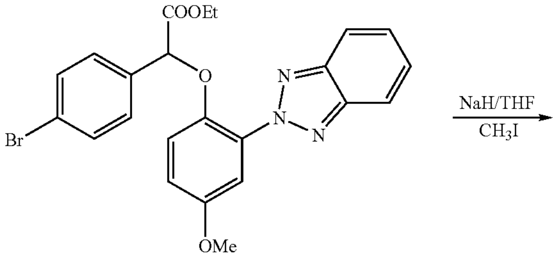

210-S1

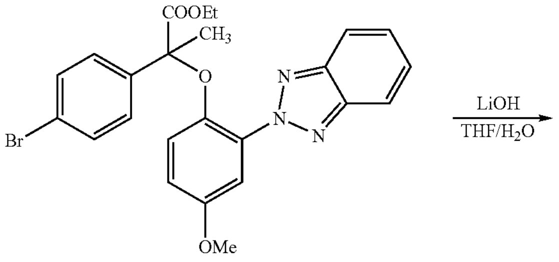

210-S2

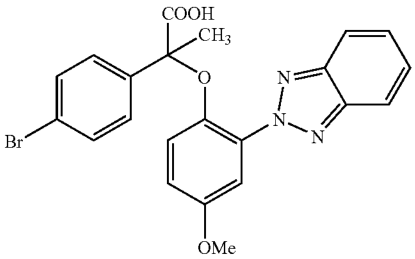

210

In the same manner as that described in Example 42 compound 210 was prepared from 210-S1. $^{1}$H NMR (400 MHz, DMSO-$d_6$): δ 13.4 (1H, br, COOH), 8.01 (2H, q, J=2.8 Hz), 7.49–7.52 (2H, m), 7.35–7.37 (3H, m), 7.26–7.28 (2H, m), 7.15 (1H, dd, J=8.8, 3.0 Hz), 7.04 (1H, d, J=8.8 Hz), 3.79 (3H, s), 1.56 (3H, s) ppm.

Example 211

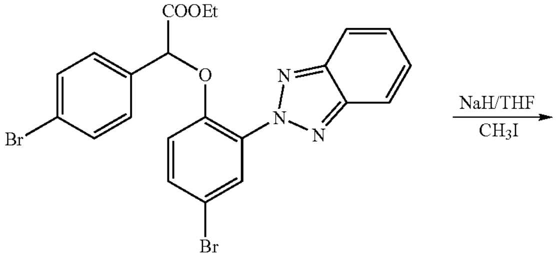

211-S1

-continued

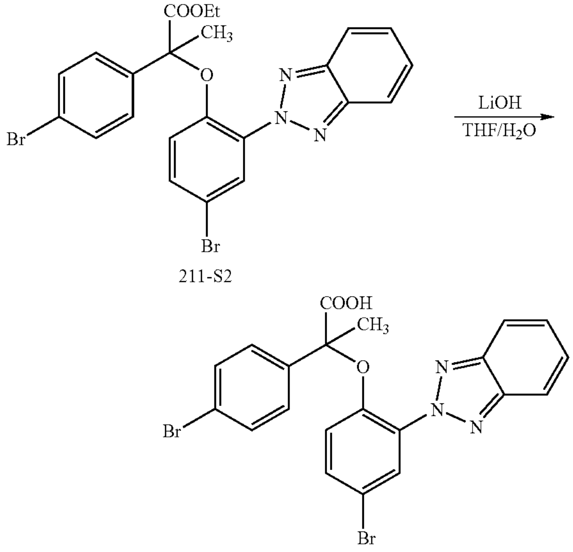

211-S2

211 (XIa-34)

In the same manner as that described in Example 42 compound 211 was prepared from 211-S1. $^{1}H$ NMR (400 MHz, DMSO-$d_6$): δ 13.7 (1H, br, COOH), 8.03–8.06 (3H, m), 7.75 (1H, dd, J=9.2, 2.8 Hz), 7.52–7.55 (2H, m), 7.40–7.42 (2H, m), 7.32–7.35 (2H, m), 6.98 (1H, d, J=9.2 Hz), 1.72 (3H, s) ppm.

Example 212

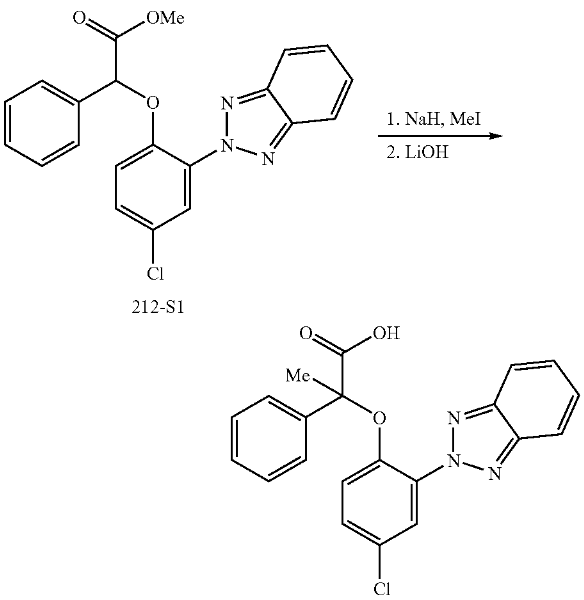

212-S1

212 (XIa-26)

In the same manner as that described in Example 42 compound 212 was prepared from 212-S1. $^{1}H$ NMR (400 MHz, DMSO-$d_6$): δ 8.0 (m, 2H), 7.81 (m, 1H), 7.54 (m, 3H), 7.34 (m, 2H), 7.15 (d, J=9.2 Hz, 1H), 7.08 (m, 3H), 1.62 (s, 3H).

Example 213

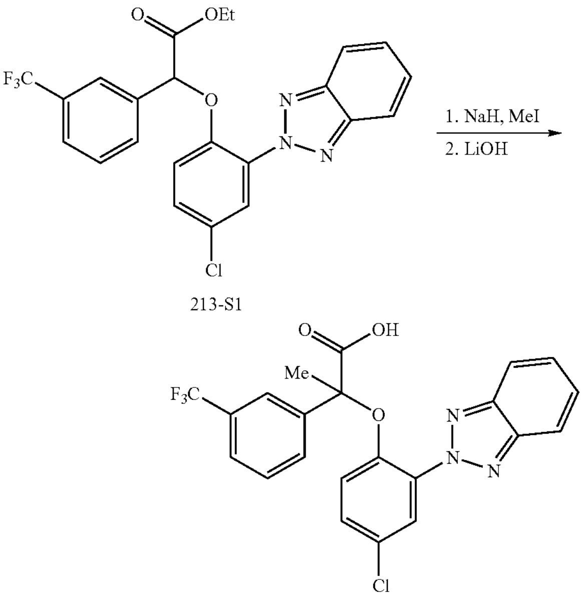

213-S1

213 (XIa-20)

In the same manner as that described in Example 42 compound 213 was prepared from 213-S1. $^{1}H$ NMR (400 MHz, DMSO-$d_6$): δ 8.0 (m, 2H), 7.95 (m, 1H), 7.69–7.61 (m, 5H), 7.53 (m, 3H), 1.82 (s, 3H).

Example 214

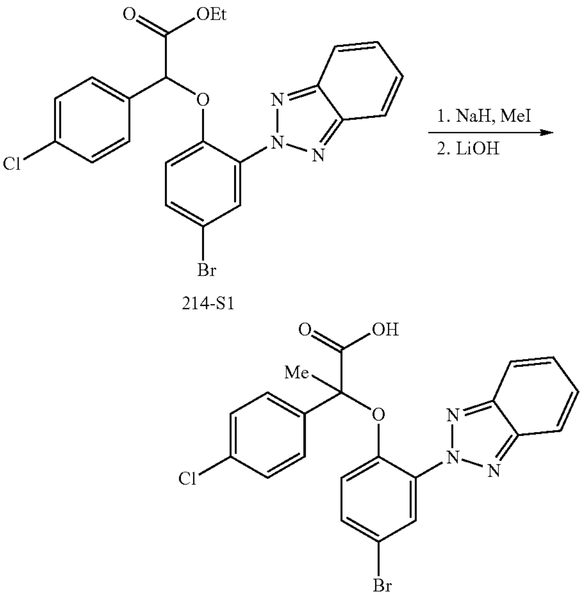

214-S1

214 (XIa-32)

In the same manner as that described in Example 42 compound 214 was prepared from 214-S1. $^{1}H$ NMR (400 MHz, DMSO-$d_6$): δ 8.06 (m, 2H), 7.76 (dd, J=2.8 and 9.2 Hz, 1H), 7.54 (m, 2H), 7.41 (m, 2H), 7.26 (m, 2H), 6.99 (d, J=9.2 Hz, 1H), 1.72 (s, 3H).

Example 215

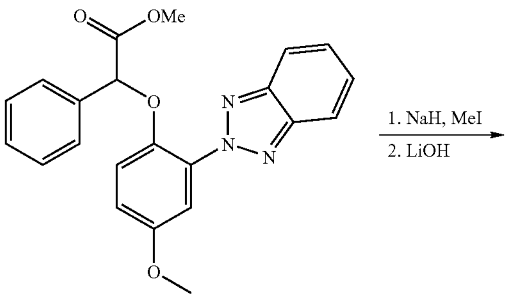

215-S1

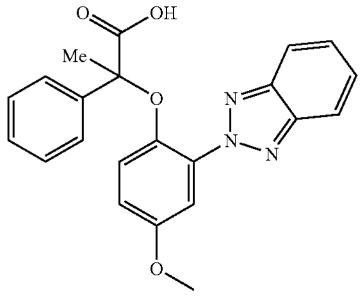

215

In the same manner as that described in Example 42 compound 215 was prepared from 215-S1. $^1$H NMR (400 MHz, DMSO-$d_6$): δ 8.02 (m, 2H), 7.51 (m, 1H), 7.32 (d, J=2.8 Hz, 1H), 7.28 (m, 2H), 7.14 (m, 4H), 7.04 (d, J=8.8 Hz, 1H), 7.38 (s, 3H), 1.57 (s, 3H).

Example 216

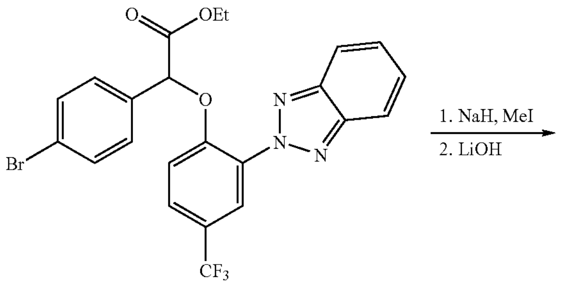

216-S1

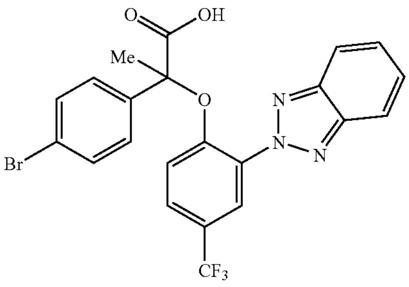

216 (XIa-52)

In the same manner as that described in Example 42 compound 216 was prepared from 216-S1. $^1$H NMR (400 MHz, DMSO-$d_6$): δ 8.21 (m, 1H), 8.09 (m, 2H), 7.95 (m, 1H), 7.56 (m, 2H), 7.45(m, 4H), 7.19 (d, J=9.2 Hz, 1H), 1.82 (s, 3H).

Example 217

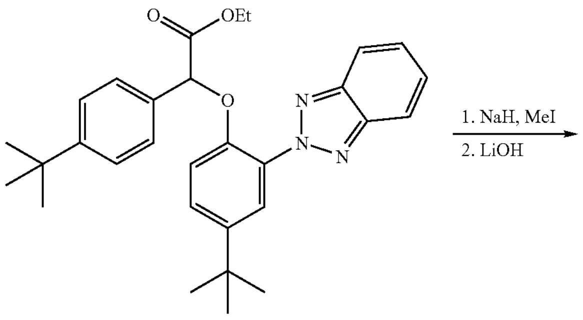

217-S1

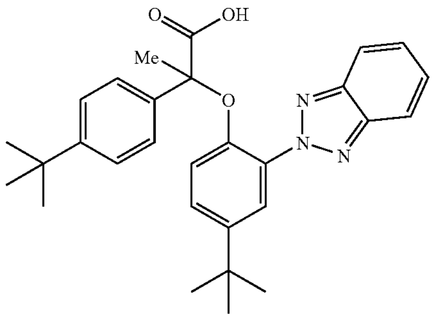

217

In the same manner as that described in Example 42 compound 217 was prepared from 217-S1. $^1$H NMR (400 MHz, DMSO-$d_6$): δ 8.05 (m, 2H), 7.68 (d, J=2.8 Hz, 1H), 7.15 (dd, J=2.8 and 8.8 Hz, 1H), 7.52 (m, 2H), 7.22 (m, 2H), 7.17 (m, 2H), 6.97 (d, J=8.8 Hz, 1H), 1.68 (s, 3H), 1.30 (s, 9H), 1.19 (s, 9H).

Example 218

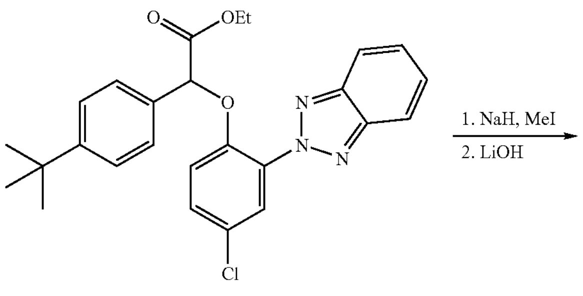

218-S1

-continued

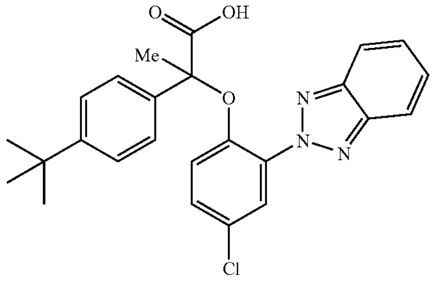

218

In the same manner as that described in Example 42 compound 218 was prepared from 218-S1. $^{1}H$ NMR (400 MHz, DMSO-$d_6$): δ 8.05 (m, 2H), 7.72 (d, J=2.4 Hz, 1H), 7.54 (m, 2H), 7.48 (dd, J=2.4 and 8.8 Hz, 1H), 7.28 (m, 2H), 7.21 (d, J=8.8 Hz, 1H), 7.03 (m, 2H), 1.60 (s, 3H), 1.21 (s, 9H).

Example 219

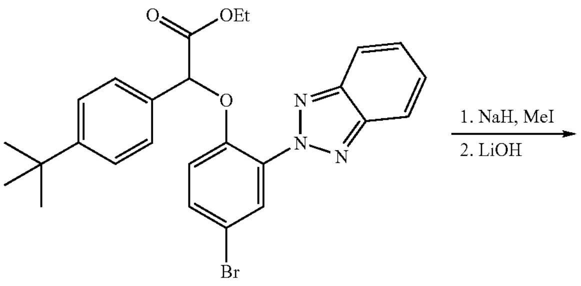

219-S1

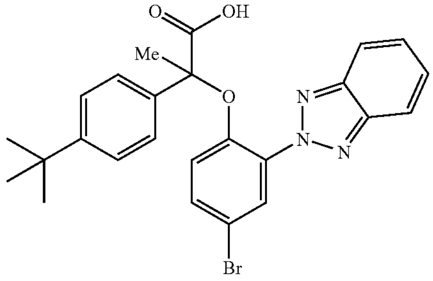

219

In the same manner as that described in Example 42 compound 219 was prepared from 219-S1. $^{1}H$ NMR (400 MHz, DMSO-$d_6$): δ 8.02 (m, 2H), 7.83 (d, J=2.8 Hz, 1H), 7.67 (dd, J=2.4 and 9.2 Hz, 1H), 7.53 (m, 2H), 7.18 (m, 2H), 7.04 (m, 3H), 1.58 (s, 3H), 1.12 (s, 9H).

Example 220

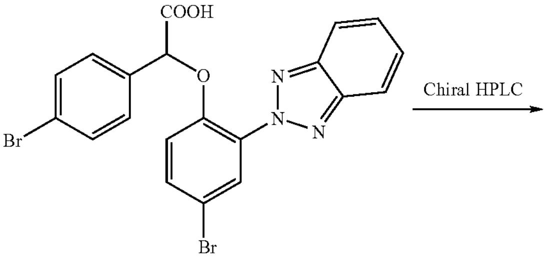

220

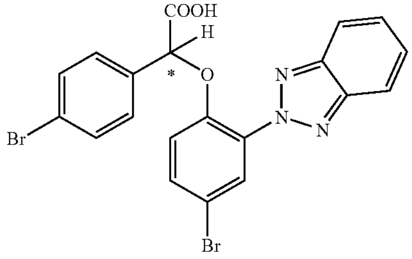

+

(+)-220 [(+)-XI-34]

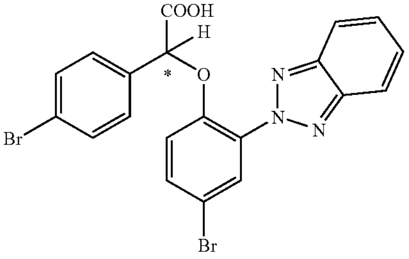

(-)-220 [(-)-XI-34]

The two enantiomers of 220 were isolated by chiral HPLC using a 25 cm×21.1 mm Regis Technologies (R,R) WHELK-O 2 10/100 column at ambient temperature. The column was eluted with (15/85/0.1) iPrOH/hexanes/TFA at a flow of 30 mL/min. Detection was at 220 nm. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (15/85/0.1) iPrOH/hexanes/TFA.

Example 221

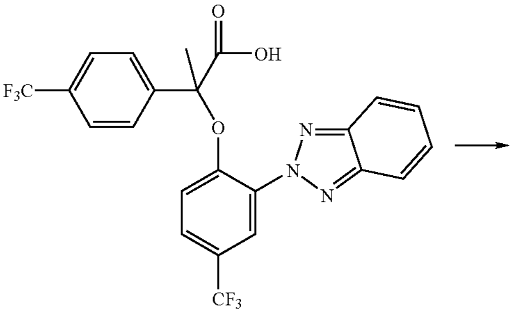

221

-continued

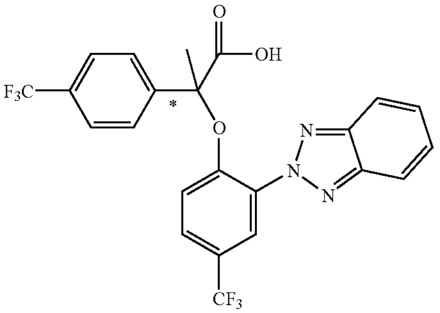

(+)-221[(+)-XIa-51]

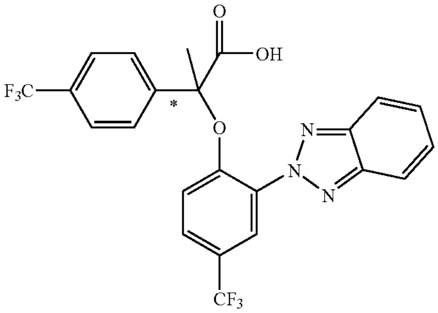

(-)-221[(-)-XIa-51]

In the same manner as that described in Example 220 compounds (+)-221 and (−)-221 were prepared from 221. $^1$H NMR (400 MHz, DMSO-$d_6$): δ 8.18–7.25 (m, 11H), 1.72 (s, 3H).

Example 222

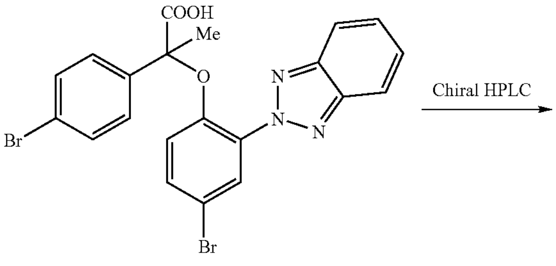

222

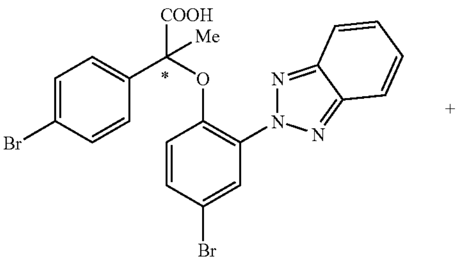

(+)-222 [(+)-XIa-34]

-continued

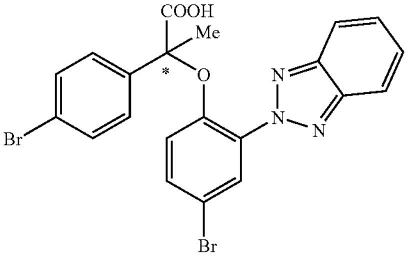

(-)-222 [(-)-XIa-34]

The two enantiomers were isolated by chiral HPLC using a 25 cm×21.1 mm Regis Technologies (R,R) WHELK-O 2 10/100 column at ambient temperature. The column was eluted with (15/85/0.1) iPrOH/hexanes/TFA at a flow of 30 mL/min. Detection was at 220 nm. One enantiomer eluted at 3.8 to 4.7 min, and the other enantiomer at 5.1 to 6.1 min. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (15/85/0.1) iPrOH/hexanes/TFA. Under these conditions, one enantiomer eluted at 4.7 min, the other enantiomer at 6.6 min.

Example 223

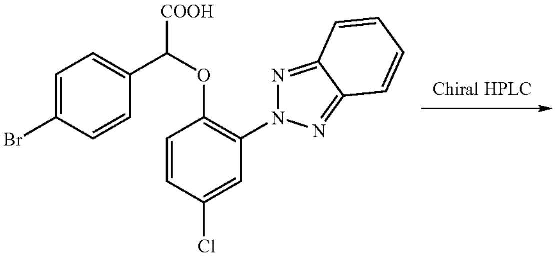

223

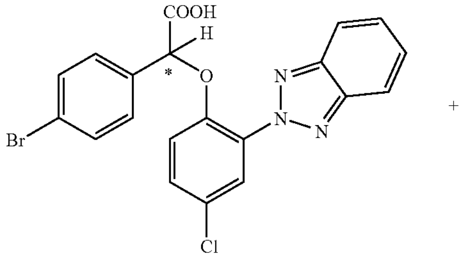

(+)-223 [(+)-XI-25]

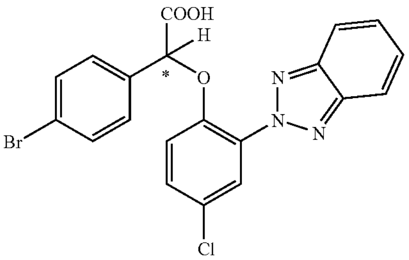

(-)-223 [(-)-XI-25]

The two enantiomers were isolated by chiral HPLC using a 25 cm×21.1 mm Regis Technologies (R,R) WHELK-O 2 10/100 column at ambient temperature. The column was eluted with (15/85/0.1) iPrOH/hexanes/TFA at a flow of 30 mL/min. Detection was at 220 nm. One enantiomer eluted at 3.6 to 4.8 min, and the other enantiomer at 5.5 to 6.9 min. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (15/85/0.1) iPrOH/hexanes/TFA. Under these conditions, one enantiomer eluted at 5.0 min, and the other enantiomer at 7.1 min.

Example 224

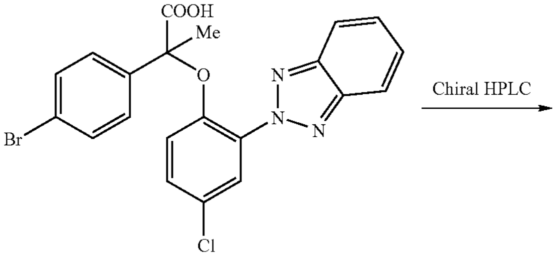

224

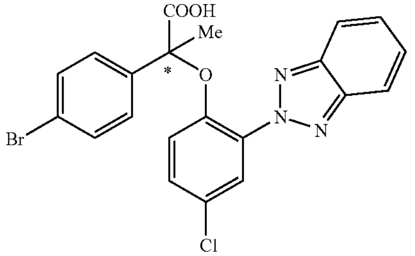

+

(+)-224 [(+)-XIa-25]

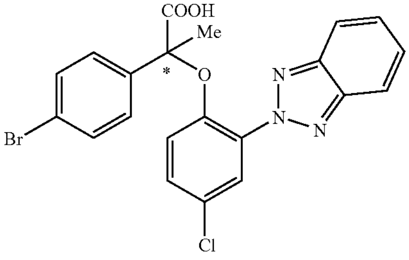

(-)-224 [(-)-XIa-25]

The two enantiomers were isolated by chiral HPLC using a 25 cm×21.1 mm Regis Technologies (R,R) WHELK-O 2 10/100 column at ambient temperature. The column was eluted with (15/85/0.1) iPrOH/hexanes/TFA at a flow of 30 mL/min. Detection was at 220 nm. One enantiomer eluted at 3.6 to 4.6 min, and the other enantiomer at 5.1 to 6.0 min. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (15/85/0.1) iPrOH/hexanes/TFA. Under these conditions, one enantiomer eluted at 4.6 min, and the other enantiomer at 6.4 min.

Example 225

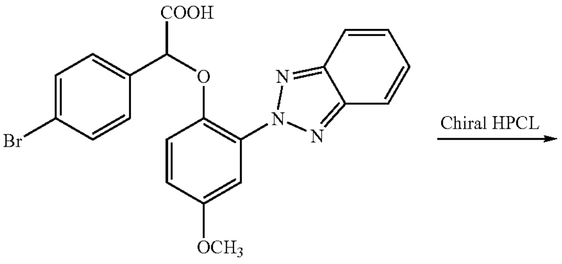

225

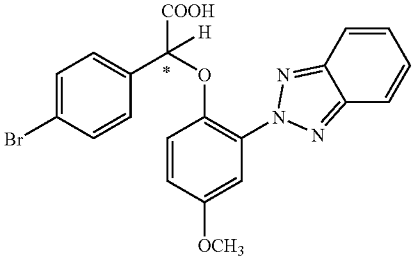

+

(+)-225

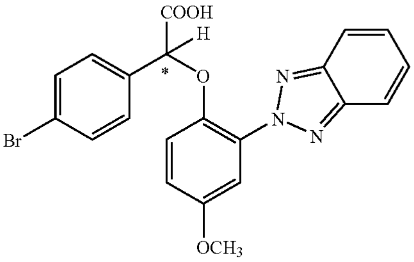

(-)-225

The two enantiomers were isolated by chiral HPLC using a 25 cm×21.1 mm Regis Technologies (R,R) WHELK-O 2 10/100 column at ambient temperature. The column was eluted with (25/75/0.1) iPrOH/hexanes/TFA at a flow of 30 mL/min. Detection was at 220 nm. One enantiomer eluted at 4.8 to 6.2 min, and the other enantiomer at 7.3 to 9.2 min. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (25/75/0.1) iPrOH/hexanes/TFA. Under these conditions, one enantiomer eluted at 6.0 min, and the other enantiomer at 9.5 min.

Example 226

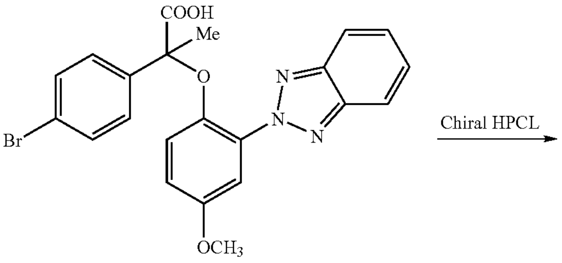

226

-continued

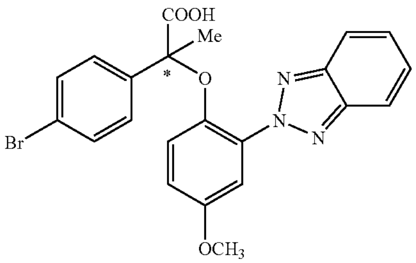

(+)-226

+

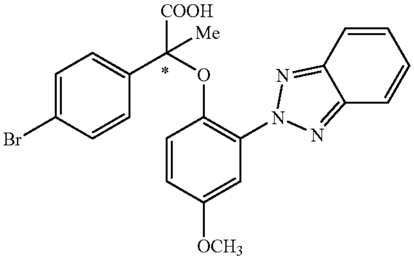

(-)-226

The two enantiomers were isolated by chiral HPLC using a 25 cm×21.1 mm Regis Technologies (R,R) WHELK-O 2 10/100 column at ambient temperature. The column was eluted with (25/75/0.1) iPrOH/hexanes/TFA at a flow of 30 mL/min. Detection was at 220 nm. One enantiomer eluted at 4.5 to 5.5 min, and the other enantiomer at 6.6 to 7.3 min. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (25/75/0.1) iPrOH/hexanes/TFA. Under these conditions, one enantiomer eluted at 5.7 min, and the other enantiomer at 8.6 min.

Example 227

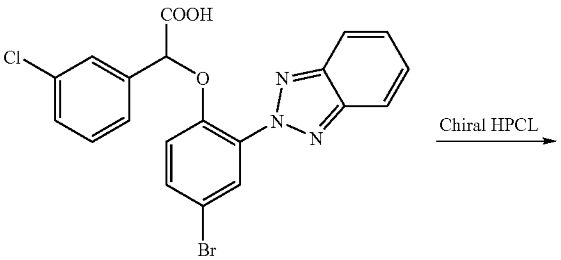

227

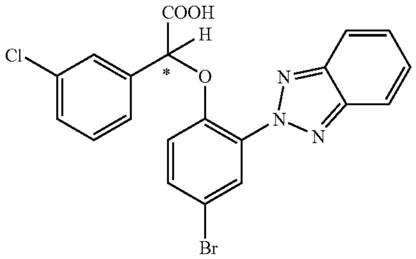

(+)-227 [(+)-XI-28]

+

-continued

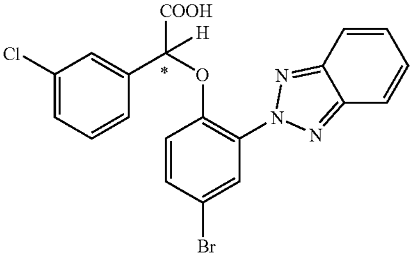

(+)-227 [(-)-XI-28]

The two enantiomers were isolated by chiral HPLC using a 25 cm×21.1 mm Regis Technologies (R,R) WHELK-O 2 10/100 column at ambient temperature. The column was eluted with (10/90/0.1) iPrOH/hexanes/TFA at a flow of 30 mL/min. Detection was at 220 nm. One enantiomer eluted at 4.8 to 5.5 min, and the other enantiomer at 6.1 to 6.9 min. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (15/85/0.1) iPrOH/hexanes/TFA. Under these conditions, one enantiomer eluted at 4.9 min, and the other enantiomer at 6.5 min.

Example 228

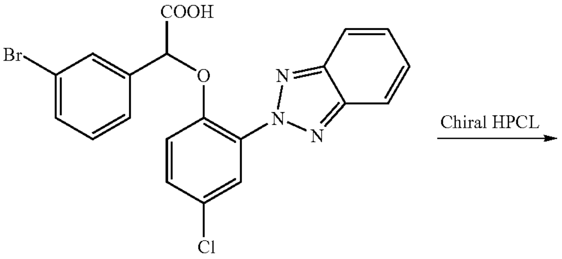

228

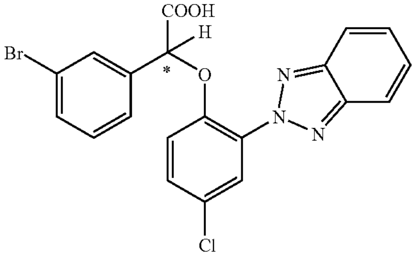

(+)-228

+

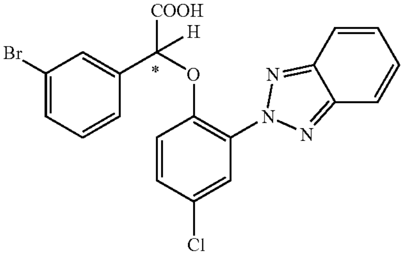

(-)-228

The two enantiomers were isolated by chiral HPLC using a 25 cm×21.1 mm Regis Technologies (R,R) WHELK-O 2

10/100 column at ambient temperature. The column was eluted with (10/90/0.1) iPrOH/hexanes/TFA at a flow of 30 mL/min. Detection was at 220 nm. One enantiomer eluted at 4.7 to 5.3 min, and the other enantiomer at 6.2 to 6.9 min. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (15/85/0.1) iPrOH/hexanes/TFA. Under these conditions, one enantiomer eluted at 4.9 min, and the other enantiomer at 6.8 min.

Example 229

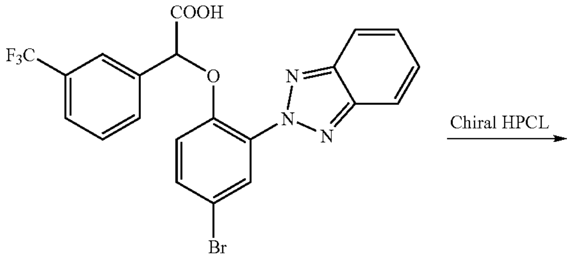

229

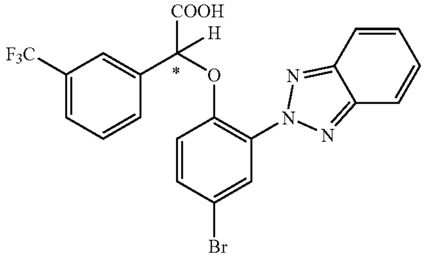

(+)-229[(+)-XI-33]

+

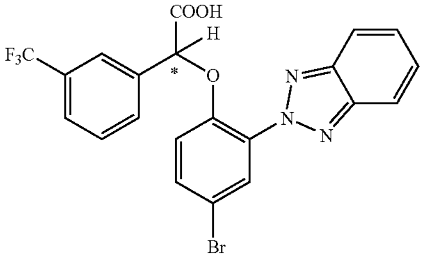

(-)-229[(-)-XI-33]

The two enantiomers were isolated by chiral HPLC using a 25 cm×21.1 mm Regis Technologies (R,R) WHELK-O 2 10/100 column at ambient temperature. The column was eluted with (5/95/0.1) iPrOH/hexanes/TFA at a flow of 30 mL/min. Detection was at 220 nm. One enantiomer eluted at 6.2 to 7.2 min, and the other enantiomer at 7.6 to 8.6 min. Chiral HPLC analysis of enantiomer was carried out at λ=220 nm by injecting 10 μL of an approximately a 0.5 mg/mL solution of the sample dissolved in mobile phase onto a 25 cm×4.6 mm Regis Technologies (R,R) Whelk-O 1 5 μm column with a 1.5 mL/min flow of (15/85/0.1) iPrOH/hexanes/TFA. Under these conditions, one enantiomer eluted at 4.1 min, and the other enantiomer at 5.0 min.

Example 230

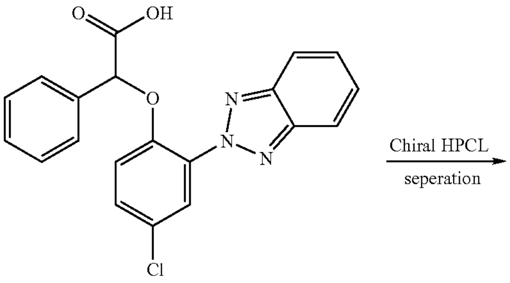

230

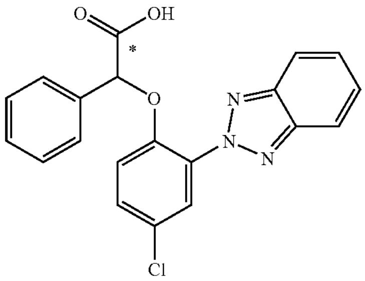

(+)-230[(+)-XI-26]

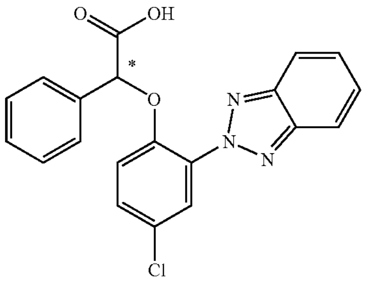

(-)-230[(-)-XI-26]

The two enantiomers were separated by chiral HPLC using a 25 cm×21.1 mm Regis Technologies (R,R) WHELK-O 2 10/100 column at ambient temperature. HPLC methods and conditions: 20% iPrOH-80% Hexanes-0.1% TFA, 30 mL/min., λ=220 nm. For (+)-enantiomer: RT 3.92 min. $[\alpha]_d$=+7.9 in acetone. For (−)-enantiomer: RT 5.0 min.

Example 231

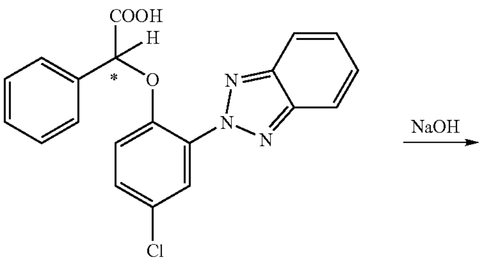

231

-continued

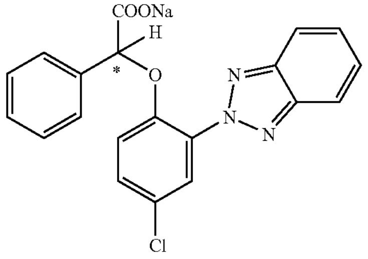

231 Na salt

To a solution of 231 (1.05 g, 2.77 mol, 98% ee) in ca. 10 mL of THF was added 2N aq. NaOH (1.384 mL, 2.77 mmol) with stirring, and then diluted with heptane (50 mL), After removal of solvents in vacuo, the residue was dissolved in 5 mL of THF and then diluted with 30 mL of heptanes. After stripping off THF and most of heptanes in vacuo, the resulting white precipitate was filtered and rinsed with heptane twice to afford desired sodium salt (1.06 g, 96%, 98+% ee) as a white solid. $^1H$ NMR (400 MHz, DMSO-$d_6$): δ 8.02 (2H, dd, J=6.8, 3.2 Hz), 7.79 (1H, d, J=2.8 Hz), 7.58 (1H, dd, J=9.2, 2.8 Hz), 7.51 (2H, dd, J=6.8, 3.2 Hz), 7.34–7.37 (2H, m), 7.17 (1H, d, J=9.2 Hz), 7.11 (3H, m), 5.26 (1H, s) ppm.

Example 232

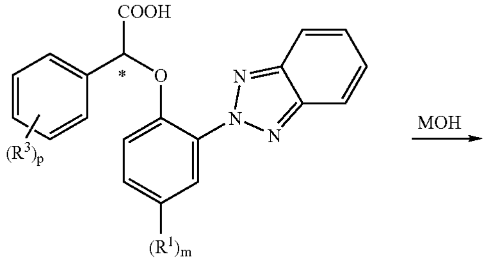

232

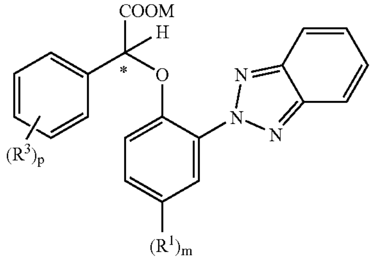

232 M salt

In the same manner as that described in Example 231 different salts of compound 232 M salts were prepared.

Example 233

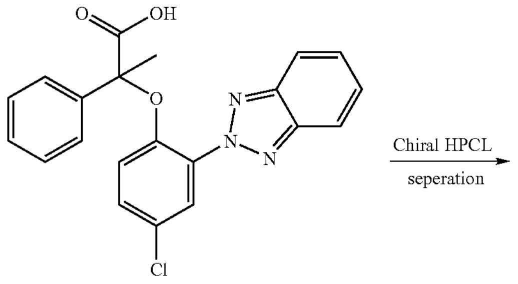

233

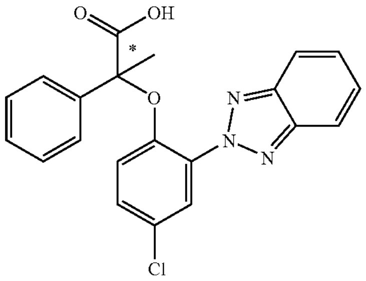

(+)-233 [(+)-XIa-26]

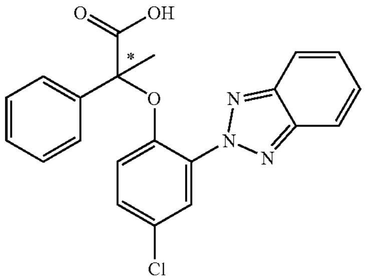

(-)-233 [(-)-XIa-26]

The two enantiomers were separated by chiral HPLC using a 25 cm×21.1 mm Regis Technologies (R,R) WHELK-O 2 10/100 column at ambient temperature. HPLC methods and conditions: 15% iPrOH-85% Hexanes-0.1% TFA, 30 mL/min., λ=220 nm. One enantiomer: RT 4.0 min. The other enantiomer: RT 4.8 min.

Example 234

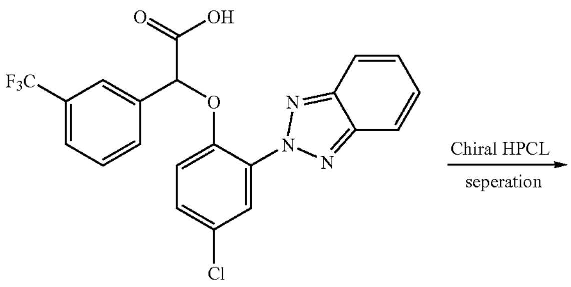

234

-continued

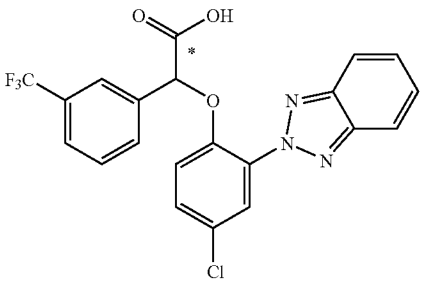

(+)-234 [(+)-XI-20]

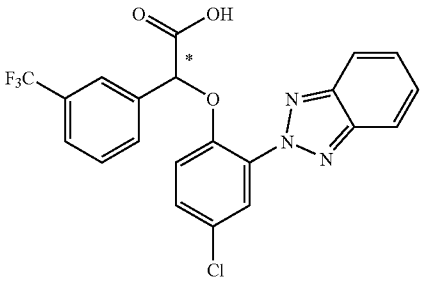

(-)-234 [(-)-XIa-20]

The two enantiomers were separated by chiral HPLC using a 25 cm×21.1 mm Regis Technologies (R,R) WHELK-O 2 10/100 column at ambient temperature. HPLC methods and conditions: 8% iPrOH-92% Hexanes-0.1% TFA, 30 mL/min., λ=220 nm. One enantiomer: RT 5.8 min. The other enantiomer: RT 6.4 min.

Example 235

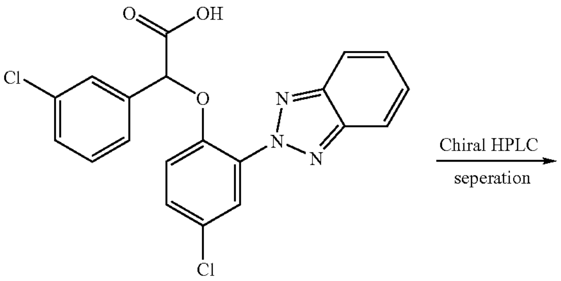

235

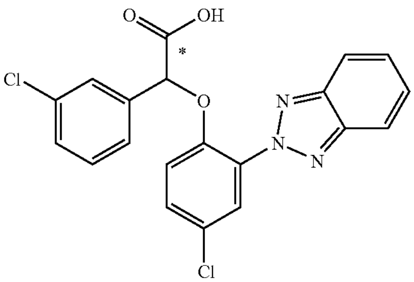

(+)-235 [(+)-XI-19]

-continued

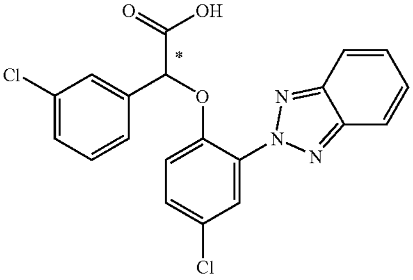

(-)-235 [(-)-XI-19]

The two enantiomers were separated by chiral HPLC using a 25 cm×21.1 mm Regis Technologies (R,R) WHELK-O 2 10/100 column at ambient temperature. HPLC methods and conditions: 15% iPrOH-85% Hexanes-0.1% TFA, 30 mL/min., λ=220 nm. One enantiomer: RT 4.5 min. The other enantiomer: RT 5.3 min.

Example 236

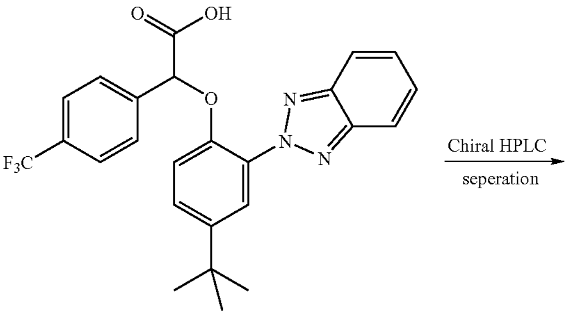

236

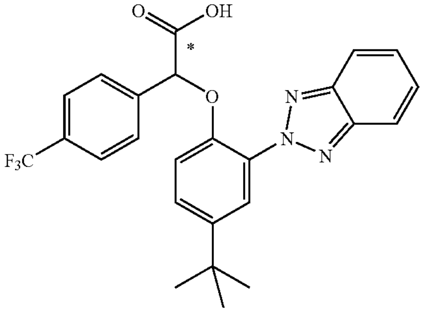

(+)-236 [(+)-XI-42]

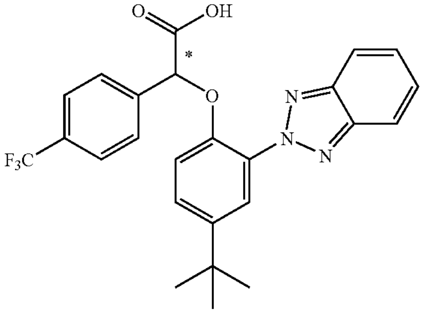

(-)-236 [(-)-XI-42]

The two enantiomers were separated by chiral HPLC using a 25 cm×21.1 mm Regis Technologies (R,R) WHELK-O 2 10/100 column at ambient temperature. HPLC methods and conditions: 15% iPrOH-85% Hexanes-0.1% TFA, 30 mL/min., λ=220 mn. One enantiomer: RT 4.0 min. The other enantiomer: RT 5.0 min.

Example 237

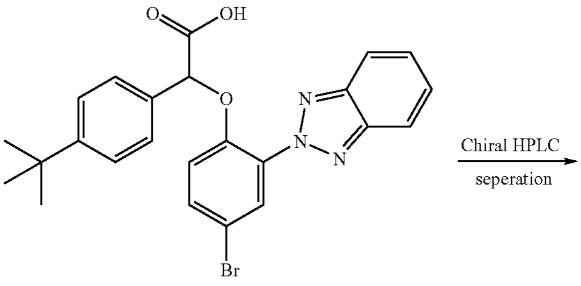

237

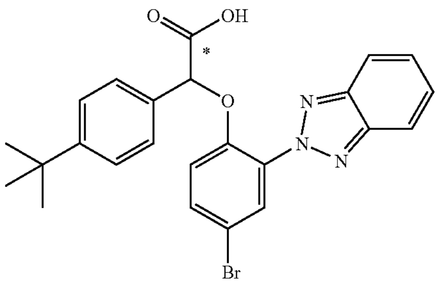

(+)-237

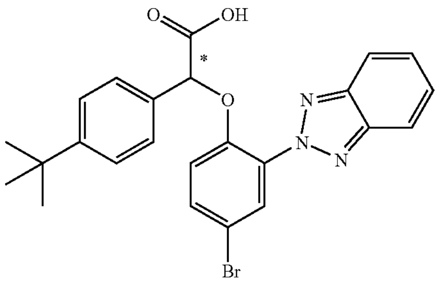

(-)-237

The two enantiomers were separated by chiral HPLC using a 25 cm×21.1 mm Regis Technologies (R,R) WHELK-O 2 10/100 column at ambient temperature. HPLC methods and conditions: 25% iPrOH-75% Hexanes-0.1% TFA, 30 mL/min., λ=220 nm. One enantiomer: RT 3.5 min. The other enantiomer: RT 4.2 min.

Example 238

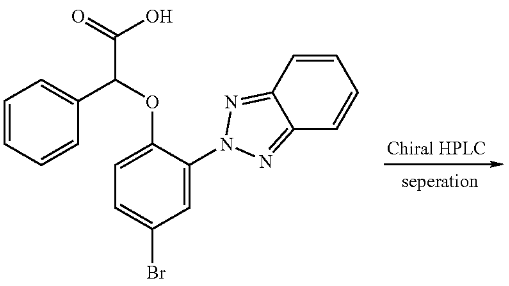

238

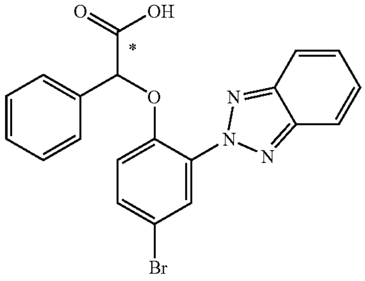

(+)-238 [(+)-XI-35]

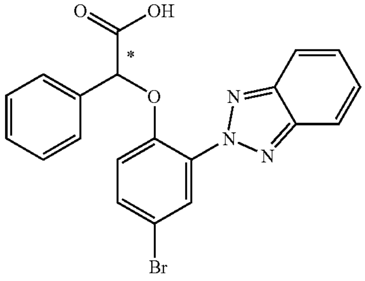

(-)-238 [(-)-XI-35]

The two enantiomers were separated by chiral HPLC using a 25 cm×21.1 mm Regis Technologies (R,R) WHELK-O 2 10/100 column at ambient temperature. HPLC methods and conditions: 20% iPrOH-80% Hexanes-0.1% TFA, 30 mL/min., λ=220 nm. One enantiomer: RT 4.2 min. The other enantiomer: RT 5.3 min.

Example 239

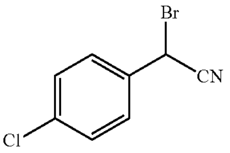

+

239-S1

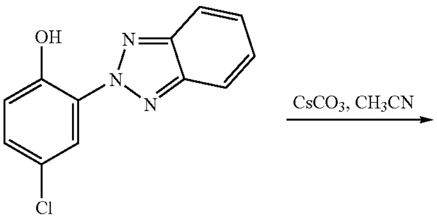

239-S2

-continued

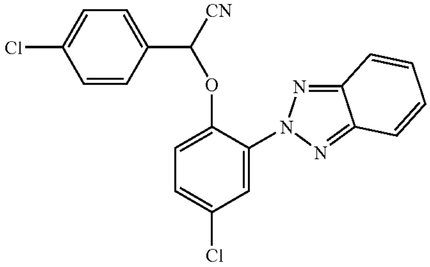

239-S3

A mixture of 239-S1 (6.6 g), 239-S2 (5.06 g) with $Cs_2CO_3$ (12 g) in $CH_3CN$ was stirred for 12 hours. The salt was filtered off. The filtrate was concentrated, and purified with chromatography (hexane/ethyl acetate 10:1) gave 239-S3 (3.2 g) as a colorless oil. $^1$H NMR (400 MHz, $CDCl_3$): δ 8.01–7.26 (m, 11H), 6.11(s, 1H), 3.49 (d, 2H).

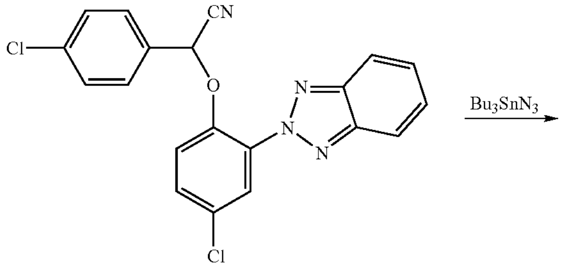

239-S3

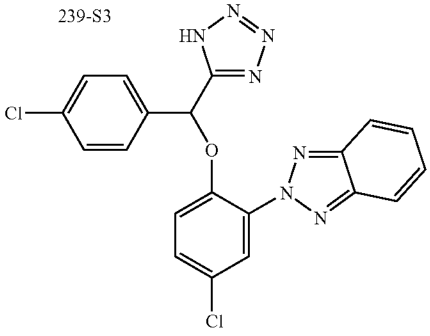

239

A solution of 239-S3 (2.0 g), $Bu_3SnN_3$ (1.7 mL) in THF was refluxed overnight, then concentrated, and treated with 1N HCl. The solution was extracted with ethyl acetate, dried and concentrated. Purification with chromatography (ethyl acetate) gave 239 (0.64 g) as a white solid. $^1$H NMR (400 MHz, $CDCl_3$): δ 8.08–7.15 (m, 11H), 6.86(s, 1H).

Example 240

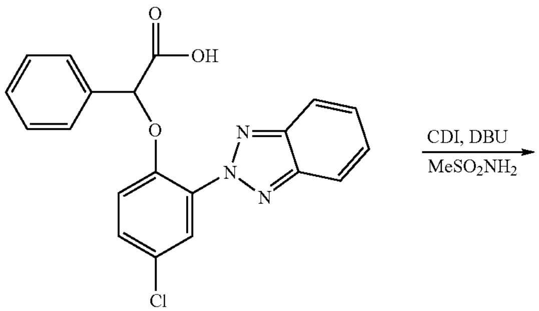

240-S1

-continued

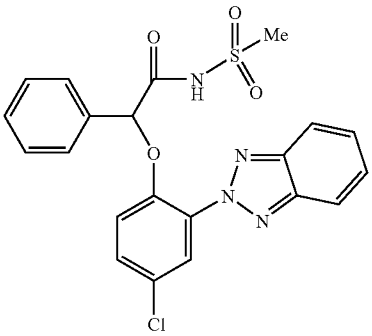

240

A solution of 240-S1 (1.1 g), CDI (0.56 g) in THF was stirred for half an hour at 60° C. After cooling down, sulfonyl amide (0.33 g) and DBU (0.65 mL) was added. The reaction mixture was stirred overnight, concentrated, diluted with ethyl acetate, washed with HCl (0.5 N), and dried. The solvent was removed, and the residue was purified by chromatography (ethyl acetate) to give 240 (1.16 g) as a white solid. $^1$H NMR (400 MHz, $CDCl_3$): δ 11.92 (s, 1H), 8.23–6.88 (m, 12H), 5.85 (s, 1H), 3.32 (s, 3H).

Example 241

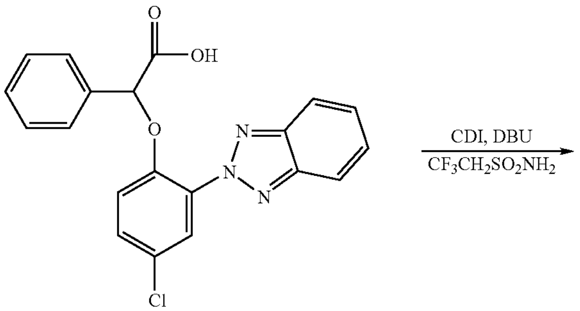

241-S1

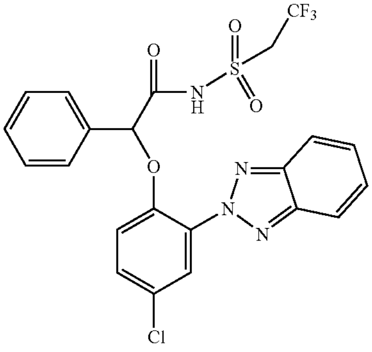

241

In the same manner as that described in Example 240 compound 241 was prepared from 241-S1. $^1$H NMR (400 MHz, $CDCl_3$): δ 12.57 (s, 1H), 8.24–6.93 (m, 12H), 5.89 (s, 1H), 4.22 (m, 2H).

Example 242

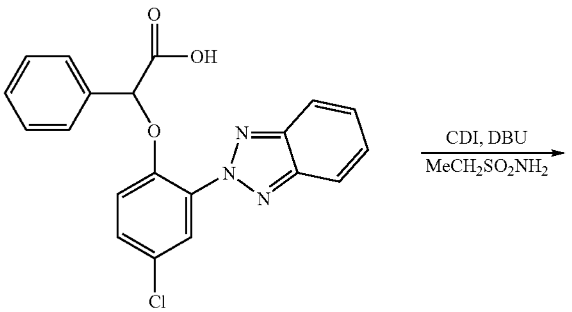

242-S1

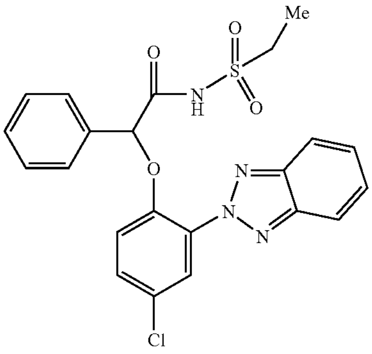

242

In the same manner as that described in Example 240 compound 242 was prepared from 242-S1. $^1H$ NMR (400 MHz, $CDCl_3$): δ 11.77 (s, 1H), 8.23–6.90 (m, 12H), 5.89 (s, 1H), 3.46 (m, 2H), 1.32 (t, 3H).

Example 243

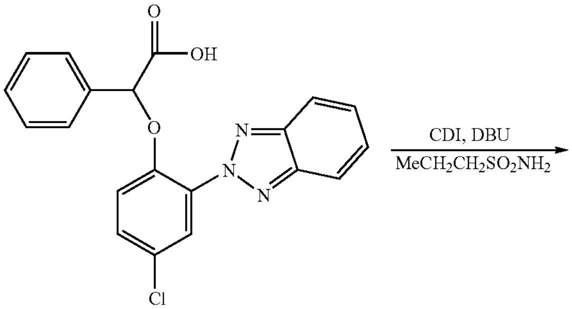

243-S1

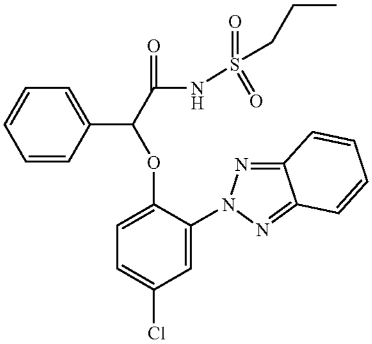

243

In the same manner as that described in Example 240 compound 243 was prepared from 243-S1. $^1H$ NMR (400 MHz, $CDCl_3$): δ 11.77 (s, 1H), 8.23–6.90 (m, 12H), 5.85 (s, 1H), 3.42 (m, 2H), 1.80 (m, 2H), 0.98 (t, 3H).

Example 244

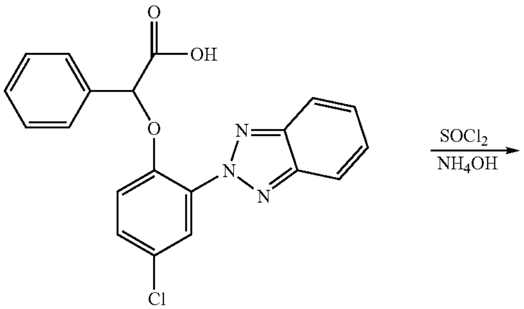

244-S1

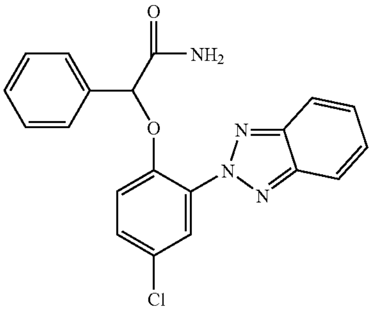

244

A mixture of acid 244-S1 (3.0 g), $SOCl_2$ in toluene was refluxed for two hours, and concentrated. The residue was diluted with THF, and the solution was drop to ammonium solution (28 N, 60 mL) at 0° C. The white precipitate was collected by filtration as the desired product. $^1H$ NMR (400 MHz, $CDCl_3$): δ 0.95 (br, 1H), 8.05–6.96 (m, 12H), 5.71 (s, 1H), 5.63 (br, 1H).

Example 245

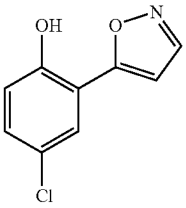

245-S1

+

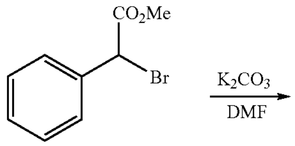

245-S2

-continued
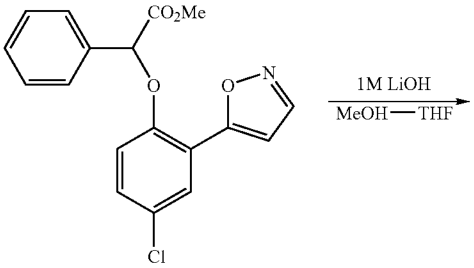
245-S3
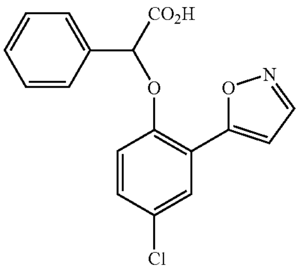
245 (IX-26)
In the same manner as that described in Example 28 compound 245 was prepared from 245-S1 and 245-S2. $^1$HNMR (400 MHz, DMSO-$d_6$) δ 8.74 (d, J=1.6 Hz, 1H), 7.86 (d, J=2.4 Hz, 1H), 7.52–7.35 (m, 7H), 7.14 (d, J=8.8 Hz, 1H), 6.21 (s, 1H).
Scheme 8
Synthesis of 2-Pyrazole phenols
a
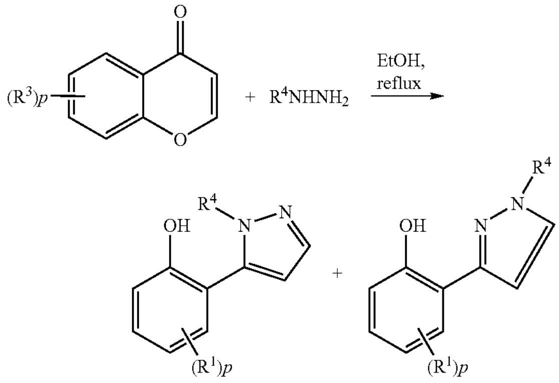
b
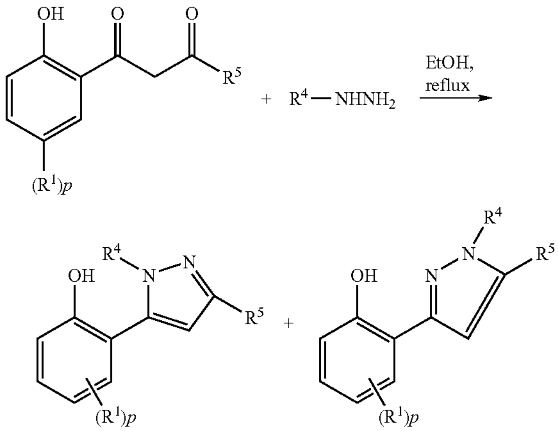
-continued
c
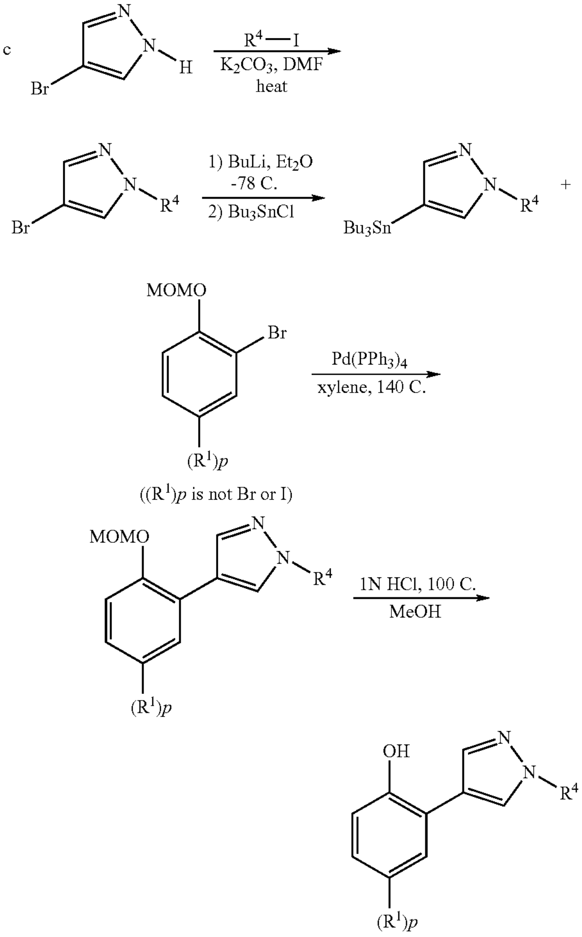
d
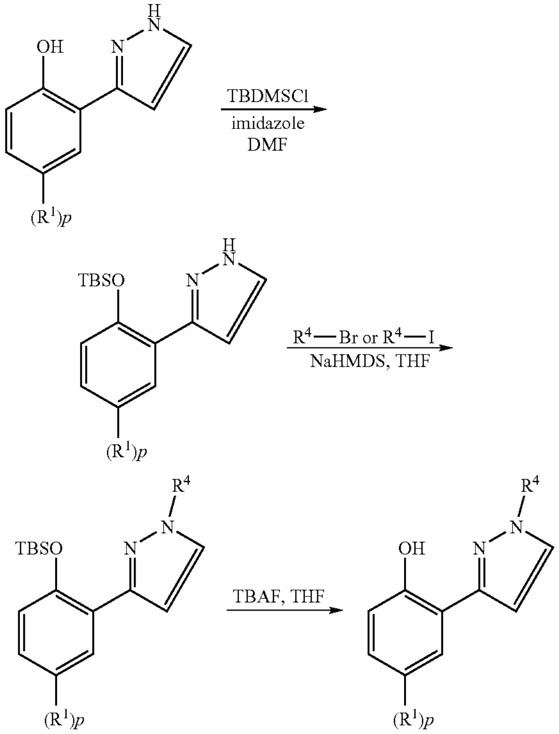

Example 246

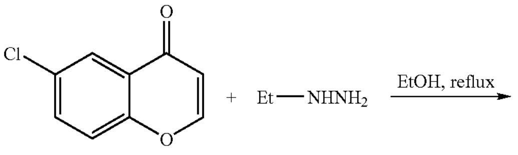

246-S1

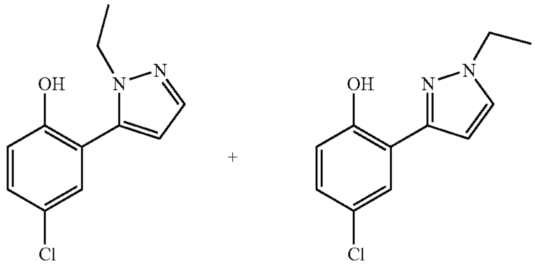

246A 246B (246A:246b = 1:4)

A solution of 6-chlorochromone 246-S1 (5.57 g, 29.91 mmol), ethylhydrazine oxalate (4.58 g, 29.91 mmol) and $Et_3N$ (10.40 mL, 74.77 mmol) in EtOH (60 mL) was refluxed overnight. The mixture was concentrated, dissolved in EtOAc, washed with 1 N HCl and brine, dried and concentrated. Purification via flash column (hexane/EtOAc 10:1 to 3:1) gave 246A (1.3 g) and 246B (5.13 g) as white solids, respectively. For 246A: $^1H$ NMR (400 MHz, $CDCl_3$): δ 7.61 (d, J=1.6 Hz, 1H), 7.31 (dd, J=2.4 and 8.8 Hz, 1H), 7.18 (d, J=2.8 Hz, 1H), 6.97 (m, 1H), 6.33 (d, J=2.0 Hz, 1H), 6.27 (s, 1H), 4.07 (q, J=7.2 Hz, 2H), 1.36 (t, J=7.2 Hz, 3H). For 246B: $^1H$ NMR (400 MHz, $CDCl_3$): δ 10.90 (s, 1H), 7.51 (d, J=2.4 Hz, 1H), 7.45 (d, J=2.0 Hz, 1H), 7.15 (dd, J=2.4 and 8.8 Hz, 1H), 6.95 (d, J=8.8 Hz, 1H), 6.58 (d, J=2.8 Hz, 1H), 4.22 (q, J=7.2 Hz, 2H), 1.54 (t, J=7.2 Hz, 3H).

Example 247

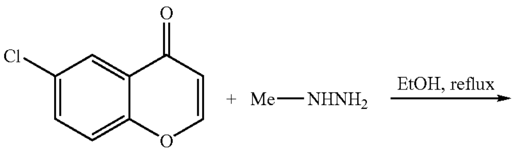

247-S1

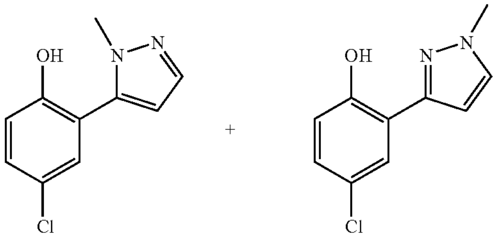

247A 247B (247A:247B = 1:6)

In the same manner as that described in Example 246 compounds 247A and 247B were prepared from 247-S1. For 247A: $^1H$ NMR (400 MHz, $CDCl_3$): δ 7.61 (d, J=1.6 Hz, 1H), 7.31 (dd, J=2.4 and 8.8 Hz, 1H), 7.19 (d, J=2.8 Hz, 1H), 6.95 (m, 1H), 6.36 (d, J=2.0 Hz, 1H), 3.80 (s, 3H).

For 247B: $^1H$ NMR (400 MHz, $CDCl_3$): δ 10.80 (s, 1H), 7.50 (d, J=2.4 Hz, 1H), 7.41 (d, J=2.0 Hz, 1H), 7.13 (dd, J=2.4 and 8.8 Hz, 1H), 6.95 (d, J=8.8 Hz, 1H), 6.58 (d, J=2.4 Hz, 1H), 3.98 (s, 3H).

Example 248

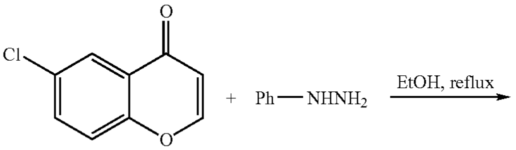

248-S1

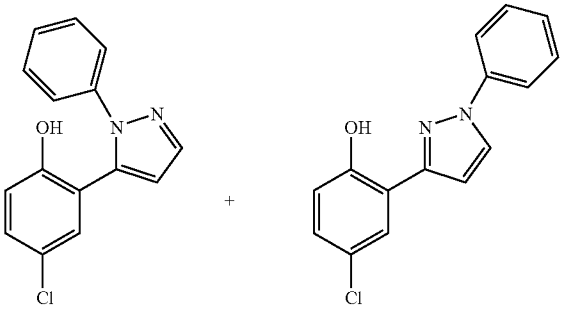

248A 248B (248A:248B = 5:1)

In the same manner as that described in Example 246 compounds 246A and 246B were prepared from 248-S1. For 248A: $^1H$ NMR (400 MHz, $CDCl_3$): δ 7.77 (d, J=2.0 Hz, 1H), 7.35–7.26 (m, 5H), 7.20 (dd, J=2.4 and 8.8 Hz, 1H), 7.02 (d, J=2.8 Hz, 1H), 6.80 (d, J=8.8 Hz, 1H), 6.55 (d, J=2.0 Hz, 1H), 5.90 (s, 1H). For 248B: $^1H$ NMR (400 MHz, $CDCl_3$): δ 10.90 (s, 1H), 8.01 (d, J=2.4 Hz, 1H), 7.70 (m, 2H), 7.58 (d, J=2.4 Hz, 1H), 7.54 (m, 2H), 7.38 (m, 1H), 7.21 (dd, J=2.8 and 8.8 Hz, 1H), 7.02 (d, J=8.4 Hz, 1H), 6.85 (d, J=2.8 Hz, 1H).

Example 249

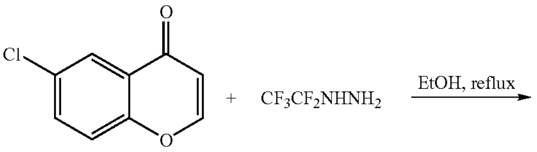

249-S1

-continued

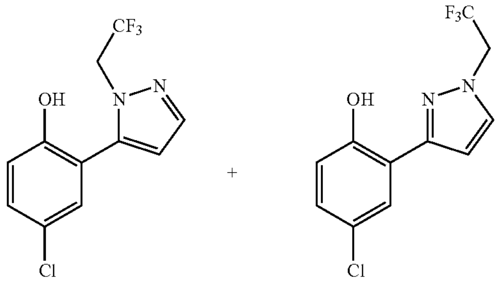

249A 249B (249A:249B = 13:1)

In the same manner as that described in Example 246 compounds 249A and 249B were prepared from 249-S1. For 249A: $^{1}H$ NMR (400 MHz, $CDCl_3$): δ 7.73 (d, J=1.6 Hz, 1H), 7.33 (dd, J=2.8 and 8.8 Hz, 1H), 7.21 (d, J=2.8 Hz, 1H), 6.95 (d, J=8.4 Hz, 1H), 6.43 (d, J=2.0 Hz, 1H), 5.64 (s, 1H), 4.70 (m, 2H). For 249B: $^{1}H$ NMR (400 MHz, $CDCl_3$): δ 10.38 (s, 1H), 7.59 (d, J=2.8 Hz, 1H), 7.52 (d, J=2.8 Hz, 1H), 7.17 (dd, J=2.8 and 8.8 Hz, 1H), 6.98 (d, J=8.4 Hz, 1H), 6.73 (d, J=2.4 Hz, 1H), 4.78 (m, 2H).

Example 250

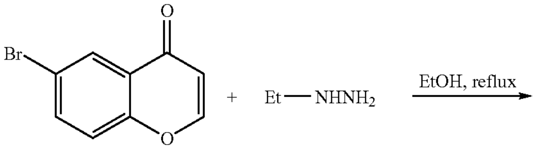

250-S1

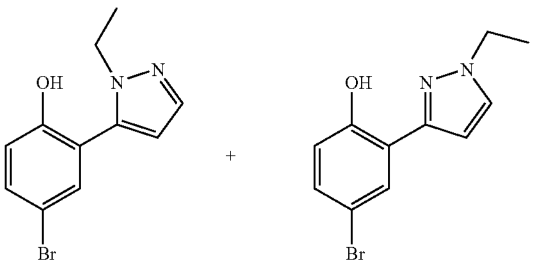

250A 250B (250A:250B = 1:4)

In the same manner as that described in Example 246 compounds 250A and 250B were prepared from 250-S1. For 250A: $^{1}H$ NMR (400 MHz, $CDCl_3$): δ 7.62 (d, J=1.6 Hz, 1H), 7.46 (dd, J=2.8 and 8.8 Hz, 1H), 7.37 (d, J=2.8 Hz, 1H), 6.94 (d, J=8.8 Hz, 1H), 6.32 (d, J=1.6 Hz, 1H), 4.09 (q, J=7.2 Hz, 2H), 1.39 (t, J=7.2 Hz, 3H). For 250B: $^{1}H$ NMR (400 MHz, $CDCl_3$): δ 10.95 (s, 1H), 7.65 (d, J=2.0 Hz, 1H), 7.44 (d, J=2.4 Hz, 1H), 7.27 (dd, J=2.8 and 9.2 Hz, 1H), 6.91 (d, J=9.2 Hz, 1H), 6.58 (d, J=2.4 Hz, 1H), 4.22 (q, J=7.2 Hz, 2H), 1.54 (t, J=7.2 Hz, 3H).

Example 251

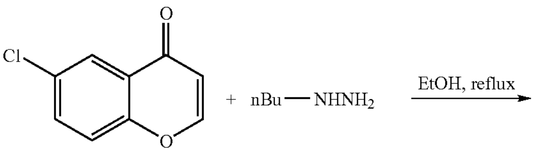

251-S1

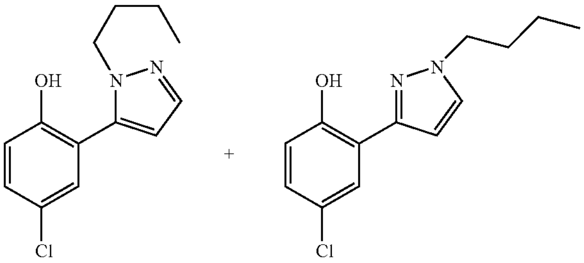

251A 251B

In the same manner as that described in Example 246 compounds 251A and 251B were prepared from 251-S1. For 251A: $^{1}H$ NMR (400 MHz, $CDCl_3$): δ 7.64 (d, J=2.0 Hz, 1H), 7.32 (dd, J=2.8 and 8.8 Hz, 1H), 7.17 (d, J=2.8 Hz, 1H), 6.98 (d, J=8.8 Hz, 1H), 6.33 (d, J=2.0 Hz, 1H), 4.05 (m, 2H), 1.75 (m, 2H), 1.22 (m, 2H), 0.85 (t, J=7.2 Hz, 3H). For 251B: $^{1}H$ NMR (400 MHz, $CDCl_3$): δ 10.92 (s, 1H), 7.51 (d, J=2.8 Hz, 1H), 7.42 (d, J=2.8 Hz, 1H), 7.13 (dd, J=2.8 and 8.8 Hz, 1H), 6.95 (d, J=8.8 Hz, 1H), 6.58 (d, J=2.8 Hz, 1H), 4.17 (m, 2H), 1.88 (m, 2H), 1.39 (m, 2H), 0.98 (t, J=7.2 Hz, 3H).

Example 252

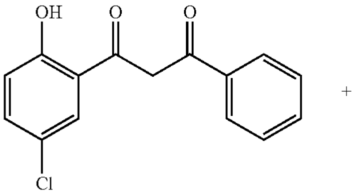

252-S1

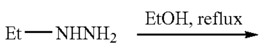

-continued

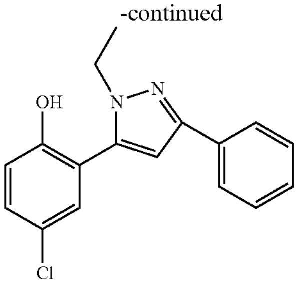

252A

+

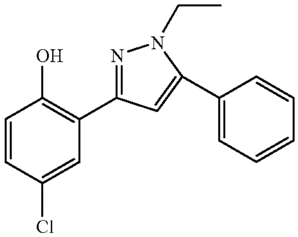

252B

A solution of 252-S1 (0.76 g, 2.76 mmol), ethylhydrazine oxalate (0.414 g, 2.76 mmol) and $Et_3N$ (0.96 mL, 6.9 mmol) in EtOH (10 mL) was refluxed overnight. The mixture was concentrated, dissolved in EtOAc, washed with 1 N HCl and brine, dried and concentrated. Purification via flash column (hexane/EtOAc 10:1) gave 252A (0.28 g) and 252B (0.23 g) as white solids, respectively. For 252A: $^1$H NMR (400 MHz, $CDCl_3$): δ 7.80 (m, 2H), 7.35–7.22 (m, 5H), 7.02 (d, J=2.8 Hz, 1H), 6.57 (s, 1H), 5.90 (s, 1H), 4.10 (q, J=7.2 Hz, 2H), 1.41 (t, J=7.2 Hz, 3H). For 252B: $^1$H NMR (400 MHz, $CDCl_3$): δ 11.05 (s, 1H), 7.5 (m, 6H), 7.20 (d, J=2.8 Hz, 1H), 6.97 (d, J=2.8 Hz, 1H), 6.64 (s, 1H), 4.22 (q, J=7.2 Hz, 2H), 1.50 (t, J=7.2 Hz, 3H).

Example 253

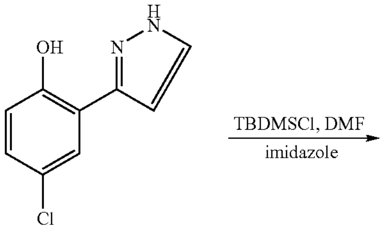

253-S1

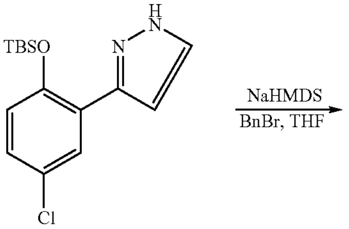

253-S2

-continued

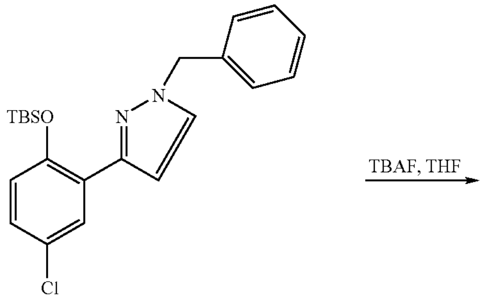

253-S3

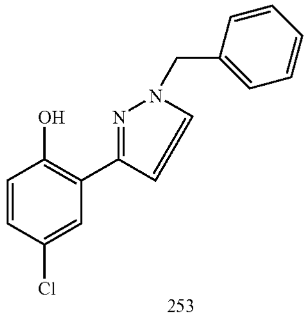

253

A mixture of 253-S1(5.116 g, 26.29 mmol), TBSCI (4.36 g, 28.92 mmol) and imidazole (2.68 g, 39.44 mmol) in DMF (100 mL) was stirred at room temperature overnight. The mixture was diluted with EtOAc, washed with brine, dried and concentrated. Purification via flash column (hexane/EtOAc 10:1) gave 253-S2 as colorless oil (7.8 g). $^1$H NMR (400 MHz, $CDCl_3$): δ 7.61 (m, 2H), 7.15 (m, 1H), 6.88 (d, J=9.2 Hz, 1H), 6.60 (m, 1H), 0.98 (s, 9H), 0.22 (s, 3H), 0.21(s, 3H).

To a solution of 253-S2 (0.6 g, 1.94 mmol) in THF (10 mL) was added NaHMDS (1.0 M in THF, 2.14 mL, 2.14 mmol) at 0° C. After 5 min. at 0° C., BnBr (242 μL, 2.04 mmol) was added. The mixture was warmed to room temperature, and kept at this temperature for 2 h. The reaction was quenched with brine, extracted with EtOAc, washed with brine, dried and concentrated. Purification via flash column (hexane/EtOAc 30:1) gave 253-S3 as colorless oil (0.4 g). $^1$H NMR (400 MHz, $CDCl_3$): δ 7.81 (m, 1H), 7.36–7.22 (m, 6H), 7.14 (m, 1H), 6.81 (m, 1H), 6.71 (m, 1H), 5.37 (s, 2H), 0.92 (s, 9H), 0.13 (s, 3H), 0.01(s, 3H).

To a solution of 253-S3 (0.4 g, 1.0 mmol) in THF (5 mL) was added TBAF (1.0 M in THF, 1.5 mL, 1.5 mmol) at 0° C. The mixture was warmed to room temperature, and kept at this temperature for 0.5 h. The reaction was quenched with brine, extracted with EtOAc, washed with brine, dried and concentrated to give 253 as a white solid (0.28 g). $^1$H NMR (400 MHz, $CDCl_3$): δ 7.51 (m, 1H), 7.44 (m, 1H), 7.40–7.33 (m, 3H), 7.24 (m, 2H), 7.15 (m, 1H), 6.93 (m, 1H), 6.62 (m, 1H), 5.34 (s, 2H).

Example 254

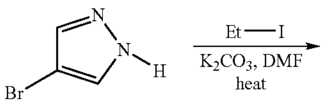

254-S1

-continued

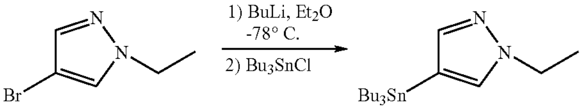

254-S2 254-S3

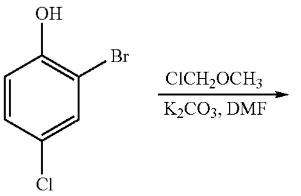

254-S4

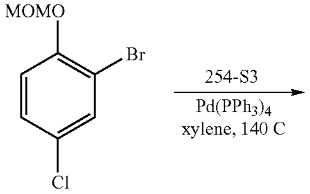

254-S5

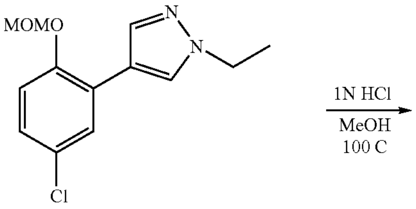

254-S6

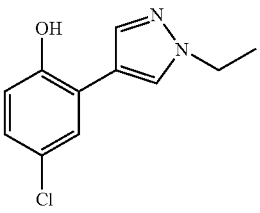

254

A mixture of 4-bromopyrazole 254-S1 (0.47 g, 3.20 mmol), iodoethane (2.5 g, 16.0 mmol) and $K_2CO_3$ (0.88 g, 6.4 mmol) in DMF (5 mL) was heated at 80° C. overnight. The mixture was diluted with ether, washed with brine, dried and concentrated. Purification via flash column (hexane/EtOAc 10:1) gave 254-S2 as colorless oil (0.45 g). $^1$H NMR (400 MHz, $CDCl_3$): δ 7.45 (s, 1H), 7.41 (s, 1H), 4.18 (q, 2H), 1.45 (t, 3H).

To a solution of 254-S2 (0.45 g, 2.57 mmol) in $Et_2O$ (5 mL) was added n-BuLi (2.5 M in hexanes, 1.13 ml, 2.83 mmol) at −78° C. After 20 min at −78□C, $Bu_3SnCl$ (852 μL, 2.83 mmol) was added drop wise. The reaction mixture was slowly warmed to room temperature over 5 h, then, quenched with saturated aqueous $NH_4Cl$ solution, extracted with $Et_2O$. The organic layer was washed with brine, dried and concentrated to give 254-S3 as a crude product, which was used for next reaction without further purification.

A mixture of 2-bromo-4-Cl-phenol 254-S4 (8.57 g, 41.31 mmol), MOMCl (3.99 g, 49.57 mmol) and $K_2CO_3$ (11.4 g, 82.62 mmol) in DMF (60 mL) was stirred overnight. The mixture was quenched with saturated aqueous $NaHCO_3$ solution, extracted with ethyl ether. The organic layer was washed with brine, dried and concentrated. Purification via flash column (hexane/EtOAc 20:1) gave 254-S5 as colorless oil (10.0 g).

A mixture of 254-S3 (ca. 1.8 mmol), 254-S5 (407 mg, 1.62 mmol) and $Pd(PPh_3)_4$ (104 mg, 0.09 mmol) in xylene (4 mL) was heated at 140° C. under nitrogen for 3 h. The mixture was concentrated, and the residue was purified by flash column (hexane/EtOAc 8:1) to give 254-S6 as colorless oil (249 mg). $^1$H NMR (400 MHz, $CDCl_3$): δ 7.88 (s, 1H), 7.84 (s, 1H), 7.47 (m, 1H), 7.11 (m, 2H), 5.24 (s, 2H), 4.22 (q, 2H), 3.50 (s, 3H), 1.53 (t, 3H).

A mixture of 254-S6(249 mg), 1N HCl aqueous solution (5 mL), THF (5 mL) and MeOH (3 mL) was heated at 100° C. for 3 h. The mixture was concentrated, extracted with ether, washed with brine, dried, and concentrated to give 254 as a pale yellow solid (208 mg). $^1$H NMR (400 MHz, $CDCl_3$): δ 7.81 (s, 1H), 7.80 (s, 1H), 7.36 (d, 1H), 7.18 (dd, 1H), 6.84 (d, 1H), 4.23 (q, 2H), 1.56 (t, 3H).

Example 255

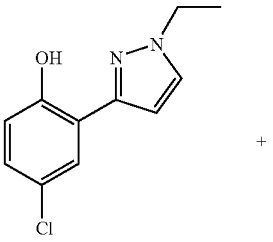

255-S1

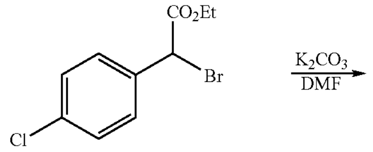

255-S2

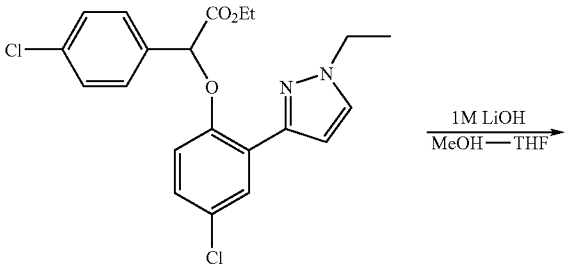

255-S3

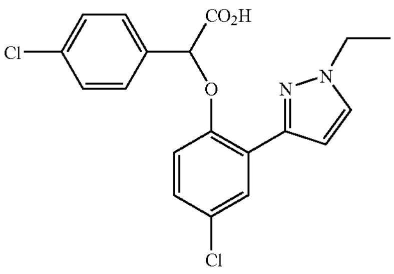

255

In the same manner as that described in Example 28 compound 255 was prepared from 255-S1 and 255-S2. $^1$H NMR (400 MHz, DMSO-$d_6$): δ 7.91 (d, J=2.8 Hz, 1H), 7.78 (d, J=2.0 Hz, 1H), 7.54 (m, 2H), 7.47 (m, 2H), 7.21 (dd, J=2.4 and 8.8 Hz, 1H), 7.09 (d, J=2.0 Hz, 1H), 6.98 (d, J=8.8 Hz, 1H), 6.09 (s, 1H), 4.18 (m, 2H), 1.42 (t, J=7.6 Hz, 3H).

Example 256

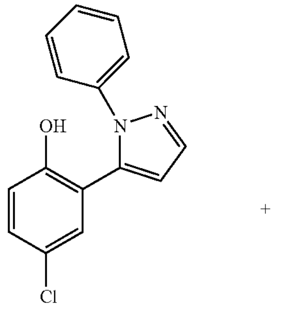

256-S1

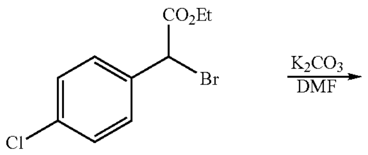

256-S2

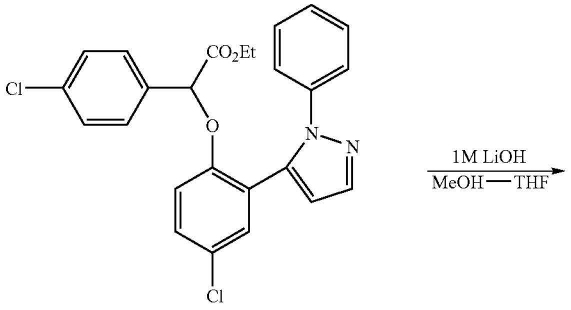

256-S3

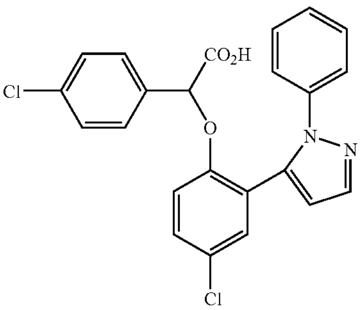

256 (X-21)

In the same manner as that described in Example 28 compound 256 was prepared from 256-S1 and 256-S2. $^1$H NMR (400 MHz, DMSO-$d_6$): δ 7.77 (d, J=1.6 Hz, 1H), 7.38 (m, 3H), 7.26 (m, 3H), 7.21 (d, J=2.4 Hz, 1H), 7.16 (m, 5H), 6.95 (d, J=9.6 Hz, 1H), 6.62 (d, J=2.0 Hz, 1H), 5.75 (s, 1H).

Example 257

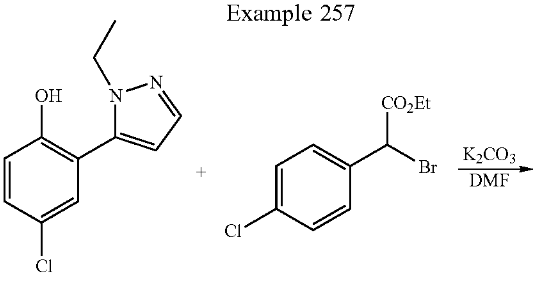

257-S1 257-S2

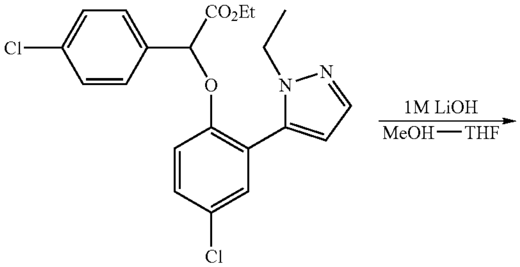

257-S3

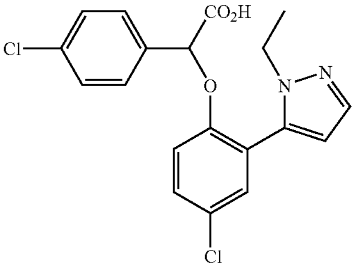

257

In the same manner as that described in Example 28 compound 257 was prepared from 257-S1 and 257-S2. $^1$H NMR (400 MHz, DMSO-$d_6$): δ 7.48 (m, 2H), 7.43 (m, 2H), 7.33 (m, 3H), 7.08 (d, J=9.6 Hz, 1H), 6.27 (d, J=2.0 Hz, 1H), 5.96 (s, 1H), 4.02 (m, 2H), 1.15 (t, J=7.2 Hz, 3H).

Example 258

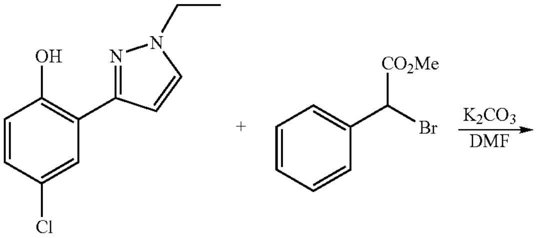

258-S1 258-S2

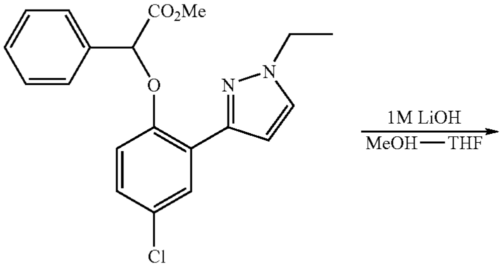

258-S3

-continued

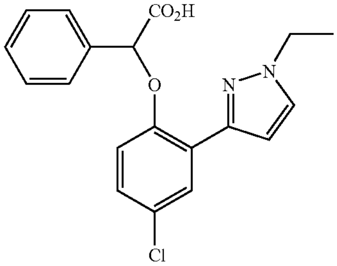

258

In the same manner as that described in Example 28 compound 258 was prepared from 258-S1 and 258-S2. $^1$H NMR (400 MHz, DMSO-$d_6$): δ 7.91 (d, J=2.8 Hz, 1H), 7.78 (d, J=2.4 Hz, 1H), 7.53 (m, 2H), 7.36 (m, 3H), 7.22 (dd, J=2.8 and 9.2 Hz, 1H), 7.11 (d, J=2.4 Hz, 1H), 7.0 (d, J=9.2 Hz, 1H), 6.04(s, 1H), 4.18 (m, 2H), 1.40 (t, J=7.6 Hz, 3H).

Example 259

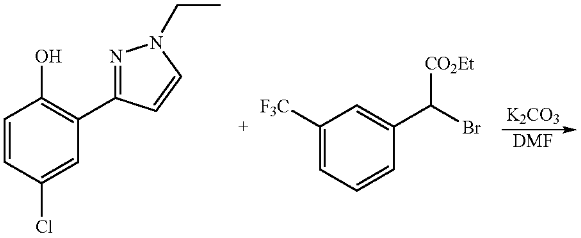

259-S1 259-S2

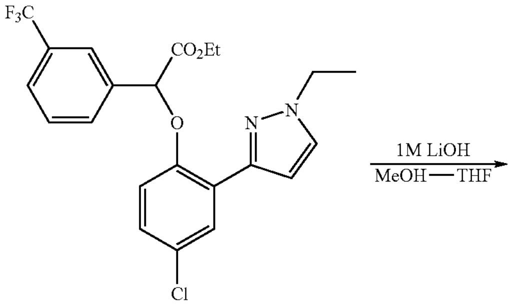

259-S3

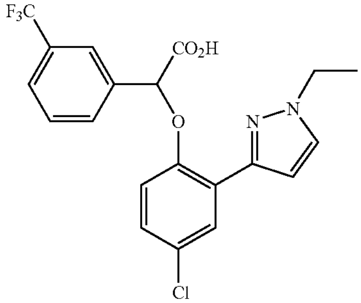

259

In the same manner as that described in Example 28 compound 259 was prepared from 259-S1 and 259-S2. $^1$H NMR (400 MHz, DMSO-$d_6$): δ 7.89 (m, 2H), 7.80 (m, 2H), 7.74 (m, 1H), 7.65 (m, 1H), 7.25 (dd, J=2.8 and 9.2 Hz, 1H), 7.05 (m, 2H), 6.25 (s, 1H), 4.19 (m, 2H), 1.40 (t, J=7.6 Hz, 3H).

Example 260

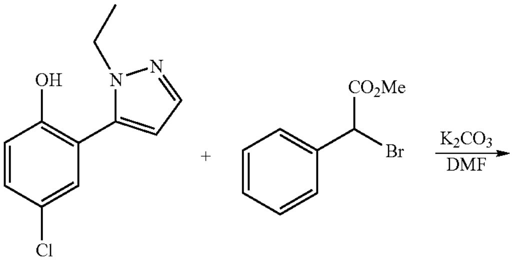

260-S1 260-S2

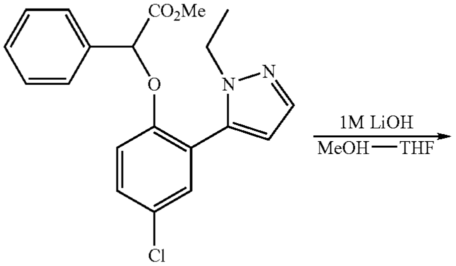

260-S3

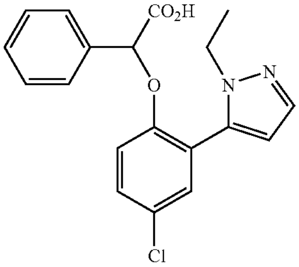

260

In the same manner as that described in Example 28 compound 260 was prepared from 260-S1 and 260-S2. $^1$H NMR (400 MHz, DMSO-$d_6$): δ 7.48 (m, 2H), 7.33 (m, 7H), 7.09 (d, J=9.6 Hz, 1H), 6.27 (d, J=2.0 Hz, 1H), 5.91(s, 1H), 4.05 (m, 2H), 1.16 (t, J=7.6 Hz, 3H).

Example 261

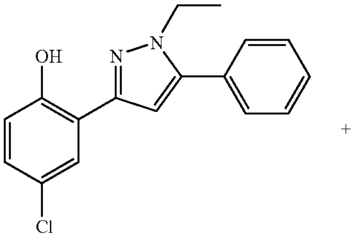

261-S1

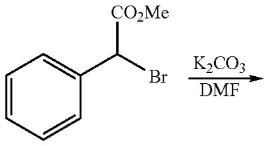

261-S2

-continued

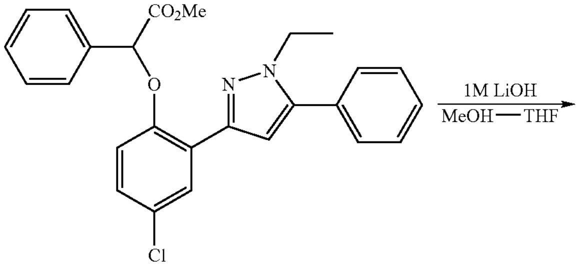

261-S3

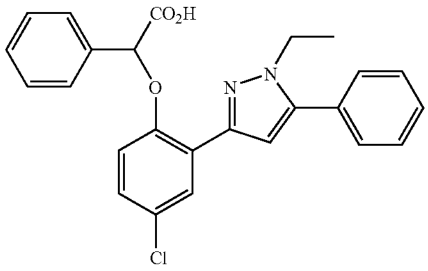

261

In the same manner as that described in Example 28 compound 261 was prepared from 261-S1 and 261-S2. $^{1}H$ NMR (400 MHz, DMSO-$d_6$): δ 7.91 (d, J=2.8 Hz, 1H), 7.59–7.20 (m, 12H), 6.98 (d, J=9.2 Hz, 1H), 5.96 (s, 1H), 4.20 (m, 2H), 1.32 (t, J=7.2 Hz, 3H).

Example 262

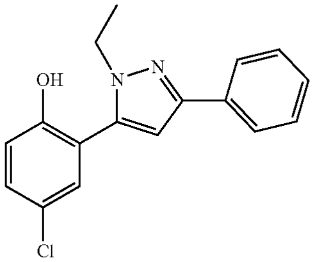

+

262-S1

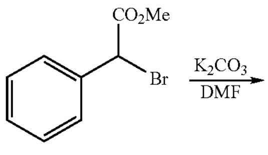

262-S2

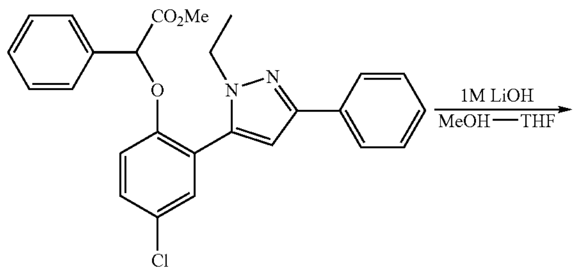

262-S3

-continued

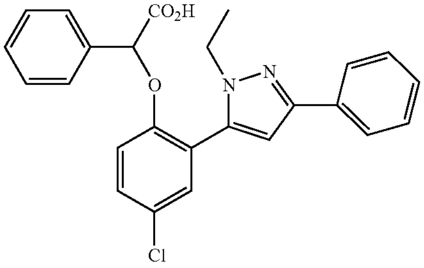

262

In the same manner as that described in Example 28 compound 262 was prepared from 262-S1 and 262-S2. $^{1}H$ NMR (400 MHz, DMSO-$d_6$): δ 7.83 (m, 2H), 7.54 (dd, J=2.8 and 8.8 Hz, 1H), 7.44–7.29 (m, 9H), 7.13 (d, J=9.2 Hz, 1H), 6.77(s, 1H), 5.96 (s, 1H), 4.08 (m, 2H), 1.24 (t, J=7.2 Hz, 3H).

Example 263

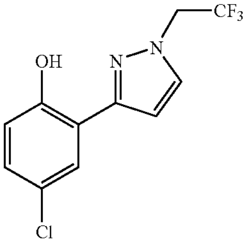

+

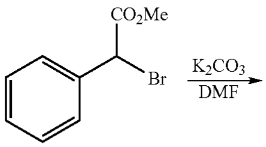

263-S1 263-S2

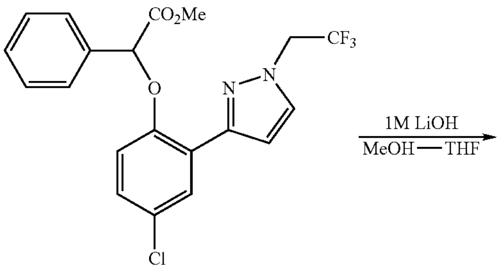

263-S3

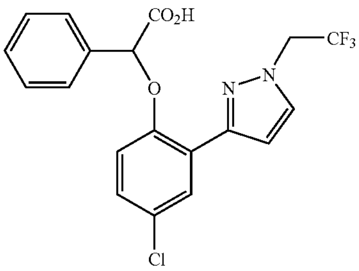

263

In the same manner as that described in Example 28 compound 263 was prepared from 263-S1 and 263-S2. $^{1}H$ NMR (400 MHz, DMSO-$d_6$): δ 7.69 (m, 2H), 7.56 (m, 2H), 7.42 (m, 3H), 7.18 (m, 1H), 6.84 (d, J=2.8 Hz, 1H), 6.76 (d, J=8.8 Hz, 1H), 5.68 (s, 1H), 4.86 (m, 2H).

Example 264
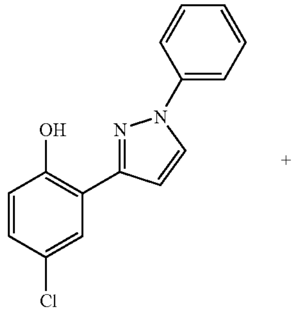
264-S1
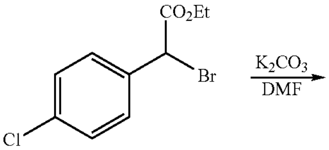
264-S2
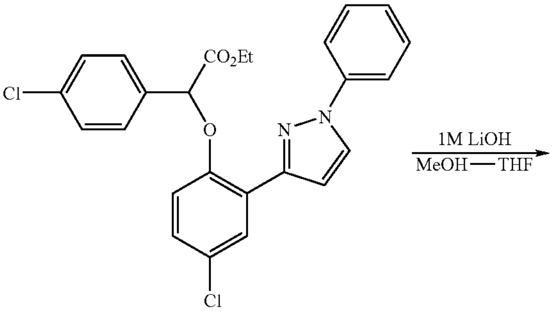
264-S3
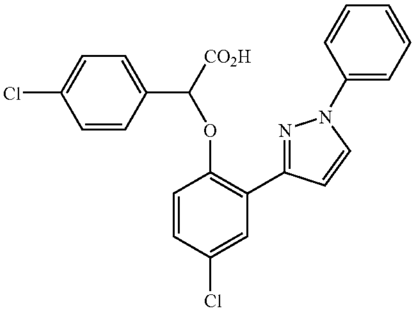
264
In the same manner as that described in Example 28 compound 264 was prepared from 264-S1 and 264-S2. $^1$H NMR (400 MHz, DMSO-$d_6$): δ 8.58 (d, J=2.8 Hz, 1H), 8.06 (d, J=3.2 Hz, 1H), 7.92 (m, 2H), 7.56–7.45 (m, 5H), 7.40 (d, J=2.8 Hz, 1H), 7.33 (m, 2H), 7.06 (d, J=8.8 Hz, 1H), 6.14 (s, 1H).
Example 265
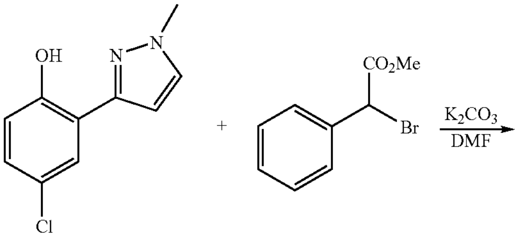
265-S1 265-S2
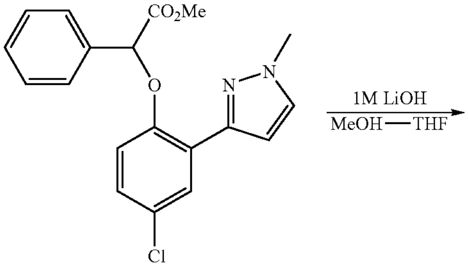
265-S3
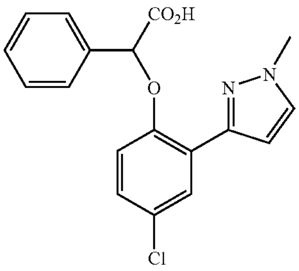
265
In the same manner as that described in Example 28 compound 265 was prepared from 265-S1 and 265-S2. $^1$H NMR (400 MHz, DMSO-$d_6$): δ 7.92 (d, J=2.8 Hz, 1H), 7.76 (d, J=2.0 Hz, 1H), 7.54 (m, 2H), 7.42–7.33 (m, 3H), 7.23 (dd, J=2.8 and 9.2 Hz, 1H), 7.15 (d, J=2.0 Hz, 1H), 7.01 (d, J=9.2 Hz, 1H), 6.07(s, 1H), 3.90 (s, 2H).
Example 266
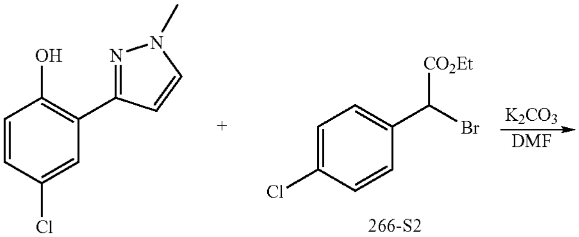
266-S2
266-S1

-continued

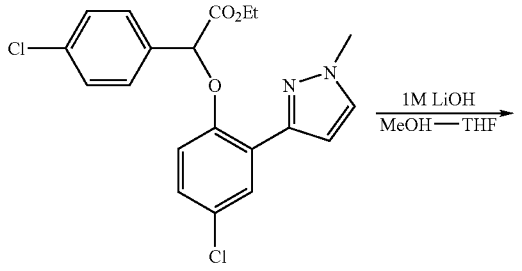

266-S3

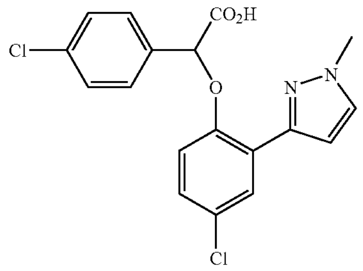

266

In the same manner as that described in Example 28 compound 266 was prepared from 266-S1 and 266-S2. $^1$H NMR (400 MHz, DMSO-$d_6$): δ 7.89 (d, J=2.4 Hz, 1H), 7.74 (d, J=2.0 Hz, 1H), 7.53 (m, 2H), 7.45 (m, 2H), 7.22 (dd, J=2.8 and 8.8 Hz, 1H), 7.11 (d, J=2.0 Hz, 1H), 7.0 (d, J=9.2 Hz, 1H), 6.09(s, 1H), 3.95 (s, 3H).

Example 267

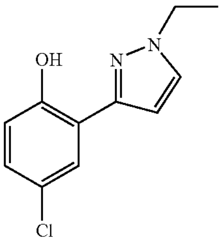

267-S1

+

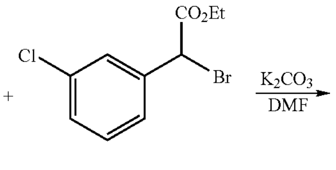

267-S2

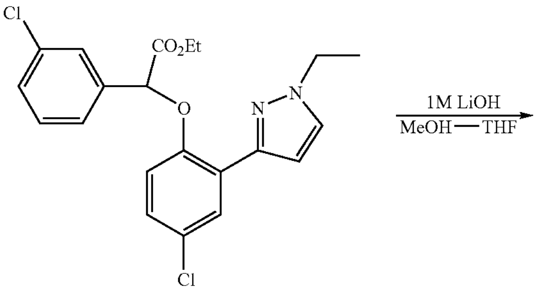

267-S3

-continued

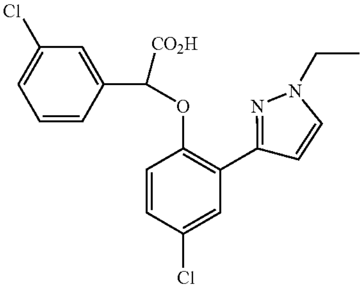

267

In the same manner as that described in Example 28 compound 267 was prepared from 267-S1 and 267-S2. $^1$H NMR (400 MHz, DMSO-$d_6$): δ 7.90 (d, J=2.8 Hz, 1H), 7.81 (d, J=2.0 Hz, 1H), 7.58 (m, 1H), 7.46–7.41 (m, 3H), 7.24 (dd, J=2.8 and 9.2 Hz, 1H), 7.10 (d, J=2.4 Hz, 1H), 6.99 (d, J=8.8 Hz, 1H), 6.11(s, 1H), 4.21 (m, 2H), 1.40 (t, J=7.6 Hz, 3H).

Example 268

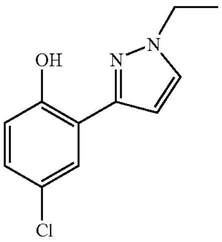

268-S1

+

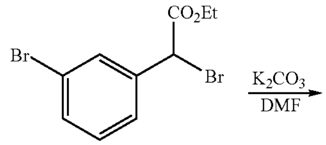

268-S2

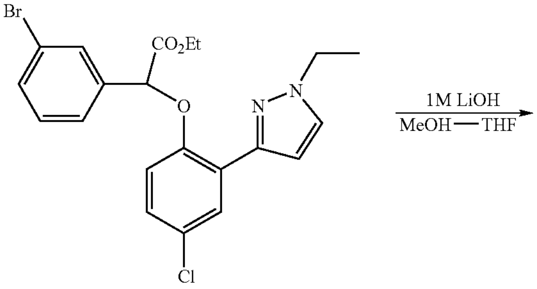

268-S3

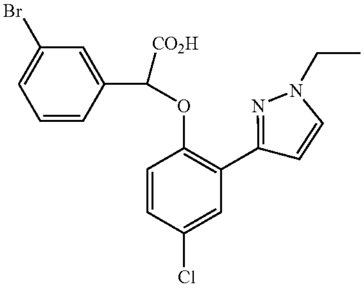

268

In the same manner as that described in Example 28 compound 268 was prepared from 268-S1 and 268-S2. $^1$H NMR (400 MHz, DMSO-$d_6$): δ 7.90 (d, J=2.8 Hz, 1H), 7.81 (d, J=2.0 Hz, 1H), 7.73 (m, 1H), 7.56 (m, 1H), 7.49 (m, 1H), 7.37 (m, 1H), 7.24 (dd, J=2.4 and 8.8 Hz, 1H), 7.09 (d, J=2.4 Hz, 1H), 7.02 (d, J=8.8 Hz, 1H), 6.10(s, 1H), 4.19 (m, 2H), 1.40 (t, J=7.6 Hz, 3H).

Example 269

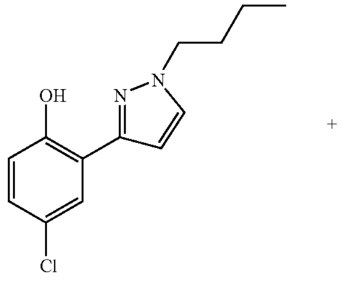

269-S1

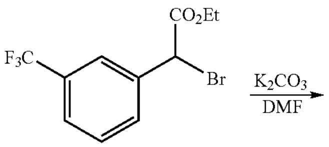

269-S2

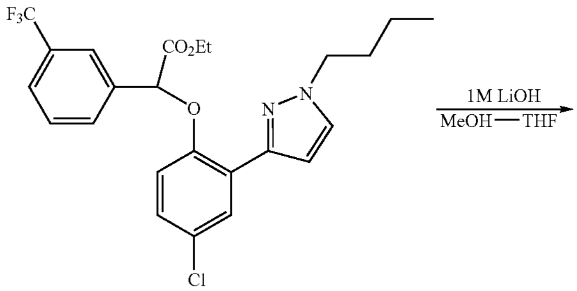

269-S3

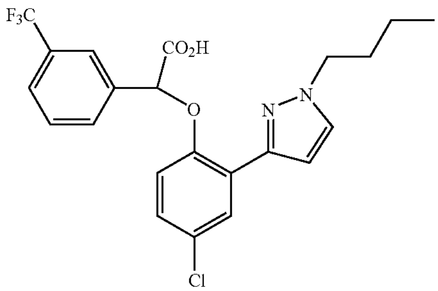

269

In the same manner as that described in Example 28 compound 269 was prepared from 269-S1 and 269-S2. $^1$H NMR (400 MHz, DMSO-$d_6$): δ 7.90 (s, 1H), 7.88 (d, J=2.8 Hz, 1H), 7.82 (s, 1H), 7.79 (d, J=2.4 Hz, 1H), 7.74 (m, 1H), 7.65 (m, 1H), 7.24 (dd, J=2.8 and 8.8 Hz, 1H), 7.05 (m, 2H), 6.25 (s, 1H), 4.14 (m, 2H), 1.78 (m, 2H), 1.25 (m, 2H), 0.88 (m, 3H).

Example 270

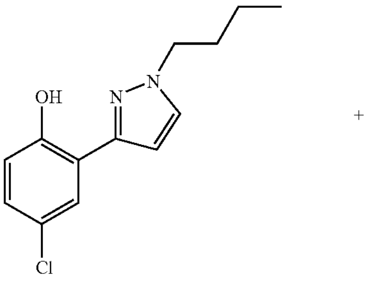

270-S1

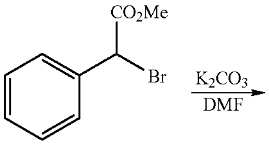

270-S2

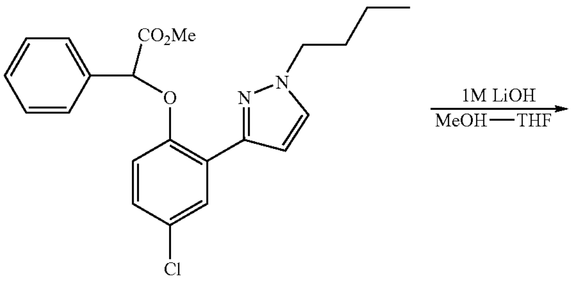

270-S2

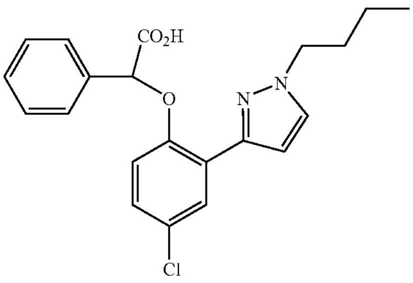

270

In the same manner as that described in Example 28 compound 270 was prepared from 270-S1 and 270-S2. $^1$H NMR (400 MHz, DMSO-$d_6$): δ 7.91 (d, J=2.8 Hz, 1H), 7.78 (d, J=2.4 Hz, 1H), 7.53 (m, 2H), 7.39 (m, 3H), 7.22 (dd, J=2.4 and 8.8 Hz, 1H), 7.12 (d, J=2.4 Hz, 1H), 7.01 (d, J=8.8 Hz, 1H), 6.03 (s, 1H), 4.15 (t, J=7.2 Hz, 2H), 1.78 (m, 2H), 1.27 (m, 2H), 0.90 (t, J=7.6 Hz, 3H).

Example 271
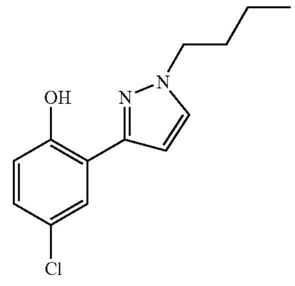
271-S1
+
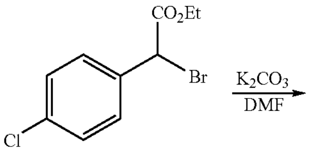
271-S2
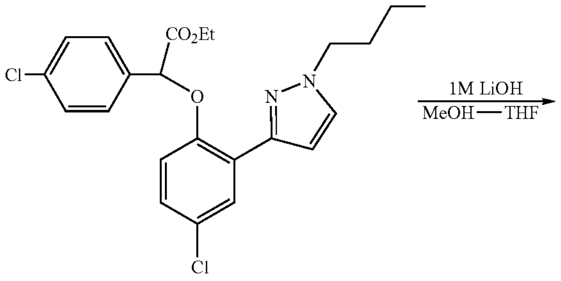
271-S3
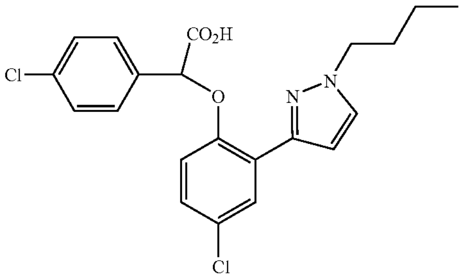
271
In the same manner as that described in Example 28 compound 271 was prepared from 271-S1 and 271-S2. $^{1}$H NMR (400 MHz, DMSO-$d_6$): δ 7.91 (d, J=2.4 Hz, 1H), 7.78 (d, J=1.6 Hz, 1H), 7.54 (m, 4H), 7.23 (dd, J=2.8 and 9.2 Hz, 1H), 7.09 (d, J=2.0 Hz, 1H), 7.0 (d, J=9.2 Hz, 1H), 6.09 (s, 1H), 4.14 (m, 2H), 1.78 (m, 2H), 1.27 (m, 2H), 0.90 (t, J=6.8 Hz, 3H).
Example 272
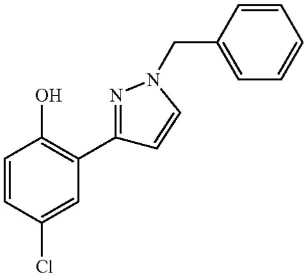
272-S1
+
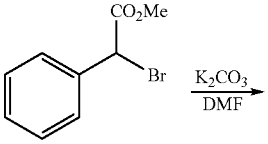
272-S2
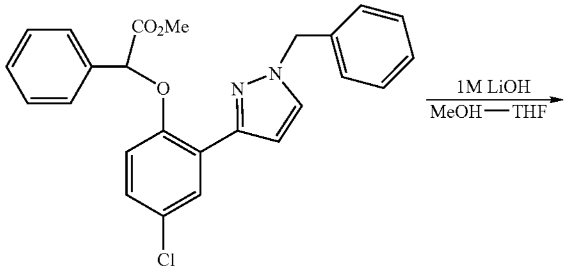
272-S3
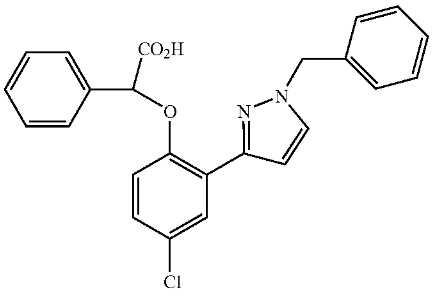
272
In the same manner as that described in Example 28 compound 272 was prepared from 272-S1 and 272-S2. $^{1}$H NMR (400 MHz, DMSO-$d_6$): δ 7.90 (m, 2H), 7.53 (m, 2H), 7.39–7.33 (m, 5H), 7.30 (m, 3H), 7.22 (dd, J=2.8 and 9.2 Hz, 1H), 7.18 (d, J=2.4 Hz, 1H), 7.02 (d, J=8.8 Hz, 1H), 6.04(s, 1H), 5.38 (s, 2H).

Example 273
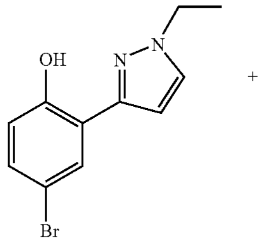
273-S1
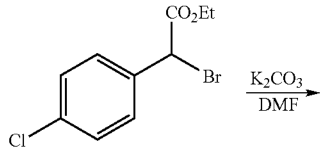
273-S2
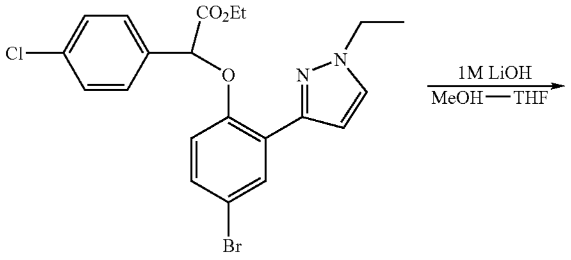
273-S3
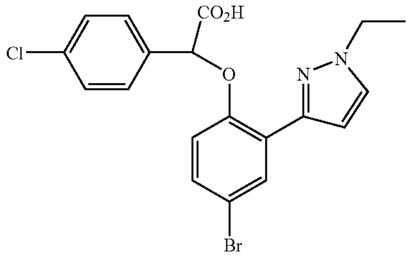
273
In the same manner as that described in Example 28 compound 273 was prepared from 273-S1 and 273-S2. $^1$H NMR (400 MHz, DMSO-d$_6$): δ 8.04 (d, J=2.8 Hz, 1H), 7.78 (d, J=2.4 Hz, 1H), 7.53 (m, 2H), 7.47 (m, 2H), 7.33 (dd, J=2.8 and 8.8 Hz, 1H), 7.09 (d, J=2.0 Hz, 1H), 6.95 (d, J=8.8 Hz, 1H), 6.09 (s, 1H), 4.19 (t, J=7.6 Hz, 2H), 1.40 (t, J=7.6 Hz, 3H).
Example 274
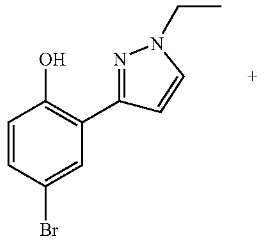
274-S1
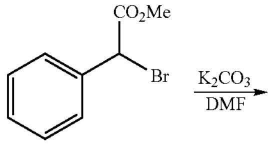
274-S2
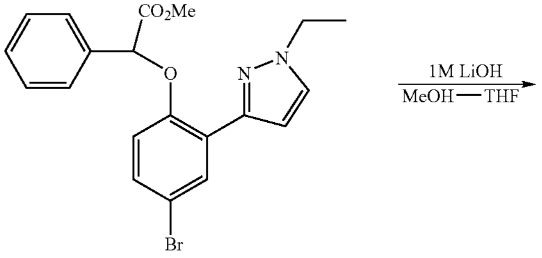
274-S3
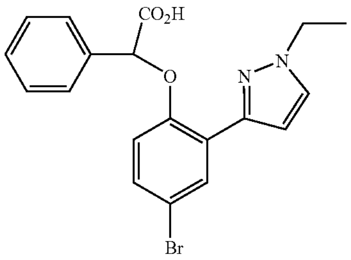
274
In the same manner as that described in Example 28 compound 274 was prepared from 274-S1 and 274-S2. $^1$H NMR (400 MHz, DMSO-d$_6$): δ (d, J=2.4 Hz, 1H), 7.53 (m, 2H), 7.41–7.32 (m, 4H), 7.11 (d, J=2.0 Hz, 1H), 6.97 (d, J=8.8 Hz, 1H), 6.04(s, 1H), 4.19 (m, 2H), 1.42 (t, J=7.6 Hz, 3H).
Example 275
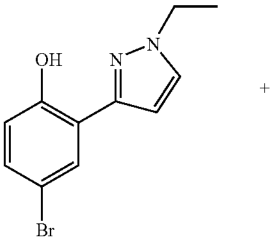
275-S1

-continued

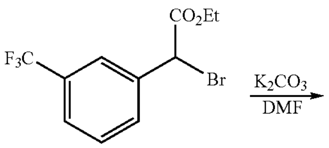

275-S2

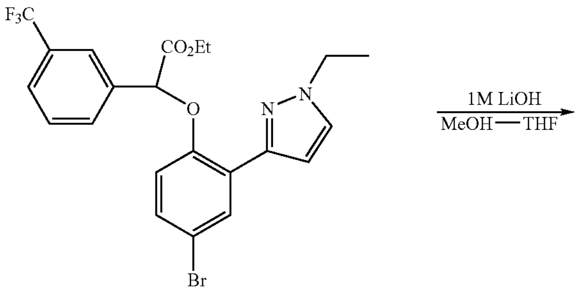

275-S3

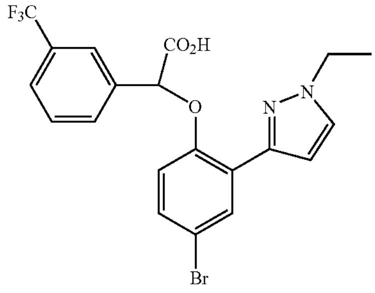

275

In the same manner as that described in Example 28 compound 275 was prepared from 275-S1 and 275-S2. $^{1}H$ NMR (400 MHz, DMSO-$d_6$): δ 8.02 (d, J=2.4 Hz, 1H), 7.89 (s, 1H), 7.80 (m, 2H), 7.73 (m, 1H), 7.64 (m, 1H), 7.37 (dd, J=2.8 and 8.8 Hz, 1H), 7.04 (d, J=2.4 Hz, 1H), 6.98 (d, J=8.8 Hz, 1H), 6.24(s, 1H), 4.19 (m, 2H), 1.40 (t, J=7.6 Hz, 3H).

Example 276

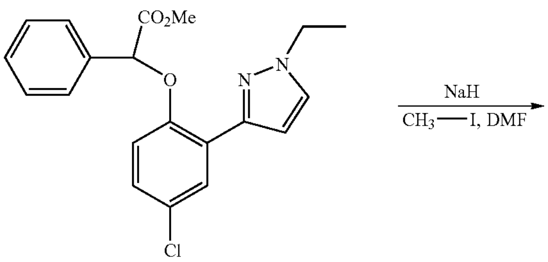

276-S1

-continued

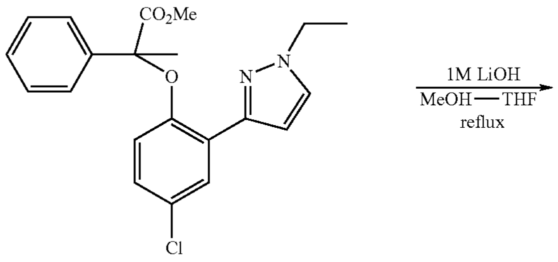

276-S2

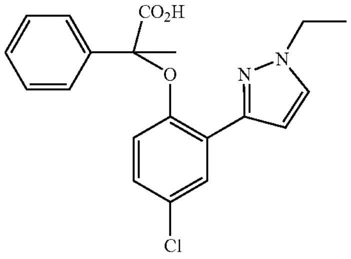

276

In the same manner as that described in Example 42 compound 276 was prepared from 276-S1 and 276-S2. $^{1}H$ NMR (400 MHz, DMSO-$d_6$): δ 7.88 (d, J=2.4 Hz, 1H), 7.80 (d, J=2.4 Hz, 1H), 7.56 (m, 2H), 7.41–7.32 (m, 3H), 7.10 (dd, J=2.8 and 9.2 Hz, 1H), 7.00 (d, J=2.0 Hz, 1H), 6.53 (d, J=8.8 Hz, 1H), 4.20 (m, 2H), 1.88 (s, 3H), 1.41 (t, J=6.8 Hz, 3H).

Example 277

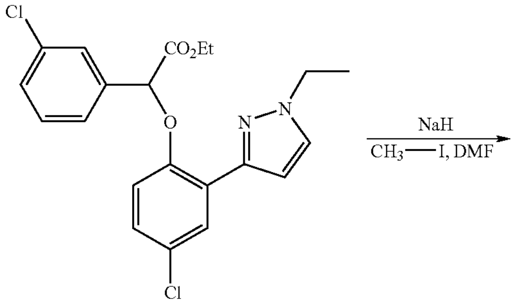

277-S1

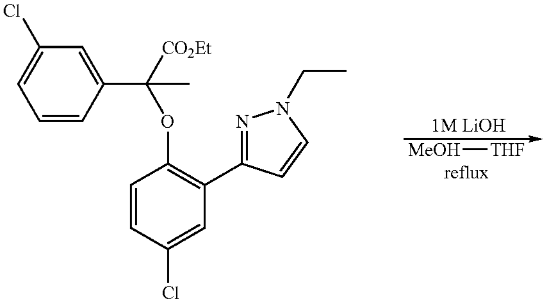

277-S2

-continued

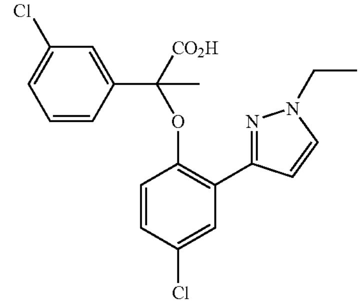

277

In the same manner as that described in Example 42 compound 277 was prepared from 277-S1 and 277-S2. $^{1}$H NMR (400 MHz, $CDCl_3$): δ 7.72 (d, J=2.8 Hz, 1H), 7.70 (d, J=2.4 Hz, 1H), 7.52 (m, 1H), 7.41–7.39 (m, 1H), 7.37–7.34 (m, 2H), 7.08 (dd, J=2.4 and 9.2 Hz, 1H), 6.84 (d, J=2.8 Hz, 1H), 6.41 (d, J=9.2 Hz, 1H), 4.46 (q, J=7.2 Hz, 2H), 2.04 (s, 3H), 1.61 (t, J=7.6 Hz, 3H).

Example 278

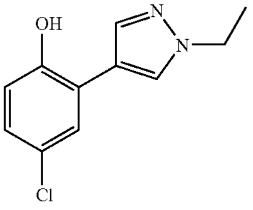

+

278-S1

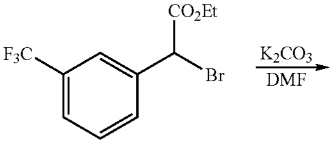

278-S2

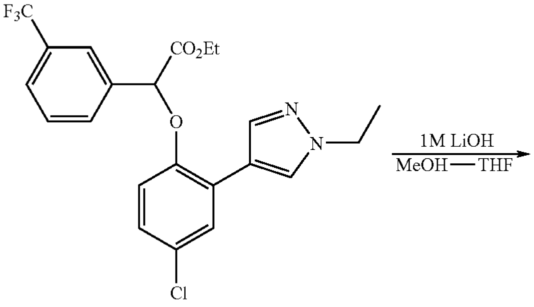

278-S3

-continued

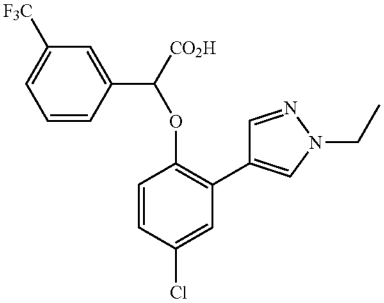

278

In the same manner as that described in Example 28 compound 278 was prepared from 278-S1 and 278-S2. $^{1}$H NMR (400 MHz, DMSO-$d_6$): δ 8.44 (s, 1H), 8.11 (s, 1H), 7.88 (s, 1H), 7.80 (d, J=8 Hz, 1H), 7.73 (d, J=7.6 Hz, 1H), 7.68 (d, J=2.8 Hz, 1H), 7.66 (m, 1H), 7.14 (dd, J=2.8 and 8.8 Hz, 1H), 6.98 (d, J=9.2 Hz, 1H), 6.24 (s, 1H), 4.14 (q, J=7.6 Hz, 2H), 1.37 (t, J=7.6 Hz, 3H).

Example 279

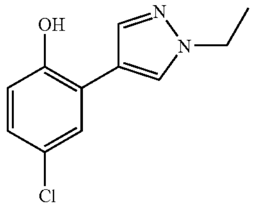

+

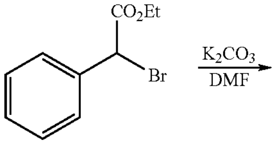

279-S1

279-S2

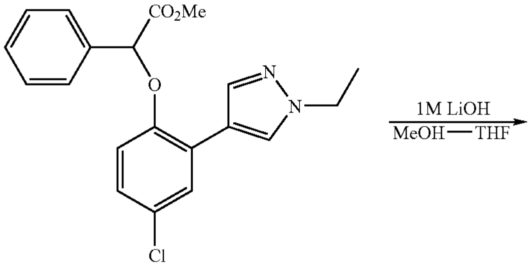

279-S3

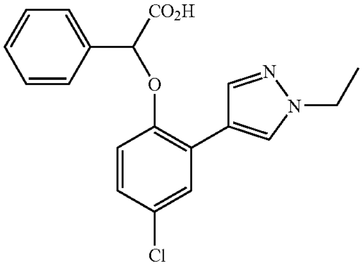

279

In the same manner as that described in Example 28 compound 279 was prepared from 279-S1 and 279-S2. $^1$H NMR (400 MHz, DMSO-$d_6$): δ 8.49 (s, 1H), 8.12 (s, 1H), 7.67 (d, J=2.4 Hz, 1H), 7.51 (m, 2H), 7.40–7.34 (m, 3H), 7.09(dd, J=2.4 and 8.4 Hz, 1H), 6.93 (d, J=8.8 Hz, 1H), 6.01 (s, 1H), 4.14 (q, J=7.6 Hz, 2H), 1.39 (t, J=7.6 Hz, 3H).

Example 280

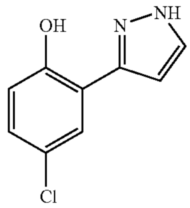

280-S1

+

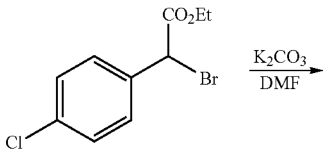

280-S2

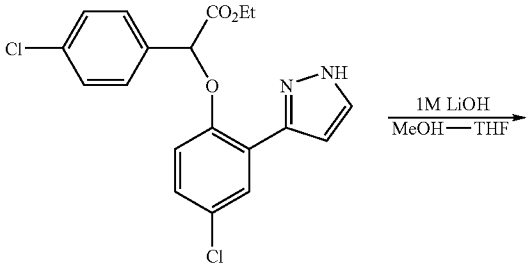

280-S3

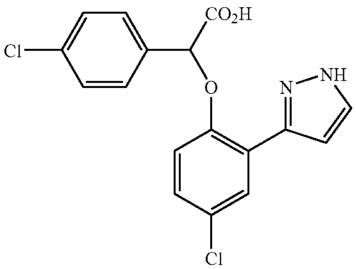

280 (X-1)

In the same manner as that described in Example 28 compound 280 was prepared from 280-S1 and 280-S2. $^1$H NMR (400 MHz, $CDCl_3$): δ 7.50–7.42 (m, 6H), 7.19 (dd, J=2.8 and 8.8 Hz, 1H), 6.97 (d, J=8.8 Hz, 1H), 6.65 (d, J=2.0 Hz, 1H), 6.21 (s, 1H).

Example 281

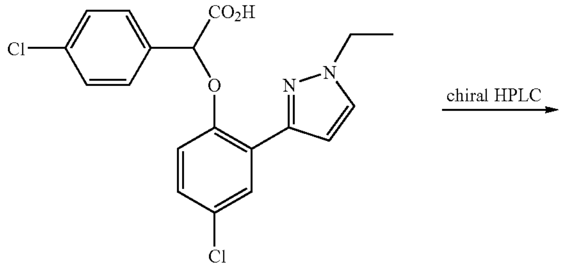

281

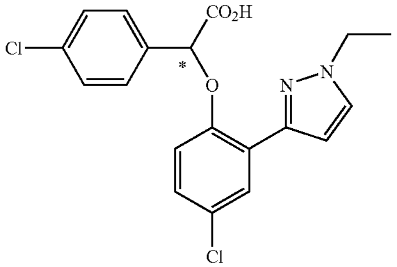

(+)-281

+

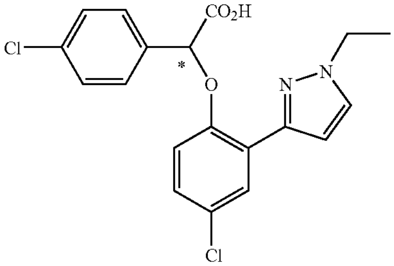

(-)-281

The two enantiomers were separated by chiral HPLC using a 25 cm×21.1 mm Regis Technologies (R,R) WHELK-O 2 10/100 column at ambient temperature. HPLC methods and conditions: 50% iPrOH-50% Hexanes-0.1% TFA, 30 mL/min., λ=220 nm. One enantiomer: RT 6.85 min. The other enantiomer: RT 9.6 min.

Example 282

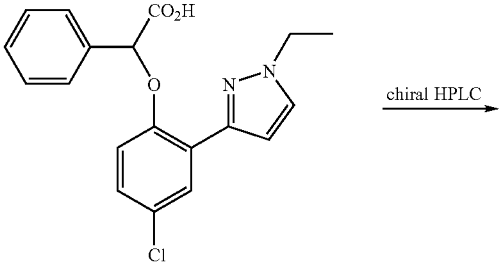

282

-continued

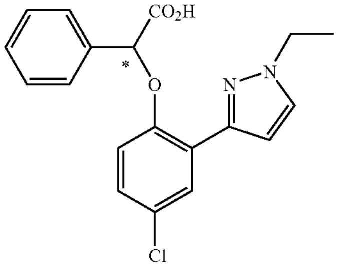

(+)-282

+

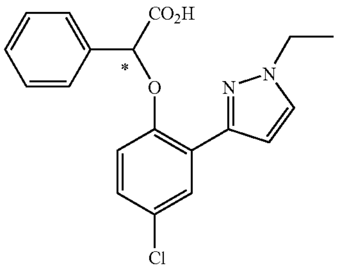

(-)-282

The two enantiomers were separated by chiral HPLC using a 25 cm×21.1 mm Regis Technologies (R,R) WHELK-O 2 10/100 column at ambient temperature. HPLC methods and conditions: 50% iPrOH-50% Hexanes-0.1% TFA, 50 mL/min., λ=220 nm. One enantiomer: RT 6.70 min. The other enantiomer: RT 8.5 min.

Example 283

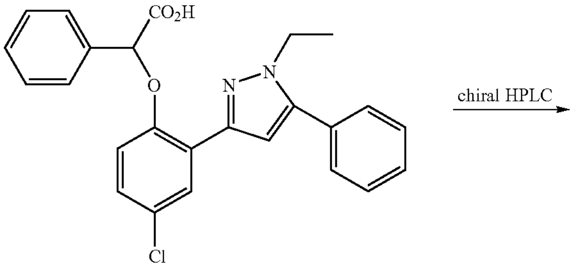

283

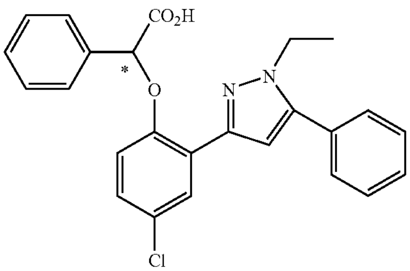

(+)-283

+

-continued

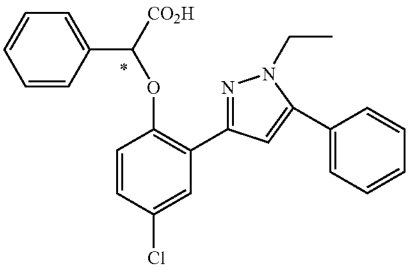

(-)-283

The two enantiomers were separated by chiral HPLC using a 25 cm×21.1 mm Regis Technologies (R,R) WHELK-O 2 10/100 column at ambient temperature. HPLC methods and conditions: 50% iPrOH-50% Hexanes-0.1% TFA, 30 mL/min., λ=220 nm. One enantiomer: RT 6.19 min. The other enantiomer: RT 8.20 min.

Example 284

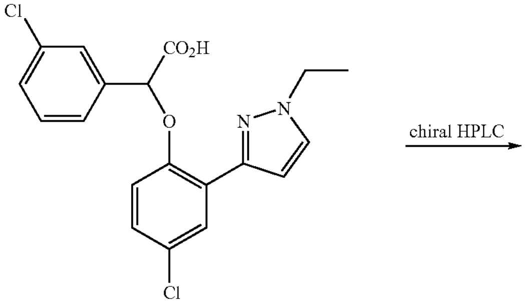

284

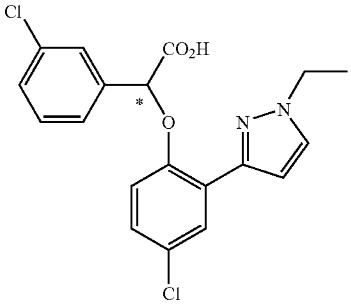

(+)-284

+

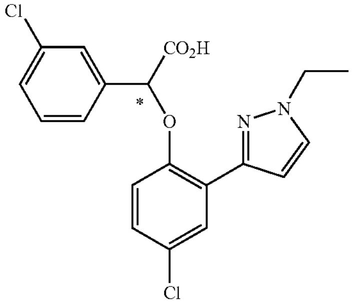

(-)-284

The two enantiomers were separated by chiral HPLC using a 25 cm×21.1 mm Regis Technologies (R,R) WHELK-O 2 10/100 column at ambient temperature. HPLC methods and conditions: 40% iPrOH-60% Hexanes-0.1% TFA, 30 mL/min., λ=220 nm. One enantiomer: RT 7.15 min. The other enantiomer: RT 10.0 min.

Example 285

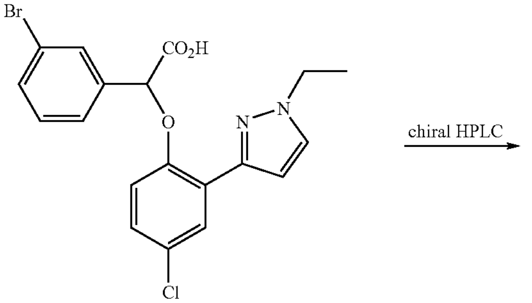

285

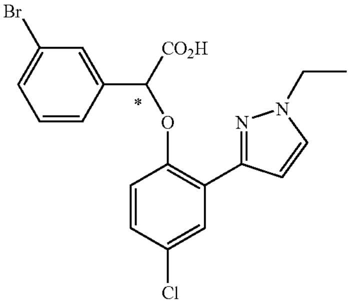

(+)-285

+

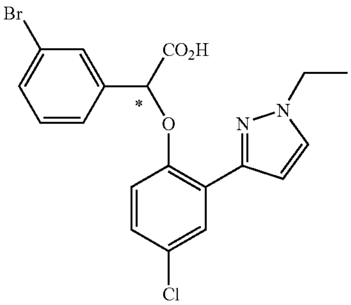

(-)-285

The two enantiomers were separated by chiral HPLC using a 25 cm×21.1 mm Regis Technologies (R,R) WHELK-O 2 10/100 column at ambient temperature. HPLC methods and condition: 40% iPrOH-60% Hexanes-0.1% TFA, 50 mL/min., λ=220 nm. One enantiomer: RT 6.0 min. The other enantiomer: RT 8.70 min.

Example 286

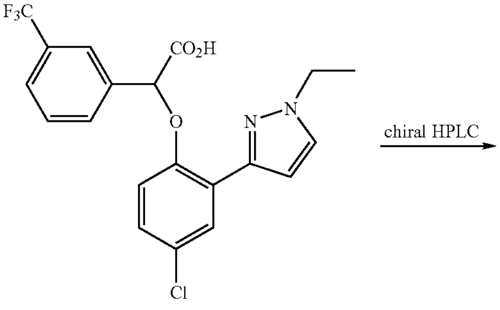

286

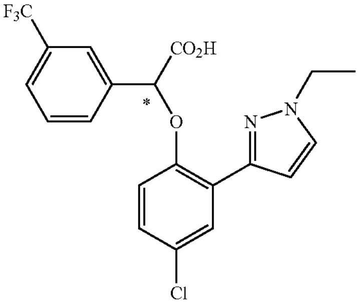

(+)-286

+

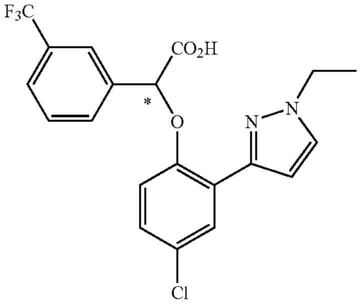

(-)-286

The two enantiomers were separated by chiral HPLC using a 25 cm×21.1 mm Regis Technologies (R,R) WHELK-O 2 10/100 column at ambient temperature. HPLC methods and conditions: 40% iPrOH-60% Hexanes-0.1% TFA, 30 mL/min., λ=220 nm. One enantiomer: RT 6.7 min. The other enantiomer: RT 8.30 min.

Example 287

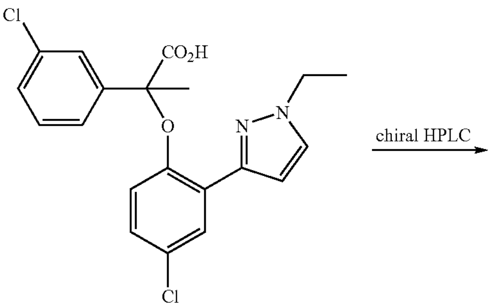

287

-continued

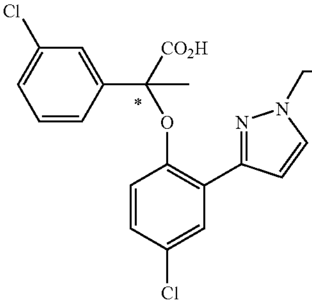

(+)-287

+

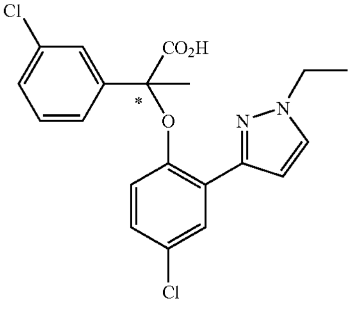

(-)-287

The two enantiomers were separated by chiral HPLC using a 25 cm×21.1 mm Regis Technologies (R,R) WHELK-O 2 10/100 column at ambient temperature. HPLC methods and conditions: 40% iPrOH-60% Hexanes-0.1% TFA, 40 mL/min., λ=220 nm. One enantiomer: RT 11.2 min. The other enantiomer: RT 14.0 min.

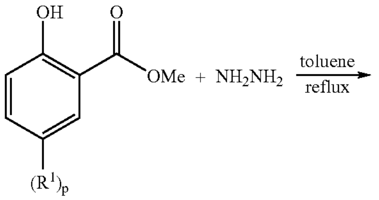

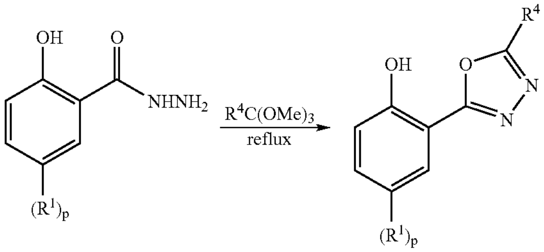

Example 288

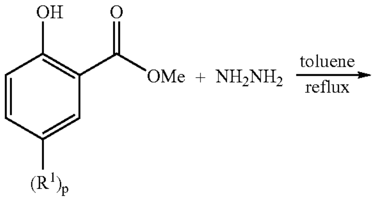

288-S1

-continued

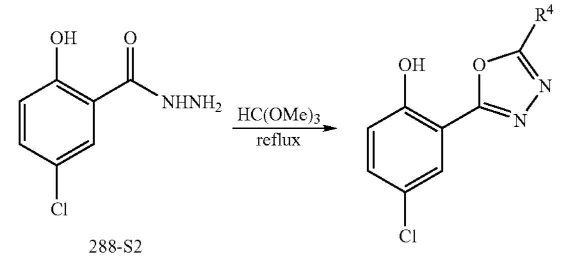

288-S2

288

A mixture of methyl-5-chloro-2-hydroxybenzoate 288 (24.9 g, 0.133 mol) and hydrazine hydrate (11.33 mL, 0.20 mol) in toluene was heated overnight at 120° C. in a sealed tube. After cooling to room temperature, the solids were collected by filtration, washed with MeOH and air dried to give a white solid (21.38 g). $^1$HNMR (400 MHz, DMSO-$d_6$) δ 7.88 (d, J=2.8 Hz, 1H), 7.38 (dd, J=2.8 and 8.8 Hz, 1H), 6.92 (d, J=8.8 Hz, 1H).

A mixture of the above product (21.38 g) and trimethyl othoformate (150 mL) was heated overnight at 110° C. The reaction mixture was concentrated to remove about 100 mL of trimethyl othoformate. Then, 300 mL of toluene was added, and the mixture was refluxed overnight. The mixture was filtered, and the filtrate was concentrated. The residue was recrystallized from McOH to give 288 as a pale yellow solid (9.0 g). $^1$HNMR (400 MHz, DMSO-$d_6$) δ 9.34 (s, 1H), 7.76 (d, J=2.8 Hz, 1H), 7.47 (dd, J=2.8 and 8.8 Hz, 1H), 7.08 (d, J=8.4 Hz, 1H).

Example 289

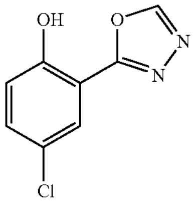

289-S1

+

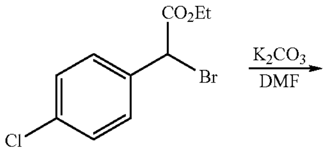

289-S2

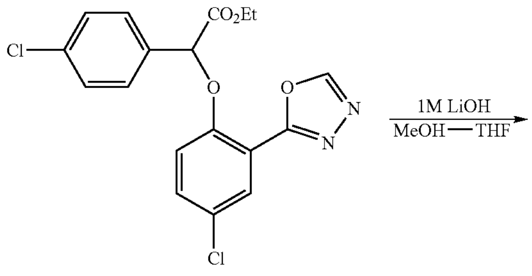

289-S3

-continued

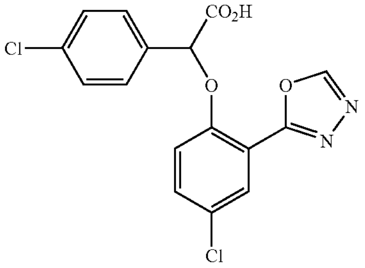

289

In the same manner as that described in Example 28 compound 289 was prepared from 289-S1 and 289-S2. $^{1}$HNMR (400 MHz, DMSO-$d_6$) δ 9.43 (s, 1H), 7.94 (d, J=2.8 Hz, 1H), 7.71 (d, J=2.8 Hz, 1H), 7.68 (m, 2H), 7.52 (m, 2H), 7.25 (d, J=9.2 Hz, 1H), 6.21 (s, 1H).

Example 290

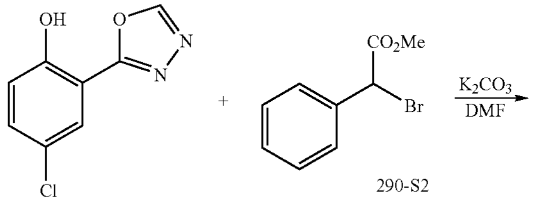

290-S1 290-S2

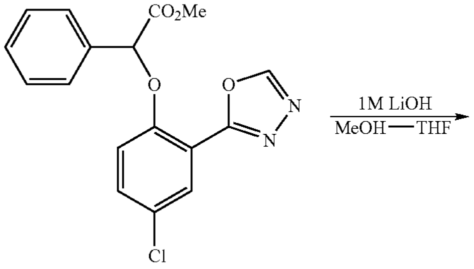

290-S3

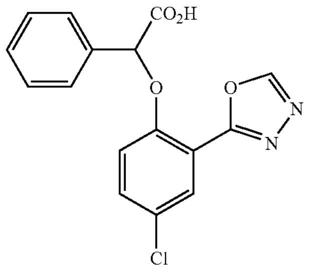

290

In the same manner as that described in Example 28 compound 290 was prepared from 290-S1 and 290-S2. $^{1}$HNMR (400 MHz, DMSO-$d_6$) δ 9.45 (s, 1H), 7.92 (d, J=2.4 Hz, 1H), 7.70 (dd, J=2.8 and 9.2 Hz, 1H), 7.65 (m, 2H), 7.39 (m, 3H), 7.26 (d, J=8.8 Hz, 1H), 6.15 (s, 1H).

Scheme 10
Synthesis of 2-Pyrrole Phenols

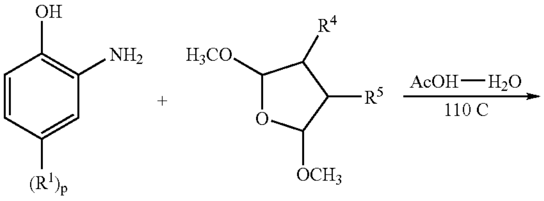

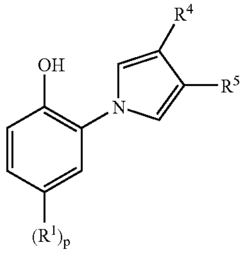

Example 291

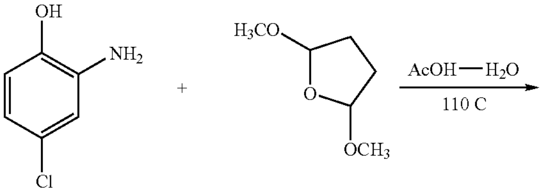

291-S1 291-S2

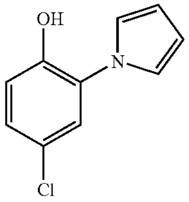

291

A mixture of 2-amino-4-chlorophenol (5.69 g, 39.63 mmol) and 2,5-dimethoxy-tetrafuran (5.24 g, 39.63 mmol) in AcOH/$H_2O$ (9:1, 200 mL) was heated for 30 min. at 110° C. under nitrogen. The mixture was concentrated, extracted with EtOAc, washed with saturated aqueous $NaUCO_3$, dried and concentrated. Purification via flash column (0–5% EtOAc in hexanes) gave 291 as a red oil (6.37 g, 83%). $^{1}$HNMR (400 MHz, $CDCl_3$) δ 7.25 (m, 2H), 6.97 (d, J=8.8 Hz, 1H), 6.85 (m, 2H), 6.41 (m, 2H), 5.26 (s, 1H).

Example 292
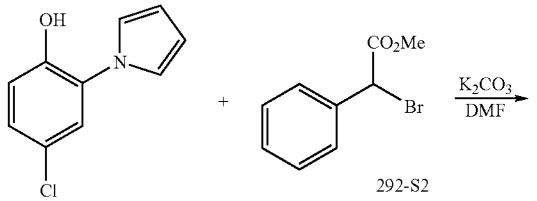
292-S1
292-S2
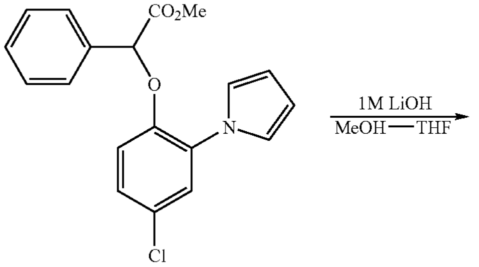
292-S3
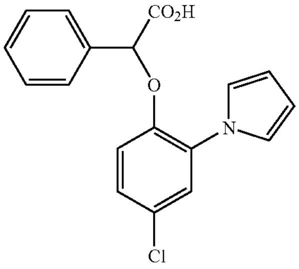
292
In the same manner as that described in Example 28 compound 292 was prepared from 292-S1 and 292-S2. $^1$HNMR (400 MHz, $CDCl_3$) δ 7.42 (m, 2H), 7.36 (m, 3H), 7.33 (d, J=2.4 Hz, 1H), 7.15 (dd, J=2.8 and 8.8 Hz, 1H), 7.06 (m, 2H), 6.90 (d, J=8.4 Hz, 1H), 6.35 (m, 2H), 5.44 (s, 1H).
Example 293
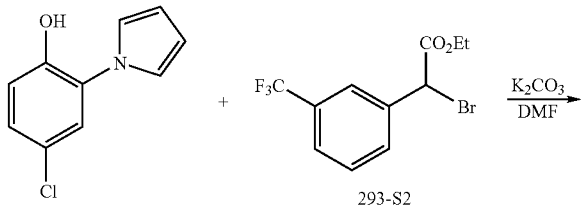
293-S1
293-S2
-continued
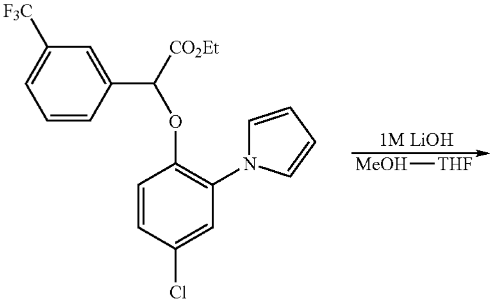
293-S3
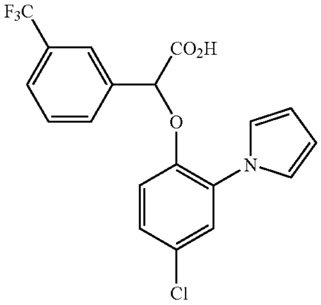
293
In the same manner as that described in Example 28 compound 293 was prepared from 293-S1 and 293-S2. $^1$HNMR (400 MHz, $CDCl_3$) δ 7.69 (s, 1H), 7.62 (m, 2H), 7.48 (m, 1H), 7.35 (d, J=2.4 Hz, 1H), 7.18 (dd, J=2.8 and 8.8 Hz, 1H), 7.01 (m, 2H), 6.92 (d, J=8.4 Hz, 1H), 6.34 (m, 2H), 5.46 (s, 1H).
Example 294
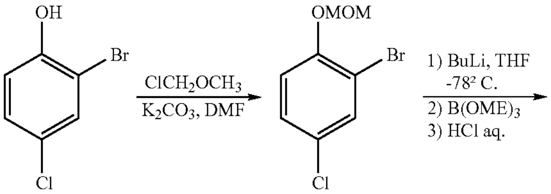
294-S1
294-S2
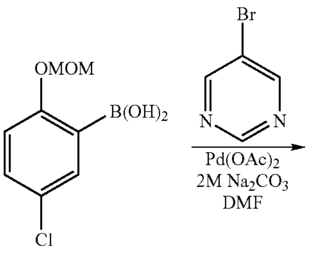
294-S3

-continued

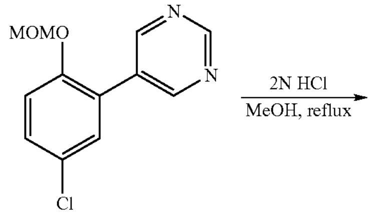

294-S4

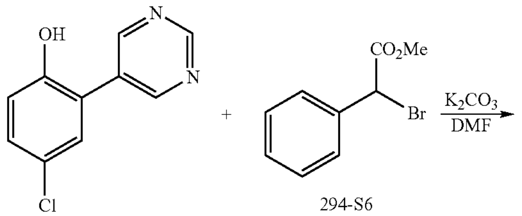

294-S5 294-S6

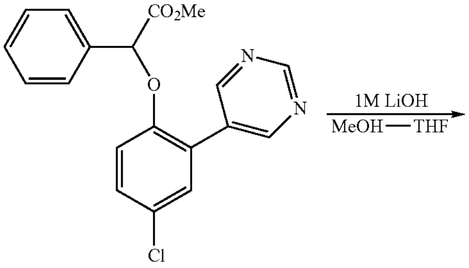

294-S7

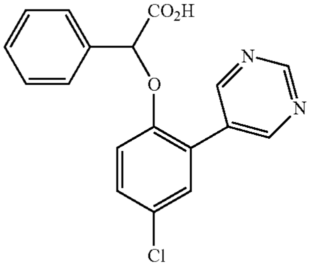

294-S8

A mixture of 2-Br-4-Cl-phenol (8.57 g, 41.31 mmol), MOMCl (3.99 g, 49.57 mmol) and $K_2CO_3$ (11.4 g, 82.62 mmol) in DMF (60 mL) was stirred overnight. The reaction was quenched with saturated aqueous $NaHCO_3$ solution, extracted with ethyl ether. The organic layer was washed with brine, dried and concentrated. Purification via flash column (hexane/EtOAc 20:1) gave 294-S2 as colorless oil (10.0 g).

To a solution of 294-S2 (1.683 g, 6.69 mmol) in THF (20 mL) was added n-BuLi (2.5 M in hexanes, 2.94 mL, 7.36 mmol) at −78° C. After 20 min. at −78° C., trimethyl boronate (1.15 mL, 10.04 mmol) was added drop wise. The mixture was slowly warmed to room temperature over 2 h. After 0.5 h at room temperature, the reaction mixture was quenched with 1 N HCl aqueous solution, and stirred for 10 min. The mixture was extracted with $Et_2O$, washed with brine, dried and concentrated to give pale yellow oil. Crystallization from $Et_2O$/hexane gave 294-S3 as a white solid (1.0 g). $^1$HNMR (400 MHz, $CDCl_3$) δ 7.80 (d, J=2.0 Hz, 1H), 7.36 (dd, J=2.4 and 8.8 Hz, 1H), 7.09 (d, J=8.8 Hz, 1H), 6.0 (br, 2H), 5.27 (s, 2H), 3.50 (s, 3H).

A mixture of 294-S3 (171 mg, 0.97 mmol), 5-bromopyrimidine (138 mg, 0.87 mmol), $Pd(OAc)_2$ and 2M $Na_2CO_3$ (0.97 mL, 1.58 mmol) in DMF (5mL) was stirred overnight at room temperature under nitrogen. The reaction mixture was quenched with brine, extracted with $Et_2O$, washed with brine, dried and concentrated. Purification via flash column (Hexane/EtOAc 10:1 to 5:1) gave 294-S4 as a white solid (31 mg). $^1$HNMR (400 MHz, $CDCl_3$) δ 9.19 (s, 1H), 8.90 (s, 2H), 7.36 (dd, J=2.4 and 8.8 Hz, 1H), 7.32 (d, J=2.4 Hz, 1H), 7.22 (d, J=8.8 Hz, 1H), 5.19 (s, 2H), 3.42 (s, 3H).

A mixture of 294-S4 (31 mg), MeOH (5 mL) and 1 N HCl (5 mL) was heated at 100° C. for 2 h. The mixture was concentrated, dissolved in EtOAc, washed with brine, dried and concentrated to give 294-S5 as a white solid (18 mg). $^1$HNMR (400 MHz, $CDCl_3$) δ 9.21 (s, 1H), 8.97 (s, 2H), 7.32–7.25 (m, 2H), 6.88 (d, J=8.8 Hz, 1H).

294 was prepared from 294-S5 and 294-S6 in the same manner as that described in Example 28. $^1$HNMR (400 MHz, DMSO-$d_6$) δ 9.16 (s, 1H), 9.07 (s, 2H), 7.61 (d, J=2.8 Hz, 1H), 7.49 (dd, J=2.8 and 8.4 Hz, 1H), 7.48–7.39 (m, 5H), 7.18 (d, J=8.8 Hz, 1), 6.10 (s, 1H).

Example 295

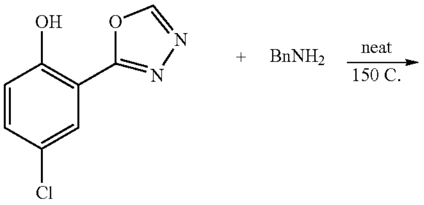

295-S1

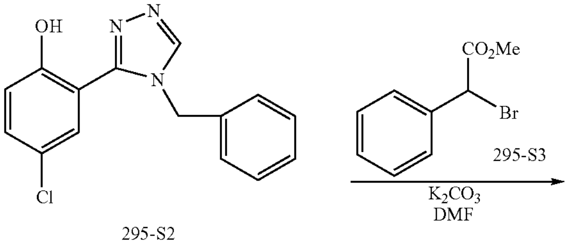

295-S2 295-S3

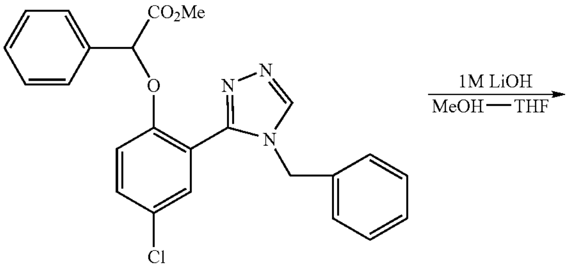

295-S4

-continued

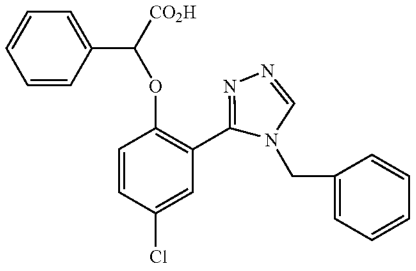

295

A mixture of 295-S1 (500 mg) and benzylamine (3 mL) was heated overnight at 150° C. in a sealed tube under nitrogen. The mixture was diluted with EtOAc, washed with 2 N HCl and brine, dried and concentrated. Purification via flash column (hexane/EtOAc 10:1 to 5:1) gave 295-S2 as a white solid (0.25 g). $^{1}$HNMR (400 MHz, DMSO-$d_6$) δ 12.50 (s, 1H), 9.37 (m, 1H), 7.96(d, J=2.4 Hz, 1H), 7.44 (dd, J=2.4 and 8.8 Hz, 1H), 7.30 (m, 4H), 7.22 (m, 1H), 6.92 (d, J=9.2 Hz, 1H), 4.49 (d, J=6 Hz, 2H).

295 was prepared from 295-S2 and 295-S3 in the same manner as that described in Example 28. $^{1}$HNMR (400 MHz, DMSO-$d_6$) δ 7.77 (d, J=2.8 Hz, 1H), 7.48–7.41 (m, 3H), 7.34–7.23 (m, 9H), 7.12 (d, J=8.8 Hz, 1H), 6.16 (s, 1H), 4.55 (m, 2H).

Example 296

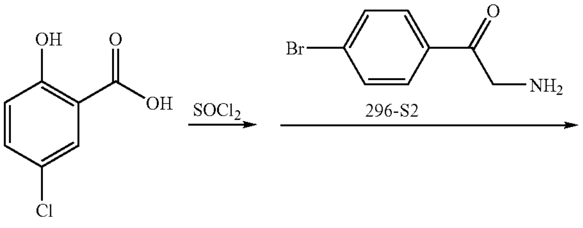

296-S1

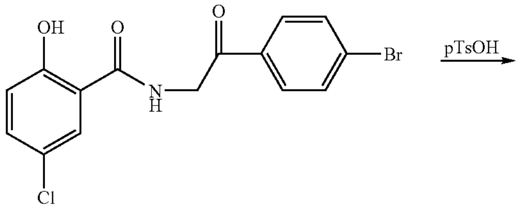

296-S3

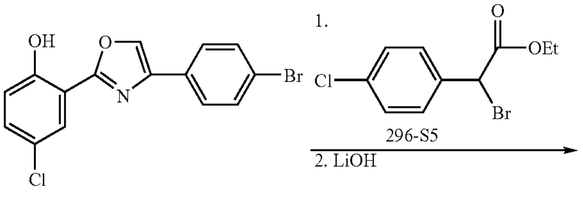

296-S4

-continued

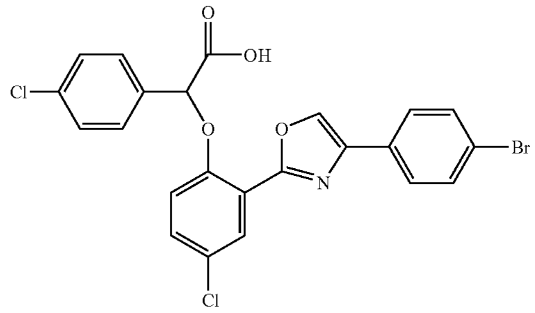

296

To a suspension of 5-chlorosalicyclic acid (2.07 g) in $CH_2Cl_2$ (50 mL) was added 2.63 mL $SOCl_2$, and refluxed for half an hour. The reaction mixture was concentrated. The residue was dissolved in $CH_2Cl_2$ (60 mL), and was charged 3 g of amino ketone followed by 5 mL of triethyl amine at 0° C. The reaction solution was stirred at room temperature for 2 hours, washed with $NaHCO_3$ solution and dried. The solvent was removed to give 296-S3 as amber oil.

A mixture of 296-S3 and pTsOH (0.5 g) in toluene (200 mL) was refluxed overnight with a Dean-Stark trap. The solvent was removed, and the residue was dissolved in ethyl acetate. The solution was washed with $NaHCO_3$ aqueous solution, dried and concentrated. Purification with chromatography (hexanes/ethyl acetate 5/1) gave 0.35 g of 296-S4 as a white solid. $^{1}$H NMR (400 MHz, $CDCl_3$): δ 11.06 (s, 1H), 7.87–7.01 (m, 8H).

The phenol 296-S4 was reacted with 0.5 g 296-S5 and 800 mg $Cs_2CO_3$ in $CH_3CN$ (60 mL) overnight. The salt was filtered off, and the filtrate was removed. Purification with chromatography (hexanes/ethyl acetate 5/1) gave the ester product, which was hydrolyzed with LiOH (1N, 30 mL) to give 296 (0.21 g) as a light yellow solid. $^{1}$H NMR (400 MHz, DMSO-d6): δ 8.01–7.13 (m, 12H), 6.14 (s, 1H).

Example 297

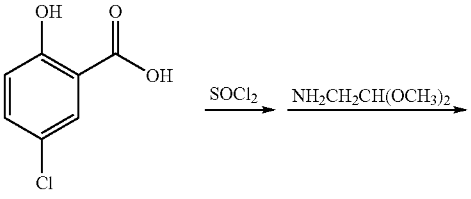

297-S1

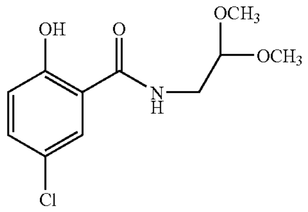

297-S2

-continued

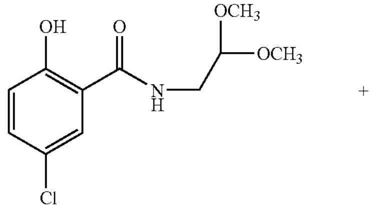

297-S2

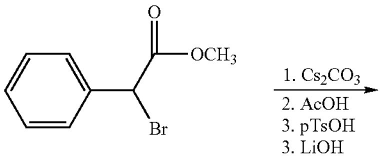

297-S3

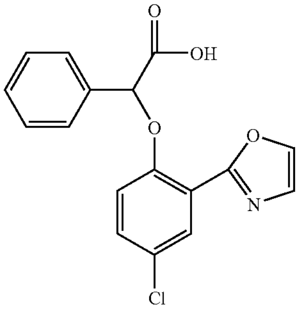

297

In the same manner as that described in Example 296 compound 297-S3 was prepared from 297-S1. $^1$H NMR (400 MHz, $CDCl_3$): δ 12.17 (s, 1H), 7.34–6.91 (m, 3H), 6.51 (br, 1H), 4.49 (m, 1H), 3.57 (m, 2H), 3.44 (ss, 6H).

A mixture of 297-S2 (1.5 g), 297-S3(1.32 g) and $Cs_2CO_3$ (1.88 g) was stir several hours. The salt was filtered out. The solution was concentrated, diluted with ethyl acetate, washed with brine and dried. The solvent was removed, and the residue was treated with 80% AcOH for several hours, concentrated and extracted with ethyl acetate. Purification with chromatography (hexanes/ethyl acetate 5/1) gave the aldehyde compound (2.2 g) as colorless oil. $^1$H NMR (400 MHz, $CDCl_3$): δ 9.73 (s, 1H), 9.29 (br, 1H), 8.19–6.66 (m, 8H), 5.75 (s, 1H), 4.36 (d, 2H), 3.76 (s, 3H).

The solution of aldehyde in toluene with 5 mL AcOH was refluxed overnight, concentrated. Purification with chromatography (hexanes/ethyl acetate 5/1) gave the ester product. The hydrolysis with LiOH (1N, 20 mL) gave 297 (0.13 g) as a white solid. $^1$H NMR (400 MHz, DMSO-d6): δ 8.35–7.15 (m, 10H), 6.26 (s, 1H).

Example 298

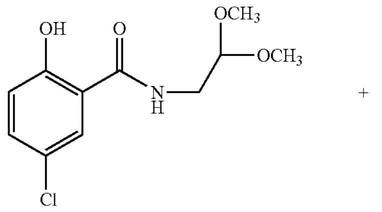

298-S1

-continued

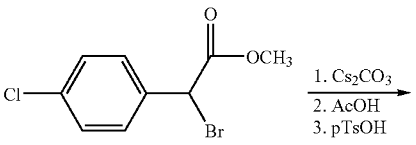

298-S2

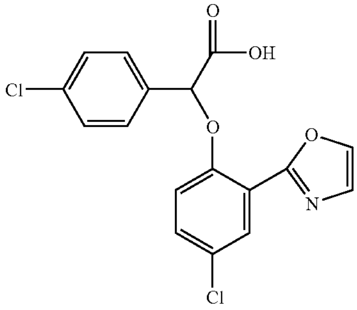

298

In the same manner as that described in Example 297 compound 298 was prepared from 298-S1 and 298-S2. $^1$H NMR (400 MHz, DMSO): δ 7.86–6.86 (m, 9H), 5.95 (s, 1H).

Example 299

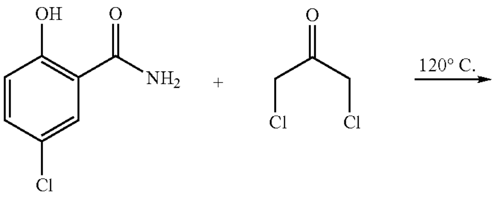

299-S1

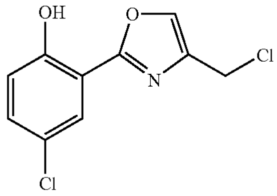

299-S2

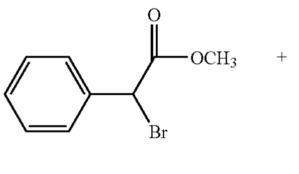

299-S3

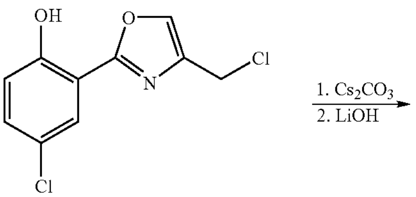

299-S2

-continued

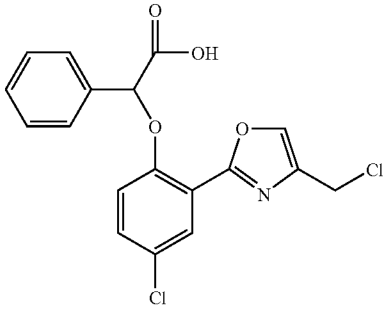

299

A mixture of 299-S1, dichloroacetone in a pressure vessel was stirred for several hours at 120° C. The resulting solid was dissolved in ethyl acetate. Purification with chromatography (hexanes/ethyl acetate 10/1) gave 299-S2 (6.2 g) as a white solid.

In the same manner as that described in Example 28 compound 299 was prepared from 299-S3 and 299-S2. $^1$H NMR (400 MHz, $CDCl_3$): δ 7.94–6.72 (m, 9H), 5.62 (s, 1H), 4.60 (s, 2H).

Example 300

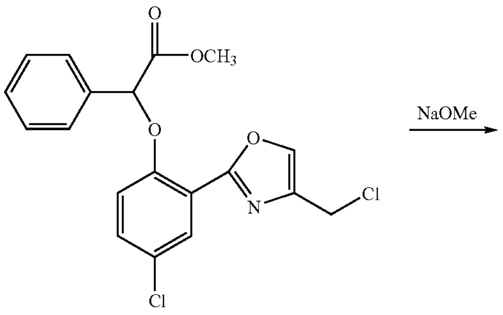

300-S1

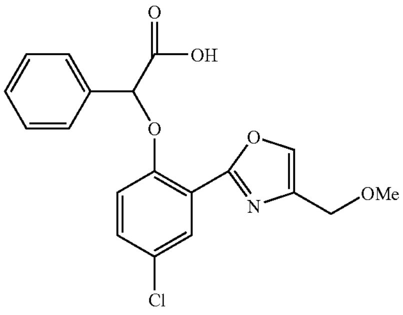

300

300-S1 (0.26 g) in DMF and 0.5 g NaOMe was stirred for one hour, quenched with HCl solution (1 N), diluted with water, extracted with ethyl acetate. The solvent was removed, and the residue was purified with chromatography (ethyl acetate) to give the acid product (0.23 g) as white solid. $^1$H NMR (400 MHz, $CDCl_3$): δ 8.00–6.50 (m, 9H), 5.62 (s, 1H), 4.54 (s, 2H), 3.50 (s, 3H).

Example 301

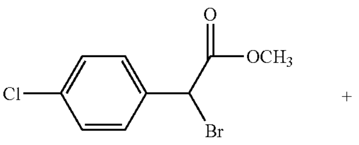

301-S1

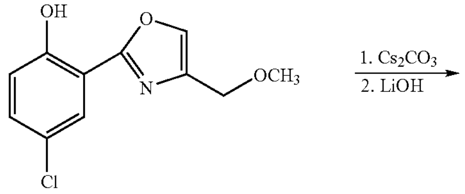

301-S2

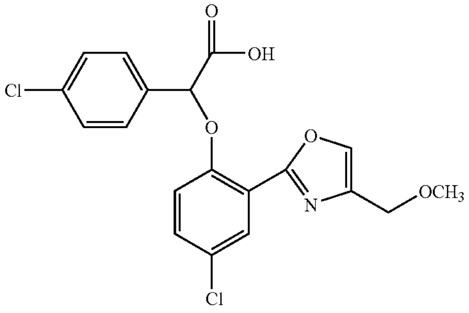

301

In the same manner as that described in Example 28 compound 301 was prepared from 301-S1 and 301-S2. $^1$H NMR (400 MHz, DMSO): δ 13.48 (br, 1H), 8.23–7.12 (m, 8H), 6.12 (s, 1H), 4.39 (s, 2H), 3.25 (s, 3H).

Example 302

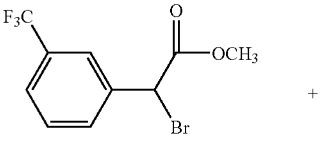

302-S1

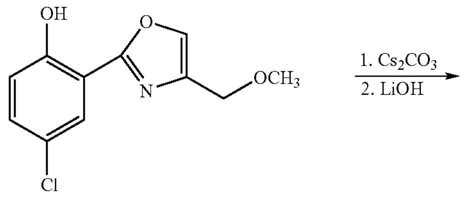

302-S2

-continued

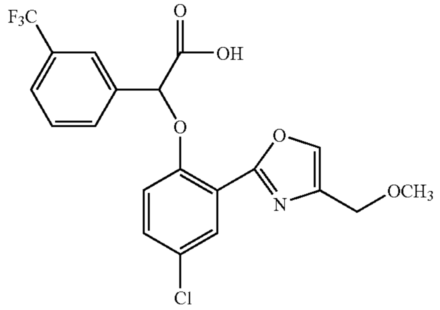

302

In the same manner as that described in Example 28 compound 302 was prepared from 302-S1 and 302-S2. $^{1}H$ NMR (400 MHz, DMSO): δ 8.17–7.16 (m, 8H), 6.29 (s, 1H), 4.39 (s, 2H), 3.45 (s, 3H).

Example 303

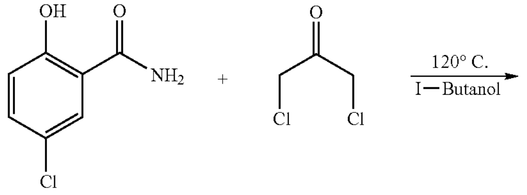

303-S1

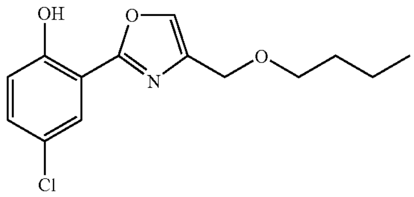

303-S2

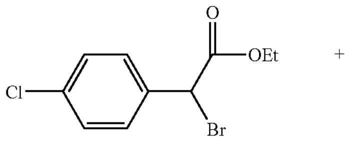

303-S3

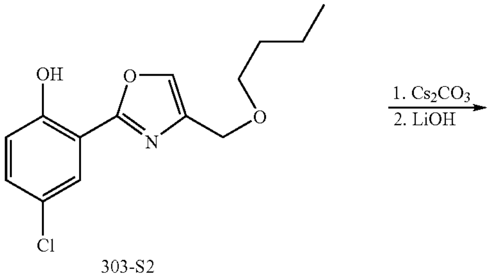

303-S2

-continued

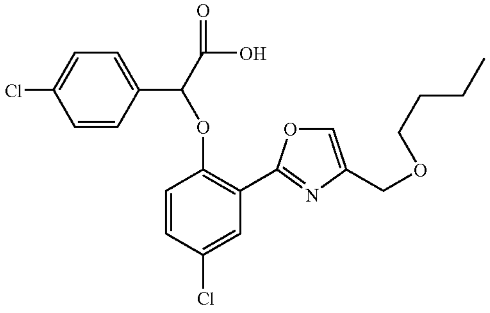

303

A mixture of 303-S1, dichloroacetone in 1-butanol was refluxed overnight. The solution was concentrated, and purified with chromatography (hexanes/ethyl acetate 5:1) to give 303-S2 (7.0 g) as colorless oil. $^{1}H$ NMR (400 MHz, $CDCl_3$): δ 11.02 (s, 1H), 7.80–7.01 (m, 4H), 4.50 (s, 2H), 3.58 (t, 2H), 1.57 (m, 2H), 1.40 (m, 2H), 0.95 (t, 3H).

In the same manner as that described in Example 28 compound 303 was prepared from 303-S2 and 303-S3. $^{1}H$ NMR (400 MHz, DMSO): δ 8.17–7.02 (m, 8H), 5.32 (s, 1H), 4.42 (s, 2H), 3.58 (m, 2H), 2.47 (m, 2H), 1.72 (m, 2H), 1.32 (m, 2H), 0.85 (t, 3H).

Example 304

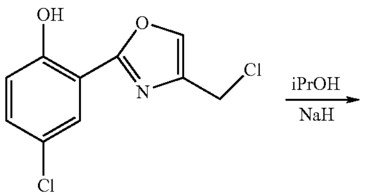

304-S1

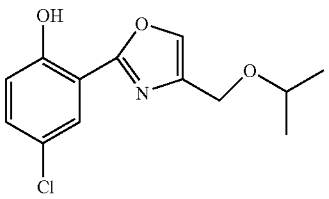

304

To a suspension of NaH (2.09 g, 60%) in DMF was added isopropanol (4 mL) drop wise at 0° C. The mixture was stirred for half an hour, and then a solution of 304-S1 (6 g) in DMF was added. The solution was stirred for several hours, diluted with ethyl acetate, washed with brine. The solvent was removed, the residue was purified with chromatography (hexanes/ethyl acetate 10:1) to give 304 (2.9 g) as a light yellow oil. $^{1}H$ NMR (400 MHz, $CDCl_3$): δ 11.07 (s, 1H), 7.79–6.99 (m, 4H), 4.51 (s, 2H), 3.78 (m, 1H), 1.24 (m, 6H).

Example 305

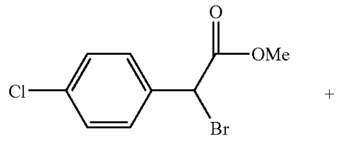

305-S1

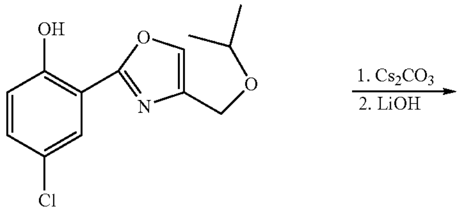

305-S2

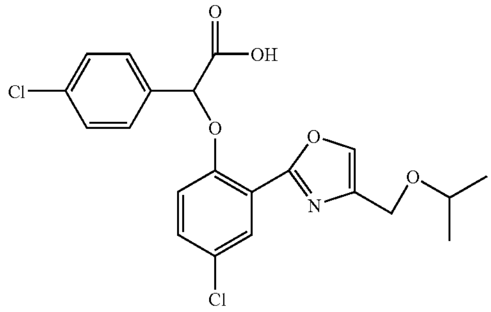

305

In the same manner as that described in Example 28 compound 305 was prepared from 305-S1 and 305-S2. $^1$H NMR (400 MHz, DMSO): δ 8.18–7.12 (m, 8H), 6.11 (s, 1H), 4.42 (s, 2H), 3.71 (m, 1H), 1.14 (d, 6H).

Example 306

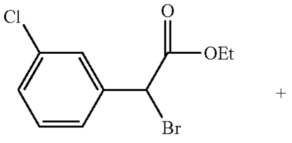

306-S1

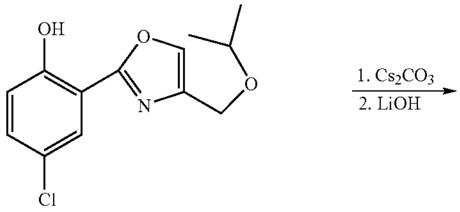

306-S2

-continued

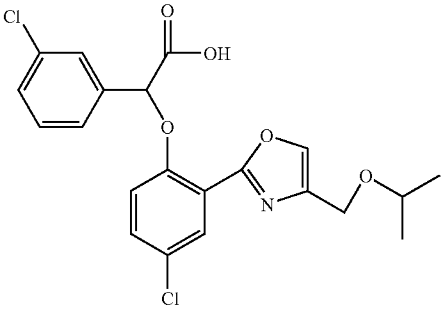

306

In the same manner as that described in Example 28 compound 306 was prepared from 306-S1 and 306-S2. $^1$H NMR (400 MHz, DMSO): δ 8.15–7.13 (m, 8H), 6.15 (s, 1H), 4.45 (s, 2H), 3.71 (m, 1H), 1.13 (d, 6H).

Example 307

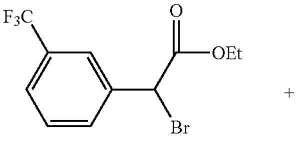

307-S1

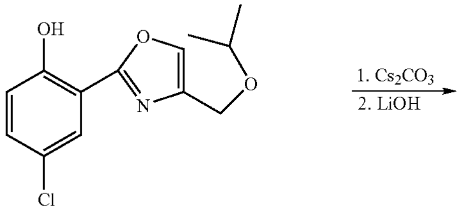

307-S2

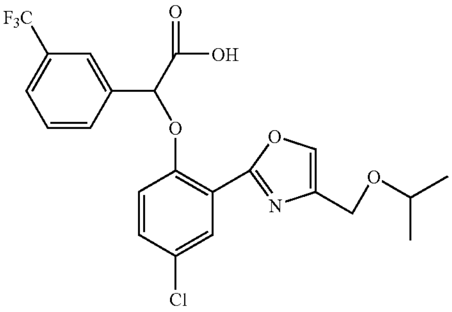

307

In the same manner as that described in Example 28 compound 307 was prepared from 307-S1 and 307-S2. $^1$H NMR (400 MHz, $CDCl_3$): δ 7.98–6.66 (m, 8H), 5.64 (s, 1H), 4.57 (s, 2H), 3.81 (m, 1H), 1.26 (d, 6H).

Example 308

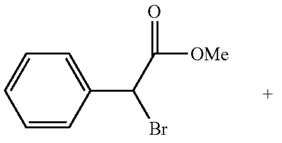

308-S1

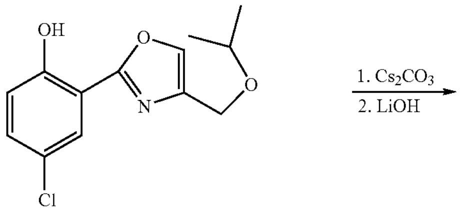

308-S2

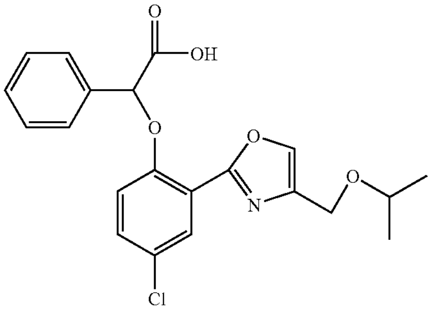

308

In the same manner as that described in Example 28 compound 308 was prepared from 308-S1 and 308-S2. $^{1}H$ NMR (400 MHz, $CDCl_3$): δ 7.96–6.70 (m, 9H), 5.61 (s, 1H), 4.57 (s, 2H), 3.81 (m, 1H), 1.27 (d, 6H).

Example 309

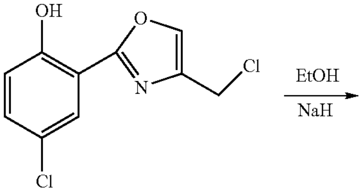

309-S1

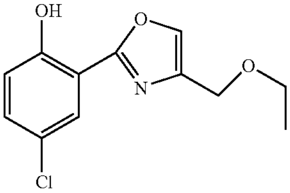

309

In the same manner as that described in Example 304 compound 309 was prepared from 309-S1. $^{1}H$ NMR (400 MHz, $CDCl_3$): δ 11.03 (s, 1H), 7.79–6.99 (m, 4H), 4.50 (s, 2H), 3.64 (q, 2H), 1.25 (t, 3H).

Example 310

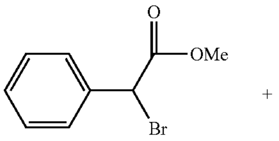

310-S1

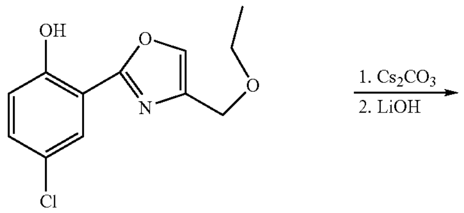

310-S2

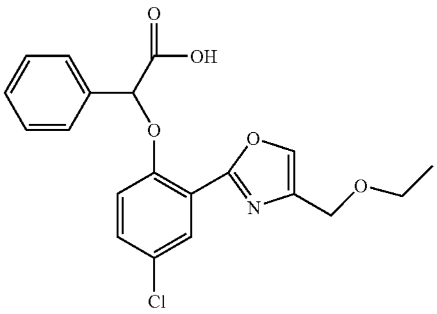

310

In the same manner as that described in Example 28 compound 310 was prepared from 310-S1 and 310-S2. $^{1}H$ NMR (400 MHz, DMSO): δ 13.37 (br, 1H), 8.21–7.14 (m, 9H), 6.07 (s, 1H), 4.41 (s, 2H), 3.54 (q, 2H), 1.13 (t, 3H).

Example 311

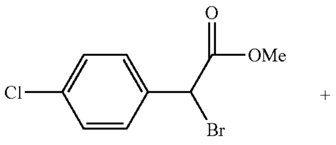

311-S1

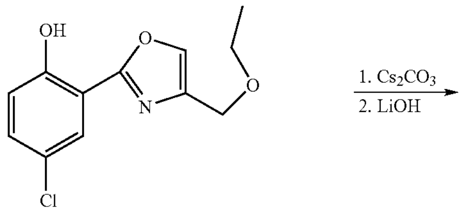

311-S2

-continued

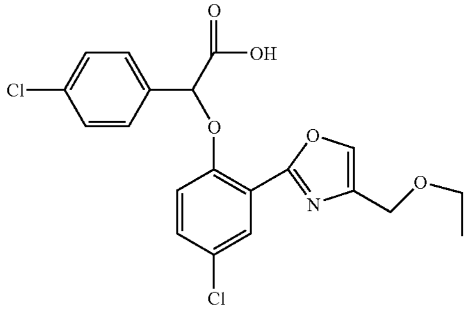

311

In the same manner as that described in Example 28 compound 311 was prepared from 311-S1 and 311-S2. $^1$H NMR (400 MHz, $CDCl_3$): δ 7.96–6.69 (m, 8H), 5.57 (s, 1H), 4.56 (s, 2H), 3.68 (q, 2H), 1.27 (t, 3H).

Example 312

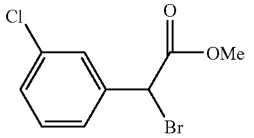

312-S1

+

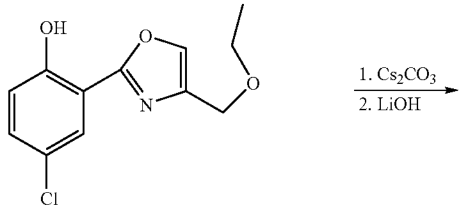

312-S2

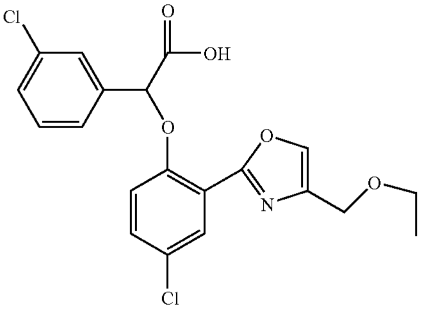

312

In the same manner as that described in Example 28 compound 312 was prepared from 312-S1 and 312-S2. $^1$H NMR (400 MHz, $CDCl_3$): δ 7.97–6.69 (m, 8H), 5.56 (s, 1H), 4.57 (s, 2H), 3.68 (q, 2H), 1.28 (t, 3H).

Example 313

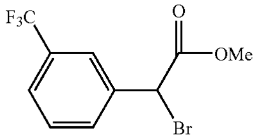

313-S1

+

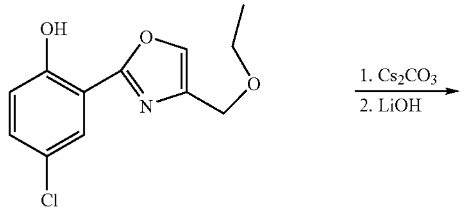

313-S2

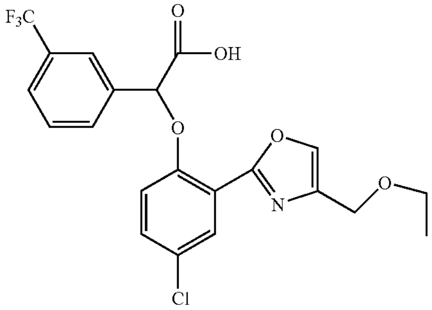

313

In the same manner as that described in Example 28 compound 313 was prepared from 313-S1 and 313-S2. $^1$H NMR (400 MHz, DMSO): δ 8.15–7.16 (m, 8H), 6.29 (s, 1H), 4.42 (s, 2H), 3.53(q, 2H), 1.12 (t, 3H).

Example 314

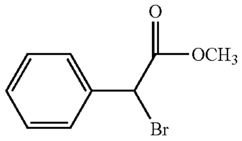

314-S1

+

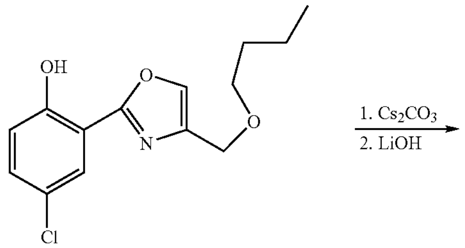

314-S2

-continued

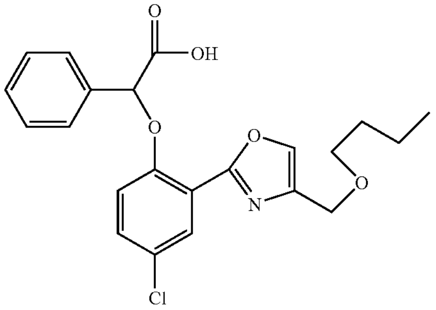

314

In the same manner as that described in Example 28 compound 314 was prepared from 314-S1 and 314-S2. $^1$H NMR (400 MHz, $CDCl_3$): 7.96–6.71 (m, 9H), 5.61 (s, 1H), 4.57 (s, 2H), 3.61 (t, 2H), 1.63 (m, 2H), 1.39 (m, 2H), 0.95 (t, 3H).

Example 315

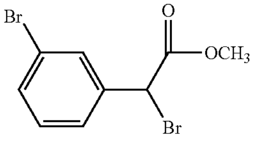

+

315-S1

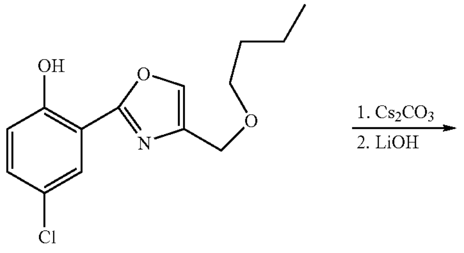

315-S2

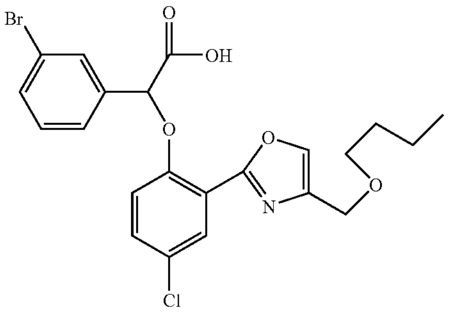

315

In the same manner as that described in Example 28 compound 315 was prepared from 315-S1 and 315-S2. $^1$H NMR (400 MHz, $CDCl_3$): δ 7.97–6.69 (m, 8H), 5.55 (s, 1H), 4.56 (s, 2H), 3.60 (t, 2H), 1.63 (m, 2H), 1.39 (m, 2H), 0.93 (t, 3H).

Example 316

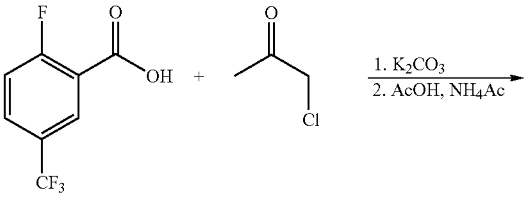

316-S1

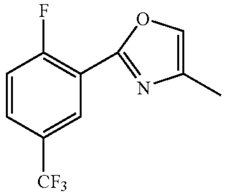

316-S2

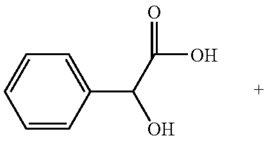

316-S3

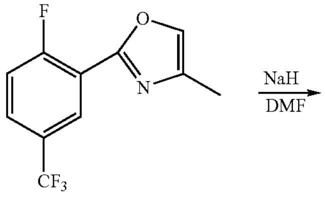

316-S2

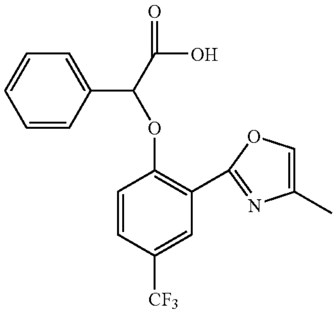

316

A mixture of acid 316-S1 (5 g), chloroacetone (2.3 mL) in DMF with $K_2CO_3$ (3.32 g) was stirred for several hours, diluted with ethyl acetate, washed with brine and dried. The solvent was removed, and the residue was dissolved in toluene. The solution was refluxed with $NH_4Ac$ (4.6 g), AcOH (50 mL) overnight. The solvent was removed. Purification with chromatography (hexanes/ethyl acetate 10:1) gave 316-S2 (0.45 g) as colorless oil. $^1$H NMR (400 MHz, $CDCl_3$): δ 8.35–7.26 (m, 4H), 2.28 (s, 3H).

To a suspension of NaH (0.13 g) in DMF (20 mL) was added drop wise a solution of 316-S3 (0.48 g) in DMF (20 mL) at 0° C. The mixture was stirred for half an hour, and was added the 316-S2 (0.43 g) in DMF (10 mL) solution. The solution was stirred for one hour, quenched with water, extracted with ethyl acetate, concentrated. Purification with chromatography (ethyl acetate) gave the acid (0.13 g) as a white solid. $^1$H NMR (400 MHz, $CDCl_3$): δ 8.28–6.92 (m, 9H), 5.73 (s, 1H), 2.37 (s, 3H).

Example 317

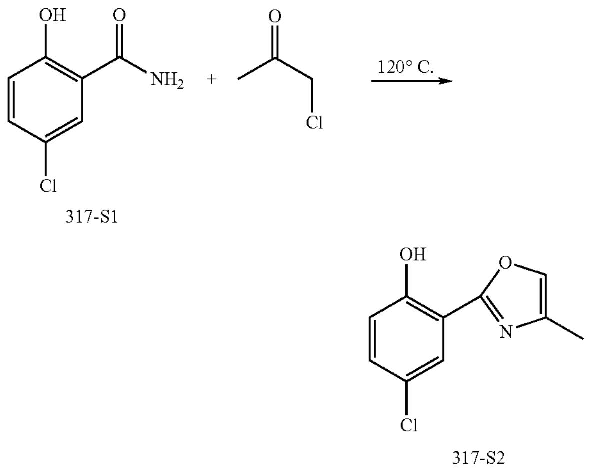

317-S1

317-S2

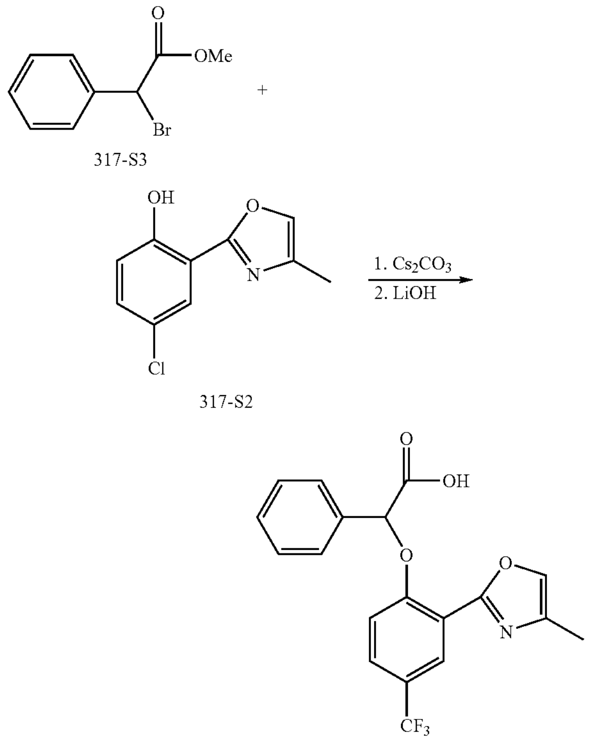

317-S3

317-S2

317

A mixture of 317-S1 (6.0 g), chloroacetone (10 mL) in a pressure vessel was stirred at 120° C. for several hours. The mixture turned to dark mud, which was dissolved in ethyl acetate. The solid left was filtered off. The solution was concentrated, and purified with chromatography (hexanes/ethyl acetate 20:3) to give 317-S2.

317-S2 was reacted with 1.5 g of317-S3 and 1 g of $Cs_2CO_3$ in $CH_3CN$. The was stirred for two hours. The solid was filtered off. The solution was concentrated and purified with chromatography (hexane/ethyl acetate 5:1) to give the ester. Hydrolysis with 1 N LiOH (20 mL) gave 317 (0.25 g) as a light yellow solid. $^1H$ NMR (400 MHz, $CDCl_3$): δ 7.95–6.72 (m, 9H), 5.61 (s, 1H), 2.33 (s, 3H).

Example 318

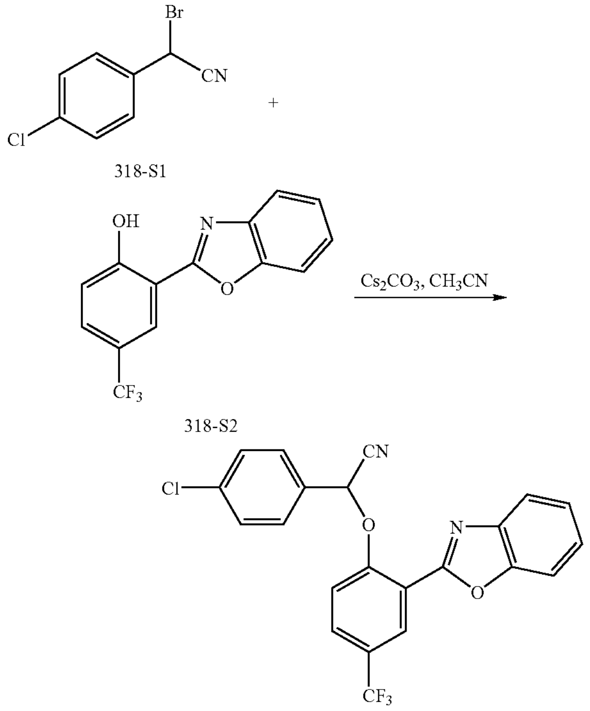

318-S1

318-S2

318

In the same manner as that described in Example 28 compound 318 was prepared from 318-S1 and 318-S2. $^1H$ NMR (400 MHz, $CDCl_3$): δ 8.01–7.26 (m, 11H), 6.11(s, 1H).

Example 319

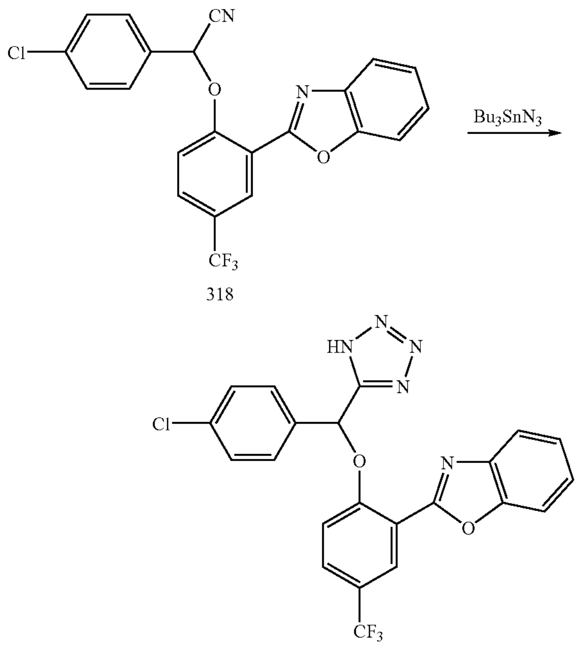

318

319

A solution of 318 (0.73 g), $Bu_3SnN_3$ (0.7 mL) in THF was refluxed overnight, then concentrated, and treated with 1N HCl. The solution was extracted with ethyl acetate, dried and concentrated. Purification with chromatography (ethyl acetate) gave 319 (0.43 g) as a white solid. $^1H$ NMR (400 MHz, DMSO): δ 8.37–7.42 (m, 12H).

Example 320

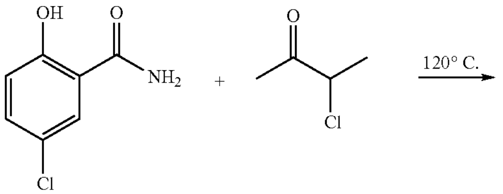

320-S1

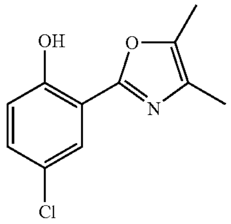

320-S2

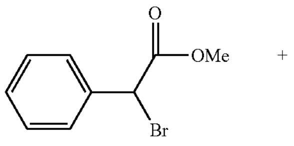

320-S3

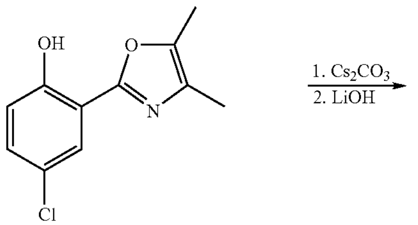

320-S2

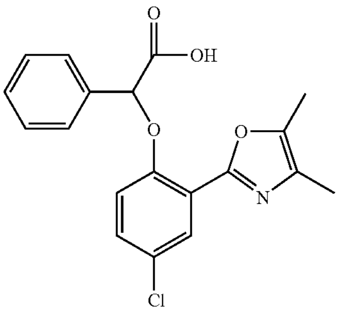

320

A mixture of 320-S1 (5.0 g), chlorobutanone (20 mL) in a pressure vessel was stirred at 120° C. for several hours. The mixture turned to dark mud, which was dissolved in ethyl acetate. The solid left was filtered off. The solution was concentrated, and purified with chromatography (hexanes/ethyl acetate 20:3) to give 320-S2 (0.19 g) as white solid. $^1H$ NMR (400 MHz, $CDCl_3$): δ 11.36 (s, 1H), 7.73–6.96 (m, 3H), 2.33 (s, 3H), 2.15 (s, 3H).

In the same manner as that described in Example 28 compound 320 was prepared from 320-S3 and 320-S2. $^1H$ NMR (400 MHz, $CDCl_3$): δ 7.90–6.68 (m, 8H), 5.57 (s, 1H), 2.38 (s, 3H), 2.23 (s, 3H).

The two enantiomers were separated by HPLC. Column: PIRKLE COVALENT, (R,R) Whelk-O 2 10/100, 25 cm×21.1 mm. Flow: 30 ml/min, 40% iPrOH/Hexanes-0.1% TFA.

Example 321

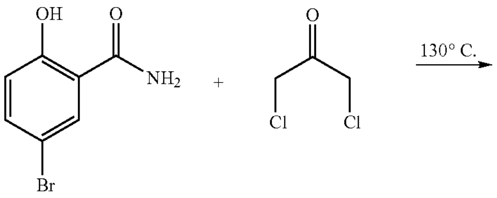

321-S1

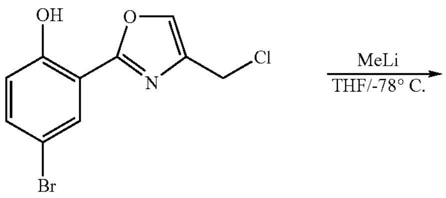

321-S2

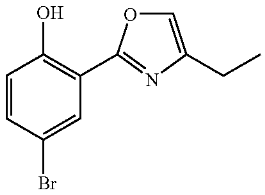

321

In the same manner as that described in Example 299 compound 321-S2 was prepared from 321-S1. $^1H$ NMR (400 MHz, $CDCl_3$): δ 10.84 (s, 1H), 7.93–6.96 (m, 4H), 4.56 (s, 2H).

To a solution of 321-S2 (1.2 g) in THF was added drop wise 6.2 mL MeLi (1.5 M) at −78° C. The solution was stirred for 30 mins, quenched with aqueous $NH_4Cl$ solution, extracted with ethyl acetate, and dried. Purification with chromatography (hexanes/ethyl acetate 5:1) gave 321 (0.72 g) as a white solid. $^1H$ NMR (400 MHz, $CDCl_3$): δ 11.35 (s, 1H), 7.90–6.93 (m, 4H), 2.62 (q, 2H), 1.27 (t, 3H).

Example 322

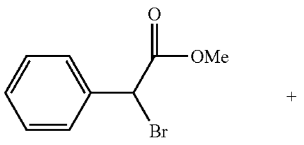

322-S1

-continued

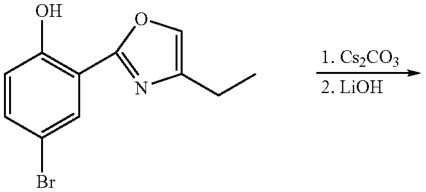

322-S2

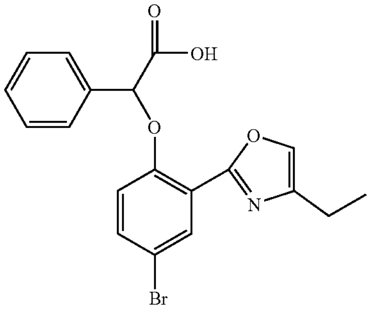

322

In the same manner as that described in Example 28 compound 322 was prepared from 322-S1 and 322-S2. $^1H$ NMR (400 MHz, $CDCl_3$): δ 8.10–6.67 (m, 9H), 5.62 (s, 1H), 2.72 (q, 2H), 1.33 (t, 3H).

Example 323

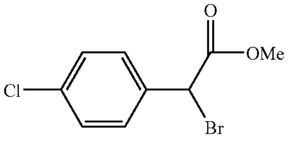

323-S1

+

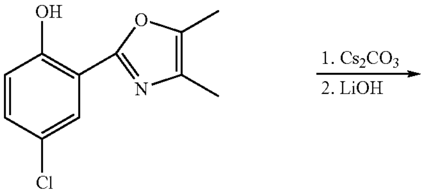

323-S2

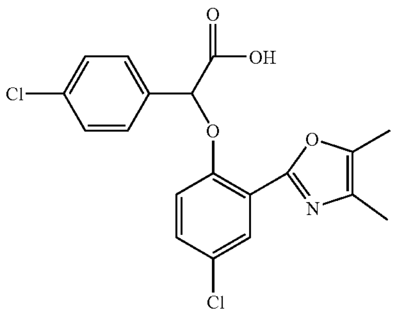

323

In the same manner as that described in Example 28 compound 323 was prepared from 323-S1 and 323-S2. $^1H$ NMR (400 MHz, $CDCl_3$): δ 7.83–6.96 (m, 7H), 6.07 (s, 1H), 2.31 (s, 3H), 2.10 (s, 3H).

Example 324

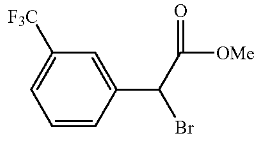

324-S1

+

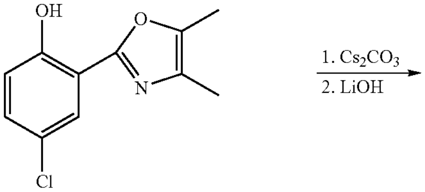

324-S2

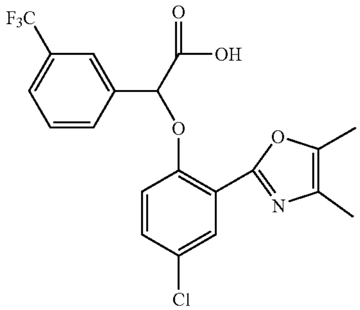

324

In the same manner as that described in Example 28 compound 324 was prepared from 324-S1 and 324-S2. $^1H$ NMR (400 MHz, $CDCl_3$): δ 8.12–6.65 (m, 7H), 5.63 (s, 1H), 2.36 (s, 2H), 2.22 (s, 3H).

Example 325

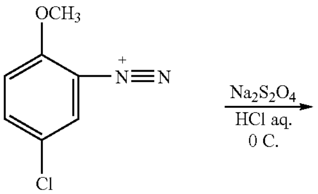

325-S1

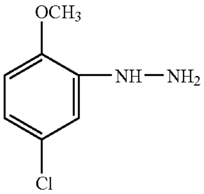

325-S2

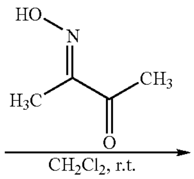

-continued

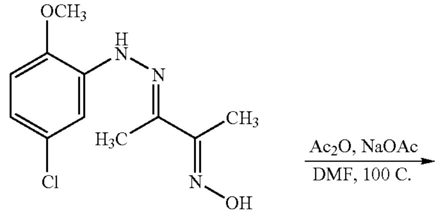

325-S3

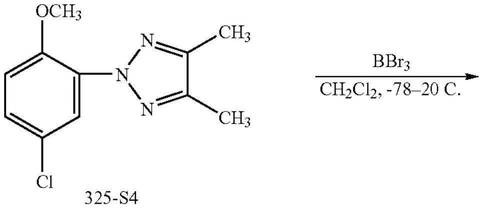

325-S4

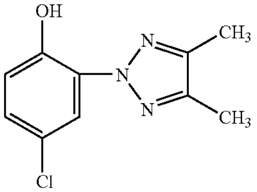

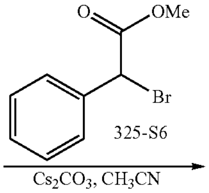

325-S6

$Cs_2CO_3$, $CH_3CN$

325-S5

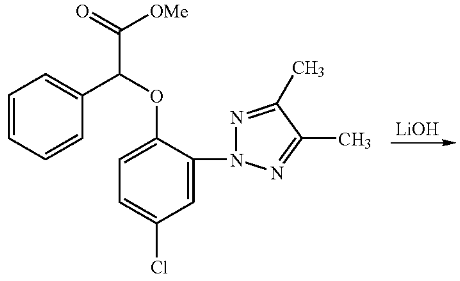

325-S7

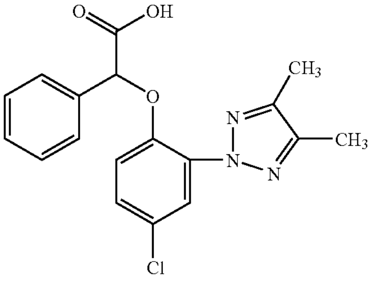

325

To a solution of diazo compound 325-S1(0.826 g, 3.02 mmol) in 1.5 N HCl (36 mL) was added slowly solid $Na_2S_2O_4$ (619 mg, 3.02 mmol) at 0° C. The mixture was stirred at 0 ° C. for 20 min, and quenched carefully with saturated aqueous $NaHCO_3$ solution. The mixture was extracted with EtOAc, washed with brine, dried and concentrated to give the phenyl hydrazine derivative 325-S2 as brown oil (156 mg) which was used for next reaction without further purification. $^1$H NMR (400 MHz, $CDCl_3$): δ 6.96 (d, J=2.0 Hz, 1H), 6.71(dd, J=2.0 and 8.4 Hz, 1H), 6.66 (d, J=8.4 Hz, 1H).

A mixture of the above hydrazine derivative (177 mg, 1.03 mmol) and diacetyl mono-oxime (104 mg, 1.03 mmol) in $CH_2Cl_2$ (5 mL) was stirred overnight at room temperature. The mixture was diluted with hexanes, and white solids were formed. After filtration and washing with hexanes, a white solid (138 mg) was obtained (325-S3). $^1$H NMR (400 MHz, $CDCl_3$): δ 7.89 (bs, 1H), 7.44 (d, J=2.4 Hz, 1H), 6.79(dd, J=2.8 and 8.8 Hz, 1H), 6.73 (d, J=8.8 Hz, 1H), 3.88 (s, 3H), 2.22(s, 3H), 2.08 (s, 3H).

A mixture of the above white solid (130 mg), acetyl anhydride (1 mL), and NaOAc (42 mg) in DMF (3 mL) was heated at 100° C. overnight. The mixture was diluted with EtOAc, washed with saturated aqueous $NaHCO_3$ solution and brine, dried and concentrated. Purification via flash column (5% to 30% EtOAc in hexanes) gave the triazole compound 325-S4 as colorless oil. $^1$H NMR (400 MHz, $CDCl_3$): δ 7.51 (d, J=2.8 Hz, 1H), 7.34 (dd, J=2.8 and 8.8 Hz, 1H), 6.98 (d, J=8.8 Hz, 1H), 3.87 (s, 3H), 2.33 (s, 6H).

To a solution of the above triazole compound (90 mg) in $CH_2Cl_2$ (5 mL) was added drop wise $BBr_3$ (0.15 mL) at −78° C. The mixture was warmed to −20° C. over 2 hours, and quenched with saturated aqueous $NaHCO_3$ solution. The mixture was extracted with EtOAc, washed with brine, dried and concentrated to give the triazole phenol compound 325-S5 as an off-white solid (80 mg). $^1$H NMR (400 MHz, $CDCl_3$): δ 10.75 (s, 1H), 8.0 (d, J=2.4 Hz, 1H), 7.14 (dd, J=2.8 and 8.8 Hz, 1H), 7.01 (d, J=8.8 Hz, 1H), 2.38 (s, 6H).

The target compound 325 was prepared from 325-S5 and 325-S6 in the same manner as that described in Example 28.

$^1$H NMR (400 MHz, $CDCl_3$): δ 7.87 (d, J=2.8 Hz, 1H), 7.47 (m, 2H), 7.36–7.32 (m, 3H), 7.08 (dd, J=2.8 and 8.8 Hz, 1H), 6.77 (d, J=8.8 Hz, 1H), 5.63 (s, 1H), 2.33 (s, 6H).

The two enantiomers were separated by HPLC. Column: PIRKLE COVALENT, (R,R) Whelk-O 2 10/100, 25 cm×21.1 mm. Flow: 30 ml/min, 25% iPrOH/Hexanes-0.1% TFA.

Example 325A

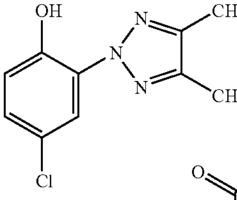

+

325A-S1

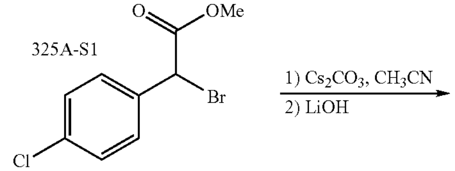

325A-S2

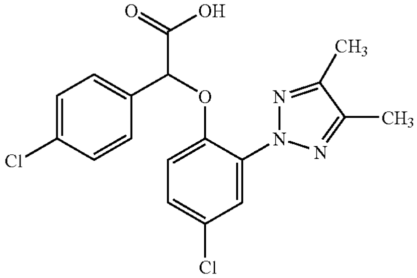

325A

Compound 325A was prepared from 325A-S1 and 325A-S2 in the same manner as that described in Exaple 28. $^1$H NMR (400 MHz, DMSO-$d_6$): δ 7.60 (d, J=2.8 Hz, 1H), 7.54–7.44 (m, 5H), 7.15 (d, J=9.2 Hz, 1H), 5.96 (s, 1H), 2.26 (s, 6H).

The two enantiomers were separated by HPLC. Column: PIRKLE COVALENT, (R,R) Whelk-O 2 10/100, 25 cm×21.1 mm. Flow: 30 ml/min, 30% iPrOH/Hexanes-0.1% TFA.

Example 325B

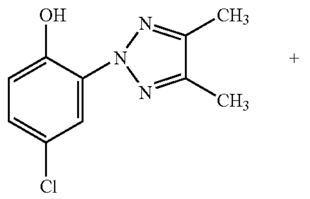

325BS-1

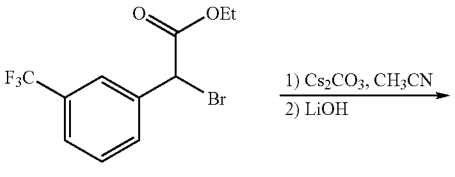

325B-S2

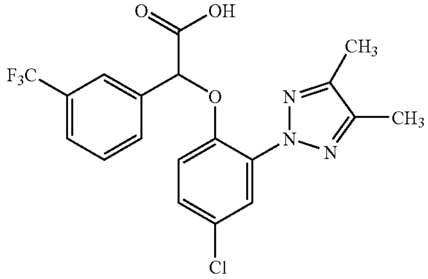

325B

Compound 325B was prepared from 325B-S1 and 325B-S2 in the same manner as that described in Example 28. $^1$H NMR (400 MHz, DMSO-$d_6$): δ 7.94 (d, J=2.4 Hz, 1H), 7.79–7.55 (m, 5H), 7.20 (dd, J=2.8 and 9.2 Hz, 1H), 6.83 (d, J=9.2 Hz, 1H), 5.78 (s, 1H), 2.42 (s, 6H).

The two enantiomers were separated by HPLC. Column: PIRKLE COVALENT, (R,R) Whelk-O 2 10/100, 25 cm×21.1 mm. Flow: 30 ml/min, 30% iPrOH/Hexanes-0.1% TFA.

Example 325C

325C-S1

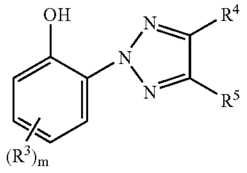

-continued

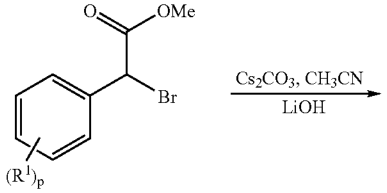

325C-S2

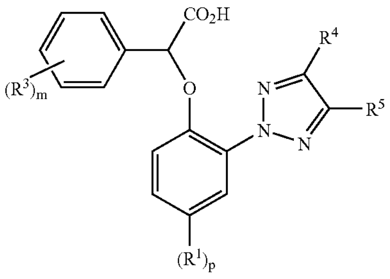

325C

In the same manner as that described in Example 28 compound 325C was prepared from 325C-S1 and 325CA-S2.

Example 326

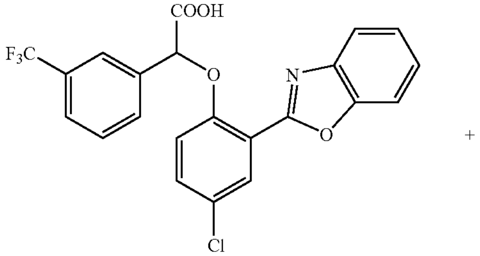

326-S1

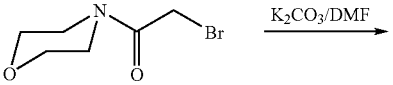

326-S2

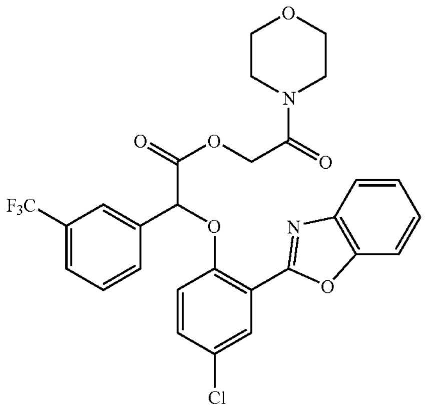

326

Bromide 326-S2 was prepared by reaction of bromoacetyl bromide (1.0 eq.) and morpholine (1.0 eq.) with triethylamine (1.02 eq.) in $CH_2Cl_2$ at 0° C. for 1.5 h. To a solution of 326-S1 (1.99 g, 4.44 mmol) in DMF (10 mL) at rt was added $K_2CO_3$ (0.64 g, 9.30 mmol), and then followed by 326-S2 (1.55 g, 7.45 mmol). After stirring for 40 min at rt, the reaction mixture was diluted with EtOAc and aq. $NH_4Cl/H_2O$. The organic layer was washed with aq. $NH_4Cl/H_2O$, and then brine/water, dried over $Na_2SO_4$, concentrated in vacuo. Purification via chromatography with EtOAc/hexanes (30% to 50%) to afforded 326 (1.34 g, 52%) as an off-white solid. $^1H$ NMR (400 MHz, $CDCl_3$): δ 8.37 (1H, s), 8.25 (1H, s), 7.99 (1H, d, J=7.2 Hz), 7.81 (1H, m), 7.68 (1H, d, J=7.2 Hz), 7.56 (2H, m), 7.48 (1H, m), 7.38 (2H, m), 7.28 (1H, m), 6.02 (1H, s), 4.92 (1H, d, J=14.0 Hz), 4.64 (1H, d, J=14.0 Hz), 3.60–3.66 (6H, m), 3.27 (2H, m) ppm.

Example 327

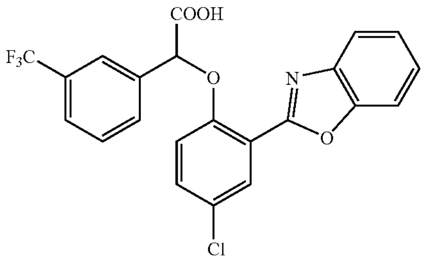

327-S1

+

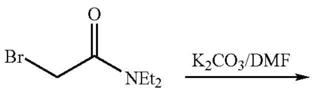

327-S2

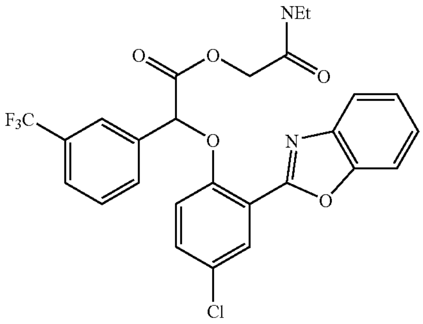

327

To a solution of 327-S1 (2.16 g, 4.82 mmol) in DMF (10 mL) at rt was added $K_2CO_3$ (0.50 g, 3.62 mmol), and then followed by 327-S2 (1.42 g, 7.32 mmol). After stirring for 30 min at rt, the reaction mixture was diluted with EtOAc and aq. $NH_4Cl/H_2O$. The organic layer was washed with aq. $NH_4Cl/H_2O$, and then brine/water, dried over $Na_2SO_4$, concentrated in vacuo. Purification via chromatography with EtOAc/hexanes (30% to 50%) to afforded 327 (2.05 g, 76%) as a white solid. $^1H$ NMR (400 MHz, $CDCl_3$): δ 8.37 (1H, s), 8.24 (1H, d, J=2.8 Hz), 8.00 (1H, d, J=7.8 Hz), 7.81 (1H, m), 7.67 (1H, d, J=7.8 Hz), 7.46–7.59 (3H, m), 7.30–7.39 (2H, m), 7.31 (1H, d, J=8.8 Hz), 6.03 (1H, s), 4.97 (1H, d, J=14.2 Hz), 4.59 (1H, d, J=14.2 Hz), 3.45 (1H, m), 3.32 (1H, m), 3.15–3.31 (2H, m), 1.15 (6H, m) ppm.

Example 328

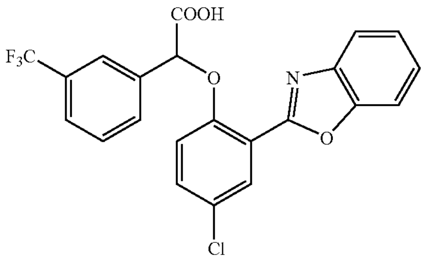

328-S1

+

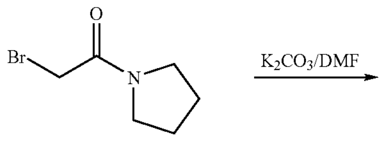

328-S2

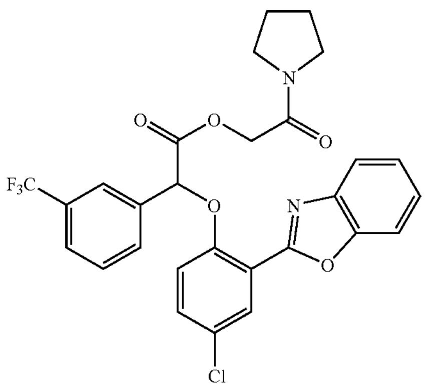

328

Bromide 328-S2 was prepared by reaction of bromoacetyl bromide (1.0 eq.) and pyrrolidine (1.0 eq.) with triethylamine (1.01 eq.) in $CH_2Cl_2$ at −5° C. for 1.5 h. To a solution of 328-S1 (2.19 g, 4.90 mmol) in DMF (20 mL) at rt was added $K_2CO_3$ (0.66 g, 4.78 mmol), and then followed by bromide (1.41 g, 7.39 mmol). After stirring for 1 h at rt, the reaction mixture was diluted with EtOAc and aq. $NH_4Cl/H_2O$. The organic layer was washed with aq. $NH_4Cl/H_2O$, and then brine/water, dried over $Na_2SO_4$, concentrated in vacuo. Purification via chromatography with EtOAc/hexanes (30% to 50%) to afforded 328 (1.91 g, 70%) as a white solid. $^1H$ NMR (400 MHz, $CDCl_3$): δ 8.38 (1H, s), 8.24 (1H, d, J=2.8 Hz), 8.01 (1H, d, J=7.4 Hz), 7.81 (1H, m), 7.68 (1H, d, J=7.4 Hz), 7.50–7.59 (3H, m), 7.37–7.39 (2H, m), 7.30 (1H, d, J=9.2 Hz), 6.04 (1H, s), 4.86 (1H, d, J=14.4 Hz), 4.53 (1H, d, J=14.4 Hz), 3.49 (2H, m), 3.28 (2H, m), 1.94 (2H, m), 1.84 (2H, m) ppm.

Example 329

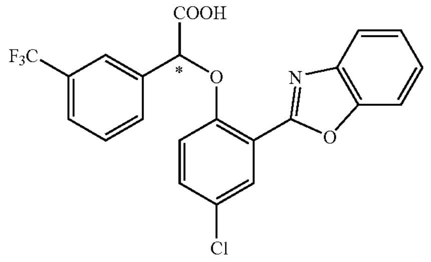

329-S1

+

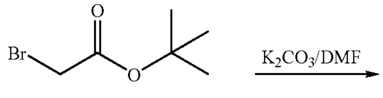

329-S2

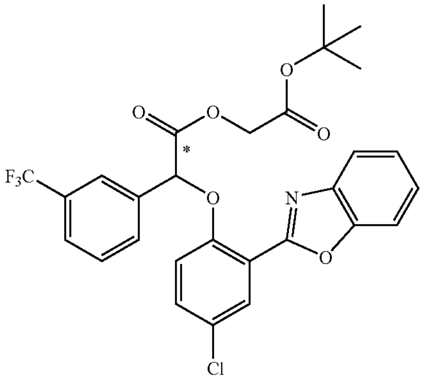

329

In the same manner as that described in Example 328 compound 329 was prepared from 329-S1 and 329-S2. (m.p. 80–82° C.). $^1$H-NMR (400 MHz, $d_6$-DMSO) δ 8.31 (s, 1H), 8.12 (d, 1H, J=2.4), 8.04 (d, 1H, J=7.6), 7.66–7.82 (m, 5H), 7.43–7.49 (m, 2), 7.34 (d, 1H, J=9.2), 6.65 (s, 1H), 4.61 (s, 2H), 1.23 (s, 9H). Chiral HPLC conditions: 4.6×250 mm Regis Whelk-O-1 column; 970:30:1 hexanes/IPA/TFA @ 1.5 mL/min @ r.t.; detection at 220 nm. Retention time of major enantiomer: 7.8 minutes. Retention time of the minor enatiomer: 8.2 minutes.

Example 330

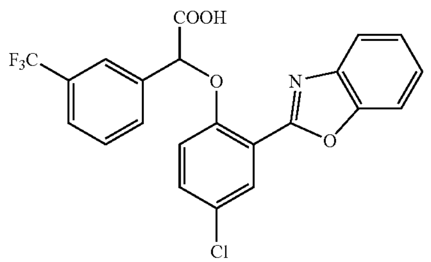

330-S1

+

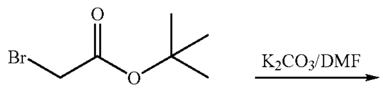

330-S2

-continued

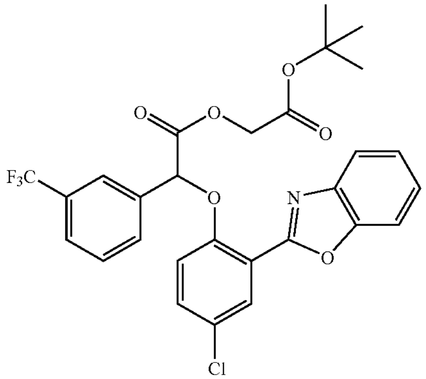

330

In the same manner as that described in Example 329 compound 330 was prepared from 330-S1 and 329-S2. Melting point: 93–95° C.

Example 331

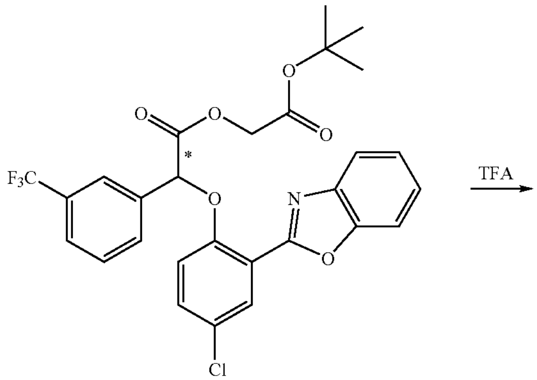

331-S1

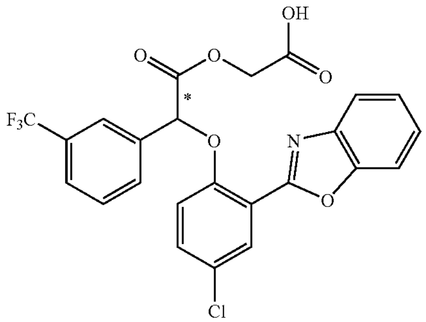

331

To a flask under air was added 15.2 g (33.9 mmol) of 331-S1, 80 mL of $CH_2Cl_2$ and 80 mL of TFA (1040 mmol; 30.6 equiv.). After stirring at room temperature for 2 hours, 500 mL of heptane was added to the reaction mixture and the volatiles were removed via a rotatory evaporator at room temperature. The resulting white solid was further dried under vacuum to give 13.9 g of 331 as a white solid (m.p. 200–202° C.). $^1$H-NMR (400 MHz, $d_6$-DMSO) δ 13.2 (br, 1H), 8.31 (s, 1H), 8.12 (d, 1H, J=2.8), 8.03 (d, 1H, J=8.0), 7.63–7.81 (m, 5H), 7.42–7.49 (m, 2H), 7.36 (d, 1H, J=9.2), 6.65 (s, 1H), 4.66 (s, 2H).

Example 332

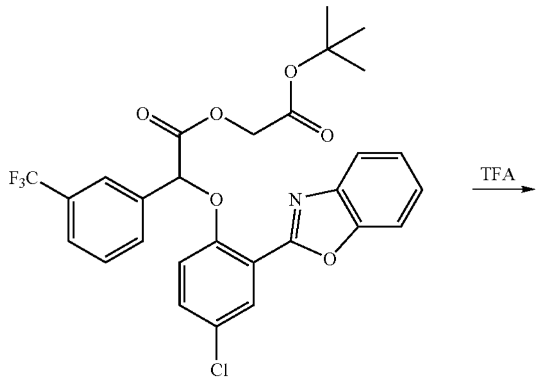

332-S1

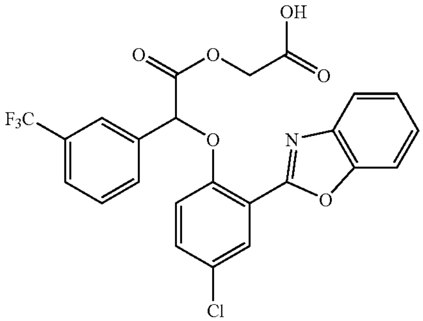

332

With the exception that 332-S1 (the racemic compound) was used as the starting material, this compound was synthesized via a procedure analogous to that used in the preparation of 331. 89% yield. Melting point: 208–210° C.

Example 333

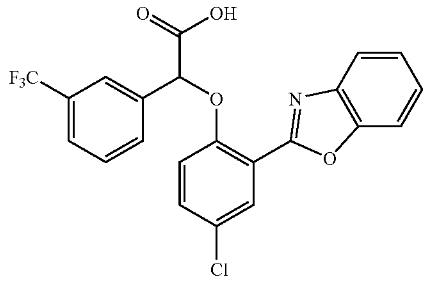

333-S1

+

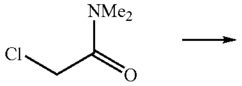

-continued

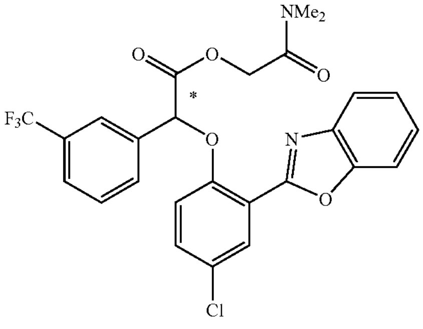

333

To a flask was added 3.08 g (22.3 mmol; 1.00 equiv.) of $K_2CO_3$, 50 mL of DMF, 10.0 g (22.3 mmol) of 333-S1 and 5.0 mL (48.4 mmol; 2.17 equiv.) of 2-chloro-N,N-dimethylacetamide. After stirring at room temperature for 6 hours, the reaction mixture was poured into 300 mL of EtOAc and washed with water 2×200 mL. To the organic phase was added 300 mL of heptane. The organic phase was concentrated to 300 mL via a rotatory evaporator and the resulting precipitate was collected in a filter funnel. After air drying, 10.6 g (89% yield) of a white solid (m.p. 145–147° C.) was obtained. $^1$H-NMR (400 MHz, $d_6$-DMSO) δ 8.30 (s, 1H), 8.13 (d, 1H, J=2.4), 8.06 (d, 1H, J=8.4), 7.67–7.76 (m, 5H), 7.43–7.47 (m, 3H), 6.62 (s, 1H), 4.92 (d, 1H, J=14.8), 4.85 (d, 1H, J=14.8), 2.83 (s, 3H), 2.77 (s, 3H).

Example 334

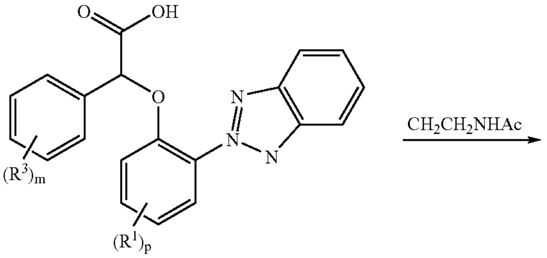

340-S1

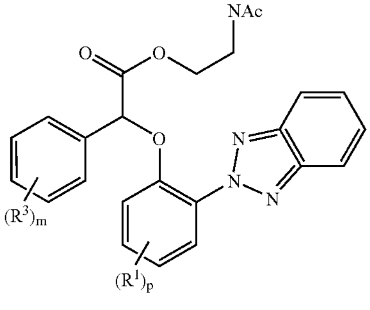

340

In the same manner as that described in Example 136 compound 340 was prepared from 340-S1.

Example 335

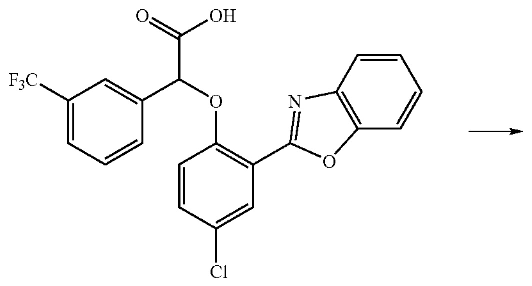

335-S1

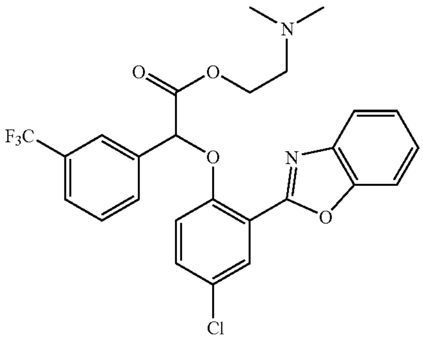

335

To a flask under air was added 8.96 g (20.0 mmol) of 335-S1, 100 mL of anhydrous DMF and 4.05 g (25.0 mmol; 1.25 equiv.) of 1,1'-carbonyldiimidazole. After stirring at room temperature for 30 minutes, 6.6 mL (49.9 mmol; 2.50 equiv.) of 2-dimethylamino-ethanol was added. After stirring for an additional 2 hours at room temperature, the reaction mixture was poured into 500 mL of EtOAc and rinsed with water 3×250 mL. After phase separation, 500 mL of heptane was added to the organic phase. The organic phase was concentrated to ~200 mL via a rotaotory evaporator. The resulting precipitate was collected in a filter funnel and rinsed with heptane 2×50 mL. After air drying, 6.62 g (61% yield) of a white solid (m.p. 78–80° C.) was obtained. $^1$H-NMR (400 MHz, $d_6$-DMSO) δ 8.29 (s, 1H), 8.12 (d, 1H, J=2.4), 8.02 (d, 1H, J=8.0), 7.66–7.83 (m, 5H), 7.43–7.49 (m, 2H), 7.31 (d, 1H, J=8.8), 6.52 (s, 1H), 4.09 (m, 2H), 2.46 (m, 2H), 2.27 (q, 4H, J=7.2), 0.71 (t, 6H, J=7.2).

Example 336

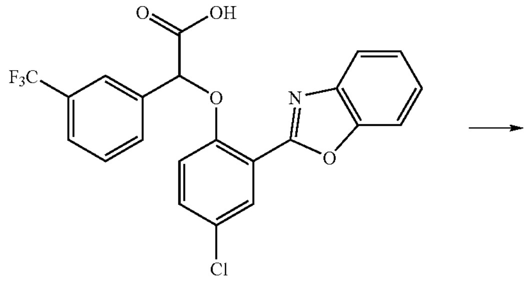

336-S1

-continued

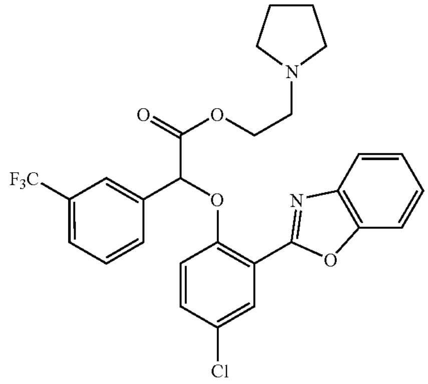

336

This compound was synthesized via a procedure analogous to that used in the preparation of 335 with the exception that 2.50 equiv. of 2-pyrrolidin-1-yl-ethanol was used instead. 77% yield. Melting point: 97–99° C. $^1$H-NMR (400 MHz, $d_6$-DMSO) δ 8.30 (s, 1H), 8.13 (d, 1H, J=2.4), 8.02 (d, 1H, J=7.6), 7.65–7.83 (m, 5H), 7.45–7.48 (m, 2H), 7.31 (d, 1H, J=8.8), 6.55 (s, 1H), 4.13 (m, 2H), 2.46 (m, 2H), 2.21 (m, 4H), 1.46 (m, 4H).

Example 337

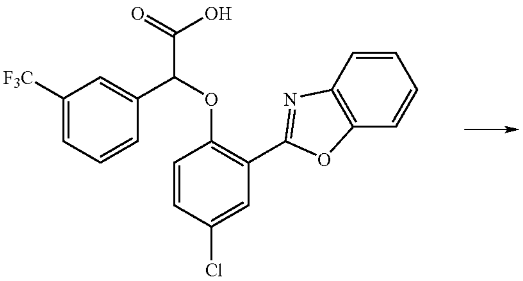

337-S1

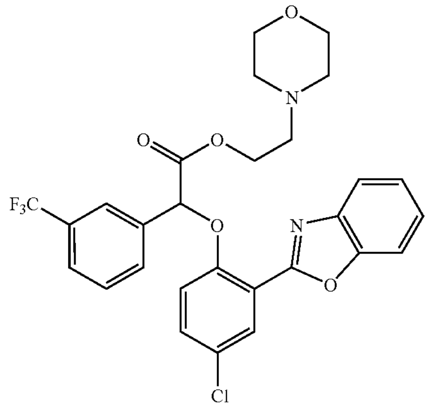

337

This compound was synthesized via a procedure analogous to that used in the preparation of 335 with the exception that 2.50 equiv. of 2-morpholin-4-yl-ethanol was used instead. 82% yield. Melting point: 93–95° C. $^1$H-NMR (400 MHz, $d_6$-DMSO) δ 8.30 (s, 1H), 8.13 (d, 1H, J=2.4), 8.02 (d, 1H, J=8.0), 7.67–7.82 (m, 5H), 7.45–7.50 (m, 2H), 7.31 (d, 1H, J=9.2), 6.55 (s, 1H), 4.19 (m, 1H), 4.11 (m, 1H), 2.46 (m, 2H), 3.28 (m, 4H), 2.32 (m, 2H), 2.10 (m, 4H).

Example 338

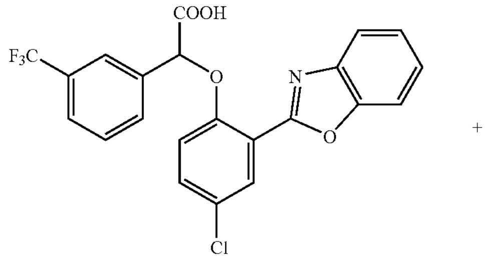

338-S1

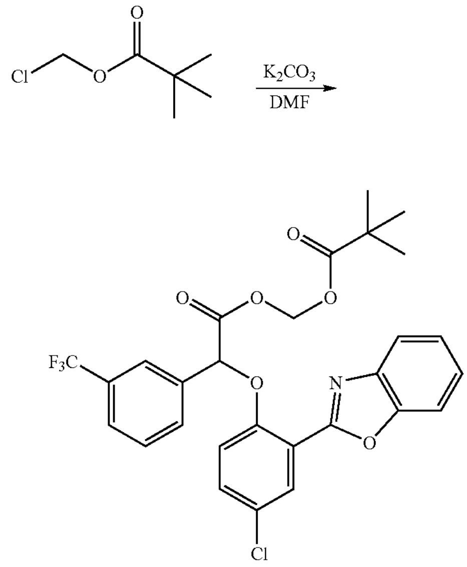

338

To a solution of 338-S1 (2.35 g, 5.25 mmol) in DMF (15 mL) at rt was added $K_2CO_3$ (1.06 g, 7.67 mmol), and then followed by chloromethyl pivalate (2.0 mL, 13.5 mmol). After stirring for 1 h at 40° C., the reaction mixture was diluted with EtOAc and aq. $NH_4Cl/H_2O$. The organic layer was washed with aq. $NH_4Cl/H_2O$, and then brine/water, dried over $Na_2SO_4$, concentrated in vacuo. Purification via chromatography with EtOAc/hexanes (10% to 20%) to afforded 338 (1.19 g, 40%) as a white solid. $^1H$ NMR (400 MHz, $CDCl_3$): δ 8.32 (1H, s), 8.27 (1H, d, J=2.8 Hz), 7.92 (1H, d, J=7.2 Hz), 7.82 (1H, m), 7.68 (1H, d, J=7.2 Hz), 7.54–7.58 (2H, m), 7.38–7.43 (3H, m), 6.97 (1H, d, J=8.8 Hz), 5.89 (1H, s), 5.81 (1H, d, J=5.4 Hz), 5.72 (1H, d, J=5.4 Hz), 1.04 (9H, s) ppm.

In Vivo Activities

The anti-diabetic activities of the compounds were evaluated in the C57BL/6j ob/ob Mice model.

A. Materials and Methods

Male, 7–9 weeks old, C57BL/6J ob/ob mice were purchased from The Jackson Laboratory (Bar Harbor, Me., USA). Animals were housed (4–5 mice/cage) under standard laboratory conditions at 22±3° C. temperature and 50±20% relative humidity, and were maintained on a diet of Purina rodent chow and water ad libitum. Prior to treatment, blood was collected from the tail vein of each animal. Mice that had non-fasting plasma glucose levels between 250 and 500 mg/dl were used. Each treatment group consisted of 8–10 mice that were distributed so that the mean glucose levels were equivalent in each group at the start of the study. Mice were dosed orally by gavage once a day for 1–4 days with vehicle and one or more dose of test compound at a dose ranging from 5 to 125 mg/kg. Compounds were delivered in a liquid formulation containing 5% (v/v) dimethyl sulfoxide (DMSO), 1% (v/v) Tween 80® and 0.9% (w/v) methylcellulose. The gavage volume was 10 ml/kg. Blood sample taken at 6 hours after the each dose and analyzed for plasma glucose. Food intake and body weight were measured daily. Plasma glucose concentrations were determined colorimetrically using a commercial glucose oxidase method (Sigma Chemical Co, St. Louis, Mo., USA). Significant difference between groups (comparing drug-treated to vehicle-treated) was evaluated using the Student unpaired t-test.

B. Results

Figure 6:
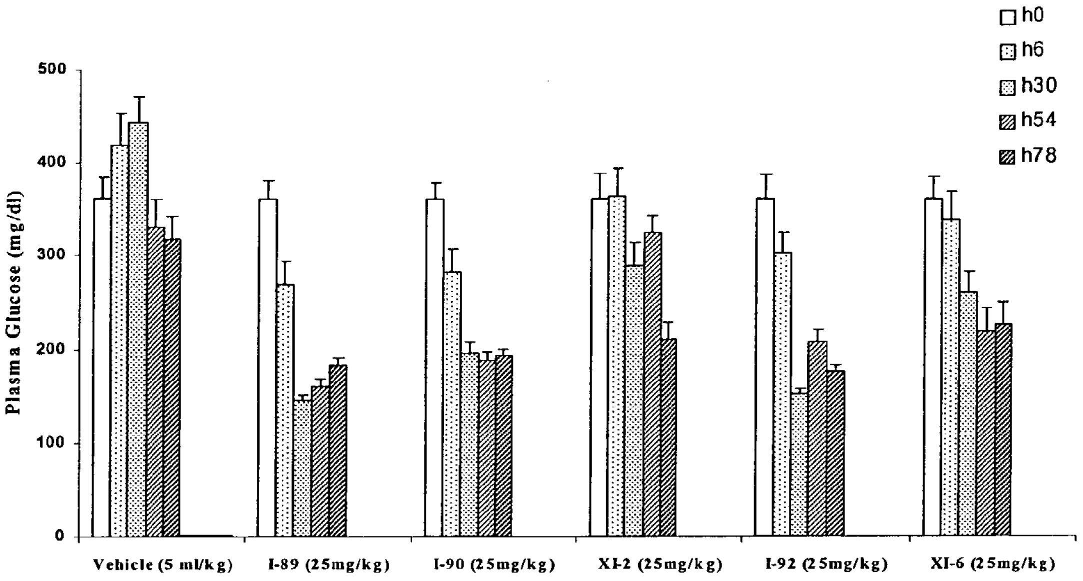
FIG. 6 is a histogram illustrating the glucose lowering effect of selected compounds of the invention in ob/ob mice.

FIG. 6 illustrates the anti-diabetic effects of selected compounds of the present invention. Table 15 provides the relative potency of some of these selected compounds. Compounds that are effective for glucose lowering at the dose of ≧125 mg/kg are assigned a potency of +; compounds that are effective for glucose lowering at a dose of >25 mg/kg but <mg/kg are assigned a potency of ++; compounds that are effective for glucose lowering at a dose of ≦5 mg/kg are assigned a potency of +++. For example, a compound at 25 mg/kg that lowered the animal glucose level from 400 mg/dL (vehicle group value) to 250 mg/dl, is assingned the potency of +++.

TABLE 13

Potency of Invention Compounds

| Number | Compound # | Potency | Insulin Level compared with vehicle |
|---|---|---|---|
| 1 | I-1 | ++ | Lower |
| 2 | I-3 | + | Lower |
| 3 | I-89 | +++ | Lower |
| 4 | I-92 | +++ | Lower |
| 5 | I-190 | +++ | Lower |
| 6 | I-191 | +++ | Lower |
| 7 | I-193 | +++ | Lower |
| 8 | I-194 | +++ | Lower |
| 9 | I-369 | +++ | Lower |
| 10 | I-372 | +++ | Lower |
| 11 | Ia-365 | +++ | Lower |
| 12 | Ia-366 | +++ | Lower |
| 13 | IX-2 | ++ | Lower |
| 14 | IX-5 | ++ | Lower |
| 15 | XI-2 | +++ | Lower |
| 16 | XI-6 | +++ | Lower |
| 17 | XI-24 | +++ | Lower |
| 18 | XI-47 | +++ | Lower |
| 19 | XI-51 | +++ | Lower |
| 20 | XIa-5 | +++ | Lower |
| 21 | XIa-51 | +++ | Lower |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent application cited herein are hereby incorporated by reference in their entirety for all purposes.

What is claimed is:

1. A compound having a formula selected from the group consisting of:

Ia

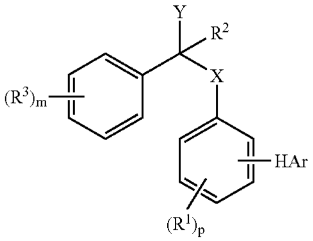

and

Ib

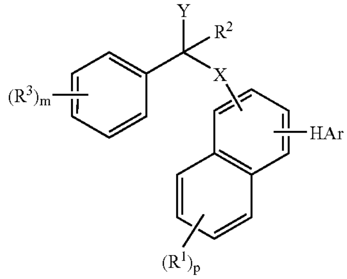

wherein

X is a member selected from the group consisting of O, S, SO, $SO_2$ and NR, wherein R is H, $(C_1-C_8)$alkyl, $COR^a$, $COOR^a$ and $CONR^aR^b$ wherein $R^a$ and $R^b$ are each independently selected from the group consisting of H and $(C_1-C_8)$alkyl;

Y is a member selected from the group consisting of $CH_2OR^c$, $CO_2R^c$, CHO, $CONR^cR^m$, $CH(=NR^c)$, $CH(=NOR^c)$, $C(O)NHSO_2R^n$,sulfonic acids, sulfinic acids, phosphonic acids, phosphinic acids, activated carboxamides, hydroxamic acids, tetrazole, triazole, hydroxypyrazole, hydroxyoxazole, acidic alcohols and $SO_2NHX^1$, wherein $X^1$ is an electron withdrawing group relative to an alkyl group, $R^c$ is a member selected from the group consisting of H, $(C_1-C_8)$alkyl, $(C_3-C_8)$alkenyl, $(C_3-C_8)$alkynyl, $(C_3-C_7)$cycloalkyl, $(C_4-C_8)$cycloalkyl-alkyl, aryl, aryl$(C_1-C_8)$alkyl and $(C_1-C_8)$alkylene-Z, wherein Z is selected from the group consisting of $COR^d$, $COOR^d$, $NR^dR^e$, $NR^dCONR^eR^f$, $NR^dCOR^e$, $NR^dCOOR^e$ and $CONR^dR^e$ wherein $R^d$, $R^e$ and $R^f$ are each independently selected from the group consisting of H, $(C_1-C_8)$alkyl and phenyl, or optionally two of $R^d$, $R^e$ and $R^f$ when attached to the same nitrogen atom are combined to form a five- or six-membered ring; and wherein $R^m$ is selected from the group consisting of H, $(C_1-C_8)$alkyl, aryl, OH and $SO_2R^n$, wherein $R^n$ is selected from the group consisting of $(C_1-C_8)$alkyl, $(C_1-C_8)$haloalkyl, aryl$(C_1-C_8)$alkyl, $(C_1-C_8)$heteroalkyl, aryl, heteroaryl, $(C_1-C_8)$alkoxy, aryloxy, alkylamino, dialkylamino, arylamino, diarylamino, haloalkylamino and di(haloalkyl)amino, and $R^m$ and $R^c$ are optionally combined with the nitrogen atom to which each is attached to form a five- or six-membered ring;

HAr is benzo-1,2,3-triazole, optionally substituted with from one to three substituents independently selected from the group consisting of halogen, hydroxy, $(C_1-C_8)$alkyl, aryl$(C_1-C_8)$alkyl, $(C_1-C_8)$alkoxy, $(C_2-C_8)$alkenyl, $(C_2-C_8)$alkynyl, $(C_3-C_7)$cycloalkyl, $(C_4-C_8)$cycloalkyl-alkyl, $(C_1-C_8)$heteroalkyl, $(C_2-C_5)$heterocyclyl, aryl, aryloxy, heterosubstituted$(C_3-C_7)$cycloalkyl, heteroalkyl substituted $(C_3-C_7)$cycloalkyl, $(C_1-C_8)$haloalkyl, $O(C_1-C_8)$haloalkyl, nitro, cyano, $CO_2R^g$, $COR^g$, $NR^gR^h$, $S(O)_qR^g$, $SO_2NR^gR^h$, $NR^gCONR^hR^i$, $NR^gCOR^h$, $NR^gCOOR^h$ and $CONR^gR^h$, wherein $R^g$, $R^h$ and $R^i$ are each independently selected from the group consisting of H and $(C_1-C_8)$alkyl, or optionally two of $R^g$, $R^h$ and $R^i$ when attached to the same nitrogen atom are combined to form a five- or six-membered ring, and the subscript q is an integer of from 0 to 2;

each $R^1$ and $R^3$ is a member independently selected from the group consisting of halogen, hydroxy, $(C_1-C_8)$alkyl, $(C_2-C_8)$alkenyl, $(C_2-C_8)$alkynyl, $(C_1-C_8)$alkoxy, $(C_3-C_7)$cycloalkyl, $(C_4-C_8)$cycloalkyl-alkyl, $(C_1-C_8)$haloalkyl, $(C_1-C_8)$heteroalkyl, $(C_2-C_5)$heterocyclyl, heterosubstituted$(C_3-C_7)$cycloalkyl, heteroalkyl substituted $(C_3-C_7)$cycloalkyl, $O(C_1-C_8)$haloalkyl, nitro, cyano, phenyl, O-phenyl, $NR^j$-phenyl, $S(O)_r$-phenyl, $COR^j$, $COOR^j$, $NR^jR^k$, $S(O)_rR^j$, $SO_2NR^jR^k$, $NR^jCONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from the group consisting of H, $(C_1-C_8)$alkyl and $(C_1-C_8)$haloalkyl, or optionally two of $R^j$, $R^k$ and $R^l$ when attached to the same nitrogen atom are combined to form a five- or six-membered ring, and the subscript r is an integer of from 0 to 2;

$R^2$ is a member selected from the group consisting of H, $(C_1-C_8)$alkyl, $(C_1-C_8)$haloalkyl, aryl$(C_1-C_8)$alkyl and $(C_1-C_4)$alkylene-Z, wherein Z is as defined above;

the subscript m is an integer of from 0 to 4;

the subscript p is an integer of from 0 to 3; and pharmaceutically acceptable salts thereof.

2. A compound of claim 1, wherein Y is selected from the group consisting of $CH_2OR^c$, $CO_2R^c$, tetrazole-5-yl, $CONHSO^2R^n$ and CHO.

3. A compound of claim 1, wherein Y is selected from the group consisting of $CH_2OR^c$, tetrazole-5-yl, $CONHSO_2R^n$ and $CO_2R^c$.

4. A compound of claim 3, wherein HAr is optionally substituted with from one to three substituents independently selected from the group consisting of halogen, $(C_1-C_4)$alkyl, aryl, aryloxy, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

5. A compound of claim 4, wherein X is selected from the group consisting of O, S and NH.

6. A compound of claim 5, wherein $R^2$ is selected from the group consisting of H, $CH_3$ and $CF_3$.

7. A compound of claim 6, wherein HAr is attached to the 2- or 3-position of the ring bearing X and is optionally substituted with from one to three substituents independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

8. A compound of claim 7, wherein the subscript m is 0 to 2 and each $R^3$ when present is independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl.

9. A compound of claim 8, wherein p is an integer of from 0 to 2 and each $R^1$ when present is independently selected from the group consisting of halogen, $(C_1-C_4)$alkyl, ($C_1$–$C_4$)alkoxy, ($C_1$–$C_4$)haloalkyl, O($C_1$–$C_4$)haloalkyl, nitro, cyano, phenyl, O-phenyl, $NR^j$-phenyl and $S(O)_r$-phenyl.

10. A compound of claim 1, wherein m is an integer of from 0 to 2; each $R^3$ when present is independently selected from the group consisting of halogen, ($C_1$–$C_4$)alkyl, ($C_1$–$C_4$)alkoxy, ($C_1$–$C_4$)haloalkyl, O($C_1$–$C_4$)haloalkyl, nitro, cyano, phenyl, O-phenyl, $NR^j$-phenyl and $S(O)_r$-phenyl; p is an integer of from 0 to 2; and each $R^1$ is independently selected from the group consisting of halogen, ($C_1$–$C_4$)alkyl, ($C_1$–$C_4$)alkoxy, ($C_1$–$C_4$)haloalkyl, O($C_1$–$C_4$)haloalkyl, nitro, cyano, phenyl, O-phenyl, $NR^j$-phenyl and $S(O)_r$-phenyl.

11. A compound of claim 7, having a formula selected from the group consisting of:

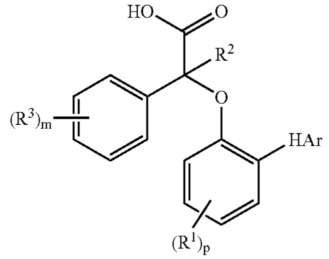

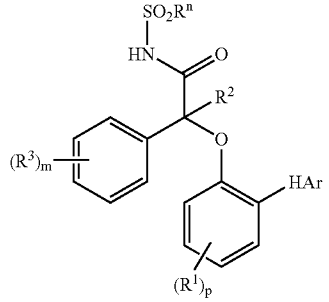

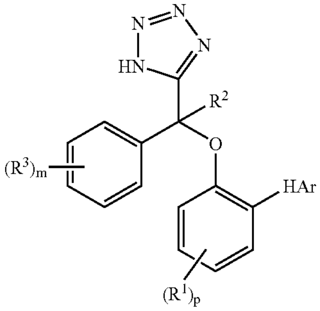

and

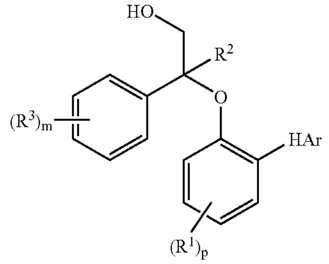

wherein the subscript m is an integer of from 0 to 2, the subscript p is an integer of from 0 to 2, and $R^1$ and $R^3$ are each independently selected from the group consisting of halogen, ($C_1$–$C_4$)alkyl, ($C_1$–$C_4$)alkoxy, ($C_1$–$C_4$)haloalkyl, O($C_1$–$C_4$)haloalkyl, nitro, cyano, phenyl, O-phenyl, $NR^j$-phenyl and $S(O)_r$-phenyl; and $R^n$ is selected from the group consisting of ($C_1$–$C_8$)alkyl, ($C_1$–$C_8$)haloalkyl, aryl($C_1$–$C_8$)alkyl, ($C_1$–$C_8$)heteroalkyl, aryl, heteroaryl, ($C_1$–$C_8$)alkoxy, aryloxy, alkylamino, dialkylamino, arylamino, diarylamino, haloalkylamino and di(haloalkyl)amino.

12. A compound of claim 11, wherein HAr is

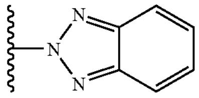

and is optionally substituted with from one to three substituents independently selected from the group consisting of halogen, ($C_1$–$C_4$)alkyl, ($C_1$–$C_4$)alkoxy, ($C_1$–$C_4$)haloalkyl, O($C_1$–$C_4$)haloalkyl, nitro, cyano, $CO_2R^g$, $COR^g$ and $CONR^gR^h$.

13. A compound of claim 12, wherein $R^2$ is H or $CH_3$; the subscript m is 0 or 1, and p is 1 or 2; and $R^1$ and $R^3$ are each independently selected from the group consisting of halogen, ($C_1$–$C_4$)alkyl, ($C_1$–$C_4$)alkoxy, ($C_1$–$C_4$)haloalkyl, O($C_1$–$C_4$)haloalkyl, nitro and cyano.

14. A composition comprising a pharmaceutically acceptable excipient and a compound having the formula:

Ia

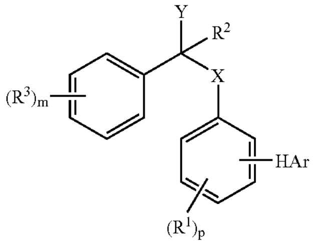

and

Ib

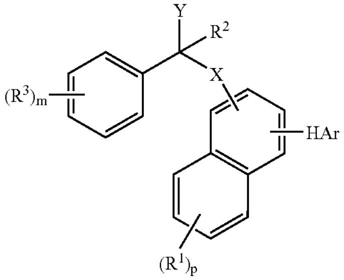

wherein

X is a member selected from the group consisting of O, S, SO, $SO_2$ and NR, wherein R is H, ($C_1$–$C_8$)alkyl, $COR^a$, $COOR^a$ and $CONR^aR^b$ wherein $R^a$and $R^b$ are each independently selected from the group consisting of H and ($C_1$–$C_8$)alkyl;

Y is a member selected from the group consisting of $CH_2OR^c$, $CO_2R^c$, CHO, $CONR^cR^m$, CH(=$NR^c$), CH(=$NOR^c$), C(O)$NHSO_2R^n$), sulfonic acids, sulfinic acids, phosphonic acids, phosphinic acids, activated carboxamides, hydroxamic acids, tetrazole, triazole, hydroxypyrazole, hydroxyoxazole, acidic alcohols and $SO_2NHX^1$, wherein $X^1$ is an electron withdrawing group relative to an alkyl group, $R^c$ is a member selected from the group consisting of H, ($C_1$–$C_8$)alkyl, ($C_3$–$C_8$)alkenyl, ($C_3$–$C_8$)alkynyl, ($C_3$–$C_7$)cycloalkyl, ($C_4$–$C_8$)cycloalkyl-alkyl, aryl, aryl($C_1$–$C_8$)alkyl and ($C_1$–$C_8$)alkylene-Z, wherein Z is selected from the group consisting of $COR^d$, $COOR^d$, $NR^dR^e$, $NR^dCONR^eR^f$, $NR^dCOR^e$, $NR^dCOOR^e$ and $CONR^dR^e$ wherein $R^d$, $R^e$ and $R^f$ are each independently selected from the group consisting of H, $(C_1–C_8)$alkyl and phenyl, or optionally two of $R^d$, $R^e$ and $R^f$ when attached to the same nitrogen atom are combined to form a five- or six-membered ring; and wherein $R^m$ is selected from the group consisting of H, $(C_1–C_8)$alkyl, aryl, OH and $SO_2R^n$, wherein $R^n$ is selected from the group consisting of $(C_1–C_8)$alkyl $(C_1–C_8)$haloalkyl, $(C_1–C_8)$aralkyl, $(C_1–C_8)$heteroalkyl, aryl, heteroaryl, $(C_1–C_8)$alkoxyl, aryloxyl, alkylamino, dialkylamino, arylamino, diarylamino, haloalkylamino and di(haloalkyl)amino; and $R^m$ and $R^c$ are optionally combined with the nitrogen atom to which each is attached to form a five- or six-membered ring;

HAr is benzo-1,2,3-triazole, optionally substituted with from one to three substituents independently selected from the group consisting of halogen, hydroxy, $(C_1–C_8)$alkyl, aryl$(C_1–C_8)$alkyl, $(C_1–C_8)$alkoxy, $(C_2–C_8)$alkenyl, $(C_2–C_8)$alkynyl, $(C_3–C_7)$cycloalkyl, $(C_4–C_8)$cycloalkyl-alkyl, $(C_1–C_8)$heteroalkyl, $(C_2–C_5)$heterocyclyl, aryl, aryloxy, heterosubstituted$(C_3–C_7)$cycloalkyl, heteroalkyl substituted $(C_3–C_7)$cycloalkyl, $(C_1–C_8)$haloalkyl, $O(C_1–C_8)$haloalkyl, nitro, cyano, $CO_2R^g$, $COR^g$, $NR^gR^h$, $S(O)_qR^g$, $SO_2NR^gR^h$, $NR^gCONR^hR^i$, $NR^gCOR^h$, $NR^gCOOR^h$ and $CONR^gR^h$, wherein $R^g$, $R^h$ and $R^i$ are each independently selected from the group consisting of H and $(C_1–C_8)$alkyl, or optionally two of $R^g$, $R^h$ and $R^i$ when attached to the same nitrogen atom are combined to form a five- or six-membered ring, and the subscript q is an integer of from 0 to 2;

each $R^1$ and $R^3$ is a member independently selected from the group consisting of halogen, hydroxy, $(C_1–C_8)$alkyl, $(C_2–C_8)$alkenyl, $(C_2–C_8)$alkynyl, $(C_1–C_8)$alkoxy, $(C_3–C_7)$cycloalkyl, $(C_4–C_8)$cycloalkyl-alkyl, $(C_1–C_8)$haloalkyl, $(C_1–C_8)$heteroalkyl, $(C_2–C_5)$heterocyclyl, heterosubstituted$(C_3–C_7)$cycloalkyl, heteroalkyl substituted $(C_3–C_7)$cycloalkyl, $O(C_1–C_8)$haloalkyl, nitro, cyano, phenyl, O-phenyl, $NR^j$-phenyl, $S(O)_r$-phenyl, $COR^j$, $COOR^j$, $NR^jR^k$, $S(O)_rR^j$, $SO_2NR^jR^k$, $NR^jCONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from the group consisting of H, $(C_1–C_8)$alkyl and $(C_1–C_8)$haloalkyl, or optionally two of $R^j$, $R^k$ and $R^l$ when attached to the same nitrogen atom are combined to form a five- or six-membered ring, and the subscript r is an integer of from 0 to 2;

$R^2$ is a member selected from the group consisting of H, $(C_1–C_8)$alkyl, $(C_1–C_8)$haloalkyl, aryl$(C_1–C_8)$alkyl and $(C_1–C_4)$alkylene-Z, wherein Z is as defined above;

the subscript m is an integer of from 0 to 4;

the subscript p is an integer of from 0 to 3; and pharmaceutically acceptable salts thereof.

15. A composition in accordance with claim 14, wherein Y is selected from the group consisting of $CH_2OR^c$, $CO_2R^c$, tetrazole-5-yl, $CONHSO_2R^n$ and CHO.

16. A composition in accordance with claim 15, wherein Y is selected from the group consisting of $CH_2OR^c$, tetrazole-5-yl, $CONHSO_2R^n$ and $CO_2R^c$.

17. A composition in accordance with claim 16, wherein HAr is optionally substituted with from one to three substituents independently selected from the group consisting of halogen, $(C_1–C_4)$alkyl, aryl, aryloxy, $(C_1–C_4)$alkoxy, $(C_1–C_4)$haloalkyl, $O(C_1–C_4)$haloalkyl, nitro, cyano, $CO_2R^g$, $COR^g$ and $CONR^gR^h$.

18. A composition in accordance with claim 17, wherein X is selected from the group consisting of O, S and NH.

19. A composition in accordance with claim 18, wherein $R^2$ is selected from the group consisting of H, $CH_3$ and $CF_3$.

20. A composition in accordance with claim 19, wherein HAr is attached to the 2- or 3-position of the ring bearing X and is optionally substituted with from one to three substituents independently selected from the group consisting of halogen, $(C_1–C_4)$alkyl, $(C_1–C_4)$alkoxy, $(C_1–C_4)$haloalkyl, $O(C_1–C_4)$haloalkyl, nitro, cyano, $CO_2R^g$, $COR^g$ and $CONR^gR^h$.

21. A composition in accordance with claim 20, wherein m is from 0 to 2; and each $R^3$ when present is independently selected from the group consisting of halogen, $(C_1–C_4)$alkyl, $(C_1–C_4)$alkoxy, $(C_1–C_4)$haloalkyl, $O(C_1–C_4)$haloalkyl, nitro, cyano, phenyl, O-phenyl, $NR^j$-phenyl and $S(O)_r$-phenyl.

22. A composition in accordance with claim 21, wherein p is from 0 to 2; and each $R^1$ when present is independently selected from the group consisting of halogen, $(C_1–C_4)$alkyl, $(C_1–C_4)$alkoxy, $(C_1–C_4)$haloalkyl, $O(C_1–C_4)$haloalkyl, nitro, cyano, phenyl, O-phenyl, $NR^j$-phenyl and $S(O)_r$-phenyl.

23. A composition in accordance with claim 14, wherein m is an integer of from 0 to 2; each $R^3$ is independently selected from the group consisting of halogen, $(C_1–C_4)$alkyl, $(C_1–C_4)$alkoxy, $(C_1–C_4)$haloalkyl, $O(C_1–C_4)$haloalkyl, nitro, cyano, phenyl, O-phenyl, $NR^j$-phenyl and $S(O)_r$-phenyl; p is an integer of from 0 to 2; and each $R^1$ is independently selected from the group consisting of halogen, $(C_1–C_4)$alkyl, $(C_1–C_4)$alkoxy, $(C_1–C_4)$haloalkyl, $O(C_1–C_4)$haloalkyl, nitro, cyano, phenyl, O-phenyl, $NR^j$-phenyl and $S(O)_r$-phenyl.

24. A composition in accordance with claim 20, having a formula selected from the group consisting of:

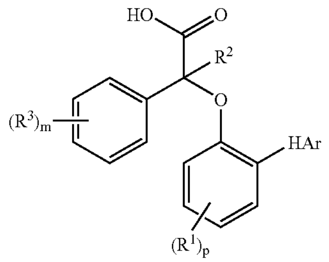

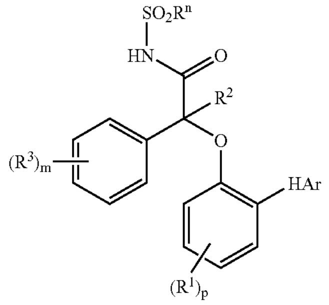

-continued

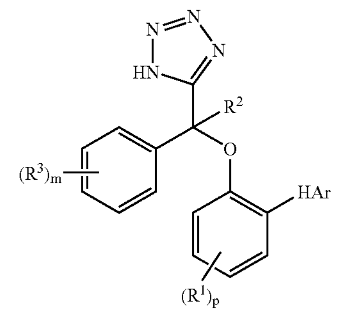

and

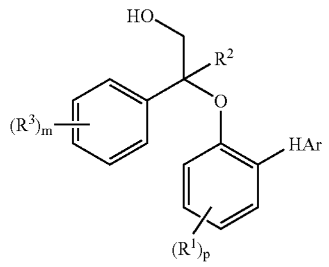

wherein the subscript m is an integer of from 0 to 2; the subscript p is an integer of from 0 to 2; $R^1$ and $R^3$ are each independently selected from the group consisting of halogen, $(C_1–C_4)$alkyl, $(C_1–C_4)$alkoxy, $(C_1–C_4)$haloalkyl, $O(C_1–C_4)$haloalkyl, nitro, cyano, phenyl, O-phenyl, $NR^j$-phenyl and $S(O)_r$-phenyl; and $R''$ is selected from the group consisting of $(C_1–C_8)$alkyl, $(C_1–C_8)$haloalkyl, aryl$(C_1–C_8)$alkyl, $(C_1–C_8)$heteroalkyl, aryl, heteroaryl, $(C_1–C_8)$alkoxy, aryloxy, alkylamino, dialkylamino, arylamino, diarylamino, haloalkylamino and di(haloalkyl)amino.

25. A composition in accordance with claim 24, wherein HAr is

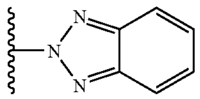

and is optionally substituted with from one to three substituents independently selected from the group consisting of halogen, $(C_1–C_4)$alkyl, $(C_1–C_4)$alkoxy, $(C_1–C_4)$haloalkyl, $O(C_1–C_4)$haloalkyl, nitro, cyano, $CO_2R^g$, $COR^g$ and $CONR^gR^h$.

26. A prodrug agent having a formula selected from the group consisting of:

Ia

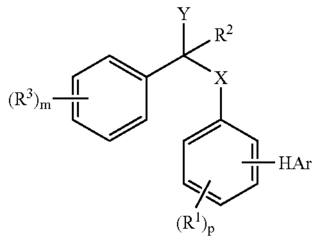

and

-continued

Ib

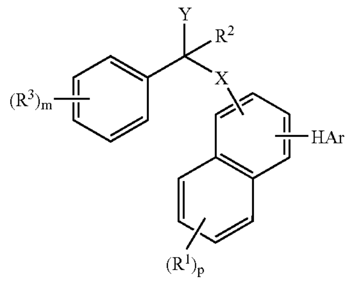

wherein

X is a member selected from the group consisting of O, S, SO, $SO_2$ and NR, wherein R is H, $(C_1–C_8)$alkyl, $COR^a$, $COOR^a$ and $CONR^aR^b$ wherein $R^a$ and $R^b$ are each independently selected from the group consisting of H and $(C_1–C_8)$alkyl;

Y is $CO_2R''$, wherein R'' is selected from the group consisting of alkyl, heteroalkyl, aryl, heteroaryl, phenyl-lower alkyl, benzamido-lower alkyl, di-lower alkylamino-lower alkyl, ureido-lower alkyl, N'-lower alkylureido-lower alkyl, carbamoyl-lower alkyl, halophenoxy substituted lower alkyl and carbamoyl substituted phenyl;

HAr is benzo-1,2,3-trizole, optionally substituted with from one to three substituents independently selected from the group consisting of halogen, hydroxy, $(C_1–C_8)$alkyl, aryl$(C_1–C_8)$alkyl, $(C_1–C_8)$alkoxy, $(C_2–C_8)$alkenyl, $(C_2–C_8)$alkynyl, $(C_3–C_7)$cycloalkyl, $(C_4–C_8)$cycloalkyl-alkyl, $(C_1–C_8)$heteroalkyl, $(C_2–C_5)$heterocyclyl, aryl, aryloxy, heterosubstituted$(C_3–C_7)$cycloalkyl, heteroalkyl substituted $(C_3–C_7)$cycloalkyl, $(C_1–C_8)$haloalkyl, $O(C_1–C_8)$haloalkyl, nitro, cyano, $CO_2R^g$, $COR^g$, $NR^gR^h$, $S(O)_qR^g$, $SO_2NR^gR^h$, $NR^gCONR^hR^i$, $NR^gCOR^h$, $NR^gCOOR^h$ and $CONR^gR^h$, wherein $R^g$, $R^h$ and $R^i$ are each independently selected from the group consisting of H and $(C_1–C_8)$alkyl, or optionally two of $R^g$, $R^h$ and $R^i$ when attached to the same nitrogen atom are combined to form a five- or six-membered ring, and the subscript q is an integer of from 0 to 2;

each $R^1$ and $R^3$ is a member independently selected from the group consisting of halogen, hydroxy, $(C_1–C_8)$alkyl, $(C_2–C_8)$alkenyl, $(C_2–C_8)$alkynyl, $(C_1–C_8)$alkoxy, $(C_3–C_7)$cycloalkyl, $(C_4–C_8)$cycloalkyl-alkyl, $(C_1–C_8)$haloalkyl, $(C_1–C_8)$heteroalkyl, $(C_2–C_5)$heterocyclyl, heterosubstituted$(C_3–C_7)$cycloalkyl, hetealkyl substituted $(C_3–C_7)$cycloalkyl, $O(C_1–C_8)$haloalkyl, nitro, cyano, phenyl, O-phenyl, $NR^j$-phenyl, $S(O)_r$-phenyl, $COR^j$, $COOR^j$, $NR^jR^k$, $S(O)_rR^j$, $SO_2NR^jR^k$, $NR^jCONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from the group consisting of H, $(C_1–C_8)$alkyl and $(C_1–C_8)$haloalkyl, or optionally two of $R^j$, $R^k$ and $R^l$ when attached to the same nitrogen atom are combined to form a five- or six-membered ring, and the subscript r is an integer of from 0 to 2;

$R^2$ is a member selected from the group consisting of H, $(C_1-C_8)$alkyl, $(C_1-C_8)$haloalkyl, aryl$(C_1-C_8)$alkyl and $(C_1-C_4)$alkylene-Z, wherein Z is as defined above;

the subscript m is an integer of from 0 to 4;

the subscript p is an integer of from 0 to 3; and pharmaceutically acceptable salts thereof.

27. A compound of claim 1, having the structure

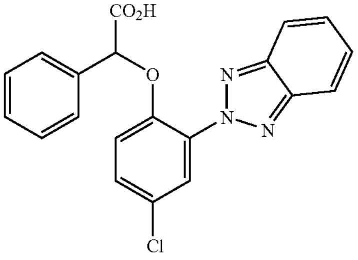

and pharmaceutically acceptable salts thereof.

28. A compound of claim 1, having the structure

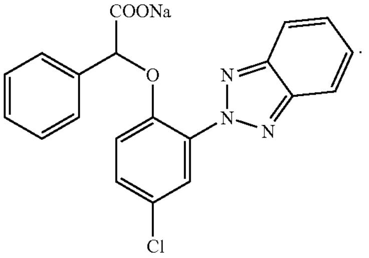

29. A compound of claim 1, selected from the group consisting of (+)-(2-Benzotriazol-2-yl-4-chloro-phenoxy)-phenylacetic acid, (−)-(2-Benzotriazol-2-yl-4-chloro-phenoxy)-phenylacetic acid, and pharmaceutically acceptable salts thereof.

30. A compound of claim 29, which is (+)-(2-Benzotriazol-2-yl-4-chloro-phenoxy)-phenylacetic acid.

31. A compound of claim 29, which is (−)-(2-Benzotriazol-2-yl-4-chloro-phenoxy)-phenylacetic acid.

* * * * *